US011998596B2

(12) United States Patent
Nikolin et al.

(10) Patent No.: US 11,998,596 B2
(45) Date of Patent: Jun. 4, 2024

(54) IMMUNOGENIC COMPOSITIONS AND VACCINES COMPRISING AFRICAN SWINE FEVER VIRUS PEPTIDES AND PROTEINS AND USES THEREOF

(71) Applicant: Boehringer Ingelheim Vetmedica GmbH, Ingelheim am Rhein (DE)

(72) Inventors: Veljko Nikolin, Hannover (DE); Egbert Siegfried Mundt, Isernhagen (DE); Fernando Rodriguez Gonzalez, Barcelona (ES); Laia Bosch Camos, Barcelona (ES); Javier Alonso Collado Miguens, Barcelona (ES)

( * ) Notice: Subject to any disclaimer, the term of this patent is extended or adjusted under 35 U.S.C. 154(b) by 0 days.

(21) Appl. No.: 18/067,614

(22) Filed: Dec. 16, 2022

(65) Prior Publication Data

US 2023/0277648 A1 Sep. 7, 2023

Related U.S. Application Data

(62) Division of application No. 16/830,412, filed on Mar. 26, 2020, now Pat. No. 11,628,214.

(30) Foreign Application Priority Data

Mar. 27, 2019 (EP) .................................... 19382216

(51) Int. Cl.

| | |
|---|---|
| *A61K 39/12* | (2006.01) |
| *C12N 15/74* | (2006.01) |
| *C12N 15/86* | (2006.01) |
| *A61K 39/00* | (2006.01) |

(52) U.S. Cl.

CPC ............ *A61K 39/12* (2013.01); *C12N 15/746* (2013.01); *C12N 15/86* (2013.01); *A61K 2039/552* (2013.01); *C12N 2710/12022* (2013.01)

(58) Field of Classification Search

None

See application file for complete search history.

(56) References Cited

U.S. PATENT DOCUMENTS

| | | | | |
|---|---|---|---|---|
| 2017/0136114 | A1 | 5/2017 | Abrams et al. | |
| 2020/0030636 | A1 | 1/2020 | Gaderlund et al. | |
| 2023/0277648 | A1* | 9/2023 | Nikolin .................. | C07K 14/01 424/204.1 |

FOREIGN PATENT DOCUMENTS

| | | | |
|---|---|---|---|
| CN | 104262484 | A | 1/2015 |
| CN | 106459931 | A | 2/2017 |
| WO | 2015091322 | A1 | 6/2015 |
| WO | 2015193685 | A1 | 12/2015 |
| WO | 2017096341 | A2 | 6/2017 |
| WO | 2020060403 | A2 | 3/2020 |
| WO | 2020102370 | A1 | 5/2020 |

OTHER PUBLICATIONS

Cadenas-Fernandez et al. (Pathogens. 2020; 9 (3): 171).*

Sequence alignment of instant SEQ ID No. 568 with UniProt db access A0A2X0TKH2 2018.*

(Continued)

*Primary Examiner* — Shanon A. Foley

(74) *Attorney, Agent, or Firm* — Steffan Finnegan

(57) ABSTRACT

The present invention relates to African swine fever virus (ASFV) peptides and/or polypeptides as well as immunogenic fragments thereof, corresponding encoding AFSV oligonucleotides and/or polynucleotides as well as immunogenic fragments thereof, immunogenic compositions, vaccines and uses thereof.

11 Claims, 3 Drawing Sheets

Specification includes a Sequence Listing.

(56) References Cited

OTHER PUBLICATIONS

Sequence alignment of instant SEQ ID No. 774 with UniProt db access A0A2X0RTS3 2018.*
Velders M.P. et al., "Defined Flanking Spacers and Enhanced Proteolysis Is Essential for Eradication of Established Tumors by an Epitope String DNA Vaccine", The Journal of Immunology, vol. 166, 2001, pp. 5366-5373.
Machuka et al., BMC Genomics, vol. 23, 2022, p. 522.
UniProt db VF145_ASFB7 2009 sequence alignment of SEQ ID 514.
Alignment with SEQ 570 with UniProt db access No. 1002L ASFWA 2009.
Alignment with SEQ 572 with UniProt db access No. 1002L ASFWA 2009.
Database Uniprot, Sep. 12, 2018, MGF 505-7R CDS protein, A0A2X0RTS3.
Database Uniprot, Sep. 12, 2018, M448R, A0A2X0TKH2.
Database Uniprot, May 18, 2010, MGF 505-7R CDS protein, D4I5L8.
Database Uniprot, Jan. 20, 2016, M448R, A0A0N7CQW3.
Yáñez R., "Analysis of the Complete Nucleotide Sequence of African Swine Fever Virus", Virology, vol. 28, Jan. 1, 1995, pp. 249-278.
Database UniProt Accession No. Q65153, May 5, 2009 (ISA).
Yáñez R., et al., "Two putative African Swine Fever Swine Fever Virus helicases similar to yeast 'DEAH' pre-mRNA processing proteins and vaccinia virus ATPases D11L and D6R", Gene, vol. 134, No. 2, 1993, pp. 161-174.
Database UniProt Accession No. Q89525, May 5, 2009 (ISA).
Alonso F. et al., "African swine fever virus-specific cytotoxic T lymphocytes recognize the 32 kDa immediate early protein (vp32)", Virus Research., vol. 49, No. 2, 1997, pp. 123-130.
Ivanov Vadimivanov, et al., "Vaccination with viral protein-mimicking peptides postpones mortality in domestic pigs Infected by African swine fever virus", Molecular Medicine Report, vol. 4, No. 3, 2011, pp. 395-401.
Leitão A., et al., "Identification of a 25-aminoacid sequence from the major African swine fever virus structural protein VP72 recognised by porcine cytotoxic T lymphocytes using a lipoprotein based expression system", Journal of Virological Methods, vol. 75, No. 1, 1998, pp. 113-119.
Leitão A., et al., "Bacterial lipoprotein based expression vectors as tools for the characterization of African swine fever virus (ASFV) antigens", Arch Virol., vol. 145, No. 8, 2000, pp. 1639-1657.
Lokhandwala S., et al., "Adenovirus-vectored African swine fever virus antigen cocktails are immunogenic but not protective against intranasal challenge with Georiga 2007/1 isolate", Vet Microbiol., vol. 235, 2019, pp. 10-20.
Arias M., et al., "Approaches and Perspectives for Development of African Swine Fever Virus Vaccines", Vaccines, vol. 5, 2017, p. 35.
Bacciu D., et al., "Genome analysis of Sardinian 26544/OG10 isolate of African Swine fever virus", Virology Reports, vol. 6, 2016, pp. 81-89.
Bao J., et al., "Genome comparison of African swine fever virus China/2018/AnhuiXCGQ strain and related European p72 Genotype II strains", Transboundary and Emerging Diseases, vol. 66, 2019, pp. 1167-1176.
Cadenas-Fernandez E., et al., "Adenovirus-vectored African Swine Fever Virus Antigens Cocktail Is Not Protective against Virulent Arm07 Isole in Eurasian Wild Boar", Pathogens, vol. 9, 2020, p. 171.
Chapman D.A., et al., "Comparison of the genome sequences of nonpathogenic and pathogenic African swine fever virus isolates", Journal of General Virology, vol. 89, 2008, pp. 387-408.
Correia S., et al., "Identification and utility of innate immune system evasion mechanisms of ASFV", Virus Research, vol. 173, 2010, pp. 87-100.

Gallardo C., et al., "Experimental Infection of Domestic Pigs with African Swine Fever Virus Lithuania 2014 Genotype II Field Isolate", Transboundary and Emerging Diseases, vol. 64, 2017, pp. 300-304.
Gaudreault N., et al., "Subunit Vaccine Approaches for African Swine Fever Virus", Vaccines, vol. 7, 2019, p. 56.
Gilliaux G., et al., "Newly emerged African swine fever virus strain Belgium/Etalle/wb/2018: Complete genomic sequence and comparative analysis with reference p72 genotype II strains", Transboundary and Emerging Diseases, vol. 66, 2019, p. 2566-2591.
Jaing C., et al., "Gene expression analysis of whole blood RNA from pigs infected with low and high pathogenic African swine fever viruses", Scientific Reports, vol. 7, 2017, p. 10115.
Jia L., et al., "Nanopore sequencing of African swine fever virus", Science China Life Science, vol. 63, No. 1, Jan. 2020, pp. 160-164.
Kollnberger S.D., et al., "Identification of the principal serological immunodeterminants of African swine fever virus by screening a virus cDNA library with antibody", Journal of General Virology, vol. 83, 2002, pp. 1331-1342.
Kovalenko G., et al., "Complete Genome Sequence of a Virulent African Swine Fever Virus from a Domestic Pig in Ukraine", Microbiology Resource Announcement, vol. 8, Issue 42, e00883-19.
Okhandwala S., et al., "Adenovirus-vectored novel African Swine Fever Virus antigens elicit robust immune response in swine", PLoS One, vol. 12, No. 5, e0177007.
Malogolovkin A., et al., "Genetic and antigenic diversity of African swine fever virus". Virus Research, vol. 271, 2019, 197673.
Olasz F., et al., "A Simple Method for Sample Preparation to Facilitate Efficient Whole-Genome Sequencing of African; Swine Fever Virus", Viruses, vol. 11, 2019, p. 1129.
Portugal R., et al., "Related strains of African swine fever virus with different virulence: genome comparison and analysis", Journal of General Virology vol. 96, 2015, pp. 408-419.
Pérez-Nuñez D., et al., "Evaluation of a viral DNA-protein immunization strategy against African swine fever in domestic pigs", Veterinary Immunology and Immunopathology, vol. 208, 2019, pp. 34-43.
Reis A. L., et al., "Systematic analysis of longitudinal serological responses of pigs infected experimentally with African swine fever virus", Journal of General Virology, vol. 88, 2007, p. 2426--2434.
Sang H., et al., "Progress Toward Development of Effective and Safe Africa Swine Fever Virus Vaccines", Frontiers in Veterinary Science., vol. 7, Article 84, Feb. 21, 2020.
Torresi C., et al., "The evolution of African swine fever virus in Sardinia (1978-2014) as revealed by whole-genome sequencing and comparative analysis", Transboundary and Emerging Diseases., vol. 00, 2020, pp. 1-10.
Wen X., et al., "Genome sequences derived from pig and dried blood pig feed samples provide important insights into the transmission of African swine fever virus in China in 2018". Emerging Microbes & Infections, vol. 8, 2019, pp. 303-306.
Xiong D., et al., "Rapid phylogenetic analysis of African swine fever virus from metagenomic sequences". bioRxiv, 2019.
Jason Farlow et al., "Intra-epidemic genome variation in highly pathogenic African swine fever virus (ASFV) from the country of Georgia", Virology Journal, vol. 15, No. 1, Dec. 1, 2018, s12985-018-1099-z.
Database Uniprot, Sep. 12, 2018, A118R, A0A2XORVA9.
De Villiers E.P., et al., "Phylogenomic analysis of 11 complete African swine fever virus genome sequences", Virology; vol. 400, No. 1, Apr. 25, 2010, pp. 128-136.
Elena G. Sanchez et al., "Development of vaccines against ASFV", Virus Research, vol. 265, May 1, 2019, pp. 150-155.
Argilaguet J.M. et al., "DNA vaccination partially protects against African swine fever virus lethal challenge in the absence of antibodies", PLoS One, vol. 7, 2012, e40942.
Calis J., et al., "Properties of MHC Class I Presented Peptides That Enhance Immunogenicity", PLoS Computational Biology, vol. 9, 2013, e1003266.
Chapman D.A et al., "Genomic Analysis of Highly Virulent Georgia 2007/1 Isolate of African Swine Fever Virus", Emerging Infectious Disease, vol. 17, No. 4, 2011, pp. 599-605.

(56) References Cited

OTHER PUBLICATIONS

Galindo-Cardiel I. et al., "Standardization of pathological investigations in the framework of experimental ASFV Infections", Virus Research, vol. 173, 2013, pp. 180-190.

Argilaguet J.M. et al., "Enhancing DNA immunization by targeting ASFV antigens to SLA-11 bearing cells", Vaccine, vol. 29, 2011, pp. 5379-5385.

Gallardo C., et al., "Comparative evaluation of novel African swine fever virus {ASF} antibody detection techniques derived from specific ASF viral genotypes with the OIE internationally prescribed serological tests", Vet Microbial, vol. 162, 2013, pp. 32-43.

Jancovich J.K. et al., "Immunization of Pigs by DNA Prime and Recombinant Vaccinia Virus Boost To Identify and Rank African Swine Fever Virus Immunogenic and Protective Proteins", J Virol., vol. 92, No. 8, 2018, e02219-17.

Jenson J.S. et al., "The cellular immune recognition of proteins expressed by an African swine fever virus random Jenomic library", J Immunol Methods, vol. 242, 2000, pp. 33-42.

Acasta A et al., "Expression library immunization can confer protection against lethal challenge with African swine fever virus", J Virol., vol. 88, 2014, pp. 13322-13332.

Lopera-Madrid J. et al., "Safety and immunogenicity of mammalian cell derived and Modified Vaccinia Ankara vectored; African swine fever subunit antigens in swine", Veterinary Immunology and Immunopathology., vol. 185, 2017, pp. 20-33.

Netherton C.L. et al., "Identification and Immunogenicity of African Swine Fever Virus Antigens", Frontier in Immunology., vol. 10, 2019, p. 1318.

O'Donnell V. et al., "African Swine Fever Virus Georgia Isolate Harboring Deletions of MGF360 and MGF505 Genes Is Attenuated in Swine and Confers Protection against Challenge with Virulent Parental Virus", Journal of Virology, vol. 89, 2015, pp. 6048-6056.

Rodriguez F. et al., "Two Overlapping Subdominant Epitopes Identified by DNA Immunization Induce Protective COB+ T-Cell Populations with Differing Cytolytic Activities", Journal of Virology., vol. 75, 2001, pp. 7399-7409.

Rodriguez J.M. et al., "Genome Sequence of African Swine Fever Virus BA71, the Virulent Parental Strain of the Nonpathogenic and Tissue-Culture Adapted BA71V", PLoS One, vol. 10, No. 11, 2015, e0142889.

Rodriguez F. and Whitton J.L., "Enhancing DNA immunization", Virology, vol. 268, 2000, pp. 233-238.

Database Uniprot accession No. A0A2X0TCF6; Sep. 12, 2018.

Database Uniprot accession No. Q07385; May 5, 2009.

* cited by examiner

Figure 5

IMMUNOGENIC COMPOSITIONS AND VACCINES COMPRISING AFRICAN SWINE FEVER VIRUS PEPTIDES AND PROTEINS AND USES THEREOF

CROSS-REFERENCE TO RELATED APPLICATIONS

This application claims priority to European patent application EP 19382216.0 filed on Mar. 27, 2019, the disclosure of which is hereby incorporated by reference.

SEQUENCE LISTING

The Sequence Listing associated with this application is provided in xml format in lieu of a paper copy, and is hereby incorporated by reference into the specification. The name of the xml file containing the Sequence Listing is 01-3357-US-2_SL.xml. The xml file is 1,008,874 bytes; it was created on May 17, 2023; and it is being submitted electronically via PatentCenter, concurrent with the filing of the specification.

This application contains a sequence listing in accordance with 37 C.F.R. 1.821-1.825. The sequence listing accompanying this application is hereby incorporated by reference in its entirety.

BACKGROUND OF THE INVENTION

A. Field of the Invention

The present invention relates to the field of veterinary vaccines, and specifically to African swine fever virus peptides and/or polypeptides, preferably full-length proteins, as well as immunogenic fragments thereof, corresponding encoding African swine fever virus oligonucleotides and/or polynucleotides as well as immunogenic fragments thereof, immunogenic compositions, vaccines and uses thereof.

B. Background and Description of the Related Art

The continuous spread of African swine fever (ASF) through Continental Europe after its introduction in Georgia in 2007, and its subsequent expansion in Asia from 2018, evidence this disease as a major threat to swine industry worldwide. ASF is a pig hemorrhagic disease of obligatory declaration to the World Organization for Animal Health (OIE) and causes enormous economic losses to the affected countries. The causative agent, African swine fever virus (ASFV), is a large, enveloped, icosahedral virus with a dsDNA genome of about 180 kbp in length. There is currently no commercial vaccine against ASFV. Early and efficient diagnosis followed by slaughtering of infected and in contact animals are the only control methods today recommended by the OIE, measures unfortunately not affordable by less favored regions.

ASF vaccine development is largely hindered by lack of knowledge about critical aspects of ASFV infection and protective immunity. In this regard, $CD8^+$ T lymphocytes have been widely shown to play a critical role in protective response against ASFV. However, the identity of the ASFV antigens capable of inducing protective $CD8^+$ T-cell responses remains largely unknown. Identification of such protective antigens could lead to rationale vaccine design as well as better understanding the mechanisms underlying ASFV immunity.

The feasibility of affording protection against the Georgia2007/1 isolate has been confirmed with the use of live attenuated viruses (Monteagudo et al., 2017; O'Donnell et al., 2015), evidencing the presence of protective Georgia2007/1 antigens. Notwithstanding, while DNA vaccination has proven successful to determine antigens or epitopes with protective potential against the E75 ASFV (Argilaguet et al., 2012; Lacasta et al., 2014), these results could not be reproduced when working with the highly virulent Georgian isolate. Other DNA-based vaccine formulations have rendered ASFV-specific response, but again failed to confer protection against Georgia2007/1 isolate/strain (Jancovich et al., 2018; Lopera-Madrid et al., 2017).

Further prior art is as follows:

Farlow J et al. (Virology Journal 2018, 15(1): 190) describe the intra-epidemic genome variation in highly pathogenic African swine fever virus (ASFV) from the country of Georgia.

Uniprot Database discloses ASFV Georgia 2007/1 full CDS protein A118R under accession number A0A2X0RVA9.

De Villiers E P et al. (Virology 2010, 400: 128-136) describe the phylogenetic analysis of 11 complete African swine fever virus genome sequences.

Netherton C L et al. (Front Immunol 2019, 10: 1318) describe the identification and immunogenicity of African swine fever virus antigens.

Sánchez E G et al. (Virus Research 2019, 265: 150-155) describe the development of vaccines against African swine fever virus.

WO 2017/096341 discloses adenovirus-vectored multivalent vaccines.

There remains an unmet need for safe ASF vaccines that in particular confer protection against the Georgia2007/1 ASFV isolate/strain.

SUMMARY OF THE INVENTION

In order to overcome the deficiencies in the prior art, the invention provides immunogenic compositions comprising
(a) one, two or more African swine fever virus peptides and/or polypeptides, preferably full-length proteins, and/or immunogenic fragments thereof; and/or
(b) one, two or more African swine fever virus oligonucleotides and/or polynucleotides and/or immunogenic fragments thereof encoding African swine fever virus peptides and/or polypeptides, preferably full-length proteins, and/or immunogenic fragments thereof; and/or
(c) a viral or bacterial vector, preferably a recombinant and/or non-naturally occurring viral or bacterial vector, comprising one, two or more African swine fever virus oligonucleotides and/or polynucleotides and/or immunogenic fragments thereof encoding African swine fever virus peptides and/or polypeptides, preferably full-length proteins, and/or immunogenic fragments thereof; and
(d) optionally, one or more pharmaceutical- or veterinary-acceptable carriers or excipients, preferably said one or more carriers or excipients being suitable for oral, intradermal, intramuscular or intranasal application.

The invention further concerns vaccines or pharmaceutical compositions comprising
(a) one, two or more African swine fever virus peptides and/or polypeptides, preferably full-length proteins, and/or immunogenic fragments thereof; and/or (b) one, two or more African swine fever virus oligonucleotides and/or polynucleotides and/or immunogenic fragments thereof encoding African swine fever virus peptides and/or polypeptides, preferably full-length proteins, and/or immunogenic fragments thereof; and/or (c) a viral or bacterial vector, preferably a recombinant and/or non-naturally occurring viral or bacterial vector, comprising one, two or more African swine fever virus oligonucleotides and/or polynucleotides and/or immunogenic fragments thereof encoding African swine fever virus peptides and/or polypeptides, preferably full-length proteins, and/or immunogenic fragments thereof; and (d) one or more pharmaceutical- or veterinary-acceptable carriers or excipients, preferably said one or more carriers or excipients being suitable for oral, intradermal, intramuscular or intranasal application;

(e) optionally, said vaccine or pharmaceutical composition further comprising an adjuvant.

The invention further concerns the immunogenic compositions or the vaccines or pharmaceutical compositions as herein described and/or claimed for use in a method of reducing or preventing the clinical signs or disease in porcines, preferably a pig, caused by an infection with at least one, preferably pathogenic, African swine fever virus or for use in a method of treating and/or preventing an infection with at least one, preferably pathogenic, African swine fever virus in porcines, preferably a pig, wherein preferably said clinical signs or disease caused by an infection with at least one, preferably pathogenic, African swine fever virus or said infection with at least one, preferably pathogenic, African swine fever virus are selected from the group consisting of: African swine fever, acute African swine fever, chronic African swine fever, mortality, death, sudden death, fever, high fever, anorexia, lethargy, weakness, loss of appetite, recumbence, erythema, cyanotic skin blotching, diarrhea, constipation, abdominal pain, respiratory signs, coughing, vomiting, dyspnea, nasal and conjunctival discharges, hemorrhages, epistaxis, abortion, leukopenia, thrombocytopenia. A corresponding method of reducing or preventing the clinical signs or disease in porcines, preferably a pig, caused by an infection with at least one, preferably pathogenic, African swine fever virus or corresponding method of treating and/or preventing an infection with at least one, preferably pathogenic, African swine fever virus in porcines, preferably a pig, comprising administering to such porcine, preferably pig, the immunogenic compositions or the vaccines or pharmaceutical compositions as herein described and/or claimed, as well as the corresponding use of the immunogenic compositions or the vaccines or pharmaceutical compositions as herein described and/or claimed for the preparation of a medicament for reducing or preventing the clinical signs or disease in porcines, preferably a pig, caused by an infection with at least one, preferably pathogenic, African swine fever virus or for treating and/or preventing an infection with at least one, preferably pathogenic, African swine fever virus in porcines, preferably a pig, are also intended to be comprised by the present invention.

The invention further concerns the immunogenic compositions or the vaccines or pharmaceutical compositions as herein described and/or claimed for use in a method of immunizing a porcine, preferably a pig, against a clinical disease caused by at least one, preferably pathogenic, African swine fever virus in said porcine, preferably pig, said method comprising the step of administering to the porcine, preferably pig, the immunogenic composition or the vaccine or pharmaceutical composition as herein described and/or claimed, wherein said immunogenic composition or vaccine or pharmaceutical composition fails to cause clinical signs of infection but is capable of inducing an immune response that immunizes the porcine, preferably pig, against, preferably pathogenic forms of, said at least one African swine fever virus, wherein preferably said clinical disease or said clinical signs of infection are selected from the group consisting of: African swine fever, acute African swine fever, chronic African swine fever, mortality, death, sudden death, fever, high fever, anorexia, lethargy, weakness, loss of appetite, recumbence, erythema, cyanotic skin blotching, diarrhea, constipation, abdominal pain, respiratory signs, coughing, vomiting, dyspnea, nasal and conjunctival discharges, hemorrhages, epistaxis, abortion, leukopenia, thrombocytopenia. A corresponding method of immunizing a porcine, preferably a pig, against a clinical disease caused by at least one, preferably pathogenic, African swine fever virus in said porcine, preferably pig, said method comprising the step of administering to the porcine, preferably pig, the immunogenic composition or the vaccine or pharmaceutical composition as herein described and/or claimed, wherein said immunogenic composition or vaccine or pharmaceutical composition fails to cause clinical signs of infection but is capable of inducing an immune response that immunizes the porcine, preferably pig, against, preferably pathogenic forms of, said at least one African swine fever virus, as well as the corresponding use of the immunogenic compositions or the vaccines or pharmaceutical composition as herein described and/or claimed for the preparation of a medicament for immunizing a porcine, preferably a pig, against a clinical disease caused by at least one, preferably pathogenic, African swine fever virus in said porcine, preferably pig, wherein said immunogenic composition or vaccine or pharmaceutical composition fails to cause clinical signs of infection but is capable of inducing an immune response that immunizes the porcine, preferably pig, against, preferably pathogenic forms of, said at least one African swine fever virus, are also intended to be comprised by the present invention.

The invention further concerns the immunogenic compositions or the vaccines or pharmaceutical compositions as herein described and/or claimed for use in a method of prime-boost immunizing a porcine, preferably a pig, against a clinical disease caused by at least one, preferably pathogenic, African swine fever virus in said porcine, preferably pig, said method comprising the step of administering to the porcine, preferably pig, once or twice an immunogenic composition or the vaccine or pharmaceutical composition as herein described and/or claimed comprising (i) one, two or more African swine fever virus oligonucleotides and/or polynucleotides and/or immunogenic fragments thereof as sole immunogenic components or (ii) a viral or bacterial vector, preferably a recombinant and/or non-naturally occurring viral or bacterial vector, comprising one, two or more African swine fever virus oligonucleotides and/or polynucleotides and/or immunogenic fragments thereof as sole immunogenic component (priming step); and subsequently—after priming once or twice—administering to the porcine, preferably pig, a live attenuated African swine fever virus, preferably BA71ΔCD2 (boosting step); wherein said immunogenic composition or vaccine or pharmaceutical composition as well as the live attenuated African swine fever virus independently from each other fail to cause clinical signs of infection but are capable of inducing an immune response that immunizes the porcine, preferably pig, against, preferably pathogenic forms of, said at least one African swine fever virus, wherein preferably said clinical disease or said clinical signs of infection are selected from the group consisting of: African swine fever, acute African swine fever, chronic African swine fever, mortality, death, sudden death, fever, high fever, anorexia, lethargy, weakness, loss of appetite, recumbence, erythema, cyanotic skin blotching, diarrhea, constipation, abdominal pain, respiratory signs, coughing, vomiting, dyspnea, nasal and conjunctival discharges, hemorrhages, epistaxis, abortion, leukopenia, thrombocytopenia. A corresponding method of prime-boost immunizing a porcine, preferably a pig, against a clinical disease caused by at least one, preferably pathogenic, African swine fever virus in said porcine, preferably pig, said method comprising the step of administering to the porcine, preferably pig, once or twice an immunogenic composition or the vaccine or pharmaceutical composition as herein described and/or claimed comprising (i) one, two or more African swine fever virus oligonucleotides and/or polynucleotides and/or immunogenic fragments thereof as sole immunogenic components or (ii) a viral or bacterial vector, preferably a recombinant and/or non-naturally occurring viral or bacterial vector, comprising one, two or more African swine fever virus oligonucleotides and/or polynucleotides and/or immunogenic fragments thereof as sole immunogenic component (priming step); and subsequently—after priming once or twice—administering to the porcine, preferably pig, a live attenuated African swine fever virus, preferably BA71ΔCD2 (boosting step); wherein said immunogenic composition or vaccine or pharmaceutical composition as well as the live attenuated African swine fever virus independently from each other fail to cause clinical signs of infection but are capable of inducing an immune response that immunizes the porcine, preferably pig, against, preferably pathogenic forms of, said at least one African swine fever virus, as well as the corresponding use of the immunogenic compositions or the vaccines or pharmaceutical compositions as herein described and/or claimed for the preparation of a medicament for prime-boost immunizing a porcine, preferably a pig, against a clinical disease caused by at least one, preferably pathogenic, African swine fever virus in said porcine, preferably pig, are also intended to be comprised by the present invention.

The invention further concerns a kit for vaccinating a porcine, preferably a pig, against a disease associated with and/or reducing the incidence or the severity of one or more clinical signs associated with or caused by at least one, preferably pathogenic, African swine fever virus in a porcine, preferably a pig, comprising:
(a) a dispenser capable of administering a vaccine to said porcine; and
(b) the immunogenic composition or the vaccine or pharmaceutical composition as herein described and/or claimed, and
(c) optionally, an instruction leaflet;
wherein preferably said disease or said clinical signs are selected from the group consisting of: African swine fever, acute African swine fever, chronic African swine fever, mortality, death, sudden death, fever, high fever, anorexia, lethargy, weakness, loss of appetite, recumbence, erythema, cyanotic skin blotching, diarrhea, constipation, abdominal pain, respiratory signs, coughing, vomiting, dyspnea, nasal and conjunctival discharges, hemorrhages, epistaxis, abortion, leukopenia, thrombocytopenia.

The invention further concerns an African swine fever virus peptide and/or polypeptide, preferably full-length-protein, and/or immunogenic fragment thereof comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: SEQ ID NOS: 1, 2, 3, 4, 5, 6, 7, 8, 9, 10, 11, 12, 13, 14, 15, 16, 17, 19, 21, 23, 25, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 1, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 272, 274, 275, 276, 277, 278, 279, 280, 281, 282, 283, 284, 285, 287, 289, 290, 291, 292, 293, 294, 295, 297, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 420, 422, 423, 424, 425, 426, 427, 428, 429, 430, 432, 434, 435, 436, 437, 438, 439, 440, 441, 442, 443, 444, 445, 446, 447, 448, 449, 450, 451, 452, 453, 454, 455, 456, 458, 460, 461, 462, 463, 464, 465, 466, 468, 470, 471, 472, 473, 474, 475, 476, 477, 478, 479, 481, 483, 484, 485, 486, 487, 489, 491, 492, 493, 494, 495, 496, 497, 498, 499, 500, 501, 502, 503, 504, 505, 506, 507, 508, 509, 510, 511, 512, 513, 514, 515, 516, 518, 520, 521, 522, 523, 524, 526, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 568, 570, 572, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 719, 721, 722, 724, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 774, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854.

The invention further concerns an African swine fever virus peptide and/or polypeptide, preferably full-length-protein, and/or immunogenic fragment thereof comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: MGF505-7R/MGF505-8R (SEQ ID NOS: 774, 772, 724, 722, 721, 719, 717), M448R (SEQ ID NOS: 568, 566, 565, 564, 563), D1133L (SEQ ID NOS: 297, 295, 294, 293, 292, 291, 290, 289, 287, 285, 284, 283, 282, 281), CP312R (SEQ ID NOS: 274, 272, 269, 268, 267), A240L (SEQ ID NOS: 854, 853, 25), A238L (SEQ ID NOS: 23, 21, 19, 17), MGF100-1L (SEQ ID NOS: 572, 570), K145R (SEQ ID NOS: 526, 524, 523, 522, 521, 520, 518, 516, 515, 514), B475L (SEQ ID NOS: 66, 65, 64, 63, 62, 61, 60, 59, 58, 57, 56, 55, 54, 53, 52, 51, 50, 49, 48), H339R (SEQ ID NOS: 468, 466, 465, 464, 463, 462, 461, 460, 458, 456, 455, 454), I226R (SEQ ID NOS: 489, 487, 486, 485, 484, 483, 481, 479, 478), CP2475L (p37) (SEQ ID NOS: 266, 265, 264, 263, 262, 261), CP2475L (p150) (SEQ ID NOS: 260, 259, 258), G1211R (SEQ ID NOS: 432, 430, 429, 428, 427, 426, 425, 424, 423, 422, 420, 418, 417, 416), M1249L (SEQ ID NOS: 562, 561, 560, 559, 558, 557, 556, 555, 554, 553, 552, 551, 550, 549, 548, 547, 546, 545, 544, 543, 542, 541, 540, 539), MGF505-9R (SEQ ID NOS: 733, 732, 731, 730, 729, 728, 727, 726), P1192R (SEQ ID NOS: 817, 816, 815, 814, 813, 812, 811, 810, 809, 808, 807, 806, 805, 804, 803, 802, 801), MGF505-1R (SEQ ID NOS: 692, 691, 690, 689, 688, 687, 686, 685, 684), MGF505-3R (SEQ ID NOS: 703, 702, 701, 700, 699), EP424R (SEQ ID NOS: 389, 388, 387, 386, 385, 384, 383, 382, 381, 380, 379), C475L (SEQ ID NOS: 201, 200, 199, 198, 197, 196, 195, 194, 193, 192, 191, 190, 189, 188), B602L (SEQ ID NOS: 75, 74, 73, 72, 71, 70, 69, 68, 67), CP530R (SEQ ID NOS: 278, 277, 276, 275), D339L (SEQ ID NOS: 322, 321, 320), D117L (SEQ ID NOS: 862, 864), I243L (SEQ ID NOS: 494, 493, 492, 491), I73R (SEQ ID NOS: 504, 503, 502), DP238L (SEQ ID NOS: 327, 326, 325), 19R (SEQ ID NOS: 513, 512, 511, 510), preferably selected from the group consisting of: MGF505-7R/MGF505-8R (SEQ ID NOS: 774, 772, 724, 722, 721, 719, 717), M448R (SEQ ID NOS: 568, 566, 565, 564, 563), D1133L (SEQ ID NOS: 297, 295, 294, 293, 292, 291, 290, 289, 287, 285, 284, 283, 282, 281), CP312R (SEQ ID NOS: 274, 272, 269, 268, 267), A240L (SEQ ID NOS: 854, 853, 25), A238L (SEQ ID NOS: 23, 21, 19, 17), MGF100-1L (SEQ ID NOS: 572, 570); and most preferably selected from the group consisting of: MGF505-7R/MGF505-8R (SEQ ID NOS: 774, 772, 724, 722, 721, 719, 717), M448R (SEQ ID NOS: 568, 566, 565, 564, 563), D1133L (SEQ ID NOS: 297, 295, 294, 293, 292, 291, 290, 289, 287, 285, 284, 283, 282, 281), CP312R (SEQ ID NOS: 274, 272, 269, 268, 267), A240L (SEQ ID NOS: 854, 853, 25).

The invention further concerns an African swine fever virus peptide and/or polypeptide, preferably full-length-protein, and/or immunogenic fragment thereof, wherein the African swine fever virus polypeptides, preferably full length proteins, comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: A238L (SEQ ID NO: 21), A238L (SEQ ID NO: 23), A240L (SEQ ID NO: 853), A240L (SEQ ID NO: 854), B475L (SEQ ID NO: 65), B475L (SEQ ID NO: 66), CP2475 (SEQ ID NO: 256), CP2475 (SEQ ID NO: 257), CP312R (SEQ ID NO: 272), CP312R (SEQ ID NO: 274), D1133L (SEQ ID NO: 295), D1133L (SEQ ID NO: 297), EP402R (SEQ ID NO: 378), EP424R (SEQ ID NO: 388), EP424R (SEQ ID NO: 389), G1211R (SEQ ID NO: 430), G1211R (SEQ ID NO: 432), H339R (SEQ ID NO: 466), H339R (SEQ ID NO: 468), I226R (SEQ ID NO: 487), I226R (SEQ ID NO: 489), K145R (SEQ ID NO: 524), K145R (SEQ ID NO: 526), M448R (SEQ ID NO: 566), M448R (SEQ ID NO: 568), M1249L (SEQ ID NO: 561), M1249L (SEQ ID NO: 562), MGF_100-1L/MGF100-1L (SEQ ID NO: 572), MGF505-1R/MGF_505-1R (SEQ ID NO: 691), MGF505-1R/MGF_505-1R (SEQ ID NO: 692), MGF505-8R/MGF_505-8R (SEQ ID NO: 722), MGF505-7R/MGF_505-7R (SEQ ID NO: 724), MGF505-8R/MGF_505-8R (SEQ ID NO: 772), MGF505-7R/MGF_505-7R (SEQ ID NO: 774), MGF505-9R/MGF_505-9R (SEQ ID NO: 732), MGF505-9R/MGF_505-9R (SEQ ID NO: 733), P1192R (SEQ ID NO: 816), P1192R (SEQ ID NO: 817) and/or wherein the African swine fever virus peptides and/or immunogenic fragments thereof and/or African swine fever virus polypeptide/full-length protein immunogenic fragments comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: A238L (SEQ ID NO: 17), A238L (SEQ ID NO: 19), A240L (SEQ ID NO: 25), B475L (SEQ ID NO: 48), B475L (SEQ ID NO: 49), B475L (SEQ ID NO: 50), B475L (SEQ ID NO: 51), B475L (SEQ ID NO: 52), B475L (SEQ ID NO: 53), B475L (SEQ ID NO: 54), B475L (SEQ ID NO: 55), B475L (SEQ ID NO: 56), B475L (SEQ ID NO: 57), B475L (SEQ ID NO: 58), B475L (SEQ ID NO: 59), B475L (SEQ ID NO: 60), B475L (SEQ ID NO: 61), B475L (SEQ ID NO: 62), B475L (SEQ ID NO: 63), B475L (SEQ ID NO: 64), CP2475 (SEQ ID NO: 235), CP2475 (SEQ ID NO: 236), CP2475 (SEQ ID NO: 237), CP2475 (SEQ ID NO: 238), CP2475 (SEQ ID NO: 239), CP2475 (SEQ ID NO: 240), CP2475 (SEQ ID NO: 241), CP2475 (SEQ ID NO: 242), CP2475 (SEQ ID NO: 243), CP2475 (SEQ ID NO: 244), CP2475 (SEQ ID NO: 245), CP2475 (SEQ ID NO: 246), CP2475 (SEQ ID NO: 247), CP2475 (SEQ ID NO: 248), CP2475 (SEQ ID NO: 249), CP2475 (SEQ ID NO: 250), CP2475 (SEQ ID NO: 251), CP2475 (SEQ ID NO: 252), CP2475 (SEQ ID NO: 253), CP2475 (SEQ ID NO: 254), CP2475 (SEQ ID NO: 255), CP2475L (p37) (SEQ ID NO: 261), CP2475L (p37) (SEQ ID NO: 262), CP2475L (p37) (SEQ ID NO: 263), CP2475L (p37) (SEQ ID NO: 264), CP2475L (p37) (SEQ ID NO: 265), CP2475L (p37) (SEQ ID NO: 266), CP2475L (p150) (SEQ ID NO: 258), CP2475L (p150) (SEQ ID NO: 259), CP2475L (p150) (SEQ ID NO: 260), CP312R (SEQ ID NO: 267), CP312R (SEQ ID NO: 268), CP312R (SEQ ID NO: 269), D1133L (SEQ ID NO: 281), D1133L (SEQ ID NO: 282), D1133L (SEQ ID NO: 283), D1133L (SEQ ID NO: 284), D1133L (SEQ ID NO: 285), D1133L (SEQ ID NO: 287), D1133L (SEQ ID NO: 289), D1133L (SEQ ID NO: 290), D1133L (SEQ ID NO: 291), D1133L (SEQ ID NO: 292), D1133L (SEQ ID NO: 293), D1133L (SEQ ID NO: 294), EP402R (SEQ ID NO: 372), EP402R (SEQ ID NO: 373), EP402R (SEQ ID NO: 374), EP402R (SEQ ID NO: 375), EP402R (SEQ ID NO: 376), EP402R (SEQ ID NO: 377), EP424R (SEQ ID NO: 379), EP424R (SEQ ID NO: 380), EP424R (SEQ ID NO: 381), EP424R (SEQ ID NO: 382), EP424R (SEQ ID NO: 383), EP424R (SEQ ID NO: 384), EP424R (SEQ ID NO: 385), EP424R (SEQ ID NO: 386), EP424R (SEQ ID NO: 387), G1211R (SEQ ID NO: 416), G1211R (SEQ ID NO: 417), G1211R (SEQ ID NO: 418), G1211R (SEQ ID NO: 420), G1211R (SEQ ID NO: 422), G1211R (SEQ ID NO: 423), G1211R (SEQ ID NO: 424), G1211R (SEQ ID NO: 425), G1211R (SEQ ID NO: 426), G1211R (SEQ ID NO: 427), G1211R (SEQ ID NO: 428), G1211R (SEQ ID NO: 429), H339R (SEQ ID NO: 454), H339R (SEQ ID NO: 455), H339R (SEQ ID NO: 456), H339R (SEQ ID NO: 458), H339R (SEQ ID NO: 460), H339R (SEQ ID NO: 461), H339R (SEQ ID NO: 462), H339R (SEQ ID NO: 463), H339R (SEQ ID NO: 464), H339R (SEQ ID NO: 465), I226R (SEQ ID NO: 478), I226R (SEQ ID NO: 479), I226R (SEQ ID NO: 481), I226R (SEQ ID NO: 483), I226R (SEQ ID NO: 484), I226R (SEQ ID NO: 485), T226R (SEQ ID NO: 486), K145R (SEQ ID NO: 514), K145R (SEQ ID NO: 515), K145R (SEQ ID NO: 516), K145R (SEQ ID NO: 518), K145R (SEQ ID NO: 520), K145R (SEQ ID NO: 521), K145R (SEQ ID NO: 522), K145R (SEQ ID NO: 523), M448R (SEQ ID NO: 563), M448R (SEQ ID NO: 564), M448R (SEQ ID NO: 565), M1249L (SEQ ID NO: 539), M1249L (SEQ ID NO: 540), M1249L (SEQ ID NO: 541), M1249L (SEQ ID NO: 542), M1249L (SEQ ID NO: 543), M1249L (SEQ ID NO: 544), M1249L (SEQ ID NO: 545), M1249L (SEQ ID NO: 546), M1249L (SEQ ID NO: 547), M1249L (SEQ ID NO: 548), M1249L (SEQ ID NO: 549), M1249L (SEQ ID NO: 550), M1249L (SEQ ID NO: 551), M1249L (SEQ ID NO: 552), M1249L (SEQ ID NO: 553), M1249L (SEQ ID NO: 554), M1249L (SEQ ID NO: 555), M1249L (SEQ ID NO: 556), M1249L (SEQ ID NO: 557), M1249L (SEQ ID NO: 558), M1249L (SEQ ID NO: 559), M1249L (SEQ ID NO: 560), MGF_100-1L/MGF100-1L (SEQ ID NO: 570), MGF505-1R/MGF_505-1R (SEQ ID NO: 684), MGF505-1R/MGF_505-1R (SEQ ID NO: 685), MGF505-1R/MGF_505-1R (SEQ ID NO: 686), MGF505-1R/MGF_505-1R (SEQ ID NO: 687), MGF505-1R/MGF_505-1R (SEQ ID NO: 688), MGF505-1R/MGF_505-1R (SEQ ID NO: 689), MGF505-1R/MGF_505-1R (SEQ ID NO: 690), MGF505-8R/MGF_505-8R (SEQ ID NO: 717), MGF505-7R/MGF_505-7R (SEQ ID NO: 719), MGF505-7R/MGF_505-7R (SEQ ID NO: 721), MGF505-9R/MGF_505-9R (SEQ ID NO: 726), MGF505-9R/MGF_505-9R (SEQ ID NO: 727), MGF505-9R/MGF_505-9R (SEQ ID NO: 728), MGF505-9R/MGF_505-9R (SEQ ID NO: 729), MGF505-9R/MGF_505-9R (SEQ ID NO: 730), MGF505-9R/MGF_505-9R (SEQ ID NO: 731), P1192R (SEQ ID NO: 801), P1192R (SEQ ID NO: 802), P1192R (SEQ ID NO: 803), P1192R (SEQ ID NO: 804), P1192R (SEQ ID NO: 805), P1192R (SEQ ID NO: 806), P1192R (SEQ ID NO: 807), P1192R (SEQ ID NO: 808), P1192R (SEQ ID NO: 809), P1192R (SEQ ID NO: 810), P1192R (SEQ ID NO: 811), P1192R (SEQ ID NO: 812), P1192R (SEQ ID NO: 813), P1192R (SEQ ID NO: 814), P1192R (SEQ ID NO: 815).

The invention further concerns an African swine fever virus peptide and/or polypeptide, preferably full-length-protein, and/or immunogenic fragment thereof, wherein the African swine fever virus polypeptides, preferably full-length proteins, comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: MGF505-7R/MGF505-8R (SEQ ID NOS: 774, 772, 724, 722), M448R (SEQ ID NOS: 568, 566), D1133L (SEQ ID NOS: 297, 295), CP312R (SEQ ID NOS: 274, 272), A240L (SEQ ID NOS: 854, 853), A238L (SEQ ID NOS: 23, 21), MGF100-1L (SEQ ID NO: 572), K145R (SEQ ID NOS: 526, 524), B475L (SEQ ID NOS: 66, 65), H339R (SEQ ID NOS: 468, 466), I226R (SEQ ID NOS: 489, 487), CP2475 (SEQ ID NO: 257), CP2475 (SEQ ID NO: 256), G1211R (SEQ ID NOS: 432, 430), M1249L (SEQ ID NOS: 562, 561), MGF505-9R (SEQ ID NOS: 733, 732), P1192R (SEQ ID NOS: 817, 816), MGF505-1R (SEQ ID NOS: 692, 691), MGF505-3R (SEQ ID NOS: 703, 702), EP424R (SEQ ID NOS: 389, 388), C475L (SEQ ID NOS: 201, 200), B602L (SEQ ID NOS: 75, 74), CP530R (SEQ ID NOS: 278, 277), D339L (SEQ ID NOS: 322, 321), D117L (SEQ ID NOS: 862, 864), I243L (SEQ ID NOS: 494, 493), I73R (SEQ ID NOS: 504, 503), DP238L (SEQ ID NOS: 327, 326), I9R (SEQ ID NOS: 513, 512) and/or wherein the African swine fever virus peptides and/or immunogenic fragments thereof and/or African swine fever virus polypeptide/full-length protein immunogenic fragments comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: MGF505-7R/MGF505-8R (SEQ ID NOS: 721, 719, 717), M448R (SEQ ID NOS: 565, 564, 563), D1133L (SEQ ID NOS: 294, 293, 292, 291, 290, 289, 287, 285, 284, 283, 282, 281), CP312R (SEQ ID NOS: 269, 268, 267), A240L (SEQ ID NO: 25), A238L (SEQ ID NOS: 19, 17), MGF100-1L (SEQ ID NO: 570), K145R (SEQ ID NOS: 523, 522, 521, 520, 518, 516, 515, 514), B475L (SEQ ID NOS: 64, 63, 62, 61, 60, 59, 58, 57, 56, 55, 54, 53, 52, 51, 50, 49, 48), H339R (SEQ ID NOS: 465, 464, 463, 462, 461, 460, 458, 456, 455, 454), I226R (SEQ ID NOS: 486, 485, 484, 483, 481, 479, 478), CP2475L (p37) (SEQ ID NOS: 266, 265, 264, 263, 262, 261), CP2475L (p150) (SEQ ID NOS: 260, 259, 258), G1211R (SEQ ID NOS: 429, 428, 427, 426, 425, 424, 423, 422, 420, 418, 417, 416), M1249L (SEQ ID NOS: 560, 559, 558, 557, 556, 555, 554, 553, 552, 551, 550, 549, 548, 547, 546, 545, 544, 543, 542, 541, 540, 539), MGF505-9R (SEQ ID NOS: 731, 730, 729, 728, 727, 726), P1192R (SEQ ID NOS: 815, 814, 813, 812, 811, 810, 809, 808, 807, 806, 805, 804, 803, 802, 801), MGF505-1R (SEQ ID NOS: 690, 689, 688, 687, 686, 685, 684), MGF505-3R (SEQ ID NOS: 701, 700, 699), EP424R (SEQ ID NOS: 387, 386, 385, 384, 383, 382, 381, 380, 379), C475L (SEQ ID NOS: 199, 198, 197, 196, 195, 194, 193, 192, 191, 190, 189, 188), B602L (SEQ ID NOS: 73, 72, 71, 70, 69, 68, 67), CP530R (SEQ ID NOS: 277, 276, 275), D339L (SEQ ID NO: 320), I243L (SEQ ID NOS: 492, 491), I73R (SEQ ID NO: 502), DP238L (SEQ ID NO: 325), I9R (SEQ ID NOS: 511, 510).

The invention further concerns an African swine fever virus oligonucleotide and/or polynucleotide and/or immunogenic fragment thereof encoding the African swine fever virus peptide and/or polypeptide, preferably full-length-protein, and/or immunogenic fragment thereof as herein described and/or claimed.

The invention further concerns an African swine fever virus oligonucleotide and/or polynucleotide and/or immunogenic fragment thereof encoding African swine fever virus peptides and/or polypeptides, preferably full-length proteins, and/or immunogenic fragments thereof; comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: SEQ ID NOS: 18, 20, 22, 24, 26, 27, 270, 271, 273, 286, 288, 296, 298, 419, 421, 431, 433, 457, 459, 467, 469, 480, 482, 488, 490, 517, 519, 525, 527, 567, 569, 571, 573, 718, 720, 723, 725, 773, 775.

The invention further concerns an African swine fever virus oligonucleotide and/or polynucleotide and/or immunogenic fragment thereof encoding African swine fever virus peptides and/or polypeptides, preferably full-length proteins, and/or immunogenic fragments thereof; comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF505-7R/MGF505-8R (SEQ ID NOS: 857, 775, 773, 725, 723, 720, 718), M448R (SEQ ID NOS: 858, 569, 567), D1133L (SEQ ID NOS: 859, 298, 296, 288, 286), CP312R (SEQ ID NOS: 861, 273, 901, 900, 271, 270), A240L (SEQ ID NOS: 860, 27, 26), A238L (SEQ ID NOS: 24, 22, 20, 18), MGF100-1L (SEQ ID NOS: 573, 571), K145R (SEQ ID NOS: 527, 525, 519, 517), B475L (SEQ ID NOS: 866, 867), H339R (SEQ ID NOS: 469, 467, 459, 457), I226R (SEQ ID NOS: 490, 488, 482, 480), CP2475L (p37) (SEQ ID NOS: 868, 869), CP2475L (p150) (SEQ ID NOS: 870, 871), G1211R (SEQ ID NOS: 433, 431, 421, 419), M1249L (SEQ ID NOS: 872, 873), MGF505-9R (SEQ ID NOS: 874, 875), P1192R (SEQ ID NOS: 876, 877), MGF505-1R (SEQ ID NOS: 878, 879), MGF505-3R (SEQ ID NOS: 880, 881), EP424R (SEQ ID NOS: 882, 883), C475L (SEQ ID NOS: 884, 885), B602L (SEQ ID NOS: 886, 887), CP530R (SEQ ID NOS: 888, 889), D339L (SEQ ID NOS: 890, 891), D117L (SEQ ID NOS: 863, 865), I243L (SEQ ID NOS: 892, 893), I73R (SEQ ID NOS: 894, 895), DP238L (SEQ ID NOS: 896, 897), I9R (SEQ ID NOS: 898, 899); preferably selected from the group consisting of: MGF505-7R/MGF505-8R (SEQ ID NOS: 857, 775, 773, 725, 723, 720, 718), M448R (SEQ ID NOS: 858, 569, 567), D1133L (SEQ ID NOS: 859, 298, 296, 288, 286), CP312R (SEQ ID NOS: 861, 273, 901, 900, 271, 270), A240L (SEQ ID NOS: 860, 27, 26), A238L (SEQ ID NOS: 24, 22, 20, 18), MGF100-1L (SEQ ID NOS: 573, 571); and most preferably selected from the group consisting of: MGF505-7R/MGF505-8R (SEQ ID NOS: 857, 775, 773, 725, 723, 720, 718), M448R (SEQ ID NOS: 858, 569, 567), D1133L (SEQ ID NOS: 859, 298, 296, 288, 286), CP312R (SEQ ID NOS: 861, 273, 901, 900, 271, 270), A240L (SEQ ID NOS: 860, 27, 26).

The invention further concerns a vector comprising one, two, three or more African swine fever virus oligonucleotides and/or polynucleotides and/or immunogenic fragments thereof as herein described and/or claimed. Preferably such vector comprises three African swine fever virus oligonucleotides and/or polynucleotides and/or immunogenic fragments thereof, preferably selected from EP402R, CP312R and A240L (multiepitope-I, ME-I), more preferably comprises, most preferably consists of, the nucleic acid sequence selected from the group consisting of SEQ ID NO: 855; or comprises thirteen African swine fever virus oligonucleotides and/or polynucleotides and/or immunogenic fragments thereof, preferably selected from D1133L, G1211R, M1249L, MGF505-9R, P1192R, CP2475L (p150), B475L, EP424R, H339R, I226R, K145R, MGF505-1R and CP2475L (p37) (multiepitope-II, ME-II), more preferably comprises, most preferably consists of, the nucleic acid sequence selected from the group consisting of SEQ ID NO: 856.

The invention further concerns a host cell, preferably a mammalian host cell, comprising the vector as herein described and/or claimed.

Thus, the solution to the above technical problem is achieved by the description and the embodiments, characterized in the claims, and the invention in its different aspects is implemented according to the claims.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3 depicts the survival percentage after Georgia2007/1 lethal challenge of pigs primed with either the selected 15 recombinant plasmids (15 clones) or the empty pCMV-Ub plasmid (Control). Both groups were immunized with a low dose of the live attenuated virus (LAV) BA71ΔCD2.

FIG. 4 depicts the percentage of surviving pigs within the M448R+MGF505-7R-primed group (solid line) and the control group (dashed line) after a Georgia2007/1 lethal challenge infection.

FIG. 5 depicts the percentage of surviving pigs after the Georgia2007/1 lethal challenge within the group primed with the multiepitopes (solid line) and the control group (dashed line).

DETAILED DESCRIPTION OF THE INVENTION

Figure 1:
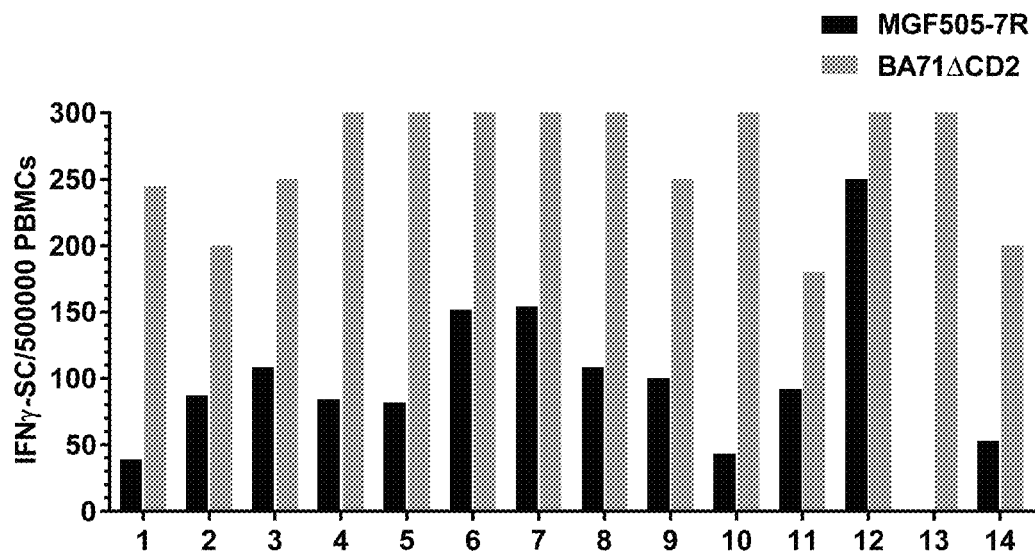
FIG. 1 depicts the following: in black, IFNγ response assessed by ELISpot assay using fibroblasts transfected with the pCMV-Ub-MGF505-7R plasmid as APCs, and PBMCs from ASF-convalescent animals as effector cells. The number of spots when stimulating with fibroblasts transfected with the pCMV-Ub empty plasmid, which never exceeded 10, were subtracted from the represented values. In grey, the levels of ASFV-specific IFNγ-SC are shown.

The present invention solves the problems inherent in the prior art and provides a distinct advance in the state of the art.

Generally, the present invention concerns immunogenic compositions comprising
(a) one, two or more African swine fever virus peptides and/or polypeptides, preferably full-length proteins, and/or immunogenic fragments thereof; and/or
(b) one, two or more African swine fever virus oligonucleotides and/or polynucleotides and/or immunogenic fragments thereof encoding African swine fever virus peptides and/or polypeptides, preferably full-length proteins, and/or immunogenic fragments thereof; and/or
(c) a viral or bacterial vector, preferably a recombinant and/or non-naturally occurring viral or bacterial vector, comprising one, two or more African swine fever virus oligonucleotides and/or polynucleotides and/or immunogenic fragments thereof encoding African swine fever virus peptides and/or polypeptides, preferably full-length proteins, and/or immunogenic fragments thereof; and
(d) optionally, one or more pharmaceutical- or veterinary-acceptable carriers or excipients, preferably said one or more carriers or excipients being suitable for oral, intradermal, intramuscular or intranasal application;
or vaccines or pharmaceutical compositions comprising
(a) one, two or more African swine fever virus peptides and/or polypeptides, preferably full-length proteins, and/or immunogenic fragments thereof; and/or (b) one, two or more African swine fever virus oligonucleotides and/or polynucleotides and/or immunogenic fragments thereof encoding African swine fever virus peptides and/or polypeptides, preferably full-length proteins, and/or immunogenic fragments thereof; and/or (c) a viral or bacterial vector, preferably a recombinant and/or non-naturally occurring viral or bacterial vector, comprising one, two or more African swine fever virus oligonucleotides and/or polynucleotides and/or immunogenic fragments thereof encoding African swine fever virus peptides and/or polypeptides, preferably full-length proteins, and/or immunogenic fragments thereof; and (d) one or more pharmaceutical- or veterinary-acceptable carriers or excipients, preferably said one or more carriers or excipients being suitable for oral, intradermal, intramuscular or intranasal application;

(e) optionally, said vaccine or pharmaceutical composition further comprising an adjuvant.

In a specific aspect, the immunogenic compositions or the vaccines or pharmaceutical compositions as described and/or claimed herein are provided, wherein the African swine fever virus is selected from the group consisting of: BA71, BA71ΔCD2 and/or Georgia2007/1 strain(s).

In another specific aspect, the immunogenic compositions or the vaccines or pharmaceutical compositions as described and/or claimed herein are provided, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: SEQ ID NOS: 1, 2, 3, 4, 5, 6, 7, 8, 9, 10, 11, 12, 13, 14, 15, 16, 17, 19, 21, 23, 25, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 1, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 272, 274, 275, 276, 277, 278, 279, 280, 281, 282, 283, 284, 285, 287, 289, 290, 291, 292, 293, 294, 295, 297, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 420, 422, 423, 424, 425, 426, 427, 428, 429, 430, 432, 434, 435, 436, 437, 438, 439, 440, 441, 442, 443, 444, 445, 446, 447, 448, 449, 450, 451, 452, 453, 454, 455, 456, 458, 460, 461, 462, 463, 464, 465, 466, 468, 470, 471, 472, 473, 474, 475, 476, 477, 478, 479, 481, 483, 484, 485, 486, 487, 489, 491, 492, 493, 494, 495, 496, 497, 498, 499, 500, 501, 502, 503, 504, 505, 506, 507, 508, 509, 510, 511, 512, 513, 514, 515, 516, 518, 520, 521, 522, 523, 524, 526, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 568, 570, 572, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 719, 721, 722, 724, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 774, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854.

In yet another specific aspect, the immunogenic compositions or the vaccines or pharmaceutical compositions as described and/or claimed herein are provided, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: MGF505-7R/MGF505-8R (SEQ ID NOS: 774, 772, 724, 722, 721, 719, 717), M448R (SEQ ID NOS: 568, 566, 565, 564, 563), D1133L (SEQ ID NOS: 297, 295, 294, 293, 292, 291, 290, 289, 287, 285, 284, 283, 282, 281), CP312R (SEQ ID NOS: 274, 272, 269, 268, 267), A240L (SEQ ID NOS: 854, 853, 25), A238L (SEQ ID NOS: 23, 21, 19, 17), MGF100-1L (SEQ ID NOS: 572, 570), K145R (SEQ ID NOS: 526, 524, 523, 522, 521, 520, 518, 516, 515, 514), B475L (SEQ ID NOS: 66, 65, 64, 63, 62, 61, 60, 59, 58, 57, 56, 55, 54, 53, 52, 51, 50, 49, 48), H339R (SEQ ID NOS: 468, 466, 465, 464, 463, 462, 461, 460, 458, 456, 455, 454), I226R (SEQ ID NOS: 489, 487, 486, 485, 484, 483, 481, 479, 478), CP2475L (p37) (SEQ ID NOS: 266, 265, 264, 263, 262, 261), CP2475L (p150) (SEQ ID NOS: 260, 259, 258), G1211R (SEQ ID NOS: 432, 430, 429, 428, 427, 426, 425, 424, 423, 422, 420, 418, 417, 416), M1249L (SEQ ID NOS: 562, 561, 560, 559, 558, 557, 556, 555, 554, 553, 552, 551, 550, 549, 548, 547, 546, 545, 544, 543, 542, 541, 540, 539), MGF505-9R (SEQ ID NOS: 733, 732, 731, 730, 729, 728, 727, 726), P1192R (SEQ ID NOS: 817, 816, 815, 814, 813, 812, 811, 810, 809, 808, 807, 806, 805, 804, 803, 802, 801), MGF505-1R (SEQ ID NOS: 692, 691, 690, 689, 688, 687, 686, 685, 684), MGF505-3R (SEQ ID NOS: 703, 702, 701, 700, 699), EP424R (SEQ ID NOS: 389, 388, 387, 386, 385, 384, 383, 382, 381, 380, 379), C475L (SEQ ID NOS: 201, 200, 199, 198, 197, 196, 195, 194, 193, 192, 191, 190, 189, 188), B602L (SEQ ID NOS: 75, 74, 73, 72, 71, 70, 69, 68, 67), CP530R (SEQ ID NOS: 278, 277, 276, 275), D339L (SEQ ID NOS: 322, 321, 320), D117L (SEQ ID NOS: 862, 864), I243L (SEQ ID NOS: 494, 493, 492, 491), I73R (SEQ ID NOS: 504, 503, 502), DP238L (SEQ ID NOS: 327, 326, 325), 19R (SEQ ID NOS: 513, 512, 511, 510), preferably selected from the group consisting of: MGF505-7R/MGF505-8R (SEQ ID NOS: 774, 772, 724, 722, 721, 719, 717), M448R (SEQ ID NOS: 568, 566, 565, 564, 563), D1133L (SEQ ID NOS: 297, 295, 294, 293, 292, 291, 290, 289, 287, 285, 284, 283, 282, 281), CP312R (SEQ ID NOS: 274, 272, 269, 268, 267), A240L (SEQ ID NOS: 854, 853, 25), A238L (SEQ ID NOS: 23, 21, 19, 17), MGF100-1L (SEQ ID NOS: 572, 570); and most preferably selected from the group consisting of: MGF505-7R/MGF505-8R (SEQ ID NOS: 774, 772, 724, 722, 721, 719, 717), M448R (SEQ ID NOS: 568, 566, 565, 564, 563), D1133L (SEQ ID NOS: 297, 295, 294, 293, 292, 291, 290, 289, 287, 285, 284, 283, 282, 281), CP312R (SEQ ID NOS: 274, 272, 269, 268, 267), A240L (SEQ ID NOS: 854, 853, 25).

In yet another specific aspect, the immunogenic composition or the vaccine or pharmaceutical composition as described and/or claimed herein are provided, wherein according to (b) the one, two or more African swine fever virus oligonucleotides and/or polynucleotides and/or immunogenic fragments thereof encode the one, two or more African swine fever virus peptides and/or polypeptides, preferably full-length proteins, and/or immunogenic fragments thereof as herein disclosed and/or claimed.

In yet another specific aspect, the immunogenic composition or the vaccine or pharmaceutical composition as described and/or claimed herein are provided, wherein according to (b) the one, two or more African swine fever virus oligonucleotides and/or polynucleotides and/or immunogenic fragments thereof encode the one, two or more African swine fever virus peptides and/or polypeptides, preferably full-length proteins, and/or immunogenic fragments thereof comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: MGF505-7R/MGF505-8R (SEQ ID NOS: 774, 772, 724, 722, 721, 719, 717), M448R (SEQ ID NOS: 568, 566, 565, 564, 563), D1133L (SEQ ID NOS: 297, 295, 294, 293, 292, 291, 290, 289, 287, 285, 284, 283, 282, 281), CP312R (SEQ ID NOS: 274, 272, 269, 268, 267), A240L (SEQ ID NOS: 854, 853, 25), A238L (SEQ ID NOS: 23, 21, 19, 17), MGF100-1L (SEQ ID NOS: 572, 570), K145R (SEQ ID NOS: 526, 524, 523, 522, 521, 520, 518, 516, 515, 514), B475L (SEQ ID NOS: 66, 65, 64, 63, 62, 61, 60, 59, 58, 57, 56, 55, 54, 53, 52, 51, 50, 49, 48), H339R (SEQ ID NOS: 468, 466, 465, 464, 463, 462, 461, 460, 458, 456, 455, 454), I226R (SEQ ID NOS: 489, 487, 486, 485, 484, 483, 481, 479, 478), CP2475L (p37) (SEQ ID NOS: 266, 265, 264, 263, 262, 261), CP2475L (p150) (SEQ ID NOS: 260, 259, 258), G1211R (SEQ ID NOS: 432, 430, 429, 428, 427, 426, 425, 424, 423, 422, 420, 418, 417, 416), M1249L (SEQ ID NOS: 562, 561, 560, 559, 558, 557, 556, 555, 554, 553, 552, 551, 550, 549, 548, 547, 546, 545, 544, 543, 542, 541, 540, 539), MGF505-9R (SEQ ID NOS: 733, 732, 731, 730, 729, 728, 727, 726), P1192R (SEQ ID NOS: 817, 816, 815, 814, 813, 812, 811, 810, 809, 808, 807, 806, 805, 804, 803, 802, 801), MGF505-1R (SEQ ID NOS: 692, 691, 690, 689, 688, 687, 686, 685, 684), MGF505-3R (SEQ ID NOS: 703, 702, 701, 700, 699), EP424R (SEQ ID NOS: 389, 388, 387, 386, 385, 384, 383, 382, 381, 380, 379), C475L (SEQ ID NOS: 201, 200, 199, 198, 197, 196, 195, 194, 193, 192, 191, 190, 189, 188), B602L (SEQ ID NOS: 75, 74, 73, 72, 71, 70, 69, 68, 67), CP530R (SEQ ID NOS: 278, 277, 276, 275), D339L (SEQ ID NOS: 322, 321, 320), D117L (SEQ ID NOS: 862, 864), I243L (SEQ ID NOS: 494, 493, 492, 491), I73R (SEQ ID NOS: 504, 503, 502), DP238L (SEQ ID NOS: 327, 326, 325), 19R (SEQ ID NOS: 513, 512, 511, 510), preferably selected from the group consisting of: MGF505-7R/MGF505-8R (SEQ ID NOS: 774, 772, 724, 722, 721, 719, 717), M448R (SEQ ID NOS: 568, 566, 565, 564, 563), D1133L (SEQ ID NOS: 297, 295, 294, 293, 292, 291, 290, 289, 287, 285, 284, 283, 282, 281), CP312R (SEQ ID NOS: 274, 272, 269, 268, 267), A240L (SEQ ID NOS: 854, 853, 25), A238L (SEQ ID NOS: 23, 21, 19, 17), MGF100-1L (SEQ ID NOS: 572, 570); and most preferably selected from the group consisting of: MGF505-7R/MGF505-8R (SEQ ID NOS: 774, 772, 724, 722, 721, 719, 717), M448R (SEQ ID NOS: 568, 566, 565, 564, 563), D1133L (SEQ ID NOS: 297, 295, 294, 293, 292, 291, 290, 289, 287, 285, 284, 283, 282, 281), CP312R (SEQ ID NOS: 274, 272, 269, 268, 267), A240L (SEQ ID NOS: 854, 853, 25).

In yet another specific aspect, the immunogenic compositions or the vaccines or pharmaceutical compositions as described and/or claimed herein are provided, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: SEQ ID NOS: 18, 20, 22, 24, 26, 27, 270, 271, 273, 286, 288, 296, 298, 419, 421, 431, 433, 457, 459, 467, 469, 480, 482, 488, 490, 517, 519, 525, 527, 567, 569, 571, 573, 718, 720, 723, 725, 773, 775.

In yet another specific aspect, the immunogenic compositions or the vaccines or pharmaceutical compositions as described and/or claimed herein are provided, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF505-7R/MGF505-8R (SEQ ID NOS: 857, 775, 773, 725, 723, 720, 718), M448R (SEQ ID NOS: 858, 569, 567), D1133L (SEQ ID NOS: 859, 298, 296, 288, 286), CP312R (SEQ ID NOS: 861, 273, 901, 900, 271, 270), A240L (SEQ ID NOS: 860, 27, 26), A238L (SEQ ID NOS: 24, 22, 20, 18), MGF100-1L (SEQ ID NOS: 573, 571), K145R (SEQ ID NOS: 527, 525, 519, 517), B475L (SEQ ID NOS: 866, 867), H339R (SEQ ID NOS: 469, 467, 459, 457), I226R (SEQ ID NOS: 490, 488, 482, 480), CP2475L (p37) (SEQ ID NOS: 868, 869), CP2475L (p150) (SEQ ID NOS: 870, 871), G1211R (SEQ ID NOS: 433, 431, 421, 419), M1249L (SEQ ID NOS: 872, 873), MGF505-9R (SEQ ID NOS: 874, 875), P1192R (SEQ ID NOS: 876, 877), MGF505-1R (SEQ ID NOS: 878, 879), MGF505-3R (SEQ ID NOS: 880, 881), EP424R (SEQ ID NOS: 882, 883), C475L (SEQ ID NOS: 884, 885), B602L (SEQ ID NOS: 886, 887), CP530R (SEQ ID NOS: 888, 889), D339L (SEQ ID NOS: 890, 891), D117L (SEQ ID NOS: 863, 865), I243L (SEQ ID NOS: 892, 893), I73R (SEQ ID NOS: 894, 895), DP238L (SEQ ID NOS: 896, 897), 19R (SEQ ID NOS: 898, 899), preferably selected from the group consisting of: MGF505-7R/MGF505-8R (SEQ ID NOS: 857, 775, 773, 725, 723, 720, 718), M448R (SEQ ID NOS: 858, 569, 567), D1133L (SEQ ID NOS: 859, 298, 296, 288, 286), CP312R (SEQ ID NOS: 861, 273, 901, 900, 271, 270), A240L (SEQ ID NOS: 860, 27, 26), A238L (SEQ ID NOS: 24, 22, 20, 18), MGF100-1L (SEQ ID NOS: 573, 571); and most preferably selected from the group consisting of: MGF505-7R/MGF505-8R (SEQ ID NOS: 857, 775, 773, 725, 723, 720, 718), M448R (SEQ ID NOS: 858, 569, 567), D1133L (SEQ ID NOS: 859, 298, 296, 288, 286), CP312R (SEQ ID NOS: 861, 273, 901, 900, 271, 270), A240L (SEQ ID NOS: 860, 27, 26).

In yet another specific aspect, the immunogenic compositions or the vaccines or pharmaceutical compositions as described and/or claimed herein are provided, wherein according to (c) the viral or bacterial vector is selected from the group consisting of: asfivirus viral vector, avipox virus viral vector, canine morbillivirus viral vector, herpes virus viral vector, varicella virus viral vector, *Lawsonia* spp., *Salmonella* spp.

In yet another specific aspect, the immunogenic compositions or the vaccines or pharmaceutical compositions as described and/or claimed herein are provided, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof as herein disclosed and/or claimed.

In yet another specific aspect, the immunogenic compositions or the vaccines or pharmaceutical compositions as described and/or claimed herein are provided, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: MGF505-7R/MGF505-8R (SEQ ID NOS: 774, 772, 724, 722, 721, 719, 717), M448R (SEQ ID NOS: 568, 566, 565, 564, 563), D1133L (SEQ ID NOS: 297, 295, 294, 293, 292, 291, 290, 289, 287, 285, 284, 283, 282, 281), CP312R (SEQ ID NOS: 274, 272, 269, 268, 267), A240L (SEQ ID NOS: 854, 853, 25), A238L (SEQ ID NOS: 23, 21, 19, 17), MGF100-1L (SEQ ID NOS: 572, 570), K145R (SEQ ID NOS: 526, 524, 523, 522, 521, 520, 518, 516, 515, 514), B475L (SEQ ID NOS: 66, 65, 64, 63, 62, 61, 60, 59, 58, 57, 56, 55, 54, 53, 52, 51, 50, 49, 48), H339R (SEQ ID NOS: 468, 466, 465, 464, 463, 462, 461, 460, 458, 456, 455, 454), I226R (SEQ ID NOS: 489, 487, 486, 485, 484, 483, 481, 479, 478), CP2475L (p37) (SEQ ID NOS: 266, 265, 264, 263, 262, 261), CP2475L (p150) (SEQ ID NOS: 260, 259, 258), G1211R (SEQ ID NOS: 432, 430, 429, 428, 427, 426, 425, 424, 423, 422, 420, 418, 417, 416), M1249L (SEQ ID NOS: 562, 561, 560, 559, 558, 557, 556, 555, 554, 553, 552, 551, 550, 549, 548, 547, 546, 545, 544, 543, 542, 541, 540, 539), MGF505-9R (SEQ ID NOS: 733, 732, 731, 730, 729, 728, 727, 726), P1192R (SEQ ID NOS: 817, 816, 815, 814, 813, 812, 811, 810, 809, 808, 807, 806, 805, 804, 803, 802, 801), MGF505-1R (SEQ ID NOS: 692, 691, 690, 689, 688, 687, 686, 685, 684), MGF505-3R (SEQ ID NOS: 703, 702, 701, 700, 699), EP424R (SEQ ID NOS: 389, 388, 387, 386, 385, 384, 383, 382, 381, 380, 379), C475L (SEQ ID NOS: 201, 200, 199, 198, 197, 196, 195, 194, 193, 192, 191, 190, 189, 188), B602L (SEQ ID NOS: 75, 74, 73, 72, 71, 70, 69, 68, 67), CP530R (SEQ ID NOS: 278, 277, 276, 275), D339L (SEQ ID NOS: 322, 321, 320), D117L (SEQ ID NOS: 862, 864), I243L (SEQ ID NOS: 494, 493, 492, 491), I73R (SEQ ID NOS: 504, 503, 502), DP238L (SEQ ID NOS: 327, 326, 325), 19R (SEQ ID NOS: 513, 512, 511, 510), preferably selected from the group consisting of: MGF505-7R/MGF505-8R (SEQ ID NOS: 774, 772, 724, 722, 721, 719, 717), M448R (SEQ ID NOS: 568, 566, 565, 564, 563), D1133L (SEQ ID NOS: 297, 295, 294, 293, 292, 291, 290, 289, 287, 285, 284, 283, 282, 281), CP312R (SEQ ID NOS: 274, 272, 269, 268, 267), A240L (SEQ ID NOS: 854, 853, 25), A238L (SEQ ID NOS: 23, 21, 19, 17), MGF100-1L (SEQ ID NOS: 572, 570); and most preferably selected from the group consisting of: MGF505-7R/MGF505-8R (SEQ ID NOS: 774, 772, 724, 722, 721, 719, 717), M448R (SEQ ID NOS: 568, 566, 565, 564, 563), D1133L (SEQ ID NOS: 297, 295, 294, 293, 292, 291, 290, 289, 287, 285, 284, 283, 282, 281), CP312R (SEQ ID NOS: 274, 272, 269, 268, 267), A240L (SEQ ID NOS: 854, 853, 25).

In yet another specific aspect, the immunogenic compositions or the vaccines or pharmaceutical compositions as described and/or claimed herein are provided, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: SEQ ID NOS: 18, 20, 22, 24, 26, 27, 270, 271, 273, 286, 288, 296, 298, 419, 421, 431, 433, 457, 459, 467, 469, 480, 482, 488, 490, 517, 519, 525, 527, 567, 569, 571, 573, 718, 720, 723, 725, 773, 775.

In yet another specific aspect, the immunogenic compositions or the vaccines or pharmaceutical compositions as described and/or claimed herein are provided, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF505-7R/MGF505-8R (SEQ ID NOS: 857, 775, 773, 725, 723, 720, 718), M448R (SEQ ID NOS: 858, 569, 567), D1133L (SEQ ID NOS: 859, 298, 296, 288, 286), CP312R (SEQ ID NOS: 861, 273, 901, 900, 271, 270), A240L (SEQ ID NOS: 860, 27, 26), A238L (SEQ ID NOS: 24, 22, 20, 18), MGF100-1L (SEQ ID NOS: 573, 571), K145R (SEQ ID NOS: 527, 525, 519, 517), B475L (SEQ ID NOS: 866, 867), H339R (SEQ ID NOS: 469, 467, 459, 457), I226R (SEQ ID NOS: 490, 488, 482, 480), CP2475L (p37) (SEQ ID NOS: 868, 869), CP2475L (p150) (SEQ ID NOS: 870, 871), G1211R (SEQ ID NOS: 433, 431, 421, 419), M1249L (SEQ ID NOS: 872, 873), MGF505-9R (SEQ ID NOS: 874, 875), P1192R (SEQ ID NOS: 876, 877), MGF505-1R (SEQ ID NOS: 878, 879), MGF505-3R (SEQ ID NOS: 880, 881), EP424R (SEQ ID NOS: 882, 883), C475L (SEQ ID NOS: 884, 885), B602L (SEQ ID NOS: 886, 887), CP530R (SEQ ID NOS: 888, 889), D339L (SEQ ID NOS: 890, 891), D117L (SEQ ID NOS: 863, 865), I243L (SEQ ID NOS: 892, 893), I73R (SEQ ID NOS: 894, 895), DP238L (SEQ ID NOS: 896, 897), I9R (SEQ ID NOS: 898, 899), preferably selected from the group consisting of: MGF505-7R/MGF505-8R (SEQ ID NOS: 857, 775, 773, 725, 723, 720, 718), M448R (SEQ ID NOS: 858, 569, 567), D1133L (SEQ ID NOS: 859, 298, 296, 288, 286), CP312R (SEQ ID NOS: 861, 273, 271, (MGF505-7R)), A240L (SEQ ID NOS: 860, 27, 26), A238L (SEQ ID NOS: 24, 22, 20, 18), MGF100-1L (SEQ ID NOS: 573, 571); and most preferably selected from the group consisting of: MGF505-7R/MGF505-8R (SEQ ID NOS: 857, 775, 773, 725, 723, 720, 718), M448R (SEQ ID NOS: 858, 569, 567), D1133L (SEQ ID NOS: 859, 298, 296, 288, 286), CP312R (SEQ ID NOS: 861, 273, 901, 900, 271, 270), A240L (SEQ ID NOS: 860, 27, 26).

In yet another specific aspect, the immunogenic compositions or the vaccines or pharmaceutical compositions as described and/or claimed herein are provided, wherein the African swine fever virus polypeptides, preferably full-length proteins, comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: A238L (SEQ ID NO: 21), A238L (SEQ ID NO: 23), A240L (SEQ ID NO: 853), A240L (SEQ ID NO: 854), B475L (SEQ ID NO: 65), B475L (SEQ ID NO: 66), CP2475 (SEQ ID NO: 256), CP2475 (SEQ ID NO: 257), CP312R (SEQ ID NO: 272), CP312R (SEQ ID NO: 274), D1133L (SEQ ID NO: 295), D1133L (SEQ ID NO: 297), EP402R (SEQ ID NO: 378), EP424R (SEQ ID NO: 388), EP424R (SEQ ID NO: 389), G1211R (SEQ ID NO: 430), G1211R (SEQ ID NO: 432), H339R (SEQ ID NO: 466), H339R (SEQ ID NO: 468), I226R (SEQ ID NO: 487), I226R (SEQ ID NO: 489), K145R (SEQ ID NO: 524), K145R (SEQ ID NO: 526), M448R (SEQ ID NO: 566), M448R (SEQ ID NO: 568), M1249L (SEQ ID NO: 561), M1249L (SEQ ID NO: 562), MGF_100-1L/MGF100-1L (SEQ ID NO: 572), MGF505-1R/MGF_505-1R (SEQ ID NO: 691), MGF505-1R/MGF_505-1R (SEQ ID NO: 692), MGF505-8R/MGF_505-8R (SEQ ID NO: 722), MGF505-7R/MGF_505-7R (SEQ ID NO: 724), MGF505-8R/MGF_505-8R (SEQ ID NO: 772), MGF505-7R/MGF_505-7R (SEQ ID NO: 774), MGF505-9R/MGF_505-9R (SEQ ID NO: 732), MGF505-9R/MGF_505-9R (SEQ ID NO: 733), P1192R (SEQ ID NO: 816), P1192R (SEQ ID NO: 817) and/or wherein the African swine fever virus peptides and/or immunogenic fragments thereof and/or African swine fever virus polypeptide/full-length protein immunogenic fragments comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: A238L (SEQ ID NO: 17), A238L (SEQ ID NO: 19), A240L (SEQ ID NO: 25), B475L (SEQ ID NO: 48), B475L (SEQ ID NO: 49), B475L (SEQ ID NO: 50), B475L (SEQ ID NO: 51), B475L (SEQ ID NO: 52), B475L (SEQ ID NO: 53), B475L (SEQ ID NO: 54), B475L (SEQ ID NO: 55), B475L (SEQ ID NO: 56), B475L (SEQ ID NO: 57), B475L (SEQ ID NO: 58), B475L (SEQ ID NO: 59), B475L (SEQ ID NO: 60), B475L (SEQ ID NO: 61), B475L (SEQ ID NO: 62), B475L (SEQ ID NO: 63), B475L (SEQ ID NO: 64), CP2475 (SEQ ID NO: 235), CP2475 (SEQ ID NO: 236), CP2475 (SEQ ID NO: 237), CP2475 (SEQ ID NO: 238), CP2475 (SEQ ID NO: 239), CP2475 (SEQ ID NO: 240), CP2475 (SEQ ID NO: 241), CP2475 (SEQ ID NO: 242), CP2475 (SEQ ID NO: 243), CP2475 (SEQ ID NO: 244), CP2475 (SEQ ID NO: 245), CP2475 (SEQ ID NO: 246), CP2475 (SEQ ID NO: 247), CP2475 (SEQ ID NO: 248), CP2475 (SEQ ID NO: 249), CP2475 (SEQ ID NO: 250), CP2475 (SEQ ID NO: 251), CP2475 (SEQ ID NO: 252), CP2475 (SEQ ID NO: 253), CP2475 (SEQ ID NO: 254), CP2475 (SEQ ID NO: 255), CP2475L (p37) (SEQ ID NO: 261), CP2475L (p37) (SEQ ID NO: 262), CP2475L (p37) (SEQ ID NO: 263), CP2475L (p37) (SEQ ID NO: 264), CP2475L (p37) (SEQ ID NO: 265), CP2475L (p37) (SEQ ID NO: 266), CP2475L (p150) (SEQ ID NO: 258), CP2475L (p150) (SEQ ID NO: 259), CP2475L (p150) (SEQ ID NO: 260), CP312R (SEQ ID NO: 267), CP312R (SEQ ID NO: 268), CP312R (SEQ ID NO: 269), D1133L (SEQ ID NO: 281), D1133L (SEQ ID NO: 282), D1133L (SEQ ID NO: 283), D1133L (SEQ ID NO: 284), D1133L (SEQ ID NO: 285), D1133L (SEQ ID NO: 287), D1133L (SEQ ID NO: 289), D1133L (SEQ ID NO: 290), D1133L (SEQ ID NO: 291), D1133L (SEQ ID NO: 292), D1133L (SEQ ID NO: 293), D1133L (SEQ ID NO: 294), EP402R (SEQ ID NO: 372), EP402R (SEQ ID NO: 373), EP402R (SEQ ID NO: 374), EP402R (SEQ ID NO: 375), EP402R (SEQ ID NO: 376), EP402R (SEQ ID NO: 377), EP424R (SEQ ID NO: 379), EP424R (SEQ ID NO: 380), EP424R (SEQ ID NO: 381), EP424R (SEQ ID NO: 382), EP424R (SEQ ID NO: 383), EP424R (SEQ ID NO: 384), EP424R (SEQ ID NO: 385), EP424R (SEQ ID NO: 386), EP424R (SEQ ID NO: 387), G1211R (SEQ ID NO: 416), G1211R (SEQ ID NO: 417), G1211R (SEQ ID NO: 418), G1211R (SEQ ID NO: 420), G1211R (SEQ ID NO: 422), G1211R (SEQ ID NO: 423), G1211R (SEQ ID NO: 424), G1211R (SEQ ID NO: 425), G1211R (SEQ ID NO: 426), G1211R (SEQ ID NO: 427), G1211R (SEQ ID NO: 428), G1211R (SEQ ID NO: 429), H339R (SEQ ID NO: 454), H339R (SEQ ID NO: 455), H339R (SEQ ID NO: 456), H339R (SEQ ID NO: 458), H339R (SEQ ID NO: 460), H339R (SEQ ID NO: 461), H339R (SEQ ID NO: 462), H339R (SEQ ID NO: 463), H339R (SEQ ID NO: 464), H339R (SEQ ID NO: 465), I226R (SEQ ID NO: 478), I226R (SEQ ID NO: 479), I226R (SEQ ID NO: 481), I226R (SEQ ID NO: 483), I226R (SEQ ID NO: 484), I226R (SEQ ID NO: 485), I226R (SEQ ID NO: 486), K145R (SEQ ID NO: 514), K145R (SEQ ID NO: 515), K145R (SEQ ID NO: 516), K145R (SEQ ID NO: 518), K145R (SEQ ID NO: 520), K145R (SEQ ID NO: 521), K145R (SEQ ID NO: 522), K145R (SEQ ID NO: 523), M448R (SEQ ID NO: 563), M448R (SEQ ID NO: 564), M448R (SEQ ID NO: 565), M1249L (SEQ ID NO: 539), M1249L (SEQ ID NO: 540), M1249L (SEQ ID NO: 541), M1249L (SEQ ID NO: 542), M1249L (SEQ ID NO: 543), M1249L (SEQ ID NO: 544), M1249L (SEQ ID NO: 545), M1249L (SEQ ID NO: 546), M1249L (SEQ ID NO: 547), M1249L (SEQ ID NO: 548), M1249L (SEQ ID NO: 549), M1249L (SEQ ID NO: 550), M1249L (SEQ ID NO: 551), M1249L (SEQ ID NO: 552), M1249L (SEQ ID NO: 553), M1249L (SEQ ID NO: 554), M1249L (SEQ ID NO: 555), M1249L (SEQ ID NO: 556), M1249L (SEQ ID NO: 557), M1249L (SEQ ID NO: 558), M1249L (SEQ ID NO: 559), M1249L (SEQ ID NO: 560), MGF_100-1L/MGF100-1L (SEQ ID NO: 570), MGF505-1R/MGF_505-1R (SEQ ID NO: 684), MGF505-1R/

MGF_505-1R (SEQ ID NO: 685), MGF505-1R/MGF_505-1R (SEQ ID NO: 686), MGF505-1R/MGF_505-1R (SEQ ID NO: 687), MGF505-1R/MGF_505-1R (SEQ ID NO: 688), MGF505-1R/MGF_505-1R (SEQ ID NO: 689), MGF505-1R/MGF_505-1R (SEQ ID NO: 690), MGF505-8R/MGF_505-8R (SEQ ID NO: 717), MGF505-7R/MGF_505-7R (SEQ ID NO: 719), MGF505-7R/MGF_505-7R (SEQ ID NO: 721), MGF505-9R/MGF_505-9R (SEQ ID NO: 726), MGF505-9R/MGF_505-9R (SEQ ID NO: 727), MGF505-9R/MGF_505-9R (SEQ ID NO: 728), MGF505-9R/MGF_505-9R (SEQ ID NO: 729), MGF505-9R/MGF_505-9R (SEQ ID NO: 730), MGF505-9R/MGF_505-9R (SEQ ID NO: 731), P1192R (SEQ ID NO: 801), P1192R (SEQ ID NO: 802), P1192R (SEQ ID NO: 803), P1192R (SEQ ID NO: 804), P1192R (SEQ ID NO: 805), P1192R (SEQ ID NO: 806), P1192R (SEQ ID NO: 807), P1192R (SEQ ID NO: 808), P1192R (SEQ ID NO: 809), P1192R (SEQ ID NO: 810), P1192R (SEQ ID NO: 811), P1192R (SEQ ID NO: 812), P1192R (SEQ ID NO: 813), P1192R (SEQ ID NO: 814), P1192R (SEQ ID NO: 815).

In yet another specific aspect, the immunogenic compositions or the vaccines or pharmaceutical compositions as described and/or claimed herein are provided, wherein the African swine fever virus polypeptides, preferably full-length proteins, comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: MGF505-7R/MGF505-8R (SEQ ID NOS: 774, 772, 724, 722), M448R (SEQ ID NOS: 568, 566), D1133L (SEQ ID NOS: 297, 295), CP312R (SEQ ID NOS: 274, 272), A240L (SEQ ID NOS: 854, 853), A238L (SEQ ID NOS: 23, 21), MGF100-1L (SEQ ID NO: 572), K145R (SEQ ID NOS: 526, 524), B475L (SEQ ID NOS: 66, 65), H339R (SEQ ID NOS: 468, 466), I226R (SEQ ID NOS: 489, 487), CP2475 (SEQ ID NO: 257), CP2475 (SEQ ID NO: 256), G1211R (SEQ ID NOS: 432, 430), M1249L (SEQ ID NOS: 562, 561), MGF505-9R (SEQ ID NOS: 733, 732), P1192R (SEQ ID NOS: 817, 816), MGF505-1R (SEQ ID NOS: 692, 691), MGF505-3R (SEQ ID NOS: 703, 702), EP424R (SEQ ID NOS: 389, 388), C475L (SEQ ID NOS: 201, 200), B602L (SEQ ID NOS: 75, 74), CP530R (SEQ ID NOS: 278, 277), D339L (SEQ ID NOS: 322, 321), D117L (SEQ ID NOS: 862, 864), I243L (SEQ ID NOS: 494, 493), I73R (SEQ ID NOS: 504, 503), DP238L (SEQ ID NOS: 327, 326), 19R (SEQ ID NOS: 513, 512) and/or wherein the African swine fever virus peptides and/or immunogenic fragments thereof and/or African swine fever virus polypeptide/full-length protein immunogenic fragments comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: MGF505-7R/MGF505-8R (SEQ ID NOS: 721, 719, 717), M448R (SEQ ID NOS: 565, 564, 563), D1133L (SEQ ID NOS: 294, 293, 292, 291, 290, 289, 287, 285, 284, 283, 282, 281), CP312R (SEQ ID NOS: 269, 268, 267), A240L (SEQ ID NO: 25), A238L (SEQ ID NOS: 19, 17), MGF100-1L (SEQ ID NO: 570), K145R (SEQ ID NOS: 523, 522, 521, 520, 518, 516, 515, 514), B475L (SEQ ID NOS: 64, 63, 62, 61, 60, 59, 58, 57, 56, 55, 54, 53, 52, 51, 50, 49, 48), H339R (SEQ ID NOS: 465, 464, 463, 462, 461, 460, 458, 456, 455, 454), I226R (SEQ ID NOS: 486, 485, 484, 483, 481, 479, 478), CP2475L (p37) (SEQ ID NOS: 266, 265, 264, 263, 262, 261), CP2475L (p150) (SEQ ID NOS: 260, 259, 258), G1211R (SEQ ID NOS: 429, 428, 427, 426, 425, 424, 423, 422, 420, 418, 417, 416), M1249L (SEQ ID NOS: 560, 559, 558, 557, 556, 555, 554, 553, 552, 551, 550, 549, 548, 547, 546, 545, 544, 543, 542, 541, 540, 539), MGF505-9R (SEQ ID NOS: 731, 730, 729, 728, 727, 726), P1192R (SEQ ID NOS: 815, 814, 813, 812, 811, 810, 809, 808, 807, 806, 805, 804, 803, 802, 801), MGF505-1R (SEQ ID NOS: 690, 689, 688, 687, 686, 685, 684), MGF505-3R (SEQ ID NOS: 701, 700, 699), EP424R (SEQ ID NOS: 387, 386, 385, 384, 383, 382, 381, 380, 379), C475L (SEQ ID NOS: 199, 198, 197, 196, 195, 194, 193, 192, 191, 190, 189, 188), B602L (SEQ ID NOS: 73, 72, 71, 70, 69, 68, 67), CP530R (SEQ ID NOS: 277, 276, 275), D339L (SEQ ID NO: 320), I243L (SEQ ID NOS: 492, 491), I73R (SEQ ID NO: 502), DP238L (SEQ ID NO: 325), 19R (SEQ ID NOS: 511, 510).

In yet another specific aspect, the immunogenic composition or the vaccine or pharmaceutical composition as described and/or claimed herein are provided, wherein the ASFV polypeptide is an ASFV full-length protein, preferably encoded by a polynucleotide sequence comprising, more preferably consisting of, any possible open reading frame (ORF), even more preferably encoded by a polynucleotide sequence comprising, most preferably consisting of, an open reading frame (ORF) with a 5'-end start codon and a 3'-end stop codon.

In yet another specific aspect, the immunogenic compositions or the vaccines or pharmaceutical compositions as described and/or claimed herein are provided, wherein the immunogenicity (and/or immunological response) of the immunogenic composition or the vaccine or pharmaceutical composition or any comprised immunogenic fragment is indicated/characterized by an induced IFN-gamma response, preferably in a porcine IFN-gamma ELISpot assay, more preferably in a porcine IFN-gamma ELISpot assay as described in Example 1.

In yet another specific aspect, the immunogenic compositions or the vaccines or pharmaceutical compositions as described and/or claimed herein are provided for use in a method of reducing or preventing the clinical signs or disease in porcines, preferably a pig, caused by an infection with at least one, preferably pathogenic, African swine fever virus or for use in a method of treating and/or preventing an infection with at least one, preferably pathogenic, African swine fever virus, wherein preferably said clinical signs or disease caused by an infection with at least one, preferably pathogenic, African swine fever virus or said infection with at least one, preferably pathogenic, African swine fever virus are selected from the group consisting of: African swine fever, acute African swine fever, chronic African swine fever, mortality, death, sudden death, fever, high fever, anorexia, lethargy, weakness, loss of appetite, recumbence, erythema, cyanotic skin blotching, diarrhea, constipation, abdominal pain, respiratory signs, coughing, vomiting, dyspnea, nasal and conjunctival discharges, hemorrhages, epistaxis, abortion, leukopenia, thrombocytopenia. A corresponding method of reducing or preventing the clinical signs or disease in porcines, preferably a pig, caused by an infection with at least one, preferably pathogenic, African swine fever virus or corresponding method of treating and/or preventing an infection with at least one, preferably pathogenic, African swine fever virus in porcines, preferably a pig, comprising administering to such porcine, preferably pig, the immunogenic compositions or the vaccines or pharmaceutical compositions as herein described and/or claimed, as well as the corresponding use of the immunogenic compositions or the vaccines or pharmaceutical compositions as herein described and/or claimed for the preparation of a medicament for reducing or preventing the clinical signs or disease in porcines, preferably a pig, caused by an infection with at least one, preferably pathogenic, African swine fever virus or for treating and/or preventing an infection with at least one, preferably pathogenic, African swine fever virus in porcines, preferably a pig, are also intended to be comprised by the present invention.

In yet another specific aspect, the immunogenic compositions or the vaccines or pharmaceutical compositions as described and/or claimed herein are provided for use in a method of immunizing a porcine, preferably a pig, against a clinical disease caused by at least one, preferably pathogenic, African swine fever virus in said porcine, preferably pig, said method comprising the step of administering to the porcine, preferably pig, the immunogenic composition or the vaccine or pharmaceutical composition as herein described and/or claimed, wherein said immunogenic composition or vaccine or pharmaceutical composition fails to cause clinical signs of infection but is capable of inducing an immune response that immunizes the porcine, preferably pig, against, preferably pathogenic forms of, said at least one African swine fever virus, wherein preferably said clinical disease or said clinical signs of infection are selected from the group consisting of: African swine fever, acute African swine fever, chronic African swine fever, mortality, death, sudden death, fever, high fever, anorexia, lethargy, weakness, loss of appetite, recumbence, erythema, cyanotic skin blotching, diarrhea, constipation, abdominal pain, respiratory signs, coughing, vomiting, dyspnea, nasal and conjunctival discharges, hemorrhages, epistaxis, abortion, leukopenia, thrombocytopenia. A corresponding method of immunizing a porcine, preferably a pig, against a clinical disease caused by at least one, preferably pathogenic, African swine fever virus in said porcine, preferably pig, said method comprising the step of administering to the porcine, preferably pig, the immunogenic composition or the vaccine or pharmaceutical composition as herein described and/or claimed, wherein said immunogenic composition or vaccine or pharmaceutical composition fails to cause clinical signs of infection but is capable of inducing an immune response that immunizes the porcine, preferably pig, against, preferably pathogenic forms of, said at least one African swine fever virus, as well as the corresponding use of the immunogenic compositions or the vaccines or pharmaceutical composition as herein described and/or claimed for the preparation of a medicament for immunizing a porcine, preferably a pig, against a clinical disease caused by at least one, preferably pathogenic, African swine fever virus in said porcine, preferably pig, wherein said immunogenic composition or vaccine or pharmaceutical composition fails to cause clinical signs of infection but is capable of inducing an immune response that immunizes the porcine, preferably pig, against, preferably pathogenic forms of, said at least one African swine fever virus, are also intended to be comprised by the present invention.

In yet another specific aspect, the immunogenic compositions or the vaccines or pharmaceutical compositions as described and/or claimed herein are provided for use in a method of prime-boost immunizing a porcine, preferably a pig, against a clinical disease caused by at least one, preferably pathogenic, African swine fever virus in said porcine, preferably pig, said method comprising the step of administering to the porcine, preferably pig, once or twice an immunogenic composition or the vaccine or pharmaceutical composition as herein described and/or claimed comprising (i) one, two or more African swine fever virus oligonucleotides and/or polynucleotides and/or immunogenic fragments thereof as sole immunogenic components or (ii) a viral or bacterial vector, preferably a recombinant and/or non-naturally occurring viral or bacterial vector, comprising one, two or more African swine fever virus oligonucleotides and/or polynucleotides and/or immunogenic fragments thereof as sole immunogenic component (priming step); and subsequently—after priming once or twice—administering to the porcine, preferably pig, a live attenuated African swine fever virus, preferably BA71ΔCD2 (boosting step); wherein said immunogenic composition or vaccine or pharmaceutical composition as well as the live attenuated African swine fever virus independently from each other fail to cause clinical signs of infection but are capable of inducing an immune response that immunizes the porcine, preferably pig, against, preferably pathogenic forms of, said at least one African swine fever virus, wherein preferably said clinical disease or said clinical signs of infection are selected from the group consisting of: African swine fever, acute African swine fever, chronic African swine fever, mortality, death, sudden death, fever, high fever, anorexia, lethargy, weakness, loss of appetite, recumbence, erythema, cyanotic skin blotching, diarrhea, constipation, abdominal pain, respiratory signs, coughing, vomiting, dyspnea, nasal and conjunctival discharges, hemorrhages, epistaxis, abortion, leukopenia, thrombocytopenia. A corresponding method of prime-boost immunizing a porcine, preferably a pig, against a clinical disease caused by at least one, preferably pathogenic, African swine fever virus in said porcine, preferably pig, said method comprising the step of administering to the porcine, preferably pig, once or twice an immunogenic composition or the vaccine or pharmaceutical composition as herein described and/or claimed comprising (i) one, two or more African swine fever virus oligonucleotides and/or polynucleotides and/or immunogenic fragments thereof as sole immunogenic components or (ii) a viral or bacterial vector, preferably a recombinant and/or non-naturally occurring viral or bacterial vector, comprising one, two or more African swine fever virus oligonucleotides and/or polynucleotides and/or immunogenic fragments thereof as sole immunogenic component (priming step); and subsequently—after priming once or twice—administering to the porcine, preferably pig, a live attenuated African swine fever virus, preferably BA71ΔCD2 (boosting step); wherein said immunogenic composition or vaccine or pharmaceutical composition as well as the live attenuated African swine fever virus independently from each other fail to cause clinical signs of infection but are capable of inducing an immune response that immunizes the porcine, preferably pig, against, preferably pathogenic forms of, said at least one African swine fever virus, as well as the corresponding use of the immunogenic compositions or the vaccines or pharmaceutical compositions as herein described and/or claimed for the preparation of a medicament for prime-boost immunizing a porcine, preferably a pig, against a clinical disease caused by at least one, preferably pathogenic, African swine fever virus in said porcine, preferably pig, are also intended to be comprised by the present invention.

In yet another specific aspect, a kit for vaccinating a porcine, preferably a pig, against a disease associated with and/or reducing the incidence or the severity of one or more clinical signs associated with or caused by at least one, preferably pathogenic, African swine fever virus in a porcine, preferably a pig, is provided comprising:
(a) a dispenser capable of administering a vaccine to said porcine; and
(b) the immunogenic composition or the vaccine or pharmaceutical composition as herein described and/or claimed, and
(c) optionally, an instruction leaflet;

wherein preferably said disease or said clinical signs are selected from the group consisting of: African swine fever, acute African swine fever, chronic African swine fever, mortality, death, sudden death, fever, high fever, anorexia, lethargy, weakness, loss of appetite, recumbence, erythema, cyanotic skin blotching, diarrhea, constipation, abdominal pain, respiratory signs, coughing, vomiting, dyspnea, nasal and conjunctival discharges, hemorrhages, epistaxis, abortion, leukopenia, thrombocytopenia.

In yet another specific aspect, an African swine fever virus peptide and/or polypeptide, preferably full-length-protein, and/or immunogenic fragment thereof is provided comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: SEQ ID NOS: 1, 2, 3, 4, 5, 6, 7, 8, 9, 10, 11, 12, 13, 14, 15, 16, 17, 19, 21, 23, 25, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 1, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 272, 274, 275, 276, 277, 278, 279, 280, 281, 282, 283, 284, 285, 287, 289, 290, 291, 292, 293, 294, 295, 297, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 420, 422, 423, 424, 425, 426, 427, 428, 429, 430, 432, 434, 435, 436, 437, 438, 439, 440, 441, 442, 443, 444, 445, 446, 447, 448, 449, 450, 451, 452, 453, 454, 455, 456, 458, 460, 461, 462, 463, 464, 465, 466, 468, 470, 471, 472, 473, 474, 475, 476, 477, 478, 479, 481, 483, 484, 485, 486, 487, 489, 491, 492, 493, 494, 495, 496, 497, 498, 499, 500, 501, 502, 503, 504, 505, 506, 507, 508, 509, 510, 511, 512, 513, 514, 515, 516, 518, 520, 521, 522, 523, 524, 526, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 568, 570, 572, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 719, 721, 722, 724, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 774, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854.

In yet another specific aspect, an African swine fever virus peptide and/or polypeptide, preferably full-length-protein, and/or immunogenic fragment thereof is provided comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: MGF505-7R/MGF505-8R (SEQ ID NOS: 774, 772, 724, 722, 721, 719, 717), M448R (SEQ ID NOS: 568, 566, 565, 564, 563), D1133L (SEQ ID NOS: 297, 295, 294, 293, 292, 291, 290, 289, 287, 285, 284, 283, 282, 281), CP312R (SEQ ID NOS: 274, 272, 269, 268, 267), A240L (SEQ ID NOS: 854, 853, 25), A238L (SEQ ID NOS: 23, 21, 19, 17), MGF100-1L (SEQ ID NOS: 572, 570), K145R (SEQ ID NOS: 526, 524, 523, 522, 521, 520, 518, 516, 515, 514), B475L (SEQ ID NOS: 66, 65, 64, 63, 62, 61, 60, 59, 58, 57, 56, 55, 54, 53, 52, 51, 50, 49, 48), H339R (SEQ ID NOS: 468, 466, 465, 464, 463, 462, 461, 460, 458, 456, 455, 454), I226R (SEQ ID NOS: 489, 487, 486, 485, 484, 483, 481, 479, 478), CP2475L (p37) (SEQ ID NOS: 266, 265, 264, 263, 262, 261), CP2475L (p150) (SEQ ID NOS: 260, 259, 258), G1211R (SEQ ID NOS: 432, 430, 429, 428, 427, 426, 425, 424, 423, 422, 420, 418, 417, 416), M1249L (SEQ ID NOS: 562, 561, 560, 559, 558, 557, 556, 555, 554, 553, 552, 551, 550, 549, 548, 547, 546, 545, 544, 543, 542, 541, 540, 539), MGF505-9R (SEQ ID NOS: 733, 732, 731, 730, 729, 728, 727, 726), P1192R (SEQ ID NOS: 817, 816, 815, 814, 813, 812, 811, 810, 809, 808, 807, 806, 805, 804, 803, 802, 801), MGF505-1R (SEQ ID NOS: 692, 691, 690, 689, 688, 687, 686, 685, 684), MGF505-3R (SEQ ID NOS: 703, 702, 701, 700, 699), EP424R (SEQ ID NOS: 389, 388, 387, 386, 385, 384, 383, 382, 381, 380, 379), C475L (SEQ ID NOS: 201, 200, 199, 198, 197, 196, 195, 194, 193, 192, 191, 190, 189, 188), B602L (SEQ ID NOS: 75, 74, 73, 72, 71, 70, 69, 68, 67), CP530R (SEQ ID NOS: 278, 277, 276, 275), D339L (SEQ ID NOS: 322, 321, 320), D117L (SEQ ID NOS: 862, 864), I243L (SEQ ID NOS: 494, 493, 492, 491), I73R (SEQ ID NOS: 504, 503, 502), DP238L (SEQ ID NOS: 327, 326, 325), 19R (SEQ ID NOS: 513, 512, 511, 510), preferably selected from the group consisting of: MGF505-7R/MGF505-8R (SEQ ID NOS: 774, 772, 724, 722, 721, 719, 717), M448R (SEQ ID NOS: 568, 566, 565, 564, 563), D1133L (SEQ ID NOS: 297, 295, 294, 293, 292, 291, 290, 289, 287, 285, 284, 283, 282, 281), CP312R (SEQ ID NOS: 274, 272, 269, 268, 267), A240L (SEQ ID NOS: 854, 853, 25), A238L (SEQ ID NOS: 23, 21, 19, 17), MGF100-1L (SEQ ID NOS: 572, 570); and most preferably selected from the group consisting of: MGF505-7R/MGF505-8R (SEQ ID NOS: 774, 772, 724, 722, 721, 719, 717), M448R (SEQ ID NOS: 568, 566, 565, 564, 563), D1133L (SEQ ID NOS: 297, 295, 294, 293, 292, 291, 290, 289, 287, 285, 284, 283, 282, 281), CP312R (SEQ ID NOS: 274, 272, 269, 268, 267), A240L (SEQ ID NOS: 854, 853, 25).

In yet another specific aspect, an African swine fever virus peptide and/or polypeptide, preferably full-length-protein, and/or immunogenic fragment thereof is provided, wherein the African swine fever virus polypeptides, preferably full-length proteins, comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: A238L (SEQ ID NO: 21), A238L (SEQ ID NO: 23), A240L (SEQ ID NO: 853), A240L (SEQ ID NO: 854), B475L (SEQ ID NO: 65), B475L (SEQ ID NO: 66), CP2475 (SEQ ID NO: 256), CP2475 (SEQ ID NO: 257), CP312R (SEQ ID NO: 272), CP312R (SEQ ID NO: 274), D1133L (SEQ ID NO: 295), D1133L (SEQ ID NO: 297), EP402R (SEQ ID NO: 378), EP424R (SEQ ID NO: 388), EP424R (SEQ ID NO: 389), G1211R (SEQ ID NO: 430), G1211R (SEQ ID NO: 432), H339R (SEQ ID NO: 466), H339R (SEQ ID NO: 468), I226R (SEQ ID NO: 487), I226R (SEQ ID NO: 489), K145R (SEQ ID NO: 524), K145R (SEQ ID NO: 526), M448R (SEQ ID NO: 566), M448R (SEQ ID NO: 568), M1249L (SEQ ID NO: 561), M1249L (SEQ ID NO: 562), MGF_100-1L/MGF100-1L (SEQ ID NO: 572), MGF505-1R/MGF_505-1R (SEQ ID NO: 691), MGF505-1R/MGF_505-1R (SEQ ID NO: 692), MGF505-8R/MGF_505-8R (SEQ ID NO: 722), MGF505-7R/MGF_505-7R (SEQ ID NO: 724), MGF505-8R/MGF_505-8R (SEQ ID NO: 772), MGF505-7R/MGF_505-7R (SEQ ID NO: 774), MGF505-9R/MGF_505-9R (SEQ ID NO: 732), MGF505-9R/MGF_505-9R (SEQ ID NO: 733), P1192R (SEQ ID NO: 816), P1192R (SEQ ID NO: 817) and/or wherein the African swine fever virus peptides and/or immunogenic fragments thereof and/or African swine fever virus polypeptide/full-length protein immunogenic fragments comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: A238L (SEQ ID NO: 17), A238L (SEQ ID NO: 19), A240L (SEQ ID NO: 25), B475L (SEQ ID NO: 48), B475L (SEQ ID NO: 49), B475L (SEQ ID NO: 50), B475L (SEQ ID NO: 51), B475L (SEQ ID NO: 52), B475L (SEQ ID NO: 53), B475L (SEQ ID NO: 54), B475L (SEQ ID NO: 55), B475L (SEQ ID NO: 56), B475L (SEQ ID NO: 57), B475L (SEQ ID NO: 58), B475L (SEQ ID NO: 59), B475L (SEQ ID NO: 60), B475L (SEQ ID NO: 61), B475L (SEQ ID NO: 62), B475L (SEQ ID NO: 63), B475L (SEQ ID NO: 64), CP2475 (SEQ ID NO: 235), CP2475 (SEQ ID NO: 236), CP2475 (SEQ ID NO: 237), CP2475 (SEQ ID NO: 238), CP2475 (SEQ ID NO: 239), CP2475 (SEQ ID NO: 240), CP2475 (SEQ ID NO: 241), CP2475 (SEQ ID NO: 242), CP2475 (SEQ ID NO: 243), CP2475 (SEQ ID NO: 244), CP2475 (SEQ ID NO: 245), CP2475 (SEQ ID NO: 246), CP2475 (SEQ ID NO: 247), CP2475 (SEQ ID NO: 248), CP2475 (SEQ ID NO: 249), CP2475 (SEQ ID NO: 250), CP2475 (SEQ ID NO: 251), CP2475 (SEQ ID NO: 252), CP2475 (SEQ ID NO: 253), CP2475 (SEQ ID NO: 254), CP2475 (SEQ ID NO: 255), CP2475L (p37) (SEQ ID NO: 261), CP2475L (p37) (SEQ ID NO: 262), CP2475L (p37) (SEQ ID NO: 263), CP2475L (p37) (SEQ ID NO: 264), CP2475L (p37) (SEQ ID NO: 265), CP2475L (p37) (SEQ ID NO: 266), CP2475L (p150) (SEQ ID NO: 258), CP2475L (p150) (SEQ ID NO: 259), CP2475L (p150) (SEQ ID NO: 260), CP312R (SEQ ID NO: 267), CP312R (SEQ ID NO: 268), CP312R (SEQ ID NO: 269), D1133L (SEQ ID NO: 281), D1133L (SEQ ID NO: 282), D1133L (SEQ ID NO: 283), D1133L (SEQ ID NO: 284), D1133L (SEQ ID NO: 285), D1133L (SEQ ID NO: 287), D1133L (SEQ ID NO: 289), D1133L (SEQ ID NO: 290), D1133L (SEQ ID NO: 291), D1133L (SEQ ID NO: 292), D1133L (SEQ ID NO: 293), D1133L (SEQ ID NO: 294), EP402R (SEQ ID NO: 372), EP402R (SEQ ID NO: 373), EP402R (SEQ ID NO: 374), EP402R (SEQ ID NO: 375), EP402R (SEQ ID NO: 376), EP402R (SEQ ID NO: 377), EP424R (SEQ ID NO: 379), EP424R (SEQ ID NO: 380), EP424R (SEQ ID NO: 381), EP424R (SEQ ID NO: 382), EP424R (SEQ ID NO: 383), EP424R (SEQ ID NO: 384), EP424R (SEQ ID NO: 385), EP424R (SEQ ID NO: 386), EP424R (SEQ ID NO: 387), G1211R (SEQ ID NO: 416), G1211R (SEQ ID NO: 417), G1211R (SEQ ID NO: 418), G1211R (SEQ ID NO: 420), G1211R (SEQ ID NO: 422), G1211R (SEQ ID NO: 423), G1211R (SEQ ID NO: 424), G1211R (SEQ ID NO: 425), G1211R (SEQ ID NO: 426), G1211R (SEQ ID NO: 427), G1211R (SEQ ID NO: 428), G1211R (SEQ ID NO: 429), H339R (SEQ ID NO: 454), H339R (SEQ ID NO: 455), H339R (SEQ ID NO: 456), H339R (SEQ ID NO: 458), H339R (SEQ ID NO: 460), H339R (SEQ ID NO: 461), H339R (SEQ ID NO: 462), H339R (SEQ ID NO: 463), H339R (SEQ ID NO: 464), H339R (SEQ ID NO: 465), I226R (SEQ ID NO: 478), I226R (SEQ ID NO: 479), I226R (SEQ ID NO: 481), I226R (SEQ ID NO: 483), I226R (SEQ ID NO: 484), I226R (SEQ ID NO: 485), I226R (SEQ ID NO: 486), K145R (SEQ ID NO: 514), K145R (SEQ ID NO: 515), K145R (SEQ ID NO: 516), K145R (SEQ ID NO: 518), K145R (SEQ ID NO: 520), K145R (SEQ ID NO: 521), K145R (SEQ ID NO: 522), K145R (SEQ ID NO: 523), M448R (SEQ ID NO: 563), M448R (SEQ ID NO: 564), M448R (SEQ ID NO: 565), M1249L (SEQ ID NO: 539), M1249L (SEQ ID NO: 540), M1249L (SEQ ID NO: 541), M1249L (SEQ ID NO: 542), M1249L (SEQ ID NO: 543), M1249L (SEQ ID NO: 544), M1249L (SEQ ID NO: 545), M1249L (SEQ ID NO: 546), M1249L (SEQ ID NO: 547), M1249L (SEQ ID NO: 548), M1249L (SEQ ID NO: 549), M1249L (SEQ ID NO: 550), M1249L (SEQ ID NO: 551), M1249L (SEQ ID NO: 552), M1249L (SEQ ID NO: 553), M1249L (SEQ ID NO: 554), M1249L (SEQ ID NO: 555), M1249L (SEQ ID NO: 556), M1249L (SEQ ID NO: 557), M1249L (SEQ ID NO: 558), M1249L (SEQ ID NO: 559), M1249L (SEQ ID NO: 560), MGF_100-1L/MGF100-1L (SEQ ID NO: 570), MGF505-1R/MGF_505-1R (SEQ ID NO: 684), MGF505-1R/MGF_505-1R (SEQ ID NO: 685), MGF505-1R/MGF_505-1R (SEQ ID NO: 686), MGF505-1R/MGF_505-1R (SEQ ID NO: 687), MGF505-1R/MGF_505-1R (SEQ ID NO: 688), MGF505-1R/MGF_505-1R (SEQ ID NO: 689), MGF505-1R/MGF_505-1R (SEQ ID NO: 690), MGF505-8R/MGF_505-8R (SEQ ID NO: 717), MGF505-7R/MGF_505-7R (SEQ ID NO: 719), MGF505-7R/MGF_505-7R (SEQ ID NO: 721), MGF505-9R/MGF_505-9R (SEQ ID NO: 726), MGF505-9R/MGF_505-9R (SEQ ID NO: 727), MGF505-9R/MGF_505-9R (SEQ ID NO: 728), MGF505-9R/MGF_505-9R (SEQ ID NO: 729), MGF505-9R/MGF_505-9R (SEQ ID NO: 730), MGF505-9R/MGF_505-9R (SEQ ID NO: 731), P1192R (SEQ ID NO: 801), P1192R (SEQ ID NO: 802), P1192R (SEQ ID NO: 803), P1192R (SEQ ID NO: 804), P1192R (SEQ ID NO: 805), P1192R (SEQ ID NO: 806), P1192R (SEQ ID NO: 807), P1192R (SEQ ID NO: 808), P1192R (SEQ ID NO: 809), P1192R (SEQ ID NO: 810), P1192R (SEQ ID NO: 811), P1192R (SEQ ID NO: 812), P1192R (SEQ ID NO: 813), P1192R (SEQ ID NO: 814), P1192R (SEQ ID NO: 815).

In yet another specific aspect, an African swine fever virus peptide and/or polypeptide, preferably full-length-protein, and/or immunogenic fragment thereof is provided, wherein the African swine fever virus polypeptides, preferably full-length proteins, comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: MGF505-7R/MGF505-8R (SEQ ID NOS: 774, 772, 724, 722), M448R (SEQ ID NOS: 568, 566), D1133L (SEQ ID NOS: 297, 295), CP312R (SEQ ID NOS: 274, 272), A240L (SEQ ID NOS: 854, 853), A238L (SEQ ID NOS: 23, 21), MGF100-1L (SEQ ID NO: 572), K145R (SEQ ID NOS: 526, 524), B475L (SEQ ID NOS: 66, 65), H339R (SEQ ID NOS: 468, 466), I226R (SEQ ID NOS: 489, 487), CP2475 (SEQ ID NO: 257), CP2475 (SEQ ID NO: 256), G1211R (SEQ ID NOS: 432, 430), M1249L (SEQ ID NOS: 562, 561), MGF505-9R (SEQ ID NOS: 733, 732), P1192R (SEQ ID NOS: 817, 816), MGF505-1R (SEQ ID NOS: 692, 691), MGF505-3R (SEQ ID NOS: 703, 702), EP424R (SEQ ID NOS: 389, 388), C475L (SEQ ID NOS: 201, 200), B602L (SEQ ID NOS: 75, 74), CP530R (SEQ ID NOS: 278, 277), D339L (SEQ ID NOS: 322, 321), D117L (SEQ ID NOS: 862, 864), I243L (SEQ ID NOS: 494, 493), I73R (SEQ ID NOS: 504, 503), DP238L (SEQ ID NOS: 327, 326), 19R (SEQ ID NOS: 513, 512) and/or wherein the African swine fever virus peptides and/or immunogenic fragments thereof and/or African swine fever virus polypeptide/full-length protein immunogenic fragments comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: MGF505-7R/MGF505-8R (SEQ ID NOS: 721, 719, 717), M448R (SEQ ID NOS: 565, 564, 563), D1133L (SEQ ID NOS: 294, 293, 292, 291, 290, 289, 287, 285, 284, 283, 282, 281), CP312R (SEQ ID NOS: 269, 268, 267), A240L (SEQ ID NO: 25), A238L (SEQ ID NOS: 19, 17), MGF100-1L (SEQ ID NO: 570), K145R (SEQ ID NOS: 523, 522, 521, 520, 518, 516, 515, 514), B475L (SEQ ID NOS: 64, 63, 62, 61, 60, 59, 58, 57, 56, 55, 54, 53, 52, 51, 50, 49, 48), H339R (SEQ ID NOS: 465, 464, 463, 462, 461, 460, 458, 456, 455, 454), I226R (SEQ ID NOS: 486, 485, 484, 483, 481, 479, 478), CP2475 (p37) (SEQ ID NOS: 266, 265, 264, 263, 262, 261), CP2475L (p150) (SEQ ID NOS: 260, 259, 258), G1211R (SEQ ID NOS: 429, 428, 427, 426, 425, 424, 423, 422, 420, 418, 417, 416), M1249L (SEQ ID NOS: 560, 559, 558, 557, 556, 555, 554, 553, 552, 551, 550, 549, 548, 547, 546, 545, 544, 543, 542, 541, 540, 539), MGF505-9R (SEQ ID NOS: 731, 730, 729, 728, 727, 726), P1192R (SEQ ID NOS: 815, 814, 813, 812, 811, 810, 809, 808, 807, 806, 805, 804, 803, 802, 801), MGF505-1R (SEQ ID NOS: 690, 689, 688, 687, 686, 685, 684), MGF505-3R (SEQ ID NOS: 701, 700, 699), EP424R (SEQ ID NOS: 387, 386, 385, 384, 383, 382, 381, 380, 379), C475L (SEQ ID NOS: 199, 198, 197, 196, 195, 194, 193, 192, 191, 190, 189, 188), B602L (SEQ ID NOS: 73, 72, 71, 70, 69, 68, 67), CP530R (SEQ ID NOS: 277, 276, 275), D339L (SEQ ID NO: 320), I243L (SEQ ID NOS: 492, 491), I73R (SEQ ID NO: 502), DP238L (SEQ ID NO: 325), 19R (SEQ ID NOS: 511, 510).

In yet another specific aspect, an African swine fever virus oligonucleotide and/or polynucleotide and/or immunogenic fragment thereof is provided encoding the African swine fever virus peptide and/or polypeptide, preferably full-length-protein, and/or immunogenic fragment thereof as herein described and/or claimed.

In yet another specific aspect, an African swine fever virus oligonucleotide and/or polynucleotide and/or immunogenic fragment thereof is provided encoding the African swine fever virus peptide and/or polypeptide, preferably full-length-protein, and/or immunogenic fragment thereof comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: SEQ ID NOS: 18, 20, 22, 24, 26, 27, 270, 271, 273, 286, 288, 296, 298, 419, 421, 431, 433, 457, 459, 467, 469, 480, 482, 488, 490, 517, 519, 525, 527, 567, 569, 571, 573, 718, 720, 723, 725, 773, 775.

In yet another specific aspect, an African swine fever virus oligonucleotide and/or polynucleotide and/or immunogenic fragment thereof is provided encoding the African swine fever virus peptide and/or polypeptide, preferably full-length-protein, and/or immunogenic fragment thereof comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF505-7R/MGF505-8R (SEQ ID NOS: 857, 775, 773, 725, 723, 720, 718), M448R (SEQ ID NOS: 858, 569, 567), D1133L (SEQ ID NOS: 859, 298, 296, 288, 286), CP312R (SEQ ID NOS: 861, 273, 901, 900, 271, 270), A240L (SEQ ID NOS: 860, 27, 26), A238L (SEQ ID NOS: 24, 22, 20, 18), MGF100-1L (SEQ ID NOS: 573, 571), K145R (SEQ ID NOS: 527, 525, 519, 517), B475L (SEQ ID NOS: 866, 867), H339R (SEQ ID NOS: 469, 467, 459, 457), I226R (SEQ ID NOS: 490, 488, 482, 480), CP2475L (p37) (SEQ ID NOS: 868, 869), CP2475L (p150) (SEQ ID NOS: 870, 871), G1211R (SEQ ID NOS: 433, 431, 421, 419), M1249L (SEQ ID NOS: 872, 873), MGF505-9R (SEQ ID NOS: 874, 875), P1192R (SEQ ID NOS: 876, 877), MGF505-1R (SEQ ID NOS: 878, 879), MGF505-3R (SEQ ID NOS: 880, 881), EP424R (SEQ ID NOS: 882, 883), C475L (SEQ ID NOS: 884, 885), B602L (SEQ ID NOS: 886, 887), CP530R (SEQ ID NOS: 888, 889), D339L (SEQ ID NOS: 890, 891), D117L (SEQ ID NOS: 863, 865), I243L (SEQ ID NOS: 892, 893), I73R (SEQ ID NOS: 894, 895), DP238L (SEQ ID NOS: 896, 897), 19R (SEQ ID NOS: 898, 899); preferably selected from the group consisting of: MGF505-7R/MGF505-8R (SEQ ID NOS: 857, 775, 773, 725, 723, 720, 718), M448R (SEQ ID NOS: 858, 569, 567), D1133L (SEQ ID NOS: 859, 298, 296, 288, 286), CP312R (SEQ ID NOS: 861, 273, 901, 900, 271, 270), A240L (SEQ ID NOS: 860, 27, 26), A238L (SEQ ID NOS: 24, 22, 20, 18), MGF100-1L (SEQ ID NOS: 573, 571); and most preferably selected from the group consisting of: MGF505-7R/MGF505-8R (SEQ ID NOS: 857, 775, 773, 725, 723, 720, 718), M448R (SEQ ID NOS: 858, 569, 567), D1133L (SEQ ID NOS: 859, 298, 296, 288, 286), CP312R (SEQ ID NOS: 861, 273, 901, 900, 271, 270), A240L (SEQ ID NOS: 860, 27, 26).

In yet another specific aspect, the African swine fever virus peptide and/or polypeptide, preferably full-length-protein, and/or immunogenic fragment thereof as herein described and/or claimed or the African swine fever virus oligonucleotide and/or polynucleotide and/or immunogenic fragment thereof encoding African swine fever virus peptide and/or polypeptide, preferably full-length-protein, and/or immunogenic fragments thereof as herein described and/or claimed is provided, wherein the ASFV polypeptide is an ASFV full-length protein, preferably encoded by a polynucleotide sequence comprising, more preferably consisting of, any possible open reading frame (ORF), even more preferably encoded by a polynucleotide sequence comprising, most preferably consisting of, an open reading frame (ORF) with a 5'-end start codon and a 3'-end stop codon.

In yet another specific aspect, the African swine fever virus peptide and/or polypeptide, preferably full-length-protein, and/or immunogenic fragment thereof as herein described and/or claimed or the African swine fever virus oligonucleotide and/or polynucleotide and/or immunogenic fragment thereof encoding African swine fever virus peptide and/or polypeptide, preferably full-length-protein, and/or immunogenic fragments thereof as herein described and/or claimed is provided, wherein the immunogenicity (and/or immunological response) of the immunogenic composition or the vaccine or pharmaceutical composition or any comprised immunogenic fragment is indicated/characterized by an induced IFN-gamma response, preferably in a porcine IFN-gamma ELISpot assay, more preferably in a porcine IFN-gamma ELISpot assay as described in Example 1.

In yet another specific aspect, a vector comprising one, two, three or more African swine fever virus oligonucleotides and/or polynucleotides and/or immunogenic fragments thereof as herein described and/or claimed is provided. Preferably, such vector comprises three African swine fever virus oligonucleotides and/or polynucleotides and/or immunogenic fragments thereof, preferably selected from EP402R, CP312R and A240L (multiepitope-I, ME-I), more preferably comprises, most preferably consists of, the nucleic acid sequence selected from the group consisting of SEQ ID NO: 855; or comprises thirteen African swine fever virus oligonucleotides and/or polynucleotides and/or immunogenic fragments thereof, preferably selected from D1133L, G1211R, M1249L, MGF505-9R, P1192R, CP2475L (p150), B475L, EP424R, H339R, I226R, K145R, MGF505-1R and CP2475L (p37) (multiepitope-II, ME-II), more preferably comprises, most preferably consists of, the nucleic acid sequence selected from the group consisting of SEQ ID NO: 856.

In yet another specific aspect, a host cell, preferably a mammalian host cell, is provided comprising the vector as herein described and/or claimed.

Definitions

Unless defined otherwise, all technical and scientific terms used herein have the same meaning as is commonly understood by one of skill in the art to which this invention belongs at the time of filing. The meaning and scope of terms should be clear; however, in the event of any latent ambiguity, definitions provided herein take precedent over any dictionary or extrinsic definition. Further, unless otherwise required by context, singular terms shall include pluralities and plural terms shall include the singular. Herein, the use of "or" means "and/or" unless stated otherwise. Furthermore, the use of the term "including", as well as other forms such as "includes" and "included" is not limiting. All patents and publications referred to herein are incorporated by reference herein.

The practice of the present invention will employ, unless otherwise indicated, conventional techniques of virology, molecular biology, microbiology, recombinant DNA technology, protein chemistry and immunology, which are within the skill of the art. Such techniques are explained fully in the literature. See, e.g., Sambrook, Fritsch & Maniatis, Molecular Cloning: A Laboratory Manual, Vols. I, II and III, Second Edition (1989); DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); Protein purification methods—a practical approach (E. L. V. Harris and S. Angal, eds., IRL Press at Oxford University Press); and Handbook of Experimental Immunology, Vols. I-IV (D. M. Weir and C. C. Blackwell eds., 1986, Blackwell Scientific Publications).

Before describing the present invention in detail, it is to be understood that this invention is not limited to particular DNA, polypeptide sequences or process parameters as such may, of course, vary. It is also to be understood that the terminology used herein is for the purpose of describing particular embodiments of the invention only, and is not intended to be limiting. It must be noted that, as used in this specification and the appended claims, the singular forms "a", "an" and "the" include plural referents unless the content clearly dictates otherwise. Thus, for example, reference to "an antigen" includes a mixture of two or more antigens, reference to "an excipient" includes mixtures of two or more excipients, and the like.

The term "viral or bacterial vector" describes a genetically modified virus or bacterium, which was manipulated by recombinant DNA technique in a way so that its entry into a host cell results in a specific biological activity, e.g. the expression of a transgene, such as an ASFV gene, carried by the vector. In a specific aspect, the transgene is an ASFV antigen. A viral or bacterial vector may or may not be replication competent in the target cell, tissue, or organism. In this context, the terms "viral vector" and "virus" are used interchangeably—as are the terms "bacterial vector" and "bacterium".

Generation of a viral or bacterial vector can be accomplished using any suitable genetic engineering techniques well known in the art, including, without limitation, the standard techniques of restriction endonuclease digestion, ligation, transformation, plasmid purification, DNA sequencing, transfection in cell cultures, for example as described in Sambrook et al. (Molecular Cloning: A Laboratory Manual. Cold Spring Harbor Laboratory Press, N.Y. (1989)) or K. Maramorosch and H. Koprowski (Methods in Virology Volume VIII, Academic Press Inc. London, UK (2014)).

A viral or bacterial vector can include coding regions for two or more proteins of interest. For example, the viral or bacterial vector can include the coding region for a first protein of interest and the coding region for a second protein of interest. The first protein of interest and the second protein of interest can be the same or different. In some embodiments, the viral or bacterial vector can include the coding region(s) for a third or a fourth protein of interest. The third and the fourth protein of interest can be the same or different. The total length of the two or more proteins of interest encoded by one viral or bacterial vector can vary. For example, the total length of the two or more proteins can be at least about 200 amino acids. At least about 250 amino acids, at least about 300 amino acids, at least about 350 amino acids, at least about 400 amino acids, at least about 450 amino acids, at least about 500 amino acids, at least about 550 amino acids, at least about 600 amino acids, at least about 650 amino acids, at least about 700 amino acids, at least about 750 amino acids, at least about 800 amino acids, or longer.

According to specific aspects of the present invention, the term "viral or bacterial vector" or alternatively "viral or bacterial construct" refers to a recombinant viral or bacterial construct derived from a virus or bacterium, which is selected from the group consisting of: asfivirus viral vector, avipox virus viral vector, canine morbillivirus viral vector, herpes virus viral vector, varicella virus viral vector, *Lawsonia* spp., *Salmonella* spp.

The terms "viral or bacterial vector" and "viral or bacterial construct" can be used interchangeably.

The term "construct," as used herein, refers to a recombinant nucleic acid such as a plasmid, a BAC, or a recombinant virus or bacterium that has been artificially generated.

The term "plasmid" refers to cytoplasmic DNA that replicates independently of the bacterial chromosome within a bacterial host cell. In a specific aspect of the present invention the term "plasmid" and/or "transfer plasmid" refers to an element of recombinant DNA technology useful for construction of e.g. an expression cassette for insertion into a viral vector. In another specific aspect the term "plasmid" may be used to specify a plasmid useful for DNA vaccination purposes.

As used herein, the terms "nucleic acid" and "polynucleotide" are interchangeable and refer to any nucleic acid.

The term "nucleic acid", "nucleic acid sequence", "nucleotide sequence", "RNA sequence", cDNA sequences or "DNA sequence" as used herein refers to an oligonucleotide, nucleotide or polynucleotide and fragments and portions thereof and to DNA or RNA of genomic or synthetic origin, which may be single or double stranded and represent the sense or antisense strand. The sequence may be a non-coding sequence, a coding sequence or a mixture of both. The nucleic acid sequences of the present invention can be prepared using standard techniques well known to one of skill in the art.

The term "nucleic acid", "nucleic acid sequence" and "nucleotide sequence" also specifically include nucleic acids composed of bases other than the five biologically occurring bases (adenine, guanine, thymine, cytosine and uracil).

The term "complementary nucleotide sequences" describes one strand of the two paired strands of polynucleotides such as DNA or RNA. The nucleotide sequence of the complementary strand mirrors the nucleotide sequence of its paired strand so that for each adenosin it contains a thymin (or uracil for RNA), for each guanine a cytosin, and vice versa. The complementary nucleotide sequence of e.g. 5'-GCATAC-3' is 3'-CGTATG-5' or for RNA 3'-CGUAUG-5'.

The term "expression" as used herein refers to transcription and/or translation of a nucleic acid sequence within a host cell. According to specific aspects of the present invention the term "expression" refers to transcription and/or translation of a heterologous and/or exogenous nucleic acid sequence within a host cell. The level of expression of a desired product in a host cell may be determined on the basis of either the amount of corresponding RNA or mRNA that is present in the cell, or the amount of the desired polypeptide encoded by the selected sequence. For example, mRNA transcribed from a selected sequence can be quantitated by Northern blot hybridization, ribonuclease RNA protection, in situ hybridization to cellular RNA or by RTqPCR (reverse transcription followed by quantitative PCR). Proteins expressed from a selected sequence can be quantitated by various methods, e.g. by ELISA, by Western blotting, by radioimmunoassays, by immunoprecipitation, by assaying for the biological activity of the protein, or by immunostaining of the protein followed by FACS analysis.

The term "virus load" is well known to the person skilled in that art. The term virus load is interchangeable used with the term "viral titer" herein. The virus load or virus titer is a measure of the severity of an active viral infection, and can be determined by methods known to the person skilled in the art. The determination can be based on the detection of viral proteins such as by antibody binding to the viral proteins and further detection or, alternatively, by detection of viral nucleic acids by amplification methods such as RT-PCR. Monitoring of virion associated viral RNA in plasma by nucleic acid amplification methods is a widely used parameter to assess the status and progression of retroviral disease, and to evaluate the effectiveness of prophylactic and therapeutic interventions. Exemplary, the virus load or virus titer can be calculated by estimating the live amount of virus in an involved body fluid such as a number of RNA copies per milliliter of blood plasma. Preferably, the term "virus load" or "virus titer" is a measure of infectious units per volume of a virus preparation. Viral titer is an endpoint in a biological procedure and is defined as the dilution at which a certain proportion of tests carried out in parallel show an effect. Specifically the tissue culture infectious dose fifty per milliliter (TCID50/ml) gives the dilution of a virus preparation at which 50% of a number of cell cultures inoculated in parallel with that dilution are infected.

By definition, every nucleotide sequence or every gene inserted in a host cell and the respective protein or RNA encoded thereby is referred to as "exogenous", "exogenous sequence", "exogenous gene", "exogenous coding sequence", "exogenous antigen encoding sequence" with respect to the host cell, when it comes from a different (virus or bacterium) species.

By definition, every nucleotide sequence or every gene inserted in a host cell and the respective protein or RNA encoded thereby is referred to as "heterologous, "heterologous sequence", "heterologous gene", "heterologous coding sequence", "transgene" or "heterologous protein" with respect to the host cell. This applies even if the sequence to be introduced or the gene to be introduced is identical to an endogenous sequence or an endogenous gene of the host cell. For example, a specific promoter sequence introduced into an viral or bacterial vector at a different site or in modified form than in the wild type virus or bacterium is by definition a heterologous sequence. As used herein in respect to a sequence or gene of interest such as an antigen, the term "heterologous" means that said sequence or gene of interest, specifically said antigen, is expressed out of its natural subspecies context.

The term "non-naturally occurring" means any sequence or gene of interest such as an antigen, which is not occurring in this context naturally, such as a hybrid sequence or a sequence or gene of interest such as an antigen from a different species, or sequence or gene of interest such as an antigen, which is not a product of nature due to artificial mutation, insertion, deletion or the like.

The term "recombinant" is used interchangeably with the terms "non-naturally occurring", "heterologous" and "exogenous" throughout the specification of this present invention. Thus, a "recombinant" protein is a protein expressed from a either a heterologous or an exogenous nucleotide sequence. The term recombinant as used with respect to a virus or bacterium means a virus or bacterium produced by artificial manipulation of the viral or bacterial genome. A virus or bacterium comprising a heterologous or an exogenous sequence such as an exogenous antigen encoding sequence is a recombinant virus or bacterium. The term recombinant virus or bacterium and the term non-naturally occurring virus or bacterium are used interchangeably.

Thus, the term "heterologous vector" means a vector that comprises a heterologous or an exogenous nucleotide sequence. The term "recombinant vector" means a vector that comprises a heterologous or a recombinant nucleotide sequence.

"Sequence homology", as used herein, refers to a method of determining the relatedness of two sequences. To determine sequence homology, two or more sequences are optimally aligned, and gaps are introduced if necessary. However, in contrast to "sequence identity", conservative amino acid substitutions are counted as a match when determining sequence homology. In other words, to obtain a polypeptide or polynucleotide having 95% sequence homology with a reference sequence, 85%, preferably 90%, 91%, 92%, 93%, 94%, even more preferably 95%, 96%, 97%, 98%, 99%, 99.9% of the amino acid residues or nucleotides in the reference sequence must match or comprise a conservative substitution with another amino acid or nucleotide, or a number of amino acids or nucleotides up to 15%, preferably up to 10%, 9%, 8%, 7%, 6%, even more preferably up to 5%, 4%, 3%, 2%, 1%, 0.1% of the total amino acid residues or nucleotides, not including conservative substitutions, in the reference sequence may be inserted into the reference sequence. Preferably the homologue sequence comprises at least a stretch of 50, even more preferred of 100, even more preferred of 250, even more preferred of 500 nucleotides.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, MD 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, 91%, 92%, 93%, 94%, even more preferably 95%, 96%, 97%, 98%, 99%, 99.9% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, 91%, 92%, 93%, 94%, even more preferably 95%, 96%, 97%, 98%, 99%, 99.9% identity relative to the reference nucleotide sequence, up to 15%, preferably 10%, 9%, 8%, 7%, 6%, even more preferably 5%, 4%, 3%, 2%, 1%, 0.1% of the nucleotides in the reference sequence may be deleted or substituted with another nucleotide, or a number of nucleotides up to 15%, preferably 10%, 9%, 8%, 7%, 6%, even more preferably 5%, 4%, 3%, 2%, 1%, 0.1% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, 91%, 92%, 93%, 94%, even more preferably 95%, 96%, 97%, 98%, 99% sequence identity to a reference amino acid sequence, it is intended that the given amino acid sequence of the polypeptide is identical to the reference sequence except that the given polypeptide sequence may include up to 15, preferably up to 10, 9, 8, 7, 6, even more preferably up to 5, 4, 3, 2, 1 amino acid alterations per each 100 amino acids of the reference amino acid sequence. In other words, to obtain a given polypeptide sequence having at least 85%, preferably 90%, 91%, 92%, 93%, 94%, even more preferably 95%, 96%, 97%, 98%, 99% sequence identity with a reference amino acid sequence, up to 15%, preferably up to 10%, 9%, 8%, 7%, even more preferably up to 5%, 4%, 3%, 2%, 1% of the amino acid residues in the reference sequence may be deleted or substituted with another amino acid, or a number of amino acids up to 15%, preferably up to 10%, 9%, 8%, 7%, even more preferably up to 5%, 4%, 3%, 2%, 1% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions, which are not identical, differ by conservative amino acid substitutions. However, conservative substitutions are not included as a match when determining sequence identity.

The terms "sequence identity" or "percent identity" are used interchangeably herein. For the purpose of this invention, it is defined here that in order to determine the percent identity of two amino acid sequences or two nucleic acid sequences, the sequences are aligned for optimal comparison purposes (e.g., gaps can be introduced in the sequence of a first amino acid or nucleic acid for optimal alignment with a second amino or nucleic acid sequence). The amino acid or nucleotide residues at corresponding amino acid or nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length.

A sequence comparison may be carried out over the entire lengths of the two sequences being compared or over fragment of the two sequences. Typically and preferred in the scope of the present invention, the comparison will be carried out over the full length of the two sequences being compared. However, sequence identity may be carried out over a region of, for example, twenty, fifty, one hundred or more contiguous amino acid residues.

As used herein, it is in particular understood that the term "having at least X % sequence identity with the nucleic acid/amino acid sequence according to SEQ ID NO:Y" (or, alternatively, the term "having at least X % sequence identity with the nucleic acid/amino acid sequence of/set forth in SEQ ID NO:Y") is equivalent to the term "having at least X % sequence identity with the nucleic acid/amino acid sequence according to SEQ ID NO:Y over the length of SEQ ID NO:Y" or to the term "having at least X % sequence identity with the nucleic acid/amino acid sequence according to SEQ ID NO:Y over the whole length of SEQ ID NO:Y", respectively.

The skilled person will be aware of the fact that several different computer programs are available to determine the homology between two sequences. For instance, a comparison of sequences and determination of percent identity between two sequences can be accomplished using a mathematical algorithm. In a specific aspect, the percent identity between two amino acid or nucleic acid sequences is determined using the Needleman and Wunsch (J. Mol. Biol. (48): 444-453 (1970)) algorithm which has been incorporated into the GAP program in the Accelrys GCG software, using either a Blosum 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

The protein sequences or nucleic acid sequences of the present invention can further be used as a "query sequence" to perform a search against public databases to, for example, identify other family members or related sequences. Such searches can be performed using the BLASTN and BLASTP programs (version 2.0) of Altschul, et al. (1990) J. Mol. Biol. 215:403-10. BLAST protein searches can be performed with the BLASTP program, score=50, wordlength=3 to obtain amino acid sequences homologous to protein molecules of the invention. To obtain gapped alignments for comparison purposes, Gapped BLAST can be utilized as described in Altschul et al. (1997) Nucleic Acids Res. 25(17): 3389-3402. When utilizing BLAST and Gapped BLAST programs, the default parameters of the respective programs (e.g., BLASTP and BLASTN) can be used. See the homepage of the National Center for Biotechnology Information.

The term "porcine" in the scope of the present invention refers to pigs and any of the animals in the genus *Sus*. The term "pigs" include the domestic pig (*Sus scrofa domesticus*) and wild pigs (*Sus scrofa scrofa*) as well as warthogs (*Potamochoerus porcus*), bushpigs (*Potamochoerus larvatus*), giant forest hogs (*Hylochoerus meinertzhageni*) and feral pigs. It has to be understood that pigs comprises female and male animals. Semen may contain ASFV, and for that reason female and male breeding animals are encompassed by the wording "porcine". Thus, the wordings "porcine" and "pig" comprises male animals such as boars as well as female animals such as gilts and sows. The term "gilt", as used herein, refers to a porcine, preferably a pig, before and during first gestation/pregnancy. In contrast, the term "sow", as used herein, refers to a porcine, preferably a pig, after first farrowing, as a positive result of its first gestation/pregnancy. Preferably, the "porcine" is a pig, in particular a domestic pig.

An "immunogenic or immunological composition" generally refers to a composition of matter that comprises at least one antigen, or immunogenic portion thereof, that elicits an immunological response in the host of a cellular or antibody-mediated immune response to the composition. Preferably, the immunogenic composition induces an immune response and, more preferably, confers protective immunity against one or more of the clinical signs of an ASFV infection. In case where the host displays a protective immunological response such that resistance to new infection will be enhanced and/or the clinical severity of the disease reduced, the immunogenic composition is described as a "vaccine".

The term "antigen" used herein is well understood in the art and includes substances which are immunogenic, i.e., immunogens, as well as substances which induce immunological unresponsiveness, or anergy, i.e., a lack of reactions by the body's defense mechanisms to foreign substances. As used herein, the term "antigen" is intended to mean full-length proteins as well as peptide fragments thereof containing or comprising epitope. Further, the term "antigen encoding sequence" relates to sequences encoding an antigen. Preferably the antigen encoding sequence is a nucleic acid sequence such as a cDNA sequence.

An "immunogenic composition" as herein specifically described and claimed comprises one, two, or more ASFV peptides and/or polypeptides, preferably full-length proteins, and/or immunogenic fragments thereof, such as for example an ASFV surface protein and/or immunogenic fragment(s) thereof; or one, two or more ASFV oligonucleotides and/or polynucleotides and/or immunogenic fragments thereof encoding ASFV peptides and/or polypeptides, preferably full-length proteins, and/or immunogenic fragments thereof; or a viral or bacterial vector, preferably a recombinant and/or non-naturally occurring viral or bacterial vector, comprising one, two or more ASFV oligonucleotides and/or polynucleotides and/or immunogenic fragments thereof encoding ASFV peptides and/or polypeptides, preferably full-length proteins, and/or immunogenic fragments thereof; that elicit an immunological response and/or immunogenicity as described herein.

The term "immunogenic fragment" or "immunogenic portion" or "immunogenic fragment(s) thereof" in the course of the present invention refers to a fragment or truncated and/or substituted form of an ASFV peptide, polypeptide or full-length protein as well as to a fragment or truncated and/or substituted form of a corresponding encoding ASFV oligonucleotide or polynucleotide, all of which including one or more epitopes and thus eliciting the immunological response and/or immunogenicity as described herein. In the course of the present invention, for instance an immunogenic fragment of an ASFV full-length protein can be either an ASFV polypeptide or an ASFV peptide. Depending on the length and/or nature of such an ASFV peptide, such ASFV peptide can also comprise more than one epitope—therefore it is even possible in the course of the present invention that one or more immunogenic fragments of a given ASFV peptide exists—depending on the number of epitopes comprised. Further, in the course of the present invention, for instance an immunogenic fragment of a corresponding encoding ASFV polynucleotide can be a corresponding encoding ASFV oligonucleotide. Depending on the length and/or nature of such an ASFV oligonucleotide, such ASFV oligonucleotide can also comprise more than one epitope—therefore it is also possible in the course of the present invention that one or more immunogenic fragments of a given ASFV oligonucleotide exists—depending on the number of epitopes comprised. Moreover, in the course of the present invention, such ASFV oligonucleotides and/or polynucleotides are either immunogenic per se, i.e. the given nucleic acid as such is immunogenic and comprises at least one epitope and thus elicits the immunological response and/or immunogenicity as described herein. Alternatively, in the course of the present invention, such ASFV oligonucleotides and/or polynucleotides are not immunogenic per se, but encode an ASFV peptide, polypeptide or full-length protein, which is immunogenic and comprises at least one epitope and thus elicits the immunological response and/or immunogenicity as described herein. Preferably, such fragment or truncated and/or substituted form of an ASFV peptide, polypeptide or full-length protein as well as fragment or truncated and/or substituted form of a corresponding encoding ASFV oligonucleotide or polynucleotide will comprise 2 to 1000, 3 to 500, 4 to 300, 5 to 200, 6 to 180 or 7 to 150 contiguous amino acid residues in length from an ASFV peptide, polypeptide or full-length protein; more preferably at least 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 120, 140, 160, 180, 200 or more contiguous amino acid residues in length from an ASFV peptide, polypeptide or full-length protein; or will comprise 6 to 3000, 9 to 1500, 12 to 900, 15 to 600, 18 to 540 or 21 to 450 contiguous nucleotides in length of the corresponding encoding ASFV oligonucleotide or polynucleotide; more preferably at least 12, 15, 18, 20, 21, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000 or more contiguous nucleotides in length of the corresponding encoding ASFV oligonucleotide or polynucleotide.

Such fragments can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, New Jersey. For example, linear epitopes may be determined by concurrently synthesizing large numbers of peptides on solid supports, the peptides corresponding to portions of the protein molecule, and reacting the peptides with antibodies while the peptides are still attached to the supports. Such techniques are known and described in the art, see e.g., U.S. Pat. No. 4,708,871; Geysen et al. (1984) Proc. Natl. Acad. Sci. USA 81:3998-4002; and Geysen et al. (1986) Molec. Immunol. 23:709-715. Similarly, conformational epitopes are readily identified by determining spatial conformation of amino acids such as by, e.g., x-ray crystallography and two-dimensional nuclear magnetic resonance. See Epitope Mapping Protocols, supra. Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996), J. Immunol. 157:3242-3249; Suhrbier, A. (1997), Immunol. and Cell Biol. 75:402-408; and Gardner et al., (1998) 12th World AIDS Conference, Geneva, Switzerland, Jun. 28-Jul. 3, 1998. The teachings and content of which are all incorporated by reference herein.

The term "ASFV peptide" in the course of the present invention refers to an amino acid sequence consisting of two or more, but no more than 50 amino acid residues, more preferably 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acid residues, comprising at least one epitope and thus eliciting the immunological response and/or immunogenicity as described herein.

The term "ASFV polypeptide" in the course of the present invention refers to an amino acid sequence consisting of more than 50 amino acid residues, comprising at least one epitope and thus eliciting the immunological response and/or immunogenicity as described herein.

The term "ASFV full-length protein" refers to an ASFV polypeptide encoded by a polynucleotide sequence comprising, more preferably consisting of, any possible open reading frame (ORF), preferably encoded by a polynucleotide sequence comprising, more preferably consisting of, an open reading frame (ORF) with a 5'-end start codon and a 3'-end stop codon.

The term "ASFV oligonucleotide" in the course of the present invention refers to a nucleotide sequence of at least two, but no more than 12 nucleotides, which can comprise at least one epitope and thus elicit the immunological response and/or immunogenicity as described herein.

The term "ASFV polynucleotide" in the course of the present invention refers to a nucleotide sequence of 13 or more nucleotides, which can comprise at least one epitope and thus elicit the immunological response and/or immunogenicity as described herein.

The term "immunizing" relates to an active immunization by the administration of an immunogenic composition to a porcine to be immunized, thereby causing an immunological response against the antigen included in such immunogenic composition.

The term "in need" or "of need", as used herein means that the administration/treatment is associated with the boosting or improvement in health or clinical signs or any other positive medicinal effect on health of the animals which receive the immunogenic composition in accordance with the present invention.

The term "vaccine" as used herein refers to a pharmaceutical composition comprising at least one immunologically active component that induces an immunological response in an animal and possibly but not necessarily one or more additional components that enhance the immunological activity of the active component. A vaccine may additionally comprise further components typical to pharmaceutical compositions. By way of distinction the immunologically active component of a vaccine may comprise complete virus particles in either their original form or as attenuated particles in a so called modified live vaccine (MLV) or particles inactivated by appropriate methods in a so called killed vaccine (KV). In another form the immunologically active component of a vaccine may comprise appropriate elements of the organisms (subunit vaccines), such as for instance peptides and/or polypeptides, preferably full-length proteins, as well as oligonucleotides and/or polynucleotides, whereby these elements are generated either by destroying the whole particle or the growth cultures containing such particles and optionally subsequent purification steps yielding the desired structure(s), or by synthetic processes including an appropriate manipulation by use of a suitable system based on, for example, bacteria, insects, mammalian, or other species plus optionally subsequent isolation and purification procedures, or by induction of the synthetic processes in the animal needing a vaccine by direct incorporation of genetic or material using suitable pharmaceutical compositions (polynucleotide vaccination). A vaccine may comprise one or simultaneously more than one of the elements described above. As used within specific aspects of the present invention "vaccine" refers to a live vaccine or live virus, also called recombinant vaccine. In another specific aspect of the present invention "vaccine" refers to an inactivated or killed virus including virus like particles (VLPs). Thus, a vaccine may be a subunit vaccine or a killed (KV) or inactivated vaccine.

The term "DNA vaccination" or "polynucleotide vaccination" means direct inoculation of genetic material using suitable pharmaceutical compositions.

Various physical and chemical methods of inactivation are known in the art. The term "inactivated" refers to a previously virulent or non-virulent virus that has been irradiated (ultraviolet (UV), X-ray, electron beam or gamma radiation), heated, or chemically treated to inactivate or kill such virus while retaining its immunogenicity. Suitable inactivating agents include beta-propiolactone, binary or beta- or acetyl-ethyleneimine, gluteraldehyde, ozone, and formalin (formaldehyde).

For inactivation by formalin or formaldehyde, formaldehyde is typically mixed with water and methyl alcohol to create formalin. The addition of methyl alcohol prevents degradation or cross reaction during the in activation process. One embodiment uses about 0.1 to 1% of a 37% solution of formaldehyde to inactivate the virus. It is critical to adjust the amount of formalin to ensure that the material is inactivated but not so much that side effects from a high dosage occur.

More particularly, the term "inactivated" in the context of a virus means that the virus is incapable of replication in vivo or in vitro. For example, the term "inactivated" may refer to a virus that has been propagated in vitro, and has then been inactivated using chemical or physical means so that it is no longer capable of replicating.

As used herein, the terms "inactivated", "killed" or "KV" are used interchangeably.

The term "live vaccine" refers to a vaccine comprising either a living organism or a replication competent virus or viral vector.

A "pharmaceutical composition" essentially consists of one or more ingredients capable of modifying physiological, e.g., immunological functions, of the organism it is administered to, or of organisms living in or on the organism. The term includes, but is not restricted to, antibiotics or antiparasitics, as well as other constituents commonly used to achieve certain other objectives such as, but not limited to, processing traits, sterility, stability, feasibility to administer the composition via enteral or parenteral routes such as oral, intranasal, intravenous, intramuscular, subcutaneous, intradermal, or other suitable route, tolerance after administration, or controlled release properties. One non-limiting example of such a pharmaceutical composition, solely given for demonstration purposes, could be prepared as follows: cell culture supernatant of an infected cell culture is mixed with a stabilizer (e.g., spermidine and/or bovine serum albumin (BSA) and the mixture is subsequently lyophilized or dehydrated by other methods. Prior to vaccination, the mixture is then rehydrated in aqueous (e.g., saline, phosphate buffered saline (PBS) or non-aqueous solutions (e.g., oil emulsion, aluminum-based adjuvant).

As used herein, "pharmaceutical- or veterinary-acceptable carrier" includes any and all solvents, dispersion media, coatings, adjuvants, stabilizing agents, diluents, preservatives, antibacterial and antifungal agents, isotonic agents, adsorption delaying agents, and the like. In some specific aspects, and especially those that include lyophilized immunogenic compositions, stabilizing agents for use in the present invention include stabilizers for lyophilization or freeze-drying.

In some embodiments, the immunogenic composition of the present invention contains an adjuvant. "Adjuvants" as used herein, can include aluminum hydroxide and aluminum phosphate, saponins e.g., Quil A, QS-21 (Cambridge Biotech Inc., Cambridge MA), GPI-0100 (Galenica Pharmaceuticals, Inc., Birmingham, AL), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed.Stewart-Tull, D. E. S.), JohnWiley and Sons, NY, pp51-94 (1995) and Todd et al., Vaccine 15:564-570 (1997). Exemplary adjuvants are the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name CARBOPOL®; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of CARBOPOL® 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta GA), SAF-M (Chiron, Emeryville CA), monophosphoryl lipid A, Avridine lipid-amine adjuvant, heat-labile enterotoxin from *E. coli* (recombinant or otherwise), cholera toxin, IMS 1314 or muramyl dipeptide, or naturally occurring or recombinant cytokines or analogs thereof or stimulants of endogenous cytokine release, among many others.

It is expected that an adjuvant can be added in an amount of about 100 µg to about 10 mg per dose, preferably in an amount of about 100 µg to about 10 mg per dose, more preferably in an amount of about 500 µg to about 5 mg per dose, even more preferably in an amount of about 750 µg to about 2.5 mg per dose, and most preferably in an amount of about 1 mg per dose. Alternatively, the adjuvant may be at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

"Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

"Attenuation" means reducing the virulence of a pathogen. In the present invention "attenuation" is synonymous with "avirulent". In the present invention, an attenuated virus is one in which the virulence has been reduced so that it does not cause clinical signs of infection but is capable of inducing an immune response in the target animal, but may also mean that the clinical signs are reduced in incidence or severity in animals infected with the attenuated virus in comparison with a "control group" of animals infected with non-attenuated virus or pathogen and not receiving the attenuated virus. In this context, the term "reduce/reduced" means a reduction of at least 10%, preferably 25%, even more preferably 50%, still more preferably 60%, even more preferably 70%, still more preferably 80%, even more preferably 90% and most preferably of 100% as compared to the control group as defined above. Thus, an attenuated, avirulent pathogen such as for example an attenuated viral or bacterial vector as claimed is suitable for the generation of a modified live vaccine (MLV) or modified live immunogenic composition.

The terms "treatment and/or prophylaxis" and "reducing or preventing the clinical signs or disease" refer to the lessening of the incidence of the particular ASFV infection or the reduction in the severity of clinical signs caused by or associated with the particular ASFV infection. Thus, the terms "treatment and/or prophylaxis" and "reducing or preventing the clinical signs or disease" also refer to the reduction of the number of animals that become infected with the particular ASFV (=lessening of the incidence of the ASFV infection) or to the reduction of the severity of clinical signs normally associated with or caused by an ASFV infection in a group of animals which animals have received an effective amount of the immunogenic composition as provided herein in comparison to a group of animals which animals have not received such immunogenic composition. The terms "treatment and/or prophylaxis" and "reducing or preventing the clinical signs or disease" generally involve the administration of an effective amount of the immunogenic composition of the present invention to an animal or animals in need of or that could benefit from such a treatment/prophylaxis/reduction/prevention. The term "treatment" refers to the administration of the effective amount of the immunogenic composition once the animal or at least some animals is/are already infected with such ASFV and wherein such animals already show some clinical signs caused by or associated with such ASFV infection. The terms "prophylaxis" and "preventing" refer to the administration to an animal prior to any infection of such animal with ASFV or at least where such animal or none of the animals in a group of animals do not show any clinical signs caused by or associated with the infection by such ASFV. The terms "prophylaxis" and "preventing" are used interchangeably in this application.

The term "clinical signs" as used herein refers to signs of infection of an animal from ASFV. The clinical signs of infection depend on the ASFV strain(s) selected. Examples for such clinical signs include but are not limited to increased thirst, increased urination, weight loss, decreased appetite, lethargy, vomiting in the subject, viremia, fever, and shedding of the virus in the environment. However, the clinical signs also include but are not limited to clinical signs that are directly observable from a live animal.

Preferably, the clinical signs lessened in incidence or severity in a treated animal compared to animals that are either not treated or treated with an immunogenic composition that was available prior to the present invention but subsequently infected by the particular ASFV refer to African swine fever, acute African swine fever, chronic African swine fever, mortality, death, sudden death, fever, high fever, anorexia, lethargy, weakness, loss of appetite, recumbence, erythema, cyanotic skin blotching, diarrhea, constipation, abdominal pain, respiratory signs, coughing, vomiting, dyspnea, nasal and conjunctival discharges, hemorrhages, epistaxis, abortion, leukopenia, thrombocytopenia.

Herein, "effective dose" means, but is not limited to, an amount of antigen that elicits, or is able to elicit, an immune response that yields a reduction of clinical symptoms in an animal to which the antigen is administered.

As used herein, the term "effective amount" means, in the context of a composition, an amount of an immunogenic composition capable of inducing an immune response that reduces the incidence of or lessens the severity of infection or incident of disease in an animal. Such effective amount is able to lessen the incidence of the particular ASFV infection in porcine or to reduce the severity of clinical signs of the particular ASFV infection. Particularly, an effective amount refers to colony forming units (CFU) per dose. Alternatively, in the context of a therapy, the term "effective amount" refers to the amount of a therapy which is sufficient to reduce or ameliorate the severity or duration of a disease or disorder, or one or more symptoms thereof, prevent the advancement of a disease or disorder, cause the regression of a disease or disorder, prevent the recurrence, development, onset, or progression of one or more symptoms associated with a disease or disorder, or enhance or improve the prophylaxis or treatment of another therapy or therapeutic agent.

An "immune response" or "immunological response" or "immunogenicity" means, but is not limited to, the development of a cellular and/or antibody-mediated immune response to the (immunogenic) composition or vaccine of interest. Usually, an immune or immunological response or immunogenicity includes, but is not limited to, one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or a protective immunological (memory) response such that resistance to new infection will be enhanced and/or the clinical severity of the disease will be reduced. Such protection will be demonstrated by either a reduction in number of symptoms, severity of symptoms, or the lack of one or more of the symptoms associated with the infection of the pathogen, a delay in the of onset of viremia, reduced viral persistence, a reduction in the overall viral load and/or a reduction of viral excretion.

In the course of the present invention an "immune response" or "immunological response" or "immunogenicity" is preferably indicated/characterized by an induced IFN-gamma response, more preferably in a porcine IFN-gamma ELISpot assay, more preferably in a porcine IFN-gamma ELISpot assay as described in Example 1. One exemplary porcine IFN-gamma ELISpot assay, which may be applied according to the present invention is as follows: IFNγ response is assessed by an ELISpot assay using purified mouse anti-pig IFNγ Clone P2G10 as capture antibody and biotinylated mouse anti-porcine IFNγ antibody P2C11 as detection antibody, following a previously reported method (Lacasta et al., 2014). Briefly, 96-well plates are coated overnight at 4° C. with 5 µg/ml capture antibody in carbonate-bicarbonate buffer, pH 9.6. Plates are washed 3× with PBS, and blocked 1 hour at 37° C. with complete RPMI with 10% FBS. $5 \times 10^5$ PBMCs/well are used in a final volume of 200 µl with the correspondent stimuli. Peptides and/or polypeptides, preferably full-length proteins, are added as a stimulus at a final concentration of 4 µg/ml. RPMI and 10 µg/ml phytohaemagglutinin-M are used as negative and positive controls, respectively. When the live attenuated virus BA71ΔCD2 is used as stimulus, $10^5$ PFU are added per well. After overnight incubation at 37° C., 5% $CO_2$, cells are washed out with PBS 0.05% Tween20, and IFNγ is detected using 0.5 µg/ml of biotinylated anti-porcine IFNγ antibody 1 hour at 37° C. After washing, the ELISpot is developed by adding 50 µl of insoluble 3,3',5,5'-tetramethylbenzidine (TMB) substrate and stopped by washing with water.

"Protection against disease", "protective immunity", "functional immunity", "reduction of clinical signs/symptoms", "induction/production of neutralizing antibodies and/or serum conversion", and similar phrases, means a partial or complete response against a disease or condition generated by administration of one or more immunogenic compositions or vaccines or pharmaceutical compositions of the invention, or a combination thereof, that results in fewer deleterious effects than would be expected in a non-immunized animal that has been exposed to disease or infection. That is, the severity of the deleterious effects of the infection is lessened in a vaccinated animal. Infection may be reduced, slowed, or possibly fully prevented, in a vaccinated animal. Herein, where complete prevention of infection is meant, it is specifically stated. If complete prevention is not stated then the term includes partial prevention. A "protective immunological response" or "protective immunity" will be demonstrated by either a reduction or lack of clinical signs/symptoms normally displayed by an infected host, a quicker recovery time and/or a lowered duration of infectivity or lowered pathogen titer in the tissues or body fluids or excretions of the infected host.

Herein, "reduction of the incidence and/or severity of clinical signs" or "reduction of clinical symptoms" or "reducing or preventing the clinical signs or disease" means, but is not limited to, reducing the number of infected animals in a group, reducing or eliminating the number of animals exhibiting clinical signs of infection, or reducing the severity of any clinical signs that are present in one or more animals, in comparison to wild-type infection. For example, it should refer to any reduction of pathogen load, pathogen shedding, reduction in pathogen transmission, or reduction of any clinical sign symptomatic of ASFV infections. Preferably, these clinical signs/symptoms are reduced in one or more animals receiving the therapeutic composition of the present invention by at least 10% in comparison to animals not receiving the composition and that become infected. More preferably, clinical signs/symptoms are reduced in animals receiving a composition of the present invention by at least 20%, preferably by at least 30%, more preferably by at least 40%, and even more preferably by at least 50%.

The term "increased protection" herein means, but is not limited to, a statistically significant reduction of one or more clinical signs or symptoms, which are associated with infection by an infectious agent in a vaccinated group of animals vs. a non-vaccinated control group of animals. The term "statistically significant reduction of clinical symptoms" means, but is not limited to, the frequency in the incidence of at least one clinical symptom in the vaccinated group of animals is at least 10%, preferably 20%, more preferably 30%, even more preferably 50%, and even more preferably 70% lower than in the non-vaccinated control group after the challenge the infectious agent.

The term "pathogen" is well known to the person skilled in the art. The term "pathogen" comprises bacteria and viruses. In the course of the present invention, the term "pathogen infecting porcines" preferably is ASFV.

"Long-lasting protection" shall refer to "improved efficacy" that persists for at least 3 weeks, but more preferably at least 3 months, still more preferably at least 6 months.

The term "shedding" refers to secretions such as nasal discharges and, further, to aerosols created by coughing or sneezing. Thus, shedding may be determined by examining the virus titer in nasal swabs or by the virus titer in the lungs. The term "shedding" further encompasses the transfer of virus to susceptible animals (i.e. sentinels). It is in the general knowledge of a person skilled in the art how to measure the viral shedding.

"Safety" refers to the absence of adverse consequences in a vaccinated animal following vaccination, including but not limited to: potential reversion of a pathogen-based vaccine to virulence, clinically significant side effects such as persistent, systemic illness or unacceptable inflammation at the site of vaccine administration.

The terms "vaccination" or "vaccinating" or variants thereof, as used herein means, but is not limited to, a process which includes the administration of an immunogenic composition of the invention that, when administered to an animal, elicits, or is able to elicit—directly or indirectly—an immune response in said animal.

"Mortality", in the context of the present invention, refers to death caused by an infection, and includes the situation where the infection is so severe that an animal is euthanized to prevent suffering and provide a humane ending to its life.

The formulations of the invention comprise an effective immunizing amount of one or more immunogenic compositions and a physiologically acceptable vehicle. Vaccines comprise an effective immunizing amount of one or more immunogenic compositions and a physiologically acceptable vehicle. The formulation should suit the mode of administration.

The immunogenic composition, if desired, can also contain minor amounts of wetting or emulsifying agents, or pH buffering agents. The immunogenic composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

Preferred routes of administration include but are not limited to intranasal, oral, intradermal, subcutaneous and intramuscular. Administration in drinking water, most preferably in a single dose, is desirable. The skilled artisan will recognize that compositions of the invention may also be administered in one, two or more doses, as well as, by other routes of administration. For example, such other routes include subcutaneously, intracutaneously, intraperitoneally, and depending on the desired duration and effectiveness of the treatment, the compositions according to the invention may be administered once or several times, also intermittently, for instance on a daily basis for several days, weeks or months and in different dosages such as about $1\times10^3$ to $1\times10^9$. In a specific aspect of the present invention, the dosage is about $1\times10^4$ to $1\times10^8$ $TCID_{50}$.

The term "sample" refers to a sample of a body fluid, to a sample of separated cells or to a sample from a tissue or an organ. Samples of body fluids can be obtained by well-known techniques and include, preferably, samples of blood, plasma, serum, or urine, more preferably, samples of blood, plasma or serum. Tissue or organ samples may be obtained from any tissue or organ by, e.g., biopsy. Separated cells may be obtained from the body fluids or the tissues or organs by separating techniques such as centrifugation or cell sorting.

The term "obtained" may comprise an isolation and/or purification step known to the person skilled in the art, preferably using precipitation, columns etc.

The term "immunotest" and "genomic analytical test" is the basis for differentiating animals vaccinated with the immunogenic composition according to the present invention and animals infected with the naturally occurring (disease-associated) ASFV. Examples of immunotests include any enzyme-immunological or immunochemical detection method such as ELISA (enzyme linked immunosorbent assay), EIA (enzyme immunoassay), RIA (radioimmunoassay), sandwich enzyme immune tests, fluorescent antibody test (FAT) electrochemiluminescence sandwich immunoassays (ECLIA), dissociation-enhanced lanthanide fluoro immuno assay (DELFIA) or solid phase immune tests, immunofluorescent test (IFT), immunohistological staining, Western blot analysis or any other suitable method available to technicians skilled in the art. Depending upon the assay used, the antigens or the antibodies can be labeled by an enzyme, a fluorophore or a radioisotope. See, e.g., Coligan et al. Current Protocols in Immunology, John Wiley & Sons Inc., New York, N.Y. (1994); and Frye et al., Oncogen 4: 1153-1157, 1987.

The term "genomic analytical test" refers to a genomic analytical method based upon the polymerase chain reaction (PCR), reverse transcription polymerase chain reaction (RT-PCR), real-time PCR (r-PCR) or real time reverse transcription PCR (rRT-PCR), Templex-PCR, nucleic-acid sequence based amplification (NASBA), and isothermal amplification methods using polymerases and specific oligonucleotides as primers. The aforementioned amplification methods are well known in the art.

Hybridization reactions can be performed under conditions of different "stringency." Conditions that increase stringency of a hybridization reaction are well known. See for examples, "Molecular Cloning: A Laboratory Manual", second edition (Sambrook et al. 1989). Examples of relevant conditions include (in order of increasing stringency): incubation temperatures of 25° C., 37° C., 50° C., and 68° C.; buffer concentrations of 10×SSC, 6×SSC, 1×SSC, 0.1×SSC (where SSC is 0.15 M NaCl and 15 mM citrate buffer) and their equivalent using other buffer systems; formamide concentrations of 0%, 25%, 50%, and 75%; incubation times from 5 minutes to 24 hours; 1, 2 or more washing steps; wash incubation times of 1, 2, or 15 minutes; and wash solutions of 6×SSC, 1×SSC, 0.1×SSC, or deionized water.

The term "epitope" refers to the site on an antigen, such as an ASFV peptide, polypeptide or full-length protein as well as an ASFV oligonucleotide or polynucleotide according to the present invention, to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

SEQUENCE LISTING

This application contains a sequence listing. The sequence listing comprises the following sequences, which are either amino acid sequences (N-terminus to C-terminus direction) or DNA sequences (5'-end to 3'-end direction):

SEQ ID NO: 1 A118R peptide Georgia 2007/1, 23-43, 21
SEQ ID NO: 2 A118R peptide Georgia 2007/1, 33-43, 11
SEQ ID NO: 3 A118R peptide Georgia 2007/1, 41-50, 10
SEQ ID NO: 4 A118R protein Georgia 2007/1
SEQ ID NO: 5 A137R peptide BA71
SEQ ID NO: 6 A137R protein BA71
SEQ ID NO: 7 A137R protein Georgia2007/1
SEQ ID NO: 8 A151R peptide BA71
SEQ ID NO: 9 A151R peptide Georgia 2007/1, 40-55, 16
SEQ ID NO: 10 A151R peptide Georgia 2007/1, 43-52, 10
SEQ ID NO: 11 A151R peptide Georgia 2007/1, 48-55, 8
SEQ ID NO: 12 A151R protein BA71
SEQ ID NO: 13 A151R protein Georgia 2007/1
SEQ ID NO: 14 A179L peptide BA71
SEQ ID NO: 15 A179L protein BA71
SEQ ID NO: 16 A179L protein Georgia 2007/1
SEQ ID NO: 17 A238L peptide BA71
SEQ ID NO: 18 A238L peptide BA71
SEQ ID NO: 19 A238L peptide Georgia 2007/1
SEQ ID NO: 20 A238L peptide Georgia 2007/1
SEQ ID NO: 21 A238L protein BA71
SEQ ID NO: 22 A238L protein BA71
SEQ ID NO: 23 A238L protein Georgia 2007/1
SEQ ID NO: 24 A238L protein Georgia 2007/1
SEQ ID NO: 25 A240L peptide Georgia 2007/1
SEQ ID NO: 26 A240L peptide Georgia 2007/1

SEQ ID NO: 27 A240L protein Georgia 2007/1
SEQ ID NO: 28 A859L peptide Georgia 2007/1, 572-580, 9
SEQ ID NO: 29 A859L peptide Georgia 2007/1, 626-636, 11
SEQ ID NO: 30 A859L protein Georgia 2007/1
SEQ ID NO: 31 B117L peptide BA71
SEQ ID NO: 32 B117L protein BA71
SEQ ID NO: 33 B117L protein Georgia 2007/1
SEQ ID NO: 34 B119L peptide Georgia 2007/1, 68-75, 8
SEQ ID NO: 35 B119L protein Georgia 2007/1
SEQ ID NO: 36 B125R peptide BA71
SEQ ID NO: 37 B125R peptide BA71
SEQ ID NO: 38 B125R protein BA71
SEQ ID NO: 39 B125R protein Georgia 2007/1
SEQ ID NO: 40 B169L peptide Georgia 2007/1, 26-34, 9
SEQ ID NO: 41 B169L protein Georgia 2007/1
SEQ ID NO: 42 B175L peptide Georgia 2007/1, 69-78, 10
SEQ ID NO: 43 B175L protein Georgia 2007/1
SEQ ID NO: 44 B318L peptide Georgia 2007/1, 155-162, 8
SEQ ID NO: 45 B318L protein Georgia 2007/1
SEQ ID NO: 46 B385R peptide Georgia 2007/1, 180-188, 9
SEQ ID NO: 47 B385R protein Georgia 2007/1
SEQ ID NO: 48 B475L peptide BA71
SEQ ID NO: 49 B475L peptide BA71
SEQ ID NO: 50 B475L peptide BA71
SEQ ID NO: 51 B475L peptide BA71
SEQ ID NO: 52 B475L peptide BA71
SEQ ID NO: 53 B475L peptide BA71
SEQ ID NO: 54 B475L peptide Georgia 2007/1
SEQ ID NO: 55 B475L peptide Georgia 2007/1
SEQ ID NO: 56 B475L peptide Georgia 2007/1
SEQ ID NO: 57 B475L peptide Georgia 2007/1
SEQ ID NO: 58 B475L peptide Georgia 2007/1
SEQ ID NO: 59 B475L peptide Georgia 2007/1
SEQ ID NO: 60 B475L peptide Georgia 2007/1, 10-18, 9
SEQ ID NO: 61 B475L peptide Georgia 2007/1, 14-24, 11
SEQ ID NO: 62 B475L peptide Georgia 2007/1, 14-28, 15
SEQ ID NO: 63 B475L peptide Georgia 2007/1, 18-28, 11
SEQ ID NO: 64 B475L peptide Georgia 2007/1, 62-70, 9
SEQ ID NO: 65 B475L protein BA71
SEQ ID NO: 66 B475L protein Georgia 2007/1
SEQ ID NO: 67 B602L peptide BA71
SEQ ID NO: 68 B602L peptide BA71
SEQ ID NO: 69 B602L peptide BA71
SEQ ID NO: 70 B602L peptide Georgia 2007/1, 54-77, 24
SEQ ID NO: 71 B602L peptide Georgia 2007/1, 61-69, 9
SEQ ID NO: 72 B602L peptide Georgia 2007/1, 61-71, 11
SEQ ID NO: 73 B602L peptide Georgia 2007/1, 73-81, 9
SEQ ID NO: 74 B602L protein BA71
SEQ ID NO: 75 B602L protein Georgia 2007/1
SEQ ID NO: 76 B646L peptide BA71
SEQ ID NO: 77 B646L peptide BA71
SEQ ID NO: 78 B646L peptide BA71
SEQ ID NO: 79 B646L peptide BA71
SEQ ID NO: 80 B646L peptide Georgia 2007/1, 455-465, 11
SEQ ID NO: 81 B646L peptide Georgia 2007/1, 457-465, 9
SEQ ID NO: 82 B646L protein BA71
SEQ ID NO: 83 B646L protein Georgia2007/1
SEQ ID NO: 84 B962L peptide Georgia 2007/1, 599-606, 8
SEQ ID NO: 85 B962L protein Georgia 2007/1
SEQ ID NO: 86 BA71V-A104R protein BA71
SEQ ID NO: 87 BA71V-A104R protein Georgia2007/1
SEQ ID NO: 88 BA71V-A118R protein BA71
SEQ ID NO: 89 BA71V-A118R protein Georgia2007/1
SEQ ID NO: 90 BA71V-A137R(p11.5) protein BA71
SEQ ID NO: 91 BA71V-A137R(p11.5) protein Georgia2007/1
SEQ ID NO: 92 BA71V-A179L(5HL)Bcl2 protein BA71
SEQ ID NO: 93 BA71V-A179L(5HL)Bcl2 protein Georgia2007/1
SEQ ID NO: 94 BA71V-A224L(4CL) protein BA71
SEQ ID NO: 95 BA71V-A224L(4CL) protein Georgia2007/1
SEQ ID NO: 96 BA71V-A238L(5EL) protein BA71
SEQ ID NO: 97 BA71V-A238L(5EL) protein Georgia2007/1
SEQ ID NO: 98 BA71V-A859L protein BA71
SEQ ID NO: 99 BA71V-A859L protein Georgia2007/1
SEQ ID NO: 100 BA71V-B175L protein BA71
SEQ ID NO: 101 BA71V-B175L protein Georgia2007/1
SEQ ID NO: 102 BA71V-B263R protein BA71
SEQ ID NO: 103 BA71V-B263R protein Georgia2007/1
SEQ ID NO: 104 BA71V-B407L protein BA71
SEQ ID NO: 105 BA71V-B407L protein Georgia2007/1
SEQ ID NO: 106 BA71V-B438L(p49) protein BA71
SEQ ID NO: 107 BA71V-B438L(p49) protein Georgia2007/1
SEQ ID NO: 108 BA71V-C62L protein BA71
SEQ ID NO: 109 BA71V-C62L protein Georgia2007/1
SEQ ID NO: 110 BA71V-D129L protein BA71
SEQ ID NO: 111 BA71V-D129L protein Georgia2007/1
SEQ ID NO: 112 BA71V-D250R(g5R) protein BA71
SEQ ID NO: 113 BA71V-D250R(g5R) protein Georgia2007/1
SEQ ID NO: 114 BA71V-D345L(i3L,i4L) protein BA71
SEQ ID NO: 115 BA71V-D345L(i3L,i4L) protein Georgia2007/1
SEQ ID NO: 116 BA71V-D79L(g7L) protein BA71
SEQ ID NO: 117 BA71V-D79L(g7L) protein Georgia2007/1
SEQ ID NO: 118 BA71V-DP96R protein BA71
SEQ ID NO: 119 BA71V-DP96R protein Georgia2007/1
SEQ ID NO: 120 BA71V-E111R(k6R) protein BA71
SEQ ID NO: 121 BA71V-E111R(k6R) protein Georgia2007/1
SEQ ID NO: 122 BA71V-E120R(p14.5) protein BA71
SEQ ID NO: 123 BA71V-E120R(p14.5) protein Georgia2007/1
SEQ ID NO: 124 BA71V-E165R(k1R) protein BA71
SEQ ID NO: 125 BA71V-E165R(k1R) protein Georgia2007/1
SEQ ID NO: 126 BA71V-E183L(p54,j13L) protein BA71
SEQ ID NO: 127 BA71V-E183L(p54,j13L) protein Georgia2007/1
SEQ ID NO: 128 BA71V-E184L(j12L) protein BA71
SEQ ID NO: 129 BA71V-E184L(i12L) protein Georgia2007/1
SEQ ID NO: 130 BA71V-E199L(j18L) protein BA71
SEQ ID NO: 131 BA71V-E199L(j18L) protein Georgia2007/1
SEQ ID NO: 132 BA71V-E248R(k2R) protein BA71
SEQ ID NO: 133 BA71V-E248R(k2R) protein Georgia2007/1
SEQ ID NO: 134 BA71V-E296R(k4R) protein BA71
SEQ ID NO: 135 BA71V-E296R(k4R) protein Georgia2007/1
SEQ ID NO: 136 BA71V-E301R(j15R) protein BA71

SEQ ID NO: 137 BA71V-E301R(j15R) protein Georgia2007/1
SEQ ID NO: 138 BA71V-EP152R protein BA71
SEQ ID NO: 139 BA71V-EP152R protein Georgia2007/1
SEQ ID NO: 140 BA71V-EP364R protein BA71
SEQ ID NO: 141 BA71V-EP364R protein Georgia2007/1
SEQ ID NO: 142 BA71V-F165R protein BA71
SEQ ID NO: 143 BA71V-F165R protein Georgia2007/1
SEQ ID NO: 144 BA71V-F317L protein BA71
SEQ ID NO: 145 BA71V-F317L protein Georgia2007/1
SEQ ID NO: 146 BA71V-H124R protein BA71
SEQ ID NO: 147 BA71V-H124R protein Georgia2007/1
SEQ ID NO: 148 BA71V-H171R(j2R) protein BA7
SEQ ID NO: 149 BA71V-H171R(j2R) protein Georgia2007/1
SEQ ID NO: 150 BA71V-H359L(j1L) protein BA71
SEQ ID NO: 151 BA71V-H359L(j1L) protein Georgia2007/1
SEQ ID NO: 152 BA71V-I177L(k14L) protein BA71
SEQ ID NO: 153 BA71V-I177L(k14L) protein Georgia2007/1
SEQ ID NO: 154 BA71V-I196L(k15L) protein BA71
SEQ ID NO: 155 BA71V-I196L(k15L) protein Georgia2007/1
SEQ ID NO: 156 BA71V-I215L(k13L) protein BA71
SEQ ID NO: 157 BA71V-I215L(k13L) protein Georgia2007/1
SEQ ID NO: 158 BA71V-I267L(k7L) protein BA71
SEQ ID NO: 159 BA71V-I267L(k7L) protein Georgia2007/
SEQ ID NO: 160 BA71V-K205R protein BA71
SEQ ID NO: 161 BA71V-K205R protein Georgia2007/1
SEQ ID NO: 162 BA71V-K78R(p10) protein BA71
SEQ ID NO: 163 BA71V-K78R(p10) protein Georgia2007/1
SEQ ID NO: 164 BA71V-KP177R protein BA71
SEQ ID NO: 165 BA71V-KP177R protein Georgia2007/1
SEQ ID NO: 166 BA71V-0174L protein BA71
SEQ ID NO: 167 BA71V-0174L protein Georgia2007/1
SEQ ID NO: 168 BA71V-S183(i5L) protein BA71
SEQ ID NO: 169 BA71V-S183(i5L) protein Georgia2007/1
SEQ ID NO: 170 BA71V-S273R(i6R) protein BA71
SEQ ID NO: 171 BA71V-S273R(i6R) protein Georgia2007/1
SEQ ID NO: 172 BA71V-X69R protein BA71
SEQ ID NO: 173 BA71V-X69R protein Georgia2007/1
SEQ ID NO: 174 C129R peptide BA71
SEQ ID NO: 175 C129R peptide BA71
SEQ ID NO: 176 C129R protein BA71
SEQ ID NO: 177 C129R protein Georgia2007/1
SEQ ID NO: 178 C147L peptide Georgia 2007/1, 10-18, 9
SEQ ID NO: 179 C147L protein Georgia 2007/1
SEQ ID NO: 180 C257L peptide BA71
SEQ ID NO: 181 C257L protein BA71
SEQ ID NO: 182 C257L protein Georgia2007/1
SEQ ID NO: 183 C315R peptide BA71
SEQ ID NO: 184 C315R peptide Georgia 2007/1, 257-267, 11
SEQ ID NO: 185 C315R peptide Georgia 2007/1, 290-299, 10
SEQ ID NO: 186 C315R protein BA71
SEQ ID NO: 187 C315R protein Georgia 2007/1
SEQ ID NO: 188 C475L peptide BA71
SEQ ID NO: 189 C475L peptide BA71
SEQ ID NO: 190 C475L peptide BA71
SEQ ID NO: 191 C475L peptide BA71
SEQ ID NO: 192 C475L peptide Georgia 2007/1, 115-123, 9
SEQ ID NO: 193 C475L peptide Georgia 2007/1, 127-137, 11
SEQ ID NO: 194 C475L peptide Georgia 2007/1, 130-137, 8
SEQ ID NO: 195 C475L peptide Georgia 2007/1, 207-217, 11
SEQ ID NO: 196 C475L peptide Georgia 2007/1, 207-221, 15
SEQ ID NO: 197 C475L peptide Georgia 2007/1, 210-217, 8
SEQ ID NO: 198 C475L peptide Georgia 2007/1, 213-221, 9
SEQ ID NO: 199 C475L peptide Georgia 2007/1, 438-445, 8
SEQ ID NO: 200 C475L protein BA71
SEQ ID NO: 201 C475L protein Georgia 2007/1
SEQ ID NO: 202 C62L peptide Georgia 2007/1, 33-51, 19
SEQ ID NO: 203 C62L peptide Georgia 2007/1, 41-51, 11
SEQ ID NO: 204 C62L protein Georgia 2007/1
SEQ ID NO: 205 C62L protein Georgia 2007/1
SEQ ID NO: 206 C717R peptide Georgia 2007/1, 104-116, 13
SEQ ID NO: 207 C717R peptide Georgia 2007/1, 356-363, 8
SEQ ID NO: 208 C717R peptide Georgia 2007/1, 356-366, 11
SEQ ID NO: 209 C717R peptide Georgia 2007/1, 388-407, 20
SEQ ID NO: 210 C717R peptide Georgia 2007/1, 394-404, 11
SEQ ID NO: 211 C717R peptide Georgia 2007/1, 425-435, 11
SEQ ID NO: 212 C717R peptide Georgia 2007/1, 47-62, 16
SEQ ID NO: 213 C717R peptide Georgia 2007/1, 495-505, 11
SEQ ID NO: 214 C717R peptide Georgia 2007/1, 543-553, 11
SEQ ID NO: 215 C717R peptide Georgia 2007/1, 543-563, 21
SEQ ID NO: 216 C717R peptide Georgia 2007/1, 546-553, 8
SEQ ID NO: 217 C717R protein Georgia 2007/1
SEQ ID NO: 218 C84L peptide Georgia 2007/1, 42-49, 8
SEQ ID NO: 219 C84L protein Georgia 2007/1
SEQ ID NO: 220 C962R peptide Georgia 2007/1, 327-335, 9
SEQ ID NO: 221 C962R peptide Georgia 2007/1, 398-407, 10
SEQ ID NO: 222 C962R peptide Georgia 2007/1, 398-417, 20
SEQ ID NO: 223 C962R peptide Georgia 2007/1, 400-409, 10
SEQ ID NO: 224 C962R peptide Georgia 2007/1, 407-416, 10
SEQ ID NO: 225 C962R peptide Georgia 2007/1, 536-544, 9
SEQ ID NO: 226 C962R peptide Georgia 2007/1, 726-742, 17
SEQ ID NO: 227 C962R peptide Georgia 2007/1, 730-738, 9
SEQ ID NO: 228 C962R protein Georgia 2007/1
SEQ ID NO: 229 CP123L peptide BA71
SEQ ID NO: 230 CP123L peptide BA71

SEQ ID NO: 231 CP123L protein BA71
SEQ ID NO: 232 CP123L protein Georgia2007/1
SEQ ID NO: 233 CP204L peptide Georgia 2007/1, 23-33, 11
SEQ ID NO: 234 CP204L protein Georgia 2007/1
SEQ ID NO: 235 CP2475L peptide BA71
SEQ ID NO: 236 CP2475L peptide BA71
SEQ ID NO: 237 CP2475L peptide BA71
SEQ ID NO: 238 CP2475L peptide BA71
SEQ ID NO: 239 CP2475L peptide BA71
SEQ ID NO: 240 CP2475L peptide BA71
SEQ ID NO: 241 CP2475L peptide BA71
SEQ ID NO: 242 CP2475L peptide BA71
SEQ ID NO: 243 CP2475L peptide BA71
SEQ ID NO: 244 CP2475L peptide Georgia 2007/1, 1540-1562, 23
SEQ ID NO: 245 CP2475L peptide Georgia 2007/1, 1547-1557, 11
SEQ ID NO: 246 CP2475L peptide Georgia 2007/1, 1795-1807, 13
SEQ ID NO: 247 CP2475L peptide Georgia 2007/1, 1889-1898, 10
SEQ ID NO: 248 CP2475L peptide Georgia 2007/1, 2019-2029, 11
SEQ ID NO: 249 CP2475L peptide Georgia 2007/1, 214-221, 8
SEQ ID NO: 250 CP2475L peptide Georgia 2007/1, 2226-2234, 9
SEQ ID NO: 251 CP2475L peptide Georgia 2007/1, 538-559, 22
SEQ ID NO: 252 CP2475L peptide Georgia 2007/1, 543-551, 9
SEQ ID NO: 253 CP2475L peptide Georgia 2007/1, 544-554, 11
SEQ ID NO: 254 CP2475L peptide Georgia 2007/1, 549-559, 11
SEQ ID NO: 255 CP2475L peptide Georgia 2007/1, 976-985, 10
SEQ ID NO: 256 CP2475L protein BA71
SEQ ID NO: 257 CP2475L protein Georgia 2007/1
SEQ ID NO: 258 CP2475L_P150 peptide Georgia 2007/1
SEQ ID NO: 259 CP2475L_P150 peptide Georgia 2007/1
SEQ ID NO: 260 CP2475L_P150 peptide Georgia 2007/1
SEQ ID NO: 261 CP2475L_P37 peptide Georgia 2007/1
SEQ ID NO: 262 CP2475L_P37 peptide Georgia 2007/1
SEQ ID NO: 263 CP2475L_P37 peptide Georgia 2007/1
SEQ ID NO: 264 CP2475L_P37 peptide Georgia 2007/1
SEQ ID NO: 265 CP2475L_P37 peptide Georgia 2007/1
SEQ ID NO: 266 CP2475L_P37 peptide Georgia 2007/1
SEQ ID NO: 267 CP312R peptide BA71
SEQ ID NO: 268 CP312R peptide Georgia 2007/1
SEQ ID NO: 269 CP312R peptide Georgia 2007/1
SEQ ID NO: 270 CP312R peptide Georgia 2007/1
SEQ ID NO: 271 CP312R peptide Georgia 2007/1
SEQ ID NO: 272 CP312R protein BA71
SEQ ID NO: 273 CP312R protein Georgia 2007/1
SEQ ID NO: 274 CP312R protein Georgia2007/1
SEQ ID NO: 275 CP530R peptide Georgia 2007/1, 225-235, 11
SEQ ID NO: 276 CP530R peptide Georgia 2007/1, 232-241, 10
SEQ ID NO: 277 CP530R peptide Georgia 2007/1, 358-365, 8
SEQ ID NO: 278 CP530R protein Georgia 2007/1
SEQ ID NO: 279 CP80R peptide Georgia 2007/1, 67-76, 10
SEQ ID NO: 280 CP80R protein Georgia 2007/1

SEQ ID NO: 281 D1133L peptide BA71
SEQ ID NO: 282 D1133L peptide BA71
SEQ ID NO: 283 D1133L peptide BA71
SEQ ID NO: 284 D1133L peptide BA71
SEQ ID NO: 285 D1133L peptide BA71
SEQ ID NO: 286 D1133L peptide BA71
SEQ ID NO: 287 D1133L peptide Georgia 2007/1
SEQ ID NO: 288 D1133L peptide Georgia 2007/1
SEQ ID NO: 289 D1133L peptide Georgia 2007/1, 1000-1008, 9
SEQ ID NO: 290 D1133L peptide Georgia 2007/1, 1111-1120, 10
SEQ ID NO: 291 D1133L peptide Georgia 2007/1, 114-124, 11
SEQ ID NO: 292 D1133L peptide Georgia 2007/1, 756-766, 11
SEQ ID NO: 293 D1133L peptide Georgia 2007/1, 782-790, 9
SEQ ID NO: 294 D1133L peptide Georgia 2007/1, 819-827, 9
SEQ ID NO: 295 D1133L protein BA71
SEQ ID NO: 296 D1133L protein BA71
SEQ ID NO: 297 D1133L protein Georgia 2007/1
SEQ ID NO: 298 D1133L protein Georgia2007/1
SEQ ID NO: 299 D133L peptide Georgia 2007/1
SEQ ID NO: 300 D133L peptide Georgia 2007/1
SEQ ID NO: 301 D133L peptide Georgia 2007/1
SEQ ID NO: 302 D133L peptide Georgia 2007/1
SEQ ID NO: 303 D205R peptide BA71
SEQ ID NO: 304 D205R peptide BA71
SEQ ID NO: 305 D205R peptide BA71
SEQ ID NO: 306 D205R peptide Georgia 2007/1, 1-19, 19
SEQ ID NO: 307 D205R peptide Georgia 2007/1, 2-11, 10
SEQ ID NO: 308 D205R peptide Georgia 2007/1, 5-13, 9
SEQ ID NO: 309 D205R peptide Georgia 2007/1, 7-17, 11
SEQ ID NO: 310 D205R peptide Georgia 2007/1, 9-16, 8
SEQ ID NO: 311 D205R protein BA71
SEQ ID NO: 312 D205R protein Georgia 2007/1
SEQ ID NO: 313 D250R peptide BA71
SEQ ID NO: 314 D250R peptide Georgia 2007/1, 168-178, 11
SEQ ID NO: 315 D250R peptide Georgia 2007/1, 176-184, 9
SEQ ID NO: 316 D250R peptide Georgia 2007/1, 32-48, 17
SEQ ID NO: 317 D250R peptide Georgia 2007/1, 3-46, 10
SEQ ID NO: 318 D250R protein BA71
SEQ ID NO: 319 D250R protein Georgia2007/1
SEQ ID NO: 320 D339L peptide BA71
SEQ ID NO: 321 D339L protein BA71
SEQ ID NO: 322 D339L protein Georgia2007/1
SEQ ID NO: 323 D345L peptide Georgia 2007/1, 125-133, 9
SEQ ID NO: 324 D345L protein Georgia 2007/1
SEQ ID NO: 325 DP238L peptide BA71
SEQ ID NO: 326 DP238L protein BA71
SEQ ID NO: 327 DP238L protein Georgia2007/1
SEQ ID NO: 328 DP96R peptide Georgia 2007/1, 46-55, 10
SEQ ID NO: 329 DP96R protein Georgia 2007/1
SEQ ID NO: 330 E111R peptide BA71
SEQ ID NO: 331 E111R protein BA71
SEQ ID NO: 332 E111R protein Georgia2007/1

SEQ ID NO: 333 E120R peptide BA71
SEQ ID NO: 334 E120R protein BA71
SEQ ID NO: 335 E120R protein Georgia2007/1
SEQ ID NO: 336 E146L peptide Georgia 2007/1, 52-64, 13
SEQ ID NO: 337 E146L peptide Georgia 2007/1, 55-64, 10
SEQ ID NO: 338 E146L protein Georgia 2007/1
SEQ ID NO: 339 E146L protein Georgia 2007/1
SEQ ID NO: 340 E183L peptide BA71
SEQ ID NO: 341 E183L protein BA71
SEQ ID NO: 342 E183L protein Georgia2007/1
SEQ ID NO: 343 E248R peptide BA71
SEQ ID NO: 344 E248R protein BA71
SEQ ID NO: 345 E248R protein Georgia2007/1
SEQ ID NO: 346 E301R peptide BA71
SEQ ID NO: 347 E301R peptide Georgia 2007/1, 290-2978
SEQ ID NO: 348 E301R protein BA71
SEQ ID NO: 349 E301R protein Georgia2007/1
SEQ ID NO: 350 E423R peptide Georgia 2007/1, 152-169, 18
SEQ ID NO: 351 E423R peptide Georgia 2007/1, 57-64, 8
SEQ ID NO: 352 E423R protein Georgia 2007/1
SEQ ID NO: 353 E66L peptide Georgia 2007/1, 18-27, 10
SEQ ID NO: 354 E66L peptide Georgia 2007/1, 4-13, 10
SEQ ID NO: 355 E66L protein BA71
SEQ ID NO: 356 E66L protein Georgia2007/1
SEQ ID NO: 357 EP1242L peptide BA71
SEQ ID NO: 358 EP1242L peptide BA71
SEQ ID NO: 359 EP1242L peptide Georgia 2007/1, 61-69, 9
SEQ ID NO: 360 EP1242L peptide Georgia 2007/1, 818-828, 11
SEQ ID NO: 361 EP1242L protein BA71
SEQ ID NO: 362 EP1242L protein Georgia 2007/1
SEQ ID NO: 363 EP152R peptide Georgia 2007/1, 40-60, 21
SEQ ID NO: 364 EP152R protein Georgia 2007/1
SEQ ID NO: 365 EP153R peptide Georgia 2007/1, 116-124, 9
SEQ ID NO: 366 EP153R protein Georgia 2007/1
SEQ ID NO: 367 EP296R peptide Georgia 2007/1, 235-245, 11
SEQ ID NO: 368 EP296R protein Georgia 2007/1
SEQ ID NO: 369 EP364R peptide BA71
SEQ ID NO: 370 EP364R protein BA71
SEQ ID NO: 371 EP364R protein Georgia2007/1
SEQ ID NO: 372 EP402R peptide Georgia 2007/1, 150-158, 9
SEQ ID NO: 373 EP402R peptide Georgia 2007/1, 189-210, 22
SEQ ID NO: 374 EP402R peptide Georgia 2007/1, 190-200, 11
SEQ ID NO: 375 EP402R peptide Georgia 2007/1, 192-202, 11
SEQ ID NO: 376 EP402R peptide Georgia 2007/1, 196-206, 11
SEQ ID NO: 377 EP402R peptide Georgia 2007/1, 279-287, 9
SEQ ID NO: 378 EP402R protein Georgia 2007/1
SEQ ID NO: 379 EP424R peptide BA71
SEQ ID NO: 380 EP424R peptide BA71
SEQ ID NO: 381 EP424R peptide Georgia 2007/1
SEQ ID NO: 382 EP424R peptide Georgia 2007/1
SEQ ID NO: 383 EP424R peptide Georgia 2007/1, 137-146, 10
SEQ ID NO: 384 EP424R peptide Georgia 2007/1, 140-156, 17
SEQ ID NO: 385 EP424R peptide Georgia 2007/1, 146-154, 9
SEQ ID NO: 386 EP424R peptide Georgia 2007/1, 215-225, 11
SEQ ID NO: 387 EP424R peptide Georgia 2007/1, 270-278, 9
SEQ ID NO: 388 EP424R protein BA71
SEQ ID NO: 389 EP424R protein Georgia2007/1
SEQ ID NO: 390 F1055L peptide Georgia 2007/1, 111-127, 17
SEQ ID NO: 391 F1055L peptide Georgia 2007/1, 112-121, 10
SEQ ID NO: 392 F1055L peptide Georgia 2007/1, 116-125, 10
SEQ ID NO: 393 F1055L peptide Georgia 2007/1, 527-535, 9
SEQ ID NO: 394 F1055L peptide Georgia 2007/1, 905-923, 19
SEQ ID NO: 395 F1055L protein Georgia 2007/1
SEQ ID NO: 396 F165R peptide Georgia 2007/1, 14-36, 23
SEQ ID NO: 397 F165R peptide Georgia 2007/1, 23-32, 10
SEQ ID NO: 398 F165R protein Georgia 2007/1
SEQ ID NO: 399 F317L peptide BA71
SEQ ID NO: 400 F317L peptide BA71
SEQ ID NO: 401 F317L peptide Georgia 2007/1, 246-256, 11
SEQ ID NO: 402 F317L peptide Georgia 2007/1, 248-256, 9
SEQ ID NO: 403 F317L peptide Georgia 2007/1, 4-13, 10
SEQ ID NO: 404 F317L protein BA71
SEQ ID NO: 405 F317L protein Georgia2007/1
SEQ ID NO: 406 F334L peptide BA71
SEQ ID NO: 407 F334L peptide Georgia 2007/1, 264-274, 11
SEQ ID NO: 408 F334L protein BA71
SEQ ID NO: 409 F334L protein Georgia 2007/1
SEQ ID NO: 410 F778R peptide Georgia 2007/1, 520-530, 11
SEQ ID NO: 411 F778R peptide Georgia 2007/1, 711-723, 13
SEQ ID NO: 412 F778R peptide Georgia 2007/1, 712-720, 9
SEQ ID NO: 413 F778R peptide Georgia 2007/1, 713-723, 11
SEQ ID NO: 414 F778R peptide Georgia 2007/1, 715-723, 9
SEQ ID NO: 415 F778R protein Georgia 2007/1
SEQ ID NO: 416 G1211R peptide BA71
SEQ ID NO: 417 G1211R peptide BA71
SEQ ID NO: 418 G1211R peptide BA71
SEQ ID NO: 419 G1211R peptide BA71
SEQ ID NO: 420 G1211R peptide Georgia 2007/1
SEQ ID NO: 421 G1211R peptide Georgia 2007/1
SEQ ID NO: 422 G1211R peptide Georgia 2007/1
SEQ ID NO: 423 G1211R peptide Georgia 2007/1
SEQ ID NO: 424 G1211R peptide Georgia 2007/1, 1043-1050, 8
SEQ ID NO: 425 G1211R peptide Georgia 2007/1, 146-157, 12
SEQ ID NO: 426 G1211R peptide Georgia 2007/1, 147-155, 9

SEQ ID NO: 427 G1211R peptide Georgia 2007/1, 206-215, 10
SEQ ID NO: 428 G1211R peptide Georgia 2007/1, 519-529, 11
SEQ ID NO: 429 G1211R peptide Georgia 2007/1, 698-707, 10
SEQ ID NO: 430 G1211R protein BA71
SEQ ID NO: 431 G1211R protein BA71
SEQ ID NO: 432 G1211R protein Georgia2007/1
SEQ ID NO: 433 G1211R protein Georgia2007/1
SEQ ID NO: 434 G1340L peptide BA71
SEQ ID NO: 435 G1340L peptide Georgia 2007/1, 229-236, 8
SEQ ID NO: 436 G1340L peptide Georgia 2007/1, 456-476, 21
SEQ ID NO: 437 G1340L peptide Georgia 2007/1, 463-473, 11
SEQ ID NO: 438 G1340L peptide Georgia 2007/1, 466-473, 8
SEQ ID NO: 439 G1340L peptide Georgia 2007/1, 534-550, 17
SEQ ID NO: 440 G1340L peptide Georgia 2007/1, 538-546, 9
SEQ ID NO: 441 G1340L peptide Georgia 2007/1, 540-548, 9
SEQ ID NO: 442 G1340L peptide Georgia 2007/1, 97-106, 10
SEQ ID NO: 443 G1340L protein BA71
SEQ ID NO: 444 G1340L protein Georgia 2007/1
SEQ ID NO: 445 H124R peptide Georgia 2007/1, 51-61, 11
SEQ ID NO: 446 H124R peptide Georgia 2007/1, 52-61, 10
SEQ ID NO: 447 H124R protein Georgia 2007/1
SEQ ID NO: 448 H233R peptide BA71
SEQ ID NO: 449 H233R peptide BA71
SEQ ID NO: 450 H233R protein BA71
SEQ ID NO: 451 H233R protein Georgia2007/1
SEQ ID NO: 452 H240R peptide Georgia 2007/1, 139-14810
SEQ ID NO: 453 H240R protein Georgia 2007/1
SEQ ID NO: 454 H339R peptide BA71
SEQ ID NO: 455 H339R peptide BA71
SEQ ID NO: 456 H339R peptide BA71
SEQ ID NO: 457 H339R peptide BA71
SEQ ID NO: 458 H339R peptide Georgia 2007/1
SEQ ID NO: 459 H339R peptide Georgia 2007/1
SEQ ID NO: 460 H339R peptide Georgia 2007/1
SEQ ID NO: 461 H339R peptide Georgia 2007/1
SEQ ID NO: 462 H339R peptide Georgia 2007/1
SEQ ID NO: 463 H339R peptide Georgia 2007/1, 200-209, 10
SEQ ID NO: 464 H339R peptide Georgia 2007/1, 84-92, 9
SEQ ID NO: 465 H339R peptide Georgia 2007/1, 87-95, 9
SEQ ID NO: 466 H339R protein BA71
SEQ ID NO: 467 H339R protein BA71
SEQ ID NO: 468 H339R protein Georgia2007/1
SEQ ID NO: 469 H339R protein Georgia2007/1
SEQ ID NO: 470 H359L peptide BA71
SEQ ID NO: 471 H359L protein BA71
SEQ ID NO: 472 H359L protein Georgia2007/1
SEQ ID NO: 473 I10L peptide Georgia 2007/1, 136-146, 11
SEQ ID NO: 474 I10L protein BA71
SEQ ID NO: 475 I10L protein Georgia 2007/1
SEQ ID NO: 476 I215L peptide Georgia 2007/1, 1-10, 10
SEQ ID NO: 477 I215L protein Georgia 2007/1
SEQ ID NO: 478 I226R peptide BA71
SEQ ID NO: 479 I226R peptide BA71
SEQ ID NO: 480 I226R peptide BA71
SEQ ID NO: 481 I226R peptide Georgia 2007/1
SEQ ID NO: 482 I226R peptide Georgia 2007/1
SEQ ID NO: 483 I226R peptide Georgia 2007/1
SEQ ID NO: 484 I226R peptide Georgia 2007/1
SEQ ID NO: 485 I226R peptide Georgia 2007/1, 150-157, 8
SEQ ID NO: 486 I226R peptide Georgia 2007/1, 51-58, 8
SEQ ID NO: 487 I226R protein BA71
SEQ ID NO: 488 I226R protein BA71
SEQ ID NO: 489 I226R protein Georgia2007/1
SEQ ID NO: 490 I226R protein Georgia2007/1
SEQ ID NO: 491 I243L peptide BA71
SEQ ID NO: 492 I243L peptide Georgia 2007/1, 81-89, 9
SEQ ID NO: 493 I243L protein BA71
SEQ ID NO: 494 I243L protein Georgia 2007/1
SEQ ID NO: 495 I267L peptide Georgia 2007/1, 246-269, 24
SEQ ID NO: 496 I267L peptide Georgia 2007/1, 252-260, 9
SEQ ID NO: 497 I267L peptide Georgia 2007/1, 66-76, 11
SEQ ID NO: 498 I267L protein Georgia 2007/1
SEQ ID NO: 499 I329L peptide Georgia 2007/1, 136-145, 10
SEQ ID NO: 500 I329L peptide Georgia 2007/1, 182-190, 9
SEQ ID NO: 501 T329L protein Georgia 2007/1
SEQ ID NO: 502 I73R peptide BA71
SEQ ID NO: 503 I73R protein BA71
SEQ ID NO: 504 I73R protein Georgia2007/1
SEQ ID NO: 505 I7L peptide Georgia 2007/1, 28-37, 10
SEQ ID NO: 506 I7L protein Georgia 2007/1
SEQ ID NO: 507 I8L peptide Georgia 2007/1, 88-95, 8
SEQ ID NO: 508 I8L protein BA71
SEQ ID NO: 509 I8L protein Georgia2007/1
SEQ ID NO: 510 I9R peptide BA7
SEQ ID NO: 511 I9R peptide Georgia 2007/1, 63-73, 11
SEQ ID NO: 512 I9R protein BA71
SEQ ID NO: 513 I9R protein Georgia 2007/1
SEQ ID NO: 514 K145R peptide BA71
SEQ ID NO: 515 K145R peptide BA71
SEQ ID NO: 516 K145R peptide BA71
SEQ ID NO: 517 K145R peptide BA71
SEQ ID NO: 518 K145R peptide Georgia 2007/1
SEQ ID NO: 519 K145R peptide Georgia 2007/1
SEQ ID NO: 520 K145R peptide Georgia 2007/1
SEQ ID NO: 521 K145R peptide Georgia 2007/1
SEQ ID NO: 522 K145R peptide Georgia 2007/1, 43-58, 16
SEQ ID NO: 523 K145R peptide Georgia 2007/1, 48-57, 10
SEQ ID NO: 524 K145R protein BA71
SEQ ID NO: 525 K145R protein BA71
SEQ ID NO: 526 K145R protein Georgia 2007/1
SEQ ID NO: 527 K145R protein Georgia2007/1
SEQ ID NO: 528 K205R peptide Georgia 2007/1, 38-48, 11
SEQ ID NO: 529 K205R protein Georgia 2007/1
SEQ ID NO: 530 K421R peptide Georgia 2007/1, 69-86, 18

SEQ ID NO: 531 K421R peptide Georgia 2007/1, 78-86, 9
SEQ ID NO: 532 K421R protein Georgia 2007/1
SEQ ID NO: 533 K78R peptide Georgia 2007/1, 36-44, 9
SEQ ID NO: 534 K78R protein Georgia 2007/1
SEQ ID NO: 535 L11L protein BA71
SEQ ID NO: 536 L11L protein Georgia2007/1
SEQ ID NO: 537 L60L protein BA71
SEQ ID NO: 538 L60L protein Georgia2007/1
SEQ ID NO: 539 M1249L peptide BA71
SEQ ID NO: 540 M1249L peptide BA71
SEQ ID NO: 541 M1249L peptide BA71
SEQ ID NO: 542 M1249L peptide Georgia 2007/1
SEQ ID NO: 543 M1249L peptide Georgia 2007/1
SEQ ID NO: 544 M1249L peptide Georgia 2007/1
SEQ ID NO: 545 M1249L peptide Georgia 2007/1, 1068-1078, 11
SEQ ID NO: 546 M1249L peptide Georgia 2007/1, 1130-1140, 11
SEQ ID NO: 547 M1249L peptide Georgia 2007/1, 1130-1144, 15
SEQ ID NO: 548 M1249L peptide Georgia 2007/1, 266-275, 10
SEQ ID NO: 549 M1249L peptide Georgia 2007/1, 266-292, 27
SEQ ID NO: 550 M1249L peptide Georgia 2007/1, 270-279, 10
SEQ ID NO: 551 M1249L peptide Georgia 2007/1, 276-284, 9
SEQ ID NO: 552 M1249L peptide Georgia 2007/1, 282-291, 10
SEQ ID NO: 553 M1249L peptide Georgia 2007/1, 555-564, 10
SEQ ID NO: 554 M1249L peptide Georgia 2007/1, 583-590, 8
SEQ ID NO: 555 M1249L peptide Georgia 2007/1, 772-782, 11
SEQ ID NO: 556 M1249L peptide Georgia 2007/1, 778-789, 12
SEQ ID NO: 557 M1249L peptide Georgia 2007/1, 780-788, 9
SEQ ID NO: 558 M1249L peptide Georgia 2007/1, 917-933, 17
SEQ ID NO: 559 M1249L peptide Georgia 2007/1, 922-932, 11
SEQ ID NO: 560 M1249L peptide Georgia 2007/1, 923-933, 11
SEQ ID NO: 561 M1249L protein BA71
SEQ ID NO: 562 M1249L protein Georgia2007/1
SEQ ID NO: 563 M448R peptide BA71
SEQ ID NO: 564 M448R peptide Georgia 2007/1, 146-156, 11
SEQ ID NO: 565 M448R peptide Georgia 2007/1, 248-257, 10
SEQ ID NO: 566 M448R protein BA71
SEQ ID NO: 567 M448R protein BA71
SEQ ID NO: 568 M448R protein Georgia 2007/1
SEQ ID NO: 569 M448R protein Georgia 2007/1
SEQ ID NO: 570 MGF_100-1L peptide Georgia 2007/1, 68-86, 19
SEQ ID NO: 571 MGF_100-1L peptide Georgia 2007/1, 68-86, 19
SEQ ID NO: 572 MGF_100-1L protein Georgia 2007/1
SEQ ID NO: 573 MGF_100-1L protein Georgia 2007/1
SEQ ID NO: 574 MGF_100-1R peptide Georgia 2007/1, 103-113, 11
SEQ ID NO: 575 MGF_100-1R peptide Georgia 2007/1, 97-115, 19
SEQ ID NO: 576 MGF_100-1R protein Georgia 2007/1
SEQ ID NO: 577 MGF_110-11L peptide Georgia 2007/1, 84-94, 11
SEQ ID NO: 578 MGF_110-11L protein Georgia 2007/1
SEQ ID NO: 579 MGF_110-12L peptide Georgia 2007/1, 19-29, 11
SEQ ID NO: 580 MGF_110-12L protein Georgia 2007/1
SEQ ID NO: 581 MGF_110-14L peptide Georgia 2007/1, 72-82, 11
SEQ ID NO: 582 MGF_110-14L protein Georgia 2007/1
SEQ ID NO: 583 MGF_110-1L peptide Georgia 2007/1, 10-19, 10
SEQ ID NO: 584 MGF_110-1L peptide Georgia 2007/1, 77-87, 11
SEQ ID NO: 585 MGF_110-1L protein Georgia 2007/1
SEQ ID NO: 586 MGF_110-6L peptide BA71
SEQ ID NO: 587 MGF_110-6L protein BA71
SEQ ID NO: 588 MGF_110-6L protein Georgia2007/1
SEQ ID NO: 589 MGF_110-8L peptide Georgia 2007/1, 81-91, 11
SEQ ID NO: 590 MGF_110-8L protein Georgia 2007/1
SEQ ID NO: 591 MGF_110-9L peptide Georgia 2007/1, 101-110, 10
SEQ ID NO: 592 MGF_110-9L peptide Georgia 2007/1, 101-118, 18
SEQ ID NO: 593 MGF_110-9L peptide Georgia 2007/1, 138-147, 10
SEQ ID NO: 594 MGF_110-9L peptide Georgia 2007/1, 140-147, 8
SEQ ID NO: 595 MGF_110-9L peptide Georgia 2007/1, 150-167, 18
SEQ ID NO: 596 MGF_110-9L peptide Georgia 2007/1, 157-167, 11
SEQ ID NO: 597 MGF_110-9L peptide Georgia 2007/1, 252-262, 11
SEQ ID NO: 598 MGF_110-9L protein Georgia 2007/1
SEQ ID NO: 599 MGF_300-1L peptide Georgia 2007/1, 172-190, 19
SEQ ID NO: 600 MGF_300-1L peptide Georgia 2007/1, 179-189, 11
SEQ ID NO: 601 MGF_300-1L peptide Georgia 2007/1, 78-87, 10
SEQ ID NO: 602 MGF_300-1L protein Georgia 2007/1
SEQ ID NO: 603 MGF_300-4L peptide Georgia 2007/1, 163-174, 12
SEQ ID NO: 604 MGF_300-4L peptide Georgia 2007/1, 165-172, 8
SEQ ID NO: 605 MGF_300-4L protein Georgia 2007/1
SEQ ID NO: 606 MGF_360-10L peptide BA71
SEQ ID NO: 607 MGF_360-10L peptide Georgia 2007/1, 136-146, 11
SEQ ID NO: 608 MGF_360-10L peptide Georgia 2007/1, 195-206, 12
SEQ ID NO: 609 MGF_360-10L peptide Georgia 2007/1, 266-274, 9
SEQ ID NO: 610 MGF_360-10L protein BA71
SEQ ID NO: 611 MGF_360-10L protein Georgia 2007/1
SEQ ID NO: 612 MGF_360-11L peptide Georgia 2007/1, 221-229, 9
SEQ ID NO: 613 MGF_360-11L peptide Georgia 2007/1, 240-260, 21
SEQ ID NO: 614 MGF_360-11L peptide Georgia 2007/1, 247-257, 11
SEQ ID NO: 615 MGF_360-11L protein Georgia 2007/1

SEQ ID NO: 616 MGF_360-12L peptide Georgia 2007/1, 165-186, 22
SEQ ID NO: 617 MGF_360-12L peptide Georgia 2007/1, 174-182, 9
SEQ ID NO: 618 MGF_360-12L peptide Georgia 2007/1, 174-184, 11
SEQ ID NO: 619 MGF_360-12L peptide Georgia 2007/1, 266-274, 9
SEQ ID NO: 620 MGF_360-12L protein Georgia 2007/1
SEQ ID NO: 621 MGF_360-13L peptide Georgia 2007/1, 271-281, 11
SEQ ID NO: 622 MGF_360-13L protein Georgia 2007/1
SEQ ID NO: 623 MGF_360-14L peptide Georgia 2007/1, 195-206, 12
SEQ ID NO: 624 MGF_360-14L protein Georgia 2007/1
SEQ ID NO: 625 MGF_360-15R peptide Georgia 2007/1, 16-25, 10
SEQ ID NO: 626 MGF_360-15R peptide Georgia 2007/1, 37-46, 10
SEQ ID NO: 627 MGF_360-15R peptide Georgia 2007/1, 71-81, 11
SEQ ID NO: 628 MGF_360-15R protein Georgia 2007/1
SEQ ID NO: 629 MGF_360-18R peptide Georgia 2007/1, 159-167, 9
SEQ ID NO: 630 MGF_360-18R peptide Georgia 2007/1, 93-100, 8
SEQ ID NO: 631 MGF_360-18R protein Georgia 2007/1
SEQ ID NO: 632 MGF_360-1L peptide Georgia 2007/1, 184-192, 9
SEQ ID NO: 633 MGF_360-1L peptide Georgia 2007/1, 188-198, 11
SEQ ID NO: 634 MGF_360-1L peptide Georgia 2007/1, 192-200, 9
SEQ ID NO: 635 MGF_360-1L peptide Georgia 2007/1, 195-203, 9
SEQ ID NO: 636 MGF_360-1L peptide Georgia 2007/1, 244-254, 11
SEQ ID NO: 637 MGF_360-1L protein Georgia 2007/1
SEQ ID NO: 638 MGF_360-21R peptide Georgia 2007/1, 176-185, 10
SEQ ID NO: 639 MGF_360-21R peptide Georgia 2007/1, 177-187, 11
SEQ ID NO: 640 MGF_360-21R peptide Georgia 2007/1, 185-193, 9
SEQ ID NO: 641 MGF_360-21R peptide Georgia 2007/1, 189-199, 11
SEQ ID NO: 642 MGF_360-21R peptide Georgia 2007/1, 197-207, 11
SEQ ID NO: 643 MGF_360-21R peptide Georgia 2007/1, 246-256, 11
SEQ ID NO: 644 MGF_360-21R protein Georgia 2007/1
SEQ ID NO: 645 MGF_360-2L peptide Georgia 2007/1, 191-198, 8
SEQ ID NO: 646 MGF_360-2L peptide Georgia 2007/1, 191-207, 17
SEQ ID NO: 647 MGF_360-2L peptide Georgia 2007/1, 196-203, 8
SEQ ID NO: 648 MGF_360-2L protein Georgia 2007/1
SEQ ID NO: 649 MGF_360-3L peptide Georgia 2007/1, 167-186, 20
SEQ ID NO: 650 MGF_360-3L protein Georgia 2007/1
SEQ ID NO: 651 MGF_360-4L peptide Georgia 2007/1, 162-170, 9
SEQ ID NO: 652 MGF_360-4L peptide Georgia 2007/1, 363-372, 10
SEQ ID NO: 653 MGF_360-4L protein Georgia 2007/1
SEQ ID NO: 654 MGF_360-6L peptide Georgia 2007/1, 150-162, 13
SEQ ID NO: 655 MGF_360-6L peptide Georgia 2007/1, 356-364, 9
SEQ ID NO: 656 MGF_360-6L protein Georgia 2007/1
SEQ ID NO: 657 MGF_360-8L peptide BA71
SEQ ID NO: 658 MGF_360-8L peptide BA71
SEQ ID NO: 659 MGF_360-8L peptide Georgia 2007/1, 189-198, 10
SEQ ID NO: 660 MGF_360-8L peptide Georgia 2007/1, 195-206, 12
SEQ ID NO: 661 MGF_360-8L peptide Georgia 2007/1, 196-206, 11
SEQ ID NO: 662 MGF_360-8L peptide Georgia 2007/1, 80-90, 11
SEQ ID NO: 663 MGF_360-8L protein BA71
SEQ ID NO: 664 MGF_360-8L protein Georgia 2007/1
SEQ ID NO: 665 MGF_360-9L peptide Georgia 2007/1, 193-203, 11
SEQ ID NO: 666 MGF_360-9L peptide Georgia 2007/1, 257-267, 11
SEQ ID NO: 667 MGF_360-9L peptide Georgia 2007/1, 257-269, 13
SEQ ID NO: 668 MGF_360-9L peptide Georgia 2007/1, 259-267, 9
SEQ ID NO: 669 MGF_360-9L peptide Georgia 2007/1, 264-274, 11
SEQ ID NO: 670 MGF_360-9L peptide Georgia 2007/1, 300-307, 8
SEQ ID NO: 671 MGF_360-9L protein Georgia 2007/1
SEQ ID NO: 672 MGF_505-10R peptide Georgia 2007/1, 499-509, 11
SEQ ID NO: 673 MGF_505-10R protein Georgia 2007/1
SEQ ID NO: 674 MGF_505-11L peptide Georgia 2007/1, 111-129, 19
SEQ ID NO: 675 MGF_505-11L peptide Georgia 2007/1, 142-149, 8
SEQ ID NO: 676 MGF_505-11L peptide Georgia 2007/1, 230-247, 18
SEQ ID NO: 677 MGF_505-11L peptide Georgia 2007/1, 231-241, 11
SEQ ID NO: 678 MGF_505-11L peptide Georgia 2007/1, 308-327, 20
SEQ ID NO: 679 MGF_505-11L peptide Georgia 2007/1, 312-322, 11
SEQ ID NO: 680 MGF_505-11L peptide Georgia 2007/1, 315-322, 8
SEQ ID NO: 681 MGF_505-11L peptide Georgia 2007/1, 319-327, 9
SEQ ID NO: 682 MGF_505-11L peptide Georgia 2007/1, 528-538, 11
SEQ ID NO: 683 MGF_505-11L protein Georgia 2007/1
SEQ ID NO: 684 MGF_505-1R peptide BA71
SEQ ID NO: 685 MGF_505-1R peptide BA71
SEQ ID NO: 686 MGF_505-1R peptide Georgia 2007/1
SEQ ID NO: 687 MGF_505-1R peptide Georgia 2007/1
SEQ ID NO: 688 MGF_505-1R peptide Georgia 2007/1, 270-280, 11
SEQ ID NO: 689 MGF_505-1R peptide Georgia 2007/1, 427-437, 11
SEQ ID NO: 690 MGF_505-1R peptide Georgia 2007/1, 76-85, 10
SEQ ID NO: 691 MGF_505-1R protein BA71
SEQ ID NO: 692 MGF_505-1R protein Georgia2007/1
SEQ ID NO: 693 MGF_505-2R peptide BA71
SEQ ID NO: 694 MGF_505-2R peptide Georgia 2007/1, 160-168, 9

SEQ ID NO: 695 MGF_505-2R peptide Georgia 2007/1, 197-206, 10
SEQ ID NO: 696 MGF_505-2R peptide Georgia 2007/1, 311-319, 9
SEQ ID NO: 697 MGF_505-2R protein BA71
SEQ ID NO: 698 MGF_505-2R protein Georgia 2007/1
SEQ ID NO: 699 MGF_505-3R peptide BA71
SEQ ID NO: 700 MGF_505-3R peptide Georgia 2007/1, 75-85, 11
SEQ ID NO: 701 MGF_505-3R peptide Georgia 2007/1, 86-95, 10
SEQ ID NO: 702 MGF_505-3R protein BA71
SEQ ID NO: 703 MGF_505-3R protein Georgia 2007/1
SEQ ID NO: 704 MGF_505-4R peptide Georgia 2007/1, 204-212, 9
SEQ ID NO: 705 MGF_505-4R peptide Georgia 2007/1, 352-362, 11
SEQ ID NO: 706 MGF_505-4R protein Georgia 2007/1
SEQ ID NO: 707 MGF_505-5R peptide BA71
SEQ ID NO: 708 MGF_505-5R peptide Georgia 2007/1, 200-208, 9
SEQ ID NO: 709 MGF_505-5R peptide Georgia 2007/1, 204-212, 9
SEQ ID NO: 710 MGF_505-5R peptide Georgia 2007/1, 346-356, 11
SEQ ID NO: 711 MGF_505-5R peptide Georgia 2007/1, 354-366, 13
SEQ ID NO: 712 MGF_505-5R protein BA71
SEQ ID NO: 713 MGF_505-5R protein Georgia 2007/1
SEQ ID NO: 714 MGF_505-6R peptide Georgia 2007/1, 102-111, 10
SEQ ID NO: 715 MGF_505-6R peptide Georgia 2007/1, 427-435, 9
SEQ ID NO: 716 MGF_505-6R protein Georgia 2007/1
SEQ ID NO: 717 MGF_505-8R peptide BA71
SEQ ID NO: 718 MGF_505-8R peptide BA71
SEQ ID NO: 719 MGF_505-7R peptide Georgia 2007/1
SEQ ID NO: 720 MGF_505-7R peptide Georgia 2007/1
SEQ ID NO: 721 MGF_505-7R peptide Georgia 2007/1, 102-111, 10
SEQ ID NO: 722 MGF_505-8R protein BA71 (A469R)
SEQ ID NO: 723 MGF_505-8R protein BA71 (A469R)
SEQ ID NO: 724 MGF_505-7R protein Georgia 2007/1
SEQ ID NO: 725 MGF_505-7R protein Georgia 2007/1
SEQ ID NO: 726 MGF_505-9R peptide BA71
SEQ ID NO: 727 MGF_505-9R peptide Georgia 2007/1
SEQ ID NO: 728 MGF_505-9R peptide Georgia 2007/1
SEQ ID NO: 729 MGF_505-9R peptide Georgia 2007/1
SEQ ID NO: 730 MGF_505-9R peptide Georgia 2007/1
SEQ ID NO: 731 MGF_505-9R peptide Georgia 2007/1, 355-355-363, 9
SEQ ID NO: 732 MGF_505-9R protein BA71
SEQ ID NO: 733 MGF_505-9R protein Georgia 2007/1
SEQ ID NO: 734 MGF110-12L protein BA71
SEQ ID NO: 735 MGF110-12L protein Georgia2007/1
SEQ ID NO: 736 MGF110-13L protein BA71
SEQ ID NO: 737 MGF110-13L protein Georgia2007/1
SEQ ID NO: 738 MGF110-14L protein BA71
SEQ ID NO: 739 MGF110-14L protein Georgia2007/1
SEQ ID NO: 740 MGF110-1L protein BA71
SEQ ID NO: 741 MGF110-1L protein Georgia2007/1
SEQ ID NO: 742 MGF300-1L protein BA71
SEQ ID NO: 743 MGF300-1L protein Georgia2007/1
SEQ ID NO: 744 MGF300-4L protein BA71
SEQ ID NO: 745 MGF300-4L protein Georgia2007/1
SEQ ID NO: 746 MGF360-10L protein BA71
SEQ ID NO: 747 MGF360-10L protein Georgia2007/1
SEQ ID NO: 748 MGF360-11L protein BA71
SEQ ID NO: 749 MGF360-11L protein Georgia2007/1
SEQ ID NO: 750 MGF360-12L protein BA71
SEQ ID NO: 751 MGF360-12L protein Georgia2007/1
SEQ ID NO: 752 MGF360-14L protein BA71
SEQ ID NO: 753 MGF360-14L protein Georgia2007/1
SEQ ID NO: 754 MGF360-15R protein BA71
SEQ ID NO: 755 MGF360-15R protein Georgia2007/1
SEQ ID NO: 756 MGF360-2L protein BA71
SEQ ID NO: 757 MGF360-2L protein Georgia2007/1
SEQ ID NO: 758 MGF360-3L protein BA71
SEQ ID NO: 759 MGF360-3L protein Georgia2007/1
SEQ ID NO: 760 MGF360-4L protein BA71
SEQ ID NO: 761 MGF360-4L protein Georgia2007/1
SEQ ID NO: 762 MGF360-6L protein BA71
SEQ ID NO: 763 MGF360-6L protein Georgia2007/1
SEQ ID NO: 764 MGF360-8L protein BA71
SEQ ID NO: 765 MGF360-8L protein Georgia2007/1
SEQ ID NO: 766 MGF505-2R protein BA71
SEQ ID NO: 767 MGF505-2R protein Georgia2007/1
SEQ ID NO: 768 MGF505-4R protein BA71
SEQ ID NO: 769 MGF505-4R protein Georgia2007/1
SEQ ID NO: 770 MGF505-7R protein BA71 (A528R)
SEQ ID NO: 771 MGF505-6R protein Georgia2007/1
SEQ ID NO: 772 MGF505-8R protein BA71
SEQ ID NO: 773 MGF505-8R protein BA71
SEQ ID NO: 774 MGF505-7R protein Georgia2007/1
SEQ ID NO: 775 MGF505-7R protein Georgia2007/1
SEQ ID NO: 776 NP1450L peptide BA71
SEQ ID NO: 777 NP1450L peptide Georgia 2007/1, 1008-1016, 9
SEQ ID NO: 778 NP1450L peptide Georgia 2007/1, 102-110, 9
SEQ ID NO: 779 NP1450L peptide Georgia 2007/1, 1032-1040, 9
SEQ ID NO: 780 NP1450L peptide Georgia 2007/1, 1136-1146, 11
SEQ ID NO: 781 NP1450L peptide Georgia 2007/1, 1327-1336, 10
SEQ ID NO: 782 NP1450L peptide Georgia 2007/1, 575-587, 13
SEQ ID NO: 783 NP1450L peptide Georgia 2007/1, 645-653, 9
SEQ ID NO: 784 NP1450L peptide Georgia 2007/1, 776-784, 9
SEQ ID NO: 785 NP1450L protein BA71
SEQ ID NO: 786 NP1450L protein Georgia 2007/1
SEQ ID NO: 787 NP419L peptide BA71
SEQ ID NO: 788 NP419L peptide Georgia 2007/1, 355-363, 9
SEQ ID NO: 789 NP419L peptide Georgia 2007/1, 363-378, 16
SEQ ID NO: 790 NP419L protein BA71
SEQ ID NO: 791 NP419L protein Georgia 2007/1
SEQ ID NO: 792 NP868R peptide Georgia 2007/1, 176-186, 11
SEQ ID NO: 793 NP868R peptide Georgia 2007/1, 184-192, 9
SEQ ID NO: 794 NP868R peptide Georgia 2007/1, 495-515, 21
SEQ ID NO: 795 NP868R peptide Georgia 2007/1, 570-579, 10
SEQ ID NO: 796 NP868R protein Georgia 2007/1
SEQ ID NO: 797 O174L peptide Georgia 2007/1, 97-105, 9
SEQ ID NO: 798 O174L protein Georgia 2007/1

SEQ ID NO: 799 O61R peptide Georgia 2007/1, 23-38, 16
SEQ ID NO: 800 O61R protein Georgia 2007/1
SEQ ID NO: 801 P1192R peptide BA71
SEQ ID NO: 802 P1192R peptide BA71
SEQ ID NO: 803 P1192R peptide BA71
SEQ ID NO: 804 P1192R peptide Georgia 2007/1
SEQ ID NO: 805 P1192R peptide Georgia 2007/1
SEQ ID NO: 806 P1192R peptide Georgia 2007/1, 1023-1040, 18
SEQ ID NO: 807 P1192R peptide Georgia 2007/1, 1026-1033, 8
SEQ ID NO: 808 P1192R peptide Georgia 2007/1, 1031-1038, 8
SEQ ID NO: 809 P1192R peptide Georgia 2007/1, 1049-1056, 8
SEQ ID NO: 810 P1192R peptide Georgia 2007/1, 1057-1067, 11
SEQ ID NO: 811 P1192R peptide Georgia 2007/1, 189-197, 9
SEQ ID NO: 812 P1192R peptide Georgia 2007/1, 372-382, 11
SEQ ID NO: 813 P1192R peptide Georgia 2007/1, 584-592, 9
SEQ ID NO: 814 P1192R peptide Georgia 2007/1, 605-614, 10
SEQ ID NO: 815 P1192R peptide Georgia 2007/1, 744-751, 8
SEQ ID NO: 816 P1192R protein BA71
SEQ ID NO: 817 P1192R protein Georgia 2007/1
SEQ ID NO: 818 Q706L peptide BA71
SEQ ID NO: 819 Q706L peptide Georgia 2007/1, 137-144, 8
SEQ ID NO: 820 Q706L peptide Georgia 2007/1, 36-46, 11
SEQ ID NO: 821 Q706L peptide Georgia 2007/1, 47-55, 9
SEQ ID NO: 822 Q706L protein BA71
SEQ ID NO: 823 Q706L protein Georgia 2007/1
SEQ ID NO: 824 QP383R peptide BA71
SEQ ID NO: 825 QP383R peptide BA71
SEQ ID NO: 826 QP383R peptide BA71
SEQ ID NO: 827 QP383R protein BA71
SEQ ID NO: 828 QP383R protein Georgia2007/1
SEQ ID NO: 829 QP509L peptide Georgia 2007/1, 384-402, 19
SEQ ID NO: 830 QP509L peptide Georgia 2007/1, 392-400, 9
SEQ ID NO: 831 QP509L peptide Georgia 2007/1, 51-63, 13
SEQ ID NO: 832 QP509L peptide Georgia 2007/1, 76-85, 10
SEQ ID NO: 833 QP509L protein Georgia 2007/1
SEQ ID NO: 834 R298L 1 protein Georgia 2007/1
SEQ ID NO: 835 R298L peptide Georgia 2007/1, 189-199, 11
SEQ ID NO: 836 R298L peptide Georgia 2007/1, 189-214, 26
SEQ ID NO: 837 R298L peptide Georgia 2007/1, 193-201, 9
SEQ ID NO: 838 R298L peptide Georgia 2007/1, 193-203, 11
SEQ ID NO: 839 R298L peptide Georgia 2007/1, 198-207, 10
SEQ ID NO: 840 R298L peptide Georgia 2007/1, 205-214, 10
SEQ ID NO: 841 R298L peptide Georgia 2007/1, 220-230, 11
SEQ ID NO: 842 R298L peptide Georgia 2007/1, 99-108, 10
SEQ ID NO: 843 R298L protein Georgia 2007/1
SEQ ID NO: 844 S183L peptide Georgia 2007/1, 10-18, 9
SEQ ID NO: 845 S183L peptide Georgia 2007/1, 128-136, 9
SEQ ID NO: 846 S183L protein Georgia 2007/1
SEQ ID NO: 847 S273R peptide Georgia 2007/1, 113-122, 10
SEQ ID NO: 848 S273R peptide Georgia 2007/1, 96-104, 9
SEQ ID NO: 849 S273R protein Georgia 2007/1
SEQ ID NO: 850 X69R peptide Georgia 2007/1, 19-29, 11
SEQ ID NO: 851 X69R peptide Georgia 2007/1, 47-54, 8
SEQ ID NO: 852 X69R protein Georgia 2007/1
SEQ ID NO: 853 A240L protein BA71
SEQ ID NO: 854 A240L protein Georgia 2007/1
SEQ ID NO: 855 Multiepitope-I (ME-I) construct
SEQ ID NO: 856 Multiepitope-II (ME-II) construct
SEQ ID NO: 857 MGF505-7R protein Georgia 2007/1
SEQ ID NO: 858 M448R protein Georgia 2007/1
SEQ ID NO: 859 D1133L protein Georgia 2007/1
SEQ ID NO: 860 A240L protein Georgia 2007/1
SEQ ID NO: 861 CP312R protein Georgia 2007/1
SEQ ID NO: 862 D117L protein Georgia 2007/1
SEQ ID NO: 863 D117L protein Georgia 2007/1
SEQ ID NO: 864 D117L protein BA71
SEQ ID NO: 865 D117L protein BA71
SEQ ID NO: 866 B475L protein Georgia 2007/1
SEQ ID NO: 867 B475L protein BA71
SEQ ID NO: 868 CP2475L (p37) protein Georgia 2007/1
SEQ ID NO: 869 CP2475L (p37) protein BA71
SEQ ID NO: 870 CP2475L (p150) protein Georgia 2007/1
SEQ ID NO: 871 CP2475L (p150) protein BA71
SEQ ID NO: 872 M1249L protein Georgia 2007/1
SEQ ID NO: 873 M1249L protein BA71
SEQ ID NO: 874 MGF-505-9R protein Georgia 2007/1
SEQ ID NO: 875 MGF-505-9R protein BA71
SEQ ID NO: 876 P1192R protein Georgia 2007/1
SEQ ID NO: 877 P1192R protein BA71
SEQ ID NO: 878 MGF-505-1R protein Georgia 2007/1
SEQ ID NO: 879 MGF-505-1R protein BA71
SEQ ID NO: 880 MGF-505-3R protein Georgia 2007/1
SEQ ID NO: 881 MGF-505-3R protein BA71
SEQ ID NO: 882 EP424R protein Georgia 2007/1
SEQ ID NO: 883 EP424R protein BA71
SEQ ID NO: 884 C475L protein Georgia 2007/1
SEQ ID NO: 885 C475L protein BA71
SEQ ID NO: 886 B602L protein Georgia 2007/1
SEQ ID NO: 887 B602L protein BA71
SEQ ID NO: 888 CP530R protein Georgia 2007/1
SEQ ID NO: 889 CP530R protein BA71
SEQ ID NO: 890 D339L protein Georgia 2007/1
SEQ ID NO: 891 D339L protein BA71
SEQ ID NO: 892 I234L protein Georgia 2007/1
SEQ ID NO: 893 I234L protein BA71
SEQ ID NO: 894 I73R protein Georgia 2007/1
SEQ ID NO: 895 I73R protein BA71
SEQ ID NO: 896 DP238L protein Georgia 2007/1
SEQ ID NO: 897 DP238L protein BA71
SEQ ID NO: 898 I9R protein Georgia 2007/1
SEQ ID NO: 899 I9R protein BA71

SEQ ID NO: 900 CP312R peptide Georgia 2007/1
SEQ ID NO: 901 CP312R peptide Georgia 2007/1

EXAMPLES

Example 1—Material and Methods

Cells and Viruses

Porcine alveolar macrophages: Porcine alveolar macrophages (PAMs) from healthy conventional pigs (Landrace× Large White) were obtained by lung lavage with PBS 1× supplemented with 1 µg/ml gentamicin (Sigma-Aldrich). The PBS solution was administered through the trachea using a sterile funnel, pulmonary lobes were gently massaged for 5 minutes, and the volume was collected into a sterile container. After three washes with 250 ml of PBS solution, the recovered fluid was centrifuged at 400×g for 10 minutes. Cell pellets were washed once with PBS 1×, and suspended in RPMI 1640 medium (Gibco) supplemented with 2 mM L-glutamine (Invitrogen), 100 IU/mL of penicillin (Invitrogen), 100 µg/ml of streptomycin (Invitrogen) and 10% heat-inactivated porcine serum (Gibco). PAMs were maintained in cell culture at 37° C., 5% CO2, or were frozen in FBS 10% DMSO (Sigma-Aldrich) and stored at −150° C.

Primary pig fibroblasts: Establishment of primary fibroblasts cultures was performed from a 2 cm² piece of ear tissue sample following previously described protocols. Briefly, tissue was cut into small sections and incubated overnight at 37° C. with a 0.5% trypsin solution in PBS. Cells were filtered through a 40 µm cell strainer (Corning) to discard the remaining tissue lumps, and centrifuged at 150×g for 10 minutes. Supernatant was discarded and cells were resuspended in complete DMEM supplemented with 10% FBS (HyClone, GE HealthCare), 100 IU/ml of penicillin (Invitrogen), 100 µg/ml of streptomycin (Invitrogen), 2 mM L-glutamine (Invitrogen), and 50 IU/ml Nystatin (Sigma-Aldrich). Primary fibroblasts were seeded in T-flasks, and maintained their viability after multiple serial passages. Cell passaging was performed following standard protocols by trypsinization.

Peripheral blood mononuclear cells (PBMCs): Porcine PBMCs were isolated from whole blood using Histopaque-1077 (Sigma-Aldrich) density gradient solution. Blood samples drawn from the jugular vein of pigs into 10 ml EDTA vacutainer tubes (Becton Dickinson), were diluted 1:1 in PBS. Diluted blood was gently layered on the top of a 10 ml Histopaque-1077 in a 50 ml conical tube and centrifuged at 400×g for 30 minutes at 20° C., without acceleration nor break. The whitish buffy coat formed in the interphase containing the mononuclear cells was aspirated and transferred to a clean 15 ml conical tube, filled with PBS, and centrifuged at 400×g for 10 minutes at 20° C. Supernatant was discarded, and red blood cells were lysed by hypotonic shock using 9 ml sterile distilled water for 30 seconds followed by addition of 3.5 mL of 3.5% NaCl solution. Afterwards cells were centrifuged 400×g for 10 minutes at 20° C., washed with PBS, and suspended in RPMI 1640 medium (Gibco) supplemented with 2 mM L-glutamine (Invitrogen), 100 IU/mL of penicillin (Invitrogen), 100 µg/ml of streptomycin (Invitrogen) and 10% heat-inactivated FBS (HyClone, GE HealthCare). For their use in the ELISpot assays, 50 µM β-mercaptoethanol (Sigma-Aldrich) was added to the medium to help maintain a reducing environment.

Rabbit kidney RK13 cells: Rabbit kidney epithelial RK13 cell line (ATCC CCL-37) was cultured at 37° C., 5% $CO_2$ in DMEM supplemented with 10% FBS (HyClone, GE HealthCare), 100 IU/ml of penicillin (Invitrogen), 100 µg/ml of streptomycin (Invitrogen), and 2 mM L-glutamine (Invitrogen).

African swine fever viruses: Two different ASFV virulent field isolates were used: BA71 (Rodriguez J M et al., PLoS One 2015; 10(11): e0142889; obtained from the spleen of an infected animal in Badajoz, Spain in 1971; GenBank accession number KP055815) and Georgia2007/1 (Chapman D A et al., Emerg Infect Dis. 2011, 17(4): 599-605; obtained from tissue samples from pigs submitted to the World Organisation for Animal Health Reference Laboratory at the Institute for Animal Health, Pirbright, UK, on Jun. 4, 2007; GenBank accession number FR682468). The live attenuated BA71ΔCD2 virus, a deletion mutant from BA71 lacking the CD2v gene (EP402R) was previously obtained (WO 2015/091322).

Multiparametric in silico predictions of $CD8^+$ T-cell epitopes: Georgia2007/1 proteome was retrieved from Uniprot (UP000141072) for in silico $CD8^+$ T cell epitope prediction. Predictions were made using the NetMHCpan 3.0 software. 42 swine leukocyte antigen (SLA) class SLA I alleles were considered, and peptides ranging from 8 to 11 amino acid residues, with an IC50 (concentration of peptide inhibiting binding of a standard peptide by 50%) below 500 nM were selected. 8,648 different sequences were obtained. To further select the most promising theoretical CTL candidates, additional features were evaluated for each peptide, including:

i) Proteasome cleavage, analyzed by using the MHC-I Processing tool from IEDB

This program allows evaluating how efficiently a peptide or its N-terminally prolonged precursors can be liberated from its source protein by the immunoproteasome.

ii) Promiscuity: Number of SLA I alleles predicted to bind the peptide with an affinity of 500 nM or lower.

iii) Overlap: Number of predicted peptides with a SLA binding affinity of 500 nM or lower, overlapping in at least one amino acid to a given polypeptide.

iv) Peptide immunogenicity: Prediction of the immunogenicity of a peptide taking into account its amino acid properties and their position within the sequence (Calis J et al., 2013).

The values of each trait were divided in 10 intervals, so that the best values received a score of and the worst ones were scored as 1. The final score consisted in the sum of all the values, and was finally used to select the best candidates.

Aiming to compare the repertoire of peptides selected, an additional list was made, incorporating TAPREG score as a new parameter, previously used to identify the CD2v CTL peptides from the E75 ASFV strain (Argilaguet et al., 2012). TAPREG server computes binding affinity of peptides to TAP using a Support Vector Machine Regression. The addition of TAPREG score provided an alternative list, and the final peptide selection was obtained combining both peptide lists. When overlapping peptides were found in both lists, both the best score and the larger peptide were selected. Additionally, larger peptides (15-27 amino acids) were selected according to the presence of more than 10 overlapping peptides in a given hot spot.

Mass Spectrometry-Based Immunopeptidomics

In vitro infection of PAMs with ASFV: $5 \times 10^6$ PAMs/well were seeded in 6-well plates for ASFV infection, using the indicated multiplicity of infection (MOI). The respective virus inoculum (0.5 ml) was diluted in complete RPMI without serum and applied to the PAMs monolayers. Following a 2-hour incubation at 37° C., 5% $CO_2$, the inoculum was discarded, and cells were replenished with complete RPMI supplemented with 10% porcine serum (Gibco). A parallel plate subjected to same conditions was used to monitor the ASFV infection. In this case, cell supernatants were harvested and the virus kinetics were analyzed by qPCR, as previously described (Lacasta et al., 2014). Cells were incubated at 37° C. and 5% $CO_2$, and harvested by scrapping when cytopathic effect was evident (dependent on the MOI used). PAMs were centrifuged at 350×g for 5 minutes at 4° C. and washed with PBS. Supernatant was discarded and pellets frozen at −80° C. until used.

Affinity purification of SLA I molecules: SLA I-peptide complexes were immunoprecipitated using 4B7/8 α-SLA I antibody-conjugated CNBr Sepharose beads (GE Healthcare). Hybridome culture supernatant of mAb α-SLA I was used. Coupling of the antibody to CNBr-activated sepharose was performed following manufacturer's instructions. A D-tube dialyzer maxi with a molecular weight cut-off of 12-14 kDa (Novagen) was used to dialyze the antibody-containing supernatant at 4° C. against 0.1 M sodium carbonate buffer pH 8.3 containing 0.5 M NaCl (coupling buffer). Lyophilized sepharose was suspended in 1 mM HCl pH 3 and incubated at RT for 20 minutes in end-over-end rotation to wash away the lyophilization additives, centrifuged at 500×g for 2 minutes at RT, and washed once with coupling buffer. The antibody in coupling solution was added to the washed sepharose at an optimal coupling concentration of 0.8-1.2 mg/ml, and rotated end-over-end overnight at 4° C. The OD of the antibody solution at 280 nm was measured before and after coupling to determine the coupling efficiency and incubate longer if necessary. The sepharose was spun down at 500×g for 2 minutes at RT, and the coupling buffer discarded. Any remaining active groups were blocked for 2 hours at 4° C. in end-over-end rotation with 0.1 M Tris-HCl pH 8. The antibody-coupled sepharose was washed with three cycles of alternating pH using 0.1 M acetic acid, pH 4 containing 0.5 M NaCl (acidic wash buffer) and 0.1 M Tris-HCl, pH 8 containing 0.5 M NaCl, (basic wash buffer). The coupled sepharose was finally resuspended in 50 mM Tris-HCl, pH 8 containing 150 mM NaCl (immunoprecipitation buffer) for the immunoprecipitation. PBS 0.1% (w/v) sodium azide was used for long-term storage of the coupled sepharose at 4° C.

Cell pellets were thawed on ice and lysed with 500 μl of 1% n-Dodecyl $-D-Maltoside (Thermo Fisher Scientific) in immunoprecipitation buffer and 1× complete protease inhibitor cocktail (Thermo Fisher Scientific), and incubated for 8 hours at 4° C. with end-over-end rotation. Cell lysates were clarified by centrifugation at 20000×g for 20 minutes at 4° C., and incubated 2 hours at 4° C. end-over-end with sepharose without antibody attached to remove any protein non-specifically interacting with the sepharose. The 500 μl of clarified lysate were then added to an equal volume of 4B7/8 α-SLA I antibody-conjugated CNBr sepharose in immunoprecipitation buffer (approximately 250 μl of sepharose in 250 μl of buffer) an incubated at 4° C. overnight with end-over-end rotation. Non-specifically bound molecules were removed by washing with 15-20 sepharose volumes of 150 mM NaCl, 50 mM ammonium bicarbonate. SLA I-peptides complexes were eluted in 4-5 sepharose volumes of 50% acetonitrile, 5% formic acid, and stored at −80° C. until analysis.

Western blot to detect immunoprecipitated SLA I-peptide complexes: Five percent of the volume of each sample was evaporated to dryness using a Concentrator 5301 (Eppendorf), suspended in 25 μl of 1× NuPAGE LDS sample buffer (Invitrogen) with 10% $-mercaptoethanol, and heated at 100° C. for 5 minutes. Half of the sample volume (2.5% of the total eluted volume) was run in a 4-12% gradient NuPAGE Bis-Tris acrylamide SDS-PAGE (Invitrogen) at 200 V during 1.5 hours in 1× NuPAGE MES SDS running buffer (Invitrogen) containing NuPAGE antioxidant (Thermofisher). His-tagged protein ladder (Thermofisher) was used as molecular weight marker. The gel was transferred to a nitrocellulose membrane (Amersham, Protran Premium) using a XCell SureLock™ Mini-Cell with a blot module (Thermofisher) during 4 hours at 50 V in transfer buffer made of 12 mM Tris-HCl (pH 8) containing 96 mM glycine, and 20% methanol (v/v). Following transfer, the nitrocellulose membrane was stained with ATX Ponceau S red staining solution (Biochemika Fluka) and destained in distilled water to confirm protein transfer. Thereafter, the nitrocellulose membrane was blocked in 3% non-fat milk (w/v) dissolved in wash buffer (TBS 0.1% Tween-20) for 1 hour at RT with gentle agitation on an orbital shaker). 4B7/8 α-SLA I antibody in blocking buffer at a concentration of 4 μg/ml was added to the membrane, and incubated for 1 hour at RT with gentle agitation, following 3 washes for 20 minutes with wash buffer. The membrane was then incubated with anti-mouse IgG HRP-conjugated (Sigma-Aldrich) diluted 1:10000 in blocking buffer for 1 hour at RT with agitation. For the His-tag marker, mouse anti-His tag HRP-conjugated (Novex) 1:100000 was used. After extensive washing as described above, the specific signal on the membrane was developed by using Western Lightning Ultra chemiluminescence substrate (PerkinElmer) for 5 minutes at RT in the dark. A Fluorchem HD2 (Alpha Innotech) was used for imaging.

On-tip desalting and LC-MS/MS analysis: Samples were desalted with TopTips C18 (PolyLC Inc), following the standard procedure. The eluates obtained from the desalting process were evaporated to dryness and reconstituted in 20 ml of 5% MeOH, 1% HCOOH for analysis by liquid chromatography coupled to mass spectrometry (LC-MS/MS). The MS system used was an LTQ XL Orbitrap (ThermoFisher) equipped with a nanoESI ion source. The total amount of each sample (20 μl) was loaded into the chromatographic system consisting in a C18 preconcentration cartridge (Agilent Technologies) connected to a 15 cm long, 100 μm i.d. C18 column (Nikkyo Technos Co Ltd). The separation was done at 0.4 μL/min in a 120-minute acetonitrile gradient from 3 to 40% (solvent A: 0.1% formic acid, solvent B: acetonitrile 0.1% formic acid). The HPLC system was composed of an Agilent 1200 capillary nano pump, a binary pump, a thermostated micro injector and a micro switch valve. The LTQ XL Orbitrap was operated in the positive ion mode with a spray voltage of 1.8 kV. The spectrometric analysis was performed in a data dependent mode, acquiring a full scan followed by 10 MS/MS scans of the 10 most intense signals detected in the MS scan from the global list. The full MS (range 400-1800) was acquired in the Orbitrap with a resolution of 60.000. The MS/MS spectra were done in the linear ion-trap.

Database search and peptide identification: All LC-MS/MS spectra were searched using SEQUEST (Proteome Discoverer v1.4, ThermoFisher) using a combined database including *Sus Scrofa*, BA71 and Georgia2007/1 ASFV, and the 6-frame translation of each virus genome (in order to identify peptides in and out of known ORFs). The following parameters were fixed: peptide confidence=High, peptide rank=1, Xcorr>2. Additionally, pig-specific 9-mers identified were used to create a sequence logo for each PAMs batch using WebLogo. Each logo consists of stacks of symbols, one stack for each position in the sequence. The overall height of the stack indicates the sequence conservation at that position, while the height of symbols within the stack indicates the relative frequency of each amino acid at that position. The binding site description given by the sequence logo was used to select or discard dubious sequences.

ASFV Gene Expression Plasmids

Plasmids encoding full-length ASFV proteins: The ASFV gene expression library used was built based on the E75 ASFV isolate (GenBank accession number FN557520.1). E75 ORFs were cloned in frame with ubiquitin into the pCMV-Ub plasmid (Rodriguez F et al., 2001). Additional construction of plasmids based on the Georgia2007/1 sequence (GenBank accession number FR682468) was done following the same strategy. A FLAG-tag sequence was added before the stop codon of the Georgia2007/1 gene in order to confirm the protein expression by immunofluorescence.

Anti-FLAG-tag immunofluorescence to check protein expression: Protein expression of Georgia2007/1 plasmids was checked by anti-FLAG-tag immunofluorescence in transfected RK13 cells. Transfection of RK13 cells was done using Lipofectamine 3000 transfection kit (Invitrogen) according to the manufacturers' instructions. Mock-transfected cells served as negative control. After 2 days of incubation at 37° C. and 5% $CO_2$, cells were fixed with 3% PFA 1 hour at 4° C. followed by permeabilization with 0.2% Tween20 in PBS 30 minutes at 37° C. AlexaFluor 488-conjugated anti-FLAG-tag monoclonal antibody (MA1-142-A488, Invitrogen) was diluted 1:100 and added to the cells for 1 hour at RT. Hoechst 33342 (Life Technologies) was used for nucleus staining. Cells were finally examined by fluorescence microscopy.

ASFV multiepitope-encoding plasmids: CTL epitope prediction of the ASFV Georgia2007/1 proteins selected to be included in the multiepitopes constructs was performed using the NetMHCpan 3.0 software. Protein sequences were retrieved from the Georgia2007/1 proteome (Uniprot access number UP000141072). The 42 SLA I alleles available in NetMHCpan 3.0 were considered, and peptides ranging from 8 to 11 amino acid residues with an IC50 below 500 nM were selected for further analysis. Protein regions containing a high density of predicted epitopes were selected. In the multiepitope-II (ME-II), each domain also included a peptide identified by previous MS-based immunopeptidomics assays. A single DNA construct was designed with the domains, linked by an optimal proteasomal cleavage site (AAY) (Velders et al., 2001) and with ubiquitin as a leader sequence to enhance their SLA I processing and presentation (Rodriguez and Whitton, 2000; Argilaguet et al., 2012; Lacasta et al., 2014). Plasmids encoding the multiepitopes were synthesized by GenScript (New Jersey, USA; SEQ ID NOS: 855 and 856).

In Vivo Experiments

Animals and animal safety: Male Landrace×Large White piglets were used in all the in vivo experiments described. Pigs were fed ad libitum and identified by numbered ear tags, and a seven-day acclimation period was established before manipulation of the animals. Animal care and procedures were carried out in accordance with the guidelines of the Good Experimental Practices and under the supervision of the Ethical and Animal Welfare Committee of the Universitat Autònoma de Barcelona (Spain).

Peptide immunization: Three- to four-week-old piglets were used for peptide immunization experiments, which were carried out at the IRTA Monells pig experimental farm (Girona, Spain). Pigs received two intramuscular administrations in the hindquarters 3-week apart. Peptide cocktails (1 ml) included 20 nM of each peptide with complete Freund's adjuvant (Thermo Fisher Scientific) in the first immunization and incomplete Freund's adjuvant (Thermo Fisher Scientific) in the second. EDTA-blood samples were drawn from the jugular vein 2 weeks after the second peptide administration for PBMCs isolation.

Source of PBMCs to be used as effector cells in different assays aiming to quantify ASFV-specific T-cell response: Pigs experimentally infected with Georgia2007/1 yields a 100% mortality, before they are capable to induce ASFV-specific T-cells. Therefore, an alternative route was followed to obtain ASFV-specific T-cells. For the isolation of PBMCs from ASF-convalescent animals, BA71ΔCD2 immunization-Georgia2007/1 challenge in vivo experiments were performed at the biosafety level 3 facilities at the Centre de Recerca en Sanitat Animal (IRTA-CReSA, Barcelona, Spain). Six- to eight-week-old piglets were used, and either $10^6$ plaque forming units (PFU) or $3.3\times10^4$ PFU of BA71ΔCD2 in 1 ml of PBS were administered intramuscularly to the animals as previously described (Monteagudo et al., 2017). Three weeks later, pigs were challenged intramuscularly with a lethal dose of $10^3$ genomic equivalent copies (GEC) of the Georgia2007/1 ASFV isolate. Three weeks after the BA71ΔCD2 immunization (before Georgia2007/1 challenge), and two to three weeks after the challenge, EDTA-blood samples were drawn and the isolated PBMCs were used in different assays to quantify ASFV-specific T-cell response.

Heterologous DNA prime-BA71ΔCD2 boost and Georgia2007/1 challenge: The high virulence of Georgia2007/1 hampers finding a lethal challenge dose allowing pig survival for more than a week, thus impeding monitoring of the immune response. To increase the chances to unmask the protective potential of specific ASFV antigens, a prime-boost protocol was established, priming animals with DNA vaccines (encoding specific ASFV antigens) and boosting with a low dose of BA71ΔCD2. Three- to four-week-old male Landrace×Large White piglets were housed together in an experimental box (12 $m^2$) of the biosafety level 3 facilities at IRTA-CReSA (Barcelona, Spain). Pigs were immunized with two doses of 0.6 mg in 1.5 ml saline of the correspondent endotoxin-free DNA plasmid or plasmid cocktail (Qiagen) two weeks apart. One-third of each vaccine dose was intramuscularly injected into the femoral quadriceps, one-third into the trapezius muscle of the neck, and the last third was subcutaneously injected into the ear, according to an optimized protocol previously described (Argilaguet et al., 2011). Control pigs received the pCMV-Ub empty plasmid following the same administration protocol. Two weeks after the second DNA dose, a suboptimal dose (partially protective) of $10^3$ PFU of the BA71ΔCD2 live attenuated ASFV was administered to the pigs as a boost. Three weeks later, pigs were challenged intramuscularly with a lethal dose of $10^3$ GEC of the Georgia2007/1 ASFV isolate. Blood samples were drawn from the jugular vein of the pigs and nasal swabs were taken before and after each of the following time points: DNA prime (0, 4 and 7 dpp), BA71ΔCD2 boost (0, 4, 7 and 14 dpb), and Georgia2007/1 challenge (0, 4, 7, 14 and 21 dpc). Post-mortem examinations were carried out to confirm or discard the presence of ASFV-compatible pathological lesions.

Monitoring of ASF-compatible clinical signs: Animals were observed daily according to a welfare schedule to monitor their health status and to record the clinical signs after the infection with ASFV. Clinical evaluation included rectal temperature, behavior, body condition (prominence of vertebrae and ribs), cyanosis, digestive signs and respiratory signs. Each parameter was scored from 0 to 3 according to the severity (0: normal, 1: mild, 2: moderate, 3: severe), as described by Galindo-Cardiel and collaborators. The humane endpoint was reached when progression of the disease led to an unacceptable loss of general welfare (Galindo-Cardiel et al., 2013).

Quantification of virus titers in serum and nasal swabs by qPCR: Viral DNA from sera and nasal swab-PBS suspensions was quantified using a SYBR Green real-time PCR (qPCR) method previously described (Lacasta et al., 2014). Briefly, the viral genomic DNA was obtained from 200 µl of sera or swab-PBS suspensions using the NucleoSpin blood kit (Macherey-Nagel), and then employed as template to amplify an 85 bp-long fragment from the ASFV serine protein kinase gene (R298L) using PowerUp SYBR Green Master Mix (Thermo Fisher Scientific). Results were expressed as $\log_{10}$ numbers of GEC per ml of sera or nasal swab, and the limit of detection of the assay was established at $10^3$ GEC/ml.

Immunological Readouts

Porcine IFNγ ELISpot: IFNγ response was assessed by ELISpot assay using purified mouse anti-pig IFNγ Clone P2G10 (BD Pharmingen) as capture antibody and biotinylated mouse anti-porcine IFNγ antibody P2C11 (BD Pharmingen) as detection antibody, following a previously reported method (Lacasta et al., 2014). Briefly, 96-well plates (Costar 3590, Corning) were coated overnight at 4° C. with 5 µg/ml capture antibody in carbonate-bicarbonate buffer, pH 9.6. Plates were washed 3× with PBS, and blocked 1 hour at 37° C. with complete RPMI with 10% FBS. $5 \times 10^5$ PBMCs/well were used in a final volume of 200 µl with the correspondent stimuli. Peptides were added as a stimulus at a final concentration of 4 µg/ml, and RPMI and 10 µg/ml phytohaemagglutinin-M (PHA-M, Sigma-Aldrich) were used as negative and positive controls, respectively. When the LAV BA71ΔCD2 were used as stimulus, $10^5$ PFU were added per well. After overnight incubation at 37° C., 5% $CO_2$, cells were washed out with PBS 0.05% Tween20, and IFNγ was detected using 0.5 µg/ml of biotinylated anti-porcine IFNγ antibody 1 hour at 37° C. After washing, the ELISpot was developed by adding 50 µl of insoluble 3,3',5,5'-tetramethylbenzidine (TMB) substrate (Calbiochem) and stopped by washing with water. The frequency of specific IFNγ-secreting cells (IFNγ-SC) represented in the graphs is the mean of two replicates, subtracting the counts in the negative control wells. 300 spots/well was considered the limit of the assay resolution (wells with more than 300 spots received a score of 300).

For the use of fibroblasts as APCs in the ELISpot assay, the ratio used was 1 APC:5 autologous PBMCs. Plasmid transfection of the fibroblasts was done by electroporation using the Neon Transfection System 10 µl Kit (Invitrogen). Fibroblasts were collected by trypsinization, centrifuged at 250×g for 5 minutes at RT and washed with PBS. The appropriate number of cells (100000 fibroblasts/condition) were placed into a clean Eppendorf tube, and suspended in 10 µl of Neon Resuspension Buffer R, and mixed with 500 ng of the corresponding plasmid or plasmid cocktail. Electroporation was done with the following pulse conditions: pulse voltage=1700 V, pulse width=20 ms, pulse number=1. Fibroblasts electroporated with the empty pCMV-Ub plasmid were used as a negative control. Finally, electroporated cells were placed in the corresponding well of a 96-well plate with the autologous PBMCs and proceeded as described above. When working with transfected fibroblasts, no replicates were made. The number of spots in a control well using fibroblasts transfected with the empty pCMV-Ub plasmid, which never exceeded 10, was subtracted from the specific IFNγ-SC represented in the graphs.

Detection of ASFV-specific antibodies by ELISA: ASFV-specific antibodies in pig sera were detected by the OIE-approved indirect ELISA assay based on the use of soluble extracts from ASFV-infected cells (Gallardo et al., 2013). The presence of positive sera was detected using peroxidase-conjugated anti-pig IgG at 1/20000 dilution (Sigma-Aldrich) as secondary antibody and soluble TMB as specific peroxidase substrate (Sigma-Aldrich). Reactions were stopped with 1 N $H_2SO_4$ (Sigma-Aldrich). Plates were read at a wavelength of 450 nm and results were expressed as optical density (OD) values.

Example 2—In Silico Predictions, Immunopeptidomics and Gene Libraries: Identification of ASFV CD8+ T-Cell Epitopes The aim of this study was to explore the effectiveness of three different strategies for identifying ASFV CD8+ T-cell epitopes with protective potential against the Georgia2007/1 ASFV isolate, the virus currently circulating in Continental Europe and China.

The first approach here explored was a multiparametric bioinformatic analysis using the Georgia2007/1 proteome as a template for the prediction of the peptide sequences more likely to be promiscuously presented by the SLA I pathway.

The second strategy here employed consisted on characterizing the repertoire of ASFV SLA I-bound peptides found in PAMs in vitro infected with the virus. The potential of each individual peptide from both in silico predictions and immunopeptidomics assays to stimulate ASFV-specific T-cells was assessed by IFNγ ELISPOT, using as effector cells PBMCs from animals inoculated with the LAV BA71ΔCD2. Since BA71ΔCD2 is capable to confer protection against the heterologous Georgia2007/1 strain, it can be assumed that protective antigens will be shared between both isolates. In this in vitro stimulation assay, peptides directly bind to the SLA I molecules exposed on the cell surface and are capable to stimulate specific CD8+ T-cells, albeit they are limited to their specific SLA I molecule match.

The third strategy here tested sought to overcome the haplotype specificity of peptide-based assays by using as in vitro stimulators full-length proteins, which might contain epitopes with multiple SLA I specificities. Aiming to enhance the SLA I processing and presentation of the antigens, gene expression plasmids each encoding individual full-length ASFV ORFs fused to ubiquitin (Rodriguez and Whitton, 2000; Rodriguez et al., 2001) were used as a source of ASFV antigens for the assay. Individual plasmids were transfected into pig skin fibroblasts thus serving as APCs in an IFNγ ELISPOT assay, using autologous PBMCs of ASF-convalescent pigs as effector cells.

Results

Evaluation of Georgia2007/1 CD8+ T-cell epitope predictions: The sequences scoring the best theoretical ratings in the multiparametric bioinformatic analysis using the Georgia2007/1 proteome as a template were synthesized. The final selected set included 330 peptides from 110 ASFV proteins. 266 peptides were a direct output of the prediction software, thus ranging from 8 to 11 amino acids in length, and 64 longer sequences (12-27 amino acids in length) were selected due to the presence of multiple peptides with 10 or more overlapping predictions.

Out of the 330 predicted peptides, only one induced an IFNγ response in PBMCs from Georgia2007/1 survivors previously immunized with BA71ΔCD2, thereby in silico predictions yielding a percentage of 0.3% of recognized peptides. The immunogenic peptide corresponded to residues 68-86 of the MGF100-1L (SEQ ID NOS: 570 and 571), and 11 out of the 20 (55%) animals tested showed a specific IFNγ secretion. It has to be taken into account that the peptide is a 19-mer, and was therefore not a direct outcome of the software used, but it was selected because peptides within that sequence had more than 9 predicted CD8+ T-cell overlapping epitopes.

Evaluation of SLA I-restricted peptides identified by mass spectrometry-based immunopeptidomics: PAMs infected with either Georgia2007/1, BA71 or the LAV BA71ΔCD2 were used for the MS-based immunopeptidomics analysis. The increase of virus titers in the supernatants assessed by qPCR evidenced the replication of the viruses in the cells. After anti-SLA I immunoprecipitation and elution, the presence of SLA I-peptide complexes was confirmed by western blot. The band located between and 50 kDa coincides with the expected molecular weight of about 45 kDa of the SLA class I heavy chain. The slightly heavier band and the 25 kDa band most probably correspond to the heavy and light chains of the anti-SLA I antibody used for immunoprecipitation, which have detached from the sepharose beads. Samples from non-infected PAMs were also analyzed by western blot to discard the possibility of an unspecific interaction of the anti-SLA I antibody.

Unfortunately, no peptides were found from Georgia2007/1-infected macrophages, independently of the PAMs used, or the multiplicity and time of infection. On the contrary, macrophages infected with BA71 or BA71ΔCD2 did render SLA I-specific peptides. These comparative assays allowed confirming that the lack of Georgia2007/1 SLA I-restricted peptides was strain-specific.

Using PAMs from three animals, 135 SLA I-bound peptides (106 different sequences) from 56 different ASFV proteins were identified. 84.3% of the sequences identified were identical for both BA71 and Georgia2007/1 isolates, 13% of the peptides only differed in 1 amino acid that theoretically did not play key roles in SLA I binding, and only 1.7% of them showed significant divergences in their sequence between both viruses, thus confirming the usefulness of this methodology to identify highly conserved peptides between ASFV strains.

Interestingly enough, while BA71-infected PAMs led to the determination of 44 ASFV sequences, 88 peptides were profiled from the BA71ΔCD2-infected samples. As expected for SLA I ligands, the length of peptides ranged from 8 to 13 amino acids, with 50% of the peptides being 9-mers. From the perspective of function, the biggest percentage was for proteins of unknown function, accounting for 35.6% of the total peptides, but peptides involved in transcription and replication, morphogenesis, host cell interaction, and from multi-gene families proteins were also identified. Regarding the temporal expression of the proteins during the infective cycle, early, intermediate and late proteins were identified, the latter ones representing the highest percentage (35.6%), although a 45.9% of the peptides came from proteins of unknown temporal expression.

With a total of 9 peptides, the ASFV protein from which the major number of peptides were identified was the uncharacterized protein B475L, followed by the structural polyprotein pp220 encoded by the CP2475L gene, and the helicase encoded by the D1133L ORF, from which 8 and 7 peptides were determined, respectively. Moreover, five SLA I peptides mapped in regions out of any known ORF, confirming results previously described (Jenson et al., 2000), and some of them without even having a conventional initiation codon. Strikingly, the five out of frame peptides were all identified from BA71ΔCD2-infected samples. Upholding the idea that these out of frame peptides could also be expressed and play a role in triggering protective response against the Georgia2007/1 ASFV, homologous sequences were found in the genome of the Georgia2007/1 isolate.

Out of the 111 different peptides identified by the immunopeptidomics approach, 5 induced an IFNγ response in PBMCs from animals surviving Georgia2007/1 challenge (Table 1), thus representing a 4.5% of the total number of peptides. Interestingly, the three peptides that were recognized by more than one tested animal were identified in BA71ΔCD2-infected PAMs, while the antigenic peptides profiled exclusively from BA71-infected samples induced an IFNγ response in only 10% of the animals. Far from being conclusive, it suggests that the peptide repertoires of BA71ΔCD2 and BA71 are slightly different.

TABLE 1

ASFV epitopes from immunopeptidomics studies in vitro inducing an IFNγ response in PBMCs from ASF-convalescent animals inoculated with the LAV BA71ΔCD2. An animal was classified as responder if 20 or more spots were counted.

| Peptide sequence | Protein | Responding animals | Sample | Georgia2007/1 homology |
|---|---|---|---|---|
| NPTIIMEQY (SEQ ID NO: 456) | H339R | 1/10 (10%) | BA71 | 100% |
| KNILNTLMF (SEQ ID NO: 478) | I226R | 1/10 (10%) | BA71 | 100% |
| DKDGNSALHYL (SEQ ID NO: 17) | A238L | 6/20 (30%) | BA71ΔCD2 | 100% |
| AKIVEEGGEES (SEQ ID NO: 514) | K145R | 4/20 (20%) | BA71/ BA71ΔCD2 | 100% |
| NSTLVIRI (SEQ ID NO: 717) | MGF505-8R | 4/20 (20%) | BA71ΔCD2 | NSTLVIRL (SEQ ID NO: 719, MGF505-7R) |

As expected, peptides were not uniformly recognized by all pigs, most probably reflecting their marked restriction for specific SLA alleles. Supporting this idea, inoculation of pigs with Freund's-adjuvanted cocktails of about 25 peptides identified by MS-based immunopeptidomics showed that some of the peptides were immunogenic but, again, not consistently recognized by all the pigs (Table 2). The peptides here employed were identified in the first immunopeptidomics analysis performed. Two immunization groups were defined depending on the theoretical binding affinity of each peptide to the SLA I alleles available at NetMHC-pan3.0. Those peptides having high binding affinities (IC50<1000 nM) to the majority of the alleles analyzed were classified as strong binders, while those with lower theoretical binding affinities (IC50>1000 nM) were grouped as weak binders. Two of the recognized peptides, from proteins D1133L and I226R, were classified as strong binders, while the third one, from protein G1211R, was a theoretical weak binder. Remarkably, opposed to what was expected according the theoretical predictions, the theoretical weak binder was recognized by 66.7% of the tested animals, while the two strong binders induced an IFNγ response in only one out of the six pigs (Table 2).

almost 100 recombinant plasmids, the 15 tested and others encoding already known immunogenic proteins were not included here. In a first screening step, mixes of 10 or 11 plasmids were electroporated into fibroblasts to, later on, test the individual plasmids from the mixes capable to specifically induce IFNγ response. Expression of similar ASFV gene expression plasmids was confirmed by adding a FLAG-tag sequence at the C-terminus of the ASFV gene and detecting it by immunofluorescence, as described in this and the following Examples.

From the ASFV gene expression library, one single clone: pCMV-Ub-MGF505-7R was identified, capable of specifically stimulating IFNγ expression in all the tested animals except for one (FIG. 1). The non-responder pig (pig 13) did show ASFV-specific IFNγ-SC, thus discarding a possible immunosuppressed state of the PBMCs. Nevertheless, a failure in some specific electroporation events (one transfection per plasmid) could not be excluded. Remarkably, an individual peptide from MGF505-8R (MGF505-7R$_{334-341}$: NSTLVIRI; SEQ ID NO: 717), was identified in the immunopeptidomics assays using PAMs infected with

TABLE 2

ASFV-specific epitopes inducing an IFNγ response assessed by ELISpot in PBMCs of animals inoculated with Freund's-adjuvanted peptide cocktails.

| Theoretical binding | Peptide sequence | Protein | Responding animals | Sample | Georgia2007/1 homology |
|---|---|---|---|---|---|
| Strong | YKDETLPYL (SEQ ID NO: 285) | D1133L | 1/6 (16.7%) | BA71/ BA71ΔCD2 | 100% |
|  | KNILNTLMF (SEQ ID NO: 478) | I226R | 1/6 (16.7%) | BA71 | 100% |
| Weak | ENIAYERLETL (SEQ ID NO: 416) | G1211R | 4/6 (66.7%) | BA71ΔCD2 | ENIVYERLETL 90.9% (SEQ ID NO: 420) |

Use of gene expression plasmids for the identification of immunodominant ASFV CD8+ T-cell antigens: As reflected supra, peptide-based approaches present a major drawback: limited presentation by restricted SLA haplotypes.

With the aim of avoiding this restriction and in an attempt to extend the studies described supra, it was aimed to identify promiscuous CD8+ T-cell determinants from ASFV, focusing on its full-length antigens. pCMV-Ub plasmids encoding full-length ASFV ORFs were transfected into primary fibroblasts and those were used as APCs in the ELISpot assay, using PBMCs from the same animal (autologous) as effector cells.

The optimal conditions for fibroblast electroporation using the Neon Transfection System were previously setup transfecting the pCMV-GFP plasmid into primary swine fibroblasts using different electroporation settings. The best condition was selected considering the percentage of transfected cells (GFP+) with respect to live cells. The conditions used gave a 36.14% of GFP+ cells and a mortality of 4.60%. Although it could not be assured that these values were constant in the following assays, it served as a proof of concept for demonstrating that the primary fibroblasts could express proteins under the pCMV promoter.

A collection of 73 recombinant plasmids belonging to an ASFV gene expression library available as described supra was used. Although the gene expression library contains BA71ΔCD2. The fact that this peptide was recognized by a small proportion of ASF-convalescent pigs confirm its SLA I-restricted nature and argue positively in favor of the advantage of using the full-length MGF505-7R protein, containing multiple CD8+ T-cell determinants, in future developments.

Figure 2:
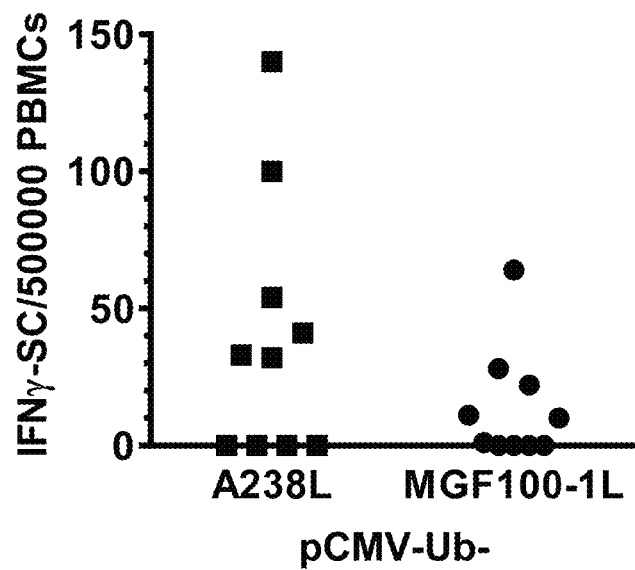
FIG. 2 depicts the IFNγ response to A238L and MGF100-1L full-length Georgia2007/1 proteins assessed by ELISpot assay using fibroblasts transfected with the pCMV-Ub-A238L and pCMV-Ub-MGF100-1L plasmids respectively as APCs and PBMCs from ASF-convalescent animals as effector cells.

Interestingly, two additional antigenic proteins were identified using this methodology: A238L and MGF100-1L. Despite those two proteins showed less promiscuity than MGF505-7R, they were still broadly recognized by ASFV-specific T-cells. Thus, fibroblasts transfected with the recombinant plasmids encoding the full-length A238L and MGF100-1L induced an IFNγ response in 60% and 50% of the animals after ASFV in vitro stimulation, respectively (FIG. 2). Interestingly, peptides previously identified from these proteins by immunopeptidomics analysis: A238L$_{81-91}$ and MGF100-1L$_{68-86}$ specifically stimulated an IFNγ response in 30% and 50% of the pigs, respectively.

Conclusion: The results displayed supra strongly suggest that immunopeptidome analysis of PAMs in vitro infected with ASFV are a more reliable strategy than in silico predictions for the identification of ASFV-specific CD8+ T-cell epitopes. However, peptides are not uniformly recognized by all pigs, probably reflecting their marked restriction for specific SLA alleles. This can be overcome by the use of full-length proteins, which here served to identify MGF505-

7R as a novel immunodominant and promiscuous ASFV antigen, and two additional antigens: A238L and MGF100-1L recognized by at least 50% of the animals tested. Therefore, focusing on full-length proteins instead of epitopes could be a more suitable approach for the identification of ASFV antigens with potential to promiscuously induce specific T-cell responses.

Example 3—M448R and MGF505-7R: Two Immunodominant ASFV Antigens with Protective Potential Since the marked restriction of peptides for specific SLA alleles is one of the major drawbacks of peptide-based vaccination approaches, in this present study there was a focus on full-length proteins. According to the identification of SLA I-restricted peptides by MS-based immunopeptidomics, 15 ASFV-encoded proteins were selected as potential inducers of $CD8^+$ T-cell responses.

In order to assess their immunogenicity and protective potential, pigs were inoculated with the selected recombinant plasmids, each encoding an ASFV antigen with an ubiquitin sequence at the N-terminus, aiming to optimize SLA I presentation and enhance the induction of $CD8^+$ T-cell responses. A heterologous regimen including the DNA prime immunization with the 15 selected antigens followed by inoculation with a low dose of the live attenuated BA71ΔCD2 ASFV was applied as explained in Example 1. The cross-protective capabilities of BA71ΔCD2, conferring protection not only against the parental BA71 but also against heterologous viruses including the Georgia2007/1 isolate, should allow the enhancement of any cross-protective response induced by the recombinant plasmids, thus increasing the chance of identifying relevant antigen-specific T-cells. In addition, this immunization protocol allowed to evaluate the capability of pigs primed with the selected 15 antigens to achieve protection against a Georgia2007/1 lethal challenge, in comparison to a control group primed with a plasmid not encoding any ASFV specific protein.

In the first experiment here described, partial protection against a Georgia2007/1 challenge in pigs receiving the 15 selected antigens as a DNA prime vaccination was observed. One protein, M448R, showed the most immunodominant nature among the antigens included in the plasmid cocktail. Moreover, M448R exhibits a promiscuous cellular response in ASFV-convalescent pigs not receiving a DNA prime vaccination. As described in Example 1, the use of fibroblasts transiently expressing ASFV antigens as APCs for autologous PBMCs from ASF-convalescent pigs, allowed identifying another ASFV protein: MGF505-7R with a promiscuous nature similar to that of M448R. Therefore, both M448R and MGF505-7R were promising candidates to be further explored for their importance in ASFV protective immunity.

In consequence, the present study describes a second in vivo experiment designed to assess the immunogenicity and protective potential of M448R and MGF505-7R combined, using a prime-boost immunization protocol as above explained.

Results

DNA immunization with a cocktail of plasmids encoding 15 ASFV pre-selected proteins confers partial protection against Georgia2007/1 challenge infection: Based on previous results of an SLA I-immunopeptidomics study of ASFV-infected PAMs, 15 ASFV antigens were selected as potential candidates to induce $CD8^+$ T-cell responses, and their immunogenicity and protective potential against a Georgia2007/1 lethal challenge was assessed.

The selected set included three ASFV potential enzymes likely involved in nucleic acid metabolism: D339L (RNA polymerase subunit 7), EP424R (putative methyl transferase), and M448R (RNA ligase); as well as I243L, an assumed transcription factor. Also, two proteins involved in virion morphogenesis were included: the structural protein p37, product of the processing of the polyprotein pp220, and the chaperon B602L. Multigene family 505 members MGF505-1R and MGF505-3R were also selected, along with seven proteins of unknown function: B475L, DP238L, H339R, I226R, I73R, 19R and K145R. All the above mentioned proteins represent early, late and intermediate proteins during the ASFV replication cycle. Expression of the ASFV proteins here tested was confirmed by anti-FLAG-tag immunofluorescence in transfected RK13 cells as described in Example 1.

Figures 3, 4:
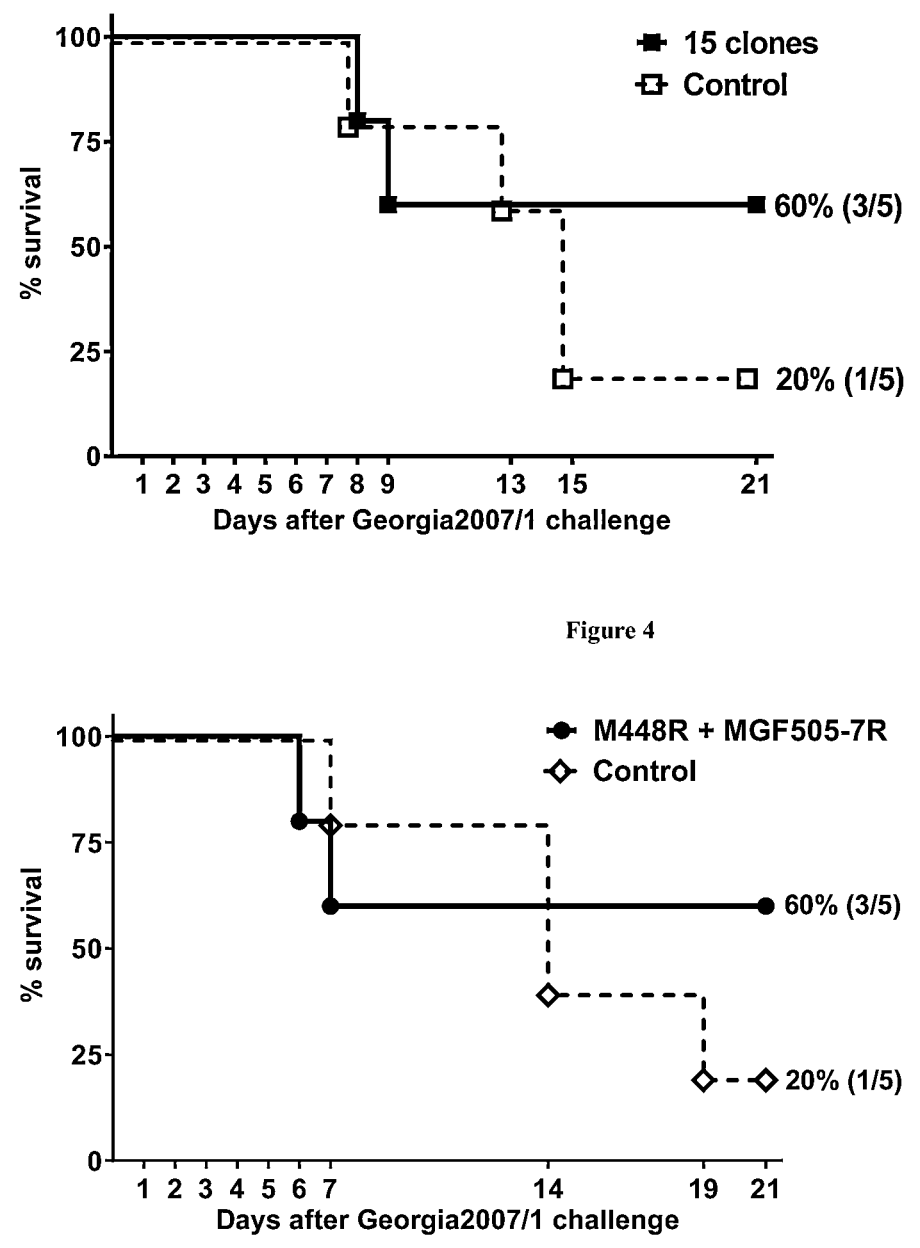

Following the immunization protocol described in Example 1, three out of five (60%) pigs primed with the 15 recombinant plasmids survived the lethal challenge with Georgia2007/01. Conversely, and in line with previous results from the lab using the low dose of BA71ΔCD2, only one out five (20%) of the control pigs immunized once with the low dose of BA71ΔCD2 survived (FIG. 3).

During the experiment, animals were monitored daily for ASF typical clinical signs, including fever, lethargy, general body condition, digestive signs, respiratory signs and cyanosis. Even though the four surviving pigs developed transient ASF-compatible symptomatology, the three primed with the 15 recombinant plasmids showed milder clinical signs compared to the survivor from the control group. These results correlated with: i) delayed and shorter viremia in serum in surviving animals in the group primed with the 15 recombinant plasmids, ii) a reduction of 1 to 2 $\log_{10}$ in their maximum titers of the challenge virus, and iii) no detectable virus at any time post-challenge. In addition, a one to two $\log_{10}$ reduction in nasal shedding was observed compared to both the non-surviving animals and the survivor in the control group.

The survivor from the control group (pig 185) showed a high and prolonged fever peak (>41° C. for 5 days) starting at 4 dpc accompanied with an apathic behavior, while the three surviving animals in the 15 recombinant plasmids-primed group had mild fever lasting at most three days. Pig 181 experienced sporadic symptoms coinciding with mild fever peaks, and pig 184 had no apparent symptomatology throughout the study. Although survivor pig 180 also showed an apathic behavior and evident dyspnea. The onset of clinical signs was delayed compared to both the control that survived and the non-survivors. Pigs 182 and 183 of the "15 clones" group succumbed at 9 and 8 dpc, respectively, and their temperature and viral load in sera and in nasal swabs were similar to those in the control group.

Immunization with the 15 recombinant plasmids induces ASFV-specific T-cells, but no antibody response is detected: Administration of the 15 recombinant plasmids did not induce any specific antibody response but it did induce detectable ASFV-specific IFNγ response at 14 dpp, thus indicating the immunogenicity of at least one of the 15 included antigens.

After the BA71ΔCD2 vaccination, all the animals seroconverted and developed ASFV-specific T response. No clear correlation of protection was observed considering the level of antibodies or T cells induced after immunization, since control animals vaccinated only once with BA71ΔCD2 did also show a notable ASFV-specific immune response. Notwithstanding, the two animals from the "15 clones" group that did not survive the Georgia2007/1 challenge showed the lowest level of antibodies and ASFV-specific T response at the time of challenge infection. The T-cell response induced directly after DNA immunization very likely contributed to a better control of ASFV infection and virus clearance in the "15 clones"-primed group.

M448R shows an immunodominant nature in ASFV-convalescent animals previously primed with the 15 recombinant plasmids: Once confirmed the immunogenicity of the administered plasmid cocktail, it was aimed to determine the immunogenic profile of each of the 15 ASFV antigens used. To this end, swine fibroblasts were electroporated with each individual recombinant plasmid contained in the immunization mix and used as APCs in an ELISpot assay with autologous PBMCs obtained at 14 dpc as effector cells.

Interestingly, high levels of IFNγ-SC (>50 spots) were exclusively detected in all the animals when PBMCs were incubated with fibroblasts transfected with pCMV-Ub-M448R. The number of M448R-specific IFNγ-SC was comparable to that obtained when transfecting the mix of the 15 recombinant plasmids. This result suggests that T-cell immunity towards M448R was largely responsible for the immunogenicity observed after immunization with the 15 recombinant plasmids. Furthermore, M448R-specific T-cells primed could have contributed to the milder course of Georgia2007/1 infection and increased survival in the "15 clones" group.

The number of spots when using ASFV as stimulus after the boost was much higher than when using swine fibroblasts transfected with the pCMV-Ub-M448R plasmid, most probably explained by different reasons. Firstly, ASFV infects APCs much better than plasmids transfect them, therefore being more efficiently processed. Secondly, PBMCs from ASFV recovered pigs might also recognize other antigens present in ASFV than those contained in the plasmid mix.

M448R induces a specific T-cell response during ASFV infection without a prior DNA prime: In a next step, it was attempted to determine if M448R induces ASFV specific $CD8^+$ T-cells not only when pigs were primed with pCMV-Ub-M448R, but also after ASFV infection. For this, PBMCs from BA71ΔCD2-immunized animals and challenged with a lethal dose of Georgia2007/1 (not previously primed with the pCMV-Ub-M448R plasmid) were tested in an ELISpot assay with autologous swine fibroblasts transfected with the pCMV-Ub-M448R plasmid. Strikingly, an IFNγ response against M448R when expressed in the pCMV-Ub plasmid was induced in 7 out of 9 animals, thus confirming the promiscuous nature of M448R and the presence of immunodominant T-cell epitopes within it.

Immunization with pCMV-Ub-M448R and pCMV-Ub-MGF505-7R confers partial protection against Georgia2007/1 lethal challenge: Given the immunodominant feature of M448R and its protective potential, it was decided to include it in future experimental vaccine formulations, together with MGF505-7R, a second antigen promiscuously recognized by ASF-convalescent pigs (Example 1). Therefore, the immunogenicity and protective potential of these two antigens was assessed by priming a group of pigs with two DNA plasmids encoding M448R and MGF505-7R proteins, with an ubiquitin sequence at the N-terminus, and boosting with a low dose of BA71ΔCD2.

In line with previous results using a low dose of BA71ΔCD2, only one animal in the control group out of five (20%) survived the Georgia2007/1 challenge infection. In contrast, in the pCMV-Ub-M448R+pCMV-Ub-MGF505-7R-immunized group three out of five pigs survived the lethal challenge infection (FIG. 4).

Surviving animals from the DNA-primed group showed lower and shorter fever peaks than the control pigs. Thus, pig number 89 showed no fever and no other clinical signs at any time after the Georgia2007/1 challenge, and pig number 90 showed a brief peak of fever at 20-21 dpc. The third survivor in this group (pig 88) showed mild apathy and the body condition was slightly affected (clinical score never exceeded 2), but was completely recovered by day 14 post-challenge. Pigs number 86 and 87 from the DNA-primed group succumbed the infection showing ASF clinical signs indistinguishable from that found in control pigs (vaccinated with BA71ΔCD2 only). These included severe ASF symptoms, such as lethargy, depression, visible vertebrae and/or ribs, dyspnea and cyanosis (scoring at least 4 in the clinical signs scale).

ASF-clinical signs in the control group were more evident with two exceptions. Pig number 97 was found dead surprisingly late (at 19 dpc), after suffering a mild ASF symptomatology and high fever (>41° C.) for at least 2 consecutive days before dying, and pig number 99 which survived the Georgia2007/1 challenge despite suffering a prolonged lethargy starting at 9 dpc and lasting until the end of the trial, and also developing cyanosis in ears and tail.

Despite the survival percentage in the M448R+MGF505-7R-primed group was the same than when priming with the 15 clones (60%), the animals seemed to cope much better with the Georgia2007/1 infection, at least according to the clinical signs observed.

Priming with pCMV-Ub-M448R and pCMV-Ub-MGF505-7R contributes to reduced virus titers in serum and reduced nasal shedding after Georgia2007/1 challenge infection: Serum and nasal swabs were collected at the indicated sampling days and then tested for the presence of ASFV DNA by qPCR. After the BA71ΔCD2 vaccination, no viral DNA was found in either serum or nasal swabs from the DNA-primed animals. Conversely, and evidencing the replication of the LAV, a peak of viral DNA in the serum was detected in one control animal after administration of BA71ΔCD2.

After Georgia2007/1 inoculation, the level of viral DNA in the serum of the animals that survived always remained below 106 GEC/ml, in contrast with the pigs that had to be sacrificed, all reaching at least 107 GEC/ml at some time point after the infection. Focusing on the surviving animals, no ASFV DNA was detected in serum from animals 89 and 90, and low levels were found in nasal swabs, except for the virus peak found at 21 dpc in animal 90. These results concurred with the absence of clinical signs reported in these animals. The detection of ASFV DNA in both serum and nasal swab from animal 88 at 7 dpc is consistent with the mild ASF symptomatology observed in this surviving animal. Despite the prolonged lethargy and cyanosis reported, the surviving animal in the control group (pig 99), was capable of controlling virus replication, showing low virus DNA levels in serum and reduced nasal shedding. The severe ASF clinical signs observed in the animals that had to be sacrificed from the DNA-primed group coincided with both high virus titers in serum and nasal swabs, and no difference was found between the succumbing animals in the immunized and the control group.

DNA immunization with pCMV-Ub-M448R and pCMV-Ub-MGF505-7R induces ASFV-specific T-cell response capable of recognizing both M488R and MGF505-7R antigens in vitro: As expected, administration of the pCMV-Ub- M448R and pCMV-Ub-MGF505-7R plasmids did not induce any detectable ASFV-specific antibody response. No difference was observed regarding antibody response among surviving and succumbing animals before Georgia2007/1 inoculation, all showing elevated levels at the day of challenge (except for pig number 100, which also showed weak T-cell response).

Also as expected, IFNγ response against swine fibroblasts transfected with pCMV-Ub-M448R and pCMV-Ub-MGF505-7R were detected 7 days after the second DNA immunization in DNA-primed animals, but not in the control group. Although low levels of IFNγ-SC were detected (likely because of low immunogenicity of DNA vaccines in large animals), this confirmed the immunogenicity of the tested antigens when administered in a DNA-based formulation. Notably, at this early time point, the two animals not showing M448R- and MGF505-7R-specific T-cell response (pigs 86 and 87) were the ones that later succumbed the Georgia2007/1 challenge.

In line with previous results showing the promiscuous and immunodominant nature of both M448R and MGF505-7R during ASFV infection, after the BA71ΔCD2 vaccination all the animals except one control (pig 100) were capable of recognizing their autologous swine fibroblasts transfected with the recombinant plasmid cocktail containing pCMV-Ub-M448R and pCMV-Ub-MGF505-7R. The control that did not respond showed low cellular and humoral responses throughout the whole experiment, reflecting perhaps an immunosuppressed state.

In order to characterize the response induced by each one of the antigens here tested, ELISpot assays were performed with swine fibroblasts transfected with either pCMV-Ub-M448R or pCMV-Ub-MGF505-7R. Simultaneous IFNγ response to M448R and MGF505-7R were detected in all the animals (except pig 86, which did not recognize MGF505-7R), thus discarding a possible immunodominance effect between M448R and MGF505-7R when administered in a DNA-based formulation. At a group level, the IFNγ response to both M448R and MGF505-7R of the three surviving animals (pigs 88, 89 and 90) was higher than the two animals that died (pigs 86 and 87) at all the analyzed time points. Again confirming the presence of M448R- and MGF505-7R-specific T-cells in Georgia2007/1-convalescent animals without a prior DNA prime immunization, the control animal that survived (pig 99) showed a notable IFNγ response to both antigens at the end of the trial.

Aiming to determine if the DNA prime immunization had an effect on the magnitude of ASFV-specific T-cell response, the number of IFNγ-secreting cells responding to BA71ΔCD2 after the vaccination with BA71ΔCD2 was assessed both early and late after the boost (at days 7 and 21 dpb, respectively). At 21 dpb, all pigs showed indistinguishable ASFV-specific T-cell response, with the exception of the low responder pig 100. IFNγ response was also detected in all the animals at 7 dpb, despite no significant differences were found between the DNA-primed animals and the control group. It is worth mentioning that the best IFNγ-responder within the control group, pig 99, was the only survivor.

Conclusion: In the present study, the feasibility of inducing ASFV-specific cellular response in pigs was confirmed by administering a cocktail of 15 plasmids encoding full-length ASFV proteins in frame with ubiquitin. It was demonstrated here that a heterologous immunization regimen including a DNA prime with the 15 recombinant plasmids followed by a low dose of the LAV BA71ΔCD2 confers partial protection against a Georgia2007/1 challenge. Protein M448R was the main responsible for the immunogenicity of the plasmid cocktail, thus suggesting its protective potential. Moreover, ASF-convalescent animals promiscuously recognized M448R, without receiving a prior DNA prime.

Following the same experimental design, DNA priming with M448R in combination with MGF505-7R, which was also shown to have an immunodominant and promiscuous nature (Example 1), did also result in a 60% survival percentage.

Example 4—Design of Multiepitope-Based DNA Constructs and Assessment of their Immunogenicity and Protective Potential Against ASFV In a first attempt to enhance the immunogenicity of the DNA constructs based on the Georgia2007/1 sequence, ASFV proteins in which the presence of CD8$^+$ T-cell determinants was previously described EP402R, CP312R and A240L, were analyzed for the presence of regions containing multiple theoretical CTL epitopes. These protein regions or "SLA I-hot spots" were selected to be included in the vaccine formulation, aiming to induce a wide repertoire of SLA I-restricted immune responses. Optimal proteasomal cleavage sites were added spacing the different protein domains, and the ubiquitin gene was used as a leader sequence. With this design, it was aimed to enhance the SLA I processing and presentation of the epitopes as previously reported, thus inducing specific CD8$^+$ T-cell responses while abolishing humoral responses. The immunogenicity of this multiepitope-encoding plasmid, referred to herein as multiepitope-I (ME-I; SEQ ID NO: 855), was confirmed in vivo. Confirming the efficacy of the strategy, pigs immunized with ME-I induced ASFV-specific T-cell response that specifically recognized peptides from EP402R, CP312R and A240L.

Extending this outcome for the identification of novel Georgia2007/1 antigens, according to Example 2, proteins with potential to induce CD8$^+$ T-cell responses were selected. Therefore, a selection was done based on analyses of the immunopeptidome profile of macrophages in vitro infected with ASFV, followed by in silico CTL epitope predictions of each one of them. Protein regions containing a high density of predicted epitopes and at least one SLA I-restricted peptide identified in the immunopeptidomics assays were selected as "SLA I-hot spots" for the design of a second multiepitope DNA construct (ME-II; SEQ ID NO: 856).

Seeking to increase the chances of success of the experimental vaccine prototype, the heterologous prime-boost immunization regimen described in Example 1 was used. Thus, animals were primed with the DNA plasmids encoding the multiepitope constructs, followed by an intramuscular inoculation with a low dose of the live attenuated BA71ΔCD2 virus. This model was useful not only to confirm the capability of the selected antigens to induce ASFV-specific CD8$^+$ T-cells, but also to evaluate their protective potential against a Georgia2007/1 lethal challenge.

Results

Selection of ASFV proteins with potential to trigger immunodominant CD8$^+$ T-cell responses and design of a multiepitope DNA construct: Results from SLA I-restricted immunopeptidomics assays were used to select ASFV proteins with potential to induce CD8$^+$ T-cell responses. The best protein candidates were selected according to three main criteria: (i) proteins from which 5 or more peptides were identified in SLA I-restricted immunopeptidomics assays, (ii) proteins from which peptides were identified using PAMs from different animals, and (iii) proteins from which a peptide had been recognized by specific T-cells obtained from pigs inoculated with the live attenuated virus (LAV) BA71ΔCD2 or with a peptide cocktail including that specific peptide (i.e. antigenic peptides).

With this data in mind, 13 proteins were finally selected for further analysis. Interestingly, 4 of these proteins corresponded to ASFV enzymes involved in nucleic acid metabolism: G1211R (DNA polymerase beta), D1133L (helicase), P1192R (DNA topoisomerase II), and EP424R (putative methyl transferase); while another two correspond to the p150 and p37 structural proteins, encoded by the CP2475L ORF as a pp220 polyprotein precursor. Additionally, two multigene family 505 members resulted selected: MGF505-1R, probably involved IFN I inhibition and absent in the non-pathogenic OURT88/3 and BA71V ASFV, and MGF505-9R. Finally, the K145R ORF, previously identified as an immunodominant antigen using sera from convalescent pigs, was selected together with four additional ORFs with unknown functions: B475L, M1249L, H339R, and I226R.

In order to encode the 13 selected proteins in a unique ORF, each one was in silico analyzed to identify regions with a high density of epitopes using the NetMHCpan 3.0 software as described in Example 1. Finally, a single DNA construct was designed with the selected protein regions, linked by an optimal proteasomal cleavage site (AAY) (Velders et al., 2001) and with ubiquitin as a leader sequence aiming to enhance their SLA I processing and presentation. The final plasmid encodes, including the ubiquitin gene, a protein of 1,884 amino acids in length, hereinafter referred to as multiepitope-II (ME-II; SEQ ID NO: 856).

Figure 5:
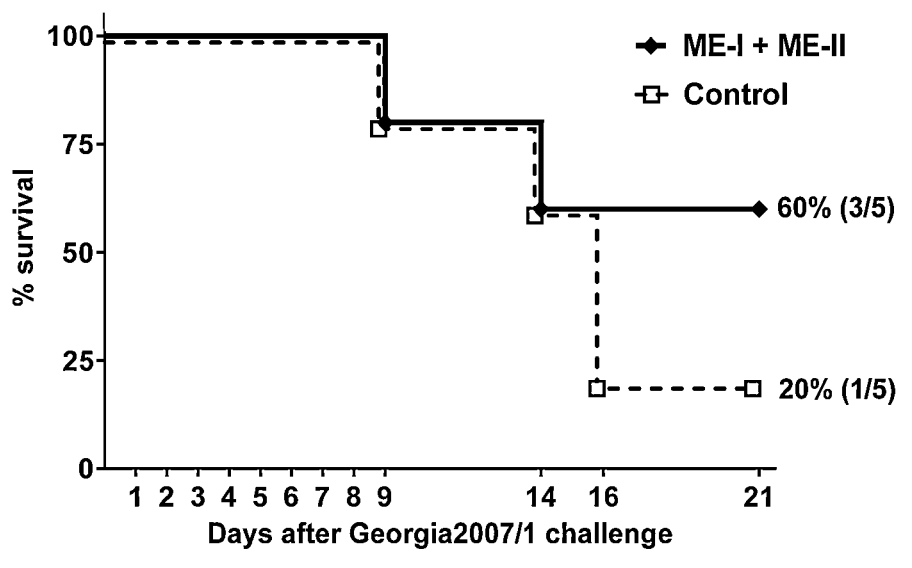

DNA immunization with ASFV multiepitope-based plasmids partially protects against Georgia2007/1 lethal challenge: To test the protective efficacy of the selected ASFV candidates, the prime-boost heterologous vaccination protocol previously described was evaluated. Both ME-I and ME-II were administered to the pigs. As represented in FIG. 5, three out of five pigs (60%) primed with the multiepitopes survived the Georgia2007/01 challenge, while only one out of the five controls (20%) did, coinciding with the expected results for the low dose of BA71ΔCD2 used.

In the group immunized with the multiepitopes, two of the three surviving animals (pigs 175 and 176) had not even two consecutive days of fever, and ASFV positive samples of serum and nasal swabs of these animals showed low virus titers, confirming the success of the DNA priming with the plasmids. Moreover, pig 175 remained free of ASF-compatible clinical signs throughout the experiment. Animal 176 showed slight apathy and evident dyspnea starting at 14 dpc until the end of the trial, but not correlating with fever nor ASFV positive serum samples or nasal shedding. The third survivor (pig 178) showed continued but minor ASF symptomatology, and transient episodes of fever starting at 5 dpc, correlating with a prolonged detection of ASFV in both serum and nasal swabs. However, at the end of the experiment this animal was almost recovered, showing no fever and only a slight dyspnea, and undetectable levels of ASFV in serum and nasal swabs. Rectal temperature and virus titers of the pigs that had to be sacrificed from the ME-I+ME-II-primed group (177 and 179) were not different from those found in most of the animals in the control group.

The course of infection in the control group was in line with previous results using a low dose of BA71ΔCD2 (Monteagudo et al., 2017). In this group, ASF-compatible clinical signs were apparent from day 3 after the Georgia2007/1 challenge, coinciding with the onset of prolonged fever (all the animals had at least five consecutive days of fever), and in agreement with the virus titers in serum and nasal swabs. The surviving control animal (pig 185) had prolonged fever compared to the survivors in the ME-I+ME-II-primed group, which also showed a delay in the appearance of symptoms of ASF.

Multiepitope-based DNA constructs encoding multiple epitopes from ASFV induce ASFV-specific T-cells in vivo: As expected, inoculation of the multiepitopes did not induce any ASFV-specific antibody response, but it did induce detectable ASFV-specific IFNγ response, confirming the successful DNA priming with the chosen antigens. After the BA71ΔCD2 boost, all the pigs seroconverted and the number of ASFV-specific T-cells increased notably. As described before, no correlation seems to exist between the level of antibodies or specific T-cells at the challenge time point and the protection afforded, at least when measured by the techniques employed here.

Confirming the antigenicity of the multiepitope DNA constructs, IFNγ response was detected by ELISpot when they were transfected into fibroblasts and these used as APCs for autologous PBMCs obtained at 21 dpb.

Identification of ASFV antigens: DNA-primed vs not-primed animals: With the aim of determining and rank the immunogenicity of the individual ASFV antigens encoded in the multiepitope-based DNA constructs, pCMV-Ub plasmids encoding each of the full-length proteins included in both ME-I and ME-II were transfected into fibroblasts, and these used as APCs in the ELISpot assay. Expression of the full-length ASFV antigens here employed was confirmed by immunofluorescence as described in Example 1. In order to determine the role that DNA-priming can have on induction and modulation of T-cell responses, PBMCs from BA71ΔCD2-inoculated animals both primed with the multiepitopes and without a prior DNA prime were used as effector cells in the ELISpot assay. While almost all the clones stimulated a specific IFN-gamma response, in both cases proteins CP312R and D1133L showed the most promiscuous nature. Strikingly, while 3 out of the 5 ASFV-infected animals not previously primed responded to CP312R and D1133L, IFN-gamma production was observed in all the DNA-primed animals, suggesting an effect of the DNA prime on the induction of specific T-cell response against these two antigens. An increase on the number of animals responding to A240L was also seen in DNA-primed animals. These results demonstrate the successful DNA priming using designed multiepitopes to characterize two not previously described immunodominant ASFV antigens: CP312R and D1133L, with potential to induce protective T-cell responses.

Conclusion: The present study has proven the feasibility of multiepitope DNA constructs to in vivo induce ASFV-specific T-cell response and increase survival after a Georgia2007/1 lethal challenge when included in a heterologous prime-boost immunization regimen using the LAV BA71ΔCD2 as a boost. The protective potential of the epitopes encoded in the DNA plasmids has therefore been confirmed, validating antigen selection based on immunopeptidomics studies of ASFV-infected macrophages. The use of allogeneic fibroblasts as APCs in the ELISpot assays allowed to narrow down the potential candidates and to identify CP312R and D1133L as highly promiscuous antigens.

All of the compositions and methods disclosed and claimed herein can be made and executed without undue experimentation in light of the present disclosure. While the compositions and methods of this invention have been described in terms of specific aspects, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the following claims.

REFERENCES

The following references, to the extent that they provide exemplary procedural or other details supplementary to those set forth herein, are specifically incorporated herein by reference.
(1) Argilaguet J M et al., Vaccine 2011, 29: 5379-5385
(2) Argilaguet J M et al., PLoS One 2012, 7: e40942
(3) Calis J et al., PLoS Comput. Biol. 2013, 9: e1003266
(4) Chapman D A et al., Emerg Infect Dis. 2011, 17(4): 599-605
(5) De Villiers E P et al., Virology 2010, 400: 128-136
(6) Farlow J et al., Virology Journal 2018, 15(1): 190
(7) Galindo-Cardiel I et al., Virus Res 2013, 173: 180-190
(8) Gallardo C et al., Vet Microbiol 2013, 162: 32-43
(9) Jancovich J K et al., J Virol 2018, 92(8): e02219-17
(10) Jenson J S et al., J Immunol Methods 2000, 242: 33-42
(11) Lacasta A et al., J Virol 2014, 88: 13322-13332
(12) Lopera-Madrid J et al., Vet Immunol Immunopthol 2017, 185: 20-33
(13) Monteagudo P L et al., J Virol 2017, 91(21): e01058-17
(14) Netherton C L et al., Front Immunol. 2019 (10): 1318
(15) O'Donnell V et al., J Virol 2015, 89: 6048-6056
(16) Rodriguez F et al., J Virol 2001, 75: 7399-7409
(17) Rodriguez J M et al., PLoS One 2015; 10(11): e0142889
(18) Rodriguez F and Whitton J L, Virology 2000, 268: 233-238
(19) Sanchez E G et al., Virus Research 2019, 265: 150-155
(20) Velders M P et al., J Immunol 2001, 166: 5366-5373
(21) Uniprot Database accession number A0A2X0RVA9
(22) WO 2015/091322
(23) WO 2017/096341

The following clauses are also comprised by the scope and spirit of the present invention:
1. An immunogenic composition comprising
(a) one, two or more African swine fever virus peptides and/or polypeptides, preferably full-length proteins, and/or immunogenic fragments thereof; and/or
(b) one, two or more African swine fever virus oligonucleotides and/or polynucleotides and/or immunogenic fragments thereof encoding African swine fever virus peptides and/or polypeptides, preferably full-length proteins, and/or immunogenic fragments thereof; and/or
(c) a viral or bacterial vector, preferably a recombinant and/or non-naturally occurring viral or bacterial vector, comprising one, two or more African swine fever virus oligonucleotides and/or polynucleotides and/or immunogenic fragments thereof encoding African swine fever virus peptides and/or polypeptides, preferably full-length proteins, and/or immunogenic fragments thereof; and
(d) optionally, one or more pharmaceutical- or veterinary-acceptable carriers or excipients, preferably said one or more carriers or excipients being suitable for oral, intradermal, intramuscular or intranasal application.
2. A vaccine or pharmaceutical composition comprising
(a) one, two or more African swine fever virus peptides and/or polypeptides, preferably full-length proteins, and/or immunogenic fragments thereof; and/or
(b) one, two or more African swine fever virus oligonucleotides and/or polynucleotides and/or immunogenic fragments thereof encoding African swine fever virus peptides and/or polypeptides, preferably full-length proteins, and/or immunogenic fragments thereof; and/or
(c) a viral or bacterial vector, preferably a recombinant and/or non-naturally occurring viral or bacterial vector, comprising one, two or more African swine fever virus oligonucleotides and/or polynucleotides and/or immunogenic fragments thereof encoding African swine fever virus peptides and/or polypeptides, preferably full-length proteins, and/or immunogenic fragments thereof; and
(d) one or more pharmaceutical- or veterinary-acceptable carriers or excipients, preferably said one or more carriers or excipients being suitable for oral, intradermal, intramuscular or intranasal application;
(e) optionally, said vaccine or pharmaceutical composition further comprising an adjuvant.
3. The immunogenic composition as disclosed in clause 1 or the vaccine or pharmaceutical composition as disclosed in clause 2, wherein the African swine fever virus is selected from the group consisting of: BA71, BA71ΔCD2 and/or Georgia2007/1 strain(s).
4. The immunogenic composition or the vaccine or pharmaceutical composition as disclosed in any one of clauses 1 to 3, wherein according to (a) the one, two or more African swine fever virus peptides and/or polypeptides, preferably full-length proteins, and/or immunogenic fragments thereof comprise, preferably consist of, an amino acid sequence which is at least 90%, 91%, 92%, 93%, 94%, 95%, 97%, 98%, 99% or 100% identical to an amino acid sequence selected from the group consisting of: SEQ ID NOS: 1, 2, 3, 4, 5, 6, 7, 8, 9, 10, 11, 12, 13, 14, 15, 16, 17, 19, 21, 23, 25, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 1, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 272, 274, 275, 276, 277, 278, 279, 280, 281, 282, 283, 284, 285, 287, 289, 290, 291, 292, 293, 294, 295, 297, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 420, 422, 423, 424, 425, 426, 427, 428, 429, 430, 432, 434, 435, 436, 437, 438, 439, 440, 441, 442, 443, 444, 445, 446, 447, 448, 449, 450, 451, 452, 453, 454, 455, 456, 458, 460, 461, 462, 463, 464, 465, 466, 468, 470, 471, 472, 473, 474, 475, 476, 477, 478, 479, 481, 483, 484, 485, 486, 487, 489, 491, 492, 493, 494, 495, 496, 497, 498, 499, 500, 501, 502, 503, 504, 505, 506, 507, 508, 509, 510, 511, 512, 513, 514, 515, 516, 518, 520, 521, 522, 523, 524, 526, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 568, 570, 572, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 719, 721, 722, 724, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 774, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854.

5. The immunogenic composition or the vaccine or pharmaceutical composition as disclosed in any one of clauses 1 to 3, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 80%, 85%, 90%, 91%, 92%, 93%, 94%, 95%, 97%, 98%, 99% or 100% identical to a nucleic acid sequence selected from the group consisting of: SEQ ID NOS: 18, 20, 22, 24, 26, 27, 270, 271, 273, 286, 288, 296, 298, 419, 421, 431, 433, 457, 459, 467, 469, 480, 482, 488, 490, 517, 519, 525, 527, 567, 569, 571, 573, 718, 720, 723, 725, 773, 775.

6. The immunogenic composition or the vaccine or pharmaceutical composition as disclosed in any one of clauses 1 to 5, wherein according to (c) the viral or bacterial vector is selected from the group consisting of: asfivirus viral vector, avipox virus viral vector, canine morbillivirus viral vector, herpes virus viral vector, varicella virus viral vector, *Lawsonia* spp., *Salmonella* spp.

7. The immunogenic composition or the vaccine or pharmaceutical composition as disclosed in clause 6, wherein the viral or bacterial vector comprises one, two or more African swine fever virus oligonucleotides and/or polynucleotides and/or immunogenic fragments thereof, which encode African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 80%, 85%, 90%, 91%, 92%, 93%, 94%, 95%, 97%, 98%, 99% or 100% identical to a nucleic acid sequence selected from the group consisting of: SEQ ID NOS: 18, 20, 22, 24, 26, 27, 270, 271, 273, 286, 288, 296, 298, 419, 421, 431, 433, 457, 459, 467, 469, 480, 482, 488, 490, 517, 519, 525, 527, 567, 569, 571, 573, 718, 720, 723, 725, 773, 775.

8. The immunogenic composition or the vaccine or pharmaceutical composition as disclosed in any one of clauses 1 to 7, wherein the African swine fever virus polypeptides, preferably full-length proteins, comprise, preferably consist of, an amino acid sequence which is at least 90%, 91%, 92%, 93%, 94%, 95%, 97%, 98%, 99% or 100% identical to an amino acid sequence selected from the group consisting of: SEQ ID NO: 21, SEQ ID NO: 23, SEQ ID NO: 853, SEQ ID NO: 854, SEQ ID NO: 65, SEQ ID NO: 66, SEQ ID NO: 256, SEQ ID NO: 257, SEQ ID NO: 272, SEQ ID NO: 274, SEQ ID NO: 295, SEQ ID NO: 297, SEQ ID NO: 378, SEQ ID NO: 388, SEQ ID NO: 389, SEQ ID NO: 430, SEQ ID NO: 432, SEQ ID NO: 466, SEQ ID NO: 468, SEQ ID NO: 487, SEQ ID NO: 489, SEQ ID NO: 524, SEQ ID NO: 526, SEQ ID NO: 566, SEQ ID NO: 568, SEQ ID NO: 561, SEQ ID NO: 562, SEQ ID NO: 572, SEQ ID NO: 691, SEQ ID NO: 692, SEQ ID NO: 722, SEQ ID NO: 724, SEQ ID NO: 772, SEQ ID NO: 774, SEQ ID NO: 732, SEQ ID NO: 733, SEQ ID NO: 816, SEQ ID NO: 817 and/or wherein the African swine fever virus peptides and/or immunogenic fragments thereof and/or African swine fever virus polypeptide/full-length protein immunogenic fragments comprise, preferably consist of, an amino acid sequence which is at least 90%, 91%, 92%, 93%, 94%, 95%, 97%, 98%, 99% or 100% identical to an amino acid sequence selected from the group consisting of: SEQ ID NO: 17, SEQ ID NO: 19, SEQ ID NO: 25, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249, SEQ ID NO: 250, SEQ ID NO: 251, SEQ ID NO: 252, SEQ ID NO: 253, SEQ ID NO: 254, SEQ ID NO: 255, SEQ ID NO: 261, SEQ ID NO: 262, SEQ ID NO: 263, SEQ ID NO: 264, SEQ ID NO: 265, SEQ ID NO: 266, SEQ ID NO: 258, SEQ ID NO: 259, SEQ ID NO: 260, SEQ ID NO: 267, SEQ ID NO: 268, SEQ ID NO: 269, SEQ ID NO: 281, SEQ ID NO: 282, SEQ ID NO: 283, SEQ ID NO: 284, SEQ ID NO: 285, SEQ ID NO: 287, SEQ ID NO: 289, SEQ ID NO: 290, SEQ ID NO: 291, SEQ ID NO: 292, SEQ ID NO: 293, SEQ ID NO: 294, SEQ ID NO: 372, SEQ ID NO: 373, SEQ ID NO: 374, SEQ ID NO: 375, SEQ ID NO: 376, SEQ ID NO: 377, SEQ ID NO:

379, SEQ ID NO: 380, SEQ ID NO: 381, SEQ ID NO: 382, SEQ ID NO: 383, SEQ ID NO: 384, SEQ ID NO: 385, SEQ ID NO: 386, SEQ ID NO: 387, SEQ ID NO: 416, SEQ ID NO: 417, SEQ ID NO: 418, SEQ ID NO: 420, SEQ ID NO: 422, SEQ ID NO: 423, SEQ ID NO: 424, SEQ ID NO: 425, SEQ ID NO: 426, SEQ ID NO: 427, SEQ ID NO: 428, SEQ ID NO: 429, SEQ ID NO: 454, SEQ ID NO: 455, SEQ ID NO: 456, SEQ ID NO: 458, SEQ ID NO: 460, SEQ ID NO: 461, SEQ ID NO: 462, SEQ ID NO: 463, SEQ ID NO: 464, SEQ ID NO: 465, SEQ ID NO: 478, SEQ ID NO: 479, SEQ ID NO: 481, SEQ ID NO: 483, SEQ ID NO: 484, SEQ ID NO: 485, SEQ ID NO: 486, SEQ ID NO: 514, SEQ ID NO: 515, SEQ ID NO: 516, SEQ ID NO: 518, SEQ ID NO: 520, SEQ ID NO: 521, SEQ ID NO: 522, SEQ ID NO: 523, SEQ ID NO: 563, SEQ ID NO: 564, SEQ ID NO: 565, SEQ ID NO: 539, SEQ ID NO: 540, SEQ ID NO: 541, SEQ ID NO: 542, SEQ ID NO: 543, SEQ ID NO: 544, SEQ ID NO: 545, SEQ ID NO: 546, SEQ ID NO: 547, SEQ ID NO: 548, SEQ ID NO: 549, SEQ ID NO: 550, SEQ ID NO: 551, SEQ ID NO: 552, SEQ ID NO: 553, SEQ ID NO: 554, SEQ ID NO: 555, SEQ ID NO: 556, SEQ ID NO: 557, SEQ ID NO: 558, SEQ ID NO: 559, SEQ ID NO: 560, SEQ ID NO: 570, SEQ ID NO: 684, SEQ ID NO: 685, SEQ ID NO: 686, SEQ ID NO: 687, SEQ ID NO: 688, SEQ ID NO: 689, SEQ ID NO: 690, SEQ ID NO: 717, SEQ ID NO: 719, SEQ ID NO: 721, SEQ ID NO: 726, SEQ ID NO: 727, SEQ ID NO: 728, SEQ ID NO: 729, SEQ ID NO: 730, SEQ ID NO: 731, SEQ ID NO: 801, SEQ ID NO: 802, SEQ ID NO: 803, SEQ ID NO: 804, SEQ ID NO: 805, SEQ ID NO: 806, SEQ ID NO: 807, SEQ ID NO: 808, SEQ ID NO: 809, SEQ ID NO: 810, SEQ ID NO: 811, SEQ ID NO: 812, SEQ ID NO: 813, SEQ ID NO: 814, SEQ ID NO: 815.

9. The immunogenic composition or the vaccine or pharmaceutical composition as disclosed in any one of clauses 1 to 8, wherein the ASFV polypeptide is an ASFV full-length protein, preferably encoded by a polynucleotide sequence comprising, more preferably consisting of, any possible open reading frame (ORF), even more preferably encoded by a polynucleotide sequence comprising, most preferably consisting of, an open reading frame (ORF) with a 5'-end start codon and a 3'-end stop codon.

10. The immunogenic composition or the vaccine or pharmaceutical composition as disclosed in any one of clauses 1 to 9, wherein the immunogenicity (and/or immunological response) of the immunogenic composition or the vaccine or pharmaceutical composition or any comprised immunogenic fragment is indicated/characterized by an induced IFN-gamma response, preferably in a porcine IFN-gamma ELISpot assay.

11. The immunogenic composition or the vaccine or pharmaceutical composition as disclosed in any one of clauses 1 to 10 for use in a method of reducing or preventing the clinical signs or disease in porcines, preferably a pig, caused by an infection with at least one pathogenic African swine fever virus or for use in a method of treating and/or preventing an infection with at least one pathogenic African swine fever virus, wherein preferably said clinical signs or disease caused by an infection with at least one pathogenic African swine fever virus or said infection with at least one pathogenic African swine fever virus are selected from the group consisting of: African swine fever, mortality, death, sudden death, fever, high fever, anorexia, lethargy, weakness, loss of appetite, recumbence, erythema, cyanotic skin blotching, diarrhea, constipation, abdominal pain, respiratory signs, coughing, vomiting, dyspnea, nasal and conjunctival discharges, hemorrhages, epistaxis, abortion, leukopenia, thrombocytopenia.

12. The immunogenic composition or the vaccine or pharmaceutical composition as disclosed in any one of clauses 1 to 10 for use in a method of immunizing a porcine, preferably a pig, against a clinical disease caused by at least one pathogenic African swine fever virus in said porcine, preferably pig, said method comprising the step of administering to the porcine, preferably pig, the immunogenic composition or the vaccine or pharmaceutical composition as claimed in any one of claims 1 to 10, wherein said immunogenic composition or vaccine or pharmaceutical composition fails to cause clinical signs of infection but is capable of inducing an immune response that immunizes the porcine, preferably pig, against pathogenic forms of said at least one African swine fever virus, wherein preferably said clinical disease or said clinical signs of infection are selected from the group consisting of: African swine fever, mortality, death, sudden death, fever, high fever, anorexia, lethargy, weakness, loss of appetite, recumbence, erythema, cyanotic skin blotching, diarrhea, constipation, abdominal pain, respiratory signs, coughing, vomiting, dyspnea, nasal and conjunctival discharges, hemorrhages, epistaxis, abortion, leukopenia, thrombocytopenia.

13. The immunogenic composition or the vaccine or pharmaceutical composition as disclosed in any one of clauses 1 to 10 for use in a method of prime-boost immunizing a porcine, preferably a pig, against a clinical disease caused by at least one pathogenic African swine fever virus in said porcine, preferably pig, said method comprising the step of administering to the porcine, preferably pig, once or twice an immunogenic composition or the vaccine or pharmaceutical composition as disclosed in any one of clauses 1 to 10 comprising (i) one, two or more African swine fever virus oligonucleotides and/or polynucleotides and/or immunogenic fragments thereof as sole immunogenic components or (ii) a viral vector, preferably a recombinant and/or non-naturally occurring viral vector, comprising one, two or more African swine fever virus oligonucleotides and/or polynucleotides and/or immunogenic fragments thereof—as sole immunogenic component (priming step); and subsequently—after priming once or twice—administering to the porcine, preferably pig, a live attenuated African swine fever virus, preferably BA71ΔCD2 (boosting step); wherein said immunogenic composition or vaccine or pharmaceutical composition as well as the live attenuated African swine fever virus independently from each other fail to cause clinical signs of infection but are capable of inducing an immune response that immunizes the porcine, preferably pig, against pathogenic forms of said at least one African swine fever virus, wherein preferably said clinical disease or said clinical signs of infection are selected from the group consisting of: African swine fever, mortality, death, sudden death, fever, high fever, anorexia, lethargy, weakness, loss of appetite, recumbence, erythema, cyanotic skin blotching, diarrhea, constipation, abdominal pain, respiratory signs, coughing, vomiting, dyspnea, nasal and conjunctival discharges, hemorrhages, epistaxis, abortion, leukopenia, thrombocytopenia.

14. A kit for vaccinating a porcine, preferably a pig, against a disease associated with and/or reducing the incidence or the severity of one or more clinical signs associated with or caused by at least one pathogenic African swine fever virus in a porcine, preferably a pig, comprising:
 (a) a dispenser capable of administering a vaccine to said porcine; and
 (b) immunogenic composition or the vaccine or pharmaceutical composition as disclosed in any one of clauses 1 to 10, and
 (c) optionally an instruction leaflet;

wherein preferably said disease or said clinical signs are selected from the group consisting of: African swine fever, mortality, death, sudden death, fever, high fever, anorexia, lethargy, weakness, loss of appetite, recumbence, erythema, cyanotic skin blotching, diarrhea, constipation, abdominal pain, respiratory signs, coughing, vomiting, dyspnea, nasal and conjunctival discharges, hemorrhages, epistaxis, abortion, leukopenia, thrombocytopenia.

15. An African swine fever virus peptide and/or polypeptide, preferably full-length-protein, and/or immunogenic fragment thereof comprising, preferably consisting of, an amino acid sequence, which is at least 90%, 91%, 92%, 93%, 94%, 95%, 97%, 98%, 99% or 100% identical to an amino acid sequence selected from the group consisting of: SEQ ID NOS: 1, 2, 3, 4, 5, 6, 7, 8, 9, 10, 11, 12, 13, 14, 15, 16, 17, 19, 21, 23, 25, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 1, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 272, 274, 275, 276, 277, 278, 279, 280, 281, 282, 283, 284, 285, 287, 289, 290, 291, 292, 293, 294, 295, 297, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 420, 422, 423, 424, 425, 426, 427, 428, 429, 430, 432, 434, 435, 436, 437, 438, 439, 440, 441, 442, 443, 444, 445, 446, 447, 448, 449, 450, 451, 452, 453, 454, 455, 456, 458, 460, 461, 462, 463, 464, 465, 466, 468, 470, 471, 472, 473, 474, 475, 476, 477, 478, 479, 481, 483, 484, 485, 486, 487, 489, 491, 492, 493, 494, 495, 496, 497, 498, 499, 500, 501, 502, 503, 504, 505, 506, 507, 508, 509, 510, 511, 512, 513, 514, 515, 516, 518, 520, 521, 522, 523, 524, 526, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 568, 570, 572, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 719, 721, 722, 724, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 774, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854.

16. The African swine fever virus peptide and/or polypeptide, preferably full-length-protein, and/or immunogenic fragment thereof as disclosed in clause 15, wherein the African swine fever virus polypeptides, preferably full-length proteins, comprise, preferably consist of, an amino acid sequence which is at least 90%, 91%, 92%, 93%, 94%, 95%, 97%, 98%, 99% or 100% identical to an amino acid sequence selected from the group consisting of: SEQ ID NO: 21, SEQ ID NO: 23, SEQ ID NO: 853, SEQ ID NO: 854, SEQ ID NO: 65, SEQ ID NO: 66, SEQ ID NO: 256, SEQ ID NO: 257, SEQ ID NO: 272, SEQ ID NO: 274, SEQ ID NO: 295, SEQ ID NO: 297, SEQ ID NO: 378, SEQ ID NO: 388, SEQ ID NO: 389, SEQ ID NO: 430, SEQ ID NO: 432, SEQ ID NO: 466, SEQ ID NO: 468, SEQ ID NO: 487, SEQ ID NO: 489, SEQ ID NO: 524, SEQ ID NO: 526, SEQ ID NO: 566, SEQ ID NO: 568, SEQ ID NO: 561, SEQ ID NO: 562, SEQ ID NO: 572, SEQ ID NO: 691, SEQ ID NO: 692, SEQ ID NO: 722, SEQ ID NO: 724, SEQ ID NO: 772, SEQ ID NO: 774, SEQ ID NO: 732, SEQ ID NO: 733, SEQ ID NO: 816, SEQ ID NO: 817 and/or wherein the African swine fever virus peptides and/or immunogenic fragments thereof and/or African swine fever virus polypeptide/full-length protein immunogenic fragments comprise, preferably consist of, an amino acid sequence which is at least 90%, 91%, 92%, 93%, 94%, 95%, 97%, 98%, 99% or 100% identical to an amino acid sequence selected from the group consisting of: SEQ ID NO: 17, SEQ ID NO: 19, SEQ ID NO: 25, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249, SEQ ID NO: 250, SEQ ID NO: 251, SEQ ID NO: 252, SEQ ID NO: 253, SEQ ID NO: 254, SEQ ID NO: 255, SEQ ID NO: 261, SEQ ID NO: 262, SEQ ID NO: 263, SEQ ID NO: 264, SEQ ID NO: 265, SEQ ID NO: 266, SEQ ID NO: 258, SEQ ID NO: 259, SEQ ID NO: 260, SEQ ID NO: 267, SEQ ID NO: 268, SEQ ID NO: 269, SEQ ID NO: 281, SEQ ID NO: 282, SEQ ID NO: 283, SEQ ID NO: 284, SEQ ID NO: 285, SEQ ID NO: 287, SEQ ID NO: 289, SEQ ID NO: 290, SEQ ID NO: 291, SEQ ID NO: 292, SEQ ID NO: 293, SEQ ID NO: 294, SEQ ID NO: 372, SEQ ID NO: 373, SEQ ID NO: 374, SEQ ID NO: 375, SEQ ID NO: 376, SEQ ID NO: 377, SEQ ID NO: 379, SEQ ID NO: 380, SEQ ID NO: 381, SEQ ID NO: 382, SEQ ID NO: 383, SEQ ID NO: 384, SEQ ID NO: 385, SEQ ID NO: 386, SEQ ID NO: 387, SEQ ID NO: 416, SEQ ID NO: 417, SEQ ID NO: 418, SEQ ID NO: 420, SEQ ID NO: 422, SEQ ID NO: 423, SEQ ID NO: 424, SEQ ID NO: 425, SEQ ID NO: 426, SEQ ID NO: 427, SEQ ID NO: 428, SEQ ID NO: 429, SEQ ID NO: 454, SEQ ID NO: 455, SEQ ID NO: 456, SEQ ID NO: 458, SEQ ID NO: 460, SEQ ID NO: 461, SEQ ID NO: 462, SEQ ID NO: 463, SEQ ID NO: 464, SEQ ID NO: 465, SEQ ID NO: 478, SEQ ID NO: 479, SEQ ID NO: 481, SEQ ID NO: 483, SEQ ID NO: 484, SEQ ID NO: 485, SEQ ID NO: 486, SEQ ID NO: 514, SEQ ID NO: 515, SEQ ID NO: 516, SEQ ID NO: 518, SEQ ID NO: 520, SEQ ID NO: 521, SEQ ID NO: 522, SEQ ID NO: 523, SEQ ID NO: 563, SEQ ID NO: 564, SEQ ID NO: 565, SEQ ID NO: 539, SEQ ID NO: 540, SEQ ID NO: 541, SEQ ID NO: 542, SEQ ID NO: 543, SEQ ID NO: 544, SEQ ID NO: 545, SEQ ID NO: 546, SEQ ID NO: 547, SEQ ID NO: 548, SEQ ID NO: 549, SEQ ID NO: 550, SEQ ID NO: 551, SEQ ID NO: 552, SEQ ID NO: 553, SEQ ID NO: 554, SEQ ID NO: 555, SEQ ID NO: 556, SEQ ID NO: 557, SEQ ID NO: 558, SEQ ID NO: 559, SEQ ID NO: 560, SEQ ID NO: 570, SEQ ID NO: 684, SEQ ID NO: 685, SEQ ID NO: 686, SEQ ID NO: 687, SEQ ID NO: 688, SEQ ID NO: 689, SEQ ID NO: 690, SEQ ID NO: 717, SEQ ID NO: 719, SEQ ID NO: 721, SEQ ID NO: 726, SEQ ID NO: 727, SEQ ID NO: 728, SEQ ID NO: 729, SEQ ID NO: 730, SEQ ID NO: 731, SEQ ID NO: 801, SEQ ID NO: 802, SEQ ID NO: 803, SEQ ID NO: 804, SEQ ID NO: 805, SEQ ID NO: 806, SEQ ID NO: 807, SEQ ID NO: 808, SEQ ID NO: 809, SEQ ID NO: 810, SEQ ID NO: 811, SEQ ID NO: 812, SEQ ID NO: 813, SEQ ID NO: 814, SEQ ID NO: 815.

17. An African swine fever virus oligonucleotide and/or polynucleotide and/or immunogenic fragment thereof encoding the African swine fever virus peptide and/or polypeptide, preferably full-length-protein, and/or immunogenic fragment thereof as disclosed in clause 16.

18. An African swine fever virus oligonucleotide and/or polynucleotide and/or immunogenic fragment thereof encoding African swine fever virus peptides and/or polypeptides, preferably full-length proteins, and/or immunogenic fragments thereof; comprising, preferably consisting of, a nucleic acid sequence which is at least 80%, 85%, 90%, 91%, 92%, 93%, 94%, 95%, 97%, 98%, 99% or 100% identical to a nucleic acid sequence selected from the group consisting of: SEQ ID NOS: 18, 20, 22, 24, 26, 27, 270, 271, 273, 286, 288, 296, 298, 419, 421, 431, 433, 457, 459, 467, 469, 480, 482, 488, 490, 517, 519, 525, 527, 567, 569, 571, 573, 718, 720, 723, 725, 773, 775.

19. The African swine fever virus peptide and/or polypeptide, preferably full-length-protein, and/or immunogenic fragment thereof as disclosed in any one of clauses 15 to 16 or the African swine fever virus oligonucleotide and/or polynucleotide and/or immunogenic fragment thereof encoding African swine fever virus peptide and/or polypeptide, preferably full-length-protein, and/or immunogenic fragments thereof as disclosed in any one of clauses 17 to 18, wherein the immunogenicity (and/or immunological response) of the immunogenic composition or the vaccine or pharmaceutical composition or any comprised immunogenic fragment is indicated/characterized by an induced IFN-gamma response, preferably in a porcine IFN-gamma ELISpot assay.

20. The African swine fever virus peptide and/or polypeptide, preferably full-length-protein, and/or immunogenic fragment thereof as disclosed in any one of clauses 15 to 16 or the African swine fever virus oligonucleotide and/or polynucleotide and/or immunogenic fragment thereof encoding African swine fever virus peptide and/or polypeptide, preferably full-length-protein, and/or immunogenic fragments thereof as disclosed in any one of clauses 17 to 18, wherein the ASFV polypeptide is an ASFV full-length protein, preferably encoded by a polynucleotide sequence comprising, more preferably consisting of, any possible open reading frame (ORF), even more preferably encoded by a polynucleotide sequence comprising, most preferably consisting of, an open reading frame (ORF) with a 5'-end start codon and a 3'-end stop codon.

21. A vector, preferably an expression vector, comprising one, two, three or more African swine fever virus oligonucleotides and/or polynucleotides and/or immunogenic fragments thereof as disclosed in any one of clauses 17 to 18.

22. The vector as disclosed in clause 21 comprising three African swine fever virus oligonucleotides and/or polynucleotides and/or immunogenic fragments thereof, preferably selected from EP402R, CP312R and A240L (multi-epitope-I, ME-I), more preferably comprising, most preferably consisting of, the nucleic acid sequence selected from the group consisting of: SEQ ID NO: 855; or comprising thirteen African swine fever virus oligonucleotides and/or polynucleotides and/or immunogenic fragments thereof, preferably selected from D1133L, G1211R, M1249L, MGF505-9R, P1192R, CP2475L (p150), B475L, EP424R, H339R, I226R, K145R, MGF505-1R and CP2475L (p37) (multiepitope-II, ME-II), more preferably comprising, most preferably consisting of, the nucleic acid sequence selected from the group consisting of: SEQ ID NO: 856.

23. A host cell, preferably a mammalian host cell, comprising the vector as disclosed in any one of clauses 21 to 22.

The following additional clauses are also comprised by the scope and spirit of the present invention:

24. An immunogenic composition comprising
   (a) one, two or more African swine fever virus peptides and/or polypeptides, preferably full-length proteins, and/or immunogenic fragments thereof; and/or
   (b) one, two or more African swine fever virus oligonucleotides and/or polynucleotides and/or immunogenic fragments thereof encoding African swine fever virus peptides and/or polypeptides, preferably full-length proteins, and/or immunogenic fragments thereof; and/or
   (c) a viral or bacterial vector, preferably a recombinant and/or non-naturally occurring viral or bacterial vector, comprising one, two or more African swine fever virus oligonucleotides and/or polynucleotides and/or immunogenic fragments thereof encoding African swine fever virus peptides and/or polypeptides, preferably full-length proteins, and/or immunogenic fragments thereof; and
   (d) optionally, one or more pharmaceutical- or veterinary-acceptable carriers or excipients, preferably said one or more carriers or excipients being suitable for oral, intradermal, intramuscular or intranasal application.

25. A vaccine or pharmaceutical composition comprising
   (a) one, two or more African swine fever virus peptides and/or polypeptides, preferably full-length proteins, and/or immunogenic fragments thereof; and/or
   (b) one, two or more African swine fever virus oligonucleotides and/or polynucleotides and/or immunogenic fragments thereof encoding African swine fever virus peptides and/or polypeptides, preferably full-length proteins, and/or immunogenic fragments thereof; and/or
   (c) a viral or bacterial vector, preferably a recombinant and/or non-naturally occurring viral or bacterial vector, comprising one, two or more African swine fever virus oligonucleotides and/or polynucleotides and/or immunogenic fragments thereof encoding African swine fever virus peptides and/or polypeptides, preferably full-length proteins, and/or immunogenic fragments thereof; and (d) one or more pharmaceutical- or veterinary-acceptable carriers or excipients, preferably said one or more carriers or excipients being suitable for oral, intradermal, intramuscular or intranasal application;

(e) optionally, said vaccine or pharmaceutical composition further comprising an adjuvant.

26. The immunogenic composition as disclosed in clause 24 or the vaccine or pharmaceutical composition as disclosed in clause 25, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: MGF505-7R/MGF505-8R (SEQ ID NOS: 774, 772, 724, 722, 721, 719, 717), M448R (SEQ ID NOS: 568, 566, 565, 564, 563), D1133L (SEQ ID NOS: 297, 295, 294, 293, 292, 291, 290, 289, 287, 285, 284, 283, 282, 281), CP312R (SEQ ID NOS: 274, 272, 269, 268, 267), A240L (SEQ ID NOS: 854, 853, 25), A238L (SEQ ID NOS: 23, 21, 19, 17), MGF100-1L (SEQ ID NOS: 572, 570), K145R (SEQ ID NOS: 526, 524, 523, 522, 521, 520, 518, 516, 515, 514), B475L (SEQ ID NOS: 66, 65, 64, 63, 62, 61, 60, 59, 58, 57, 56, 55, 54, 53, 52, 51, 50, 49, 48), H339R (SEQ ID NOS: 468, 466, 465, 464, 463, 462, 461, 460, 458, 456, 455, 454), I226R (SEQ ID NOS: 489, 487, 486, 485, 484, 483, 481, 479, 478), CP2475L (p37) (SEQ ID NOS: 266, 265, 264, 263, 262, 261), CP2475L (p150) (SEQ ID NOS: 260, 259, 258), G1211R (SEQ ID NOS: 432, 430, 429, 428, 427, 426, 425, 424, 423, 422, 420, 418, 417, 416), M1249L (SEQ ID NOS: 562, 561, 560, 559, 558, 557, 556, 555, 554, 553, 552, 551, 550, 549, 548, 547, 546, 545, 544, 543, 542, 541, 540, 539), MGF505-9R (SEQ ID NOS: 733, 732, 731, 730, 729, 728, 727, 726), P1192R (SEQ ID NOS: 817, 816, 815, 814, 813, 812, 811, 810, 809, 808, 807, 806, 805, 804, 803, 802, 801), MGF505-1R (SEQ ID NOS: 692, 691, 690, 689, 688, 687, 686, 685, 684), MGF505-3R (SEQ ID NOS: 703, 702, 701, 700, 699), EP424R (SEQ ID NOS: 389, 388, 387, 386, 385, 384, 383, 382, 381, 380, 379), C475L (SEQ ID NOS: 201, 200, 199, 198, 197, 196, 195, 194, 193, 192, 191, 190, 189, 188), B602L (SEQ ID NOS: 75, 74, 73, 72, 71, 70, 69, 68, 67), CP530R (SEQ ID NOS: 278, 277, 276, 275), D339L (SEQ ID NOS: 322, 321, 320), D117L (SEQ ID NOS: 862, 864), I243L (SEQ ID NOS: 494, 493, 492, 491), I73R (SEQ ID NOS: 504, 503, 502), DP238L (SEQ ID NOS: 327, 326, 325), 19R (SEQ ID NOS: 513, 512, 511, 510), preferably selected from the group consisting of: MGF505-7R/ MGF505-8R (SEQ ID NOS: 774, 772, 724, 722, 721, 719, 717), M448R (SEQ ID NOS: 568, 566, 565, 564, 563), D1133L (SEQ ID NOS: 297, 295, 294, 293, 292, 291, 290, 289, 287, 285, 284, 283, 282, 281), CP312R (SEQ ID NOS: 274, 272, 269, 268, 267), A240L (SEQ ID NOS: 854, 853, 25), A238L (SEQ ID NOS: 23, 21, 19, 17), MGF100-1L (SEQ ID NOS: 572, 570); and most preferably selected from the group consisting of: MGF505-7R/MGF505-8R (SEQ ID NOS: 774, 772, 724, 722, 721, 719, 717), M448R (SEQ ID NOS: 568, 566, 565, 564, 563), D1133L (SEQ ID NOS: 297, 295, 294, 293, 292, 291, 290, 289, 287, 285, 284, 283, 282, 281), CP312R (SEQ ID NOS: 274, 272, 269, 268, 267), A240L (SEQ ID NOS: 854, 853, 25).

27. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: MGF505-7R/MGF505-8R (SEQ ID NOS: 774, 772, 724, 722, 721, 719, 717).

28. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: MGF505-7R (SEQ ID NO: 774).

29. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: MGF505-8R (SEQ ID NO: 772).

30. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: MGF505-7R (SEQ ID NO: 724).

31. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: MGF505-8R (SEQ ID NO: 722).

32. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: MGF505-7R (SEQ ID NO: 721).

33. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: MGF505-7R (SEQ ID NO: 719).

34. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: MGF505-8R (SEQ ID NO: 717).

35. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: M448R (SEQ ID NOS: 568, 566, 565, 564, 563).

36. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: M448R (SEQ ID NO: 568).

37. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: M448R (SEQ ID NO: 566).

38. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: M448R (SEQ ID NO: 565).

39. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: M448R (SEQ ID NO: 564).

40. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: M448R (SEQ ID NO: 563).

41. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NOS: 297, 295, 294, 293, 292, 291, 290, 289, 287, 285, 284, 283, 282, 281).

42. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 297).

43. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 295).

44. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 294).

45. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 293).

46. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 292).

47. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 291).

48. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 290).

49. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 289).

50. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 287).

51. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 285).

52. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 284).

53. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 283).

54. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 282).

55. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 281).

56. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: CP312R (SEQ ID NOS: 274, 272, 269, 268, 267).

57. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: CP312R (SEQ ID NO: 274).

58. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: CP312R (SEQ ID NO: 272).

59. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: CP312R (SEQ ID NO: 269).

60. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: CP312R (SEQ ID NO: 268).

61. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: CP312R (SEQ ID NO: 267).

62. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: A240L (SEQ ID NOS: 854, 853, 25).

63. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: A240L (SEQ ID NO: 854).

64. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: A240L (SEQ ID NO: 853).

65. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: A240L (SEQ ID NO: 25).

66. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: A238L (SEQ ID NOS: 23, 21, 19, 17).

67. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: A238L (SEQ ID NO: 23).

68. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: A238L (SEQ ID NO: 21).

69. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: A238L (SEQ ID NO: 19).

70. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: A238L (SEQ ID NO: 17).

71. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: MGF100-1L (SEQ ID NOS: 572, 570).

72. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: MGF100-1L (SEQ ID NO: 572).

73. The immunogenic composition or the vaccine or pharmaceutical composition as disclosed in clause 26, wherein according to (a) the one, two or more African swine fever virus peptides and/or polypeptides, preferably full-length proteins, and/or immunogenic fragments thereof comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: MGF100-1L (SEQ ID NOS: 570).

74. The immunogenic composition or the vaccine or pharmaceutical composition as disclosed in any one of clauses 24 to 73, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: MGF505-7R/MGF505-8R (SEQ ID NOS: 774, 772, 724, 722, 721, 719, 717), M448R (SEQ ID NOS: 568, 566, 565, 564, 563), D1133L (SEQ ID NOS: 297, 295, 294, 293, 292, 291, 290, 289, 287, 285, 284, 283, 282, 281), CP312R (SEQ ID NOS: 274, 272, 269, 268, 267), A240L (SEQ ID NOS: 854, 853, 25), A238L (SEQ ID NOS: 23, 21, 19, 17), MGF100-1L (SEQ ID NOS: 572, 570), K145R (SEQ ID NOS: 526, 524, 523, 522, 521, 520, 518, 516, 515, 514), B475L (SEQ ID NOS: 66, 65, 64, 63, 62, 61, 60, 59, 58, 57, 56, 55, 54, 53, 52, 51, 50, 49, 48), H339R (SEQ ID NOS: 468, 466, 465, 464, 463, 462, 461, 460, 458, 456, 455, 454), I226R (SEQ ID NOS: 489, 487, 486, 485, 484, 483, 481, 479, 478), CP2475L (p37) (SEQ ID NOS: 266, 265, 264, 263, 262, 261), CP2475L (p150) (SEQ ID NOS: 260, 259, 258), G1211R (SEQ ID NOS: 432, 430, 429, 428, 427, 426, 425, 424, 423, 422, 420, 418, 417, 416), M1249L (SEQ ID NOS: 562, 561, 560, 559, 558, 557, 556, 555, 554, 553, 552, 551, 550, 549, 548, 547, 546, 545, 544, 543, 542, 541, 540, 539), MGF505-9R (SEQ ID NOS: 733, 732, 731, 730, 729, 728, 727, 726), P1192R (SEQ ID NOS: 817, 816, 815, 814, 813, 812, 811, 810, 809, 808, 807, 806, 805, 804, 803, 802, 801), MGF505-1R (SEQ ID NOS: 692, 691, 690, 689, 688, 687, 686, 685, 684), MGF505-3R (SEQ ID NOS: 703, 702, 701, 700, 699), EP424R (SEQ ID NOS: 389, 388, 387, 386, 385, 384, 383, 382, 381, 380, 379), C475L (SEQ ID NOS: 201, 200, 199, 198, 197, 196, 195, 194, 193, 192, 191, 190, 189, 188), B602L (SEQ ID NOS: 75, 74, 73, 72, 71, 70, 69, 68, 67), CP530R (SEQ ID NOS: 278, 277, 276, 275), D339L (SEQ ID NOS: 322, 321, 320), D117L (SEQ ID NOS: 862, 864), I243L (SEQ ID NOS: 494, 493, 492, 491), I73R (SEQ ID NOS: 504, 503, 502), DP238L (SEQ ID NOS: 327, 326, 325), I9R (SEQ ID NOS: 513, 512, 511, 510), preferably selected from the group consisting of: MGF505-7R/MGF505-8R (SEQ ID NOS: 774, 772, 724, 722, 721, 719, 717), M448R (SEQ ID NOS: 568, 566, 565, 564, 563), D1133L (SEQ ID NOS: 297, 295, 294, 293, 292, 291, 290, 289, 287, 285, 284, 283, 282, 281), CP312R (SEQ ID NOS: 274, 272, 269, 268, 267), A240L (SEQ ID NOS: 854, 853, 25), A238L (SEQ ID NOS: 23, 21, 19, 17), MGF100-1L (SEQ ID NOS: 572, 570); and most preferably selected from the group consisting of: MGF505-7R/MGF505-8R (SEQ ID NOS: 774, 772, 724, 722, 721, 719, 717), M448R (SEQ ID NOS: 568, 566, 565, 564, 563), D1133L (SEQ ID NOS: 297, 295, 294, 293, 292, 291, 290, 289, 287, 285, 284, 283, 282, 281), CP312R (SEQ ID NOS: 274, 272, 269, 268, 267), A240L (SEQ ID NOS: 854, 853, 25).

75. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: MGF505-7R/MGF505-8R (SEQ ID NOS: 774, 772, 724, 722, 721, 719, 717).

76. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: MGF505-7R (SEQ ID NO: 774).

77. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: MGF505-8R (SEQ ID NO: 772).

78. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: MGF505-7R (SEQ ID NO: 724).

79. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: MGF505-8R (SEQ ID NO: 722).

80. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: MGF505-7R (SEQ ID NO: 721).

81. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: MGF505-7R (SEQ ID NO: 719).

82. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: MGF505-8R (SEQ ID NO: 717).

83. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: M448R (SEQ ID NOS: 568, 566, 565, 564, 563).

84. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: M448R (SEQ ID NO: 568).

85. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: M448R (SEQ ID NO: 566).

86. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: M448R (SEQ ID NO: 565).

87. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: M448R (SEQ ID NO: 564).

88. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: M448R (SEQ ID NO: 563).

89. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NOS: 297, 295, 294, 293, 292, 291, 290, 289, 287, 285, 284, 283, 282, 281).

90. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 297).

91. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 295).

92. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 294).

93. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 293).

94. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 292).

95. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 291).

96. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 290).

97. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 289).

98. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 287).

99. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 285).

100. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 284).

101. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 283).

102. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 282).

103. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 281).

104. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: CP312R (SEQ ID NOS: 274, 272, 269, 268, 267).

105. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: CP312R (SEQ ID NO: 274).

106. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: CP312R (SEQ ID NO: 272).

107. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: CP312R (SEQ ID NO: 269).

108. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: CP312R (SEQ ID NO: 268).

109. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: CP312R (SEQ ID NO: 267).

110. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: A240L (SEQ ID NOS: 854, 853, 25).

111. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: A240L (SEQ ID NO: 854).

112. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: A240L (SEQ ID NO: 853).

113. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: A240L (SEQ ID NO: 25).

114. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: A238L (SEQ ID NOS: 23, 21, 19, 17).

115. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: A238L (SEQ ID NO: 23).

116. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: A238L (SEQ ID NO: 21).

117. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: A238L (SEQ ID NO: 19).

118. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: A238L (SEQ ID NO: 17).

119. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: MGF100-1L (SEQ ID NOS: 572, 570).

120. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: MGF100-1L (SEQ ID NO: 572).

121. The immunogenic composition or the vaccine or pharmaceutical composition as disclosed in clause 74, wherein according to (b) the one, two or more African swine fever virus oligonucleotides and/or polynucleotides and/or immunogenic fragments thereof encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: MGF100-1L (SEQ ID NOS: 570).

122. The immunogenic composition or the vaccine or pharmaceutical composition as disclosed in any one of clauses 24 to 121, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF505-7R/MGF505-8R (SEQ ID NOS: 857, 775, 773, 725, 723, 720, 718), M448R (SEQ ID NOS: 858, 569, 567), D1133L (SEQ ID NOS: 859, 298, 296, 288, 286), CP312R (SEQ ID NOS: 861, 273, 901, 900, 271, 270), A240L (SEQ ID NOS: 860, 27, 26), A238L (SEQ ID NOS: 24, 22, 20, 18), MGF100-1L (SEQ ID NOS: 573, 571), K145R (SEQ ID NOS: 527, 525, 519, 517), B475L (SEQ ID NOS: 866, 867), H339R (SEQ ID NOS: 469, 467, 459, 457), I226R (SEQ ID NOS: 490, 488, 482, 480), CP2475L (p37) (SEQ ID NOS: 868, 869), CP2475L (p150) (SEQ ID NOS: 870, 871), G1211R (SEQ ID NOS: 433, 431, 421, 419), M1249L (SEQ ID NOS: 872, 873), MGF505-9R (SEQ ID NOS: 874, 875), P1192R (SEQ ID NOS: 876, 877), MGF505-1R (SEQ ID NOS: 878, 879), MGF505-3R (SEQ ID NOS: 880, 881), EP424R (SEQ ID NOS: 882, 883), C475L (SEQ ID NOS: 884, 885), B602L (SEQ ID NOS: 886, 887), CP530R (SEQ ID NOS: 888, 889), D339L (SEQ ID NOS: 890, 891), D117L (SEQ ID NOS: 863, 865), I243L (SEQ ID NOS: 892, 893), I73R (SEQ ID NOS: 894, 895), DP238L (SEQ ID NOS: 896, 897), I9R (SEQ ID NOS: 898, 899), preferably selected from the group consisting of: MGF505-7R/MGF505-8R (SEQ ID NOS: 857, 775, 773, 725, 723, 720, 718), M448R (SEQ ID NOS: 858, 569, 567), D1133L (SEQ ID NOS: 859, 298, 296, 288, 286), CP312R (SEQ ID NOS: 861, 273, 901, 900, 271, 270), A240L (SEQ ID NOS: 860, 27, 26), A238L (SEQ ID NOS: 24, 22, 20, 18), MGF100-1L (SEQ ID NOS: 573, 571); and most preferably selected from the group consisting of: MGF505-7R/MGF505-8R (SEQ ID NOS: 857, 775, 773, 725, 723, 720, 718), M448R (SEQ ID NOS: 858, 569, 567), D1133L (SEQ ID NOS: 859, 298, 296, 288, 286), CP312R (SEQ ID NOS: 861, 273, 901, 900, 271, 270), A240L (SEQ ID NOS: 860, 27, 26).

123. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF505-7R/MGF505-8R (SEQ ID NOS: 857, 775, 773, 725, 723, 720, 718).

124. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF505-7R (SEQ ID NO: 857).

125. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF505-7R (SEQ ID NO: 775).

126. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF505-8R (SEQ ID NO: 773).

127. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF505-7R (SEQ ID NO: 725).

128. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF505-8R (SEQ ID NO: 723).

129. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF505-7R (SEQ ID NO: 720).

130. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF505-8R (SEQ ID NO: 718).

131. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: M448R (SEQ ID NOS: 858, 569, 567).

132. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: M448R (SEQ ID NO: 858).

133. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: M448R (SEQ ID NO: 569).

134. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: M448R (SEQ ID NO: 567).

135. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: D1133L (SEQ ID NOS: 859, 298, 296, 288, 286).

136. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: D1133L (SEQ ID NO: 859).

137. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: D1133L (SEQ ID NO: 298).

138. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: D1133L (SEQ ID NO: 296).

139. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: D1133L (SEQ ID NO: 288).

140. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: D1133L (SEQ ID NO: 286).

141. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: CP312R (SEQ ID NOS: 861, 273, 901, 900, 271, 270).

142. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: CP312R (SEQ ID NO: 861).

143. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: CP312R (SEQ ID NO: 273).

144. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: CP312R (SEQ ID NO: 901, 271).

145. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: CP312R (SEQ ID NO: 900, 270).

146. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: A240L (SEQ ID NOS: 860, 27, 26).

147. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: A240L (SEQ ID NO: 860).

148. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: A240L (SEQ ID NO: 27).

149. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: A240L (SEQ ID NO: 26).

150. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: A238L (SEQ ID NOS: 24, 22, 20, 18).

151. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: A238L (SEQ ID NO: 24).

152. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: A238L (SEQ ID NO: 22).

153. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: A238L (SEQ ID NO: 20).

154. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: A238L (SEQ ID NO: 18).

155. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF100-1L (SEQ ID NOS: 573, 571).

156. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF100-1L (SEQ ID NO: 573).

157. The immunogenic composition or the vaccine or pharmaceutical composition as disclosed in clause 122, wherein according to (b) the one, two or more African swine fever virus oligonucleotides and/or polynucleotides and/or immunogenic fragments thereof encoding African swine fever virus peptides and/or polypeptides, preferably full-length proteins, and/or immunogenic fragments thereof; comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF100-1L (SEQ ID NO: 571).

158. The immunogenic composition or the vaccine or pharmaceutical composition as disclosed in any one of clauses 24 to 157, wherein according to (c) the viral or bacterial vector is selected from the group consisting of: asfivirus viral vector, avipox virus viral vector, canine morbillivirus viral vector, herpes virus viral vector, varicella virus viral vector, *Lawsonia* spp., *Salmonella* spp.

159. The immunogenic composition or the vaccine or pharmaceutical composition as disclosed in any one of clauses 24 to 158, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: MGF505-7R/MGF505-8R (SEQ ID NOS: 774, 772, 724, 722, 721, 719, 717), M448R (SEQ ID NOS: 568, 566, 565, 564, 563), D1133L (SEQ ID NOS: 297, 295, 294, 293, 292, 291, 290, 289, 287, 285, 284, 283, 282, 281), CP312R (SEQ ID NOS: 274, 272, 269, 268, 267), A240L (SEQ ID NOS: 854, 853, 25), A238L (SEQ ID NOS: 23, 21, 19, 17), MGF100-1L (SEQ ID NOS: 572, 570), K145R (SEQ ID NOS: 526, 524, 523, 522, 521, 520, 518, 516, 515, 514), B475L (SEQ ID NOS: 66, 65, 64, 63, 62, 61, 60, 59, 58, 57, 56, 55, 54, 53, 52, 51, 50, 49, 48), H339R (SEQ ID NOS: 468, 466, 465, 464, 463, 462, 461, 460, 458, 456, 455, 454), I226R (SEQ ID NOS: 489, 487, 486, 485, 484, 483, 481, 479, 478), CP2475L (p37) (SEQ ID NOS: 266, 265, 264, 263, 262, 261), CP2475L (p150) (SEQ ID NOS: 260, 259, 258), G1211R (SEQ ID NOS: 432, 430, 429, 428, 427, 426, 425, 424, 423, 422, 420, 418, 417, 416), M1249L (SEQ ID NOS: 562, 561, 560, 559, 558, 557, 556, 555, 554, 553, 552, 551, 550, 549, 548, 547, 546, 545, 544, 543, 542, 541, 540, 539), MGF505-9R (SEQ ID NOS: 733, 732, 731, 730, 729, 728, 727, 726), P1192R (SEQ ID NOS: 817, 816, 815, 814, 813, 812, 811, 810, 809, 808, 807, 806, 805, 804, 803, 802, 801), MGF505-1R (SEQ ID NOS: 692, 691, 690, 689, 688, 687, 686, 685, 684), MGF505-3R (SEQ ID NOS: 703, 702, 701, 700, 699), EP424R (SEQ ID NOS: 389, 388, 387, 386, 385, 384, 383, 382, 381, 380, 379), C475L (SEQ ID NOS: 201, 200, 199, 198, 197, 196, 195, 194, 193, 192, 191, 190, 189, 188), B602L (SEQ ID NOS: 75, 74, 73, 72, 71, 70, 69, 68, 67), CP530R (SEQ ID NOS: 278, 277, 276, 275), D339L (SEQ ID NOS: 322, 321, 320), D117L (SEQ ID NOS: 862, 864), I243L (SEQ ID NOS: 494, 493, 492, 491), I73R (SEQ ID NOS: 504, 503, 502), DP238L (SEQ ID NOS: 327, 326, 325), 19R (SEQ ID NOS: 513, 512, 511, 510), preferably selected from the group consisting of: MGF505-7R/MGF505-8R (SEQ ID NOS: 774, 772, 724, 722, 721, 719, 717), M448R (SEQ ID NOS: 568, 566, 565, 564, 563), D1133L (SEQ ID NOS: 297, 295, 294, 293, 292, 291, 290, 289, 287, 285, 284, 283, 282, 281), CP312R (SEQ ID NOS: 274, 272, 269, 268, 267), A240L (SEQ ID NOS: 854, 853, 25), A238L (SEQ ID NOS: 23, 21, 19, 17), MGF100-1L (SEQ ID NOS: 572, 570); and most preferably selected from the group consisting of: MGF505-7R/MGF505-8R (SEQ ID NOS: 774, 772, 724, 722, 721, 719, 717), M448R (SEQ ID NOS: 568, 566, 565, 564, 563), D1133L (SEQ ID NOS: 297, 295, 294, 293, 292, 291, 290, 289, 287, 285, 284, 283, 282, 281), CP312R (SEQ ID NOS: 274, 272, 269, 268, 267), A240L (SEQ ID NOS: 854, 853, 25).

160. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: MGF505-7R/MGF505-8R (SEQ ID NOS: 774, 772, 724, 722, 721, 719, 717).

161. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: MGF505-7R (SEQ ID NO: 774).

162. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: MGF505-8R (SEQ ID NO: 772).

163. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: MGF505-7R (SEQ ID NO: 724).

164. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: MGF505-8R (SEQ ID NO: 722).

165. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: MGF505-7R (SEQ ID NO: 721).

166. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: MGF505-7R (SEQ ID NO: 719).

167. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: MGF505-8R (SEQ ID NO: 717).

168. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: M448R (SEQ ID NOS: 568, 566, 565, 564, 563).

169. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: M448R (SEQ ID NO: 568).

170. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: M448R (SEQ ID NO: 566).

171. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: M448R (SEQ ID NO: 565).

172. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: M448R (SEQ ID NO: 564).

173. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: M448R (SEQ ID NO: 563).

174. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NOS: 297, 295, 294, 293, 292, 291, 290, 289, 287, 285, 284, 283, 282, 281).

175. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 297).

176. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 295).

177. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 294).

178. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 293).

179. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 292).

180. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 291).

181. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 290).

182. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 289).

183. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 184. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 285).

185. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 284).

186. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 283).

187. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 282).

188. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: D1133L (SEQ ID NO: 281).

189. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: CP312R (SEQ ID NOS: 274, 272, 269, 268, 267).

190. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: CP312R (SEQ ID NO: 274).

191. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: CP312R (SEQ ID NO: 272).

192. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: CP312R (SEQ ID NO: 269).

193. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 194. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: CP312R (SEQ ID NO: 267).

195. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: A240L (SEQ ID NOS: 854, 853, 25).

196. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: A240L (SEQ ID NO: 854).

197. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: A240L (SEQ ID NO: 853).

198. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: A240L (SEQ ID NO: 25).

199. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: A238L (SEQ ID NOS: 23, 21, 19, 17).

200. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: A238L (SEQ ID NO: 23).

201. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: A238L (SEQ ID NO: 21).

202. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: A238L (SEQ ID NO: 19).

203. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: A238L (SEQ ID NO: 17).

204. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: MGF100-1L (SEQ ID NOS: 572, 570).

205. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: MGF100-1L (SEQ ID NO: 572).

206. The immunogenic composition or the vaccine or pharmaceutical composition as disclosed in clause 159, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof; comprising, preferably consisting of, an amino acid sequence which is at least 80%, 85%, 90%, 91%, 92%, 93%, 94%, 95%, 97%, 98%, 99% or 100% identical to an amino acid sequence selected from the group consisting of: MGF100-1L (SEQ ID NOS: 570).

207. The immunogenic composition or the vaccine or pharmaceutical composition as disclosed in any one of clauses 24 to 206, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF505-7R/MGF505-8R (SEQ ID NOS: 857, 775, 773, 725, 723, 720, 718), M448R (SEQ ID NOS: 858, 569, 567), D1133L (SEQ ID NOS: 859, 298, 296, 288, 286), CP312R (SEQ ID NOS: 861, 273, 901, 900, 271, 270), A240L (SEQ ID NOS: 860, 27, 26), A238L (SEQ ID NOS: 24, 22, 20, 18), MGF100-1L (SEQ ID NOS: 573, 571), K145R (SEQ ID NOS: 527, 525, 519, 517), B475L (SEQ ID NOS: 866, 867), H339R (SEQ ID NOS: 469, 467, 459, 457), I226R (SEQ ID NOS: 490, 488, 482, 480), CP2475L (p37) (SEQ ID NOS: 868, 869), CP2475L (p150) (SEQ ID NOS: 870, 871), G1211R (SEQ ID NOS: 433, 431, 421, 419), M1249L (SEQ ID NOS: 872, 873), MGF505-9R (SEQ ID NOS: 874, 875), P1192R (SEQ ID NOS: 876, 877), MGF505-1R (SEQ ID NOS: 878, 879), MGF505-3R (SEQ ID NOS: 880, 881), EP424R (SEQ ID NOS: 882, 883), C475L (SEQ ID NOS: 884, 885), B602L (SEQ ID NOS: 886, 887), CP530R (SEQ ID NOS: 888, 889), D339L (SEQ ID NOS: 890, 891), D117L (SEQ ID NOS: 863, 865), I243L (SEQ ID NOS: 892, 893), I73R (SEQ ID NOS: 894, 895), DP238L (SEQ ID NOS: 896, 897), 19R (SEQ ID NOS: 898, 899); preferably selected from the group consisting of: MGF505-7R/MGF505-8R (SEQ ID NOS: 857, 775, 773, 725, 723, 720, 718), M448R (SEQ ID NOS: 858, 569, 567), D1133L (SEQ ID NOS: 859, 298, 296, 288, 286), CP312R (SEQ ID NOS: 861, 273, 901, 900, 271, 270), A240L (SEQ ID NOS: 860, 27, 26), A238L (SEQ ID NOS: 24, 22, 20, 18), MGF100-1L (SEQ ID NOS: 573, 571); and most preferably selected from the group consisting of: MGF505-7R/MGF505-8R (SEQ ID NOS: 857, 775, 773, 725, 723, 720, 718), M448R (SEQ ID NOS: 858, 569, 567), D1133L (SEQ ID NOS: 859, 298, 296, 288, 286), CP312R (SEQ ID NOS: 861, 273, 901, 900, 271, 270), A240L (SEQ ID NOS: 860, 27, 26).

208. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF505-7R/MGF505-8R (SEQ ID NOS: 857, 775, 773, 725, 723, 720, 718).

209. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF505-7R (SEQ ID NO: 857).

210. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF505-7R (SEQ ID NO: 775).

211. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF505-8R (SEQ ID NO: 773).

212. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF505-7R (SEQ ID NO: 725).

213. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF505-8R (SEQ ID NO: 723).

214. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF505-7R (SEQ ID NO: 720).

215. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF505-8R (SEQ ID NO: 718).

216. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: M448R (SEQ ID NOS: 858, 569, 567).

217. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: M448R (SEQ ID NOS: 858).

218. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: M448R (SEQ ID NO: 569).

219. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: M448R (SEQ ID NO: 567).

220. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: D1133L (SEQ ID NOS: 859, 298, 296, 288, 286).

221. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: D1133L (SEQ ID NO: 859).

222. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: D1133L (SEQ ID NO: 298).

223. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: D1133L (SEQ ID NO: 296).

224. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: D1133L (SEQ ID NO: 288).

225. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: D1133L (SEQ ID NO: 286).

226. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: CP312R (SEQ ID NOS: 861, 273, 901, 900, 271, 270).

227. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: CP312R (SEQ ID NO: 861).

228. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: CP312R (SEQ ID NO: 273).

229. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: CP312R (SEQ ID NO: 901, 271).

230. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: CP312R (SEQ ID NO: 900, 270).

231. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: A240L (SEQ ID NOS: 860, 27, 26).

232. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: A240L (SEQ ID NO: 860).

233. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: A240L (SEQ ID NO: 27).

234. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: A240L (SEQ ID NO: 26).

235. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: A238L (SEQ ID NOS: 24, 22, 20, 18).

236. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: A238L (SEQ ID NO: 24).

237. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: A238L (SEQ ID NO: 22).

238. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: A238L (SEQ ID NO: 20).

239. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: A238L (SEQ ID NO: 18).

240. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF100-1L (SEQ ID NOS: 573, 571).

241. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF100-1L (SEQ ID NO: 573).

242. The immunogenic composition or the vaccine or pharmaceutical composition as disclosed in clause 207, wherein according to (c) the viral or bacterial vector comprises one, two or more African swine fever virus oligonucleotides and/or polynucleotides and/or immunogenic fragments thereof, which encode one, two or more African swine fever virus peptides and/or polypeptides, preferably full-length proteins, and/or immunogenic fragments thereof, wherein the one, two or more African swine fever virus oligonucleotides and/or polynucleotides and/or immunogenic fragments thereof comprise, preferably consist of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF100-1L (SEQ ID NO: 571).

243. The immunogenic composition or the vaccine or pharmaceutical composition as disclosed in any one of clauses 24 to 242, wherein the ASFV polypeptide is an ASFV full-length protein, preferably encoded by a polynucleotide sequence comprising, more preferably consisting of, any possible open reading frame (ORF), even more preferably encoded by a polynucleotide sequence comprising, most preferably consisting of, an open reading frame (ORF) with a 5'-end start codon and a 3'-end stop codon.

244. The immunogenic composition or the vaccine or pharmaceutical composition as disclosed in any of clauses 24 to 243, wherein the African swine fever virus is selected from the group consisting of: BA71, BA71ΔCD2 and/or Georgia2007/1 strain(s).

245. The immunogenic composition or the vaccine or pharmaceutical composition as disclosed in any one of clauses 24 to 244, wherein the immunogenicity (and/or immunological response) of the immunogenic composition or the vaccine or pharmaceutical composition or any comprised immunogenic fragment is indicated/characterized by an induced IFN-gamma response, preferably in a porcine IFN-gamma ELISpot assay, more preferably in a porcine IFN-gamma ELISpot assay as described in Example 1.

246. The immunogenic composition or the vaccine or pharmaceutical composition as disclosed in any one of clauses 24 to 245 for use in a method of reducing or preventing the clinical signs or disease in porcines, preferably a pig, caused by an infection with at least one, preferably pathogenic, African swine fever virus or for use in a method of treating and/or preventing an infection with at least one, preferably pathogenic, African swine fever virus, wherein preferably said clinical signs or disease caused by an infection with at least one, preferably pathogenic, African swine fever virus or said infection with at least one, preferably pathogenic, African swine fever virus are selected from the group consisting of: African swine fever, acute African swine fever, chronic African swine fever, mortality, death, sudden death, fever, high fever, anorexia, lethargy, weakness, loss of appetite, recumbence, erythema, cyanotic skin blotching, diarrhea, constipation, abdominal pain, respiratory signs, coughing, vomiting, dyspnea, nasal and conjunctival discharges, hemorrhages, epistaxis, abortion, leukopenia, thrombocytopenia.

247. The immunogenic composition or the vaccine or pharmaceutical composition as disclosed in any one of clauses 24 to 245 for use in a method of immunizing a porcine, preferably a pig, against a clinical disease caused by at least one, preferably pathogenic, African swine fever virus in said porcine, preferably pig, said method comprising the step of administering to the porcine, preferably pig, the immunogenic composition or the vaccine or pharmaceutical composition as disclosed in any one of clauses 24 to 245, wherein said immunogenic composition or vaccine or pharmaceutical composition fails to cause clinical signs of infection but is capable of inducing an immune response that immunizes the porcine, preferably pig, against, preferably pathogenic forms of, said at least one African swine fever virus, wherein preferably said clinical disease or said clinical signs of infection are selected from the group consisting of: African swine fever, acute African swine fever, chronic African swine fever, mortality, death, sudden death, fever, high fever, anorexia, lethargy, weakness, loss of appetite, recumbence, erythema, cyanotic skin blotching, diarrhea, constipation, abdominal pain, respiratory signs, coughing, vomiting, dyspnea, nasal and conjunctival discharges, hemorrhages, epistaxis, abortion, leukopenia, thrombocytopenia.

248. The immunogenic composition or the vaccine or pharmaceutical composition as disclosed in any one of clauses 24 to 245 for use in a method of prime-boost immunizing a porcine, preferably a pig, against a clinical disease caused by at least one, preferably pathogenic, African swine fever virus in said porcine, preferably pig, said method comprising the step of administering to the porcine, preferably pig, once or twice an immunogenic composition or the vaccine or pharmaceutical composition as disclosed in any one of clauses 24 to 245 comprising (i) one, two or more African swine fever virus oligonucleotides and/or polynucleotides and/or immunogenic fragments thereof as sole immunogenic components or (ii) a viral vector, preferably a recombinant and/or non-naturally occurring viral vector, comprising one, two or more African swine fever virus oligonucleotides and/or polynucleotides and/or immunogenic fragments thereof—as sole immunogenic component (priming step); and subsequently—after priming once or twice—administering to the porcine, preferably pig, a live attenuated African swine fever virus, preferably BA71ΔCD2 (boosting step); wherein said immunogenic composition or vaccine or pharmaceutical composition as well as the live attenuated African swine fever virus independently from each other fail to cause clinical signs of infection but are capable of inducing an immune response that immunizes the porcine, preferably pig, against, preferably pathogenic forms of, said at least one African swine fever virus, wherein preferably said clinical disease or said clinical signs of infection are selected from the group consisting of: African swine fever, acute African swine fever, chronic African swine fever, mortality, death, sudden death, fever, high fever, anorexia, lethargy, weakness, loss of appetite, recumbence, erythema, cyanotic skin blotching, diarrhea, constipation, abdominal pain, respiratory signs, coughing, vomiting, dyspnea, nasal and conjunctival discharges, hemorrhages, epistaxis, abortion, leukopenia, thrombocytopenia.

249. A kit for vaccinating a porcine, preferably a pig, against a disease associated with and/or reducing the incidence or the severity of one or more clinical signs associated with or caused by at least one, preferably pathogenic, African swine fever virus in a porcine, preferably a pig, comprising:
  (a) a dispenser capable of administering a vaccine to said porcine; and
  (b) the immunogenic composition or the vaccine or pharmaceutical composition as disclosed in any one of clauses 24 to 245, and
  (c) optionally, an instruction leaflet;
  wherein preferably said disease or said clinical signs are selected from the group consisting of: African swine fever, acute African swine fever, chronic African swine fever, mortality, death, sudden death, fever, high fever, anorexia, lethargy, weakness, loss of appetite, recumbence, erythema, cyanotic skin blotching, diarrhea, constipation, abdominal pain, respiratory signs, coughing, vomiting, dyspnea, nasal and conjunctival discharges, hemorrhages, epistaxis, abortion, leukopenia, thrombocytopenia.

250. An African swine fever virus peptide and/or polypeptide, preferably full-length-protein, and/or immunogenic fragment thereof comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: MGF505-7R/MGF505-8R (SEQ ID NOS: 774, 772, 724, 722, 721, 719, 717), M448R (SEQ ID NOS: 568, 566, 565, 564, 563), D1133L (SEQ ID NOS: 297, 295, 294, 293, 292, 291, 290, 289, 287, 285, 284, 283, 282, 281), CP312R (SEQ ID NOS: 274, 272, 269, 268, 267), A240L (SEQ ID NOS: 854, 853, 25), A238L (SEQ ID NOS: 23, 21, 19, 17), MGF100-1L (SEQ ID NOS: 572, 570), K145R (SEQ ID NOS: 526, 524, 523, 522, 521, 520, 518, 516, 515, 514), B475L (SEQ ID NOS: 66, 65, 64, 63, 62, 61, 60, 59, 58, 57, 56, 55, 54, 53, 52, 51, 50, 49, 48), H339R (SEQ ID NOS: 468, 466, 465, 464, 463, 462, 461, 460, 458, 456, 455, 454), I226R (SEQ ID NOS: 489, 487, 486, 485, 484, 483, 481, 479, 478), CP2475L (p37) (SEQ ID NOS: 266, 265, 264, 263, 262, 261), CP2475L (p150) (SEQ ID NOS: 260, 259, 258), G1211R (SEQ ID NOS: 432, 430, 429, 428, 427, 426, 425, 424, 423, 422, 420, 418, 417, 416), M1249L (SEQ ID NOS: 562, 561, 560, 559, 558, 557, 556, 555, 554, 553, 552, 551, 550, 549, 548, 547, 546, 545, 544, 543, 542, 541, 540, 539), MGF505-9R (SEQ ID NOS: 733, 732, 731, 730, 729, 728, 727, 726), P1192R (SEQ ID NOS: 817, 816, 815, 814, 813, 812, 811, 810, 809, 808, 807, 806, 805, 804, 803, 802, 801), MGF505-1R (SEQ ID NOS: 692, 691, 690, 689, 688, 687, 686, 685, 684), MGF505-3R (SEQ ID NOS: 703, 702, 701, 700, 699), EP424R (SEQ ID NOS: 389, 388, 387, 386, 385, 384, 383, 382, 381, 380, 379), C475L (SEQ ID NOS: 201, 200, 199, 198, 197, 196, 195, 194, 193, 192, 191, 190, 189, 188), B602L (SEQ ID NOS: 75, 74, 73, 72, 71, 70, 69, 68, 67), CP530R (SEQ ID NOS: 278, 277, 276, 275), D339L (SEQ ID NOS: 322, 321, 320), D117L (SEQ ID NOS: 862, 864), I243L (SEQ ID NOS: 494, 493, 492, 491), I73R (SEQ ID NOS: 504, 503, 502), DP238L (SEQ ID NOS: 327, 326, 325), I9R (SEQ ID NOS: 513, 512, 511, 510), preferably selected from the group consisting of: MGF505-7R/MGF505-8R (SEQ ID NOS: 774, 772, 724, 722, 721, 719, 717), M448R (SEQ ID NOS: 568, 566, 565, 564, 563), D1133L (SEQ ID NOS: 297, 295, 294, 293, 292, 291, 290, 289, 287, 285, 284, 283, 282, 281), CP312R (SEQ ID NOS: 274, 272, 269, 268, 267), A240L (SEQ ID NOS: 854, 853, 25), A238L (SEQ ID NOS: 23, 21, 19, 17), MGF100-1L (SEQ ID NOS: 572, 570); and most preferably selected from the group consisting of: MGF505-7R/MGF505-8R (SEQ ID NOS: 774, 772, 724, 722, 721, 719, 717), M448R (SEQ ID NOS: 568, 566, 565, 564, 563), D1133L (SEQ ID NOS: 297, 295, 294, 293, 292, 291, 290, 289, 287, 285, 284, 283, 282, 281), CP312R (SEQ ID NOS: 274, 272, 269, 268, 267), A240L (SEQ ID NOS: 854, 853, 25).

251. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: MGF505-7R/MGF505-8R (SEQ ID NOS: 774, 772, 724, 722, 721, 719, 717).

252. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: MGF505-7R (SEQ ID NO: 774).

253. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: MGF505-8R (SEQ ID NO: 772).

254. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: MGF505-7R (SEQ ID NO: 724).

255. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: MGF505-8R (SEQ ID NO: 722).

256. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: MGF505-7R (SEQ ID NO: 721).

257. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: MGF505-7R (SEQ ID NO: 719).

258. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: MGF505-8R (SEQ ID NO: 717).

259. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: M448R (SEQ ID NOS: 568, 566, 565, 564, 563).

260. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: M448R (SEQ ID NO: 568).

261. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: M448R (SEQ ID NO: 566).

262. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: M448R (SEQ ID NO: 565).

263. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: M448R (SEQ ID NO: 564).

264. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: M448R (SEQ ID NO: 563).

265. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: D1133L (SEQ ID NOS: 297, 295, 294, 293, 292, 291, 290, 289, 287, 285, 284, 283, 282, 281).

266. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: D1133L (SEQ ID NO: 297).

267. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: D1133L (SEQ ID NO: 295).

268. The African swine fever virus peptide and/or polypeptide, preferably full-length-protein, and/or immunogenic 268. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: D1133L (SEQ ID NO: 294).

269. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: D1133L (SEQ ID NO: 293).

270. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: D1133L (SEQ ID NO: 292).

271. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: D1133L (SEQ ID NO: 291).

272. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: D1133L (SEQ ID NO: 290).

273. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: D1133L (SEQ ID NO: 289).

274. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: D1133L (SEQ ID NO: 287).

275. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: D1133L (SEQ ID NO: 285).

276. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: D1133L (SEQ ID NO: 284).

277. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: D1133L (SEQ ID NO: 283).

278. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: D1133L (SEQ ID NO: 282).

279. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: D1133L (SEQ ID NO: 281).

280. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: CP312R (SEQ ID NOS: 274, 272, 269, 268, 267).

281. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: CP312R (SEQ ID NO: 274).

282. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: CP312R (SEQ ID NO: 272).

283. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: CP312R (SEQ ID NO: 269).

284. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: CP312R (SEQ ID NO: 268).

285. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: CP312R (SEQ ID NO: 267).

286. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: A240L (SEQ ID NOS: 854, 853, 25).

287. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: A240L (SEQ ID NO: 854).

288. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: A240L (SEQ ID NO: 853).

289. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: A240L (SEQ ID NO: 25).

290. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: A238L (SEQ ID NOS: 23, 21, 19, 17).

291. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: A238L (SEQ ID NO: 23).

292. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: A238L (SEQ ID NO: 21).

293. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: A238L (SEQ ID NO: 19).

294. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: A238L (SEQ ID NO: 17).

295. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: MGF100-1L (SEQ ID NOS: 572, 570).

296. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: MGF100-1L (SEQ ID NO: 572).

297. The African swine fever virus peptide and/or polypeptide, preferably full-length-protein, and/or immunogenic fragment thereof as disclosed in clause 250 comprising, preferably consisting of, an amino acid sequence, which is at least 80%, 85%, 90%, 91%, 92%, 93%, 94%, 95%, 97%, 98%, 99% or 100% identical to an amino acid sequence selected from the group consisting of: MGF100-1L (SEQ ID NOS: 570).

298. The African swine fever virus peptide and/or polypeptide, preferably full-length-protein, and/or immunogenic fragment thereof as disclosed in any one of clauses 250 to 297, wherein the African swine fever virus polypeptides, preferably full-length proteins, comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: MGF505-7R/MGF505-8R (SEQ ID NOS: 774, 772, 724, 722), M448R (SEQ ID NOS: 568, 566), D1133L (SEQ ID NOS: 297, 295), CP312R (SEQ ID NOS: 274, 272), A240L (SEQ ID NOS: 854, 853), A238L (SEQ ID NOS: 23, 21), MGF100-1L (SEQ ID NO: 572), K145R (SEQ ID NOS: 526, 524), B475L (SEQ ID NOS: 66, 65), H339R (SEQ ID NOS: 468, 466), I226R (SEQ ID NOS: 489, 487), CP2475 (SEQ ID NO: 257), CP2475 (SEQ ID NO: 256), G1211R (SEQ ID NOS: 432, 430), M1249L (SEQ ID NOS: 562, 561), MGF505-9R (SEQ ID NOS: 733, 732), P1192R (SEQ ID NOS: 817, 816), MGF505-1R (SEQ ID NOS: 692, 691), MGF505-3R (SEQ ID NOS: 703, 702), EP424R (SEQ ID NOS: 389, 388), C475L (SEQ ID NOS: 201, 200), B602L (SEQ ID NOS: 75, 74), CP530R (SEQ ID NOS: 278, 277), D339L (SEQ ID NOS: 322, 321), D117L (SEQ ID NOS: 862, 864), I243L (SEQ ID NOS: 494, 493), I73R (SEQ ID NOS: 504, 503), DP238L (SEQ ID NOS: 327, 326), 19R (SEQ ID NOS: 513, 512) and/or wherein the African swine fever virus peptides and/or immunogenic fragments thereof and/or African swine fever virus polypeptide/full-length protein immunogenic fragments comprise, preferably consist of, an amino acid sequence which is at least 80%, 85%, 90%, 91%, 92%, 93%, 94%, 95%, 97%, 98%, 99% or 100% identical to an amino acid sequence selected from the group consisting of: MGF505-7R/ MGF505-8R (SEQ ID NOS: 721, 719, 717), M448R (SEQ ID NOS: 565, 564, 563), D1133L (SEQ ID NOS: 294, 293, 292, 291, 290, 289, 287, 285, 284, 283, 282, 281), CP312R (SEQ ID NOS: 269, 268, 267), A240L (SEQ ID NO: 25), A238L (SEQ ID NOS: 19, 17), MGF100-1L (SEQ ID NO: 570), K145R (SEQ ID NOS: 523, 522, 521, 520, 518, 516, 515, 514), B475L (SEQ ID NOS: 64, 63, 62, 61, 60, 59, 58, 57, 56, 55, 54, 53, 52, 51, 50, 49, 48), H339R (SEQ ID NOS: 465, 464, 463, 462, 461, 460, 458, 456, 455, 454), I226R (SEQ ID NOS: 486, 485, 484, 483, 481, 479, 478), CP2475L (p37) (SEQ ID NOS: 266, 265, 264, 263, 262, 261), CP2475L (p150) (SEQ ID NOS: 260, 259, 258), G1211R (SEQ ID NOS: 429, 428, 427, 426, 425, 424, 423, 422, 420, 418, 417, 416), M1249L (SEQ ID NOS: 560, 559, 558, 557, 556, 555, 554, 553, 552, 551, 550, 549, 548, 547, 546, 545, 544, 543, 542, 541, 540, 539), MGF505-9R (SEQ ID NOS: 731, 730, 729, 728, 727, 726), P1192R (SEQ ID NOS: 815, 814, 813, 812, 811, 810, 809, 808, 807, 806, 805, 804, 803, 802, 801), MGF505-1R (SEQ ID NOS: 690, 689, 688, 687, 686, 685, 684), MGF505-3R (SEQ ID NOS: 701, 700, 699), EP424R (SEQ ID NOS: 387, 386, 385, 384, 383, 382, 381, 380, 379), C475L (SEQ ID NOS: 199, 198, 197, 196, 195, 194, 193, 192, 191, 190, 189, 188), B602L (SEQ ID NOS: 73, 72, 71, 70, 69, 68, 67), CP530R (SEQ ID NOS: 277, 276, 275), D339L (SEQ ID NO: 320), I243L (SEQ ID NOS: 492, 491), I73R (SEQ ID NO: 502), DP238L (SEQ ID NO: 325), 19R (SEQ ID NOS: 511, 510).

299. An African swine fever virus oligonucleotide and/or polynucleotide and/or immunogenic fragment thereof encoding the African swine fever virus peptide and/or polypeptide, preferably full-length-protein, and/or immunogenic fragment thereof as disclosed in any one of clauses 250 to 298.

300. An African swine fever virus oligonucleotide and/or polynucleotide and/or immunogenic fragment thereof encoding African swine fever virus peptides and/or polypeptides, preferably full-length proteins, and/or immunogenic fragments thereof; comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF505-7R/MGF505-8R (SEQ ID NOS: 857, 775, 773, 725, 723, 720, 718), M448R (SEQ ID NOS: 858, 569, 567), D1133L (SEQ ID NOS: 859, 298, 296, 288, 286), CP312R (SEQ ID NOS: 861, 273, 901, 900, 271, 270), A240L (SEQ ID NOS: 860, 27, 26), A238L (SEQ ID NOS: 24, 22, 20, 18), MGF100-1L (SEQ ID NOS: 573, 571), K145R (SEQ ID NOS: 527, 525, 519, 517), B475L (SEQ ID NOS: 866, 867), H339R (SEQ ID NOS: 469, 467, 459, 457), I226R (SEQ ID NOS: 490, 488, 482, 480), CP2475L (p37) (SEQ ID NOS: 868, 869), CP2475L (p150) (SEQ ID NOS: 870, 871), G1211R (SEQ ID NOS: 433, 431, 421, 419), M1249L (SEQ ID NOS: 872, 873), MGF505-9R (SEQ ID NOS: 874, 875), P1192R (SEQ ID NOS: 876, 877), MGF505-1R (SEQ ID NOS: 878, 879), MGF505-3R (SEQ ID NOS: 880, 881), EP424R (SEQ ID NOS: 882, 883), C475L (SEQ ID NOS: 884, 885), B602L (SEQ ID NOS: 886, 887), CP530R (SEQ ID NOS: 888, 889), D339L (SEQ ID NOS: 890, 891), D117L (SEQ ID NOS: 863, 865), I243L (SEQ ID NOS: 892, 893), I73R (SEQ ID NOS: 894, 895), DP238L (SEQ ID NOS: 896, 897), 19R (SEQ ID NOS: 898, 899); preferably selected from the group consisting of: MGF505-7R/MGF505-8R (SEQ ID NOS: 857, 775, 773, 725, 723, 720, 718), M448R (SEQ ID NOS: 858, 569, 567), D1133L (SEQ ID NOS: 859, 298, 296, 288, 286), CP312R (SEQ ID NOS: 861, 273, 901, 900, 271, 270), A240L (SEQ ID NOS: 860, 27, 26), A238L (SEQ ID NOS: 24, 22, 20, 18), MGF100-1L (SEQ ID NOS: 573, 571); and most preferably selected from the group consisting of: MGF505-7R/MGF505-8R (SEQ ID NOS: 857, 775, 773, 725, 723, 720, 718), M448R (SEQ ID NOS: 858, 569, 567), D1133L (SEQ ID NOS: 859, 298, 296, 288, 286), CP312R (SEQ ID NOS: 861, 273, 901, 900, 271, 270), A240L (SEQ ID NOS: 860, 27, 26).

301. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF505-7R/MGF505-8R (SEQ ID NOS: 857, 775, 773, 725, 723, 720, 718).

302. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF505-7R (SEQ ID NO: 857).

303. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF505-7R (SEQ ID NO: 775).

304. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF505-8R (SEQ ID NO: 773).

305. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF505-7R (SEQ ID NO: 725).

306. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence 307. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF505-7R (SEQ ID NO: 720).

308. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF505-8R (SEQ ID NO: 718).

309. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: M448R (SEQ ID NOS: 858, 569, 567).

310. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: M448R (SEQ ID NO: 858).

311. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: M448R (SEQ ID NO: 569).

312. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: M448R (SEQ ID NO: 567).

313. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: D1133L (SEQ ID NOS: 859, 298, 296, 288, 286).

314. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: D1133L (SEQ ID NO: 859).

315. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: D1133L (SEQ ID NO: 298).

316. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: D1133L (SEQ ID NO: 296).

317. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: D1133L (SEQ ID NO: 288).

318. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: D1133L (SEQ ID NO: 286).

319. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: CP312R (SEQ ID NOS: 861, 273, 901, 900, 271, 270).

(page begins) which is at least 70%, 75%, 80%, 85%, 90%, 91%, 92%, 93%, 94%, 95%, 97%, 98%, 99% or 100% identical to a nucleic acid sequence selected from the group consisting of: MGF505-8SEQ ID NO:).

320. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: CP312R (SEQ ID NO: 861).

321. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: CP312R (SEQ ID NO: 273).

322. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: CP312R (SEQ ID NO: 901, 271).

323. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: CP312R (SEQ ID NO: 900, 270).

324. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: A240L (SEQ ID NOS: 860, 27, 26).

325. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: A240L (SEQ ID NO: 860).

326. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: A240L (SEQ ID NO: 27).

327. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: A240L (SEQ ID NO: 26).

328. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: A238L (SEQ ID NOS: 24, 22, 20, 18).

329. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: A238L (SEQ ID NO: 24).

330. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: A238L (SEQ ID NO: 22).

331. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: A238L (SEQ ID NO: 20).

332. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: A238L (SEQ ID NO: 18).

333. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF100-1L (SEQ ID NOS: 573, 571).

334. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF100-1L (SEQ ID NO: 573).

335. The African swine fever virus oligonucleotide and/or polynucleotide and/or immunogenic fragment thereof encoding African swine fever virus peptides and/or polypeptides, preferably full-length proteins, and/or immunogenic fragments thereof; as disclosed in clause 300 comprising, preferably consisting of, a nucleic acid sequence which is at least 70%, 75%, 80%, 85%, 90%, 91%, 92%, 93%, 94%, 95%, 97%, 98%, 99% or 100% identical to a nucleic acid sequence selected from the group consisting of: MGF100-1L (SEQ ID NO: 571).

336. The African swine fever virus peptide and/or polypeptide, preferably full-length-protein, and/or immunogenic fragment thereof as disclosed in any one of clauses 250 to 298 or the African swine fever virus oligonucleotide and/or polynucleotide and/or immunogenic fragment thereof encoding African swine fever virus peptide and/or polypeptide, preferably full-length-protein, and/or immunogenic fragments thereof as disclosed in any one of clauses 299 to 335, wherein the immunogenicity (and/or immunological response) of the immunogenic composition or the vaccine or pharmaceutical composition or any comprised immunogenic fragment is indicated/characterized by an induced IFN-gamma response, preferably in a porcine IFN-gamma ELISpot assay, more preferably in a porcine IFN-gamma ELISpot assay as described in Example 1.

337. The African swine fever virus peptide and/or polypeptide, preferably full-length-protein, and/or immunogenic fragment thereof as disclosed in any one of clauses 250 to 298 and 336 or the African swine fever virus oligonucleotide and/or polynucleotide and/or immunogenic fragment thereof encoding African swine fever virus peptide and/or polypeptide, preferably full-length-protein, and/or immunogenic fragments thereof as disclosed in any one of clauses 299 to 336, wherein the ASFV polypeptide is an ASFV full-length protein, preferably encoded by a polynucleotide sequence comprising, more preferably consisting of, any possible open reading frame (ORF), even more preferably encoded by a polynucleotide sequence comprising, most preferably consisting of, an open reading frame (ORF) with a 5'-end start codon and a 3'-end stop codon.

338. A viral or bacterial vector, preferably selected from the group consisting of: asfivirus viral vector, avipox virus viral vector, canine morbillivirus viral vector, herpes virus viral vector, varicella virus viral vector, *Lawsonia* spp., *Salmonella* spp., comprising one, two, three or more African swine fever virus oligonucleotides and/or polynucleotides and/or immunogenic fragments thereof as disclosed in any one of clauses 299 to 335.

339. A vector, preferably an expression vector, comprising one, two, three or more African swine fever virus oligonucleotides and/or polynucleotides and/or immunogenic fragments thereof as disclosed in any one of clauses 299 to 335.

340. The viral or bacterial vector as disclosed in clause 338 or the vector as disclosed in clause 339 comprising three African swine fever virus oligonucleotides and/or polynucleotides and/or immunogenic fragments thereof, preferably selected from EP402R, CP312R and A240L (multi-epitope-I, ME-I), more preferably comprising, most preferably consisting of, the nucleic acid sequence selected from the group consisting of: SEQ ID NO: 855; or comprising thirteen African swine fever virus oligonucleotides and/or polynucleotides and/or immunogenic fragments thereof, preferably selected from D1133L, G1211R, M1249L, MGF505-9R, P1192R, CP2475L (p150), B475L, EP424R, H339R, I226R, K145R, MGF505-1R and CP2475L (p37) (multiepitope-II, ME-II), more preferably comprising, most preferably consisting of, the nucleic acid sequence selected from the group consisting of: SEQ ID NO: 856.

341. A host cell, preferably a mammalian host cell, comprising the viral or bacterial vector or the vector as disclosed in any one of clauses 338 to 340.

342. The immunogenic composition or the vaccine or pharmaceutical composition as disclosed in any one of clauses 24 to 341, wherein the viral or bacterial vector is a genetically modified virus or bacterium, which was manipulated by recombinant DNA technique in a way so that its entry into a host cell results in a specific biological activity, e.g. the expression of a transgene, such as an ASFV gene, carried by the vector, wherein preferably the transgene is an ASFV antigen and wherein preferably the viral or bacterial vector may or may not be replication competent in the target or host cell.

The invention claimed is:

1. An immunogenic composition comprising an adjuvant, and further comprising
two African swine fever virus peptides, polypeptides, and/or full-length proteins, comprising
one amino acid sequence which is at least 95% identical to MGF505-7R (SEQ ID NO: 774) and one amino acid sequence which is at least 95% identical to M448R (SEQ ID NOS: 568, 566).

2. The immunogenic composition according claim 1, further comprising one or more pharmaceutical- or veterinary-acceptable carriers or excipients, wherein said one or more carriers or excipients are suitable for oral, intradermal, intramuscular or intranasal application.

3. An immunogenic composition, comprising a viral or bacterial vector, an exogenous and/or heterologous viral or bacterial vector, comprising one or two African swine fever virus oligonucleotides, and/or polynucleotides, encoding the African swine fever virus peptides, polypeptides, and/or full-length proteins, as claimed in claim 1.

4. The immunogenic composition as claimed in claim 3, wherein the viral or bacterial vector is selected from the group consisting of: avipox virus viral vector, canine morbillivirus viral vector, herpes virus viral vector, varicella virus viral vector, Lawsonia spp., Salmonella spp.

5. The immunogenic composition as claimed in claim 1, wherein the ASFV polypeptide is an ASFV full-length protein, encoded by a polynucleotide sequence comprising an open reading frame (ORF).

6. Immunogenic composition as claimed in claim 1, wherein the ASFV is selected from the group consisting of: BA71, BA71ΔCD2 and/or Georgia2007/1 strain(s).

7. The immunogenic composition as claimed in claim 1, wherein the immunogenicity of the immunogenic composition is indicated by an induced IFN-gamma response when administered to pigs.

8. A method of reducing or preventing the clinical signs or disease in pigs caused by an infection with at least one pathogenic African swine fever virus or for use in a method of treating and/or preventing an infection with at least one pathogenic African swine fever virus comprising administering the immunogenic composition of claim 1.

9. A method of immunizing a pig against a clinical disease caused by at least one pathogenic African swine fever virus in said pig comprising the step of administering to the pig the immunogenic composition of claim 1, wherein said immunogenic composition fails to cause significant clinical signs of infection but is capable of inducing an immune response that immunizes the pig against pathogenic forms of said at least one African swine fever virus.

10. A method of prime-boost immunizing a pig against a clinical disease caused by at least one pathogenic African swine fever virus in said pig comprising the step of administering to the pig once or twice the immunogenic composition of claim 1—as sole immunogenic component (priming step); and subsequently—after priming once or twice—administering to the pig a live attenuated African swine fever virus, such as BA71ΔCD2 (boosting step); wherein said immunogenic composition as well as the live attenuated African swine fever virus independently from each other fail to cause clinical signs of infection but are capable of inducing an immune response that immunizes the pig against pathogenic forms of said at least one African swine fever virus.

11. A kit for vaccinating a pig against a disease associated with and/or reducing the incidence or the severity of one or more clinical signs associated with or caused by at least one pathogenic African swine fever virus in a pig, comprising:
(a) a dispenser capable of administering a vaccine to said pig; and
(b) the immunogenic composition as claimed in claim 1.

* * * * *

SEQUENCE LISTING

```
Sequence total quantity: 901
SEQ ID NO: 1            moltype = AA  length = 21
FEATURE                 Location/Qualifiers
source                  1..21
                        mol_type = protein
                        organism = African swine fever virus
SEQUENCE: 1
MAMSIPRMIN KRKKRIQFLT F                                              21

SEQ ID NO: 2            moltype = AA  length = 11
FEATURE                 Location/Qualifiers
source                  1..11
                        mol_type = protein
                        organism = African swine fever virus
SEQUENCE: 2
```

```
KRKKRIQFLT F                                                                       11

SEQ ID NO: 3               moltype = AA   length = 10
FEATURE                    Location/Qualifiers
source                     1..10
                           mol_type = protein
                           organism = African swine fever virus
SEQUENCE: 3
LTFLTNLFLY                                                                         10

SEQ ID NO: 4               moltype = AA   length = 60
FEATURE                    Location/Qualifiers
source                     1..60
                           mol_type = protein
                           organism = African swine fever virus
SEQUENCE: 4
MHSNVSFNFI ACVLFPTPLI PSMAMSIPRM INKRKKRIQF LTFLTNLFLY NIVQHCISGI                   60

SEQ ID NO: 5               moltype = AA   length = 9
FEATURE                    Location/Qualifiers
source                     1..9
                           mol_type = protein
                           organism = African swine fever virus
SEQUENCE: 5
NSYTKKMEL                                                                          9

SEQ ID NO: 6               moltype = AA   length = 137
FEATURE                    Location/Qualifiers
source                     1..137
                           mol_type = protein
                           organism = African swine fever virus
SEQUENCE: 6
MEAVLTKLDQ EEKKALQNFH RCAWEETKNI INDFLEIPEE RCTYKFNSYT KKMELLFTPE                   60
FHTAWHEVPE CREFILNFLR LISGHRVVLK GPTFVFTKET KNLGIPSTIN VDFQANIENM                   120
DDLQKGNLIG KMNIKEG                                                                 137

SEQ ID NO: 7               moltype = AA   length = 137
FEATURE                    Location/Qualifiers
source                     1..137
                           mol_type = protein
                           organism = African swine fever virus
SEQUENCE: 7
MEAVLTKLDQ EEKKALQNFH RCAWEETKNI INDFLEIPEE RCTYKFNSYT KKMELLFTPE                   60
FHTAWHEVPE CREFILNFLR LISGHRVVLK GPTFVFTKEI KNLGIPSTIN VDFQANIENM                   120
DDLQKGNLIG KMNIKEG                                                                 137

SEQ ID NO: 8               moltype = AA   length = 9
FEATURE                    Location/Qualifiers
source                     1..9
                           mol_type = protein
                           organism = African swine fever virus
SEQUENCE: 8
ENDLYHTNY                                                                          9

SEQ ID NO: 9               moltype = AA   length = 16
FEATURE                    Location/Qualifiers
source                     1..16
                           mol_type = protein
                           organism = African swine fever virus
SEQUENCE: 9
VSEISYIGNT YKYFTF                                                                  16

SEQ ID NO: 10              moltype = AA   length = 10
FEATURE                    Location/Qualifiers
source                     1..10
                           mol_type = protein
                           organism = African swine fever virus
SEQUENCE: 10
ISYIGNTYKY                                                                         10

SEQ ID NO: 11              moltype = AA   length = 8
FEATURE                    Location/Qualifiers
source                     1..8
                           mol_type = protein
                           organism = African swine fever virus
SEQUENCE: 11
NTYKYFTF                                                                           8

SEQ ID NO: 12              moltype = AA   length = 151
```

```
FEATURE               Location/Qualifiers
source                1..151
                      mol_type = protein
                      organism = African swine fever virus
SEQUENCE: 12
MMALLHKEKL IECIENEVLS GGTVLLLVKN IVVSEISYID NSYKYFTFNA NHDLKSKEDL    60
KGATSNNIAK MIYNWIIKNP QNNKIWSGEP RTQIYFENDL YHTNYNHECI KDFWDVSTSV   120
GPCIFNDRSI WCTKCTSFYP FTNIMSPNIF Q                                  151

SEQ ID NO: 13         moltype = AA  length = 158
FEATURE               Location/Qualifiers
source                1..158
                      mol_type = protein
                      organism = African swine fever virus
SEQUENCE: 13
MNKKIIVMMA LLHKEKLIEC IYHELENGGT ILLLTKNIVV SEISYIGNTY KYFTFNDNHD    60
LISKEDLKGA TSKNIAKMIY NWIIKNPQNN KIWSGEPRTQ IYFENDLYHT NYNHKCIKDF   120
WNVSTSVGPH IFNDRSIWCT KCTSFYPFTN IMSPNIFQ                           158

SEQ ID NO: 14         moltype = AA  length = 9
FEATURE               Location/Qualifiers
source                1..9
                      mol_type = protein
                      organism = African swine fever virus
SEQUENCE: 14
VIFNIKYFL                                                             9

SEQ ID NO: 15         moltype = AA  length = 179
FEATURE               Location/Qualifiers
source                1..179
                      mol_type = protein
                      organism = African swine fever virus
SEQUENCE: 15
MEGEELIYHN IINEILVGYI KYYINDISEH ELSPYQQQIK KILTYYDECL NKQVTITFSL    60
TSVQEIKTQF TGVVTELFKD LINWGRICGF IVFSAKMAKY CKDANNHLES TVITTAYNFM   120
KHNLLPWMIS HGGQEEFLAF SLHSDMYSVI FNIKYFLSKF CNHMFFRSCV QLLRNCNLI    179

SEQ ID NO: 16         moltype = AA  length = 179
FEATURE               Location/Qualifiers
source                1..179
                      mol_type = protein
                      organism = African swine fever virus
SEQUENCE: 16
MEGEELIYHN IINEILVGYI KYYINDISEH ELSPYQQQIK KILTYYDECL NKQVTITFSL    60
TSVQEIKTQF TGVVTELFKD LINWGRICGF IVFSAKMAKY CKDANNHLES TVITTAYNFM   120
KHNLLPWMIS HGGQEEFLAF SLHSDMYSVI FNIKYFLSKF CNHMFFRSCV QLLRNCNLI    179

SEQ ID NO: 17         moltype = AA  length = 11
FEATURE               Location/Qualifiers
source                1..11
                      mol_type = protein
                      organism = African swine fever virus
SEQUENCE: 17
DKDGNSALHY L                                                         11

SEQ ID NO: 18         moltype = DNA  length = 33
FEATURE               Location/Qualifiers
source                1..33
                      mol_type = unassigned DNA
                      organism = African swine fever virus
SEQUENCE: 18
gataaagatg gaaactctgc tttacattat tta                                 33

SEQ ID NO: 19         moltype = AA  length = 11
FEATURE               Location/Qualifiers
source                1..11
                      mol_type = protein
                      organism = African swine fever virus
SEQUENCE: 19
DKDGNSALHY L                                                         11

SEQ ID NO: 20         moltype = DNA  length = 33
FEATURE               Location/Qualifiers
source                1..33
                      mol_type = unassigned DNA
                      organism = African swine fever virus
SEQUENCE: 20
gataaagatg gaaactctgc tttacattat tta                                 33
```

| | | |
|---|---|---|
| SEQ ID NO: 21 | moltype = AA   length = 238 | |
| FEATURE | Location/Qualifiers | |
| source | 1..238 | |
| | mol_type = protein | |
| | organism = African swine fever virus | |

SEQUENCE: 21
```
MEHMFPEREI ENLFVKWIKK HIRNGNLTLF EEFFKTDPWI VNRCDKNGSS VFMWICIYGR    60
IDFLKFLFEQ ESYPGEIINP HRRDKDGNSA LHYLAEKKNH LILEEVLGYF GKNGTKICLP   120
NFNGMTPVMK AAIRGRTSNV LSLIKFGADP TQKDYHRGFT AWDWAVFTGN MELVKSLNHD   180
YQKPLYMHFP LYKLDVFHRW FKKKPKIIIT GCKNNVYEKL PEQNPNFLCV KKLNKYGK    238
```

| | | |
|---|---|---|
| SEQ ID NO: 22 | moltype = DNA   length = 717 | |
| FEATURE | Location/Qualifiers | |
| source | 1..717 | |
| | mol_type = unassigned DNA | |
| | organism = African swine fever virus | |

SEQUENCE: 22
```
atggaacaca tgtttccaga aagggagata gaaaacttgt ttgttaaatg gattaaaaaa    60
catatcagaa atggaaatct tacactattt gaggaatttt ttaaaacaga tccgtggatt   120
gtcaatagat gcgataaaaa tggatcctcg gtattcatgt ggatatgcat ctacggacgt   180
atagacttttt taaaatttct ttttgaacaa gaatcttatc ccggagaaat aattaaccct   240
cataggaggg ataaagatgg aaactctgct ttacattatt tagctgagaa aaaaaatcat   300
ttaatcctgg aagaggtgtt gggctatttc ggaaaaaatg ggaccaaaat ttgtttaccg   360
aattttaatg gatgactcc tgtgatgaag gccgcaatac ggggccgtac ttcaaatgtg   420
cttttctctca taaaatttgg agcagatccg actcaaaaag actatcatag aggctttact   480
gcttgggact gggcagtctt tacaggaaat atggagttag tcaaatctct taaccatgac   540
taccaaaaac ctctctacat gcatttccct ctttacaagc tggatgtttt ccaccggtgg   600
tttaagaaaa agcccaaaat tattattact ggctgtaaaa ataatgtcta tgaaaaactt   660
cctgaacaga atccaaactt cctgtgtgta aaaaaactga caagtatgg aaagtaa      717
```

| | | |
|---|---|---|
| SEQ ID NO: 23 | moltype = AA   length = 226 | |
| FEATURE | Location/Qualifiers | |
| source | 1..226 | |
| | mol_type = protein | |
| | organism = African swine fever virus | |

SEQUENCE: 23
```
MFPEREIENL FVKWIKKHIR NGNLTLFEEF FKTDPWIVNR CDKNGSSVFM WICIYGRIDF    60
LKFLFEQESY PGEIINPHRR DKDGNSALHY LAEKKNHLIL EGVLGYFGKN GTRICLPNFN   120
GMTPVMKAAI RGRSLNMLSL IKFGADPTQK DYHRGFTAWD WAVFTGNMEL VKSLNHDYQN   180
LSTCISLFTS WMFSTGGLRK SPKLLLLAVN IMSMKNFLNR IQSSCV                 226
```

| | | |
|---|---|---|
| SEQ ID NO: 24 | moltype = DNA   length = 681 | |
| FEATURE | Location/Qualifiers | |
| source | 1..681 | |
| | mol_type = unassigned DNA | |
| | organism = African swine fever virus | |

SEQUENCE: 24
```
atgtttccag aaagggagat agaaaacttg tttgttaaat ggattaaaaa acatattaga    60
aatgggaatc ttacactatt tgaggaattt tttaaaacag atccgtggat tgtcaataga   120
tgcgataaaa atggatcctc ggtattcatg tggatatgca tctacggacg tatagacttt   180
ttaaaatttc tttttgaaca agaatcttat cctggagaaa taattaaccc tcataggagg   240
gataaagatg gaaactctgc tttacattat ttagctgaga aaaaaaatca tttaatcctg   300
gaaggggtgt tgggctattt cggaaaaaat gggaccagaa tttgtttacc gaattttaat   360
gggatgactc ctgtgatgaa ggccgcaata cggggccgtt cttaaatat gctttctctc   420
ataaaatttg gagcagatcc gactcaaaaa gactatcata gaggttttac tgcttgggac   480
tgggcagtct tttacaggaaa catggagtta gtcaaatctc ttaaccatga ctaccaaaac   540
ctctctacat gcatttccct ctttacaagc tggatgtttt ccaccggtgg tttaagaaaa   600
agcccaaaat tattattact ggctgtaaac ataatgtcta tgaaaaactt cctgaacaga   660
atccaaagtt cctgtgtgta a                                            681
```

| | | |
|---|---|---|
| SEQ ID NO: 25 | moltype = AA   length = 11 | |
| FEATURE | Location/Qualifiers | |
| source | 1..11 | |
| | mol_type = protein | |
| | organism = African swine fever virus | |

SEQUENCE: 25
```
SEFIAEIAVL L                                                        11
```

| | | |
|---|---|---|
| SEQ ID NO: 26 | moltype = DNA   length = 33 | |
| FEATURE | Location/Qualifiers | |
| source | 1..33 | |
| | mol_type = unassigned DNA | |
| | organism = African swine fever virus | |

SEQUENCE: 26
```
agtgaattta tcgcagaaat tgcagtgcta ctt                                33
```

| | | |
|---|---|---|
| SEQ ID NO: 27 | moltype = DNA   length = 711 | |
| FEATURE | Location/Qualifiers | |
| source | 1..711 | |

```
                          mol_type = unassigned DNA
                          organism = African swine fever virus
SEQUENCE: 27
atgcgtggaa tactcattgc catcgaggga atcaatggtg tgggaaaaag cacacaggca    60
atgaaattaa aagaaacatt ggaatgcatg gattataatg ctatatgtat acatttttcct  120
aatccagaca cgaccaccgg tgatcttata ttgcaggtgt taaataaaac catagaaatg   180
tcatcggaac aattacataa attatttaca aacatcgta gtgaatttat cgcagaaatt    240
gcagtgctac ttaagctaaa ttatattgta atagtggacc gttatatttg gtctggttta   300
gtatatgctc aagcagatgg aatcacgatt gaaaccaaaa ataccttaa accagattat    360
acattctttt tatcttcaaa gaaccattg aacgagaaac ctttaacctt acaacgttta    420
tttgaaacaa aagaaaaaca agaaacaatt tttactaatt ttactattat catggatgat   480
gtacctaaaa ataggttttg tattattccg gcaactctta taaggaaat tattcatatg    540
ataatttaa caaaaacgct aaaagttttt gacaacaact catgttttaaa ttatattaaa   600
atgtacgatg ataagtattt aaatgtccag gatctgaatt tattcgattt cgattggcaa   660
aaatatattg aagataataa cgataaagaa gaatatgact ttatagttta g            711

SEQ ID NO: 28             moltype = AA  length = 9
FEATURE                   Location/Qualifiers
source                    1..9
                          mol_type = protein
                          organism = African swine fever virus
SEQUENCE: 28
QLARHAIRY                                                              9

SEQ ID NO: 29             moltype = AA  length = 11
FEATURE                   Location/Qualifiers
source                    1..11
                          mol_type = protein
                          organism = African swine fever virus
SEQUENCE: 29
ATLRFDTWYK W                                                          11

SEQ ID NO: 30             moltype = AA  length = 858
FEATURE                   Location/Qualifiers
source                    1..858
                          mol_type = protein
                          organism = African swine fever virus
SEQUENCE: 30
MCAGFYVAVH PWLEAQSLHK VGHTGNLAAR LHDGSYTTCF TDEWKYCFTL ETSTKKDAQK     60
IEAGVLYCAQ FFRVKNKELV CLLPEKIKQL AEDVANCLDI SYTLCDSPAY EMNDSTIVVE    120
PSLPSDPLIS KEKLRHLVIT PVEDEHFADD VLFFSTDETR TAIEDRLYQK EAANMGYQEL    180
RRSGRAILQM ACRCGKTRVA YLILSNYLQG KVLYLVPGLS LLRQTLEKLY QYGISLKNVL    240
LVGSDQTRIV LNHDNIEMTT NPVFIAKRIR EAPSLLVIAT YQSSTLLVDD FDLIISDECH    300
RICGEWETRP FTHVLLNFKK GHRLFLTATP RYDTPLSMKN RELFGGVAFR YYLREGIEAG    360
YVNDFELQMV AAPKLAHQPS TKEETTKQII VKQIIMALAY LKTNIPAPKM LVFTRDIKQA    420
KELYAALVDQ GVYALIAHST LPRQVILKTF TEFCSSKEPV ILLNCRLFQE GVEVPELNAV    480
FFAAPRHSPR DIIQSICRPL NKQVQKPHAT IFLPLEVNTE NVCLDRFSSI IPFADALASE    540
DPRFYEHLLN PSEVAYPINW IGAHGSVSEL LQLARHAIRY GTQGKIDRLT RSERLPWKAA    600
FAELKRTVEI CCRYPKINDG FHFGGATLRF DTWYKWVIKS YLQYKNKEPS SLEPYQVSDL    660
ESLQDWTTRG VGGPYPWEES MAFLETWLAQ NKGELVAIDI HQGGWIGLDA TPMERLSGVL    720
TTVSQRDGRS YGKNKKLRPK KGFMIPPQQA QDLDRIFGKH NLKWRKDRVN GFLKEDEHGN    780
YTGEPTCIQE AYRTFKEYVK TNPEYIEKYW PGYAKGKHKH QELPHIWEKG LAPPRYKAFK    840
DGNKQLIQRS PKKKDIKN                                                  858

SEQ ID NO: 31             moltype = AA  length = 9
FEATURE                   Location/Qualifiers
source                    1..9
                          mol_type = protein
                          organism = African swine fever virus
SEQUENCE: 31
LTRHIYNTV                                                              9

SEQ ID NO: 32             moltype = AA  length = 117
FEATURE                   Location/Qualifiers
source                    1..117
                          mol_type = protein
                          organism = African swine fever virus
SEQUENCE: 32
MGYTIQLDKD GDYCWDEDPT HHDPYMQANA TSHVATSYAT TSHAAVAAPH AAAHHTFHEP     60
FIKLNLTDKN IFNGLGFILI VIFIYLLLIT LQQMLTRHIY NTVQHCVKAH LDSKNLQ       117

SEQ ID NO: 33             moltype = AA  length = 115
FEATURE                   Location/Qualifiers
source                    1..115
                          mol_type = protein
                          organism = African swine fever virus
SEQUENCE: 33
MGYTIQLDKD GDYCWDEDPT HHDPYMQANA TSHVATSYAT TSHAATPHAA AHHTFHEPFI     60
KLNLTDKNIF NGLGFILIVI FIYLLLITLQ QMLTRHIYNT VQHCVKAHLD SKNLQ         115
```

```
SEQ ID NO: 34            moltype = AA   length = 8
FEATURE                  Location/Qualifiers
source                   1..8
                         mol_type = protein
                         organism = African swine fever virus
SEQUENCE: 34
FQYWTFAF                                                                 8

SEQ ID NO: 35            moltype = AA   length = 119
FEATURE                  Location/Qualifiers
source                   1..119
                         mol_type = protein
                         organism = African swine fever virus
SEQUENCE: 35
MLHWGPKYWR SLHLYAIFFS DAPSWKEKYE AIQWILNFIE SLPCTRCQHH AFSYLTKNPL        60
TLNNSEDFQY WTFAFHNNVN NRLNKKIISW SEYKNIYEQS ILKTIEYGKT DFIGAWSSL        119

SEQ ID NO: 36            moltype = AA   length = 10
FEATURE                  Location/Qualifiers
source                   1..10
                         mol_type = protein
                         organism = African swine fever virus
SEQUENCE: 36
AKDLDNNKEL                                                              10

SEQ ID NO: 37            moltype = AA   length = 9
FEATURE                  Location/Qualifiers
source                   1..9
                         mol_type = protein
                         organism = African swine fever virus
SEQUENCE: 37
NKKEEYLRM                                                                9

SEQ ID NO: 38            moltype = AA   length = 125
FEATURE                  Location/Qualifiers
source                   1..125
                         mol_type = protein
                         organism = African swine fever virus
SEQUENCE: 38
MAVYAKDLDN NKELNQKLIN DQLKIIDTLL LAEKKNFLVY ELPAPFDFSS GDPLASQRDI        60
YYAIIKSLEE RGFTVKICMK GDRALLFITW KKIQSIEINK KEEYLRMHFI QDEEKAFYCK       120
FLESR                                                                  125

SEQ ID NO: 39            moltype = AA   length = 125
FEATURE                  Location/Qualifiers
source                   1..125
                         mol_type = protein
                         organism = African swine fever virus
SEQUENCE: 39
MAVYAKDLDN NKELNQKLIN DQLKIIDTLL LAEKKNFLVY ELPAPFDFSS GDPLASQRDI        60
YYAIIKSLEE RGFTVKICMK GDRALLFITW KKIQSIEINK KEEYLRMHFI QDEEKAFYCK       120
FLESR                                                                  125

SEQ ID NO: 40            moltype = AA   length = 9
FEATURE                  Location/Qualifiers
source                   1..9
                         mol_type = protein
                         organism = African swine fever virus
SEQUENCE: 40
FQNPFIVAL                                                                9

SEQ ID NO: 41            moltype = AA   length = 164
FEATURE                  Location/Qualifiers
source                   1..164
                         mol_type = protein
                         organism = African swine fever virus
SEQUENCE: 41
MNVDFIAGIN NLGEKIYTCE PFKTSFQNPF IVALIITAVV LVVFFAICNP PVDKKRKTKT        60
AIYVYICIVA LLFLHYYVLN HQLNDIYNKS NMDVIVSSIH DKYKGGDEII PPISPPSVSN       120
ELEEDQPKKI PAGPKPADSK PVSLPDSKPL VPLQEVIMPS QYNN                       164

SEQ ID NO: 42            moltype = AA   length = 10
FEATURE                  Location/Qualifiers
source                   1..10
                         mol_type = protein
                         organism = African swine fever virus
SEQUENCE: 42
KTVPKFVPTY                                                              10
```

```
SEQ ID NO: 43            moltype = AA   length = 175
FEATURE                  Location/Qualifiers
source                   1..175
                         mol_type = protein
                         organism = African swine fever virus
SEQUENCE: 43
METNCPNILY LSGITIEECL QSKKTATDTL NTNDDEAEVE KKLPSVFTTV SKWVTHSSFK    60
CWTCHLYFKT VPKFVPTYMR ENERGEIEMG VLGNFCSFSC AASYVDVHYT EPKRWEAREL   120
LNMLYRFFTS QWISYIKPAP SYTMRKEYGG KLSEEAFISE LHTLEESISS KHIFI        175

SEQ ID NO: 44            moltype = AA   length = 8
FEATURE                  Location/Qualifiers
source                   1..8
                         mol_type = protein
                         organism = African swine fever virus
SEQUENCE: 44
AQMSALAL                                                              8

SEQ ID NO: 45            moltype = AA   length = 318
FEATURE                  Location/Qualifiers
source                   1..318
                         mol_type = protein
                         organism = African swine fever virus
SEQUENCE: 45
MLHLIYISII VVLIIILISY TRKPKYFRIT APRSVALFHG IHPLNPKNYK TFSEEFETIL    60
NNAIEDGDFK GQLTEPCSYA LRGGKYIRPI ILMEIVRACQ LQHSFGAPIY PAEAALAAEY   120
FHVASLIIDD MPSFDNDVKR RNKDTVWARF GVAKAQMSAL ALTMQGFQNI CRQIDWIKEH   180
CPRFPDPNQL GALLCTFVSH SLNSAGSGQL VDTPEKTIPF FKIAFIMGWV LGTGSVEDIG   240
MIERAAHCFG HAFQLADDIK DHDTDTGWNY AKIHGKQKTF DDVAQSLQEC KKILHGKKIF   300
TSIWNEIFQK VINVALGT                                                 318

SEQ ID NO: 46            moltype = AA   length = 9
FEATURE                  Location/Qualifiers
source                   1..9
                         mol_type = protein
                         organism = African swine fever virus
SEQUENCE: 46
TIFDETHFY                                                             9

SEQ ID NO: 47            moltype = AA   length = 385
FEATURE                  Location/Qualifiers
source                   1..385
                         mol_type = protein
                         organism = African swine fever virus
SEQUENCE: 47
MDEIINKYQA VEKLFKEIQQ GLAAYDQYKT LISEMMHYNN HIKQEYFNFL MIISPYLIRA    60
HSGETLRNKV NNEIKRLILV ENINTKISKT LVSVNFLLQK KLSTDGVKTK NMWCTNNPML   120
QVKTAHNLFK QLCDTQSKTQ WVQTLKYKEC KYCHTDMVFN TTQFGLQCPN CGCIQELMGT   180
IFDETHFYNH DGQKAKSGIF NPNRHYRFWI EHILGRNPEQ ELGTKQDPCG TKVLQQLKKI   240
IKRDNKCIAL LTVENIRKML KEINRTDLNN CVSLILRKLT GVGPPQISES ILLRGEYIFT   300
EAIKIREKVC KKGRINRNYY PYYIYKIFDA ILPPNDTTNR RILQYIHLQG NDTLANNDSE   360
WESICMELPE IKWKPTDRTH CVHFF                                         385

SEQ ID NO: 48            moltype = AA   length = 12
FEATURE                  Location/Qualifiers
source                   1..12
                         mol_type = protein
                         organism = African swine fever virus
SEQUENCE: 48
DSFIPKEYSQ SI                                                        12

SEQ ID NO: 49            moltype = AA   length = 12
FEATURE                  Location/Qualifiers
source                   1..12
                         mol_type = protein
                         organism = African swine fever virus
SEQUENCE: 49
LPFIIKNRKE NY                                                        12

SEQ ID NO: 50            moltype = AA   length = 11
FEATURE                  Location/Qualifiers
source                   1..11
                         mol_type = protein
                         organism = African swine fever virus
SEQUENCE: 50
LPSEHFSNEE Y                                                         11

SEQ ID NO: 51            moltype = AA   length = 9
```

-continued

```
FEATURE                 Location/Qualifiers
source                  1..9
                        mol_type = protein
                        organism = African swine fever virus
SEQUENCE: 51
NKKLYEKML                                                                       9

SEQ ID NO: 52           moltype = AA  length = 11
FEATURE                 Location/Qualifiers
source                  1..11
                        mol_type = protein
                        organism = African swine fever virus
SEQUENCE: 52
RKQELLTSQE L                                                                   11

SEQ ID NO: 53           moltype = AA  length = 11
FEATURE                 Location/Qualifiers
source                  1..11
                        mol_type = protein
                        organism = African swine fever virus
SEQUENCE: 53
SQELTSKSPN N                                                                   11

SEQ ID NO: 54           moltype = AA  length = 9
FEATURE                 Location/Qualifiers
source                  1..9
                        mol_type = protein
                        organism = African swine fever virus
SEQUENCE: 54
NKKLYEKML                                                                       9

SEQ ID NO: 55           moltype = AA  length = 12
FEATURE                 Location/Qualifiers
source                  1..12
                        mol_type = protein
                        organism = African swine fever virus
SEQUENCE: 55
DSFIPKEYSQ SI                                                                  12

SEQ ID NO: 56           moltype = AA  length = 12
FEATURE                 Location/Qualifiers
source                  1..12
                        mol_type = protein
                        organism = African swine fever virus
SEQUENCE: 56
LPFIIKNRKE NY                                                                  12

SEQ ID NO: 57           moltype = AA  length = 11
FEATURE                 Location/Qualifiers
source                  1..11
                        mol_type = protein
                        organism = African swine fever virus
SEQUENCE: 57
LPSEHFSNEE Y                                                                   11

SEQ ID NO: 58           moltype = AA  length = 11
FEATURE                 Location/Qualifiers
source                  1..11
                        mol_type = protein
                        organism = African swine fever virus
SEQUENCE: 58
RKQELLTSQE L                                                                   11

SEQ ID NO: 59           moltype = AA  length = 11
FEATURE                 Location/Qualifiers
source                  1..11
                        mol_type = protein
                        organism = African swine fever virus
SEQUENCE: 59
SQELTSKSPN N                                                                   11

SEQ ID NO: 60           moltype = AA  length = 9
FEATURE                 Location/Qualifiers
source                  1..9
                        mol_type = protein
                        organism = African swine fever virus
SEQUENCE: 60
SIFETLGAY                                                                       9
```

-continued

| | | |
|---|---|---|
| SEQ ID NO: 61 | moltype = AA   length = 11 | |
| FEATURE | Location/Qualifiers | |
| source | 1..11 | |
| | mol_type = protein | |
| | organism = African swine fever virus | |
| SEQUENCE: 61 | | |
| TLGAYFINIF Y | | 11 |
| | | |
| SEQ ID NO: 62 | moltype = AA   length = 15 | |
| FEATURE | Location/Qualifiers | |
| source | 1..15 | |
| | mol_type = protein | |
| | organism = African swine fever virus | |
| SEQUENCE: 62 | | |
| TLGAYFINIF YNFLY | | 15 |
| | | |
| SEQ ID NO: 63 | moltype = AA   length = 11 | |
| FEATURE | Location/Qualifiers | |
| source | 1..11 | |
| | mol_type = protein | |
| | organism = African swine fever virus | |
| SEQUENCE: 63 | | |
| YFINIFYNFL Y | | 11 |
| | | |
| SEQ ID NO: 64 | moltype = AA   length = 9 | |
| FEATURE | Location/Qualifiers | |
| source | 1..9 | |
| | mol_type = protein | |
| | organism = African swine fever virus | |
| SEQUENCE: 64 | | |
| KMLDSFYKY | | 9 |
| | | |
| SEQ ID NO: 65 | moltype = AA   length = 475 | |
| FEATURE | Location/Qualifiers | |
| source | 1..475 | |
| | mol_type = protein | |
| | organism = African swine fever virus | |
| SEQUENCE: 65 | | |
| MDQEESHVIS IFETLGAYFI NIFYNFLYKN ALYKKHSIVT EYQYQVKGYI LGVKQNKKLY | | 60 |
| EKMLDSFYKY FCNITQINSK TLNFSNFITT IVDSFIPKEY SQSISLEKKE SILELLLCDY | | 120 |
| ISNLGTFITT EKMLPFIIKN RKENYHKVTK EMQDYSLTFL LKKRMELYNK FLRKQAYVEP | | 180 |
| ETELEETYAR LSSYNRSLLH QIEELTSEKK SLLADLSTLR KKYEKRQSEY RRLVQLLYQQ | | 240 |
| IQRSSTSKSS YPLTKFIETL PSEHFSNEEY QKETPADQKE VVEMELLRKQ ELLTSQELTS | | 300 |
| KSPNNYPVPH SRTIVSKPPD NYPVPRSRTT TKLDFDNSLQ NQELHTKNGF SEKDIVEFGQ | | 360 |
| DKPEEENILA IDQDKPEEEN ILAIKQDIPE EENILAIDQD KPEFNQDTPE FKEAVLDTKE | | 420 |
| NILEEENQDE PIVQNPFLEN FWKPEQKTFN QSGLFEESSN FSNDWSGGDV TLNFS | | 475 |
| | | |
| SEQ ID NO: 66 | moltype = AA   length = 475 | |
| FEATURE | Location/Qualifiers | |
| source | 1..475 | |
| | mol_type = protein | |
| | organism = African swine fever virus | |
| SEQUENCE: 66 | | |
| MDQEESHVIS IFETLGAYFI NIFYNFLYKN ALYKKHSIVT EYQYQVKGYI LGVKQNKKLY | | 60 |
| EKMLDSFYKY FCNITQINSK TLNFSNFVTT IVDSFIPKEY SQSISLEKKE SILELLLCDY | | 120 |
| ISNLGTFITT EKMLPFIIKN RKENYHKVTK EMQDYSLTFL LKKRMELYNK FLRKQAYVEP | | 180 |
| ETELEETYAR LSSYNRSLLH QIEELTSENK SLLADLSTLR KKYEKRQSEY RRLVQLLYQQ | | 240 |
| IQRSSTSKSS YPLTKFIETL PSEHFSNEEY QKETPADQKE VVEMELLRKQ ELLTSQELTS | | 300 |
| KSPNNYPVPH SRTIVSKPLD NYPVPRSRTT TKIDFDNSLQ NQELHTKNGF SEKDIVEFGQ | | 360 |
| DKPEEENILA IDQDKPEEET ILAIKQDISE EDNIFAIDQD KPEFNQDTPE FKEAVLDIKE | | 420 |
| NILEEENQDE PIVQNPFLEN FWKPEQKTFN QSGLFEESSN FSNDWSGGDV TLNFS | | 475 |
| | | |
| SEQ ID NO: 67 | moltype = AA   length = 9 | |
| FEATURE | Location/Qualifiers | |
| source | 1..9 | |
| | mol_type = protein | |
| | organism = African swine fever virus | |
| SEQUENCE: 67 | | |
| KVDEFYYKY | | 9 |
| | | |
| SEQ ID NO: 68 | moltype = AA   length = 11 | |
| FEATURE | Location/Qualifiers | |
| source | 1..11 | |
| | mol_type = protein | |
| | organism = African swine fever virus | |
| SEQUENCE: 68 | | |
| SKPTHTTKTL L | | 11 |
| | | |
| SEQ ID NO: 69 | moltype = AA   length = 8 | |

```
FEATURE                Location/Qualifiers
source                 1..8
                       mol_type = protein
                       organism = African swine fever virus
SEQUENCE: 69
VDEFYYKY                                                                    8

SEQ ID NO: 70          moltype = AA  length = 24
FEATURE                Location/Qualifiers
source                 1..24
                       mol_type = protein
                       organism = African swine fever virus
SEQUENCE: 70
REQYIRRLIM TSFIGYVFKA LQEW                                                 24

SEQ ID NO: 71          moltype = AA  length = 9
FEATURE                Location/Qualifiers
source                 1..9
                       mol_type = protein
                       organism = African swine fever virus
SEQUENCE: 71
LIMTSFIGY                                                                   9

SEQ ID NO: 72          moltype = AA  length = 11
FEATURE                Location/Qualifiers
source                 1..11
                       mol_type = protein
                       organism = African swine fever virus
SEQUENCE: 72
LIMTSFIGYV F                                                               11

SEQ ID NO: 73          moltype = AA  length = 9
FEATURE                Location/Qualifiers
source                 1..9
                       mol_type = protein
                       organism = African swine fever virus
SEQUENCE: 73
ALQEWMPSY                                                                   9

SEQ ID NO: 74          moltype = AA  length = 602
FEATURE                Location/Qualifiers
source                 1..602
                       mol_type = protein
                       organism = African swine fever virus
SEQUENCE: 74
MAEFNIDELL KNVLEDPSTE ISEETLKQLY QRTNPYKQFK NDSRVAFCSF TNLREQYIRR           60
LIMTSFIGYV FKALQEWMPS YSKPTHTTKT LLSELITLVD TLKQETNDVP SESVVNTILS          120
IADSCKTQTQ KSKEAKTTID SFLREHFVFD PNLHAQSAYT CASTCADTNV DTCASTCAST          180
CASTCASTGA STCADTNVDT CASTCADTNV DTCASTCADT NVDTCASTCA DTNVDTCAST          240
CADTNVNTCA SMCADTNVDT CASTCANTCA STEYTDLADP ERIPLHIMQK TLNVPNELQA          300
DIDAITQTPQ GYRAAAHILQ NIELHQSIKH MLENPRAFKP ILFNTKITRY LSQHIPPQDT          360
FYKWNYYIED NYEELRAATE SIYPEKPDLE FAFIIYDVVD SSNQQKVDEF YYKYKDQIFS          420
EVSSIQLGNW TLLGSFKANR ERYNYFNQNN EIIKRILDRH EEDLKIGKEI LRNTIYHKKA          480
KNIQETGPDA PGLSIYNSTF HTDSGIKGLL SFKELKNLEK ASGNIKKARE YDFIDDCEEK          540
IKQLLSKENL TPDEESELIK TKKQLNNALE MLNVPDDTIR VDMWVNNNNK LEKEILYTKA          600
EL                                                                        602

SEQ ID NO: 75          moltype = AA  length = 530
FEATURE                Location/Qualifiers
source                 1..530
                       mol_type = protein
                       organism = African swine fever virus
SEQUENCE: 75
MAEFNIDELL KNVLEDPSTE ISEETLKQLY QRTNPYKQFK NDSRVAFCSF TNLREQYIRR           60
LIMTSFIGYV FKALQEWMPS YSKPTHTTKT LLSELITLVD TLKQETNDVP SESVVNTILS          120
IADSCKTQTQ KSKEAKTTID SFLREHFVFD PNLHAQSAYT CADTNVDTCA SMCADTNVDT          180
CASMCADTNV DTCASTCTST EYTDLADPER IPLHIMQKTL NVPNELQADI DAITQTPQGY          240
RAAAHILQNI ELHQSIKHML ENPRAFKPIL FNTKITRYLS QHIPPQDTFY KWNYYIEDNY          300
EELRAATESI YPEKPDLEFA FIIYDVVDSS NQQKVDEFYY KYKDQIFSEV SSIQLGNWTL          360
LGSFKANRER YNYFNQNNEI IKRILDRHEE DLKIGKEILR NTIYHKKAKN IQETGPDAPG          420
LSIYNSTFHT DSGIKGLLSF KELKNLEKAS GNIKKAREYD FIDDCEEKIK QLLSKENLTP          480
DEESELIKTK KQLDNALEML NVPDDTIRVD MWVNNNNKLE KEILYTKAEL                     530

SEQ ID NO: 76          moltype = AA  length = 13
FEATURE                Location/Qualifiers
source                 1..13
                       mol_type = protein
                       organism = African swine fever virus
SEQUENCE: 76
```

```
LLQNGSAVLR YST                                                            13

SEQ ID NO: 77           moltype = AA  length = 12
FEATURE                 Location/Qualifiers
source                  1..12
                        mol_type = protein
                        organism = African swine fever virus
SEQUENCE: 77
LQNGSAVLRY ST                                                             12

SEQ ID NO: 78           moltype = AA  length = 11
FEATURE                 Location/Qualifiers
source                  1..11
                        mol_type = protein
                        organism = African swine fever virus
SEQUENCE: 78
NVRFDVNGNS L                                                              11

SEQ ID NO: 79           moltype = AA  length = 10
FEATURE                 Location/Qualifiers
source                  1..10
                        mol_type = protein
                        organism = African swine fever virus
SEQUENCE: 79
KPYVPVGFEY                                                                10

SEQ ID NO: 80           moltype = AA  length = 11
FEATURE                 Location/Qualifiers
source                  1..11
                        mol_type = protein
                        organism = African swine fever virus
SEQUENCE: 80
LMSALKWPIE Y                                                              11

SEQ ID NO: 81           moltype = AA  length = 9
FEATURE                 Location/Qualifiers
source                  1..9
                        mol_type = protein
                        organism = African swine fever virus
SEQUENCE: 81
SALKWPIEY                                                                  9

SEQ ID NO: 82           moltype = AA  length = 646
FEATURE                 Location/Qualifiers
source                  1..646
                        mol_type = protein
                        organism = African swine fever virus
SEQUENCE: 82
MASGGAFCLI ANDGKADKII LAQDLLNSRI SNIKNVNKSY GKPDPEPTLS QIEETHLVHF   60
NAHFKPYVPV GFEYNKVRPH TGTPTLGNKL TFGIPQYGDF FHDMVGHHIL GACHSSWQDA  120
PIQGTAQMGA HGQLQTFPRN GYDWDNQTPL EGAVYTLVDP FGRPIVPGTK NAYRNLVYYC  180
EYPGERLYEN VRFDVNGNSL DEYSSDVTTL VRKFCIPGDK MTGYKHLVGQ EVSVEGTSGP  240
LLCNIHDLHK PHQSKPILTD ENDTQRTCSH TNPKFLSQHF PENSHNIQTA GKQDITPITD  300
ATYLDIRRNV HYSCNGPQTP KYYQPPLALW IKLRFWFNEN VNLAIPSVSI PFGERFITIK  360
LASQKDLVNE FPGLFIRQSR FIPGRPSRRN IRFKPWFIPG VINEISLTNN ELYINNLFVT  420
PEIHNLFVKR VRFSLIRVHK TQVTHTNNNH HDEKLMSALK WPIEYMFIGL KPTWNISDQN  480
PHQHRDWHKF GHVVNAIMQP THHAEISFQD RDTALPDACS SISDISPVTY PITLPIIKNI  540
SVTAHGINLI DKFPSKFCSS YIPFHYGGNA IKTPDDPGAM MITFALKPRE EYQPSGHINV  600
SRAREFYISW DTDYVGSITT ADLVVSASAI NFLLLQNGSA VLRYST              646

SEQ ID NO: 83           moltype = AA  length = 646
FEATURE                 Location/Qualifiers
source                  1..646
                        mol_type = protein
                        organism = African swine fever virus
SEQUENCE: 83
MASGGAFCLI ANDGKADKII LAQDLLNSRI SNIKNVNKSY GKPDPEPTLS QIEETHLVHF   60
NAHFKPYVPV GFEYNKVRPH TGTPTLGNKL TFGIPQYGDF FHDMVGHHIL GACHSSWQDA  120
PIQGTSQMGA HGQLQTFPRN GYDWDNQTPL EGAVYTLVDP FGRPIVPGTK NAYRNLVYYC  180
EYPGERLYEN VRFDVNGNSL DEYSSDVTTL VRKFCIPGDK MTGYKHLVGQ EVSVEGTSGP  240
LLCNIHDLHK PHQSKPILTD ENDTQRTCSH TNPKFLSQHF PENSHNIQTA GKQDITPITD  300
ATYLDIRRNV HYSCNGPQTP KYYQPPLALW IKLRFWFNEN VNLAIPSVSI PFGERFITIK  360
LASQKDLVNE FPGLFVRQSR FIAGRPSRRN IRFKPWFIPG VINEISLTNN ELYINNLFVT  420
PEIHNLFVKR VRFSLIRVHK TQVTHTNNNH HDEKLMSALK WPIEYMFIGL KPTWNISDQN  480
PHQHRDWHKF GHVVNAIMQP THHAEISFQD RDTALPDACS SISDISPVTY PITLPIIKNI  540
SVTAHGINLI DKFPSKFCSS YIPFHYGGNA IKTPDDPGAM MITFALKPRE EYQPSGHINV  600
SRAREFYISW DTDYVGSITT ADLVVSASAI NFLLLQNGSA VLRYST              646

SEQ ID NO: 84           moltype = AA  length = 8
```

```
FEATURE                  Location/Qualifiers
source                   1..8
                         mol_type = protein
                         organism = African swine fever virus
SEQUENCE: 84
FQHAIVYF                                                                            8

SEQ ID NO: 85            moltype = AA   length = 962
FEATURE                  Location/Qualifiers
source                   1..962
                         mol_type = protein
                         organism = African swine fever virus
SEQUENCE: 85
MGKPTLLEPG HLYNVPAEHK NDVPIHYIIT WIKQRLPEFG GAIPTSLADR VLIIKSRTGS                   60
GKSTALPVHV FRILRNENTH SFQKYLGRSV ICTQPRVLTA VTLAKDIGAS THYPDMILGQ                  120
TVGYQTKPLT EKPNRGLIYA TAGVLLAQLH TMTDDEIASR YAFMIIDEAH ERALGIDLML                  180
MYIKSMLQRM LQRGSIGALR IPFVILTSAT IDTHKYSTYF GIGKENIILV EGRQYGVETH                  240
WPLYNTNNYI KTACETALTI HKENIHDRPT EADILIFMPG MAEIRFLSML LNNANMDLAK                  300
EKLPLMLILP IDSEAIAQEN EAYLGLKAEI KNLWVKNPLT AKVEKPLRRV IVSTVVAETG                  360
LTIETLKYVI DPGWNRSIET YYPEWAGGLI TRPAAQSRIE QRKGRVGRVF PGHFYPLYTK                  420
HVFEQIPVQQ YPEIITEGPG AIFLSIVVET IKKNKEGVFK AEEIDMLDPP PTDALASAIE                  480
RAIVAGLLTR GEKGLQLTQL GDIASRFSFL SIEEARMCFS GYFWQAAISD IATILAVVSV                  540
ADKKLTNLLD SKQRNGAMLA EAVLAGIPPF LQNIDNAYTN IHLLLADDLL EGLFIFEGFQ                  600
HAIVYFINNK VNNVAKHLRE WCEKKMLKYS SMVQILARRE DILNELAIVG LNPFHQWQNR                  660
LASANAETFL KRVCTLKQCM YEAYRLNCFC YDEHRLLYTG RNGIHFSYHD AVIKNPSCIV                  720
TPRIMLSPVS KQYMEWRLEP SFVSVLDGFV NVDINFLLPR QEIPNILGGV ENEEEEPPLP                  780
IQVFLHKYVK THFHFSGKSF KELKMKPSQM IKFPETTLIN MIPDIPKNVV QTYLEINVCH                  840
RYSFKRLIYC ETFYTDMDDV QHENSVELIG LPMAAHHLTI NDFNKLYHLL KPDGFLIMYD                  900
LHQGQEAFWL HSLQDALGHH TIRRDMDFHT IPEWETIFKE CGFTPIFSKQ PSEHELFIVF                  960
KK                                                                                962

SEQ ID NO: 86            moltype = AA   length = 104
FEATURE                  Location/Qualifiers
source                   1..104
                         mol_type = protein
                         organism = African swine fever virus
SEQUENCE: 86
MSTKKKPTIT KQELYSLVAA DTQLNKALIE RIFTSQQKII QNALKHNQEV IIPPGIKFTV                   60
VTVKAKPARQ GHNPATGEPI QIKAKPEHKA VKIRALKPVH DMLN                                  104

SEQ ID NO: 87            moltype = AA   length = 104
FEATURE                  Location/Qualifiers
source                   1..104
                         mol_type = protein
                         organism = African swine fever virus
SEQUENCE: 87
MSTKKKPTIT KQELYSLVAA DTQLNKALIE RIFTSQQKII QNALKHNQEV IIPPGIKFTV                   60
VTVKAKPARQ GHNPATGEPI QIKAKPEHKA VKIRALKPVH DMLN                                  104

SEQ ID NO: 88            moltype = AA   length = 118
FEATURE                  Location/Qualifiers
source                   1..118
                         mol_type = protein
                         organism = African swine fever virus
SEQUENCE: 88
MHSNAFFNLI ACVLFPTPLI PSMVISIPRM INKWVKRVQF LTFLTNLFLY NIVQHYINRI                   60
RCYSFIKYLL LYNLYRPIFG RSLQMAITKI KIISDATAAV LLKSCAAMYD VLIDKKFK                   118

SEQ ID NO: 89            moltype = AA   length = 60
FEATURE                  Location/Qualifiers
source                   1..60
                         mol_type = protein
                         organism = African swine fever virus
SEQUENCE: 89
MHSNVSFNFI ACVLFPTPLI PSMAMSIPRM INKRKKRIQF LTFLTNLFLY NIVQHCISGI                   60

SEQ ID NO: 90            moltype = AA   length = 137
FEATURE                  Location/Qualifiers
source                   1..137
                         mol_type = protein
                         organism = African swine fever virus
SEQUENCE: 90
MEAVLTKLDQ EEKKALQNFH RCAWEETKNI INDFLEIPEE RCTYKFNSYT KKMELLFTPE                   60
FHTAWHEVPE CREFILNFLR LISGHRVVLK GPTFVFTKET KNLGIPSTIN VDFQANIENM                  120
DDLQKGNLIG KMNIKEG                                                                137

SEQ ID NO: 91            moltype = AA   length = 137
FEATURE                  Location/Qualifiers
source                   1..137
```

```
                        mol_type = protein
                        organism = African swine fever virus
SEQUENCE: 91
MEAVLTKLDQ EEKKALQNFH RCAWEETKNI INDFLEIPEE RCTYKFNSYT KKMELLFTPE    60
FHTAWHEVPE CREFILNFLR LISGHRVVLK GPTFVFTKEI KNLGIPSTIN VDFQANIENM   120
DDLQKGNLIG KMNIKEG                                                  137

SEQ ID NO: 92           moltype = AA  length = 179
FEATURE                 Location/Qualifiers
source                  1..179
                        mol_type = protein
                        organism = African swine fever virus
SEQUENCE: 92
MEGEELIYHN IINEILVGYI KYYINDISEH ELSPYQQQIK KILTYYDECL NKQVTITFSL    60
TSVQEIKTQF TGVVTELFKD LINWGRICGF IVFSAKMAKY CKDANNHLES TVITTAYNFM   120
KHNLLPWMIS HGGQEEFLAF SLHSDMYSVI FNIKYFLSKF CNHMFFRSCV QLLRNCNLI    179

SEQ ID NO: 93           moltype = AA  length = 179
FEATURE                 Location/Qualifiers
source                  1..179
                        mol_type = protein
                        organism = African swine fever virus
SEQUENCE: 93
MEGEELIYHN IINEILVGYI KYYINDISEH ELSPYQQQIK KILTYYDECL NKQVTITFSL    60
TSVQEIKTQF TGVVTELFKD LINWGRICGF IVFSAKMAKY CKDANNHLES TVITTAYNFM   120
KHNLLPWMIS HGGQEEFLAF SLHSDMYSVI FNIKYFLSKF CNHMFFRSCV QLLRNCNLI    179

SEQ ID NO: 94           moltype = AA  length = 224
FEATURE                 Location/Qualifiers
source                  1..224
                        mol_type = protein
                        organism = African swine fever virus
SEQUENCE: 94
MFPKINTIDP YISLRLFEVK PKYVGYSSID ARNQSFAIHG IKNYEKFSNA GFFYTSPTEI    60
TCYCCGMKFC NWLYEKHPLQ VHGFWSRNCG FMRATLGIIG LKKMIDSYND YYNNEVFVKH   120
KNRVYTHKRL EDMGFSKPFM RFILANAFIP PYRKYIHKII LNERYFTFKF AAHLLSFHKV   180
NLDNQTTYCM TCGIEPIKKD ENFCNACKTL NYKHYKTLNF SVKL                    224

SEQ ID NO: 95           moltype = AA  length = 224
FEATURE                 Location/Qualifiers
source                  1..224
                        mol_type = protein
                        organism = African swine fever virus
SEQUENCE: 95
MFPKINTIDP YISLRLFEVK PKYVGYSSID ARNQSFAIHD IKNYEKFSNA GLFYTSPTEI    60
TCYCCGMKFC NWLYEKHPLQ VHAFWSRNCG FMRATLGIIG LKKMIDSYND YYNNEVFVKH   120
QNRVYTHKRL EDMGFSKPFM RFILANAFIP PYRKYIHKII LNERYFTFKF AAHLLSFHKV   180
NLDNQTTYCM TCGIEPIKKD ENFCNACKTL NYKHYKTLNF SVKL                    224

SEQ ID NO: 96           moltype = AA  length = 238
FEATURE                 Location/Qualifiers
source                  1..238
                        mol_type = protein
                        organism = African swine fever virus
SEQUENCE: 96
MEHMFPEREI ENLFVKWIKK HIRNGNLTLF EEFFKTDPWI VNRCDKNGSS VFMWICIYGR    60
IDFLKFLFEQ ESYPGEIINP HRRDKDGNSA LHYLAEKKNH LILEEVLGYF GKNGTKICLP   120
NFNGMTPVMK AAIRGRTSNV LSLIKFGADP TQKDYHRGFT AWDWAVFTGN MELVKSLNHD   180
YQKPLYMHFP LYKLDVFHRW FKKKPKIIIT GCKNNVYEKL PEQNPNFLCV KKLNKYGK     238

SEQ ID NO: 97           moltype = AA  length = 226
FEATURE                 Location/Qualifiers
source                  1..226
                        mol_type = protein
                        organism = African swine fever virus
SEQUENCE: 97
MFPEREIENL FVKWIKKHIR NGNLTLFEEF FKTDPWIVNR CDKNGSSVFM WICIYGRIDF    60
LKFLFEQESY PGEIINPHRR DKDGNSALHY LAEKKNHLIL EGVLGYFGKN GTRICLPNFN   120
GMTPVMKAAI RGRSLNMLSL IKFGADPTQK DYHRGFTAWD WAVFTGNMEL VKSLNHDYQN   180
LSTCISLFTS WMFSTGGLRK SPKLLLLAVN IMSMKNFLNR IQSSCV                  226

SEQ ID NO: 98           moltype = AA  length = 859
FEATURE                 Location/Qualifiers
source                  1..859
                        mol_type = protein
                        organism = African swine fever virus
SEQUENCE: 98
MCAGFYVAVH PWLEAQSLHK VGHTGNLAAR LHDGSYTTCF TDEWKYCFTL ETSTKKDAQK    60
IEAGVLYCAQ FFRVKNKELV CLLPEKIKQL AEDVANCLDI SYTLCDSPTY EMNDSTIVVE   120
```

```
PSLPSDPLIS KEKLRHLVIT PVEDEEHFAD DVLFFSTDET RTAIEDRLYQ KEAANMGYQE    180
LRRSGRAILQ MACRCGKTRV AYLILSNYLQ GKVLYLVPGL SLLRQTLEKL YQYGISLKNV    240
LLVGSDQTRI VLNHDNIEMT TNPVFIAKRI REAPSLLVIA TYQSSTLLVD DFDLIISDEC    300
HRICGEWETR PFTHVLLNFK KGHRLFLTAT PRYDTPLSMK NRELFGGVAF RYYLREGIEA    360
GYVNDFELQM VAAPKLAHQP SNREETTKQI IVKQIIMALA YLKTNIPAPK MLVFTRDIKQ    420
ARELYAELVD QGVYALIAHS TLPRQVILKT FTEFCSSKEP VILLNCRLFQ EGVEVPELNA    480
VFFAAPRHSP RDIIQSICRP LNKQVQKPHA TIFLPLEVNT ENVCLDRFSS IIPFADALAS    540
EDPRFYEHLL NPSEVAYPIN WIGAHGSVSE LLQLARHAIR YGTQGKIDRL TRSERLPWKA    600
APAELKRTVE ICCRYPKIND GFHFGGATLR FDTWYKWVIK SYLQYKNKEP SSLEPYQVSD    660
LESLQDWTTR GVGGPYPWEE SMAFLETWLA QNKGELVAID IHQGGWIGLD ATPMERLSGV    720
LTTVSQRDGR SYGKNKKLRP KKGFMIPPQQ AEDLDRIFGK HNLKWRKDRV NGFLKEDEHG    780
NYTGEPTCIQ EAYRTFKEYV KTNPEYIEKY WPGYAKGKHK HQELPHIWES GLAPPRYKAF    840
KDGNKQLIQR SPKKKDIKN                                                 859

SEQ ID NO: 99              moltype = AA  length = 858
FEATURE                    Location/Qualifiers
source                     1..858
                           mol_type = protein
                           organism = African swine fever virus
SEQUENCE: 99
MCAGFYVAVH PWLEAQSLHK VGHTGNLAAR LHDGSYTTCF TDEWKYCFTL ETSTKKDAQK    60
IEAGVLYCAQ FFRVKNKELV CLLPEKIKQL AEDVANCLDI SYTLCDSPAY EMNDSTIVVE    120
PSLPSDPLIS KEKLRHLVIT PVEDEHFADD VLFFSTDETR TAIEDRLYQK EAANMGYQEL    180
RRSGRAILQM ACRCGKTRVA YLILSNYLQG KVLYLVPGLS LLRQTLEKLY QYGISLKNVL    240
LVGSDQTRIV LNHDNIEMTT NPVFIAKRIR EAPSLLVIAT YQSSTLLVDD FDLIISDECH    300
RICGEWETRP FTHVLLNFKK GHRLFLTATP RYDTPLSMKN RELFGGVAFR YYLREGIEAG    360
YVNDFELQMV AAPKLAHQPS TKEETTKQII VKQIIMALAY LKTNIPAPKM LVFTRDIKQA    420
KELYAALVDQ GVYALIAHST LPRQVILKTF TEFCSSKEPV ILLNCRLFQE GVEVPELNAV    480
FFAAPRHSPR DIIQSICRPL NKQVQKPHAT IFLPLEVNTE NVCLDRFSSI IPFADALASE    540
DPRFYEHLLN PSEVAYPINW IGAHGSVSEL LQLARHAIRF GTQGKIDRLT RSERLPWKAA    600
FAELKRTVEI CCRYPKINDG FHFGGATLRF DTWYKWVIKS YLQYKNKEPS SLEPYQVSDL    660
ESLQDWTTRG VGGPYPWEES MAFLETWLAQ NKGELVAIDI HQGGWIGLDA TPMERLSGVL    720
TTVSQRDGRS YGKNKKLRPK KGFMIPPQQA QDLDRIFGKH NLKWRKDRVN GFLKEDEHGN    780
YTGEPTCIQE AYRTFKEYVK TNPEYIEKYW PGYAKGKHKH QELPHIWEKG LAPPRYKAFK    840
DGNKQLIQRS PKKKDIKN                                                  858

SEQ ID NO: 100             moltype = AA  length = 175
FEATURE                    Location/Qualifiers
source                     1..175
                           mol_type = protein
                           organism = African swine fever virus
SEQUENCE: 100
METNCPNILY LSGITIEECL QTKKTATDTL NTNDDEAEVE KKLPSVFTTV SKWVTHSSFK    60
CWTCHLYFKT VPKFVPTYMR ENERGEIEMG VLGNFCSFSC AASYVDVHYT EPKRWEAREL    120
LNMLYRFFTS QWISYIKPAP SYTMRKEYGG KLSEEAFISE LHTLEESISS KHIFI         175

SEQ ID NO: 101             moltype = AA  length = 175
FEATURE                    Location/Qualifiers
source                     1..175
                           mol_type = protein
                           organism = African swine fever virus
SEQUENCE: 101
METNCPNILY LSGITIEECL QSKKTATDTL NTNDDEAEVE KKLPSVFTTV SKWVTHSSFK    60
CWTCHLYFKT VPKFVPTYMR ENERGEIEMG VLGNFCSFSC AASYVDVHYT EPKRWEAREL    120
LNMLYRFFTS QWISYIKPAP SYTMRKEYGG KLSEEAFISE LHTLEESISS KHIFI         175

SEQ ID NO: 102             moltype = AA  length = 263
FEATURE                    Location/Qualifiers
source                     1..263
                           mol_type = protein
                           organism = African swine fever virus
SEQUENCE: 102
MEDETELCFR SNKVTRLEMF VCTYGGKITS LACSHMELIK MLQIAEPVKA LNCNFGHQCL    60
PGYESLIKTP KKTKNMLRRP RKTEGDGTCF NSAIEASILF KDKMYKLKCF PSTGEIQVPG    120
VIFPDFEDGK NIIQQWVDFL QHQPIEKKIQ IIEFKTIMIN FKFQINPVSP RVIIHLKKFA    180
ALLEHIPTPY PIREIKPPLE DSKVSAKFMV SPGKKVRINV FLKGKINILG CNTKESAEII    240
YTFLKDLISV HWQEILCVLP VPD                                            263

SEQ ID NO: 103             moltype = AA  length = 263
FEATURE                    Location/Qualifiers
source                     1..263
                           mol_type = protein
                           organism = African swine fever virus
SEQUENCE: 103
MEDETELCFR SNKVTRLEMF VCTYGGKITS LACSHMELIK MLQIAEPVKA LNCNFGHQCL    60
PGYESLIKTP KKTKNMLRRP RKTEGDGTCF NSAIEASILF KDKMYKLKCF PSTGEIQVPG    120
VIFPDFEDGK NIIQQWVDFL QHQPIEKKIQ IIEFKTIMIN FKFQINPVSP RVIIHLKKFA    180
ALLEHIPTPY PIREIKPPLE DSKVSAKFMV SPGKKVRINV FLKGKINILG CNTKESAETI    240
YTFLKDLISV HWQEILCVLP VPD                                            263
```

```
SEQ ID NO: 104          moltype = AA   length = 407
FEATURE                 Location/Qualifiers
source                  1..407
                        mol_type = protein
                        organism = African swine fever virus
SEQUENCE: 104
MEDTTFLEGA NLAGITTLMN NLHINEQANL EELEKQVMGK QQSFPTDHFD EELNGLAKSL    60
GINFNDPEFS LDSPHSVISK KPSGRGRDKV HGGIRRDSVC TDSICSDSVC SGSIRSGSIR   120
SGSIRNGSIR SGSVRDDSVR SGKTRRGLAC NSSSRNDRGY SLSTHRKKYA ESEASQKTAF   180
SKRDRKNHYA ESEYSEKSIK PSTKQVDRLI NHLRSNGDPN SFYKKDHDYE RKTKLVKLEK   240
INMLLTYLGN EQISTDDIKI PTIDSSMQEI DDVIEMLTLR NVGIRYSSIA EEILIGLARG   300
LEIVFDGTRE IPFLNYRPDY TGLHNTFMIK LFKMRYETSQ VVGNLVQNMS PLSKICLELG   360
PSLLLYPALI RTKHKASEDL YNLLQKGPED PFTAYNEIHE TLKKNNK                 407

SEQ ID NO: 105          moltype = AA   length = 412
FEATURE                 Location/Qualifiers
source                  1..412
                        mol_type = protein
                        organism = African swine fever virus
SEQUENCE: 105
MEDTTFLEGA NLAGITTLMN NLHINEQANL EELEKQVMGK QQSFPTDHFD EELNGLAKSL    60
GINFNDPEFS LDSPHSIISK KPSGRGGDKV HGGIRRDSVC TDSICSDSVC SGSIRSGSIR   120
SGSIRNGSIR SGSVRDGSIR NGSVRSGKTR RGLACNSSSR NDRGYSLSTH RKKYAESEAS   180
QKTAISKRDR KNHYAESEYS EKSIKPSTKQ VDRLINHLRS NGDPNSFYKK DHDYERKTKL   240
VKLEKINMLL TYLGNEQIST DDIKIPTIDS SMQEIDDVIE MLTLRNVGIR YSSIAEEILI   300
GLARGLEIVF DGTREIPFLN YRPDYTGLHN TFMIKLFKMR YETSQVVGNL VQNMSPLSKI   360
CLELGPSLLL YPALIRTKHK ASEDLYNLLQ KGPEDPFTAY NEIHETLKKN NK           412

SEQ ID NO: 106          moltype = AA   length = 438
FEATURE                 Location/Qualifiers
source                  1..438
                        mol_type = protein
                        organism = African swine fever virus
SEQUENCE: 106
MYHDYASKLL ADYRSDPPLW ESDLPRHNRY SDNILNSRYC GNKNGAAPVY NEYTNSPEKA    60
EKGLQLSDLR NFSFMLNPQH KNIGYGDAQD LEPYSSIPKN KLFNHFKNHR PAFSTHTENL   120
IRRNVVRTEK KTFPQVASLK GTQKNCLTQP SSLPSLKNPK NSSVPSTRFS EHTKFFSYED   180
IPKLKTKGTI KHEQHLGDQM PGQHYNGYIP HKDVYNILCL AHNLPASVEK GIAGRGIPLG   240
NPHVKPNIEQ ELIKSTSTYT GVPMLGPLPP KDSQHGREYQ EFSANRHMLQ VANILHSVFA   300
NHSIKPQILE DIPVLNAQLT SIKPVSPFLN KAYQTHYMEN IVTLVPRFKS IANYSSPIPN   360
YSKRNSGQAE YFDTSKQTIS RHNNYIPKYT GGIGDSKLDS TFPKDFNASS VPLTSAEKDH   420
SLRGDNSACC ISSISPSL                                                 438

SEQ ID NO: 107          moltype = AA   length = 438
FEATURE                 Location/Qualifiers
source                  1..438
                        mol_type = protein
                        organism = African swine fever virus
SEQUENCE: 107
MYHDYASKLL ADYRSDPPLW ESDLPRHNRY SDNILNSRYC GNKNGAAPVY NEYTNSPEKA    60
EKGLQLSDLR NFSFMLNPQH KNIGYGDAQD LEPYSSIPKN KLFNHFKNHR PAFSTHTENL   120
IRRNVVRTEK KTFPQVASLK GTQKNCLTQP SSLPSLKNPK NSSVPSTRFS EHTKFFSYED   180
LPKLRTKGTI KHEQHLGDQM PGQHYNGYIP HKDVYNILCL AHNLPASVEK GIAGRGIPLG   240
NPHVKPNIEQ ELIKSTSTYT DVPMLGPLPP KDSQHGREYQ EFSANRHMLQ VSNILHSVFA   300
NHSIKPQILE DIPVLNAQLT SIKPVSPFLN KAYQTHYMEN IVTLVPRFKS IANYSSPIPN   360
YSKRNSGQAE YFDTSKQTIS RHNNYIPKYT GGIGDSKLDS TFPKDFNASS VPLTSAEKDH   420
SLRGDNSACC ISSISPSL                                                 438

SEQ ID NO: 108          moltype = AA   length = 62
FEATURE                 Location/Qualifiers
source                  1..62
                        mol_type = protein
                        organism = African swine fever virus
SEQUENCE: 108
MNWGSISSGT PGLFVESIRN TPSVVKINVI FLKVISNTAV SVFWRDRRIR FESDWLNSYF    60
QK                                                                   62

SEQ ID NO: 109          moltype = AA   length = 62
FEATURE                 Location/Qualifiers
source                  1..62
                        mol_type = protein
                        organism = African swine fever virus
SEQUENCE: 109
MNWGSISSGT PGLFVESIRN TPSVVKINVI FLKVISNTAV SVFWRDRRIR FESDWLNSYF    60
QK                                                                   62

SEQ ID NO: 110          moltype = AA   length = 129
FEATURE                 Location/Qualifiers
```

```
source                  1..129
                        mol_type = protein
                        organism = African swine fever virus
SEQUENCE: 110
MDINPLLYLQ AFNNDATTFN TQGHILEQQS DSPYFDTFAN AMQAYLDTKQ GGNDEEGTII    60
LMDDEDFNDS ESLEDFLQML SEEELNDGFS SDDEPEEHVI LTEDNQGEPS ETPQATFDIT   120
EFIKIDDED                                                          129

SEQ ID NO: 111          moltype = AA  length = 129
FEATURE                 Location/Qualifiers
source                  1..129
                        mol_type = protein
                        organism = African swine fever virus
SEQUENCE: 111
MDINPLLYLQ AFNNDATTFN TQGHILEQQS DSAYFDTFAN AMQAYLDTKQ GGNDEEGTII    60
LMDDEDFNDS ESLEDFLQML SEEELNDGFS SDDEPEEHVI LTEDNQGEPS ETPQATFDIT   120
EFIKTDDED                                                          129

SEQ ID NO: 112          moltype = AA  length = 250
FEATURE                 Location/Qualifiers
source                  1..250
                        mol_type = protein
                        organism = African swine fever virus
SEQUENCE: 112
MDTAMQLKTS IGLITCRMNT QNNQIETILV QKRYSLAFSE FIHCHYSINA NQGHLIKMFN    60
NMTINERLLV KTLDFDRMWY HIWIETPVYE LYHKKYQKFR KNWLLPDNGK KLISLINQAK   120
GSGTLLWEIP KGKPKEDESD LTCAIREFEE ETGITREYYQ ILPEFKKSMS YFDGKTEYKH   180
IYFLAMLCKS LEEPNMNLSL QYENRIAEIS KISWQNMEAV RFISKRQSFN LEPIIGPAFN   240
FIKNYLRYKH                                                         250

SEQ ID NO: 113          moltype = AA  length = 250
FEATURE                 Location/Qualifiers
source                  1..250
                        mol_type = protein
                        organism = African swine fever virus
SEQUENCE: 113
MDTAMQLKTS IGLITCRMNT QNNQIETILV QKRYSLAFSE FIHCHYSINA NQGHLIKMFN    60
NMTINERLLV KTLDFDRMWY HIWIETPVYE LYHKKYQKFR KNWLLPDNGK KLISLINQAK   120
GSGTLLWEIP KGKPKEDESD LTCAIREFEE ETGITREYYQ ILPEFKKSMS YFDGKTEYKH   180
IYFLAMLCKS LEEPNMNLSL QYENRIAEIS KISWQNMEAV RFISKRQSLN LEPIIGPAFN   240
FIKNYLRYKH                                                         250

SEQ ID NO: 114          moltype = AA  length = 345
FEATURE                 Location/Qualifiers
source                  1..345
                        mol_type = protein
                        organism = African swine fever virus
SEQUENCE: 114
METFVRLFKD SPQQRSDAWH AIRRTQVGGS DLASVLGLNP YKSYYIILAE KANLFKKNLN    60
RAACSWGTLF ERVSKDLLEL FCQTTVIGDN IHIDGTYLGY PGHSNSPDGF CHLTLGYTQQ   120
SWEIKTIFNN VRYEATKRIP VLVEIKSPFN RKIKNSVPSY YMPQIQSGLA LSPPISMGIY   180
VEAMFRVCGI HQLGSNNETN TDIHPPESML PLAWGIITIC STQEHTEAPQ DFGTLDAETF   240
RQLLETLYQK DQYTIHYSMP YETACPEMPN VVGYFGWKVF IFQIIPVMKH PQFLKDKYPI   300
IQQFLRDLHT IKASPSPMET YEKICCSEES ALSTEDIDNF TDMLT                  345

SEQ ID NO: 115          moltype = AA  length = 345
FEATURE                 Location/Qualifiers
source                  1..345
                        mol_type = protein
                        organism = African swine fever virus
SEQUENCE: 115
METFVRLFKD SPQQRSDAWH AIRRTQVGGS DLASVLGLNP YKSYYITLAE KANLFKKNLN    60
RAACSWGTLF ERVSKDLLEL FCQTTVIGDN IHIDGTYLGY PGHSNSPDGF CHLTLGYTQQ   120
SWEIKTIFNN VRYEATKRIP VLVEIKSPFN RKIKNSVPSY YMPQIQSGLA LSPPISMGIY   180
VEAMFRVCGI HQLGSNNETN TDIHPPESML PLAWGIITIC STQEHTEAPQ DFGTLDAETF   240
RQLLETLYQK DQYTIHYSMP YETACPEMPN VVGYFGWKVF IFQIIPVMKH PQFLKDKYPI   300
IQQFLRDLHT IKASPSPMEM YEKICCSEES ALSTEDIDNF TDMLT                  345

SEQ ID NO: 116          moltype = AA  length = 79
FEATURE                 Location/Qualifiers
source                  1..79
                        mol_type = protein
                        organism = African swine fever virus
SEQUENCE: 116
MNKTIEYQKE FLKENNQLLS IPVKKNILKE ILQNDEQDTI ITNCITKEVS INLDLIKNPK    60
VLYSIYIMVV EYLKSINIA                                                79

SEQ ID NO: 117          moltype = AA  length = 79
FEATURE                 Location/Qualifiers
```

```
                              source          1..79
                                              mol_type = protein
                                              organism = African swine fever virus
SEQUENCE: 117
MNKTIEYQKE FLKENNQLLS IPVKKNILKE ILQNDEQDTI ITNCITKEVS INLDLIKNPK    60
VLYSIYIMVV EYLKSINIA                                                79

SEQ ID NO: 118                moltype = AA   length = 96
FEATURE                       Location/Qualifiers
source                        1..96
                              mol_type = protein
                              organism = African swine fever virus
SEQUENCE: 118
MSTHDCFSKE KPVDMNDISE KSSVVDNAPE KPAGANHIPE KSAREMTSSE WIAEYWKGIK    60
RGNDVPCCCP RKMTSADKKF SVFGKGSLIR SIQKNN                             96

SEQ ID NO: 119                moltype = AA   length = 96
FEATURE                       Location/Qualifiers
source                        1..96
                              mol_type = protein
                              organism = African swine fever virus
SEQUENCE: 119
MSTHDCSLKE KPVDMNDISE KSVVVDNAPE KPAGANHIPE KSAREMTSSE WIAEYWKGIK    60
RGNDVPCCCP RKMTSADKKF SVFGKGSLMR SIQKNN                             96

SEQ ID NO: 120                moltype = AA   length = 111
FEATURE                       Location/Qualifiers
source                        1..111
                              mol_type = protein
                              organism = African swine fever virus
SEQUENCE: 120
MSFSECPLVI SACKKFLQKR ITIENEALIN ALITALAQTS TLNDLCLLPI QTYLLSYKNA    60
FEWIHFVCIA ITTILDNKYN WKDCTVDINY IFLHVTYIYN IKTKEYLDYC S            111

SEQ ID NO: 121                moltype = AA   length = 111
FEATURE                       Location/Qualifiers
source                        1..111
                              mol_type = protein
                              organism = African swine fever virus
SEQUENCE: 121
MSFSECPLVI SACKKFLQKR ITIENEALIN ALITALAQTS TLNDLCLLPI QTYLLSYKNA    60
FEWIHFVCIA ITTILDNKYN WKDCTVDINY IFLHVTYIYN IKTKEYLDYC S            111

SEQ ID NO: 122                moltype = AA   length = 120
FEATURE                       Location/Qualifiers
source                        1..120
                              mol_type = protein
                              organism = African swine fever virus
SEQUENCE: 122
MADFNSPIQY LKEDSRDRTS IGSLEYDENS DTIIPSFAAG LEDFEPIPSP TTSTSLYSQL    60
THNMEKIAEE EDINFLHDTR EFTSLVPDEA DNKPEDDEES GAKPKKKKHL FPKLSSHKSK   120

SEQ ID NO: 123                moltype = AA   length = 122
FEATURE                       Location/Qualifiers
source                        1..122
                              mol_type = protein
                              organism = African swine fever virus
SEQUENCE: 123
MADFNSPIQY LKEDSRDRTS IGSLEYDENA DTMIPSFAAG LEEFEPIPDY DPTTSTSLYS    60
QLTHNMEKIA EEEDSNFLHD TREFTSLVPD EADNKPEDDE ESGAKPKKKK HLFPKLSSHK   120
SK                                                                 122

SEQ ID NO: 124                moltype = AA   length = 165
FEATURE                       Location/Qualifiers
source                        1..165
                              mol_type = protein
                              organism = African swine fever virus
SEQUENCE: 124
MATNFFIQPI TQEAEAYYPP SVITNKRKDL GVDVYCCSDL VLQPGLNIVR LHIKVACEHM    60
GKKCGFKIMA RSSMCTHERL LILANGIGLI DPGYVGELML KIINLGDTPV QIWAKECLVQ   120
LVAQGDHVPD HINILKRNQI FPLFAPTPRG EGRFGSTGEA GIMRT                  165

SEQ ID NO: 125                moltype = AA   length = 165
FEATURE                       Location/Qualifiers
source                        1..165
                              mol_type = protein
                              organism = African swine fever virus
SEQUENCE: 125
MATNFFIQPI TEEAEAYYPP SVITNKRKDL GVDVYCCSDL VLQPGLNIVR LHIKVACEHM    60
```

```
GKKCGFKIMA RSSMCTHERL LILANGIGLI DPGYVGELML KIINLGDTPV QIWAKECLVQ    120
LVAQGDHVPD HINILKRNQI FPLFAPTPRG EGRFGSTGEA GIMRT                    165

SEQ ID NO: 126          moltype = AA  length = 183
FEATURE                 Location/Qualifiers
source                  1..183
                        mol_type = protein
                        organism = African swine fever virus
SEQUENCE: 126
MDSEFFQPVY PRHYGECLSP VTPPSFFSTH MYTILIAIVV LVIIIIVLIY LFSSRKKKAA    60
AAIEEEDIQF INPYQDQQWA EVTPQPGTSK PAGATTASAG KPVTGRPATN RPATNKPVTD    120
NPVTDRLVMA TGGPAAAPAA ASAHPTEPYT TVTTQNTASQ TMSAIENLRQ RNTYTHKDLE    180
NSL                                                                  183

SEQ ID NO: 127          moltype = AA  length = 184
FEATURE                 Location/Qualifiers
source                  1..184
                        mol_type = protein
                        organism = African swine fever virus
SEQUENCE: 127
MDSEFFQPVY PRHYGECLSP VTPSFFSTH MYTILIAIVV LVIIIIVLIY LFSSRKKKAA     60
AIEEEDIQFI NPYQDQQWVE VTPQPGTSKP AGATTASVGK PVTGRPATNR PATNKPVTDN    120
PVTDRLVMAT GGPAAAPAAA SAPAHPAEPY TTVTTQNTAS QTMSAIENLR QRNTYTHKDL    180
ENSL                                                                 184

SEQ ID NO: 128          moltype = AA  length = 184
FEATURE                 Location/Qualifiers
source                  1..184
                        mol_type = protein
                        organism = African swine fever virus
SEQUENCE: 128
MKTFITCTSV KNYFRQHLKT NQRISSELIS YVCTILNHIC HQYLQNPQAQ EEEWFALIKE    60
LPIIKDGLSK EERFFSSGVK HFLHEYKITP ENQEKFQKML NAITEQLMSR LCKVFSIMIQ    120
RQGFLKTQTL MYSHLFTILS ILMVADNLYG EQDPTEFFSL IIEQTKTIKK KKKSSSEEEE    180
SHEE                                                                 184

SEQ ID NO: 129          moltype = AA  length = 184
FEATURE                 Location/Qualifiers
source                  1..184
                        mol_type = protein
                        organism = African swine fever virus
SEQUENCE: 129
MKTFITCTSV KNYFRQHLKT NQRISSELIS YVCTILNHIC HQYLQNPQAQ EEEWFALIKE    60
LPIIKDGLSK EERFFSSGVK HFLHEYKITP ENQEKFQKML NAITEQLMSR LCKVFSIMIQ    120
RQGFLKTQTL MYSHLFTILS ILMVADNLYG EQDPTEFFSL IIEQTKTIKK KKKSGSEEEE    180
SHEE                                                                 184

SEQ ID NO: 130          moltype = AA  length = 199
FEATURE                 Location/Qualifiers
source                  1..199
                        mol_type = protein
                        organism = African swine fever virus
SEQUENCE: 130
MSCMPVSTKC NDIWVDFSCT GPSISELQKK EPKAWAAILR SHTNQQTAED DNIIGSICDK    60
QGLCSKDEYA YSQYCACVNS GTLWAECAFA PCNGNKNAYK TTEQRNILTN KQCPSGLTIC    120
QNIAEYRGSG NISDLYQNFN CNSVINTFLI NVMNHPFLTL ILIILILIII YRLMPSSGGK    180
HNDDKLPPPS LIFSNLNNF                                                 199

SEQ ID NO: 131          moltype = AA  length = 199
FEATURE                 Location/Qualifiers
source                  1..199
                        mol_type = protein
                        organism = African swine fever virus
SEQUENCE: 131
MSCMPVSTKC NDIWVDFSCT GPSISELQKK EPKAWAAILR SHTNQQTAED DNIIGSICDK    60
QGLCSKDEYA YSQYCACVNS GTLWAECAFA PCNGNKNAYK TTEQRNILTN KQCPSGLTIC    120
QNIAEYGGSG NISDLYQNFN CNSVINTFLI NVMNHPFLTL ILIILILIII YRLMSSSGGK    180
HNDDKLPPPS LIFSNLNNF                                                 199

SEQ ID NO: 132          moltype = AA  length = 248
FEATURE                 Location/Qualifiers
source                  1..248
                        mol_type = protein
                        organism = African swine fever virus
SEQUENCE: 132
MGGSTSKNSF KNTTNIISNS IFNQMQNCIS MLDGKNYIGV FGDGNILNHV FQDLNLSLDT    60
SCVQKHVNEE NFITNLSNQI TQNLKDQEVA LTQWMDAGHH DQKTDIEENI KVNLTTTLIQ    120
NCVSSLSGMN VLVVKGNGNI VENATQKQSQ QIISNCLQGS KQAIDTTTGI TNTVNQYSHY    180
TSKNFFDFIA DAISAVFKNI MVAAVVIVLI IVGFIAVFYF LHSRHRHEEE EEAEPLISNK    240
```

```
VLKNAAVS                                                                  248

SEQ ID NO: 133           moltype = AA   length = 248
FEATURE                  Location/Qualifiers
source                   1..248
                         mol_type = protein
                         organism = African swine fever virus
SEQUENCE: 133
MGGSTSKNSF KNTTNIISNS IFNQMQSCIS MLDGKNYIGV FGDGNILNHV FQDLNLSLNT           60
SCVQKHVNEE NFITNLSNQI TQNLKDQEVA LTQWMDAGTH DQKTDIEENI KVNLTTTLIQ          120
NCVSSLSGMN VLVVKGNGNI VENATQKQSQ QIISNCLQGS KQAIDTTTGI TNTVNQYSHY          180
TSKNFFDFIA DAISAVFKNI MVAAVVIVLI IVGFIAVFYF LHSRHRHEEE EEAEPLISNK          240
VLKNAAVS                                                                  248

SEQ ID NO: 134           moltype = AA   length = 296
FEATURE                  Location/Qualifiers
source                   1..296
                         mol_type = protein
                         organism = African swine fever virus
SEQUENCE: 134
MFGAFVSHRL WSDSGCTTTC ITNSIANYVA FGEQIGFPFK SAQVFIAGPR KAVINIQEDD           60
KVELLKMIVK HNLWVVAHGT YLDVPWSRRS AFVTHFIQQE GLVLHLGVVE                     120
PELIVEGLKK IKPVEGVVIY LETPHNKHHT YKYSTMEQIK ELFLRIRNTR LKQIGLCIDT          180
AHIWSSGVNI SSYNDAGQWL RSLENIHSVI PPSHIMFHLN DAATECGSGI DRHASLFEGM          240
IWKSYSHKIK KSGLYCFVEY ITRHQCPAIL ERNLGSSMQL QTALTAEFTT LKSLLK              296

SEQ ID NO: 135           moltype = AA   length = 296
FEATURE                  Location/Qualifiers
source                   1..296
                         mol_type = protein
                         organism = African swine fever virus
SEQUENCE: 135
MFGAFVSHRL WSDSGCTTTC ITNSIANYVA FGEQIGFPFK SAQVFIAGPR KAVINIQEDD           60
KVELLKMIVK HNLWVVAHGT YLDVPWSRKS AFVTHFIQQE LLICKEVGIK GLVLHLGAVE          120
PELIMEGLKK IKPVEGVVIY LETPHNKHHT YKYSTIEQIK ELFLRIRNTR LKQIGLCIDT          180
AHIWSSGVNI SSYNDAGQWL RSLENIHSVI PPSHIMFHLN DAATECGSGI DRHASLFEGM          240
IWKSYSHKIK QSGLYCFVEY VTRHQCPAIL ERNLGSSMQL QTALTAEFTT LKSLLK              296

SEQ ID NO: 136           moltype = AA   length = 301
FEATURE                  Location/Qualifiers
source                   1..301
                         mol_type = protein
                         organism = African swine fever virus
SEQUENCE: 136
MSEDIRRGPG RPPKKRVVPN FERKGILEKP VRPQSRLEFS YDNPLIFKNL FIYFKNLKSK           60
NILVRCTPTE ITFFSRDQSQ ASFVIATIDG KNVNHYYASD VFWLGINREL VEKMFNSIDR          120
SFLKITIVHR YDKPETLFFI FTDFDIDKEC TYQITVSEPE LDMDLIEMEK SISEERLKNY          180
PLRWEFTSKQ LKKTFSDLSN YTELVTIEKL GGDTPLHLYF QKFNSISYHE MYKSSNKINL          240
TSTIPKSQVF QINVKIAHIK SLASAMVTDK IRILCEENGN LIFQSEMDAL MLNTITLNNT          300
I                                                                         301

SEQ ID NO: 137           moltype = AA   length = 301
FEATURE                  Location/Qualifiers
source                   1..301
                         mol_type = protein
                         organism = African swine fever virus
SEQUENCE: 137
MSEDIRRGPG RPPKKRVVPN FERKGILEKP VRPQSRLEFS YDNPLIFKNL FIYFKNLKSK           60
NILVRCTPTE ITFFSRDQSQ ASFVIATIDG KNVNHYYASD VFWLGINREL VEKMFNSIDR          120
SFLKITIVHR YDKPETLFFI FTDFDIDKEC TYQITVSEPE LDMDLIEMEK SISEERLKNY          180
PLRWEFTSKQ LKKTFSDLSN YTELVTIEKL GGDTPLHLYF QKFNSISYHE MYKSSNKINL          240
TSTIPKSQVF QINVKIAHIK SLASAMVTDK IRILCEENGN LIFQSEMDAL MLNTITLNNT          300
I                                                                         301

SEQ ID NO: 138           moltype = AA   length = 152
FEATURE                  Location/Qualifiers
source                   1..152
                         mol_type = protein
                         organism = African swine fever virus
SEQUENCE: 138
MYSILIACLV LLLCLVIYVG HRADHARKYL EGMWHGDPVF LKQSGLQSFY LYIQPGHTCF           60
FSIVNKNGEK LMETKIPCTI TNKIYMFFKP IFEFHVVMED IHRYLPKQFN FLLDSAEGKL         120
ILENNHVIYA VLYKDNFATA LGKTVEKYIT QN                                       152

SEQ ID NO: 139           moltype = AA   length = 152
FEATURE                  Location/Qualifiers
source                   1..152
                         mol_type = protein
                         organism = African swine fever virus
```

-continued

```
SEQUENCE: 139
MYSILIACLV LLLCLVIYVG HRADHARKYL EGMWHGDPVF LKQSGLQSFY LYIQPDHTCF      60
FSIVNKNGEK LMETKIPCTI TNKIYMFFKP IFEFHVVMED IHSYFPKQFN FLLDSTEGKL     120
ILENNHVIYA VLYKDNFATA LGKTVEKYIT QN                                    152

SEQ ID NO: 140          moltype = AA   length = 364
FEATURE                 Location/Qualifiers
source                  1..364
                        mol_type = protein
                        organism = African swine fever virus
SEQUENCE: 140
MYFLVADHRE HHVIPFLKTD FHDMQHNPMF TQKQALLEIK QLFTGDYLIC KSPTTILACI      60
ERKTYKDFAA SLKDGRYKNR QKMLSLREQT NCQLYFFVEG PAFPNPQKKI NHVAYASIIT     120
AMTHLMVRDH IFVIQTKNEA HSSQKLVQLF YAFSKEMCVV VPTSLTPTDE ELCIKLWSSL     180
SGISGVIGKI LANTCSVAHL VSGKLSSQNI DQLKTPSNRP FPKKVKRMLI SISKGNKELE     240
IKLLSGVPNI GKKLAAEILK DHALLFFLNQ PVECLANIQI VQKTRTIKLG MKRAEAIHYF     300
LNWCGSAHVT DDSQNITEAS RPATQPAATQ PLHEVSDDAT SNASDTSSPI GHQTLSKEML     360
LNTA                                                                  364

SEQ ID NO: 141          moltype = AA   length = 369
FEATURE                 Location/Qualifiers
source                  1..369
                        mol_type = protein
                        organism = African swine fever virus
SEQUENCE: 141
MYFLVADHRE HHVIPFLKTD FHHMHQNPIQ KNQALLEIKQ LFTGDYLICK SPSTILACIE      60
RKTYKDFAAS LKDGRYKNRQ KMLSLREQTN CQLYFFVEGP AFPNPQKKIN HVAYASIITA     120
MTHLMVRDHI FVIQTKNEAH SSQKLVQLFY AFSKEMCVVV PTSLTPTDEE LCIKLWSSLS     180
GISGVIGKIL ANTCSVAHLV HGKLSSQNID QLKTPSNRPF PKKVKRMLIS ISKGNKELEI     240
KLLSGVPNIG KKLAAEILKD HALLFFLNQP VECLANIQIV QKTRTIKLGM KRAEAIHYFL     300
NWCGSAHVTD DSQNITEASR STMQVATQSA AIQPAATQPL HEVSDDASSD ASSPVGYQTL     360
SKEMLLNTA                                                             369

SEQ ID NO: 142          moltype = AA   length = 165
FEATURE                 Location/Qualifiers
source                  1..165
                        mol_type = protein
                        organism = African swine fever virus
SEQUENCE: 142
MANPNKRIMN KKSKQASISS ILNFFFFYIM EYFVAVDNET PLGVFTSIEQ CEETMKQYPG      60
LHYVVFKYTC PADAENTDVV YLIPSLTLHT PMFVDHCPNR TKQARHVLKK INLVFEEESI     120
ENWKVSVNTV FPHVHNRLSA PKFSIDEANE AVEKFLIQAG RLMSL                     165

SEQ ID NO: 143          moltype = AA   length = 165
FEATURE                 Location/Qualifiers
source                  1..165
                        mol_type = protein
                        organism = African swine fever virus
SEQUENCE: 143
MVNPNKRIMN KKSKQASISS ILNFFFFYIM EYFVAVDNET SLGVFTSIEQ CEETMKQYPG      60
LHYVVFKYMC PADAENTDVV YLIPSLTLHT PMFVDHCPNR TKQARHVLKK INLVFEEESI     120
ENWKVSVNTV FPHVHNRLSA PKLSIDEANE AVEKFLIQAG RLMSL                     165

SEQ ID NO: 144          moltype = AA   length = 317
FEATURE                 Location/Qualifiers
source                  1..317
                        mol_type = protein
                        organism = African swine fever virus
SEQUENCE: 144
MVETQMDKLG FLLNHIGKQV TTKVLSNAHI TQTMKEIILE NHGVDGGAAK NVSKGKSSPK      60
EKKHWTEFES WEQLSKSKRS FKEYWAERNE IVNTLLLNWD NVRGAIKKFL DDDREWCGRI     120
NMINGVPEIV EIIPSPYRAG ENIYFGSEAM MPADIYSRVA NKPAMFVFHT HPNLGSCCGG     180
MPSICDISTT LRYLLMGWTA GHLIISSNQV GMLTVDKRII VDLWANENPR WLMAQKILDI     240
FMMLTSRRSL VNPWTLRDLK KILQDYGIEY IIFPSNDFFI YEDERLLMFS KKWTNFFTLH     300
ELLDDDLETIE TKASSTT                                                    317

SEQ ID NO: 145          moltype = AA   length = 317
FEATURE                 Location/Qualifiers
source                  1..317
                        mol_type = protein
                        organism = African swine fever virus
SEQUENCE: 145
MVETQMDKLG FLLNHIGKQV TTKVLSNAHI TQTMKEIILE NHSVDGGAAK NVSKGKSSPK      60
EKKHWTEFES WEQLSKSKRS FKEYWAERNE IVNTLLLNWD NVRGAIKKFL DDDREWCGRI     120
NMINGVPEIV EIIPSPYRAG ENIYFGSEAM MPADIYSRVA NKPAMFVFHT HPNLGSCCGG     180
MPSICDISTT LRYLLMGWTA GHLIISSNQV GMLTVDKRII VDLWANENPR WLMAQKILDI     240
FMMLTSRRSL VNPWTLRDLK KILQDYGIEY IIFPSNDFFI YEDERLLMFS KKWTNFFTLH     300
ELLDDDLETIE TKASSTT                                                    317
```

```
SEQ ID NO: 146          moltype = AA  length = 124
FEATURE                 Location/Qualifiers
source                  1..124
                        mol_type = protein
                        organism = African swine fever virus
SEQUENCE: 146
MNLEYVQVVQ KFNQVLLELT KKVCTVVGGS KPTYWYHHIR RVCSECPSMP MSMIGPYLNV   60
YKAQILTRDK NFFMNFDPAH NEYTFIIQKL KEAARNMPED ELEQYWVKLL FLLKSYIKCK  120
PFIN                                                               124

SEQ ID NO: 147          moltype = AA  length = 124
FEATURE                 Location/Qualifiers
source                  1..124
                        mol_type = protein
                        organism = African swine fever virus
SEQUENCE: 147
MNLEYVQVVQ KFNQVLLELT KKVCTVVGGS KPTYWYHHIR RVCSECPSMP MSMIGPYLNV   60
YKAQILTRDK NFFMNFDPAH NEYTFIIQKL KEAARNMPED ELEQYWVKLL FLLKSYIKCK  120
PFIN                                                               124

SEQ ID NO: 148          moltype = AA  length = 171
FEATURE                 Location/Qualifiers
source                  1..171
                        mol_type = protein
                        organism = African swine fever virus
SEQUENCE: 148
MVVYDLLVSL SKESIDVLRF VEANLAAFNQ QYIFFNIQRK NSITTPLLIT PQQEKISQIV   60
EFLMDEYNKN NRRPSGPPRE QPMHPLLPYQ QSSDEQPMMP YQQPPGNDDQ PYEQIYHKKH  120
ASQQVNTELN DYYQHILALG DEDKGMDSML KLPEKAKRGS DDEDDMFSIK N           171

SEQ ID NO: 149          moltype = AA  length = 171
FEATURE                 Location/Qualifiers
source                  1..171
                        mol_type = protein
                        organism = African swine fever virus
SEQUENCE: 149
MVVYDLLVSL SKESIDVLRF VEANLAAFNQ QYIFFNIQRK NSITTPLLIT PQQEKISQIV   60
EFLMDEYNKN NRRPSGPPRE QPMHPLLPYQ QSSDEQPMMP YQQPPGNDDQ PYEQIYHKKH  120
ASQQVNTELN DYYQHILALG DEDKGMDSML KLPEKAKRDS DDEDDMFSIK N           171

SEQ ID NO: 150          moltype = AA  length = 359
FEATURE                 Location/Qualifiers
source                  1..359
                        mol_type = protein
                        organism = African swine fever virus
SEQUENCE: 150
MEKIFQNVEI KPFLIDFSNP FIKNAAKRLF QLEEQLPLVP VNVVMDFKGI SRAAVHGLSR   60
VLQDEIPNYM LDIKPGGYKI EDSTDLFMTE QFIRNRINFI PIYAKNETLV FALRSLNNSC  120
EVKTIYSRDL IQVAGPKLKY PIFNPTFEIG FLQPGKSLII EDIYIKKGIG RKHAAFNLAV  180
KTHFSHLDIE QYPTDKKEYM ALSGYKQSSM TSDPRHHRLG LCFPAVPLPH INQAVRTYLK  240
NACRIIIGRI QSIQKIYENF EEPQPELVLF SLDEEKTKAI ITIKDETHTI GNLLKTCIYE  300
MIPDISFVGY QCVPHKQEMV LTIIHKASQE DLITLLEKSI QNIIQTFQIL EKNVDELIA   359

SEQ ID NO: 151          moltype = AA  length = 359
FEATURE                 Location/Qualifiers
source                  1..359
                        mol_type = protein
                        organism = African swine fever virus
SEQUENCE: 151
MEKIFQNVEI KPFLIDFSNL FIKNAAKKLF QLEEQLPLVP VNVVMDFKGI SRAAVHGLSR   60
VLQDEIPNYM LDIKPGGYKI EDSTDLFMTE QFIRNRINFI PIYAKNETLV FALRSLNNSC  120
EVKTIYSRDL IQVAGPKLKY PIFNPTFEIG FLQPGKSLII EDIYIKKGIG RKHAAFNLAV  180
KTHFSHLDIE QYPTDKKEYM ALSGYKQSSM TSDPRHHRLG LCFPAVPLPH INQAVRTYLK  240
NACRIIIGRI QSIQKIYENF EEPQPELVLF SMDEEKTKAI ITIKDETHTI GNLLKTYIYE  300
MIPDISFVGY QCVPHKQEMV LTIIHKASQE DLITLLEKSI QNIIQTFQIL EKNVDELIA   359

SEQ ID NO: 152          moltype = AA  length = 177
FEATURE                 Location/Qualifiers
source                  1..177
                        mol_type = protein
                        organism = African swine fever virus
SEQUENCE: 152
MYEIILAIII ILLTIIIFYF YKTPFKCITT TKTPVLFIKF QLIAADNYQA ITWKNGVLSY   60
EKIDQPTPLY LSVNGLIFDC AKLQPLTTNT NVISGDKDIH IGQTFEYNNL LMWKVNDQGF  120
LNITVTGTKF NLIAITGKLG FYTDPPSHLM IMPLKIFPVH KFSKNEPNKK QKRFIYF     177

SEQ ID NO: 153          moltype = AA  length = 66
FEATURE                 Location/Qualifiers
source                  1..66
```

```
                            mol_type = protein
                            organism = African swine fever virus
SEQUENCE: 153
MWKVNDQGFL NISVTGTKFN LIAITGKLGF YTDPPSHLII MPLKFFPVHK FSKNEPNKKQ    60
KRFIYF                                                              66

SEQ ID NO: 154              moltype = AA  length = 196
FEATURE                     Location/Qualifiers
source                      1..196
                            mol_type = protein
                            organism = African swine fever virus
SEQUENCE: 154
MLFRYLVWLF RFIEVKNVVS ISLLVIGSNY LTTAISNNTS TTISPTTSSN YLLTAISNNT    60
STTILPTTTS SNYLTSAIPN IISDKEDDTP FSTDKTVSDG LSPITLYRAI RSTLNDTMTD   120
ILTRPYRPTT VIFHSDTPQP VKNATQGNII KKTYRQVLTF FIQPNPLFPC FKNHEVFLNL   180
ANILNTILCI ILIKNV                                                  196

SEQ ID NO: 155              moltype = AA  length = 202
FEATURE                     Location/Qualifiers
source                      1..202
                            mol_type = protein
                            organism = African swine fever virus
SEQUENCE: 155
MLFRYLVWLF RFIEVKNVVS ISLLVIGSNY LTTAISNNTS TTISPTTTSS NYLMTAISNN    60
TSTTISPTTT SSNYLMTAIP NIISDKEDDI HFSTDKTVFD RLSPITLYRA IRSTLNDTST   120
KTMTDHILTR PYRPTTVIFH SDTPQPVKNA TQGNIVKKIY RQVLTFFIQP NPLFPCFKNH   180
EVFLNLANIL NTILCIILIK NV                                           202

SEQ ID NO: 156              moltype = AA  length = 215
FEATURE                     Location/Qualifiers
source                      1..215
                            mol_type = protein
                            organism = African swine fever virus
SEQUENCE: 156
MVSRFLIAEY RHLIENPSEN FKISVNENNI TEWDVILRGP PDTLYEGGLF KAKVAFPPEY    60
PYAPPKLTFT SEMWHPNIYP DGRLCISILH GDNAEEQGMT WSPAQKIDTI LLSVISLLNE   120
PNPDSPANVD AAKSYRKYVY KEDLESYPME VKKTVKKSLD ECSPEDIEYF KNAASNVPPI   180
PSDAYEDECE EMEDDTYILT YDDDEEEEDE EMDDE                             215

SEQ ID NO: 157              moltype = AA  length = 212
FEATURE                     Location/Qualifiers
source                      1..212
                            mol_type = protein
                            organism = African swine fever virus
SEQUENCE: 157
MVSRFLIAEY RHLIENPSEN FKISVNEKDM TEWDVILRGP PDTFYEGGLF KAKIAFPPEY    60
PYAPPRLTFT SEMWHPNIYS DGKLCISILH GDNAEEQGMT WSPAQKIDTI LLSVISLLNE   120
PNPDSPANVD AAKSYRKLLY KEDLESYPME VKRTVKKSLD ECSPEDIEYF KNAASNVPPI   180
PSDAYEDECE EMEDDTYILT YDDEDEEEED DE                                212

SEQ ID NO: 158              moltype = AA  length = 267
FEATURE                     Location/Qualifiers
source                      1..267
                            mol_type = protein
                            organism = African swine fever virus
SEQUENCE: 158
MLLVLIDVDG FMGQLYNENG TQTILIPREV VIFYWEKNTA SKILQLFFHG GIDPIFEKIN    60
QRSFSFQSRH IHHFTLDESP LPNSIALPTD TLQAFKAGKK MIFQHLVKIT KDHEQILLLH   120
KGGPEGEWVR SFNIPNATVQ NLNDLCCPSV EKLVLKKRDY ISSSIGCPKH IQGSNHCPVF   180
ECHVLFKWIQ ENTSIVQGVL KRPSLPYEEA VLFIEHRINM VDNHPFKKDS VKQNQKKKNW   240
IATQFVQHGI YVDNGILSKI YNKYSLF                                      267

SEQ ID NO: 159              moltype = AA  length = 279
FEATURE                     Location/Qualifiers
source                      1..279
                            mol_type = protein
                            organism = African swine fever virus
SEQUENCE: 159
MLLVLIDVDG FMGQLYNENG TQTILIPREV VIFYWEKNTP SKILQLFFHG GIDPIFEKIN    60
QRSFSFQSRH IHHFTLDESP LPNSIALPTD TLQAFKAGKK MIFQHLVKIT KDHEQILLLH   120
KGGPEGEWIR SFNIPNATVQ NLNDLCCPSV EKLVLKKRDY ISSSIGCPKH IQGSNHCPVF   180
ECHVLFKWIQ ENTSIVQGVL ERPSLPYEKA DLFIEHRINM VDNHPFKKDS IKQNQKKRTG   240
SQRNLSNMGY MLTMASLARF IINTASFNKC IYPLSQDIR                         279

SEQ ID NO: 160              moltype = AA  length = 205
FEATURE                     Location/Qualifiers
source                      1..205
                            mol_type = protein
                            organism = African swine fever virus
```

```
SEQUENCE: 160
MVEPREQFFQ DLLSAVDQQM DTVKNDIKDI MKEKTSFMVS FENFIERYDT MEKNIQDLQN    60
KYEEMAANLM TVMTDTKIQL GAIIAQLEIL MINGTPLPAK KTTIKEAMPL PSSNTNNDQT   120
SPPASGKTSE TPKKNPTNAM FFTRSEWASS KTFREKFLTP EIQAILDEQF ANKTGIERLH   180
AEGLYMWRTQ FSDEQKKMVK EMMKK                                        205

SEQ ID NO: 161          moltype = AA  length = 205
FEATURE                 Location/Qualifiers
source                  1..205
                        mol_type = protein
                        organism = African swine fever virus
SEQUENCE: 161
MVEPREQFFQ DLLSAVDQQM DTVKNDIKDI MKEKTSFMVS FENFIERYDT MEKNIQDLQN    60
KYEEMAANLM TVMTDTKIQL GAIIAQLEIL MINGTPLPAK KTTIKEAMPL PSSNTNNEQT   120
SPPASGKTSE TPKKNPTNAM FFTRSEWASS NTFREKFLTP EIQAILDEQF ANKTGIERLH   180
AEGLYMWRTQ FSDEQKKMVK EMMKK                                        205

SEQ ID NO: 162          moltype = AA  length = 78
FEATURE                 Location/Qualifiers
source                  1..78
                        mol_type = protein
                        organism = African swine fever virus
SEQUENCE: 162
MPTKAGTKST ANKKTTKGSS KSGSSRGHTG KTHASSSMHS GMLYKDMVNI ARSRGIPIYQ    60
NGSRLTKSEL EKKIKRPK                                                 78

SEQ ID NO: 163          moltype = AA  length = 78
FEATURE                 Location/Qualifiers
source                  1..78
                        mol_type = protein
                        organism = African swine fever virus
SEQUENCE: 163
MPTKAGTKST ANKKTTKGSS KSGSSRGHTG KTHASSSMHS GMLYKDMVNI ARSRGIPIYQ    60
NGSRLTKSEL EKKIKRSK                                                 78

SEQ ID NO: 164          moltype = AA  length = 177
FEATURE                 Location/Qualifiers
source                  1..177
                        mol_type = protein
                        organism = African swine fever virus
SEQUENCE: 164
MFNIKMTIST LLIALIILVI IILVVFLYYK KQQPPKKVCK VDKDCGSGEH CVRGTCSTLS    60
CLDAVKMDKR NIKIDSKISS CEFTPNFYRF TDTAADEQQE FGKTRHPIKI TPSPSESHSP   120
QEVCEKYCSW GTDDCTGWEY VGDEKEGTCY VYNNPHHPVL KYGKDHIIAL PRNHKHA      177

SEQ ID NO: 165          moltype = AA  length = 189
FEATURE                 Location/Qualifiers
source                  1..189
                        mol_type = protein
                        organism = African swine fever virus
SEQUENCE: 165
MRSSKKINNK KNMFNIKMTI STLLIALIIL LIIILVVFLY YKKQQPPKKV CKVDKDCGSG    60
EHCVRGSCSS LSCLDAVKMD KRNIKIDSKI SSCEFTPNFY RFTDTAADEQ QEFGKTRHPI   120
KITPSPSESH SPQEVCEKYC SWGTDDCTGW EYVGDEKEGT CYVYNNPHHP VLKYGKDHII   180
ALPRNHKHA                                                          189

SEQ ID NO: 166          moltype = AA  length = 174
FEATURE                 Location/Qualifiers
source                  1..174
                        mol_type = protein
                        organism = African swine fever virus
SEQUENCE: 166
MLTLIQGKKI VNHLRSRLAF EYNGQLIKIL SKNIVAVGSL RREEKMLNDV DLLIIVPEKK    60
LLKHVLPNIR IKGLSFSVKV CGERKCVLFI EWKKTYQLD LFTALAEEKP YAIFHFTGPV   120
SYLIRIRAAL KKKNYKLNQY GLFKNQTLVP LKITTEKELI KELGFTYRIP KKRL         174

SEQ ID NO: 167          moltype = AA  length = 174
FEATURE                 Location/Qualifiers
source                  1..174
                        mol_type = protein
                        organism = African swine fever virus
SEQUENCE: 167
MLTLIQGKKI VNDLRSRLAF EYNGQLIKIL SKNIVAVGSL RREEKMLNDV DLLIIVPEKK    60
LLKHVLPNIR IKDLSFSVKV CGERKCVLFI EWKKNTYQLD LFTALAEEKP YAVLHFTGPV   120
SYLIRIRAAL KKKNYKLNQY GLFKNQTLVP LKITTEKELI KELGFTYRIP KKRL         174

SEQ ID NO: 168          moltype = AA  length = 183
FEATURE                 Location/Qualifiers
source                  1..183
```

```
                       mol_type = protein
                       organism = African swine fever virus
SEQUENCE: 168
MSVVVGGVEY SLNNWARYEI KRRAAELESV NYYPHCEYIM PEDIVVSILG SKPNCPFLEA    60
LKRFHDFLKK RRIIFKGEYL VIPWMGAQDV ADMIHHVENR INLDHLEDLA HMLKLITYHK   120
SFDTCINQAF EHLYAFKFPD ANIETHELKH IRQLEKKMYG YILRLEKLQT VLTFYIEFLL   180
KQV                                                                 183

SEQ ID NO: 169         moltype = AA   length = 183
FEATURE                Location/Qualifiers
source                 1..183
                       mol_type = protein
                       organism = African swine fever virus
SEQUENCE: 169
MSVVVGGVEY SLNNWARYEI KRRAAELESV NYYPHCEYIM PEDIVVSILG SKPNCPFLEA    60
LKRFHDFLKK RRIIFKGEYL VIPWMGAQDV ADMIHHVENR INLDHLEDLA HMLKLITYHR   120
SFDTCINQAF EHLYAFKFPD ANIETHELKH IRQLEKKMYG YILRLEKLQT VLTFYIEFLL   180
KQV                                                                 183

SEQ ID NO: 170         moltype = AA   length = 208
FEATURE                Location/Qualifiers
source                 1..208
                       mol_type = protein
                       organism = African swine fever virus
SEQUENCE: 170
MSILEKITSS PSECAEHLTN KDSCLSKKIQ KELTSFLEKK ETLGCDSESC VITHPAVKAY    60
AQQKGLDLSK ELETRFKAPG PRNNTGLLTN FNIDETLQRW AIKYTKFFNC PFSMMDFERV   120
HYKFNQVDMV KVYKGEELQY VEGKVVKRPC NTFGCVLNTD FSTGTGKHWV AIFVDMRGDC   180
WSIEYFNSAG NSPQVPLFAG WNGSNSSY                                      208

SEQ ID NO: 171         moltype = AA   length = 273
FEATURE                Location/Qualifiers
source                 1..273
                       mol_type = protein
                       organism = African swine fever virus
SEQUENCE: 171
MSILEKITSS PSECAEHLTN KDSCLSKKIQ KELTSFLEKK ETLGCDSESC VITHPAVKAY    60
AQQKGLDLSK ELETRFKAPG PRNNTGLLTN FNIDETLQRW AIKYTKFFNC PFSMMDFERV   120
HYKFNQVDMV KVYKGEELQY VEGKVVKRPC NTFGCVLNTD FSTGTGKHWV AIFVDMRGDC   180
WSIEYFNSTG NSPPGPVIRW MERVKQQLLK IHHTVKTLAV TNIRHQRSQT ECGPYSLFYI   240
RARLDNVSYA HFISARITDE DMYKFRTHLF RIA                                273

SEQ ID NO: 172         moltype = AA   length = 69
FEATURE                Location/Qualifiers
source                 1..69
                       mol_type = protein
                       organism = African swine fever virus
SEQUENCE: 172
MLLYIVIIVA CIISKLVPNE YWAIHLFFII MIFMVYMYEK LDIHQKYQFW NYTMSGLSGH    60
NVQVICKCY                                                            69

SEQ ID NO: 173         moltype = AA   length = 69
FEATURE                Location/Qualifiers
source                 1..69
                       mol_type = protein
                       organism = African swine fever virus
SEQUENCE: 173
MLLYIVIIVA CIISKLVPNE YWAIHLFFII MIFMVYMYEK LDIHQKSQFW NYTMSGLSGH    60
NVQVTCKCY                                                            69

SEQ ID NO: 174         moltype = AA   length = 10
FEATURE                Location/Qualifiers
source                 1..10
                       mol_type = protein
                       organism = African swine fever virus
SEQUENCE: 174
VPYDNISKLY                                                           10

SEQ ID NO: 175         moltype = AA   length = 9
FEATURE                Location/Qualifiers
source                 1..9
                       mol_type = protein
                       organism = African swine fever virus
SEQUENCE: 175
YAKPDAIML                                                             9

SEQ ID NO: 176         moltype = AA   length = 129
FEATURE                Location/Qualifiers
source                 1..129
```

```
                          mol_type = protein
                          organism = African swine fever virus
SEQUENCE: 176
MEHPSTNYTP EQQHEKLKYY VLIPKHLWSY IKYGTHVRYY TTQNVFRVGG FVLQNPYEAV    60
IKNEVKTAIR LQNSFNTKAK GHVTWAVPYD NISKLYAKPD AIMLTIQENV EKALHALNQN   120
VLTLASKIR                                                           129

SEQ ID NO: 177            moltype = AA   length = 129
FEATURE                   Location/Qualifiers
source                    1..129
                          mol_type = protein
                          organism = African swine fever virus
SEQUENCE: 177
MEHPSTNYTP EQQHEKLKHY VLIPKHLWSY IKYGTHVRYY TTQNVFRVGG FVLQNPYEAV    60
IKNEVKTAIR LQNSFNTKAK GHVTWAVPYD NISKLYAKPD AIMLTIQENV EKALHALNQN   120
VLTLASKIR                                                           129

SEQ ID NO: 178            moltype = AA   length = 9
FEATURE                   Location/Qualifiers
source                    1..9
                          mol_type = protein
                          organism = African swine fever virus
SEQUENCE: 178
IMDDLVEEY                                                             9

SEQ ID NO: 179            moltype = AA   length = 147
FEATURE                   Location/Qualifiers
source                    1..147
                          mol_type = protein
                          organism = African swine fever virus
SEQUENCE: 179
MADNDNEDLI MDDLVEEYVE TEEENLVDSE EESEDKDEIV ESPSICEGFV QASSQTLVII    60
PDNERITSNV LTTFEATRLV AVRAQQLAIN GSTMLKKKYS SPIDIAKQEL FNRKIPLLVM   120
RCIKVTPEGQ KIVEIWNPRE MGIPLLD                                       147

SEQ ID NO: 180            moltype = AA   length = 9
FEATURE                   Location/Qualifiers
source                    1..9
                          mol_type = protein
                          organism = African swine fever virus
SEQUENCE: 180
NKYLERQDL                                                             9

SEQ ID NO: 181            moltype = AA   length = 257
FEATURE                   Location/Qualifiers
source                    1..257
                          mol_type = protein
                          organism = African swine fever virus
SEQUENCE: 181
MYSVCDVVRD AVAQSHLCAC PNDKLPQCKG VTKAPPKCSV FHVAKLQDTK FKWKYTLDPL    60
KAQKLSQIDK DIEKDAITLK LIYGIELSPE DLEWWKMQRC LINKKTGAKG GQFANKYLER   120
QDLELLGYSP TPIIGGDFMF TALPDKVLRT IPVAWDRFLN PAMMIFFLII LLCVILGIFY   180
VLVRNTLRRK QKSKQHQMEI KRFIKEKEQD PYIHTSFESW PADPNKEWKD LIPMYEAQGY   240
CMADYRKKLG MPPGPNC                                                  257

SEQ ID NO: 182            moltype = AA   length = 257
FEATURE                   Location/Qualifiers
source                    1..257
                          mol_type = protein
                          organism = African swine fever virus
SEQUENCE: 182
MYSVCDVVRD AVAQSHLCAC PNDKLPQCKG VTKAPPKCSV FHVAKLQDTK FKWKYTLDPL    60
KAQKLSQIDK DIEKDAITLK LIYGIELSPE DLEWWKMQRC LINKKTGAKG GQFANKYLER   120
QDLELLGYSP TPIIGGDFMF TALPDKVLRT IPVAWDRFLN PAMMIFFLII LLCVILGIFY   180
VLVRNTLRRK QKSKQHQMEI KRFIKEKEQD PYIHTSFESW PADPNKEWKD LIPVYEAQGY   240
CMADYRKKLG MPPGPNC                                                  257

SEQ ID NO: 183            moltype = AA   length = 9
FEATURE                   Location/Qualifiers
source                    1..9
                          mol_type = protein
                          organism = African swine fever virus
SEQUENCE: 183
KKISNYQLL                                                             9

SEQ ID NO: 184            moltype = AA   length = 11
FEATURE                   Location/Qualifiers
source                    1..11
                          mol_type = protein
```

```
                               -continued organism = African swine fever virus
SEQUENCE: 184
TMYNVLRRAY Y                                                         11

SEQ ID NO: 185          moltype = AA   length = 10
FEATURE                 Location/Qualifiers
source                  1..10
                        mol_type = protein
                        organism = African swine fever virus
SEQUENCE: 185
KMYEDYYSHF                                                           10

SEQ ID NO: 186          moltype = AA   length = 315
FEATURE                 Location/Qualifiers
source                  1..315
                        mol_type = protein
                        organism = African swine fever virus
SEQUENCE: 186
MDALLKEIEK LSQPSLQKEN NDVCDLCFMQ MKKISNYQLL CEECGQLKDW FEPEYNEKFT    60
VYSRLKIVGA NSSYHQRDLD KANSSDYSSL QFHHILEELK SLNVKYMDAG QKPFPIQVLK   120
ETAHSYNQVQ QHRVIRSITK LQILASILRS ICLKLNIACT VADAARFTQL NTKGISRGMD   180
LLRSLFVDNK ITLNVDLNPI DSFINSTYSA LQIKQIHQEL QEENVYNLKE IVKSFILYAD   240
EKNIGVDLNR RTVVIATMYN VLRRAYYPIE IDTVVYQCKI RKNTITRALK MYEDYYSHFK   300
SLYEQYHLNA AKKLI                                                   315

SEQ ID NO: 187          moltype = AA   length = 315
FEATURE                 Location/Qualifiers
source                  1..315
                        mol_type = protein
                        organism = African swine fever virus
SEQUENCE: 187
MDALLKEIEK LSQPSLQKEN NDVCDLCFMQ MKKISNYQLL CEECGQLKDW FEPEYNEKFT    60
VYSRLKIVGA NSSYHQRDLD KANSSDYSSL QFHHILEELK SLNVKYMDAG QKPFPIQVLK   120
ETAHSYNQVQ QHRVIRSITK LQILASILRS ICLKLNIACT VADAARFTQL NTKGISRGMD   180
LLRSLFVDNK ITLNVDLNPI DSFINSTYSA LQIKQIHQEL QEENVYNLKE IVKSFILYAD   240
EKNIGVDLNR RTVVIATMYN VLRRAYYPIE IDTVVYQCKI RKNTITRALK MYEDYYSHFK   300
SLYEQYHLNA AKKLI                                                   315

SEQ ID NO: 188          moltype = AA   length = 9
FEATURE                 Location/Qualifiers
source                  1..9
                        mol_type = protein
                        organism = African swine fever virus
SEQUENCE: 188
HKNDKNITL                                                            9

SEQ ID NO: 189          moltype = AA   length = 11
FEATURE                 Location/Qualifiers
source                  1..11
                        mol_type = protein
                        organism = African swine fever virus
SEQUENCE: 189
LPDVSTLPYN Y                                                        11

SEQ ID NO: 190          moltype = AA   length = 9
FEATURE                 Location/Qualifiers
source                  1..9
                        mol_type = protein
                        organism = African swine fever virus
SEQUENCE: 190
SPNHVEDAY                                                            9

SEQ ID NO: 191          moltype = AA   length = 11
FEATURE                 Location/Qualifiers
source                  1..11
                        mol_type = protein
                        organism = African swine fever virus
SEQUENCE: 191
TPADKSLFLF Y                                                        11

SEQ ID NO: 192          moltype = AA   length = 9
FEATURE                 Location/Qualifiers
source                  1..9
                        mol_type = protein
                        organism = African swine fever virus
SEQUENCE: 192
FVWVADLSY                                                            9

SEQ ID NO: 193          moltype = AA   length = 11
```

| FEATURE | Location/Qualifiers |
|---|---|
| source | 1..11<br>mol_type = protein<br>organism = African swine fever virus |

SEQUENCE: 193
NIFNTIPTLT Y                                                              11

| SEQ ID NO: 194 | moltype = AA length = 8 |
|---|---|
| FEATURE | Location/Qualifiers |
| source | 1..8<br>mol_type = protein<br>organism = African swine fever virus |

SEQUENCE: 194
NTIPTLTY                                                                  8

| SEQ ID NO: 195 | moltype = AA length = 11 |
|---|---|
| FEATURE | Location/Qualifiers |
| source | 1..11<br>mol_type = protein<br>organism = African swine fever virus |

SEQUENCE: 195
KQVAIHGFAA Y                                                              11

| SEQ ID NO: 196 | moltype = AA length = 15 |
|---|---|
| FEATURE | Location/Qualifiers |
| source | 1..15<br>mol_type = protein<br>organism = African swine fever virus |

SEQUENCE: 196
KQVAIHGFAA YALLY                                                          15

| SEQ ID NO: 197 | moltype = AA length = 8 |
|---|---|
| FEATURE | Location/Qualifiers |
| source | 1..8<br>mol_type = protein<br>organism = African swine fever virus |

SEQUENCE: 197
AIHGFAAY                                                                  8

| SEQ ID NO: 198 | moltype = AA length = 9 |
|---|---|
| FEATURE | Location/Qualifiers |
| source | 1..9<br>mol_type = protein<br>organism = African swine fever virus |

SEQUENCE: 198
GFAAYALLY                                                                 9

| SEQ ID NO: 199 | moltype = AA length = 8 |
|---|---|
| FEATURE | Location/Qualifiers |
| source | 1..8<br>mol_type = protein<br>organism = African swine fever virus |

SEQUENCE: 199
STLPYNYY                                                                  8

| SEQ ID NO: 200 | moltype = AA length = 475 |
|---|---|
| FEATURE | Location/Qualifiers |
| source | 1..475<br>mol_type = protein<br>organism = African swine fever virus |

SEQUENCE: 200
MSSLLKTDFN VSKYRLIAQK REANAVEIEA ALEVVREFII KKKLILYGGI AIDYALHLKG    60
SSIYPEGERP DFDMFSPNHV EDAYELADIL YEKGFKQVGT VRAIHVQTMR VRTDFVWVAD   120
LSYMPPNIFN TIPTLTYKNL KIIHPDYQRA GLHLAFCFPF DNPPREDVFS RFKKDLQRYN   180
LIEKYYPIPV VPVKSIYESK TFSIPFKQVA IHGFAAYALL YQTLNELRIT CKVPEWKTEF   240
PQPSYSYHKN DKNITLTVDM PKAYPALVLA TYNPEEVIKE MGLHLTEICE PYMDYSPPIF   300
KTNDIHFFST MFKELAISII QDNLIVVSPQ YLLLYFLYGA FATPADKSLF LFYYNATLWI   360
LEKADSLLNI IQKQTSPEEF TRFANTSPFV LTTRVLSCSQ ERCTFSPAYR ISLANDVQQS   420
QLPLPKTHFL SNSLPDVSTL PYNYYPGKGK DRPTNFSYEK NLLFNIGGKC TPSAM        475

| SEQ ID NO: 201 | moltype = AA length = 475 |
|---|---|
| FEATURE | Location/Qualifiers |
| source | 1..475<br>mol_type = protein<br>organism = African swine fever virus |

SEQUENCE: 201
MTSLLKTDFN VSKYRLIAQK REANAVEIEA ALEVVREFII KKKLILYGGI AIDYALHLKG    60
SSIYPEGERP DFDMFSPNHV EDAYELADIL YEKGFKQVGT VRAIHVQTMR VRTDFVWVAD   120
LSYMPPNIFN TIPTLTYKNL KIIHPDYQRA GLHLAFCFPF DNPPREDVFS RFKKDLQRYN   180

```
LIEKYYPIPV VPVKSTYESK TFSIPFKQVA IHGFAAYALL YQTLNELRIT CKVPEWKTEF    240
PQPSYSYHKN DKNITLTVDM PKAYPALVLA TYNPEEVIKE MGLHLTEICE PYMDYSPPIF    300
KTNDIHFFST MFKELAISII QDNLIVVSPQ YLLLYFLYGA FATPADKSLF LFYYNATLWI    360
LEKADSLLNI IQKQTSPEEF TRFANTSPFV LTTRVLSCSQ ERCTFSPAYR ISLANDVQQS    420
QLPLPKTHFL SNSLPDVSTL PYNYYPGKGK DRPTNFSYEK NLLFNIGGKC TPSAM         475

SEQ ID NO: 202           moltype = AA   length = 19
FEATURE                  Location/Qualifiers
source                   1..19
                         mol_type = protein
                         organism = African swine fever virus
SEQUENCE: 202
KVISNTAVSV FWRDRRIRF                                                  19

SEQ ID NO: 203           moltype = AA   length = 11
FEATURE                  Location/Qualifiers
source                   1..11
                         mol_type = protein
                         organism = African swine fever virus
SEQUENCE: 203
SVFWRDRRIR F                                                          11

SEQ ID NO: 204           moltype = AA   length = 62
FEATURE                  Location/Qualifiers
source                   1..62
                         mol_type = protein
                         organism = African swine fever virus
SEQUENCE: 204
MNWGSISSGT PGLFVESIRN TPSVVKINVI FLKVISNTAV SVFWRDRRIR FESDWLNSYF     60
QK                                                                    62

SEQ ID NO: 205           moltype = AA   length = 62
FEATURE                  Location/Qualifiers
source                   1..62
                         mol_type = protein
                         organism = African swine fever virus
SEQUENCE: 205
MNWGSISSGT PGLFVESIRN TPSVVKINVI FLKVISNTAV SVFWRDRRIR FESDWLNSYF     60
QK                                                                    62

SEQ ID NO: 206           moltype = AA   length = 13
FEATURE                  Location/Qualifiers
source                   1..13
                         mol_type = protein
                         organism = African swine fever virus
SEQUENCE: 206
GEYRYRFVWY QPF                                                        13

SEQ ID NO: 207           moltype = AA   length = 8
FEATURE                  Location/Qualifiers
source                   1..8
                         mol_type = protein
                         organism = African swine fever virus
SEQUENCE: 207
AIMITTEY                                                               8

SEQ ID NO: 208           moltype = AA   length = 11
FEATURE                  Location/Qualifiers
source                   1..11
                         mol_type = protein
                         organism = African swine fever virus
SEQUENCE: 208
AIMITTEYVG Y                                                          11

SEQ ID NO: 209           moltype = AA   length = 20
FEATURE                  Location/Qualifiers
source                   1..20
                         mol_type = protein
                         organism = African swine fever virus
SEQUENCE: 209
ILMDEDSFMS LLFDLCYGAY                                                 20

SEQ ID NO: 210           moltype = AA   length = 11
FEATURE                  Location/Qualifiers
source                   1..11
                         mol_type = protein
                         organism = African swine fever virus
SEQUENCE: 210
SFMSLLFDLC Y                                                          11
```

```
SEQ ID NO: 211            moltype = AA   length = 11
FEATURE                   Location/Qualifiers
source                    1..11
                          mol_type = protein
                          organism = African swine fever virus
SEQUENCE: 211
MTYYHFNPTS F                                                           11

SEQ ID NO: 212            moltype = AA   length = 16
FEATURE                   Location/Qualifiers
source                    1..16
                          mol_type = protein
                          organism = African swine fever virus
SEQUENCE: 212
AFDILKYGYP MQQSGY                                                      16

SEQ ID NO: 213            moltype = AA   length = 11
FEATURE                   Location/Qualifiers
source                    1..11
                          mol_type = protein
                          organism = African swine fever virus
SEQUENCE: 213
RQYGLAFVNT F                                                           11

SEQ ID NO: 214            moltype = AA   length = 11
FEATURE                   Location/Qualifiers
source                    1..11
                          mol_type = protein
                          organism = African swine fever virus
SEQUENCE: 214
FFNSITAIDF Y                                                           11

SEQ ID NO: 215            moltype = AA   length = 21
FEATURE                   Location/Qualifiers
source                    1..21
                          mol_type = protein
                          organism = African swine fever virus
SEQUENCE: 215
FFNSITAIDF YAIARNLRSM L                                                21

SEQ ID NO: 216            moltype = AA   length = 8
FEATURE                   Location/Qualifiers
source                    1..8
                          mol_type = protein
                          organism = African swine fever virus
SEQUENCE: 216
SITAIDFY                                                               8

SEQ ID NO: 217            moltype = AA   length = 717
FEATURE                   Location/Qualifiers
source                    1..717
                          mol_type = protein
                          organism = African swine fever virus
SEQUENCE: 217
MTKLAQWMFE QYVKDLNLKN RGSPSFRKWL TLQPSLLRYS GVMRANAFDI LKYGYPMQQS        60
GYTVATLEIH FKNIRSSFAN IYWNRDSEEP EYVCCCATYQ SHDGEYRYRF VWYQPFIEAY       120
NAIEAALDPL ETIILNLIAA RDLDFVVHIF PYNKGHEDYL ASTQLILKIF IATLLMDILR       180
IKDNTLDVHL NSDYIIVMER LWPHIKDAIE HFFEAHKDLL GYLIAFRNGG NFAGSLRPSC       240
GQKIVPLTIR EVLQMNDINL AVWREVFIMQ ECSDLVINGI APCFPIFNTW TYLQGINQIF       300
FENTSLQEKF KKDFIARELS KEIIKGQKTL NDKEFKKLSL HQIQYMESFL LMSDVAIMIT       360
TEYVGYTLQS LPGIISRSSY LSPIVKNILM DEDSFMSLLF DLCYGAYVLH KKENVIHADL       420
HLNNMTYYHF NPTSFTDRNK PGKYTLKVKN PVIAFITGPK VETETYVFKH IDGFGCIIDF       480
SRAIMGPNHA IKLERQYGLA FVNTFYRNQS EHILKVLRYY FPEMLTNREN EIQGVILSNF       540
NFFFNSITAI DFYAIARNLR SMLSDYLHT SEVKRNVEIS QTFLDTCQFL EEKAVEFLFK        600
NLHTVLSGKP VEKTAGDVLL PIVFKKFLYP NIPKNILRSF TVIDVYNYNN IKRYSGKAIQ       660
TFPPWAQTKE ILTHAEGRTF EDIFPRGELV FKKAYAENNH LDKILQRIRE QLANENL          717

SEQ ID NO: 218            moltype = AA   length = 8
FEATURE                   Location/Qualifiers
source                    1..8
                          mol_type = protein
                          organism = African swine fever virus
SEQUENCE: 218
MMMFITVY                                                               8

SEQ ID NO: 219            moltype = AA   length = 79
FEATURE                   Location/Qualifiers
source                    1..79
```

```
                              mol_type = protein
                              organism = African swine fever virus
SEQUENCE: 219
MDQEQLFDKL YSLNLQLTAK NDQKKENRFF IRSGKKIQRI QMMMFITVYD INQKQKKRYG    60
LRGCNLNLKA TVLPLHKRI                                                 79

SEQ ID NO: 220                moltype = AA   length = 9
FEATURE                       Location/Qualifiers
source                        1..9
                              mol_type = protein
                              organism = African swine fever virus
SEQUENCE: 220
ALANTSANY                                                             9

SEQ ID NO: 221                moltype = AA   length = 10
FEATURE                       Location/Qualifiers
source                        1..10
                              mol_type = protein
                              organism = African swine fever virus
SEQUENCE: 221
YFSILAEYVY                                                           10

SEQ ID NO: 222                moltype = AA   length = 20
FEATURE                       Location/Qualifiers
source                        1..20
                              mol_type = protein
                              organism = African swine fever virus
SEQUENCE: 222
YFSILAEYVY SYNGMLEHYM                                                20

SEQ ID NO: 223                moltype = AA   length = 10
FEATURE                       Location/Qualifiers
source                        1..10
                              mol_type = protein
                              organism = African swine fever virus
SEQUENCE: 223
SILAEYVYSY                                                           10

SEQ ID NO: 224                moltype = AA   length = 10
FEATURE                       Location/Qualifiers
source                        1..10
                              mol_type = protein
                              organism = African swine fever virus
SEQUENCE: 224
YSYNGMLEHY                                                           10

SEQ ID NO: 225                moltype = AA   length = 9
FEATURE                       Location/Qualifiers
source                        1..9
                              mol_type = protein
                              organism = African swine fever virus
SEQUENCE: 225
RQRSFIQTL                                                             9

SEQ ID NO: 226                moltype = AA   length = 17
FEATURE                       Location/Qualifiers
source                        1..17
                              mol_type = protein
                              organism = African swine fever virus
SEQUENCE: 226
FQMTATMVAA SNYNFII                                                   17

SEQ ID NO: 227                moltype = AA   length = 9
FEATURE                       Location/Qualifiers
source                        1..9
                              mol_type = protein
                              organism = African swine fever virus
SEQUENCE: 227
ATMVAASNY                                                             9

SEQ ID NO: 228                moltype = AA   length = 962
FEATURE                       Location/Qualifiers
source                        1..962
                              mol_type = protein
                              organism = African swine fever virus
SEQUENCE: 228
MREESWEDHD TIQLTAQRKY LAEVQALETL LTRELSVFLT EPGSKKTNII NRITGKTYAL    60
PSTELLRLYE HLEQCRKQGA LMYFLERQGT YSGLMLDYDL KLNTNAVPPL EPPALSRLCH   120
RIFVHIKNSS VLPEGSHKIH FFFTLKPEVV QGKYGFHVLI PGLKLAASTK KSIIGSLQHD   180
```

```
ATVQKILHEQ GVTNPESCLD PHSASVPSLL YGSSKLNHKP YQLKTGFELV FDSSDPDYIP  240
IHQIKNLESY NLVSELSLTN EQGSLVRPVY CAADIAAEKE EEIPTEDHSL SILMLHDPEA  300
RYLHKILNLL PPEYYVEYPL WSNVVFALAN TSANYRPLAE WFSQKCPEKW NTGGKEKLEK  360
LWNDASHHTE KKITKRSIMY WAHKHAPQQY KEIVEQGYFS ILAEYVYSYN GMLEHYMIAK  420
VIYAMMGNKF VVDVDSNGKY VWFEFVLPGQ PMNQGEIWKW RKEVNPDELH IYISENFSRV  480
MDRITEHIKY HLSQPHESNI LNYYKKLLKA FERSKSKIFN DSFKKGVIRQ AEFLFRQRSF  540
IQTLDTNPHL LGVGNGVLSI ETIPAKLINH FHEHPIHQYT HICYVPFNPE NPWTKLLLNA  600
LQDIIPELDA RLWIMFYLST AIFRGLKEAL MLLWLGGGCN GKTFLMRLVA MVLGDHYASK  660
LNISLLTSCR ETAEKPNSAF MRLKGRGYGY FEETNKSEVL NTSRLKEMVN PGDVTARELN  720
QKQESFQMTA TMVAASNYNF IIDTTDHGTW RRLRHYRSKV KFCHNPDPSN PYEKKEDPRF  780
IHEYIMDPDC QNAFFSILVY FWEKLQKEYN GQIKKVFCPT IESETEAYRK SQDTLHRFIT  840
ERVVESPSAE TVYNLSEVVT AYAEWYNTNI NVKRHIALEL SQELENSVLE KYLQWSPNKT  900
RILKGCRILH KFETLQPGES YIGVSTAGTL LNTPICEPKN KWWEWSPNPS APPEKEASAP  960
TP                                                                962

SEQ ID NO: 229        moltype = AA  length = 9
FEATURE               Location/Qualifiers
source                1..9
                      mol_type = protein
                      organism = African swine fever virus
SEQUENCE: 229
AKSLFKEFL                                                           9

SEQ ID NO: 230        moltype = AA  length = 9
FEATURE               Location/Qualifiers
source                1..9
                      mol_type = protein
                      organism = African swine fever virus
SEQUENCE: 230
WANEAEHLI                                                           9

SEQ ID NO: 231        moltype = AA  length = 123
FEATURE               Location/Qualifiers
source                1..123
                      mol_type = protein
                      organism = African swine fever virus
SEQUENCE: 231
MPSTGTLVII FAIVLILCIM LLFFYKTVEA EKPGVLPPPI PPPTPPPSKK KYDHNEYMEK   60
TDLEPEVKKN HRKWANEAEH LISSSVKGLE NLDETAFLAN HKGHGFRTFE HAKSLFKEFL  120
KKY                                                                123

SEQ ID NO: 232        moltype = AA  length = 122
FEATURE               Location/Qualifiers
source                1..122
                      mol_type = protein
                      organism = African swine fever virus
SEQUENCE: 232
MPSTGTLVII FAIVLILCIM LLFFYKTVEA GKSGVLPPPI PPPTPPPKKK YDHNEYMEKT   60
DLEPEVKKNH RKWANEAEHL ISSSVKGLEN LDETAFLANH KGHGFRTFDH AKSLFKEFLK  120
KY                                                                 122

SEQ ID NO: 233        moltype = AA  length = 11
FEATURE               Location/Qualifiers
source                1..11
                      mol_type = protein
                      organism = African swine fever virus
SEQUENCE: 233
SQVVFHAGSL Y                                                        11

SEQ ID NO: 234        moltype = AA  length = 201
FEATURE               Location/Qualifiers
source                1..201
                      mol_type = protein
                      organism = African swine fever virus
SEQUENCE: 234
MDFILNISMK MEVIFKTDLR SSSQVVFHAG SLYNWFSVEI INSGRIVTTA IKTLLSTVKY    60
DIVKSARIYA GQGYTEHQAQ EEWNMILHVL FEEETESSAS SENIHEKNDN ETNECTSSFE  120
TLFEQEPSSE VPKDSKLYML AQKTVQHIEQ YGKAPDFNKV IRAHNFIQTI YGTPLKEEEK  180
EVVRLMVIKL LKKISFYLTY I                                            201

SEQ ID NO: 235        moltype = AA  length = 9
FEATURE               Location/Qualifiers
source                1..9
                      mol_type = protein
                      organism = African swine fever virus
SEQUENCE: 235
DNAPAGHYY                                                           9

SEQ ID NO: 236        moltype = AA  length = 9
```

```
FEATURE                 Location/Qualifiers
source                  1..9
                        mol_type = protein
                        organism = African swine fever virus
SEQUENCE: 236
EFYQKLFSF                                                                        9

SEQ ID NO: 237          moltype = AA  length = 9
FEATURE                 Location/Qualifiers
source                  1..9
                        mol_type = protein
                        organism = African swine fever virus
SEQUENCE: 237
HNKQEFQSY                                                                        9

SEQ ID NO: 238          moltype = AA  length = 9
FEATURE                 Location/Qualifiers
source                  1..9
                        mol_type = protein
                        organism = African swine fever virus
SEQUENCE: 238
IPIYLKENY                                                                        9

SEQ ID NO: 239          moltype = AA  length = 9
FEATURE                 Location/Qualifiers
source                  1..9
                        mol_type = protein
                        organism = African swine fever virus
SEQUENCE: 239
ITKTFVNNI                                                                        9

SEQ ID NO: 240          moltype = AA  length = 9
FEATURE                 Location/Qualifiers
source                  1..9
                        mol_type = protein
                        organism = African swine fever virus
SEQUENCE: 240
NKALQKVGL                                                                        9

SEQ ID NO: 241          moltype = AA  length = 10
FEATURE                 Location/Qualifiers
source                  1..10
                        mol_type = protein
                        organism = African swine fever virus
SEQUENCE: 241
TPEEAAQRVY                                                                      10

SEQ ID NO: 242          moltype = AA  length = 9
FEATURE                 Location/Qualifiers
source                  1..9
                        mol_type = protein
                        organism = African swine fever virus
SEQUENCE: 242
VNDALSTRW                                                                        9

SEQ ID NO: 243          moltype = AA  length = 9
FEATURE                 Location/Qualifiers
source                  1..9
                        mol_type = protein
                        organism = African swine fever virus
SEQUENCE: 243
YINQALHEL                                                                        9

SEQ ID NO: 244          moltype = AA  length = 23
FEATURE                 Location/Qualifiers
source                  1..23
                        mol_type = protein
                        organism = African swine fever virus
SEQUENCE: 244
IQNNRSMMMV FNQLIASYIT RFY                                                       23

SEQ ID NO: 245          moltype = AA  length = 11
FEATURE                 Location/Qualifiers
source                  1..11
                        mol_type = protein
                        organism = African swine fever virus
SEQUENCE: 245
MMVFNQLIAS Y                                                                    11
```

-continued

| | | |
|---|---|---|
| SEQ ID NO: 246<br>FEATURE<br>source | moltype = AA  length = 13<br>Location/Qualifiers<br>1..13<br>mol_type = protein<br>organism = African swine fever virus | |
| SEQUENCE: 246<br>YMSRYNKEPL MPF | | 13 |
| SEQ ID NO: 247<br>FEATURE<br>source | moltype = AA  length = 10<br>Location/Qualifiers<br>1..10<br>mol_type = protein<br>organism = African swine fever virus | |
| SEQUENCE: 247<br>YTHAIQALRF | | 10 |
| SEQ ID NO: 248<br>FEATURE<br>source | moltype = AA  length = 11<br>Location/Qualifiers<br>1..11<br>mol_type = protein<br>organism = African swine fever virus | |
| SEQUENCE: 248<br>YSFEEIACLM Y | | 11 |
| SEQ ID NO: 249<br>FEATURE<br>source | moltype = AA  length = 8<br>Location/Qualifiers<br>1..8<br>mol_type = protein<br>organism = African swine fever virus | |
| SEQUENCE: 249<br>VTMIEAVY | | 8 |
| SEQ ID NO: 250<br>FEATURE<br>source | moltype = AA  length = 9<br>Location/Qualifiers<br>1..9<br>mol_type = protein<br>organism = African swine fever virus | |
| SEQUENCE: 250<br>AIQNWVQQY | | 9 |
| SEQ ID NO: 251<br>FEATURE<br>source | moltype = AA  length = 22<br>Location/Qualifiers<br>1..22<br>mol_type = protein<br>organism = African swine fever virus | |
| SEQUENCE: 251<br>SQVDLNQAIN TFMYYYYVAQ IY | | 22 |
| SEQ ID NO: 252<br>FEATURE<br>source | moltype = AA  length = 9<br>Location/Qualifiers<br>1..9<br>mol_type = protein<br>organism = African swine fever virus | |
| SEQUENCE: 252<br>NQAINTFMY | | 9 |
| SEQ ID NO: 253<br>FEATURE<br>source | moltype = AA  length = 11<br>Location/Qualifiers<br>1..11<br>mol_type = protein<br>organism = African swine fever virus | |
| SEQUENCE: 253<br>QAINTFMYYY Y | | 11 |
| SEQ ID NO: 254<br>FEATURE<br>source | moltype = AA  length = 11<br>Location/Qualifiers<br>1..11<br>mol_type = protein<br>organism = African swine fever virus | |
| SEQUENCE: 254<br>FMYYYYVAQI Y | | 11 |
| SEQ ID NO: 255<br>FEATURE<br>source | moltype = AA  length = 10<br>Location/Qualifiers<br>1..10<br>mol_type = protein<br>organism = African swine fever virus | |
| SEQUENCE: 255<br>VIYQHFNLEY | | 10 |

```
SEQ ID NO: 256         moltype = AA  length = 2475
FEATURE                Location/Qualifiers
source                 1..2475
                       mol_type = protein
                       organism = African swine fever virus
SEQUENCE: 256
MGNRGSSTSS RPPLSSEANL YAKLQDHIQR QTRPFSGGGY FNGGGDKNPV QHIKDYHIDS    60
VSSKAKLRVI EGIIRAIAKI GFKVDTKQPI EDILKDIKKQ LPDPRAGSTF VKNAEKQETV   120
CKMIADAINQ EFIDLGQDKL IDTTDGAASI CRQIVLYINS LTHGLRAEYL DVHGSIENTL   180
ENIKLLNDAI KQLHERMVTE VTKAAPNEEV INAVTMIEAV YRRLLNEQNL QINILTNFID   240
NILTPTQKEL DKLQTDEVDI IKLLNDTNSV LGTKNFGKVL SYTLCNLGIA ASVANKINKA   300
LQKVGLKVEQ YLQSKNWAEF DKELDLKRFS GLVSAENIAE FEKAVNLLRQ TFNERHKILE   360
NSCAKKGGDE EKTPLDRRIE AQRLDRKHIL MEFLNKSTQA YNDFLENVKK IGIKLVKEIA   420
LTPNITRLRD ALSRINDMGT IALDLSLIGF YTNAAAREER ETFLTQFMLV KNVLEEQSKI   480
DPNFKNLYDS CSRLLQIIDF YTDIVQKKYG GGEDCECTRV GGAALTVEEL GLSKAARSQV   540
DLNQAINTFM YYYYVAQIYS NLTHNKQEFQ SYEENYATIL GDAIAGRLMQ LDTEKNARIN   600
SPAVDLARGH VGPNPGGAQE ADWKAAVSAI ELEYDVKRRF YRALEGLDLY LKNITKTFVN   660
NIDSIQTVQQ MLDGVRIIGR WFTEATGDTL AQVFESFPTS AGNDSNVFTD NAPAGHYYEK   720
VAAEIQQGRS VGTLRPVRAS QAKNIRDLIG RSLSNFQALK NIINAFARIG DMLGGEELRQ   780
MVPMSPLQIY KTLLEYIQHS ALSVGLKNLN QSEIGGQRVA LARTPEEAAQ RVYLSTVRVN   840
DALSTRWETE DVFFTPMLKS MAAKIFIVLG IYDMFERPEP VYKLIPTRMI LGGADELEPE   900
VIPEAAELYF RLPRLAEFYQ KLFSFRDENV QISMLPELEG IFSGLIRIIF MRPIELINIG   960
DYSETEIRQL IKEINVIYQH FNLEYGEQEA TKKALIHFVN EINRRFGVIT RTEWEKFQRI  1020
VQEARTMNDF GMMNQTNYSI LPDEDGYTQS SQLLPSDRFI SPSTQPTPKW RPALYNIDSV  1080
DVQTGMLQPN SQWDLVQKFR KQLSEMFEDP SLQQELGKVS YQELIRQAIN ELKKEHTDKI  1140
QIVSKLIQGS ESLADTDVNK IFLFHETVIT GLNLLSAIYV LLNNFRNNIK GLDLDTIQKS  1200
IIEWLRETQA ANVNRANLID WLGRKHGAIS EIRNPGLVVK ENDVRLSRVY PDPTTNATAP  1260
QDQNLVTETL FAWIVPYVGI PAGGGVRAEQ ELAARYLVDN QRIMQLLLTN IFEMTSSFNK  1320
MVQVRFPETS TAQVHLDFTG LISLIDSLMA DTKYFLNLLR PHIDKNIIQY YENRSNPGSF  1380
YWLEEHLIDK LIKPPTDAGG RPLPGGELGL EGVNQIINKT YILLTKPYNV LQLRGGVQPR  1440
DAANIQINNN PQPSERFEQY GRVFSRLVFY DALENNSGLR VEQVVLGDFR LSNLIRTNNA  1500
QEEENTLSYWD NMAPRTYANV NDAANNLRRY RLYGSDYGIQ NNRSMMMVFN QLVASYIARF  1560
YDAPSGKIYL NLINAFANGN FSQAVMELGY THPDLARDNI AFGHRGDPTE QSVLLLSLGL  1620
MLQRLIKDTN RQGLSQHLIS TLTEIPIYLK ENYRANLPLF NKMFNILISQ GELLKQFIQY  1680
TNVQLARPNL MGLLGANNDS VIYYNNNINV PMTGLSVGQA ALRGIGGVFR PNVTLMPLGD  1740
AQNNTSDVVR KRLVAVIDGI IRGSHTLADS AMEVLHELTD HPIYLETEEH FIQNYMSRYN  1800
KEPLMPFSLS LYYLRDLRIE NNEVYDPLLY PNLESGSPEF KLLYGTRKLL GNDPVQLSDM  1860
PGVQLIMKNY NETVVAREQI TPTRFEHFYT HAIQALRFIV NIRSFKTVMM YNENTFGGVN  1920
LISENRDDKP IITAGIGMNA VYSLRKTLQD VISFVESSYQ EEQINHIHKI VSPKGQTRTL  1980
GSNRERERIF NLFDMNIIPI NVNALMRSIP LANIYNYDYS FEEIACLMYG ISAEKVRSLN  2040
TAAPQPDIAE VLNIPNRPPM NTREFMLKLL INPYVSVSIT QYGNELMSKG SAGYMSRIFR  2100
GDNALNMGRP KFLSDQIFNK VLFGSLYPTQ FDYDEAGPGL AAGIQRGREQ WGQPLSEYIN  2160
QALHELVRTI RIPQKLRVLR NIIVKNQLIA DLTTIREQLV SMRREVENMI QTPEIQNNPT  2220
PEVIAAAQNW TQQYRARVDT LINFIGNIGQ PNSMLDLIQT ITPVTVRAQL GVIFNRHGIP  2280
VPHPRQILQT DDEATQWFMT NILNIPAIIM TPFTDLANDL RTFLETLERY VFNVPRWLGP  2340
STGRVARAPV RMAPRDMRHP ISYTENSVLT YITEQNREEG PWSIVKQVGV GIQKPTLVQI  2400
GKDRFDTRLI RNLIFITNIQ RLLRLRLNLE LSQFRNVLVS PDHIINPSIT EYGFSITGPS  2460
ETFSDKQYDS DIRIL                                                 2475

SEQ ID NO: 257         moltype = AA  length = 2476
FEATURE                Location/Qualifiers
source                 1..2476
                       mol_type = protein
                       organism = African swine fever virus
SEQUENCE: 257
MGNRGSSTSS RPLPSSEANI YAKLQDHIQR QTRPFSGGGY FNGGGDKNPV QHIKDYHIDS    60
VSSKAKLRII EGIIRAIAKI GFKVDTKQPI EDILKDIKKQ LPDPRAGSTF VKNAEKQETV   120
CKMIADAINQ EFIDLGQDKL IDTTEGAASI CRQIVLYINS LTHGLRAEYL DVHGSIENTL   180
ENIKLLNDAI KQLHERMVTE VTKAAPNEEV INAVTMIEAV YRRLLNEQNL QINILTNFID   240
NILTPTQKEL DKLQTDEVDI IKLLNDTNSV LGTKNFGKVL SYTLCNLGIA ASVANKINKA   300
LQKVGLKVEQ YLQSKNWAEF DKELDLKRFS GLVSAENIAE FEKAVNLLRQ TFNERHKILE   360
NSCAKKGGDE EKTPLDRRIE AQRLDRKHIL MEFLNKSTQA YNDFLENVKK IGIKLVKEIA   420
LTPNITRLRD ALSRINDMGT IALDLSLIGF YTNAAAREER ETFLTQLTLV KNVLEEISKT   480
DPNFKNLYDS CSRLLQIIDF YTDIVQKKYG GEEDCECTRV GGAALTVEEL GLSKAARSQV   540
DLNQAINTFM YYYYVAQIYS NLTHNKQEFQ SYEENYATIL GDAIAGRLMQ LDTEKNARIN   600
SPAVDLARGH VGPNPGGAQE VDWKATVSAI ELEYDVKRRF YRALEGLDLY LKNITKTFVN   660
NIDSIQTVQQ MLDGVRIIGR WFTETTGDTL AQVFESFPTS TGNDSNVFTD NAPAGHYYEK   720
VAAEIQQGRS VGTLRPVRAS QAKNIRDLIG RSLSNFQALK NIINAFARIG DMLGGEELRQ   780
MVPMSPLQIY KTLLEYLQHS ALSVGLKNLN QSEIGGQRMA LAQTAEEEAQ RVYLSTVRVN   840
DALSTRWETE DVFFTPMLKS MAAKIFIVLG IYDMFERPEP VYKLIPTRMI LGGADELEPE   900
VIPEAAELYF RLPRLAEFYQ KLFSFRDENV QISMLPELEG IFSGLIRIIF MRPIELINIG   960
DYSETEIRQL IKEINVIYQH FNLEYGEQEA TKKALIHFVN EINRRFGVIT RTEWEKFQRI  1020
VQEARTMNDF GMMNQTNYSI LPDEDGYTQS SQLLPSDRFI SPSTQPTPKW RPALYNIDSV  1080
DVQTGMLQPN SQWDLVQKFR KQLSEMFEDP SLQQELGKIS YQELIRQAIN ELKKEHTDKI  1140
QIVSKLIQGS ESLADTDVNK IFLFHETVIT GLNLLSAIYV LLNNFRNNIK GLDLDTIQKS  1200
IIEWLRETQA ANVNRANLID WLGRKHGAIS EIRNPGLVIK EINMRLSMVY PDPTTEAAAA  1260
AQDRNLTTET LFAWIVPYVG IPAGGGVRPE QELAARYLVD NQRIMQLLLT NIFEMTSSFN  1320
KMVQVRFPET STAQVHLDFT GLISLIDSLM ADTKYFLDLL RPHIDKNIIQ YYENRSNPGS  1380
```

```
FYWLEEHLID KLIKPPTDAG GRPLPGGELG LEGVNQIINK TYTLLTKPYN VLQLRGGAQR   1440
RDAANIQINN NPQSSERFEQ YGRVFSRLVF YDALENNSGL RVEQVALGDF RLSNLIRTNN   1500
AQEENTLSYW DNIALRTYAN VNDAANNLRR YRLYGSDYGI QNNRSMMMVF NQLIASYITR   1560
FYDAPSGKIY LNLINAFANG NFSQAVMEMG YAHPDLARNN NVFGHRGDPT EQSVLLLSLG   1620
LILQRLIKDT NRQGLSQHLI STLTEIPIYL KENYRANLPL FNKMFNILIS QGELLKQFIQ   1680
YTNVQLARPN LTALLGANND SVIYYNNNNV PATGLSVGQA ALRGIGGVFR PNVTLMPLGD   1740
AQNNTSDVVR KRLVAVIDGI IRGSHTLADS AMEVLHELTD HPIYLETEEH FIQNYMSRYN   1800
KEPLMPFSLS LYYLHDLRIE NNEVYDPLLY PNLESGSPEF KLLYGTRKLL GNDPVQLSDM   1860
PGVQLIMKNY NETVVAREQI TPTRFEHFYT HAIQALRFII NIRSFKTVMM YNENTFGGVN   1920
LISENRDDKP IITAGIGMNA VYSLRKTLQD VISFVESSYQ EEQINHIHKI VSPKGQTRTL   1980
GSNREREIF NLFDMNIIPI NVNALMRSIP LANIYNYDYS FEEIACLMYG ISAEKVRSLD    2040
TTAPQPDVAE VLNIPNRPPI NTREFMLKLL INPYVSVSIT QYGNELLSKG NAGYMSRIFR   2100
GDNALNMGRP KFLSDQIFNK VLFGSLYPTQ FDYDEAGPSL AAGIQRGRER WGHPMSIYIN   2160
QALHEIVRTI RLAETVRGLR NVIDRNQIIG ELNAFRTQLE DTRREVNNLI QTPEIQNNPT   2220
PEIIAAIQNW VQQYRGQITN LIDLIGNAGQ ANSMINLIQN ITPQTAGAQL TALFNIRGLP   2280
APPPRQALQN DIEAMQWFMT MVINHPPVLI APFMLLVNNL KEFLNTLERY VYKTPRWLGP   2340
GTARIAQPPV GMAPGINMRH HTSYTENSVL TYITEQNREE GPWSIVKQVG VGIQKPTLVQ   2400
IGKDRFDTRL IRNLIFITNI QRLLRLRLNL ELSQFRNVLV SPDHIINPSI TEYGFSITGP   2460
SETFSDKQYD SDIRIL                                                  2476

SEQ ID NO: 258          moltype = AA  length = 9
FEATURE                 Location/Qualifiers
source                  1..9
                        mol_type = protein
                        organism = African swine fever virus
SEQUENCE: 258
EFYQKLFSF                                                             9

SEQ ID NO: 259          moltype = AA  length = 9
FEATURE                 Location/Qualifiers
source                  1..9
                        mol_type = protein
                        organism = African swine fever virus
SEQUENCE: 259
IPIYLKENY                                                             9

SEQ ID NO: 260          moltype = AA  length = 9
FEATURE                 Location/Qualifiers
source                  1..9
                        mol_type = protein
                        organism = African swine fever virus
SEQUENCE: 260
YINQALHEI                                                             9

SEQ ID NO: 261          moltype = AA  length = 9
FEATURE                 Location/Qualifiers
source                  1..9
                        mol_type = protein
                        organism = African swine fever virus
SEQUENCE: 261
HNKQEFQSY                                                             9

SEQ ID NO: 262          moltype = AA  length = 9
FEATURE                 Location/Qualifiers
source                  1..9
                        mol_type = protein
                        organism = African swine fever virus
SEQUENCE: 262
ITKTFVNNI                                                             9

SEQ ID NO: 263          moltype = AA  length = 9
FEATURE                 Location/Qualifiers
source                  1..9
                        mol_type = protein
                        organism = African swine fever virus
SEQUENCE: 263
DNAPAGHYY                                                             9

SEQ ID NO: 264          moltype = AA  length = 10
FEATURE                 Location/Qualifiers
source                  1..10
                        mol_type = protein
                        organism = African swine fever virus
SEQUENCE: 264
NIRDLIGRSL                                                           10

SEQ ID NO: 265          moltype = AA  length = 10
FEATURE                 Location/Qualifiers
source                  1..10
```

-continued

```
                            mol_type = protein
                            organism = African swine fever virus
SEQUENCE: 265
TAEEAAQRVY                                                            10

SEQ ID NO: 266          moltype = AA   length = 9
FEATURE                 Location/Qualifiers
source                  1..9
                        mol_type = protein
                        organism = African swine fever virus
SEQUENCE: 266
VNDALSTRW                                                             9

SEQ ID NO: 267          moltype = AA   length = 9
FEATURE                 Location/Qualifiers
source                  1..9
                        mol_type = protein
                        organism = African swine fever virus
SEQUENCE: 267
MKTKHVIKL                                                             9

SEQ ID NO: 268          moltype = AA   length = 15
FEATURE                 Location/Qualifiers
source                  1..15
                        mol_type = protein
                        organism = African swine fever virus
SEQUENCE: 268
SFPLCLEMGV VKVFE                                                      15

SEQ ID NO: 269          moltype = AA   length = 15
FEATURE                 Location/Qualifiers
source                  1..15
                        mol_type = protein
                        organism = African swine fever virus
SEQUENCE: 269
KNNGIDVNSI YGSDD                                                      15

SEQ ID NO: 270          moltype = DNA   length = 45
FEATURE                 Location/Qualifiers
source                  1..45
                        mol_type = unassigned DNA
                        organism = African swine fever virus
SEQUENCE: 270
tccttccccc tgtgcctgga gatgggcgtg gtcaaagtct tcgag                     45

SEQ ID NO: 271          moltype = DNA   length = 45
FEATURE                 Location/Qualifiers
source                  1..45
                        mol_type = unassigned DNA
                        organism = African swine fever virus
SEQUENCE: 271
aaaaacaacg gcatcgacgt gaacagcatt tatggcagcg atgat                     45

SEQ ID NO: 272          moltype = AA   length = 312
FEATURE                 Location/Qualifiers
source                  1..312
                        mol_type = protein
                        organism = African swine fever virus
SEQUENCE: 272
MLLVKMTTHI FHADDLLQAL QQAKAEKNFS SVFSLDWDKL RTAKRNTTVK YVTVNVIVKG     60
KKAPLMFNFQ NEKHVGTIPP STDEEVIRMN AENPKFLVKK RDRDPCLQFN KYKISPPLED    120
DGLTVKKNEQ GEEIYPGDEE KSKLFQIIEL LEEAFEDAVQ KGPEAMKTKH VIKLIQRKIS    180
NSAVKNADKP LPNPIARIRI KINPATSILT PILLDKNKPI TLQNGKTSFE ELKDEDGVKA    240
NPDNIHKLIE SHSMHDGIIN ARSICISNMG ISFPLCLEMG VVKVFEKNNG IDVNSIYGSD    300
DISTLVNQIA IA                                                        312

SEQ ID NO: 273          moltype = DNA   length = 924
FEATURE                 Location/Qualifiers
source                  1..924
                        mol_type = unassigned DNA
                        organism = African swine fever virus
SEQUENCE: 273
atgactacac acatctttca cgcagatgat ctcctacaag cattgcaaca agcaaaagca     60
gaaaaaaatt tttcatctgt attttcttta gattgggata aattacgcac agcgaagcgt    120
aatacaacgg ttaaatatgt tacggtcaat gtcatagtaa aaggcaaaaa agctccgcta    180
atgtttaact ttcaaaatga aaacatgta ggaaccattc ctcccagtac cgatgaagag     240
gttatacgga tgaatgctga aaatccaaag ttttggtga aaaacgtga cagggatccc      300
tgtttgcagt tcaacaaata caaatctcg ccgccattgg aagatgatgg tctcactgtt     360
aaaaagaatg agcagggtga agaaatatac cccggcgacg aagaaaatc taagttgttt     420
```

```
caaattattg aactgttaga agaagccttt gaagacgctg tgcaaaaagg tcctgaagcc    480
atgaaaacga acatgttat aaaattaatt caaagaaaaa tttctaatag cgcggttaaa    540
aacgcagaca aacctttgcc gaatcctatc gcacgcattc gtattaaaat caatcccgct    600
acaagtatac taacaccaat attgcttgat aaaaataagc ccattacttt acagaatggt    660
aaaacaagct ttgaagagtt aaaagatgaa gacggcgtta aggccaatcc ggataatatt    720
cataagctta tagaatcgca ttctatacat gatggcatca ttaatgctag atctatttgt    780
atcagcaata tggcatttc atttccgctt tgcttggaaa tgggagttgt aaaagttttt    840
gaaaaaaata tgggattga tgtgaactcc atttatggct cagacgatat ttcaactctt    900
gttaatcaga ttgctattgc ttaa                                            924

SEQ ID NO: 274          moltype = AA  length = 307
FEATURE                 Location/Qualifiers
source                  1..307
                        mol_type = protein
                        organism = African swine fever virus
SEQUENCE: 274
MTTHIFHADD LLQALQQAKA EKNFSSVFSL DWDKLRTAKR NTTVKYVTVN VIVKGKKAPL     60
MFNFQNEKHV GTIPPSTDEE VIRMNAENPK FLVKKRDRDP CLQFNKYKIS PPLEDDGLTV    120
KKNEQGEEIY PGDEEKSKLF QIIELLEEAF EDAVQKGPEA MKTKHVIKLI QRKISNSAVK    180
NADKPLPNPI ARIRIKINPA TSILTPILLD KNKPITLQNG KTSFEELKDE DGVKANPDNI    240
HKLIESHSIH DGIINARSIC ISNMGISFPL CLEMGVVKVF EKNNGIDVNS IYGSDDISTL    300
VNQIAIA                                                              307

SEQ ID NO: 275          moltype = AA  length = 11
FEATURE                 Location/Qualifiers
source                  1..11
                        mol_type = protein
                        organism = African swine fever virus
SEQUENCE: 275
LIDFDPLVTF Y                                                          11

SEQ ID NO: 276          moltype = AA  length = 10
FEATURE                 Location/Qualifiers
source                  1..10
                        mol_type = protein
                        organism = African swine fever virus
SEQUENCE: 276
VTFYLLLEPY                                                            10

SEQ ID NO: 277          moltype = AA  length = 8
FEATURE                 Location/Qualifiers
source                  1..8
                        mol_type = protein
                        organism = African swine fever virus
SEQUENCE: 277
STINALRF                                                               8

SEQ ID NO: 278          moltype = AA  length = 530
FEATURE                 Location/Qualifiers
source                  1..530
                        mol_type = protein
                        organism = African swine fever virus
SEQUENCE: 278
MPSNMKQFCK ISVWLQQHDP DLLEIINNLC MLGNLSAAKY KHGVTFIYPK QAKIRDEIKK     60
HAYSNDPSQA IKTLESLILP FYIPTPAEFT GEIGSYTGVK LEVEKTEANK VILKNGEAVL    120
VPAADFKPFP DRRLAVWIME SGSMPLEGPP YKRKKEGGGN DPPVPKHISP YTPRTRIAIE    180
VEKAFDDCMR QNWCSVNNPY LAKSVSLLSF LSLNHPTEFI KVLPLIDFDP LVTFYLLLEP    240
YKTHGDDFLI PETILFGPTG WNGTDLYQSA MLEFKKFFTQ ITRQTFMDIA DSATKEVDVP    300
ICYSDPETVH SYANHVRTEI LHHNAVNKVT TPNLVVQAYN ELEQTNTIRH YGPIFPESTI    360
NALRFWKKLW QDEQRFVIHG LHRTLMDQPT YETSEFAEIV RNLRFSRPGN NYINELNITS    420
PAMYGDKHTT GDIAPNDRFA MLVAFINSTD FLYTAIPEEK VGGNETQTSS LTDLVPTRLH    480
SFLNHNLSKL KILNRAQQTV RNILSNDCLN QLKHYVKHTG KNEILKLLQE                530

SEQ ID NO: 279          moltype = AA  length = 10
FEATURE                 Location/Qualifiers
source                  1..10
                        mol_type = protein
                        organism = African swine fever virus
SEQUENCE: 279
RTHLITTLDY                                                            10

SEQ ID NO: 280          moltype = AA  length = 80
FEATURE                 Location/Qualifiers
source                  1..80
                        mol_type = protein
                        organism = African swine fever virus
SEQUENCE: 280
MLIPVVCFTC GFPIGTYAAI FDKARTEYIK TKMGGTLPQN IPLDASLQIE LKDLITALGI     60
PMRVCCRTHL ITTLDYRKYY                                                 80
```

```
SEQ ID NO: 281           moltype = AA   length = 10
FEATURE                  Location/Qualifiers
source                   1..10
                         mol_type = protein
                         organism = African swine fever virus
SEQUENCE: 281
EPMEQVLIHY                                                                    10

SEQ ID NO: 282           moltype = AA   length = 11
FEATURE                  Location/Qualifiers
source                   1..11
                         mol_type = protein
                         organism = African swine fever virus
SEQUENCE: 282
GPDPKISSNA Y                                                                  11

SEQ ID NO: 283           moltype = AA   length = 10
FEATURE                  Location/Qualifiers
source                   1..10
                         mol_type = protein
                         organism = African swine fever virus
SEQUENCE: 283
HNAQLFVQNF                                                                    10

SEQ ID NO: 284           moltype = AA   length = 11
FEATURE                  Location/Qualifiers
source                   1..11
                         mol_type = protein
                         organism = African swine fever virus
SEQUENCE: 284
TPDGGPELAK Y                                                                  11

SEQ ID NO: 285           moltype = AA   length = 9
FEATURE                  Location/Qualifiers
source                   1..9
                         mol_type = protein
                         organism = African swine fever virus
SEQUENCE: 285
YKDETLPYL                                                                      9

SEQ ID NO: 286           moltype = DNA   length = 27
FEATURE                  Location/Qualifiers
source                   1..27
                         mol_type = unassigned DNA
                         organism = African swine fever virus
SEQUENCE: 286
tataaagacg aaacattgcc gtactta                                                 27

SEQ ID NO: 287           moltype = AA   length = 9
FEATURE                  Location/Qualifiers
source                   1..9
                         mol_type = protein
                         organism = African swine fever virus
SEQUENCE: 287
YKDETLPYL                                                                      9

SEQ ID NO: 288           moltype = DNA   length = 27
FEATURE                  Location/Qualifiers
source                   1..27
                         mol_type = unassigned DNA
                         organism = African swine fever virus
SEQUENCE: 288
tataaagacg aaacattgcc gtactta                                                 27

SEQ ID NO: 289           moltype = AA   length = 9
FEATURE                  Location/Qualifiers
source                   1..9
                         mol_type = protein
                         organism = African swine fever virus
SEQUENCE: 289
KTWHEIPLY                                                                      9

SEQ ID NO: 290           moltype = AA   length = 10
FEATURE                  Location/Qualifiers
source                   1..10
                         mol_type = protein
                         organism = African swine fever virus
SEQUENCE: 290
```

```
GMQDGIRWFY                                                                    10

SEQ ID NO: 291          moltype = AA  length = 11
FEATURE                 Location/Qualifiers
source                  1..11
                        mol_type = protein
                        organism = African swine fever virus
SEQUENCE: 291
RQFMNHYMNF I                                                                  11

SEQ ID NO: 292          moltype = AA  length = 11
FEATURE                 Location/Qualifiers
source                  1..11
                        mol_type = protein
                        organism = African swine fever virus
SEQUENCE: 292
TVLNTFEAYG Y                                                                  11

SEQ ID NO: 293          moltype = AA  length = 9
FEATURE                 Location/Qualifiers
source                  1..9
                        mol_type = protein
                        organism = African swine fever virus
SEQUENCE: 293
FMARPVWTY                                                                      9

SEQ ID NO: 294          moltype = AA  length = 9
FEATURE                 Location/Qualifiers
source                  1..9
                        mol_type = protein
                        organism = African swine fever virus
SEQUENCE: 294
ALALISLCY                                                                      9

SEQ ID NO: 295          moltype = AA  length = 1133
FEATURE                 Location/Qualifiers
source                  1..1133
                        mol_type = protein
                        organism = African swine fever virus
SEQUENCE: 295
MAYPELDAAD FLQQLARRKE FKSLISPPVD QKELIRDLRA HFVQIGGPGC EKGGRAFFPC     60
DPYASPFPSI KGLQLHNAQL FVQNFQNPNT PYSRLLLNWQ TGTGKSIAAI AIARQFMNHY    120
MNFIENAPWI FVVGFTRAII QTEMLRRPEL GFVSYKEVAE LHRLLHIAKQ SGSTTSVESR    180
HLNGFVSTLK RRLTDRNRGG FFQFYGYKEF ASKLFNITSK GEEKNFDVLS LFHRSDEAED    240
TLNENDISQF VQKISEAETN GLIRVNQKIM EQLRGGLLIA DEIHNVYNIQ ERNNYGIALQ    300
YVLDAFPPHQ APRAVFMSAT PVTGSVMEYV DLLNLLVPRH ELPNGQPLQR QQLFDSSGHS    360
VKWKKDALAL VERLSTGRVS FLLDTNTNFY PERIFAGKML SYKDETLPYL HFIECPMSEY    420
QLETLKQLGP DPKISSNAYS IYDMVFPNPK FSKQTEPKAY GLFNSTETPT ALSMASTDWL    480
LENGVQIIEP SRRAPFNVSG SFLSLQPPTH ISGLAFYSGK YTQMMKDILS IIRQGRGKIL    540
IYHNRVRMSG VLILQEILQS NGILNEVSSP VGTTRCSICA AIRDEHTHSD HQFIPVRFTI    600
LHSEIEPAVR ERSLALFNAS SNLEGHQLRI LIGSKVIVEG LNFQAVRYEM IMSLPLDIPR    660
LIQVFGRVVR KNSHMELPPS ERNVTIYLYV STTPDGGPEL AKYAQKLKEY ILIQEGDKAL    720
RKHAIDGFTN QIKIDKPMLE SLPLSPSITP ANVGATVLNT FEAYGYGEQE VKTISNIIIS    780
LFMARPVWTY SELWKAVSTP KLIQGITIDN KLFSEDNFAL ALISLCYSKN QCKELWIQNR    840
LCTIMHVPAK PEHLYVAAVL NHKKEPVLDI ETYIRDFQTP AMHSIRITKY LEHSQTKEPF    900
QVLYEKFQKD FQDEPMEQVL IHYPASFHYT MLEALIIDNL AGMGALVEVY KKFFIAFSKK    960
DIQPFPDIFK IISHVPGDDN TLVGYATEDS VRLITSREDK TWHEIPLYML NINVKRKEND   1020
IVIGYMESKG KALKFKIRPP IQVLKKNEIT DIRMLNRGAV CETRGREEQQ KIADQLGISL   1080
NLTKISAIKL CLLIRNNLLQ KEMEARNQPN GMQDGIRWFY LFNDKMPSLV HTS           1133

SEQ ID NO: 296          moltype = DNA  length = 3402
FEATURE                 Location/Qualifiers
source                  1..3402
                        mol_type = unassigned DNA
                        organism = African swine fever virus
SEQUENCE: 296
atggcgtatc ccgaattgga tgccgcagac tttttgcagc agttggcgcg aagaaaggag     60
tttaagtcgt tgatttcccc tcctgtcgac caaaaagagc tcattcgtga tctgcgggct    120
cattttgtcc agatcggggg gcctggctgc gagaagggg ggcgagcgtt ttttccgtgt    180
gaccccacgc gtcgcccttt ccttccatc aagggtctcc aattgcataa tgcccagctt    240
ttcgtccaaa actttcaaaa ccccaacaca ccctactcgc gtctttttatt aaactggcag    300
accgggacgg gaaaaagcat tgccgcgatt gccattgcgc gccaattcat gaaccactac    360
atgaatttta ttgaaaatgc ggcctggatt ttgtggtga gctttacacg cgccatcatt    420
caaacagaaa tgctaagacg tcctgagctg ggatttgttt cttacaagga ggtcgctgaa    480
ctacaccggc ttcttcacat tgcaaagcag tctggcagca ccacgtcggt tgaatcacgg    540
catctaaatg ggttcgttag tacgttaaag cgccgtttaa ccgatagaaa ccgcggaggc    600
ttttttcagt tttacggcta taggaatttt gcatccaagc ttttcaatat tacgagtaag    660
ggtgaagaga aaaactttga tgtgcttcct ctgtttcatc gttctgacga agcagaagat    720
acattgaatg agaacgatat atctcagttc gtgcaaaaaa tcagcgaggc cgagacaaac    780
```

```
ggcctcatcc gggtgaatca aaaaatcatg gagcagctta ggggaggact gctcattgcg    840
gatgaaatac acaacgtgta caatatccga gaacgaaata attatggcat cgctttacag    900
tatgtcctgg atgcctttcc acctcaccag gcccccaggg ccgtcttcat gtcggcaacg    960
cccgtaaccg ggagtgtcat ggaatacgtc gacctgttaa accttttggt tccgcggcat   1020
gagctgccca acggccagcc cctccagcgc cagcaactgt ttgacagcag tgggcattcc   1080
gttaaatgga aaaggacgc cctggctctt gtggaaagac tcagcaccgg aagggtatct   1140
tttttgttgg ataccaacac caattttta cctgaaagaa tatttgccgg aaagatgttg   1200
tcctataaag acgaaacatt gccgtactta catttcatcg aatgccccat gtctgagtat   1260
cagctcgaaa cgcttaaaca gctgggccct gaccctaaaa tctcgagtaa tgcgtacagc   1320
atttatgaca tggtgtttcc caacccaaaa ttttcaaaac aaacggaacc caaggcttac   1380
ggcctgttta actcgacgga aaccccact gcccttccta tggcaagcac agactggctt   1440
ctggaaaacg gggtacagat tattgagcct tcgcgtagag ccccctttaa tgtgagtggc   1500
agcttttgt cgctgcagcc accaacgcac atctcgggat tggccttta tagcggaaaa   1560
tacactcaaa tgatgaaaga cattcttttc attattcggc aaggccgggg gaaaatttta   1620
atttaccaca atcgggtccg catgtcgggg gttcttatcc tgcaagaaat tttacaaagt   1680
aatggcattt taaatgaagt ttcgtcccct gtgggaacga cccgctgctc catctgcgcc   1740
gcgattcgcg atgagcacac acatagcgac catcagttta ttccagtacg gttcaccatt   1800
ctgcacagcg aaatagagcc cgctgtacgc gaacgaagcc tggctctttt taacgcctcg   1860
tccaacctgg aaggccacca gctgcgtatt ctcatcgggt ccaaggtgat tgtggagggt   1920
ttgaactttc aggccgtgcg gtacgagatg attatgtcat tgcccctga tattcccgg    1980
cttattcagg tatttgggag ggtggtgcga aaaaattcac acatggagct tcccccagt   2040
gagcgcaacg tgacaatcta tttgtacgta tcgacaaccc cgatggggag gccagagctt   2100
gctaagtacg cacaaaatt aaagaatac attttaatac aggaggggga taaggcgctg   2160
cgaaagcacg ccattgatgg gttcaccaac cagattaaga ttgataagcc tatgctggaa   2220
agtctgcccc ttagtccatc catcacgccg gcaaacgtcg gagccaccgt cctcaatacc   2280
tttgaggcct atggatacgg ggagcaagag gtaaaaacaa tttctaatat tattatatct   2340
ttgtttatgg cacgccccgt gtggacgtac tccgagctat ggaaggcagt ttccacgccc   2400
aagctcatac agggaattac catcgataat aaactcttct cagaggacaa cttcgcgctg   2460
gcgctcattt ctctatgcta ctcaaaaaac cagtgcaagg aattatggat acagaatcgt   2520
ctttgcacca ttatgcatgt gccggcaaag cctgagcatt tgtacgtcgc tgcggtgctt   2580
aaccataaaa aggaaccggt attagatatt gaaacatata ttcgggattt tcagcttccc   2640
gcgatgcaca gcatccgtat taccaaatac ctcgaacact cgcagaccaa gaaccctttt   2700
caagtattgt atgaaaagtt tcagaaggat tttcaggatg agccaatgga gcaggtactc   2760
atccattatc ccgcttcatt tcactatacg atgctagaag cacttattat agataatctt   2820
gcaggtatgg gggcccttgt cgaggtttat aaaaagtttt tcatcgcttt ttcaaaaaaa   2880
gatattcagc catttccgga cattttaaa attataagcc acgtgcctgg ggatgacaac   2940
actctggtgg gctatgccac ggaggactcc gtgcgactta ttacctcgcg agaagataaa   3000
acctggcatg aaattccgct ctatatgctt aatattaatg ttaaacgaaa agaaaacgac   3060
attgtcatag gctatatgga aagcaaggga aaggccctta aattttaaaat ccgcccaact   3120
atccaggttt taaaaaagaa cgagattact gatattcgca tgctaaaccg gggagccgta   3180
tgcgaaacac gcggacggga ggagcaacaa aaaattgctg accaattggg cataagttta   3240
aaccttacaa agattagtgc catcaagctc tgcttactca ttcgcaataa ccttttgcaa   3300
aaagaaatgg aggctcgtaa tcaacccaat ggaatgcagg atggaatccg ctggttttac   3360
cttttttaacg acaaaatgcc gtcacttgtg cacacatctt ag                     3402
```

```
SEQ ID NO: 297          moltype = AA  length = 1133
FEATURE                 Location/Qualifiers
source                  1..1133
                        mol_type = protein
                        organism = African swine fever virus
SEQUENCE: 297
MAYPELDAAD FLQQLARRKE FKSLISPPVD QKELIRDLRA HFVQIGGPGC EKGGRAFFPC     60
DPYASPFPSI KGLQLHNAQL FVQNFQNPNT PYSRLLLNWQ TGTGKSIAAI AIARQFMNHY    120
MNFIENAPWI FVVGFTRAII QTEMLRRPEL GFVSYKEVAE LHRLLHIAKQ SGSTTSVESR    180
HLNGFVSTLK RRLTDRNRGG FFQFYGYKEF ASKLFNITSK GEEKNFDVLS LFHRSDEAED   240
TLNENDISQF VQKISEAETN GLIRVNQKIM EQLRGGLLIA DEIHNVYNIQ ERNNYGIALQ    300
YVLDAFPPHQ APRAVPMSAT PVTGSVMEYV DLLNLLVPRH ELPNGQPLQR QQLFDSSGHS    360
VKWKKDALAL VERLSTGRVS FLLDTNTNFY PERIFAGKML SYKDETLPYL HFIECPMSEY    420
QLETLKQLGP DPKISSNAYS IYDMVFPNPK FSKQTEPKAY GLFNSTETPT ALSMASTDWL    480
LENGVQIIEP SRRAPFNVSG SFLSLQPPTH ISGLAFYSGK YTQMMKDILS IIRQGRGKIL    540
IYHNRVRMSG VLILQEILQS NGILNEVSSP VGTTRCSICA AIRDEHTHSD HQFIPVRFTI    600
LHSEIEPAVR ERSLALFNAS SNLEGHQLRI LIGSKVIVEG LNFQAVRYEM IMSLPLDIPR    660
LIQVFGRVVR KNSHMELPPS ERNVTIYLYV STTPDGGPEL AKYAQKLKEY ILIQEGDKAL    720
RKHAIDGFTN QIKIDKPMLE SLPLSPSITP ANVGATVLNT FEAYGYGEQE VKTISNIIIS    780
LFMARPVWTY SELWKAVSTP KLIQGITIDN KLFSEDNFAL ALISLCYSKN QCKELWIQNR    840
LCTIMHVPAK PEHLYVAAVL NHKKEPVLDI ETYIRDFQPP AMHSIRITKY LEHSQTKEPF    900
QVLYEKFQKD FQDEPMEQVL IHYPASFHYT MLEALIIDNL AGMGALVEVY KKFFIAFSKK    960
DIQPFPDIFK IISHVPGDDN TLVGYATEDS VRLITSREDK TWHEIPLYML NINVKRKEND   1020
IVIGYMESKG KALKFKIRPP IQVLKKNEIT DIRMLNRGAV CETRGREEQQ KIADQLGISL   1080
NLTKISAIKL CLLIRNNLLQ KEMEARNQPN GMQDGIRWFY LFNDKMPSLV HTS          1133

SEQ ID NO: 298          moltype = DNA  length = 3402
FEATURE                 Location/Qualifiers
source                  1..3402
                        mol_type = unassigned DNA
                        organism = African swine fever virus
SEQUENCE: 298
atggcgtatc ccgaattgga tgccgcagac ttttttgcagc agttggcgcg aagaaaggag     60
tttaaatcgt tgatttcccc tcctgtcgac caaaaagagc tcattcgtga tctgcgggct    120
```

```
cattttgtcc agatcggtgg gcctggctgc gagaagggg ggcgagcgtt ttttccgtgt     180
gacccctacg cgtcgccctt tccttccatc aagggtctcc aattgcataa tgcccagctt    240
ttcgtccaaa actttcaaaa tcccaacacg ccctactcgc gtcttttatt aaactggcag    300
accgggacgg gaaaaagcat tgccgcgatt gccatcgcgc gtcaatttat gaaccactac    360
atgaatttta ttgaaaatgc gccctggatt tttgtggtag gcttacacg cgccatcatt     420
caaacagaaa tgctaagacg tcctgagctg ggatttgttt cttacaagga ggtcgctgag    480
ctacaccggc ttcttcacat tgcaaagcag tctggcagca ccacgtcggt cgaatcacgg    540
catctaaatg ggtcgttag tacgttaaag cgccgtttaa ccgatagaaa ccgcggaggc     600
ttttttcagt tttacggcta taaggaattt gcatccaagc ttttcaatat tacgagtaag    660
ggtgaagaga aaacttttga tgtgcttttct ctgtttcatc gttctgacga agcagaagat    720
acattgaatg agaacgatat atctcagttc gtgcaaaaaa ttagcgaggc cgagacaaac    780
ggcctcatcc gggtgaatca aaaaatcatg gagcaactta ggggaggact gctcattgcg    840
gatgaaatac acaacgtgta caatatccag gaacgaaata attatggcat cgctttacag    900
tatgtcctgg atgcctttcc acctcaccag gcccccaggg ccgtcttcat gtcggcaacg    960
cccgtaaccg ggagtgtcat ggaatacgtc gacctgttaa acctttggt tccgcggcat    1020
gagctgccca acgccagcc cctccagcgc cagcaactgt ttgacagcag tgggcattcc   1080
gttaaatgga aaaggacgc cctagctctt gtggaaagac tgagcaccgg aagggtatct    1140
ttttgttgg ataccaacac caatttttac cccgaaagaa tatttgccgg aaagatgttg   1200
tcctataaag acgaaacatt gccgtactta catttcatcg aatgccccat gtctgagtat   1260
cagcttgaaa cgcttaaaca gctgggccct gaccctaaaa tctcgagtaa tgcgtacagc    1320
atttatgaca tggtgtttcc caacccaaaa ttttcaaaac aaacgaacc caaggcttac   1380
ggcctgttta actcgacgga aaccccсcacc gccctttcta tggcaagcac agactggctt    1440
ctggaaaacg gggtacagat tattgagcct tcgcgtagag cccccttaa tgtgagtggc    1500
agctttttgt cgctgcagcc accaacgcac atctcgggat tggccttta tagcggaaaa    1560
tacactcaaa tgatgaaaga cattcttttcc attattcggc aaggccgggg gaaaatttta   1620
atttaccaca atcgggtccg catgtcgggg gttcttatct tgcaagaaat tttacaaagt    1680
aatggcattt taaatgaagt ttcgtcccct gtgggaacga cccgctgctc catctgcgcc    1740
gcgattcgcg atgagcacac acatagcgac catcagttta ttccagtacg gttcaccatt    1800
ctgcacagcg aaatagagcc cgctgtacgc gaacgaagcc tggctctttt taacgcctcg    1860
tccaacctgg aagccacca gctgcgtatt ctcatcgggt ccaaggtgat tgtggagggt    1920
ttgaactttc aggccgtgcg gtacgagatg attatgtcat tgcсccсttga tattccccgg   1980
cttattcagg tatttgggag ggtggtgcga aaaaattcac acatggagct cccccccagt    2040
gagcgcaacg tgacaattta tttgtacgta tcgacaacac ccgatggagg gccagagctc    2100
gctaagtacg cacaaaaatt aaaagaatac attttaatac aggaggggga taaggcgctg    2160
cgaaagcacg ccattgatgg gttcaccaac cagattaaga ttgataagcc tatgttggaa    2220
agtctgcccc ttagtccatc catcacgccg gcaaacgtcg gagccaccgt cctcaatacc    2280
tttgaggcct atggatacgg ggagcaagag gtaaaaacaa tttctaatat tattatatct    2340
ttgtttatgg cacgccccgt gtggacgtac tccgagctat ggaaggctgt ttccactccc    2400
aagctcatac agggaattac catcgataat aaactctctt cagaggacaa cttcgccctg    2460
gcgctcatttt ctctatgcta ctcaaaaaac cagtgcaagg aattatggat acagaatcgt   2520
ctttgcacca ttatgcatgt gccggcaaag cctgagcatt tgtacgtcgc tgcggtgctt   2580
aaccataaaa aggaaccggt attagatatt gaaacatata ttcgggattt tcagcctccc    2640
gcgatgcaca gcatccgtat taccaaatac ctcgaacact cgcagaccaa agaacccctt    2700
caagtattgt atgaaaagtt tcagaaggat tttcaggatg agccaatgga gcaggtactc    2760
atccactacc ccgcttcatt tcactatacg atgctagaag cacttattat agataatctt    2820
gcaggtatgg gggcccttgt cgaggtttat aaaaagtttt tcatcgcttt ttcaaaaaaaa    2880
gatattcagc catttccgga cattttttaaa attataagcc acgtgcctgg ggatgacaac    2940
actctagtgg gctatgccac ggaggactcc gtgcgactta ttacctcgcg agaagataaa    3000
acctggcatg aaattccgct ttatatgctt aatattaatg ttaaacgaaa agaaaacgac    3060
atcgtccatg gctatatgga aagcaaggga aaggccctta aatttaaaat ccgcccсcсct    3120
atccaggtttt taaaaagaa tgagattact gatattcgca tgctaaaccg gggagcgtta    3180
tgcgaaacac gcggacggga ggagcaacaa aaaattgctg accaattggg cataagttta   3240
aaccttacaa agattagtgc catcaagctc tgcttactca ttcgcaataa cctttttgcaa    3300
aaagaaatga aggctcgtaa tcaaccaaat ggaatgcagg atggaatccg ctggttttac   3360
cttttttaacg acaaaatgcc gtcacttgtg cacacatctt ag                      3402
```

```
SEQ ID NO: 299        moltype = AA   length = 10
FEATURE               Location/Qualifiers
source                1..10
                      mol_type = protein
                      organism = African swine fever virus SEQUENCE: 299
HNAQLFVQNF                                                              10

SEQ ID NO: 300        moltype = AA   length = 9
FEATURE               Location/Qualifiers
source                1..9
                      mol_type = protein
                      organism = African swine fever virus SEQUENCE: 300
YKDETLPYL                                                                9

SEQ ID NO: 301        moltype = AA   length = 11
FEATURE               Location/Qualifiers
source                1..11
                      mol_type = protein
                      organism = African swine fever virus SEQUENCE: 301
GPDPKISSNA Y                                                            11
```

```
SEQ ID NO: 302          moltype = AA   length = 10
FEATURE                 Location/Qualifiers
source                  1..10
                        mol_type = protein
                        organism = African swine fever virus
SEQUENCE: 302
EPMEQVLIHY                                                                  10

SEQ ID NO: 303          moltype = AA   length = 10
FEATURE                 Location/Qualifiers
source                  1..10
                        mol_type = protein
                        organism = African swine fever virus
SEQUENCE: 303
EFIEYRKMVL                                                                  10

SEQ ID NO: 304          moltype = AA   length = 11
FEATURE                 Location/Qualifiers
source                  1..11
                        mol_type = protein
                        organism = African swine fever virus
SEQUENCE: 304
EFIEYRKMVL L                                                                11

SEQ ID NO: 305          moltype = AA   length = 9
FEATURE                 Location/Qualifiers
source                  1..9
                        mol_type = protein
                        organism = African swine fever virus
SEQUENCE: 305
VPYDKFVQM                                                                    9

SEQ ID NO: 306          moltype = AA   length = 19
FEATURE                 Location/Qualifiers
source                  1..19
                        mol_type = protein
                        organism = African swine fever virus
SEQUENCE: 306
MAMQKLFTYI YEFIEYRKM                                                        19

SEQ ID NO: 307          moltype = AA   length = 10
FEATURE                 Location/Qualifiers
source                  1..10
                        mol_type = protein
                        organism = African swine fever virus
SEQUENCE: 307
AMQKLFTYIY                                                                  10

SEQ ID NO: 308          moltype = AA   length = 9
FEATURE                 Location/Qualifiers
source                  1..9
                        mol_type = protein
                        organism = African swine fever virus
SEQUENCE: 308
KLFTYIYEF                                                                    9

SEQ ID NO: 309          moltype = AA   length = 11
FEATURE                 Location/Qualifiers
source                  1..11
                        mol_type = protein
                        organism = African swine fever virus
SEQUENCE: 309
FTYIYEFIEY R                                                                11

SEQ ID NO: 310          moltype = AA   length = 8
FEATURE                 Location/Qualifiers
source                  1..8
                        mol_type = protein
                        organism = African swine fever virus
SEQUENCE: 310
YIYEFIEY                                                                     8

SEQ ID NO: 311          moltype = AA   length = 205
FEATURE                 Location/Qualifiers
source                  1..205
                        mol_type = protein
                        organism = African swine fever virus
SEQUENCE: 311
```

```
MAMQKLFTYI YEFIEYRKMV LLEEKVPYDK FVQMVLNTGF FRINAETLNH GIVSVFIFGA   60
NGKYVHHGGD MRTLLTNTLN EKKHYEELIL IVDKPVLSKK NILDIIVEQR AANPTIVINI  120
YPYHLFCINI PKVSAIPKHK LITQEEAQEF LGREYLQPQD LMQISASDPP VVWLGGRPGD  180
FVQIERPSET AMHAVVIRFI TKSKI                                       205

SEQ ID NO: 312          moltype = AA   length = 205
FEATURE                 Location/Qualifiers
source                  1..205
                        mol_type = protein
                        organism = African swine fever virus
SEQUENCE: 312
MAMQKLFTYI YEFIEYRKMV LLEEKVPYDK FVQMVLNTGF FRINAETLNH GIVSVFIFGA   60
NGKYVHHGGD MRTLLTNTLN EKKHYEELIL IVDKPVLSKK NILDIIVEQR AANPTIVINI  120
YPYHLFCINI PKVSAIPKHK LITQEEAQEF LGREYLQPQD LMQISASDPP VVWLGGRPGD  180
FVQIERPSET AMHAVVIRFI TKSKI                                       205

SEQ ID NO: 313          moltype = AA   length = 9
FEATURE                 Location/Qualifiers
source                  1..9
                        mol_type = protein
                        organism = African swine fever virus
SEQUENCE: 313
TAMQLKTSI                                                           9

SEQ ID NO: 314          moltype = AA   length = 11
FEATURE                 Location/Qualifiers
source                  1..11
                        mol_type = protein
                        organism = African swine fever virus
SEQUENCE: 314
SMSYFDGKTE Y                                                       11

SEQ ID NO: 315          moltype = AA   length = 9
FEATURE                 Location/Qualifiers
source                  1..9
                        mol_type = protein
                        organism = African swine fever virus
SEQUENCE: 315
TEYKHIYFL                                                           9

SEQ ID NO: 316          moltype = AA   length = 17
FEATURE                 Location/Qualifiers
source                  1..17
                        mol_type = protein
                        organism = African swine fever virus
SEQUENCE: 316
KRYSLAFSEF IHCHYSI                                                 17

SEQ ID NO: 317          moltype = AA   length = 10
FEATURE                 Location/Qualifiers
source                  1..10
                        mol_type = protein
                        organism = African swine fever virus
SEQUENCE: 317
AFSEFIHCHY                                                         10

SEQ ID NO: 318          moltype = AA   length = 250
FEATURE                 Location/Qualifiers
source                  1..250
                        mol_type = protein
                        organism = African swine fever virus
SEQUENCE: 318
MDTAMQLKTS IGLITCRMNT QNNQIETILV QKRYSLAFSE FIHCHYSINA NQGHLIKMFN   60
NMTINERLLV KTLDFDRMWY HIWIETPVYE LYHKKYQKFR KNWLLPDNGK KLISLINQAK  120
GSGTLLWEIP KGKPKEDESD LTCAIREFEE ETGITREYYQ ILPEFKKSMS YFDGKTEYKH  180
IYFLAMLCKS LEEPNMNLSL QYENRIAEIS KISWQNMEAV RFISKRQSFN LEPIIGPAFN  240
FIKNYLRYKH                                                        250

SEQ ID NO: 319          moltype = AA   length = 250
FEATURE                 Location/Qualifiers
source                  1..250
                        mol_type = protein
                        organism = African swine fever virus
SEQUENCE: 319
MDTAMQLKTS IGLITCRMNT QNNQIETILV QKRYSLAFSE FIHCHYSINA NQGHLIKMFN   60
NMTINERLLV KTLDFDRMWY HIWIETPVYE LYHKKYQKFR KNWLLPDNGK KLISLINQAK  120
GSGTLLWEIP KGKPKEDESD LTCAIREFEE ETGITREYYQ ILPEFKKSMS YFDGKTEYKH  180
IYFLAMLCKS LEEPNMNLSL QYENRIAEIS KISWQNMEAV RFISKRQSLN LEPIIGPAFN  240
FIKNYLRYKH                                                        250
```

```
SEQ ID NO: 320          moltype = AA  length = 9
FEATURE                 Location/Qualifiers
source                  1..9
                        mol_type = protein
                        organism = African swine fever virus
SEQUENCE: 320
RSKKDFKQI                                                                 9

SEQ ID NO: 321          moltype = AA  length = 339
FEATURE                 Location/Qualifiers
source                  1..339
                        mol_type = protein
                        organism = African swine fever virus
SEQUENCE: 321
MIDQKIFETT LNIDDPTNFC TNVEAHLLKE LENIYVGKCF KNSFILNITG VIQRSPCFIM   60
RTNNSGRGYM HVRFSAVVSY LNAFDLIAAV KIIKNDSNII LGESLLTEPV TIVIPSSESQ  120
NNVAEVGQIV PVQLANSSVY YIPGRQQASA TGSIFIPKHT FSVYHVQEEL TQEQALNLTK  180
LVNIIEMLLE SRSKKDFKQI CFFEKLYYTY SISSDEILDL KIWGPKGKE MSRLKPCNVL   240
SFLYDALKNK SSSLGFWARP PNLLKSSPLA YQQDQNSFNA TELPIICSAE VMFVTLLKEI  300
INYLQFMNDL CDTFNNEQLI KRHENIWMLI EQRKIGHDF                         339

SEQ ID NO: 322          moltype = AA  length = 339
FEATURE                 Location/Qualifiers
source                  1..339
                        mol_type = protein
                        organism = African swine fever virus
SEQUENCE: 322
MIDQKIFETT LNIDDPTNFC TNVEAHLLKE LENIYVGKCF KNSFILNITG VIQRSPCFIM   60
RTNNSGRGYM HVRFSAVVSY LNAFDLIAAV KIIKNDSNII LGESLLTEPV TIVIPSSESQ  120
NNVAEVGQIV PVQLANSSVY YIPGRQQASA TGSIFIPKHT FSVYHVQEEL TQEQALNLTK  180
LVNIIEMLLE SRSKKDFKQI CFFEKLYYTY SISSDEILDL KIWGPKGKE MSRLKPCNVL   240
SFLYDALKNK NSSLGFWARP PNLLKSSPLA YQQDQNSFNA TELPIICSAE VMFVTLLKEI  300
INYLQFINDL CDTFNNEQLI KRHENIWMLI EQRKIGHDF                         339

SEQ ID NO: 323          moltype = AA  length = 9
FEATURE                 Location/Qualifiers
source                  1..9
                        mol_type = protein
                        organism = African swine fever virus
SEQUENCE: 323
KTIFNNVRY                                                                 9

SEQ ID NO: 324          moltype = AA  length = 345
FEATURE                 Location/Qualifiers
source                  1..345
                        mol_type = protein
                        organism = African swine fever virus
SEQUENCE: 324
METFVRLFKD SPQQRSDAWH AIRRTQVGGS DLASVLGLNP YKSYYITLAE KANLFKKNLN   60
RAACSWGTLF ERVSKDLLEL FCQTTVIGDN IHIDGTYLGY PGHSNSPDGF CHLTLGYTQQ  120
SWEIKTIFNN VRYEATKRIP VLVEIKSPFN RKIKNSVPSY YMPQIQSGLA LSPPISMGIY  180
VEAMFRVCGI HQLGSNNETN TDIHPPESML PLAWGIITIC STQEHTEAPQ DFGTLDAETF  240
RQLLETLYQK DQYTIHYSMP YETACPEMPN VVGYFGWKVF IFQIIPVMKH PQFLKDKYPI  300
IQQFLRDLHT IKASPSPMEM YEKICCSEES ALSTEDIDNF TDMLT                  345

SEQ ID NO: 325          moltype = AA  length = 9
FEATURE                 Location/Qualifiers
source                  1..9
                        mol_type = protein
                        organism = African swine fever virus
SEQUENCE: 325
YSEKEKETI                                                                 9

SEQ ID NO: 326          moltype = AA  length = 238
FEATURE                 Location/Qualifiers
source                  1..238
                        mol_type = protein
                        organism = African swine fever virus
SEQUENCE: 326
MARGQNIRKR TFSDMDTPSD KNIGIHTNSL PKNNLYRRIL FKGKISNYSI SKDSLAKDHS   60
SKHSISKNGL IGKKRPAPLD ISFQSMNSSI SSSTQKKTRI LDEEIKDQSL SNENDTDSPV  120
IVDITLKPSY MSKTSRITEI IHKMKELNMN RIEDGSSFNK KRSEHDDKNI LLHTMEMEEE  180
DCEIEEDIAI DSPYLNTSLS EDDTDSIVGT DYSEKEKETI SETESSSDDE SYSLYDSF    238

SEQ ID NO: 327          moltype = AA  length = 238
FEATURE                 Location/Qualifiers
source                  1..238
                        mol_type = protein
```

```
                        organism = African swine fever virus
SEQUENCE: 327
MARGQNIRKR TFSDMDTPSD KNIGIHTNSL PKNNLYRRIL FKGKISNYSI SKDSLAKDHS    60
SNHSISKNGL IGKKRPAPLD ISFQNMNSSI SSSTQKKTRI LDEEIKDQSL SNENDRDSPV   120
IVDITLKPSY MSKTSRITEI IHKMKELNMN RIEDGSSFNK KRSEHDDKNI LLHTMEMEEE   180
DCEIEEDIAI DSPYLNTSLS EDDTDSIVGT DYSEEEKETI SETESSSDDE SYSLYDSF     238

SEQ ID NO: 328          moltype = AA  length = 10
FEATURE                 Location/Qualifiers
source                  1..10
                        mol_type = protein
                        organism = African swine fever virus
SEQUENCE: 328
MTSSEWIAEY                                                           10

SEQ ID NO: 329          moltype = AA  length = 96
FEATURE                 Location/Qualifiers
source                  1..96
                        mol_type = protein
                        organism = African swine fever virus
SEQUENCE: 329
MSTHDCSLKE KPVDMNDISE KSVVVDNAPE KPAGANHIPE KSAREMTSSE WIAEYWKGIK    60
RGNDVPCCCP RKMTSADKKF SVFGKGSLMR SIQKNN                              96

SEQ ID NO: 330          moltype = AA  length = 8
FEATURE                 Location/Qualifiers
source                  1..8
                        mol_type = protein
                        organism = African swine fever virus
SEQUENCE: 330
YNIKTKEY                                                              8

SEQ ID NO: 331          moltype = AA  length = 111
FEATURE                 Location/Qualifiers
source                  1..111
                        mol_type = protein
                        organism = African swine fever virus
SEQUENCE: 331
MSFSECPLVI SACKKFLQKR ITIENEALIN ALITALAQTS TLNDLCLLPI QTYLLSYKNA    60
FEWIHFVCIA ITTILDNKYN WKDCTVDINY IFLHVTYIYN IKTKEYLDYC S            111

SEQ ID NO: 332          moltype = AA  length = 111
FEATURE                 Location/Qualifiers
source                  1..111
                        mol_type = protein
                        organism = African swine fever virus
SEQUENCE: 332
MSFSECPLVI SACKKFLQKR ITIENEALIN ALITALAQTS TLNDLCLLPI QTYLLSYKNA    60
FEWIHFVCIA ITTILDNKYN WKDCTVDINY IFLHVTYIYN IKTKEYLDYC S            111

SEQ ID NO: 333          moltype = AA  length = 8
FEATURE                 Location/Qualifiers
source                  1..8
                        mol_type = protein
                        organism = African swine fever virus
SEQUENCE: 333
LTHNMEKI                                                              8

SEQ ID NO: 334          moltype = AA  length = 120
FEATURE                 Location/Qualifiers
source                  1..120
                        mol_type = protein
                        organism = African swine fever virus
SEQUENCE: 334
MADFNSPIQY LKEDSRDRTS IGSLEYDENS DTIIPSFAAG LEDFEPIPSP TTSTSLYSQL    60
THNMEKIAEE EDINFLHDTR EFTSLVPDEA DNKPEDDEES GAKPKKKKHL PPKLSSHKSK   120

SEQ ID NO: 335          moltype = AA  length = 122
FEATURE                 Location/Qualifiers
source                  1..122
                        mol_type = protein
                        organism = African swine fever virus
SEQUENCE: 335
MADFNSPIQY LKEDSRDRTS IGSLEYDENA DTMIPSFAAG LEEFEPIPDY DPTTSTSLYS    60
QLTHNMEKIA EEEDSNFLHD TREFTSLVPD EADNKPEDDE ESGAKPKKKK HLFPKLSSHK   120
SK                                                                  122

SEQ ID NO: 336          moltype = AA  length = 13
FEATURE                 Location/Qualifiers
```

```
source                     1..13
                           mol_type = protein
                           organism = African swine fever virus
SEQUENCE: 336
IAYMRFRNCV FTF                                                          13

SEQ ID NO: 337             moltype = AA  length = 10
FEATURE                    Location/Qualifiers
source                     1..10
                           mol_type = protein
                           organism = African swine fever virus
SEQUENCE: 337
MRFRNCVFTF                                                              10

SEQ ID NO: 338             moltype = AA  length = 146
FEATURE                    Location/Qualifiers
source                     1..146
                           mol_type = protein
                           organism = African swine fever virus
SEQUENCE: 338
MGGTTDFVLS ITIVLVILII IAFIWYNFTG WSPFKYSKGN TVTFKTPDES SIAYMRFRNC        60
VFTFTDPKGS LHSIDVTEVL NNMAKGFRDA QNPPSSFTLG GHCQAPLNAF SFVLPGVNDR       120
ATVATADEAK KWENCDATLT GLQRII                                           146

SEQ ID NO: 339             moltype = AA  length = 146
FEATURE                    Location/Qualifiers
source                     1..146
                           mol_type = protein
                           organism = African swine fever virus
SEQUENCE: 339
MGGTTDFVLS ITIVLVILII IAFIWYNFTG WSPFKYSKGN TVTFKTPDES SIAYMRFRNC        60
VFTFTDPKGS LHSIDVTEVL NNMAKGFRDA QNPPSSFTLG GHCQAPLNAF SFVLPGVNDR       120
ATVATADEAK KWENCDATLT GLQRII                                           146

SEQ ID NO: 340             moltype = AA  length = 10
FEATURE                    Location/Qualifiers
source                     1..10
                           mol_type = protein
                           organism = African swine fever virus
SEQUENCE: 340
YTHKDLENSL                                                              10

SEQ ID NO: 341             moltype = AA  length = 183
FEATURE                    Location/Qualifiers
source                     1..183
                           mol_type = protein
                           organism = African swine fever virus
SEQUENCE: 341
MDSEFFQPVY PRHYGECLSP VTPPSFFSTH MYTILIAIVV LVIIIIVLIY LFSSRKKKAA        60
AAIEEEDIQF INPYQDQQWA EVTPQPGTSK PAGATTASAG KPVTGRPATN RPATNKPVTD       120
NPVTDRLVMA TGGPAAAPAA ASVHPTEPYT TVTTQNTASQ TMSAIENLRQ RNTYTHKDLE       180
NSL                                                                    183

SEQ ID NO: 342             moltype = AA  length = 184
FEATURE                    Location/Qualifiers
source                     1..184
                           mol_type = protein
                           organism = African swine fever virus
SEQUENCE: 342
MDSEFFQPVY PRHYGECLSP VTTPSFFSTH MYTILIAIVV LVIIIIVLIY LFSSRKKKAA        60
AIEEEDIQFI NPYQDQQWVE VTPQPGTSKP AGATTASVGK PVTGRPATNR PATNKPVTDN       120
PVTDRLVMAT GGPAAAPAAA SAPAHPAEPY TTVTTQNTAS QTMSAIENLR QRNTYTHKDL       180
ENSL                                                                   184

SEQ ID NO: 343             moltype = AA  length = 10
FEATURE                    Location/Qualifiers
source                     1..10
                           mol_type = protein
                           organism = African swine fever virus
SEQUENCE: 343
TNTVNQYSHY                                                              10

SEQ ID NO: 344             moltype = AA  length = 248
FEATURE                    Location/Qualifiers
source                     1..248
                           mol_type = protein
                           organism = African swine fever virus
SEQUENCE: 344
MGGSTSKNSF KNTTNIISNS IFNQMQNCIS MLDGKNYIGV FGDGNILNHV FQDLNLSLDT        60
```

```
                                                      -continued

SCVQKHVNEE NFITNLSNQI TQNLKDQEVA LTQWMDAGHH DQKTDIEENI KVNLTTTLIQ    120
NCVSSLSGMN VLVVKGNGNI VENATQKQSQ QIISNCLQGS KQAIDTTTGI TNTVNQYSHY    180
TSKNFFDFIA DAISAVFKNI MVAAVVIVLI IVGFIAVFYF LHSRHRHEEE EEAEPLISNK    240
VLKNAAVS                                                            248

SEQ ID NO: 345          moltype = AA   length = 248
FEATURE                 Location/Qualifiers
source                  1..248
                        mol_type = protein
                        organism = African swine fever virus
SEQUENCE: 345
MGGSTSKNSF KNTTNIISNS IFNQMQSCIS MLDGKNYIGV FGDGNILNHV FQDLNLSLNT    60
SCVQKHVNEE NFITNLSNQI TQNLKDQEVA LTQWMDAGTH DQKTDIEENI KVNLTTTLIQ    120
NCVSSLSGMN VLVVKGNGNI VENATQKQSQ QIISNCLQGS KQAIDTTTGI TNTVNQYSHY    180
TSKNFFDFIA DAISAVFKNI MVAAVVIVLI IVGFIAVFYF LHSRHRHEEE EEAEPLISNK    240
VLKNAAVS                                                            248

SEQ ID NO: 346          moltype = AA   length = 9
FEATURE                 Location/Qualifiers
source                  1..9
                        mol_type = protein
                        organism = African swine fever virus
SEQUENCE: 346
NTITLNNTI                                                           9

SEQ ID NO: 347          moltype = AA   length = 8
FEATURE                 Location/Qualifiers
source                  1..8
                        mol_type = protein
                        organism = African swine fever virus
SEQUENCE: 347
LMLNTITL                                                            8

SEQ ID NO: 348          moltype = AA   length = 301
FEATURE                 Location/Qualifiers
source                  1..301
                        mol_type = protein
                        organism = African swine fever virus
SEQUENCE: 348
MSEDIRRGPG RPPKKRVVPN FERKGILEKP VRPQSRLEFS YDNPLIFKNL FIYFKNLKSK    60
NILVRCTPTE ITFFSRDQSQ ASFVIATIDG KNVNHYYASD VFWLGINREL VEKMFNSIDR    120
SFLKITIVHR YDKPETLFFI FTDFDIDKEC TYQITVSEPE LDMDLIEMEK SISEERLKNY    180
PLRWEFTSKQ LKKTFSDLSN YTELVTIEKL GGDTPLHLYF QKFNSISYHE MYKSSNKINL    240
TSTIPKSQVF QINVKIAHIK SLASAMVTDK IRILCEENGN LIFQSEMDAL MLNTITLNNT    300
I                                                                   301

SEQ ID NO: 349          moltype = AA   length = 301
FEATURE                 Location/Qualifiers
source                  1..301
                        mol_type = protein
                        organism = African swine fever virus
SEQUENCE: 349
MSEDIRRGPG RPPKKRVVPN FERKGILEKP VRPQSRLEFS YDNPLIFKNL FIYFKNLKSK    60
NILVRCTPTE ITFFSRDQSQ ASFVIATIDG KNVNHYYASD VFWLGINREL VEKMFNSIDR    120
SFLKITIVHR YDKPETLFFI FTDFDIDKEC TYQITVSEPE LDMDLIEMEK SISEERLKNY    180
PLRWEFTSKQ LKKTFSDLSN YTELVTIEKL GGDTPLHLYF QKFNSISYHE MYKSSNKINL    240
TSTIPKSQVF QINVKIAHIK SLASAMVTDK IRILCEENGN LIFQSEMDAL MLNTITLNTT    300
I                                                                   301

SEQ ID NO: 350          moltype = AA   length = 18
FEATURE                 Location/Qualifiers
source                  1..18
                        mol_type = protein
                        organism = African swine fever virus
SEQUENCE: 350
RSRTASSAEL YRKMLYAY                                                 18

SEQ ID NO: 351          moltype = AA   length = 8
FEATURE                 Location/Qualifiers
source                  1..8
                        mol_type = protein
                        organism = African swine fever virus
SEQUENCE: 351
LVDHIFNY                                                            8

SEQ ID NO: 352          moltype = AA   length = 423
FEATURE                 Location/Qualifiers
source                  1..423
                        mol_type = protein
```

```
                        organism = African swine fever virus
SEQUENCE: 352
MLWRNEITEF MDQLSKYSQE ILKTFKQLRP SEYKQYNEFL TQVTPLLQKT PEKIPELVDH    60
IFNYLDNVEK ICELLVNASS IIISSKIREQ VKHGMSFSYK ADLDSLADIL SQKQYVLMHL   120
SKNIAAEYFN TCLNQGKSKL DLKAASVFYS SRSRTASSAE LYRKMLYAYG SPQEINYYTE   180
KARNKTLDVE ESDSMAIIER TARHNLSLMH PLEAMGLTFG ATNTDADPED LKDKTVINLT   240
LPQATESITY HLKSLMQLKK VSTASGLNTN ILKAFDNIIS TPVKKNKMAS KLAPGMDVVF   300
TSDNGKTFFT KNILSKNMLA GPKERVFAYN NLISNLNNSC FIQNHNDFLR QQDSWPFYDA   360
HNFTNKFLMQ PIFSGQTRPR LQGAMEAAHV ETHLTAFLQS IQPSRPQDPS VLASPKLSAL   420
ILN                                                                423

SEQ ID NO: 353          moltype = AA  length = 10
FEATURE                 Location/Qualifiers
source                  1..10
                        mol_type = protein
                        organism = African swine fever virus
SEQUENCE: 353
LTHNHILFTY                                                          10

SEQ ID NO: 354          moltype = AA  length = 10
FEATURE                 Location/Qualifiers
source                  1..10
                        mol_type = protein
                        organism = African swine fever virus
SEQUENCE: 354
SIITRYTLKY                                                          10

SEQ ID NO: 355          moltype = AA  length = 66
FEATURE                 Location/Qualifiers
source                  1..66
                        mol_type = protein
                        organism = African swine fever virus
SEQUENCE: 355
MLTMVSLARF IINTASFNKS IYPLSQVYVK IHLSHKYNHI LFTYNMRIYL IKRNHMLFTH    60
MLISCN                                                              66

SEQ ID NO: 356          moltype = AA  length = 50
FEATURE                 Location/Qualifiers
source                  1..50
                        mol_type = protein
                        organism = African swine fever virus
SEQUENCE: 356
MHISIITRYT LKYIYMHLTH NHILFTYIMR IYLIKHNHML FTTHVYTYIM               50

SEQ ID NO: 357          moltype = AA  length = 9
FEATURE                 Location/Qualifiers
source                  1..9
                        mol_type = protein
                        organism = African swine fever virus
SEQUENCE: 357
RVHGSGVSL                                                            9

SEQ ID NO: 358          moltype = AA  length = 10
FEATURE                 Location/Qualifiers
source                  1..10
                        mol_type = protein
                        organism = African swine fever virus
SEQUENCE: 358
TNAFELAQRY                                                          10

SEQ ID NO: 359          moltype = AA  length = 9
FEATURE                 Location/Qualifiers
source                  1..9
                        mol_type = protein
                        organism = African swine fever virus
SEQUENCE: 359
QMFNVDITY                                                            9

SEQ ID NO: 360          moltype = AA  length = 11
FEATURE                 Location/Qualifiers
source                  1..11
                        mol_type = protein
                        organism = African swine fever virus
SEQUENCE: 360
RVDMNRFFQF Y                                                        11

SEQ ID NO: 361          moltype = AA  length = 1242
FEATURE                 Location/Qualifiers
source                  1..1242
```

```
                        mol_type = protein
                        organism = African swine fever virus
SEQUENCE: 361
MEPLRPQITY GPIETVDNEE LTEADMLSFI SAAVNSTGLI GYNIKSFDDL MDNGIPQIVK    60
QMFNVDITYK DQRDHTEIDK LRESVQIQFN FTDVNIERPQ HRNYSQGNKI NLLPNKARLC   120
GLSYSGPVNL AAEVILTAHY SNGRQEVKRA SIPPFQVSTF PIMRGSNRCH THHLSKTAKK   180
EIGEDPNEPG GYFIARGGEW VVDLLENIRF NTLHIHYHTM QQGNNEIIRG EFISQPGGAF   240
ENSSQIIIRY MTTGAITIEI NSTKFSKLRI PWYLIFRMFG MTGDDSIIEQ VVFDLESNSP   300
VNTFMIEILE KSIHVLDPIF QPVQHELNRE KIIQFLSEKV SKFVSNPSAY KSDENAVQYL   360
NERQLTILDK ILLPHMGQTA DTRVRKLRFL GLLIHKILLV IMNVFPPTDR DSYRTKRVHG   420
SGVSLAKAFK AIFNTSVIAP IINGFKELLK QTAFEELTQR NIIEAFSAAL SKNTASDLNR   480
SMEQSIISGN KTIMVRQRPI VNRVSTQSLE RKNLLNTISA LRTVNTHNTT NASKQTERAD   540
MMRRVHASYP GYICVAQSAD TGEKVGMSKQ LAITANVCTA GEVLSLKQRL LSDPAIQQLA   600
DVSNKDIVRK GLARVFINGE WIGCCTNAFE LAQRYRMFRR EGKIVHPHTT IYWDSMVDEV   660
EFWLDVGRLT RPLLIVDNNI EKYNQACYKA AEARKKGDKD WEKHKIPFIQ NTRFTSQMAK   720
DILAGTLTLE DLVAQGICEF ITPEEAENCL VAFSIIELRK HKHDVTRRFT HVDVPQAILG   780
LAALVSPYAN CTQPARVTYE TNQGRQTGGW YCFSWPYRVD MNRFFQFYNE MPLVKTIAHN   840
YVIPNGLNTI VAYMIYGGYN QEDSVIVSQS FIDRGGFAGT FYREEKVELE SDIESFGKPD   900
PLITKNLKPG ANYEKLVDGF VPVGTVVKKG DIIIGKVAKI RGEKDELNKY IDRSVMYGFD   960
EPAVVDAVMR PHGPNDEIFG LMRLRYERNL NIGDKMSSRS GNKGIAALAL PTSDMPFTED  1020
GLQPDLIVNH HSHPSRMTNG QMIETTVGLA NALQGVVTDG TAFLPINVQL LSERLAQEGL  1080
RFNGCQKMFN GQTGEYFDAA IFIGPTYHQR LQKFVLDDRY AVASYGPTDA LTGQPLDGKR  1140
SHGGLRLGEM EHWVLTAQGA MQTIIEKSHD DSDGCISYIC RNCGEPAIYN ASHPIYKCMN  1200
CDVQADIGMV DSRRSSIVFQ HEMRAANVNI TSVLSPRVFQ PA                    1242

SEQ ID NO: 362          moltype = AA  length = 1242
FEATURE                 Location/Qualifiers
source                  1..1242
                        mol_type = protein
                        organism = African swine fever virus
SEQUENCE: 362
MEPLRPQITY GPIETVDNEE LTEADMLSFI SAAVNSTGLI GYNIKSFDDL MDNGIPQIVK    60
QMFNVDITYK DQRDHTEIDK LRESVQIQFN FTDVNIERPQ HRNYSQGNKI NLLPNKARLC   120
GLSYSGPVNL AAEVILTAHY SNGRQEVKRA SIPPFQVSTF PIMRGSNRCH THHLSKTAKK   180
EIGEDPNEPG GYFIARGGEW VVDLLENIRF NTLHIHYHTM QQGNNEIIRG EFISQPGGAF   240
ENSSQIIIRY MTTGAITIEI NSTKFSKLRI PWYLIFRMFG MTGDDSIIEQ VVFDLESNSL   300
VNTFMIEILE KSIHVLDPIF QPVQHELNRE KIIQFLSEKV SKFVSNPSAY KSDENAVQYL   360
NERQLTILDK ILLPHMGQTA DTRVRKLRFL GLLIHKILLV IMNVFPPTDR DSYRTKRVHG   420
SGVSLAKAFK AIFNTSVIAP IINGFKELLK QTAFEELTQR NIIEAFSAAL SKNTASDLNR   480
SMEQSIISGN KTIMVRQRPI VNRVSTQSLE RKNLLNTISA LRTVNTHNTT NASKQTERAD   540
MMRRVHASYP GYICVAQSAD TGEKVGMSKQ LAITANVCTA GEVLSLKQRL LSDPAIQQLA   600
DVSNKDIVRK GLARVFINGE WIGCCTNAFE LAQRYRMLRR EGKIVHPHTT IYWDSMVDEV   660
EFWLDVGRLT RPLLIVDNNI EKYNQACYKA AEARKKGDKD WEKHKIPFIQ NTRFTPQMAK   720
DILAGTLTLE DLVAQGICEF ITPEEAENCL VAFSIIELRK HKHDVTRRFT HVDVPQAILG   780
LAALVSPYAN CTQPARVTYE TNQGRQTGGW YCFSWPYRVD MNRFFQFYNE MPLVKTIAHN   840
YVIPNGLNTI VAYMIYGGYN QEDSVIVSQS FIDRGGFAGT FYREEKVELE SDIESFGKPD   900
PLITKNLKPG ANYEKLVDGF VPVGTVVKKG DIIIGKVAKI RGEKDELNKY IDRSVMYGFD   960
EPAVVDAVMR PHGPNDEIFG LMRLRYERNL NIGDKMSSRS GNKGIAALAL PTSDMPFTED  1020
GLQPDLIVNP HSHPSRMTNG QMIETTVGLA NALQGVVTDG TAFLPINVQL LSERLAQEGL  1080
RFNGCQKMFN GQTGEYFDAA IFIGPTYHQR LQKFVLDDRY AVASYGPTDA LTGQPLDGKR  1140
SHGGLRLGEM EHWVLTAQGA MQTIIEKSHD DSDGCISYIC RNCGEPAIYN ASHPIYKCMN  1200
CDVQADIGMV DSRRSSIVFQ HEMRAANVNI TSVLSPRVFQ PA                    1242

SEQ ID NO: 363          moltype = AA  length = 21
FEATURE                 Location/Qualifiers
source                  1..21
                        mol_type = protein
                        organism = African swine fever virus
SEQUENCE: 363
FLKQSGLQSF YLYIQPDHTC F                                             21

SEQ ID NO: 364          moltype = AA  length = 152
FEATURE                 Location/Qualifiers
source                  1..152
                        mol_type = protein
                        organism = African swine fever virus
SEQUENCE: 364
MYSILIACLV LLLCLVIYVG HRADHARKYL EGMWHGDPVF LKQSGLQSFY LYIQPDHTCF    60
FSIVNKNGEK LMETKIPCTI TNKIYMFFKP IFEFHVVMED IHSYFPKQFN FLLDSTEGKL   120
ILENNHVIYA VLYKDNFATA LGKTVEKYIT QN                                152

SEQ ID NO: 365          moltype = AA  length = 9
FEATURE                 Location/Qualifiers
source                  1..9
                        mol_type = protein
                        organism = African swine fever virus
SEQUENCE: 365
KTYNHESNY                                                            9
```

```
SEQ ID NO: 366          moltype = AA  length = 158
FEATURE                 Location/Qualifiers
source                  1..158
                        mol_type = protein
                        organism = African swine fever virus
SEQUENCE: 366
MFSNKKYIGL INKKEGLKKK IDDYSILIIG ILIGTNILSL IINIIGEINK PICYQNDDKI    60
FYCPKDWVGY NNVCYYFGNE EKNYNNASNY CKQLNSTLTN NNTILVNLTK TLNLTKTYNH   120
ESNYWVNYSL IKNESVLLRD SGYYKKQKHV SLLYICSK                           158

SEQ ID NO: 367          moltype = AA  length = 11
FEATURE                 Location/Qualifiers
source                  1..11
                        mol_type = protein
                        organism = African swine fever virus
SEQUENCE: 367
SLFEGMIWKS Y                                                         11

SEQ ID NO: 368          moltype = AA  length = 296
FEATURE                 Location/Qualifiers
source                  1..296
                        mol_type = protein
                        organism = African swine fever virus
SEQUENCE: 368
MFGAFVSHRL WSDSGCTTTC ITNSIANYVA FGEQIGFPPK SAQVFIAGPR KAVINIQEDD    60
KVELLKMIVK HNLWVVAHGT YLDVPWSRKS AFVTHFIQQE LLICKEVGIK GLVLHLGAVE   120
PELIMEGLKK IKPVEGVVIY LETPHNKHHT YKYSTIEQIK ELFLRIRNTR LKQIGLCIDT   180
AHIWSSGVNI SSYNDAGQWL RSLENIHSVI PPSHIMFHLN DAATECGSGI DRHASLFEGM   240
IWKSYSHKIK QSGLYCFVEY VTRHQCPAIL ERNLGSSMQL QTALTAEFTT LKSLLK       296

SEQ ID NO: 369          moltype = AA  length = 10
FEATURE                 Location/Qualifiers
source                  1..10
                        mol_type = protein
                        organism = African swine fever virus
SEQUENCE: 369
PAFPNPQKKI                                                           10

SEQ ID NO: 370          moltype = AA  length = 364
FEATURE                 Location/Qualifiers
source                  1..364
                        mol_type = protein
                        organism = African swine fever virus
SEQUENCE: 370
MYFLVADHRE HHVIPFLKTD FHDMQHNPMF TQKQALLEIK QLFTGDYLIC KSPTTILACI    60
ERKTYKDFAA SLKDGRYKNR QKMLSLREQT NCQLYFFVEG PAFPNPQKKI NHVAYASIIT   120
AMTHLMVRDH IFVIQTKNEA HSSQKLVQLF YAFSKEMVCV VPTSLTPTDE ELCIKLWSSL   180
SGISGVIGKI LANTCSVAHL VSGKLSSQNI DQLKTPSNRP FPKKVKRMLI SISKGNKELE   240
IKLLSGVPNI GKKLAAEILK DHALLFFLNQ PVECLANIQI VQKTRTIKLG MKRAEAIHYF   300
LNWCGSAHVT DDSQNITEAS RPATQPAATQ PLHEVSDDAT SNASDTSSPI GHQTLSKEML   360
LNTA                                                                364

SEQ ID NO: 371          moltype = AA  length = 369
FEATURE                 Location/Qualifiers
source                  1..369
                        mol_type = protein
                        organism = African swine fever virus
SEQUENCE: 371
MYFLVADHRE HHVIPFLKTD FHHMHQNPIQ KNQALLEIKQ LFTGDYLICK SPSTILACIE    60
RKTYKDFAAS LKDGRYKNRQ KMLSLREQTN CQLYFFVEGP AFPNPQKKIN HVAYASIITA   120
MTHLMVRDHI FVIQTKNEAH SSQKLVQLFY AFSKEMVCVV PTSLTPTDEE LCIKLWSSLS   180
GISGVIGKIL ANTCSVAHLV HGKLSSQNID QLKTPSNRPF PKKVKRMLIS ISKGNKELEI   240
KLLSGVPNIG KKLAAEILKD HALLFFLNQP VECLANIQIV QKTRTIKLGM KRAEAIHYFL   300
NWCGSAHVTD DSQNITEASR STMQVATQSA AIQPAATQPL HEVSDDASSD ASSPVGYQTL   360
SKEMLLNTA                                                           369

SEQ ID NO: 372          moltype = AA  length = 9
FEATURE                 Location/Qualifiers
source                  1..9
                        mol_type = protein
                        organism = African swine fever virus
SEQUENCE: 372
YTNESILEY                                                            9

SEQ ID NO: 373          moltype = AA  length = 22
FEATURE                 Location/Qualifiers
source                  1..22
                        mol_type = protein
                        organism = African swine fever virus
```

```
SEQUENCE: 373
CTYLTLSSNY FYTFFKLYYI PL                                                      22

SEQ ID NO: 374          moltype = AA  length = 11
FEATURE                 Location/Qualifiers
source                  1..11
                        mol_type = protein
                        organism = African swine fever virus
SEQUENCE: 374
TYLTLSSNYF Y                                                                  11

SEQ ID NO: 375          moltype = AA  length = 11
FEATURE                 Location/Qualifiers
source                  1..11
                        mol_type = protein
                        organism = African swine fever virus
SEQUENCE: 375
LTLSSNYFYT F                                                                  11

SEQ ID NO: 376          moltype = AA  length = 11
FEATURE                 Location/Qualifiers
source                  1..11
                        mol_type = protein
                        organism = African swine fever virus
SEQUENCE: 376
SNYFYTFFKL Y                                                                  11

SEQ ID NO: 377          moltype = AA  length = 9
FEATURE                 Location/Qualifiers
source                  1..9
                        mol_type = protein
                        organism = African swine fever virus
SEQUENCE: 377
YQYNTPIYY                                                                      9

SEQ ID NO: 378          moltype = AA  length = 360
FEATURE                 Location/Qualifiers
source                  1..360
                        mol_type = protein
                        organism = African swine fever virus
SEQUENCE: 378
MIILIFLIFS NIVLSIDYWV SFNKTIILDS NITNDNNDIN GVSWNFFNNS FNTLATCGKA              60
GNFCECSNYS TSIYNITNNC SLTIFPHNDV FDTTYQVVWN QIINYTIKLL TPATPPNITY             120
NCTNFLITCK KNNGTNTNIY LNINDTFVKY TNESILEYNW NNSNINNFTA TCIINNTIST             180
SNETTLINCT YLTLSSNYFY TFFKLYYIPL SIIIGITISI LLISIITFLS LRKRKKHVEE             240
IESPPPESNE EEQCQHDDTT SIHEPSPREP LLPKPYSRYQ YNTPIYYMRP STQPLNPFPL             300
PKPCPPPKPC PPPKPCPPPK PCPSAESYSP PKPLPSIPLL PNIPPLSTQN ISLIHVDRII             360

SEQ ID NO: 379          moltype = AA  length = 10
FEATURE                 Location/Qualifiers
source                  1..10
                        mol_type = protein
                        organism = African swine fever virus
SEQUENCE: 379
NKIKLLNEYL                                                                    10

SEQ ID NO: 380          moltype = AA  length = 9
FEATURE                 Location/Qualifiers
source                  1..9
                        mol_type = protein
                        organism = African swine fever virus
SEQUENCE: 380
YVLEKKHKL                                                                      9

SEQ ID NO: 381          moltype = AA  length = 10
FEATURE                 Location/Qualifiers
source                  1..10
                        mol_type = protein
                        organism = African swine fever virus
SEQUENCE: 381
NKIKLLNDYL                                                                    10

SEQ ID NO: 382          moltype = AA  length = 9
FEATURE                 Location/Qualifiers
source                  1..9
                        mol_type = protein
                        organism = African swine fever virus
SEQUENCE: 382
YVLEKKHKL                                                                      9
```

```
SEQ ID NO: 383             moltype = AA   length = 10
FEATURE                    Location/Qualifiers
source                     1..10
                           mol_type = protein
                           organism = African swine fever virus
SEQUENCE: 383
FISAINHFNY                                                                 10

SEQ ID NO: 384             moltype = AA   length = 17
FEATURE                    Location/Qualifiers
source                     1..17
                           mol_type = protein
                           organism = African swine fever virus
SEQUENCE: 384
AINHFNYTMM HYPTFNW                                                         17

SEQ ID NO: 385             moltype = AA   length = 9
FEATURE                    Location/Qualifiers
source                     1..9
                           mol_type = protein
                           organism = African swine fever virus
SEQUENCE: 385
YTMMHYPTF                                                                   9

SEQ ID NO: 386             moltype = AA   length = 11
FEATURE                    Location/Qualifiers
source                     1..11
                           mol_type = protein
                           organism = African swine fever virus
SEQUENCE: 386
ATQRLTPIHL Y                                                               11

SEQ ID NO: 387             moltype = AA   length = 9
FEATURE                    Location/Qualifiers
source                     1..9
                           mol_type = protein
                           organism = African swine fever virus
SEQUENCE: 387
YTLNHAFTL                                                                   9

SEQ ID NO: 388             moltype = AA   length = 424
FEATURE                    Location/Qualifiers
source                     1..424
                           mol_type = protein
                           organism = African swine fever virus
SEQUENCE: 388
MSNYYYYYGG GRYDWLKTVE PTNFLKIGLP YQAHPLHLQH QATTTPPSIL EKFKRADILL           60
NEVKAEMDPL MLQPETEKKL YQILGSIDMF KGLRKKVEFT YNAQIVTNAW LKMYELLNTM          120
NFNNTSQAFC NCELPGGFIS AINHFNYTMM HYPTFNWVAS SLYPSSETDA LEDHYGLYQC          180
NPDNWLMQSP LLKKNVDYND GDVTIASNVK NLALRATQRL TPIHLYTADG GINVGHDYNK          240
QEELNLKLHF GQALTGLLSL SKGGNMILKH YTLNHAFTLS LICVFSHFFE ELYITKPTSS          300
RPTNSETYIV GKNRLRLFTP KEEQILLKRL EFFNDTPLVD LSLYQNLLES IYFAVETIHL          360
KQQIEFLNFG MKCYRHFYNK IKLLNEYLAP KKKIFQDRWR VLNKLYVLEK KHKLKLCAPQ          420
GSVA                                                                      424

SEQ ID NO: 389             moltype = AA   length = 418
FEATURE                    Location/Qualifiers
source                     1..418
                           mol_type = protein
                           organism = African swine fever virus
SEQUENCE: 389
MSNYYYYYGG GRYDWLKTVE PTNFLKIGLP YQAHPLHLQH QATTPPSILE KFKRADILLN           60
EVKAEMDPLM LQPETEKKLF QILSSIDMFK GLRKKVEFTY NAQIVTNAWL KMYELLNTMN          120
FNNTSQAFCN CELPGGFISA INHFNYTMMH YPTFNWVASS LYPSSETDAL EDHYGLYQCN          180
PDNWLMQSPL LKKNIDYNNG DVTIASNVKN LALRATQRLT PIHLYTADGG INVGHDYNKQ          240
EELNLKLHFG QALTGLLSLS KGGNMILKHY TLNHAFTLSL ICVFSHFFEE LYITKPTSSR          300
PTNSETYIVG KNRLRLFTPK EEQVLLKRLE FFNDTPLVDL SLYQNLLESV YPAVETIHLK          360
QQIEFLNFGM KCYRHFYNKI KLLNDYLAPK KKIFQDRWRV LNKLYVLEKK HKLKLCAS            418

SEQ ID NO: 390             moltype = AA   length = 17
FEATURE                    Location/Qualifiers
source                     1..17
                           mol_type = protein
                           organism = African swine fever virus
SEQUENCE: 390
NVIMDVFYET YSLPYNI                                                         17

SEQ ID NO: 391             moltype = AA   length = 10
```

```
FEATURE              Location/Qualifiers
source               1..10
                     mol_type = protein
                     organism = African swine fever virus
SEQUENCE: 391
VIMDVFYETY                                                                   10

SEQ ID NO: 392       moltype = AA  length = 10
FEATURE              Location/Qualifiers
source               1..10
                     mol_type = protein
                     organism = African swine fever virus
SEQUENCE: 392
VFYETYSLPY                                                                   10

SEQ ID NO: 393       moltype = AA  length = 9
FEATURE              Location/Qualifiers
source               1..9
                     mol_type = protein
                     organism = African swine fever virus
SEQUENCE: 393
RTYNILQRF                                                                     9

SEQ ID NO: 394       moltype = AA  length = 19
FEATURE              Location/Qualifiers
source               1..19
                     mol_type = protein
                     organism = African swine fever virus
SEQUENCE: 394
LQFNYSFQSH MYAIMLLTK                                                         19

SEQ ID NO: 395       moltype = AA  length = 1048
FEATURE              Location/Qualifiers
source               1..1048
                     mol_type = protein
                     organism = African swine fever virus
SEQUENCE: 395
MQETFKFLRC NSQGEAVEDK YSLETLKNHF VVRDEYNNLF RVFSSRDDFW EWEAAQPFEQ             60
KCFHEVVFGF LPQRLKFDID FPVNKSYSDD NVDDNDNVED NVYDILDMII NVIMDVFYET            120
YSLPYNINLT REQILLTDSI GLNKKRELKY SFHIILYTYS VLNNNEAKVF TSKVLENLPK            180
HVYPFVDPQV NKSIQNFRII GSHKKGSMRV KMFNEELAEV FETSTTTKKS DTLIATPFET            240
TCLPCIFTNV KETTPSSCDT IQQSELEEVL KFAGTLCKNH CFLRVHKNLV LFKRTSPSYC            300
EICKRMHDKD NTLILRVTGN KVYQHCRHDN KHSLLMGSLS GTNNFVETYV DQVMTKSIEV            360
HESILFEELP DTQKHIYDES SMREYERVPT LVVKAQMKIG KTVQLRNYLQ KYYGNNSISK            420
QQTIRFVTFR QIFSKNIQSR LPNFTLYSEV TGDLDSYERV IIQVESLFRL TSTAEPVDLL            480
ILDEVESIFN QFNSGLHKYF APSFAIFMWM LETANYVICL DANLGNRTYN ILQRFRGDVP            540
IFFHWNQYKR AQHDTYYFTS SRETWLNNLL KDLLEDKKIV IPTNSLMEAR LLQSFIQKKF            600
PEKKIGFYSS KSTAHERESH FNNVSYYWGL VDILIYTPTI SAGVSYEDKR FDVLYGFFNN            660
MSCDVETCCQ MLGRVRELKS KCYKICLQGK QNYYPETIED IEMFTLQKRD TLFQTISNHQ            720
LSFTYSKETG RPIYYKTPYY HLWLETMRIQ HLSKNHFITR FINQIADTGA KVFILTGEKL            780
ETVKQYTSIK MEIKHQDYVN IASAETIDAN KALQIKQNLK EGITVDQQDL FAYEKYKLLE            840
FYAWHGHKIT PKFVEQYNSF MTKQNYTGRV QISRGKTVYE SLTMLQTQEL NFHQWAMQHA            900
EHHDLQFNYS FQSHMYAIML LTKCGFKCVQ DPNILTNEQL MTKLVDEFVQ YDLSAISFEF            960
KLKKPNKTDP QTILKFINKV LGLRYGLKIH HNKGNYYIKN TKAGSLIPFV RQQIKQSPCV           1020
VSNLLPITET SSAKEETSPI KEETFTET                                             1048

SEQ ID NO: 396       moltype = AA  length = 23
FEATURE              Location/Qualifiers
source               1..23
                     mol_type = protein
                     organism = African swine fever virus
SEQUENCE: 396
KQASISSILN FFFFYIMEYF VAV                                                    23

SEQ ID NO: 397       moltype = AA  length = 10
FEATURE              Location/Qualifiers
source               1..10
                     mol_type = protein
                     organism = African swine fever virus
SEQUENCE: 397
NFFFFYIMEY                                                                   10

SEQ ID NO: 398       moltype = AA  length = 165
FEATURE              Location/Qualifiers
source               1..165
                     mol_type = protein
                     organism = African swine fever virus
SEQUENCE: 398
MVNPNKRIMN KKSKQASISS ILNFFFFYIM EYFVAVDNET SLGVFTSIEQ CEETMKQYPG             60
```

```
LHYVVFKYMC PADAENTDVV YLIPSLTLHT PMFVDHCPNR TKQARHVLKK INLVFEEESI    120
ENWKVSVNTV FPHVHNRLSA PKLSIDEANE AVEKFLIQAG RLMSL                   165

SEQ ID NO: 399              moltype = AA   length = 10
FEATURE                     Location/Qualifiers
source                      1..10
                            mol_type = protein
                            organism = African swine fever virus
SEQUENCE: 399
DFFIYEDERL                                                          10

SEQ ID NO: 400              moltype = AA   length = 13
FEATURE                     Location/Qualifiers
source                      1..13
                            mol_type = protein
                            organism = African swine fever virus
SEQUENCE: 400
DFFIYEDERL LMF                                                      13

SEQ ID NO: 401              moltype = AA   length = 11
FEATURE                     Location/Qualifiers
source                      1..11
                            mol_type = protein
                            organism = African swine fever virus
SEQUENCE: 401
SRRSLVNPWT L                                                        11

SEQ ID NO: 402              moltype = AA   length = 9
FEATURE                     Location/Qualifiers
source                      1..9
                            mol_type = protein
                            organism = African swine fever virus
SEQUENCE: 402
RSLVNPWTL                                                           9

SEQ ID NO: 403              moltype = AA   length = 10
FEATURE                     Location/Qualifiers
source                      1..10
                            mol_type = protein
                            organism = African swine fever virus
SEQUENCE: 403
TQMDKLGFLL                                                          10

SEQ ID NO: 404              moltype = AA   length = 317
FEATURE                     Location/Qualifiers
source                      1..317
                            mol_type = protein
                            organism = African swine fever virus
SEQUENCE: 404
MVETQMDKLG FLLNHIGKQV TTKVLSNAHI TQTMKEIILE NHGVDGGAAK NVSKGKSSPK    60
EKKHWTEFES WEQLSKSKRS FKEYWAERNE IVNTLLLNWD NVRGAIKKFL DDDREWCGRI   120
NMINGVPEIV EIIPSPYRAG ENIYFGSEAM MPADIYSRVA NKPAMFVFHT HPNLGSCCGG   180
MPSICDISTT LRYLLMGWTA GHLIISSNQV GMLTVDKRII VDLWANENPR WLMAQKILDI   240
FMMLTSRRSL VNPWTLRDLK KILQDYGIEY IIFPSNDFFI YEDERLLMFS KKWTNFFTLH   300
ELLDDLETIE TKASSTT                                                  317

SEQ ID NO: 405              moltype = AA   length = 317
FEATURE                     Location/Qualifiers
source                      1..317
                            mol_type = protein
                            organism = African swine fever virus
SEQUENCE: 405
MVETQMDKLG FLLNHIGKQV TTKVLSNAHI TQTMKEIILE NHSVDGGAAK NVSKGKSSPK    60
EKKHWTEFES WEQLSKSKRS FKEYWAERNE IVNTLLLNWD NVRGAIKKFL DDDREWCGRI   120
NMINGVPEIV EIIPSPYRAG ENIYFGSEAM MPADIYSRVA NKPAMFVFHT HPNLGSCCGG   180
MPSICDISTT LRYLLMGWTA GHLIISSNQV GMLTVDKRII VDLWANENPR WLMAQKILDI   240
FMMLTSRRSL VNPWTLRDLK KILQDYGIEY IIFPSNDFFI YEDERLLMFS KKWTNFFTLH   300
ELLDDLETIE TKASSTT                                                  317

SEQ ID NO: 406              moltype = AA   length = 9
FEATURE                     Location/Qualifiers
source                      1..9
                            mol_type = protein
                            organism = African swine fever virus
SEQUENCE: 406
EFISRDEGM                                                           9

SEQ ID NO: 407              moltype = AA   length = 11
FEATURE                     Location/Qualifiers
```

```
source              1..11
                    mol_type = protein
                    organism = African swine fever virus
SEQUENCE: 407
FQYIRYFTDN L                                                        11

SEQ ID NO: 408      moltype = AA  length = 334
FEATURE             Location/Qualifiers
source              1..334
                    mol_type = protein
                    organism = African swine fever virus
SEQUENCE: 408
MLIFISNMEE LLIENSQRFT IFPIQHPECW NWYKKLESLT WTAQEVDMCK DIDDWEAMPK    60
PQREFYKQIL AFFVVADEIV IENLLTNFMR EIKVKEVLYF YTMQAAQECV HSEAYSIQVK   120
TLIPDEKEQQ RIFSGIEKHP IIKKMAQWVR QWMDPDRNTL GERLVGFAAV EGILFQNHFV   180
AIQFLKEQNI MPGLVSYNEF ISRDEGMHCS FACFLISNYV YNIPEEKIIH KILKEAVELV   240
DEFINYAFDK ARGRVPGFSK EMLFQYIRYF TDNLCFMMQC KSIYKVGNPF PQMTKFFLNE   300
VEKTNFFELR PTQYQNCVKD DAFAFKLFLN DDDF                               334

SEQ ID NO: 409      moltype = AA  length = 334
FEATURE             Location/Qualifiers
source              1..334
                    mol_type = protein
                    organism = African swine fever virus
SEQUENCE: 409
MLIFISNMEE LLIENSQRFT IFPIQHPECW NWYKKLESLT WTAQEVDMCK DIDDWEAMPK    60
PQREFYKQIL AFFVVADEIV IENLLTNFMR EIKVKEVLYF YTMQAAQECV HSEAYSIQVK   120
TLIPDEKEQQ RIFSGIEKHP IIKKMAQWVR QWMDPDRNTL GERLVGFAAV EGILFQNHFV   180
AIQFLKEQNI MPGLVSYNEF ISRDEGMHCS FACFLISNYV YNIPEEKIIH KILKEAVELV   240
DEFINYAFDK ARGRVPGFSK EMLFQYIRYF TDNLCFMMQC KSIYKVGNPF PQMTKFFLNE   300
VEKTNFFELR PTQYQNCVKD DAFAFKLFLN DDDF                               334

SEQ ID NO: 410      moltype = AA  length = 11
FEATURE             Location/Qualifiers
source              1..11
                    mol_type = protein
                    organism = African swine fever virus
SEQUENCE: 410
AMDEAIHAAL Y                                                        11

SEQ ID NO: 411      moltype = AA  length = 13
FEATURE             Location/Qualifiers
source              1..13
                    mol_type = protein
                    organism = African swine fever virus
SEQUENCE: 411
FVSQSMSLNY YFY                                                      13

SEQ ID NO: 412      moltype = AA  length = 9
FEATURE             Location/Qualifiers
source              1..9
                    mol_type = protein
                    organism = African swine fever virus
SEQUENCE: 412
VSQSMSLNY                                                            9

SEQ ID NO: 413      moltype = AA  length = 11
FEATURE             Location/Qualifiers
source              1..11
                    mol_type = protein
                    organism = African swine fever virus
SEQUENCE: 413
SQSMSLNYYF Y                                                        11

SEQ ID NO: 414      moltype = AA  length = 9
FEATURE             Location/Qualifiers
source              1..9
                    mol_type = protein
                    organism = African swine fever virus
SEQUENCE: 414
SMSLNYYFY                                                            9

SEQ ID NO: 415      moltype = AA  length = 778
FEATURE             Location/Qualifiers
source              1..778
                    mol_type = protein
                    organism = African swine fever virus
SEQUENCE: 415
METFFIETLA SDVYGKALNV DLDRLSQAQV KYTLQELISY CSALTILHYD YSTLAARLSV    60
```

-continued

```
YQLHQSTASS FSKAVRLQAA QSCSRLSPQF VDVVYKYKAI FDSYIDYSRD YKLSLLGIET    120
MKNSYLLKNK DGVIMERPQD AYMRVAIMIY GMGRVVNMKM ILLTYDLLSQ HVITHASPTM    180
FNAGTKKPQL SSCFLLNVND NLENLYDMVK TAGIISGGGG GIGLCLSGIR AKNSFISGSG    240
LKSNGIQNYI VLQNASQCYA NQGGLRPGAY AVYLELWHQD IFTFLQMPRL KGQMAEQRLN    300
APNLKYGLWV PDLFMEILED QIHNRGDGKW YLFSPDQAPN LHKVFDLERS QHENAHREFK    360
KLYYQYVAEK RYTGVTTAKE IIKEWFKTVV QVGNPYIGFK DAINRKSNLS HVGTITNSNL    420
CIEVTIPCWE GDKAEQGVCN LAAVNLAAFI RENGYDYRGL IEASGNVTEN LDNIIDNGYY    480
PTEATRRSNM RHRPIGIGVF GLADVFASLK MKFGSPEAIA MDEAIHAALY YGAMRRSIEL    540
AKEKGSHPSF PGSAASKGLL QPDLWVRCGD LVSSWEERVA QTTQGVLTPK RWSQLRLAAM    600
QGLRNGYVTA LMPTATSSNS TGKNECFEPF TSNLYTRRTL SGEFIVLNKY LIDDLKEINL    660
WTEAIQQQLL NAGGSIQHIL DIPAEIRDRY KTSREMNQKI LTKHAAARNP FVSQSMSLNY    720
YFYEPELSQV LTVLVLGWKK GLTTGSYYCH FSPGAGTQKK IIRNSEKACN ADCEACLL     778

SEQ ID NO: 416         moltype = AA   length = 11
FEATURE                Location/Qualifiers
source                 1..11
                       mol_type = protein
                       organism = African swine fever virus
SEQUENCE: 416
ENIAYERLET L                                                         11

SEQ ID NO: 417         moltype = AA   length = 10
FEATURE                Location/Qualifiers
source                 1..10
                       mol_type = protein
                       organism = African swine fever virus
SEQUENCE: 417
EPEPGERFSY                                                           10

SEQ ID NO: 418         moltype = AA   length = 10
FEATURE                Location/Qualifiers
source                 1..10
                       mol_type = protein
                       organism = African swine fever virus
SEQUENCE: 418
MPIDIHEVRY                                                           10

SEQ ID NO: 419         moltype = DNA   length = 33
FEATURE                Location/Qualifiers
source                 1..33
                       mol_type = unassigned DNA
                       organism = African swine fever virus
SEQUENCE: 419
gaaaatattg cgtatgaacg gctggagacg ctc                                 33

SEQ ID NO: 420         moltype = AA   length = 11
FEATURE                Location/Qualifiers
source                 1..11
                       mol_type = protein
                       organism = African swine fever virus
SEQUENCE: 420
ENIVYERLET L                                                         11

SEQ ID NO: 421         moltype = DNA   length = 33
FEATURE                Location/Qualifiers
source                 1..33
                       mol_type = unassigned DNA
                       organism = African swine fever virus
SEQUENCE: 421
gaaaatattg tgtatgaacg gctggagacg ctc                                 33

SEQ ID NO: 422         moltype = AA   length = 10
FEATURE                Location/Qualifiers
source                 1..10
                       mol_type = protein
                       organism = African swine fever virus
SEQUENCE: 422
MPIDIHEVRY                                                           10

SEQ ID NO: 423         moltype = AA   length = 11
FEATURE                Location/Qualifiers
source                 1..11
                       mol_type = protein
                       organism = African swine fever virus
SEQUENCE: 423
ENIVYERLET L                                                         11

SEQ ID NO: 424         moltype = AA   length = 8
FEATURE                Location/Qualifiers
```

```
source                    1..8
                          mol_type = protein
                          organism = African swine fever virus
SEQUENCE: 424
STQFMIQY                                                                    8

SEQ ID NO: 425            moltype = AA  length = 12
FEATURE                   Location/Qualifiers
source                    1..12
                          mol_type = protein
                          organism = African swine fever virus
SEQUENCE: 425
TAADDTTCYY RM                                                              12

SEQ ID NO: 426            moltype = AA  length = 9
FEATURE                   Location/Qualifiers
source                    1..9
                          mol_type = protein
                          organism = African swine fever virus
SEQUENCE: 426
AADDTTCYY                                                                   9

SEQ ID NO: 427            moltype = AA  length = 10
FEATURE                   Location/Qualifiers
source                    1..10
                          mol_type = protein
                          organism = African swine fever virus
SEQUENCE: 427
IVMAYDIETY                                                                 10

SEQ ID NO: 428            moltype = AA  length = 11
FEATURE                   Location/Qualifiers
source                    1..11
                          mol_type = protein
                          organism = African swine fever virus
SEQUENCE: 428
ASLYPSLIMA Y                                                               11

SEQ ID NO: 429            moltype = AA  length = 10
FEATURE                   Location/Qualifiers
source                    1..10
                          mol_type = protein
                          organism = African swine fever virus
SEQUENCE: 429
SLYTEVTDAY                                                                 10

SEQ ID NO: 430            moltype = AA  length = 1211
FEATURE                   Location/Qualifiers
source                    1..1211
                          mol_type = protein
                          organism = African swine fever virus
SEQUENCE: 430
MISIMDRSEI VARENPVITQ RVTNLLQTNA PLLFMPIDIH EVRYGAYTLF MYGSLENGYK           60
AEVRIENIPV FFDVQIEFND TNQLFLKSLL TAENIAYERL ETLTQRPVMG YREKEKEFAP          120
YIRIFFKSLY ERRKAITYLN NMGYNTAADD TTCYYRMVSR ELKLPLTSWI QLQHYSYEPR          180
GLVHRFSVTP EDLVSYQDDG PTDHSIVMAY DIETYSPVKG TVPDPNQAND VVFMICMRIF          240
WIHSTEPLAS TCITMAPCKK SSEWTTILCS SEKNLLLSFA EQFSRWAPDI CTGFNDSRYD          300
WPFIVEKSMQ HGILEEIFNK MSLFWHQKLD TILKCYYVKE KRVKISAEKS IISSFLHTPG          360
CLPIDVRNMC MQLYPKAEKT SLKAFLENCG LDSKVDLPYH LMWKYYETRD SEKMADVAYY          420
CIIDAQRCQD LLVRHNVIPD RREVGILSYT SLYDCIYYAG GHKVCNMLIA YAIHDEYGRI          480
ACSTIARGKR EHGKYPGAFV IDPVKGLEQD KPTTGLDFAS LYPSLIMAYN FSPEKFVASR          540
DEAKSLMAKG ESLHYVSFHF NNRLVEGWFV RHNNVPDKMG LYPKVLIDLL NKRTALKQEL          600
KKLGEKKECI HESHPGFKEL QFRHAMVDAK QKALKIFMNT FYGEAGNNLS PFFLLPLAGG          660
VTSSGQYNLK LVYNFVINKG YGIKYGDTDS LYITCPDSLY TEVTDAYLNS QKTIKHYEQL          720
CHEKVLLSMK AMSTLCAEVN EYLRQDNGTS YLRMAYEEVL FPVCFTGKKK YYGIAHVNTP          780
NFNTKELFIR GIDIIKQGQT KLTKTIGTRI MEESMKLRRP EDHRPPLIEI VKTVLKDAVV          840
NMKQWNFEDF IQTDAWRPDK DNKAVQIFMS RMHARREQLK KHGAAASQFA EPEPGERFSY          900
VIVEKQVQFD IQGHRTDSSR KGDKMEYVSE AKAKNLPIDI LFYINNYVLG LCARFINENE          960
EFQPPPDNVSN KDEYAQRRAK SYLQKFVQSI HPKDKSVIKQ GIVHRQCYKY VHQEIKKKIG        1020
IFADLYKEFF NNTTNPIESF IQSARFMIQY SDGEQKVNHS MKKMVEQRAT LASKPAGKPA        1080
GNPAGNPAGN ALMRAIFTQL ITEEKKIVQA LYNKGDAIHD LLTYIINNIN YKIATFQTKQ        1140
MLTFEFSSTH VELLLKLNKT WLILAGIHVA KKHLQALLDS YNNEPPSRTF IQQAIEEECG        1200
SIKPSCYDFI S                                                            1211

SEQ ID NO: 431            moltype = DNA  length = 3636
FEATURE                   Location/Qualifiers
source                    1..3636
                          mol_type = unassigned DNA
                          organism = African swine fever virus
```

SEQUENCE: 431

```
atgatatcta tcatggaccg ttctgagatt gttgcacggg agaacccggt gattacccaa    60
cgagttacaa atctcctaca aaccaatgct cctctactat tcatgcccat tgatatccat   120
gaagtacgat atggagccta cacactttc atgtatggtt ccctcgaaaa cggttacaaa   180
gcagaagtaa ggattgaaaa catcccagtt ttctttgacg tacagattga gttcaatgat   240
acaaaccagc ttttttttaaa gtcgctactg acggctgaaa atattgcgta tgaacggctg   300
gagacgctca cccagcgtcc tgtaatgggg taccgcgaga aggaaaaaga gtttgcacca   360
tacattcgaa tatttttaa aagcctgtat gagcgacgaa aagccattac ttacttgaat   420
aatatgggtt acaacaccgc cgcggacgac acaacctgtt actaccgaat ggtttcccga   480
gagctaaaac tgcctcttac aagttggata cagcttcagc actattccta cgagcctcgc   540
ggcttggtac acaggtttc cgtaaccccc gaggatcttg tttcctatca ggatgatggc   600
cccacagacc acagcatcgt tatggcctac gatatagaga cctatagcc tgttaaggga   660
accgttccgg acccaaatca ggcaaacgac gtggtgttca tgatatgcat gcgcattttt   720
tggattcact ccacagagcc tctagcgagc acgtgcatca ctatgccac ctgcaaaaag   780
tcctcagagt ggaccaccat tctatgctcc tctgaaaaaa atttgctgtt aagctttgct   840
gaacagttca gccgctgggc tcctgatata tgcacagggt caatgattc tcggtacgac   900
tggccctta tcgttgaaaa atctatgcag acggtattc tagaagaaat ctttaacaaa   960
atgagccttt tctggcacca aagctggat accattctaa aatgctatta tgtgaaggaa  1020
aagagagtca aaatctcggc cgaaaaatcg atcatttcct cctttttgca tacccctgga  1080
tgcctaccca ttgatgtccg caacatgtgt atgcagcttt accctaaagc cgaaaaaaca  1140
agcctaaaag cgttttttaga aaattgtggg ttagattcga aggtagacct gcctaccat  1200
ctcatgtgga agtattatga aacgcagcac agtgaaaaga tggccgacgt ggcctactac  1260
tgcattatag atgcccagcg ctgtcaggac cttctggtgc gccacaatgt tatccccgat  1320
cgcagagagg taggaatctt gtcatacacc tcgttgtatg actgtatcta ctacgcggga  1380
ggacataagg tatgtaatat gctcattgcc tatgctatcc atgatgagta cggccgtatt  1440
gcttgcagca ccattgctcg gggtaagcgg gaacacggaa aatatccggg cgccttttgt  1500
attgaccccg ttaaagggct tgaacaggat aaacccacca ccggcctcga ttttgcgtcg  1560
ctgtaccct cactcatcat ggcctacaac tttcgccag aaaaatttgt agcctctcgg  1620
gatgaggcaa aagcctcat ggccaagggt gaatctcttc actacgtctc ctttcacttt  1680
aacaatcgtc tcgtgaagg atggtttgtg cgactataa cgttcctga taaaatgga  1740
ttatacccaa aagtactcat cgatctactt aacaaacgaa ccgcccttaa acaagagctt  1800
aaaaaactag gtgagaaaaa agaatgtatc catgaatccc atcctgggtt taaggaacta  1860
cagtttcgcc atgccatggt agacgcgaag caaaaggcgt tgaaaatttt catgaacacg  1920
ttttacggcg aggcaggtaa caatttgtcg cccttctttc tgcttcctct agccggagga  1980
gtcaccagtt cgggtcaata taatcttaaa ctcgtctata actttgttat caataaaggt  2040
tacggcatca agtacggtga caccgactca ttatacatta catgcccaga tagtctttat  2100
acagaggtaa cagacgcata tttaaatagc caaaaaacaa taaaacatta tgagcaactc  2160
tgccacgaaa aagtgcttct gtctatgaaa gccatgtcta cactatgcgc cgaggtgaat  2220
gaatacctgc ggcaagataa tggcaccagt tacctacgta tggcctacga ggaagtactc  2280
tttcctgtgt gctttacagg caagaaaag tattacggta ttgctcatgt aaacacaccc  2340
aatttttaata caaagaatt attcatccgc ggaatagata tcattaagca gggtcaaaca  2400
aaactcacca aaacgatagg tacgcgaatt atggaagaat ccatgaaact cgccgcccct  2460
gaggaccatc gcccccctct tattgaaatc gttaaaacgg ttttgaagga tgctgtggtt  2520
aacatgaagc agtggaattt tgaagacttc atccaaacag atgcgtggag accggacaaa  2580
gacaacaaag cagtccaaat cttatgtct cgcatgcacg ctcggcgtga gcaactaaaa  2640
aaacacggcg ccgcagcatc gcaatttgct gagcctgagc cggagaacg cttctcctac  2700
gttatcgtgg aaaaacaagt acagttgat attcagggcc accgcacaga ttcctccaga  2760
aagggggaca agatggaata cgtctctgaa gcaaaggcta aaaatcttcc aattgatata  2820
ttgtttttata tcaacaacta tgttctaggc ttgtgcgcga gattcattaa tgaaaatgaa  2880
gaatttcaac cccctgacaa tgtcagcaat aaggatgaat acgctcagcg ccgagccaaa  2940
tcctacctac aaaaattcgt acaatccatt caccctaaca caagtctgt cattaagcaa  3000
ggcattgttc atcgacagtg ctacaaatac gttcaccaag aaattaaaaa aaaataggc  3060
atctttgccg accttttataa ggaatttttt aacaacacca caaacccat cgaaagcttt  3120
attcaaagcg ctcggtttat gatacaatac tctgatggag aacaaaaagt aaaccattct  3180
atgaaaaaaa tggttgaaca gcgtgctact ttggcaagta agcccgctgg taagcccgct  3240
ggtaatccag ctggcaaccc agccggcaat gcgctgatgc gggctatatt tacgcagctg  3300
attacggaag aaaaaaaaat tgtacaagcc ttatacaata aggggggatgc aatacacgat  3360
cttctcacct atatcattaa caatataaat tacaaaattg ccacgtttca gacgaaacag  3420
atgttgacgt tcgagttttc tagtactcat gtagaactgc tattaaagct gaataaggca  3480
tggcttattt tggctggaat tcatgtggcg aaaaaacatc tgcaagctct tttggattca  3540
tataatatatg aaccaccgtc tagaacattc attcagcagg ctatagagga agaatgtggc  3600
agtattaaac catcttgcta cgactttatt tcctaa                             3636
```

SEQ ID NO: 432         moltype = AA   length = 1206
FEATURE             Location/Qualifiers
source              1..1206
                   mol_type = protein
                   organism = African swine fever virus

SEQUENCE: 432

```
MISIMDRSEI VARENPVITQ RVTNLLQTNA PLLFMPIDIH EVRYGAYTLF MYGSLENGYK    60
AEVRIENIPV FFDVQIEFND TNQLFLKSLL TAENIVYERL ETLTQRPVMG YREKEKEFAP   120
YIRIFFKSLY ERRKAITYLN NMGYNTAADD TTCYYRMVSR ELKLPLTSWI QLQHYSEPR   180
GLVHRFSVTP EDLVSYQNDG PTDHSIVMAY DIETYSPVKG TVPDPNQAND VVFMICMRIF   240
WIHSTEPLAS TCITMAPCKK SSEWTTILCS SEKNLLLSFA EQFSRWAPDI CTGFNDSRYD   300
WPFIVEKSMQ HGILEEIFNK MSLFWHQKLD TILKCYYVKE KRVKISAEKS IISSFLHTPG   360
CLPIDVRNMC MQLYPKAEKT SLKAFLENCG LDSKVDLPYH LMWKYYETRD SEKIADVAYY   420
CIIDAQRCQD LLVRHNVIPD RREVGILSYT SLYDCIYYAG GHKVCNMLIA YAIHDEYGRI   480
ACSTIARGKR EHGKYPGAFV IDPVKGLEQD KPTTGLDFAS LYPSLIMAYN FSPEKFVASR   540
DEANSLMAKG ESLHYVSFHF NNRLVEGWFV RHNNVPDKMG LYPKVLIDLL NKRTALKQEL   600
```

```
KKLGEKKECI HESHPGFKEL QFRHAMVDAK QKALKIFMNT FYGEAGNNLS PFFLLPLAGG    660
VTSSGQYNLK LVYNFVINKG YGIKYGDTDS LYITCPDSLY TEVTDAYLNS QKTIKHYEQL    720
CHEKVLLSMK AMSTLCAEVN EYLRQDNGTS YLRMAYEEVL FPVCFTGKKK YYGIAHVNTP    780
NFNTKELFIR GIDIIKQGQT KLTKTIGTRI MEESMKLRRP EDHRPPLIEI VKTVLKDAVV    840
NMKQWNFEDF IQTDAWRPDK DNKAVQIFMS RMHARREQLK KHGAAASQFA EPEPGERFSY    900
VIVEKQVQFD IQGHRTDSSR KGDKMEYVSE AKAKNLPIDI LFYINNYVLG LCARFINENE    960
EFQPPDNVSN KDEYAQRRAK SYLQKFVQSI HPKDKSVIKQ GNVHRQCYKY IHQEIKKKIG   1020
IFADLYKEFF NNTTNPIESF IQSTQFMIQY FDGEQKVNHS MKKMVEQHAT ASNRAGKPAG   1080
NPAGNALMRA IFTQLITEEK KIVQALYNKG DAIHDLLTYI INNINYKIAT FQTKQMLTFE   1140
FSSTHVELLL KLNKTWLILA GIHVAKKHLQ AFLDSYNNES PSRTFIQQAI EEECGSIKPS   1200
CYDFIS                                                              1206

SEQ ID NO: 433          moltype = DNA  length = 3621
FEATURE                 Location/Qualifiers
source                  1..3621
                        mol_type = unassigned DNA
                        organism = African swine fever virus
SEQUENCE: 433
atgatatcta tcatggaccg ttctgagatt gttgcacggg agaacccggt gattacccaa     60
cgagttacaa atctcctaca aaccaatgct cctctactat tcatgcccat tgatatccat    120
gaagtacgat atggagccta cacacttttc atgtatggtt ccctcgaaaa cggttacaaa    180
gcagaagtaa ggattgaaaa catcccagtt ttctttgagt tacagattga gttcaatgat    240
acaaaccagc ttttttttaa gtcgctactg acggctgaaa atattgtgta tgaacggctg    300
gagacgctca cccagcgtcc tgtaatgggg taccgcgaga aggaaaaaga gtttgcacca    360
tacattcgaa tattttttaa aagcctgtat gagcgacgaa aagccattac ttacttaaat    420
aatatgggct acaacacggc cgcggacgac acaacctgtt attaccgaat ggtttcccga    480
gaattaaaac tacctcttac aagttggata cagcttcagc actattccta cgagcctcgc    540
ggcttggtac acaggttttc cgtaaccccc gaggatcttg tttcctatca gaatgatggc    600
cccacagacc acagcatcgt tatggcctac gatatagaac ctatagccc tgttaaggga    660
accgttccgg acccaaatca ggcaaacgac gtggtgttca tgatatgcat gcgcattttt    720
tggattcact ccacagagcc tctagcgagc acgtgcatca ccatggcacc ctgcaaaaag    780
tcctcagagt ggaccaccat tctatgctcc tctgaaaaaa atttgttgtt aagctttgct    840
gaacagtttta gccgctgggc tcctgatata tgcacagggt tcaatgattc tcggtacgac    900
tggccctta tcgttgaaaa atctatgcag cacggtattc tgaagaaat ctttaacaaa    960
atgagccttt tctggcacca aaagctggat accattctaa agtgctatta cgtaaaggaa   1020
aagagagtca aaatctcggc cgaaaaatcg atcatttcct cctttttgca tacccctgga   1080
tgcctaccca ttgatgtccg caacatgtgt atgcagcttt accctaaagc cgaaaaaaca   1140
agcttgaaag cgttttttaga aaattgtggg ttagattcga aggtagacct gccgtaccat   1200
ctcatgtgga agtattatga aacacgagc agcgaaaaaa tagccgacgt ggcctattac   1260
tgcattatag atgcccagcg ctgtcaggac cttctggtgc gccacaatgt tatccccgat   1320
cgcagagagg taggaattct gtcatacacc tcgctgtatg actgtatcta ctacgcggga   1380
ggacacaagg tatgcaatat gctcattgcc tatgccatcc atgatgaata cggccgtatt   1440
gcttgcagta ccattgcccg aggtaagcgg gaacacgaaa aatatcccgg cgccttttga   1500
atagaccccg ttaaagggct tgaacaggat aaacccacca caggtctcga ctttgcgtcg   1560
ctgtacccct cactcatcat ggcctacaac ttttcgccag aaaaatttgt agcctctcgg   1620
gatgaggcaa atagcctcat ggccaagggt gaatctcttc actacgtctc ctttcacttt   1680
aacaatcgtc tcgtggaagg atggtttgtg cggcataata cgttcctga taaaatgggga   1740
ttgtacccaa aagtactcat cgatctactt aacaaacgga ccgccttaa acaagagctt   1800
aaaaaaactag gtgagaaaaa agaatgtatc catgaatccc atcctgggtt taaggaacta   1860
cagtttcgcc atgccatggt agacgcgaag caaaaggcgt tgaaaatttt catgaacacg   1920
ttttacggcg aggcaggtaa caatttgtcg cccttctttc tgcttcctct agccggagga   1980
gtcaccagtt cgggtcaata taatcttaaa ctttgtctata actttgttat caataaaggt   2040
tacggcatca agtacggtga caccgactca ttatacatta tcgcccaga tagtctttat   2100
acagaggtaa cagacgcata tttaaacagc caaaaaacga taaaacatta tgagcaactc   2160
tgccacgaaa aagtgcttct gtctatgaaa gccatgtcta cactatgcgc cgaggtgaat   2220
gaatacctgc gacaagataa tggcaccagt tacctacgta tggcctacga ggaagtactc   2280
tttcctgtgt gctttacagg caagaaaaag tattatggta ttgctcatgt aaacacaccc   2340
aattttaata caaagaatt attcatccgc ggaatagata tcattaagca gggtcaaaca   2400
aaactcacca aaacgatagg aacgcgaatt atggaagaat ccatgaaact agccgccct   2460
gaggaccatc gccccctct tattgaaatc gttaaaacgg ttttgaagga tgctgtggtt   2520
aacatgaagc agtggaattt tgaagacttc atccaaacag atgcgtggag accggacaaa   2580
gacaacaaag cagtccaaat cttttatgtct cgcatgcacg ctcggcgtga gcaactaaaa   2640
aaacacggcg ctgcagcatc gcaatttgct gagcccgagc cggagaacg cttctcctac   2700
gttatcgtgg aaaaacaggt acagtttgat atcccaggac accgcacaga ttcctccaga   2760
aagggggaca agatgggata cgtctctgaa gcaaaggcta aaaatcttcc tattgatata   2820
ttgttttata tcaacaacta tgttctaggc ttgtgcgcga gattcattaa tgaaaatgaa   2880
gaatttcaac ccccctgacaa cgtcagcaat aaggatgaat acgctcagcg ccgagctaaa   2940
tcctacctac aaaaattcgt gcaatccatt cacctaaag acaagtctgt cattaagcaa   3000
ggcaatgttc atcgacagtg ctacaaatac attcaccaag aaattaaaaa aaaaatggc   3060
atctttgccg acctttataa ggaatttttt aacaacacca caaacccat cgaaagctttt   3120
attcaaagca ctcagtttat gatacaatac tttgatggag aacaaaagt aaaccattct   3180
atgaaaaaaa tggttgaaca gcatgctacg gctagtaatc gagctggtaa gcccgctggt   3240
aatccagccg gcaatgcgct gatgcgggct atatttacgc agctgattac ggaagaaaaa   3300
aaaattgtac aagcctttata caataagggg gatgcaatct cacctatatc   3360
attaacaata taaattacaa aattgccacg tttcagacga aacagatgtt gacgttcgag   3420
ttttccagta ctcatgtaga actgcttatta agctgaataa aacgtggct tatttttggct   3480
ggaattcatg tggcaaaaaa acatctgcaa gctttttttgg attcatataa caatgaatcg   3540
ccgtctagaa cattcattca gcaggctata gaggaagaat gtggcagtat taaaccatct   3600
tgctacgact ttatttccta a                                              3621
```

```
SEQ ID NO: 434         moltype = AA  length = 11
FEATURE                Location/Qualifiers
source                 1..11
                       mol_type = protein
                       organism = African swine fever virus
SEQUENCE: 434
DFVDLNDIHT I                                                          11

SEQ ID NO: 435         moltype = AA  length = 8
FEATURE                Location/Qualifiers
source                 1..8
                       mol_type = protein
                       organism = African swine fever virus
SEQUENCE: 435
YQFDLLYY                                                               8

SEQ ID NO: 436         moltype = AA  length = 21
FEATURE                Location/Qualifiers
source                 1..21
                       mol_type = protein
                       organism = African swine fever virus
SEQUENCE: 436
IQISISSMSV STFWPYTLSS K                                               21

SEQ ID NO: 437         moltype = AA  length = 11
FEATURE                Location/Qualifiers
source                 1..11
                       mol_type = protein
                       organism = African swine fever virus
SEQUENCE: 437
MSVSTFWPYT L                                                          11

SEQ ID NO: 438         moltype = AA  length = 8
FEATURE                Location/Qualifiers
source                 1..8
                       mol_type = protein
                       organism = African swine fever virus
SEQUENCE: 438
STFWPYTL                                                               8

SEQ ID NO: 439         moltype = AA  length = 17
FEATURE                Location/Qualifiers
source                 1..17
                       mol_type = protein
                       organism = African swine fever virus
SEQUENCE: 439
KMDINVALLQ NTYAYLF                                                    17

SEQ ID NO: 440         moltype = AA  length = 9
FEATURE                Location/Qualifiers
source                 1..9
                       mol_type = protein
                       organism = African swine fever virus
SEQUENCE: 440
NVALLQNTY                                                              9

SEQ ID NO: 441         moltype = AA  length = 9
FEATURE                Location/Qualifiers
source                 1..9
                       mol_type = protein
                       organism = African swine fever virus
SEQUENCE: 441
ALLQNTYAY                                                              9

SEQ ID NO: 442         moltype = AA  length = 10
FEATURE                Location/Qualifiers
source                 1..10
                       mol_type = protein
                       organism = African swine fever virus
SEQUENCE: 442
VMMPEIETMY                                                            10

SEQ ID NO: 443         moltype = AA  length = 1340
FEATURE                Location/Qualifiers
source                 1..1340
                       mol_type = protein
                       organism = African swine fever virus
SEQUENCE: 443
```

```
MDFQNDFLTN PLRVTLYNPA ENEYTKTFIF LGSVPANVLQ ACRKDLQRTP KDKEILQNFY    60
GKDWEKKLSQ YVVGGDSDDL DEFEKLFVED SGEETNVMMP EIETMYSEYS IFPEDTFKDI   120
REKIYVATGI PPYRQHIFFF QNNALQVTYR LLLSGSGVAL DIRDYKKEFQ QVGGLNIDAS   180
MESQKDELYV EALDSFQLIK NIHHIFVADL NTLVAPMRRQ ISIAMEDNYQ FDLLYYGLIM   240
KYWPLLSPDA FKLLVQSPLQ MEKQYPALSP SLTSLKKRLL LEQKLINFTY ARAQQVIAKS   300
EGNRLTRGTL AVTSAMIKIS PLVNIQINVR NVFDLFPATP DIPQLVVFFY SKTGPTVVSK   360
HHITSTEPEK FSNKTFRVPT IILIRFINKK AFILTIQNNG HYFIESNWSE NERHDFNSVV   420
STLNNFINPI IHTINDMGPA AFPRGGSLPL PSNEDIQISI SSMSVSTFWP YTLSSKGFTE   480
LKSRWREYEQ AGIISVRGLQ QTGIYNFLFK KGIYSYDPHE IERMIIISSG PGRKMDINVA   540
LLQNTYAYLF DANVAARWET IYGGRNIRIY HRVTDIKIEM FNITQEEFNY LWVYLFVFLD   600
NLITGPDKIL VNKLSQLHDK QQGKGASQLR ALQEQDPDLY DLRKYDTQAT VYSVLCQHPR   660
PPVIYSEAEV KSMPPAKRKE LVKYWNFTEG VPAYYSCPHP DYPHLSLLEG RHPLNYCLPC   720
CQKTKALLGT KRFYINNTCL TKHTFVEQDL EDLNTQTSRH TLSYGKKIPV NRIAFLPHQI   780
ADELFLNTIK EPDIFCIVGV EQTMLGISNA GLFYSLARIL DLAPKALAIE IAKAANTPQY   840
YILGNGAGNM FSSGAELANL ILQTFVEQKN QLLQWDTTWQ DIFLDLVAIC YDLHCVFFKD   900
KQGDIEFEVS PSTIQKILSP SKKIAIIFDT DEGIYPMAIT QQKRFLKNSE AQYIFTEDDP   960
VMEVVQSMSE FMCKDNWWDI HDVKNIPGYT VGKKLINRFN FCYALLIDSD TDRPIYFPIR  1020
LSSYIHDDIP IDFDLRPTQI ASFEETWKFI TLFNKQYKQY EIVPSAVLQN IKKEFVGFLS  1080
EGKTGLYFYY APTQTLPATL EKLPIATLTI DPRDIDQAIL YPLEEPYPQQ NKANKAFYIN  1140
HLYKFLLIEF FDVLYGLQSN STRKHIENLF QKTDFQKITS VTEFYTKLSD FVDLNDIHTI  1200
KHILETTDAE HALKVLQKNI FNFDYTLLSP LQSYTYDELC QHLKKLLTPR IEFYEDIETI  1260
DRGLINIYTS CQYSTLNQPQ CKKKRLRIPV NHFENYIHIL AADILNPLKH STLLLTGLGV  1320
IDDLQFILRP QEIISVKNKF                                              1340

SEQ ID NO: 444          moltype = AA   length = 1340
FEATURE                 Location/Qualifiers
source                  1..1340
                        mol_type = protein
                        organism = African swine fever virus
SEQUENCE: 444
MDFQNDFLTN PLRVTLYNPV ENEYTKTFIF LGSVPANVLQ ACRKDLQRTP KDKEILQNFY    60
GEDWEKKLSQ YVVGGDSDDL DEFEKLFVED RGEETNVMMP EIETMYSEYS IFPEDTFKDI   120
REKIYVATGI PPYRQHIFFF QNNALQVTYR LLLSGSGVAL DIRDYKKEFQ QVGGVNIDAS   180
MESQKDELYV EALDSFQLIK NIHHIFVADL NTLVAPMRRQ ISIAIEDNYQ FDLLYYGLIM   240
KYWPLLSPDA FKLLVQSPLQ MEKQYPALSP SLTSLKKRLL LEQKLINFTY ARAQQVIAKY   300
EGNRLTRGTL AVTSAMIKIS PLVNIQINVR NVFDLFPATP DIPQLVVFFY SKTGPTVVSK   360
HHITSTEPEK FSNKTFRVPT IILIRFINKK AFILTIQNNG HYFIESNWSE NERHDFNSVV   420
STLNNFINPI IHTINDMGPA AFPRGGSLPL PSNEDIQISI SSMSVSTFWP YTLSSKGFTE   480
LKSRWREYEQ AGIISVRGLQ QTGVYNFLFK KGIYSYDPHE IERMIIISSG PGRKMDINVA   540
LLQNTYAYLF DTNVAARWET IYGGRNIRIY HRVTDIKIEM FNITQEEFNY LWVYLFVFLD   600
NLITGPDKIL VNKLSQLHDK QQGKGASQLR ALQEQDPDLY DLRKYDTQAT VYSVLCQHPR   660
PPVIYSEAEV KSMPPAKRKE LVKYWNFTEG VPAYYSCPHP DYPHLSLLEG RHPLNYCLPC   720
CQKTKALLGT KRFYINNTCL TKHTFVEQDL EDLNTQTSRH TLSYGKKIPV NRIAFLPHQI   780
ADELFLNTIK EPDIFCIVGV EQTMLGISNA GLFYSLARIL DLAPKALAIE IAKAANTPQY   840
YILGNGAGNM FSSGAELANL ILQTFVEQKN QLLQWDTTWQ DIFLDLVAIC YDLHCVFFKD   900
KQGDIGFEVS PSTIQKILSP SKKIAIIFDT DEGIYPMAIT QQKRFLKNSE AQYIFTEDDP   960
VMEVIQSMSE FMCKDNWWDI HDVKNIPGYT VGKKLINRFN FCYALLIDSD TDRPIYFPIR  1020
LSSYIHDDIP IDFDLRPTQI ASFEETWKFI TLFNKQYKQY EIVPSAVLQN IKKEFVGFLS  1080
EGKTGLYFYY APTQTLPATL EKLPIATLTI DPRDIDQAIL YPLEEPYPQQ NKANKAFYIN  1140
HLYKFLLIEF FDVLYGLQSN STRKHIENLF QKTDFQKITS VTEFYTKLSD FVDLNDIHTI  1200
KHILETTDAE HALKVLQKNI FNFDYTLLSP LQSYTYDELC QHLKKLLTPR IEFYEDIETI  1260
DRGLINIYTS CQYSTLNQPQ CKKKRLRIPV NHFENYIHIL AADILNPLKH STLLLTGLGV  1320
IDDLQFILRP QEIISVKNKF                                              1340

SEQ ID NO: 445          moltype = AA   length = 11
FEATURE                 Location/Qualifiers
source                  1..11
                        mol_type = protein
                        organism = African swine fever virus
SEQUENCE: 445
MSMIGPYLNV Y                                                         11

SEQ ID NO: 446          moltype = AA   length = 10
FEATURE                 Location/Qualifiers
source                  1..10
                        mol_type = protein
                        organism = African swine fever virus
SEQUENCE: 446
SMIGPYLNVY                                                           10

SEQ ID NO: 447          moltype = AA   length = 124
FEATURE                 Location/Qualifiers
source                  1..124
                        mol_type = protein
                        organism = African swine fever virus
SEQUENCE: 447
MNLEYVQVVQ KFNQVLLELT KKVCTVVGGS KPTYWHHIR RVCSECPSMP MSMIGPYLNV    60
YKAQILTRDK NFFMNFDPAH NEYTFIIQKL KEAARNMPED ELEQYWVKLL FLLKSYIKCK   120
PFIN                                                                124
```

```
SEQ ID NO: 448          moltype = AA   length = 9
FEATURE                 Location/Qualifiers
source                  1..9
                        mol_type = protein
                        organism = African swine fever virus
SEQUENCE: 448
NAYAHKLNI                                                                  9

SEQ ID NO: 449          moltype = AA   length = 10
FEATURE                 Location/Qualifiers
source                  1..10
                        mol_type = protein
                        organism = African swine fever virus
SEQUENCE: 449
SPFSLAHLEY                                                                 10

SEQ ID NO: 450          moltype = AA   length = 233
FEATURE                 Location/Qualifiers
source                  1..233
                        mol_type = protein
                        organism = African swine fever virus
SEQUENCE: 450
MILIASPFSL AHLEYLHTWH VTIKNIAQQH GLDIKVAIVV STSHLNNFLP ISGALNIECI   60
TFPSCGIKEI DLLWARIKLF QHYCAIGARL LWLVSADIRP PVSAWPAIAD SLKKGADAVV   120
IPYPSRWNNL IPTVIKEIVV HQKKCLVAVD ARHLDTDTQI VGAGMGCIVL TLKALMVRLS   180
IGKQPVKILW PDLHGTAEGI PLEGVEVGWF LNAYAHKLNI RCLGADHIAQ HLT         233

SEQ ID NO: 451          moltype = AA   length = 233
FEATURE                 Location/Qualifiers
source                  1..233
                        mol_type = protein
                        organism = African swine fever virus
SEQUENCE: 451
MILIASPFSL AHLEYLHTWH VTIKNIAQQH GLDIKVAIVV STSHLNNFLP ISGALNIECI   60
TFPSCGIKEI DLLWARIKLF QHYCAIGARL LWLVSADIRP PVSAWPAIAD SLKKGADAVV   120
IPYPSRWNNL IPTVIKEIVV HQKKCLVAVD ARHLDTDTQI VGAGMGCIVL TLKALMVRLS   180
IGKQPVKILW PDLHGTAEGI PLEGVEVGWF LNAYAHKLNI RCLGADHIAQ HLT         233

SEQ ID NO: 452          moltype = AA   length = 10
FEATURE                 Location/Qualifiers
source                  1..10
                        mol_type = protein
                        organism = African swine fever virus
SEQUENCE: 452
VVQYLTPIFY                                                                 10

SEQ ID NO: 453          moltype = AA   length = 241
FEATURE                 Location/Qualifiers
source                  1..241
                        mol_type = protein
                        organism = African swine fever virus
SEQUENCE: 453
MAANIIATRA VPKMASKKEH QYCLLDSQEK RHGHYPFSFE LKPYGQTGAN IIGVQGSLTH   60
VIKMTVFPFM IPFPLQKTHI DDFIGGRIYL FFKELDMQAV SDVNGMQYHF EFKVVPVSPN   120
QVELLPVNNK YKFTYAIPVV QYLTPIFYDL SGPLDFPLDT LSVHVDILSN HIQLPIQNHN   180
LTTGDRVFIS GYKHLQTIEL CKNNKIFIKN IPPLSSEKIK LYILKNRIRI PLYFKSLKTS   240
K                                                                          241

SEQ ID NO: 454          moltype = AA   length = 9
FEATURE                 Location/Qualifiers
source                  1..9
                        mol_type = protein
                        organism = African swine fever virus
SEQUENCE: 454
DSKNISPRI                                                                  9

SEQ ID NO: 455          moltype = AA   length = 10
FEATURE                 Location/Qualifiers
source                  1..10
                        mol_type = protein
                        organism = African swine fever virus
SEQUENCE: 455
NKIESSVHLL                                                                 10

SEQ ID NO: 456          moltype = AA   length = 9
FEATURE                 Location/Qualifiers
source                  1..9
                        mol_type = protein
```

```
                                      -continued organism = African swine fever virus
SEQUENCE: 456
NPTIIMEQY                                                                      9

SEQ ID NO: 457          moltype = DNA  length = 27
FEATURE                 Location/Qualifiers
source                  1..27
                        mol_type = unassigned DNA
                        organism = African swine fever virus
SEQUENCE: 457
aacccaacca tcattatgga acagtac                                                 27

SEQ ID NO: 458          moltype = AA  length = 9
FEATURE                 Location/Qualifiers
source                  1..9
                        mol_type = protein
                        organism = African swine fever virus
SEQUENCE: 458
NPTIIMEQY                                                                      9

SEQ ID NO: 459          moltype = DNA  length = 27
FEATURE                 Location/Qualifiers
source                  1..27
                        mol_type = unassigned DNA
                        organism = African swine fever virus
SEQUENCE: 459
aacccaacca tcattatgga acagtac                                                 27

SEQ ID NO: 460          moltype = AA  length = 10
FEATURE                 Location/Qualifiers
source                  1..10
                        mol_type = protein
                        organism = African swine fever virus
SEQUENCE: 460
NKIESSVHLL                                                                    10

SEQ ID NO: 461          moltype = AA  length = 9
FEATURE                 Location/Qualifiers
source                  1..9
                        mol_type = protein
                        organism = African swine fever virus
SEQUENCE: 461
NPTIIMEQY                                                                      9

SEQ ID NO: 462          moltype = AA  length = 9
FEATURE                 Location/Qualifiers
source                  1..9
                        mol_type = protein
                        organism = African swine fever virus
SEQUENCE: 462
DSKNISPRI                                                                      9

SEQ ID NO: 463          moltype = AA  length = 10
FEATURE                 Location/Qualifiers
source                  1..10
                        mol_type = protein
                        organism = African swine fever virus
SEQUENCE: 463
KLYTAALGVY                                                                    10

SEQ ID NO: 464          moltype = AA  length = 9
FEATURE                 Location/Qualifiers
source                  1..9
                        mol_type = protein
                        organism = African swine fever virus
SEQUENCE: 464
KLWAAYEGY                                                                      9

SEQ ID NO: 465          moltype = AA  length = 9
FEATURE                 Location/Qualifiers
source                  1..9
                        mol_type = protein
                        organism = African swine fever virus
SEQUENCE: 465
AAYEGYFKY                                                                      9

SEQ ID NO: 466          moltype = AA  length = 339
FEATURE                 Location/Qualifiers
source                  1..339
```

```
                        mol_type = protein
                        organism = African swine fever virus
SEQUENCE: 466
MAGRVKIKQK ELIDSTVKNK NVMNLFHEII GSKGNINFSV VWPKFKKIKQ SVYDYISTLS    60
VLEKASVMQN FEADKKLLEL FVQKLWAAYE GYFKYPEIEK YEVEGQVNFN LVPQCVLEKF   120
SQLYRIRINS ELVTLILNSC AFMSKYNDYI LKKDPYILTI TPGLCFSPIP NFEDLNFKHL   180
YNSDKNSQHD KEFIMFILYK LYTAALGVYN AISIPDIDVE DLENIILSSV SQIKKQIPRC   240
KDAFNKIESS VHLLRKNFNT YYSDYVGSGY NPTIIMEQYI KDISQDSKNI SPRISYQFRT   300
IIKYYRDMIA TRHQTMDPQV LNLVKHVEKK LDMLDREKN                          339

SEQ ID NO: 467          moltype = DNA  length = 1020
FEATURE                 Location/Qualifiers
source                  1..1020
                        mol_type = unassigned DNA
                        organism = African swine fever virus
SEQUENCE: 467
atggccggtc gtgttaaaat aaaacagaaa gagctcatag actctactgt aaaaaacaaa    60
aatgtgatga atctgttcca tgaaattata ggctcaaaag gcaatattaa ttttagcgtt   120
gtctggccca gtttaaaaa aatcaaacag agcgtttatg actacatttc cactcttttct   180
gtgctggaaa agcaagcgt tatgcaaaac tttgaagctg ataagaaact gttggaactt   240
tttgtacaaa agctgtgggc tgcctatgaa ggctatttca aatatcccga gattgaaaaa   300
tatgaggtgg aaggccaggt aaatttcaat ctcgtacctc agtgcgtcct cgaaaagttt   360
agccagttgt ataggataag aatcaattca gagcttgtca cactcatcct gaacagctgt   420
gcctttatga gtaaatataa cgattatatt ctcaaaaaag atccctacat actaaccata   480
accccggcc tatgcttttc ccccattccc aacttcgagg acctaaattt taaacatctt   540
tacaacagtg ataaaaattc tcagcatgac aaagagttta tcatgttttat attatataag   600
ctttatacgg ctgccctagg agtgtacaat gccatctcga ttccagacat cgacgtagaa   660
gaccttgaaa atattatcct atcctcggtg agccagatta aaaaacaaat tccgcgctgc   720
aaagacgcct tcaacaaaat tgaatcttcg gtacacctgc tgcgcaaaaa ttttaacaca   780
tattacagtg actatgtggg ctcaggctac aacccaacca tcattatgga acagtacatt   840
aaagacatat cacaggattc caagaacata tcaccacgca tttcctacca gtttagaacc   900
atcatcaagt attaccgcga catgatcgcc accaggcatc aaacgatgga ccccaggta    960
ttaaacctcg taaagcacgt cgaaaagaaa ttagatatgc ttgatagaga aaaaaattag  1020

SEQ ID NO: 468          moltype = AA  length = 339
FEATURE                 Location/Qualifiers
source                  1..339
                        mol_type = protein
                        organism = African swine fever virus
SEQUENCE: 468
MAGRVKIKQK ELIDSTVKNK NVMNLFHEII GSKGNINFSV VWPKFKKIKQ SVYDYISTLS    60
VLEKANVMQN FEADKKLLEL FVQKLWAAYE GYFKYPEIEK YEVEGQVNFN LVPQCVLEKF   120
SQLYRIRINS ELVTLILNSC AFMSKYNDYI LKKDPYILTI TPGLCFSPIP NFEDLNFKHL   180
YNSDKNSQHD KEFIMFILYK LYTAALGVYN AISIPDIDVE DLENIILSSV SQIKKQIPRC   240
KDAFNKIESS VHLLRKNFNT YYSDYVGSGY NPTIIMEQYI KDISQDSKNI SPRISYQFRT   300
IIKYYRDMIA TRHQTMDPQV LNLVKHVEKK LDMLDREKN                          339

SEQ ID NO: 469          moltype = DNA  length = 1020
FEATURE                 Location/Qualifiers
source                  1..1020
                        mol_type = unassigned DNA
                        organism = African swine fever virus
SEQUENCE: 469
atggccggtc gtgttaaaat aaaacagaaa gagctcatag actctactgt aaaaaacaaa    60
aatgtgatga atctgttcca tgaaattata ggctcaaaag gcaatattaa ttttagcgtt   120
gtctggccca gtttaaaaa aatcaaacag agcgtttatg actacatttc cactcttttct   180
gtgctggaaa agcaaacgt tatgcaaaac tttgaagctg ataagaaact gttggaactt   240
tttgtacaaa agctgtgggc tgcctatgaa ggctatttca aatatcccga gattgaaaaa   300
tatgaggtgg aaggccaggt aaatttcaat ctcgtacctc agtgcgtcct cgaaaagttt   360
agccagttgt ataggataag aatcaattca gagcttgtca cactcatcct aaacagctgt   420
gcctttatga gtaaatataa cgattatatt ctcaaaaaag atccctacat actaaccata   480
accccggcc tatgcttttc ccccattccc aacttcgagg acctaaattt taaacatctt   540
tacaacagtg ataaaaattc tcagcatgac aaagagttta tcatgtttat attatataag   600
ctttatacgg ctgccctagg agtgtacaat gccatctcga ttccagacat cgacgtagaa   660
gaccttgaaa atatcatcct atcctcggtg agccagatta aaaaacaaat tccgcgctgc   720
aaagacgcct tcaacaaaat tgaatcttcg gtacacctgt tgcgcaaaaa ttttaacaca   780
tattacagtg actatgtggg ctcaggctac aacccaacca tcattatgga acagtacatt   840
aaagacatat cacaggattc caagaacata tcaccacgca tttcctacca gtttagaacc   900
atcatcaagt attaccgcga catgattgcc accaggcatc aaacgatgga ccccaggta    960
ttaaacctcg taaagcacgt cgaaaagaaa ttagatatgc ttgatagaga aaaaaattag  1020

SEQ ID NO: 470          moltype = AA  length = 9
FEATURE                 Location/Qualifiers
source                  1..9
                        mol_type = protein
                        organism = African swine fever virus
SEQUENCE: 470
FNLAVKTHF                                                             9
```

```
SEQ ID NO: 471          moltype = AA   length = 359
FEATURE                 Location/Qualifiers
source                  1..359
                        mol_type = protein
                        organism = African swine fever virus
SEQUENCE: 471
MEKIFQNVEI KPFLIDFSNP FIKNAAKRLF QLEEQLPLVP VNVVMDFKGI SRAAVHGLSR   60
VLQDEIPNYM LDIKPGGYKI EDSTDLFMTE QFIRNRINFI PIYAKNETLV FALRSLNNSC  120
EVKTIYSRDL IQVAGPKLKY PIFNPTFEIG FLQPGKSLII EDIYIKKGIG RKHAAFNLAV  180
KTHFSHLDIE QYPTDKKEYM ALSGYKQSSM TSDPRHHRLG LCFPAVPLPH INQAVRTYLK  240
NACRIIIGRI QSIQKIYENF EEPQPELVLF SLDEEKTKAI ITIKDETHTI GNLLKTCIYE  300
MIPDISFVGY QCVPHKQEMV LTIIHKASQE DLITLLEKSI QNIIQTFQIL EKNVDELIA   359

SEQ ID NO: 472          moltype = AA   length = 359
FEATURE                 Location/Qualifiers
source                  1..359
                        mol_type = protein
                        organism = African swine fever virus
SEQUENCE: 472
MEKIFQNVEI KPFLIDFSNL FIKNAAKKLF QLEEQLPLVP VNVVMDFKGI SRAAVHGLSR   60
VLQDEIPNYM LDIKPGGYKI EDSTDLFMTE QFIRNRINFI PIYAKNETLV FALRSLNNSC  120
EVKTIYSRDL IQVAGPKLKY PIFNPTFEIG FLQPGKSLII EDIYIKKGIG RKHAAFNLAV  180
KTHFSHLDIE QYPTDKKEYM ALSGYKQSSM TSDPRHHRLG LCFPAVPLPH INQAVRTYLK  240
NACRIIIGRI QSIQKIYENF EEPQPELVLF SMDEEKTKAI ITIKDETHTI GNLLKTYIYE  300
MIPDISFVGY QCVPHKQEMV LTIIHKASQE DLITLLEKSI QNIIQTFQIL EKNVDELIA   359

SEQ ID NO: 473          moltype = AA   length = 11
FEATURE                 Location/Qualifiers
source                  1..11
                        mol_type = protein
                        organism = African swine fever virus
SEQUENCE: 473
VSLGGTGECY Y                                                        11

SEQ ID NO: 474          moltype = AA   length = 170
FEATURE                 Location/Qualifiers
source                  1..170
                        mol_type = protein
                        organism = African swine fever virus
SEQUENCE: 474
MFYPAIQVLI GIILVIILIL GFYHIKHKLP KKKCKTDTDC KDKGHHCVRG TCTDKSCLEA   60
VKQDIDIKL DPTIRSCDYT PGFYRFNATT ADLQSPFGKT RIDLGKIWTS WGREADYCQS   120
LCLQHKGCIG WEFDEMSLGG EGKCYCYTNP HPALKNSNNT TVMEIARNVL             170

SEQ ID NO: 475          moltype = AA   length = 170
FEATURE                 Location/Qualifiers
source                  1..170
                        mol_type = protein
                        organism = African swine fever virus
SEQUENCE: 475
MFYPVVQVLI GIILVIILIL GFYHLKHKPP KKKCKTDTDC KDKGHHCVRG TCTDKSCLEA   60
VKQDIDIKL DPTIRSCDYA PGFYRFNATT ADLQSPFGKT RIDLGRIWTT WSKEDECCQS   120
LCLQHKGCIG WEFDEVSLGG TGECYYYLNP HLALKNSNNN TVMGIARNVL             170

SEQ ID NO: 476          moltype = AA   length = 10
FEATURE                 Location/Qualifiers
source                  1..10
                        mol_type = protein
                        organism = African swine fever virus
SEQUENCE: 476
MVSRFLIAEY                                                          10

SEQ ID NO: 477          moltype = AA   length = 212
FEATURE                 Location/Qualifiers
source                  1..212
                        mol_type = protein
                        organism = African swine fever virus
SEQUENCE: 477
MVSRFLIAEY RHLIENPSEN FKISVNEKDM TEWDVILRGP PDTFYEGGLF KAKIAFPPEY   60
PYAPPRLTFT SEMWHPNIYS DGKLCISILH GDNAEEQGMT WSPAQKIDTI LLSVISLLNE  120
PNPDSPANVD AAKSYRKLLY KEDLESYPME VKRTVKKSLD ECSPEDIEYF KNAASNVPPI  180
PSDAYEDECE EMEDDTYILT YDDEDEEEED DE                                212

SEQ ID NO: 478          moltype = AA   length = 9
FEATURE                 Location/Qualifiers
source                  1..9
                        mol_type = protein
                        organism = African swine fever virus
SEQUENCE: 478
```

```
KNILNTLMF                                                                        9

SEQ ID NO: 479         moltype = AA  length = 9
FEATURE                Location/Qualifiers
source                 1..9
                       mol_type = protein
                       organism = African swine fever virus
SEQUENCE: 479
TNLYLKQEL                                                                        9

SEQ ID NO: 480         moltype = DNA  length = 27
FEATURE                Location/Qualifiers
source                 1..27
                       mol_type = unassigned DNA
                       organism = African swine fever virus
SEQUENCE: 480
aaaaacattt taaatacgtt gatgttt                                                   27

SEQ ID NO: 481         moltype = AA  length = 9
FEATURE                Location/Qualifiers
source                 1..9
                       mol_type = protein
                       organism = African swine fever virus
SEQUENCE: 481
KNILNTLMF                                                                        9

SEQ ID NO: 482         moltype = DNA  length = 27
FEATURE                Location/Qualifiers
source                 1..27
                       mol_type = unassigned DNA
                       organism = African swine fever virus
SEQUENCE: 482
aaaaacattt taaatacgtt gatgttt                                                   27

SEQ ID NO: 483         moltype = AA  length = 9
FEATURE                Location/Qualifiers
source                 1..9
                       mol_type = protein
                       organism = African swine fever virus
SEQUENCE: 483
TNLYLKQEL                                                                        9

SEQ ID NO: 484         moltype = AA  length = 8
FEATURE                Location/Qualifiers
source                 1..8
                       mol_type = protein
                       organism = African swine fever virus
SEQUENCE: 484
KNILNTLM                                                                         8

SEQ ID NO: 485         moltype = AA  length = 8
FEATURE                Location/Qualifiers
source                 1..8
                       mol_type = protein
                       organism = African swine fever virus
SEQUENCE: 485
TLMFAVRY                                                                         8

SEQ ID NO: 486         moltype = AA  length = 8
FEATURE                Location/Qualifiers
source                 1..8
                       mol_type = protein
                       organism = African swine fever virus
SEQUENCE: 486
RQLSFVLL                                                                         8

SEQ ID NO: 487         moltype = AA  length = 226
FEATURE                Location/Qualifiers
source                 1..226
                       mol_type = protein
                       organism = African swine fever virus
SEQUENCE: 487
MKMETFLVCL PHNADGLHQQ IQEILYLLRM HIYETNLYLK QELSRLIYPN RQLSFVLLMP                60
LSLLRNWDDI EYLTDVVDDK QTLHYAANLL TNYVLHLSMF QKLTKPYFLL AVKRVSEKLN               120
KRQRHSFYEV LVTSETLNNY ENLSKNILNT LMFAVRYVFK PTPNYSEILA ELEKKNKIHH               180
IIFNMVIADF AQIRKQQMDK HLCETNNELR QECKETIFDL KVVGNV                              226

SEQ ID NO: 488         moltype = DNA  length = 681
FEATURE                Location/Qualifiers
```

```
source                  1..681
                        mol_type = unassigned DNA
                        organism = African swine fever virus
SEQUENCE: 488
atgaaaatgg aaacattttt agtctgttta tttcacaatg ctgatggttt acatcaacag    60
attcaggaaa ttttgtattt attgcggatg catatttatg agacaaatct ttacttaaag   120
caggaactat cacggcttat atatccaaat aggcagcttt cttttgtgtt acttatgccc   180
cttccccttc taagaaactg ggatgacatt gaatatttga cggacgttgt agacgataag   240
cagactctac attacgcggc aaatttgctg acaaactacg ttctacatct atccatgttt   300
caaaagctga caaaccata cttccttta gcggtaaagc gggtcagcga aaaactcaac    360
aaaaggcagc gacattcatt ttacgaggta ttggtaaccct ctgaacctt gaataattat   420
gaaaacctat ctaaaaacat tttaaatacg ttgatgtttg ccgtgcgcta cgtatttaaa   480
cctacaccga actattcaga aattctcgca gagttggaaa aaaaaaataa aattcaccat   540
attatttta atatggtaat tgcggatttt gcgcaaatcc gtaaacaaca aatggataaa   600
catctgtgcg aaacaaataa tgagcttcgt caggaatgta agaaactat ttttgattta    660
aaggtggtag gaaatgttta g                                             681

SEQ ID NO: 489          moltype = AA   length = 226
FEATURE                 Location/Qualifiers
source                  1..226
                        mol_type = protein
                        organism = African swine fever virus
SEQUENCE: 489
MKMETFLVCL FHNADGLHQQ IQEILYLLRM HIYETNLYLK QELSRLIYPN RQLSFVLLMP    60
LSLLRNWDDI EYLTDVVDDK QTLHYAANLL TNYVLHLSMF QKLTKPYFLL AVKRVSEKLN   120
KKQRHSFYEV LVTSETLNNY ENLSKNILNT LMFAVRYVFK PTPNYSEILA ELEKKNKIHH   180
IIFNMVITDF AQIREQQMDK HLCETNNELR QECKETIFDL KVVGNV                  226

SEQ ID NO: 490          moltype = DNA   length = 681
FEATURE                 Location/Qualifiers
source                  1..681
                        mol_type = unassigned DNA
                        organism = African swine fever virus
SEQUENCE: 490
atgaaaatgg aaacattttt agtctgttta tttcacaatg cagatggttt acatcaacag    60
attcaggaaa ttttgtattt attgcggatg catatttacg aaacaaatct ttacttaaag   120
caggaactat cacggcttat atatccaaat aggcaactt cttttgtgtt acttatgccc    180
cttccccttc taagaaactg ggatgacatt gaatatttaa cggacgttgt agatgataag   240
cagactctac attacgcggc aaatttgctg acaaactacg ttctacatct atccatgttt   300
caaaagctga caaaccata cttccttta gcggtcaagc gggtcagcga aaaactcaac    360
aaaaagcagc gacattcatt ttacgaggta ttggtaaccct ccgaacctt gaataattat   420
gaaaacctat ctaaaaacat tttaaatacg ttgatgtttg ccgtgcgcta cgtatttaaa   480
cctacgccga actattcaga aattctcgca gagttggaaa aaaaaaataa aattcaccat   540
attatttta atatggtaat tacgattttt gcgcaaatcc gtaacaaca aatggataaa    600
catctgtgtg aaacaaataa tgagcttcgt caggaatgta agaaactat ttttgattta    660
aaggtggtag gaaatgttta g                                             681

SEQ ID NO: 491          moltype = AA   length = 8
FEATURE                 Location/Qualifiers
source                  1..8
                        mol_type = protein
                        organism = African swine fever virus
SEQUENCE: 491
NTILTNKI                                                              8

SEQ ID NO: 492          moltype = AA   length = 9
FEATURE                 Location/Qualifiers
source                  1..9
                        mol_type = protein
                        organism = African swine fever virus
SEQUENCE: 492
IQMMFFRTL                                                             9

SEQ ID NO: 493          moltype = AA   length = 243
FEATURE                 Location/Qualifiers
source                  1..243
                        mol_type = protein
                        organism = African swine fever virus
SEQUENCE: 493
MKMHIARDSI VFLLNKHLQN TILTNKIEQE CFLQADTPKK YLQYIKPFLI NCMTKNITTD    60
LVMKDSKRLE PYIILEMRDI IQMMFFRTLQ KHMFFKEHTD LCTEYAQKIE ASCYHYTYQQ   120
QEKTFLEEYS TRCGTINHII NCEKKSHQQQ DNDALNKLIS GELKPEAIGS MTFAELCPSA   180
ALKEKTEITL RSQQKVAEKT SQLYKCPNCK QRMCTYREVQ TRALDEPSTI FCTCKKCGHE   240
FIG                                                                 243

SEQ ID NO: 494          moltype = AA   length = 243
FEATURE                 Location/Qualifiers
source                  1..243
                        mol_type = protein
```

```
                            organism = African swine fever virus
SEQUENCE: 494
MKMHIARDSI VFLLNKYLQN TILTNKIEQE CFLQADTPKK YLQYIKPFLI NCMTKNITTD   60
LVMKDSKRLE PYIILEMRDI IQMMFFRTLQ KHMFFKEHTD LCTEYAQKIE ASCYHYTYQQ  120
QEKTFLEEYS TRCGTINHII NCEKKSHQQQ DNDALNKLIS GELKPEAIGS MTFAELCPSA  180
ALKEKTEITL RSQQKVAEKT SQLYKCPNCK QRMCTYREVQ TRALDEPSTI FCTCKKCGHE  240
FIG                                                               243

SEQ ID NO: 495             moltype = AA   length = 24
FEATURE                    Location/Qualifiers
source                     1..24
                           mol_type = protein
                           organism = African swine fever virus
SEQUENCE: 495
SNMGYMLTMA SLARFIINTA SFNK                                         24

SEQ ID NO: 496             moltype = AA   length = 9
FEATURE                    Location/Qualifiers
source                     1..9
                           mol_type = protein
                           organism = African swine fever virus
SEQUENCE: 496
LTMASLARF                                                           9

SEQ ID NO: 497             moltype = AA   length = 11
FEATURE                    Location/Qualifiers
source                     1..11
                           mol_type = protein
                           organism = African swine fever virus
SEQUENCE: 497
FQSRHIHHFT L                                                       11

SEQ ID NO: 498             moltype = AA   length = 279
FEATURE                    Location/Qualifiers
source                     1..279
                           mol_type = protein
                           organism = African swine fever virus
SEQUENCE: 498
MLLVLIDVDG FMGQLYNENG TQTILIPREV VIFYWEKNTP SKILQLFFHG GIDPIFEKIN   60
QRSFSFQSRH IHHFTLDESP LPNSIALPTD TLQAFKAGKK MIFQHLVKIT KDHEQILLLH  120
KGGPEGEWIR SFNIPNATVQ NLNDLCCPSV EKLVLKKRDY ISSSIGCPKH IQGSNHCPVF  180
ECHVLFKWIQ ENTSIVQGVL ERPSLPYEKA DLFIEHRINM VDNHPFKKDS IKQNQKKRTG  240
SQRNLSNMGY MLTMASLARF IINTASFNKC IYPLSQDIR                        279

SEQ ID NO: 499             moltype = AA   length = 10
FEATURE                    Location/Qualifiers
source                     1..10
                           mol_type = protein
                           organism = African swine fever virus
SEQUENCE: 499
RSNTPTYLYY                                                         10

SEQ ID NO: 500             moltype = AA   length = 9
FEATURE                    Location/Qualifiers
source                     1..9
                           mol_type = protein
                           organism = African swine fever virus
SEQUENCE: 500
FSNNNTFLY                                                           9

SEQ ID NO: 501             moltype = AA   length = 329
FEATURE                    Location/Qualifiers
source                     1..329
                           mol_type = protein
                           organism = African swine fever virus
SEQUENCE: 501
MLRVFIFFVF LGSGLTGRIK PQVTCKYFIS ENNTWYKYNV TILNSSIVLP AYNTIPSNAA   60
GISCTCHDID YLQKNNISIH YNTSILKTFQ DIRIIRCGMK NISEIAGGFG KELKFLDLRY  120
NDLQVIDYNI LRKLIRSNTP TYLYYNNLMC GKRNCPLYYF LLKQEQTYLK RLPQFFLRRI  180
NFSNNNTFLY HFLSCGNKPG HEFLEYQTKY CRTKFPEINI TVNQLIAKKN TERYKSCYPL  240
VFISILCSCI SFLFLFICLL RSICKKYSCT KQDKSSHNYI PLIPSYTFSL KKHRHPETAV  300
VEDHTTSANS PIVYIPTTEE KKVSCSRRK                                   329

SEQ ID NO: 502             moltype = AA   length = 9
FEATURE                    Location/Qualifiers
source                     1..9
                           mol_type = protein
                           organism = African swine fever virus
SEQUENCE: 502
```

```
TAKNIKVVI                                                                    9

SEQ ID NO: 503          moltype = AA  length = 73
FEATURE                 Location/Qualifiers
source                  1..73
                        mol_type = protein
                        organism = African swine fever virus
SEQUENCE: 503
METQKLISMV KEALEKYQYP LTAKNIKVVI QKEYNVVLPT GSINSILYSN SELFEKIDKT            60
NTIYPPLWIR KTN                                                              73

SEQ ID NO: 504          moltype = AA  length = 72
FEATURE                 Location/Qualifiers
source                  1..72
                        mol_type = protein
                        organism = African swine fever virus
SEQUENCE: 504
METQKLISMV KEALEKYQYP LTAKNIKVVI QKEHNVVLPT GSINSILYSN SELFEKIDKT            60
NTIYPPLWIR KN                                                               72

SEQ ID NO: 505          moltype = AA  length = 10
FEATURE                 Location/Qualifiers
source                  1..10
                        mol_type = protein
                        organism = African swine fever virus
SEQUENCE: 505
MLYNEPLGTY                                                                  10

SEQ ID NO: 506          moltype = AA  length = 102
FEATURE                 Location/Qualifiers
source                  1..102
                        mol_type = protein
                        organism = African swine fever virus
SEQUENCE: 506
MGNHPIKQDM KTCDYYHGEK KLKYMRRMLY NEPLGTYAVS SLFGCDMIVL TWNCTISGRT            60
LHRRIHTRFG QYYHNNCYYT KIDDIIGDYP DTFYRPLYRY KP                              102

SEQ ID NO: 507          moltype = AA  length = 8
FEATURE                 Location/Qualifiers
source                  1..8
                        mol_type = protein
                        organism = African swine fever virus
SEQUENCE: 507
RLYPHIFY                                                                    8

SEQ ID NO: 508          moltype = AA  length = 103
FEATURE                 Location/Qualifiers
source                  1..103
                        mol_type = protein
                        organism = African swine fever virus
SEQUENCE: 508
MGNRLIKKDL KKCEYYYGEQ QNLKQIWRLL FNEPLGTYVV SSFLKKNYVV ISFSCPTNTR            60
IMHLRINICY DLYCINGEYY EKIDDFIRLY PHIFYRPLYR YKS                             103

SEQ ID NO: 509          moltype = AA  length = 103
FEATURE                 Location/Qualifiers
source                  1..103
                        mol_type = protein
                        organism = African swine fever virus
SEQUENCE: 509
MGNRLIKKDL KKCEYYYGEQ QNLKQIWRLL FNEPLGTYVV SSFLKKNYVV ISFSCPTNTR            60
IMHLRINICY DLYCINGEYY EKIDDFIRLY PHIFYRPLYR YKS                             103

SEQ ID NO: 510          moltype = AA  length = 9
FEATURE                 Location/Qualifiers
source                  1..9
                        mol_type = protein
                        organism = African swine fever virus
SEQUENCE: 510
YKIYIHSDL                                                                   9

SEQ ID NO: 511          moltype = AA  length = 11
FEATURE                 Location/Qualifiers
source                  1..11
                        mol_type = protein
                        organism = African swine fever virus
SEQUENCE: 511
STFSSQDFDE Y                                                                11
```

| | |
|---|---|
| SEQ ID NO: 512 | moltype = AA length = 98 |
| FEATURE | Location/Qualifiers |
| source | 1..98 |
| | mol_type = protein |
| | organism = African swine fever virus |

SEQUENCE: 512
```
METFSVTASA KSDDAVCKYL EEPIDENKNS RNILRNEHGK KKLNEALNRH IIAYNPVVDW   60
CNNYSTYSSQ YFDEYKIYIH SDLMDGRPRP KKTWCVIM                          98
```

| | |
|---|---|
| SEQ ID NO: 513 | moltype = AA length = 96 |
| FEATURE | Location/Qualifiers |
| source | 1..96 |
| | mol_type = protein |
| | organism = African swine fever virus |

SEQUENCE: 513
```
MGTFSVTASA KSDDAVCKYL EEPIDENYRN ILRNEHVKKN LNEALNRHIT TYNPVVDWCN   60
NYSTFSSQDF DEYKIYIHSD LMDGRPRPKK TWCVIM                            96
```

| | |
|---|---|
| SEQ ID NO: 514 | moltype = AA length = 11 |
| FEATURE | Location/Qualifiers |
| source | 1..11 |
| | mol_type = protein |
| | organism = African swine fever virus |

SEQUENCE: 514
```
AKIVEEGGEE S                                                       11
```

| | |
|---|---|
| SEQ ID NO: 515 | moltype = AA length = 10 |
| FEATURE | Location/Qualifiers |
| source | 1..10 |
| | mol_type = protein |
| | organism = African swine fever virus |

SEQUENCE: 515
```
KLDPIGFINY                                                         10
```

| | |
|---|---|
| SEQ ID NO: 516 | moltype = AA length = 10 |
| FEATURE | Location/Qualifiers |
| source | 1..10 |
| | mol_type = protein |
| | organism = African swine fever virus |

SEQUENCE: 516
```
YIKTSKQEYL                                                         10
```

| | |
|---|---|
| SEQ ID NO: 517 | moltype = DNA length = 33 |
| FEATURE | Location/Qualifiers |
| source | 1..33 |
| | mol_type = unassigned DNA |
| | organism = African swine fever virus |

SEQUENCE: 517
```
gcaaagattg ttgaagaagg aggagaagaa tcc                               33
```

| | |
|---|---|
| SEQ ID NO: 518 | moltype = AA length = 11 |
| FEATURE | Location/Qualifiers |
| source | 1..11 |
| | mol_type = protein |
| | organism = African swine fever virus |

SEQUENCE: 518
```
AKIVEEGGEE S                                                       11
```

| | |
|---|---|
| SEQ ID NO: 519 | moltype = DNA length = 33 |
| FEATURE | Location/Qualifiers |
| source | 1..33 |
| | mol_type = unassigned DNA |
| | organism = African swine fever virus |

SEQUENCE: 519
```
gcaaagattg ttgaagaagg aggagaagaa tcc                               33
```

| | |
|---|---|
| SEQ ID NO: 520 | moltype = AA length = 10 |
| FEATURE | Location/Qualifiers |
| source | 1..10 |
| | mol_type = protein |
| | organism = African swine fever virus |

SEQUENCE: 520
```
KLDPIGFINY                                                         10
```

| | |
|---|---|
| SEQ ID NO: 521 | moltype = AA length = 10 |
| FEATURE | Location/Qualifiers |
| source | 1..10 |
| | mol_type = protein |
| | organism = African swine fever virus |

-continued

```
SEQUENCE: 521
YIKTSKQEYL                                                              10

SEQ ID NO: 522         moltype = AA  length = 16
FEATURE                Location/Qualifiers
source                 1..16
                       mol_type = protein
                       organism = African swine fever virus
SEQUENCE: 522
TQLYRSIQQL FLTMYK                                                       16

SEQ ID NO: 523         moltype = AA  length = 10
FEATURE                Location/Qualifiers
source                 1..10
                       mol_type = protein
                       organism = African swine fever virus
SEQUENCE: 523
SIQQLFLTMY                                                              10

SEQ ID NO: 524         moltype = AA  length = 145
FEATURE                Location/Qualifiers
source                 1..145
                       mol_type = protein
                       organism = African swine fever virus
SEQUENCE: 524
MDHYLKKLQD IYTKLEGHPF LFSPSKTNEK EFITLLNQAL ASTQLYRSIQ QLFLTMYKLD        60
PIGFINYIKT SKQEYLCLLI NPKLVTKFLK ITSFKIYINF RLKTFYISPN KYNNFYTAPS       120
EEKTNHLLKE EKTWAKIVEE GGEES                                            145

SEQ ID NO: 525         moltype = DNA  length = 438
FEATURE                Location/Qualifiers
source                 1..438
                       mol_type = unassigned DNA
                       organism = African swine fever virus
SEQUENCE: 525
atggatcatt atcttaaaaa attacaagat atttatacga agctcgaggg ccatcccttt        60
cttttttagcc cgtcgaaaac caatgaaaaa gagtttatta ctctgctaaa ccaggccttg     120
gcctcaacgc agctttaccg cagcatacaa cagctgtttt taacgatgta taagctagat     180
cccattgggt ttattaacta tattaaaacg agtaaacaag agtatttatg cctgttgatt     240
aatcctaaac tcgttactaa gttttttaaa ataacgagct ttaaaattta cattaatttc     300
agactgaaaa cttttttatat aagtcctaat aagtataata attttttacac tgctcccctct   360
gaagaaaaga ctaaccatct cctaaaagaa gaaaaaactt gggcaaagat tgttgaagaa     420
ggaggagaag aatcctaa                                                   438

SEQ ID NO: 526         moltype = AA  length = 145
FEATURE                Location/Qualifiers
source                 1..145
                       mol_type = protein
                       organism = African swine fever virus
SEQUENCE: 526
MDHYLKKLQD IYTKLEGHPF LFSPSKTNEK EFITLLNQAL ASTQLYRSIQ QLFLTMYKLD        60
PIGFINYIKT SKQEYLCLLI NPKLVTKFLK ITSFKIYINF RLKTFYISPN KYNNFYTAPS       120
EEKTNHLLKE EKTWAKIVEE GGEES                                            145

SEQ ID NO: 527         moltype = DNA  length = 438
FEATURE                Location/Qualifiers
source                 1..438
                       mol_type = unassigned DNA
                       organism = African swine fever virus
SEQUENCE: 527
atggatcatt atcttaaaaa attacaagat atttatacga agctcgaggg tcatcccttt        60
cttttttagcc cgtcgaaaac caatgaaaaa gagtttatta ctctgctaaa ccaggccttg     120
gcctcaacgc agctttaccg cagcatacaa cagctgtttt taacgatgta taagctagat     180
cccattgggt ttattaacta tattaaaacg agtaaacaag agtatttatg cctgttaatt     240
aatcctaaac tcgttactaa gttttttaaa ataacgagct ttaaaattta cattaatttc     300
aggctgaaaa cttttttatat aagtcctaat aagtataata attttttacac cgctcccctct   360
gaagaaaaga ctaaccatct tctaaaagaa gaaaaaactt gggcaaagat tgttgaagaa     420
ggaggagaag aatcctaa                                                   438

SEQ ID NO: 528         moltype = AA  length = 11
FEATURE                Location/Qualifiers
source                 1..11
                       mol_type = protein
                       organism = African swine fever virus
SEQUENCE: 528
MVSFENFIER Y                                                            11

SEQ ID NO: 529         moltype = AA  length = 205
FEATURE                Location/Qualifiers
```

```
source                  1..205
                        mol_type = protein
                        organism = African swine fever virus
SEQUENCE: 529
MVEPREQFFQ DLLSAVDQQM DTVKNDIKDI MKEKTSFMVS FENFIERYDT MEKNIQDLQN   60
KYEEMAANLM TVMTDTKIQL GAIIAQLEIL MINGTPLPAK KTTIKEAMPL PSSNTNNEQT  120
SPPASGKTSE TPKKNPTNAM FFTRSEWASS NTFREKFLTP EIQAILDEQF ANKTGIERLH  180
AEGLYMWRTQ FSDEQKKMVK EMMKK                                       205

SEQ ID NO: 530          moltype = AA   length = 18
FEATURE                 Location/Qualifiers
source                  1..18
                        mol_type = protein
                        organism = African swine fever virus
SEQUENCE: 530
AEHSKALATL LYKLDPEY                                                18

SEQ ID NO: 531          moltype = AA   length = 9
FEATURE                 Location/Qualifiers
source                  1..9
                        mol_type = protein
                        organism = African swine fever virus
SEQUENCE: 531
LLYKLDPEY                                                           9

SEQ ID NO: 532          moltype = AA   length = 422
FEATURE                 Location/Qualifiers
source                  1..422
                        mol_type = protein
                        organism = African swine fever virus
SEQUENCE: 532
MYTHVDVVGI AEASAALYVQ KDRDRYLDVL TTIENFIYQH KCIITGESAH LLFLKKNIYL   60
YEFYSNNVAE HSKALATLLY KLDPEYLTRY TVLITKIPNH WYVINVDQRE FVRLYAIPAV  120
KQHLPIPILP FYCTSALTQQ ELFCLGPELQ LIQIYSKLCN PNFVEEWPTL LDYEKSMRML  180
FLEQFPQRLE MTGGKKEEKE KHESIIKKII LEMVSTRQRI VVGGYIQKNL YNHVLKNRNR  240
LQLITSLNIY EEKDIIQQFC DSNGLKIKIR INNPLLPTNP ELRRLTIYFN HNNDDDQSYL  300
IVDMYNTGSY ELVPTNQINT LDGSFLIGTP FVQARFLLVE IWVLMLIAQQ TKKDTKKIIQ  360
FFINQYEMLM NSPWPSMEAL FPSSSKRYLG NYVDPNALIK WAQLKLKRIP PFYPGKPDEE  420
SC                                                                422

SEQ ID NO: 533          moltype = AA   length = 9
FEATURE                 Location/Qualifiers
source                  1..9
                        mol_type = protein
                        organism = African swine fever virus
SEQUENCE: 533
SSMHSGMLY                                                           9

SEQ ID NO: 534          moltype = AA   length = 78
FEATURE                 Location/Qualifiers
source                  1..78
                        mol_type = protein
                        organism = African swine fever virus
SEQUENCE: 534
MPTKAGTKST ANKKTTKGSS KSGSSRGHTG KTHASSSMHS GMLYKDMVNI ARSRGIPIYQ   60
NGSRLTKSEL EKKIKRSK                                                78

SEQ ID NO: 535          moltype = AA   length = 77
FEATURE                 Location/Qualifiers
source                  1..77
                        mol_type = protein
                        organism = African swine fever virus
SEQUENCE: 535
MLEPILVMAP IPLVLIFLYS YFKIKLHKLI TIALFLGCLF FILRDFCFPP MLWTQLHNIT   60
SSINILGNNS FQVKCNK                                                 77

SEQ ID NO: 536          moltype = AA   length = 93
FEATURE                 Location/Qualifiers
source                  1..93
                        mol_type = protein
                        organism = African swine fever virus
SEQUENCE: 536
MDFFLLKKIF FFVDNRMLEP MLVMAPIPLV LIFLYSYFKI KLHKLITIAL FLGCLFFILR   60
DFCFPPMLWT QLHNITSSIN ILGNKSFQVQ CNK                               93

SEQ ID NO: 537          moltype = AA   length = 67
FEATURE                 Location/Qualifiers
source                  1..67
                        mol_type = protein
```

```
                          organism = African swine fever virus
SEQUENCE: 537
MDDTLPKQMT PTDTSPLKEE QAHCNNKTLE NQPKNINDNK CTDSQNTDLQ NTESQNTDLQ    60
NTEPSKV                                                              67

SEQ ID NO: 538            moltype = AA  length = 52
FEATURE                   Location/Qualifiers
source                    1..52
                          mol_type = protein
                          organism = African swine fever virus
SEQUENCE: 538
MDDTLPKQMT PTDTSSSKEE QAHCNNKTLE KQPKNINDNK CTDSQNTESS KV             52

SEQ ID NO: 539            moltype = AA  length = 8
FEATURE                   Location/Qualifiers
source                    1..8
                          mol_type = protein
                          organism = African swine fever virus
SEQUENCE: 539
KNIRLIDF                                                             8

SEQ ID NO: 540            moltype = AA  length = 12
FEATURE                   Location/Qualifiers
source                    1..12
                          mol_type = protein
                          organism = African swine fever virus
SEQUENCE: 540
TPAELLSQKE FY                                                        12

SEQ ID NO: 541            moltype = AA  length = 8
FEATURE                   Location/Qualifiers
source                    1..8
                          mol_type = protein
                          organism = African swine fever virus
SEQUENCE: 541
YAATVARI                                                             8

SEQ ID NO: 542            moltype = AA  length = 8
FEATURE                   Location/Qualifiers
source                    1..8
                          mol_type = protein
                          organism = African swine fever virus
SEQUENCE: 542
KNIRLIDF                                                             8

SEQ ID NO: 543            moltype = AA  length = 8
FEATURE                   Location/Qualifiers
source                    1..8
                          mol_type = protein
                          organism = African swine fever virus
SEQUENCE: 543
YAATVARI                                                             8

SEQ ID NO: 544            moltype = AA  length = 12
FEATURE                   Location/Qualifiers
source                    1..12
                          mol_type = protein
                          organism = African swine fever virus
SEQUENCE: 544
TPAELLSQKE FY                                                        12

SEQ ID NO: 545            moltype = AA  length = 11
FEATURE                   Location/Qualifiers
source                    1..11
                          mol_type = protein
                          organism = African swine fever virus
SEQUENCE: 545
AVDSAVRIFL Y                                                         11

SEQ ID NO: 546            moltype = AA  length = 11
FEATURE                   Location/Qualifiers
source                    1..11
                          mol_type = protein
                          organism = African swine fever virus
SEQUENCE: 546
RVTDPASALL Y                                                         11

SEQ ID NO: 547            moltype = AA  length = 15
FEATURE                   Location/Qualifiers
```

```
source                   1..15
                         mol_type = protein
                         organism = African swine fever virus
SEQUENCE: 547
RVTDPASALL YSIEF                                                   15

SEQ ID NO: 548           moltype = AA   length = 10
FEATURE                  Location/Qualifiers
source                   1..10
                         mol_type = protein
                         organism = African swine fever virus
SEQUENCE: 548
STMYSVSPVF                                                         10

SEQ ID NO: 549           moltype = AA   length = 27
FEATURE                  Location/Qualifiers
source                   1..27
                         mol_type = protein
                         organism = African swine fever virus
SEQUENCE: 549
STMYSVSPVF TSGYMPLLYD LYRAGYL                                      27

SEQ ID NO: 550           moltype = AA   length = 10
FEATURE                  Location/Qualifiers
source                   1..10
                         mol_type = protein
                         organism = African swine fever virus
SEQUENCE: 550
SVSPVFTSGY                                                         10

SEQ ID NO: 551           moltype = AA   length = 9
FEATURE                  Location/Qualifiers
source                   1..9
                         mol_type = protein
                         organism = African swine fever virus
SEQUENCE: 551
TSGYMPLLY                                                           9

SEQ ID NO: 552           moltype = AA   length = 10
FEATURE                  Location/Qualifiers
source                   1..10
                         mol_type = protein
                         organism = African swine fever virus
SEQUENCE: 552
LLYDLYRAGY                                                         10

SEQ ID NO: 553           moltype = AA   length = 10
FEATURE                  Location/Qualifiers
source                   1..10
                         mol_type = protein
                         organism = African swine fever virus
SEQUENCE: 553
AVNVCLPLVY                                                         10

SEQ ID NO: 554           moltype = AA   length = 8
FEATURE                  Location/Qualifiers
source                   1..8
                         mol_type = protein
                         organism = African swine fever virus
SEQUENCE: 554
AVIYIYAY                                                            8

SEQ ID NO: 555           moltype = AA   length = 11
FEATURE                  Location/Qualifiers
source                   1..11
                         mol_type = protein
                         organism = African swine fever virus
SEQUENCE: 555
KTSTLIYLRA Y                                                       11

SEQ ID NO: 556           moltype = AA   length = 12
FEATURE                  Location/Qualifiers
source                   1..12
                         mol_type = protein
                         organism = African swine fever virus
SEQUENCE: 556
YLRAYELFLK YL                                                      12

SEQ ID NO: 557           moltype = AA   length = 9
```

```
FEATURE                 Location/Qualifiers
source                  1..9
                        mol_type = protein
                        organism = African swine fever virus
SEQUENCE: 557
RAYELFLKY                                                                          9

SEQ ID NO: 558          moltype = AA  length = 17
FEATURE                 Location/Qualifiers
source                  1..17
                        mol_type = protein
                        organism = African swine fever virus
SEQUENCE: 558
QTALKASLEF NTFYAFY                                                                17

SEQ ID NO: 559          moltype = AA  length = 11
FEATURE                 Location/Qualifiers
source                  1..11
                        mol_type = protein
                        organism = African swine fever virus
SEQUENCE: 559
ASLEFNTFYA F                                                                      11

SEQ ID NO: 560          moltype = AA  length = 11
FEATURE                 Location/Qualifiers
source                  1..11
                        mol_type = protein
                        organism = African swine fever virus
SEQUENCE: 560
SLEFNTFYAF Y                                                                      11

SEQ ID NO: 561          moltype = AA  length = 1249
FEATURE                 Location/Qualifiers
source                  1..1249
                        mol_type = protein
                        organism = African swine fever virus
SEQUENCE: 561
MEEVITIAQI VHRGTDILSL NNEEIEALVD EIYSTLKGSN DIKNIRLIDF LFTLKDFVNH    60
VRAEQSKLPD LSMPMEAYIR QLLVDPDVVP IVSEKKKELR VRPSTRKEIF LINGTHLAVP   120
AEAPIEIYGL KLRLKSFSPQ CFMRMAEIGS FSPETLGYVA SGANLTNFIR VPMKCVDQET   180
WKKNGEGVVV TTKENIIQFT HQYIELYKFL RSGGHSWLIN RLAEEMVHRK LDREDQGSHI   240
SNIVETEEIE PEENIKRVIF FLKELSTMYS VSPVFTSGYM PLLYDLYRAG YLEVLWNPVE   300
QKFLQHAEQR EKEQMILQQV DMKLTEVITQ ARQYFKIMEE KIGRVQSDAI REILTMEGKV   360
DDPNSILQEV IKACGKQEAE LITTEYLNIK QWELQEKNA CAHLKLVKQL RSGLQYAELL    420
KVLESIRVLY KEKNNTTNWN LCKACGFKLL CPHVDMLIQL QAAEASYDTM RTKLMKFSGI   480
NKEKENNQGL IYSYFCKICG EELAHFIQED RTADVGVIGD LNSKLRIFIW QETMKACTFI   540
HFGKLVDVKQ FANIAVNVCL PLVYSIENIK KEEDYDPLTQ LYAVIYIYAY ILNLIYSSQK   600
NKEFLTITIH GMKADSSLNA YVTFLLEKMM QQYSGIINQL SEITDQWIAN NFREAFKKII   660
HQNGLQGLSV QDDTKVLLTE ILLDPMYDYA ATVARIDGSI PMHKPRTPKE AEYEFKTVIG   720
RTPAELLSQK EFYDKIYTSK YRPDFTQLAR LNDIYFQEES LRVWWGGRDE EKTSTLIYLR   780
AYELFLKYLQ NAPNFNSELA EFKTYENAYG EQKALLAQQG FYNIFDPNTG RADQRTRLFE   840
YKRLPISTLY DERGLPHKWT IYVYKAVDSS QKPAEIEVTR KDVIKKIDNH YALADLRCSV   900
CHVLQHEVGQ LNIKKVQTAL KASLEFNTFY AFYESRCPKG GLHDFQDKKC VKCGLFTYII   960
YDHLSQPELV HDYYNNYKDQ YDKEKMSIRS IQIKKDMTTP SSETQPKPPQ EPWTFDGYKI  1020
IKTAKILDIS PAVIEAIGAM EGRSYADIRE GQGAPPPPTS MDDPRLMAVD SAVRIFLYNY  1080
NCLRHVSTFN KPPMHVERLV KHLSYEEKED LEKVLPNVVN EYHTTFKHLR VTDPASALLY  1140
SIEFLCVSFL TLYEIKEPSW VVNIVREFAL TELNTIIQSE KLLSKPGAFN FMIFGEDFVC  1200
SGEDSSMDYI SAYSSPGLFG EDIIDRLDDP FSIEDVDISL DVLDNLAPQ              1249

SEQ ID NO: 562          moltype = AA  length = 1249
FEATURE                 Location/Qualifiers
source                  1..1249
                        mol_type = protein
                        organism = African swine fever virus
SEQUENCE: 562
MEEVITIAQI VHRGTDILSL NNEEIEALVD EIYSTLKGSN DIKNIRLIDF LFTLKDFVNH    60
VRAEQSKLPD LSMPIEAYIR QLLVDPDVVP IVSEKKKELR VRPSTRKEIF LINGTHLAVP   120
AEAPIEIYGL KLRLKTFSPQ CFMRMAEIGS FSPETLGYVA SGANLTNFIR VPMKCVDQET   180
WKKNGEGVVV TTKENIIQFT HQYIELYKFL RSGGHSWLIN RLAEEMVHRK LDREDQGSHI   240
SNIVETEEIE PEENIKRVIF FLKELSTMYS VSPVFTSGYM PLLYDLYRAG YLEVLWNPVE   300
QKFLQHAEQR EKEQMILQQV DMKLTEVITQ ARQYFKIMEE KIGRVQSDAI REILTMEGKV   360
DDPNSILQEV IKACGKQEAE LITTEYLNIK QWELQEKNA CAHLKLVKQL RSGLQYAELL    420
KVLESIRVLY KEKNNTTNWN LCKACGFKLL CPHVDMLIQL QAAEASYDTM RTKLMKFSGI   480
NKEKENNQGL IYSYFCKICG EELAHFIQED RTADVGIIGD LNSKLRVFIW QETMKACTFI   540
HFGKLVDVKQ FANIAVNVCL PLVYSIENIK KEEDYDPLTQ LYAVIYIYAY ILNLIYSSQK   600
NKEFLTITIH GMKADSSLNA YVTFLLEKMM QQYSGIINQL SEITDQWIAN NFREAFKKII   660
HQNGLQGLSV QDDTKVLLTE ILLDPMYDYA ATVARIDGSI PMHKPRTPKE AEYEFKTVIG   720
RTPAELLSQK EFYDKIYTSK YRPDFTQLTR LNDIYFQEES LRVWWGGRDE EKTSTLIYLR   780
AYELFLKYLQ NAPNFNSELA EFKTYENAYG EQKALLAQQG FYNIFDPNTG RADQRTRLFE   840
```

-continued

```
YKRLPISTLY DERGLPHKWT IYVYKAVDSS QKPAEIEVTR KDVIKKIDNH YALADLRCSV    900
CHVLQHEVGQ LNIKKVQTAL KASLEFNTFY AFYESRCPKG GLHDFQDKKC VKCGLFTYII    960
YDHLSQPELV HDYYNNYKDQ YDKEKMSIRS IQIKKDMTTP STETQPKPPQ EPWTFDYGKI   1020
IKTAKILDIS PAVIEAIGAM EGRSYADIRE GQGAPPPPTS MDDPRLMAVD SAVRIFLYNY   1080
NCLRHVSTFN KPPIHVERLV KHLSYEEKED LEKVLPNVVN EYHTTFKHLR VTDPASALLY   1140
SIEFLCISFL TLYEIKEPSW VVNIVREFAL TELNTIIQSE KLLSKPGAFN FMIFGEDFVC   1200
SGEDSSMDDI SAYSSPGLFG EDIIDRLDDP FSIEDVDISL DVLDNLAPQ              1249

SEQ ID NO: 563         moltype = AA  length = 9
FEATURE                Location/Qualifiers
source                 1..9
                       mol_type = protein
                       organism = African swine fever virus
SEQUENCE: 563
RAKIPAQEI                                                             9

SEQ ID NO: 564         moltype = AA  length = 11
FEATURE                Location/Qualifiers
source                 1..11
                       mol_type = protein
                       organism = African swine fever virus
SEQUENCE: 564
LTIYHWDDPE Y                                                         11

SEQ ID NO: 565         moltype = AA  length = 10
FEATURE                Location/Qualifiers
source                 1..10
                       mol_type = protein
                       organism = African swine fever virus
SEQUENCE: 565
KTLKTVYPEY                                                           10

SEQ ID NO: 566         moltype = AA  length = 448
FEATURE                Location/Qualifiers
source                 1..448
                       mol_type = protein
                       organism = African swine fever virus
SEQUENCE: 566
MSNESFPETL ENLLSTLQTK QQNAIQSEVI EWLHSFCETF HLKIHCHKQF IPSGEKKRAK    60
IPAQEIQGNT QPSHHVHRVV LSRAQPVKAQ ESLLTTMCNG LVLDANTWTC LAIPPPAPFQ   120
QATRQVQHFY RNNFYEVVPI QDGTLLTIYY WDDPEHGPSW CLASTHGYDV SNYCWIGDKT   180
FAELVYELLQ QHSTCDVTLE KNKTRGTRLF FNNLNPDYCY TIGIRHHNLQ PLIYDPQNIW   240
AIQSTNLKTL KTVYPEYYGY IGIPGIQSQV PELPQYDLPY LIRSYKTAMN QAKNAIKNGK   300
KDKEYFNYGY LLISRAPAIT KSTSNVLLKS PLLVFLQKSV YQKKHNISNS QRLEFIILQN   360
YLMQHFRDHF IALFPQYISY YTKYQNMLNM IIHSIATKDK DHPFAGAVVK KVLEDIENAE   420
NIIDHTTIQN YAHQSKYAML YLSIISHF                                      448

SEQ ID NO: 567         moltype = DNA  length = 1347
FEATURE                Location/Qualifiers
source                 1..1347
                       mol_type = unassigned DNA
                       organism = African swine fever virus
SEQUENCE: 567
atgtcaaatg aaagttttcc cgaaacgttg gaaaacctac tttcgacgtt acagaccaaa    60
cagcaaaacg caattcagtc agaggtgatt gaatggctgc acagcttttg tgaaacctttt  120
cacttaaaaa tacactgcca taaacagttg attcctagcg gggaaaaaaa acgagctaaa   180
atacctgctc aggaaataca gggaaacacg cagccctccc accatgtgca ccgggttgtt   240
cttttccagag cacagccggt caaagcgcag gaatctctgc taacaaccat gtgcaacgga   300
ctggtgctag atgcaaacac atggacatgt ctagccattc ctccgcctgc gcccttttcaa  360
caggcgaccc gtcaagtcca acactttttac cgtaacaatt tctacgaagt ggttcccatc   420
caggatggca cccttctcac aatctactac tgggatgacc ccgagcatgg ccctcctgg    480
tgcctagcaa gtacccacgg atatgatgtg agtaactact gttggatagg cgacaaaacc    540
ttcgccgagc ttgtatacga attgctacag cagcactcta cctgcgacgt caccctggaa   600
aaaaataaaa cgcggggaac acgtcttttc tttaacaact taaatcccga ttactgctat   660
acgattggaa ttcggcacca taatttacag ccgcttatct atgacctca aaatatttg    720
gcgattcaat ctacaaacct aaaaacgctt aaaacggtat atccagaata ctacggctat    780
ataggcattc aggaattca gagtcaagtt cctgagcttc cccagtatga tttacctatt     840
ctaatacgat cctataagac tgctatgaat caagccaaaa atgctataaa aatgggcaaa   900
aaagacaagg aatactttaa ttatggctat ttactcattt cgcgagcgcc tgccattact   960
aaaagtactt ctaatgtttt gttaaaatcg cctctgctgg tattttttaca aaaaagtgtg  1020
taccagaaaa aacacaatat ctctaacagc cagcggctag aatttattat actgcaaaac  1080
tacttgatgc agcattttcg agatcatttc attgctctat ttccgcagta catatcctat  1140
tatacgaaat accaaaacat gttgaatatg attatccata gtattgcaac caagatgaaa   1200
gatcatccct ttgcaggagc cgtggtaaaa aaagtattgg aagatattga aaacgccgaa   1260
aacattattg atcatacaac cattcaaaac tatgcccatc aaagcaagta cgctatgctt   1320
tacttgtcaa ttatttccca ttttttaa                                     1347

SEQ ID NO: 568         moltype = AA  length = 448
FEATURE                Location/Qualifiers
```

```
source                  1..448
                        mol_type = protein
                        organism = African swine fever virus
SEQUENCE: 568
MSNESFPETL ENLLSMLQTK QQNAIQSEVI EWLHSFCETF HLKIHCHKQF IPSGEKKRAK    60
IPAQETQGNT QPSHHVYRVV LSRAQPVKAQ ESLLTTMCNG LVLDANTWTC LAIPPPAPFQ   120
QATRQVQHFY RNNFYEVVPI QDGTLLTIYH WDDPEYGPSW CLASTHGYDV SNYCWIGDKT   180
FAELVYELLQ QHSTCDVTLE KNKTRGTRLF FDNLNPDYCY TIGIRHHNLQ PLIYDPQNIW   240
AIQSTNLKTL KTVYPEYYGY IGIPGIQSQV PELPQYDLPY LIRSYKTAMN QAKNAIKNGK   300
KDKGYFNYGY LLISRAPAIT KSTSNVLLKS PLLVFLQKSV YQKKHNISNS QRLEFIILQN   360
YLMQHFRDHF IALFPQYISY YTKYQNMLNM IIHSIATKDK DHPFAGAVVK KVLEDIENAE   420
NIIDHTTIQN YAHQSKYAML YLSIISHF                                     448

SEQ ID NO: 569          moltype = DNA  length = 1347
FEATURE                 Location/Qualifiers
source                  1..1347
                        mol_type = unassigned DNA
                        organism = African swine fever virus
SEQUENCE: 569
atgtcaaatg aaagttttcc cgaaacgttg gaaaacttac tttcaatgtt acagaccaaa    60
cagcaaaacg caattcagtc agaggtgatt gaatggctgc acagcttttg tgaaaccttt   120
cacttaaaaa tacactgcca taaacagttt attcctagcg gggaaaaaaa acgagctaaa   180
ataccgctc aagaaacaca gggaaacacg cagccctccc accatgtgta ccgggttgtt   240
ctctccagag cacagccagt caaagcacag gaatctctgc taacaaccat gtgcaacgga   300
ctggtgctag atgcaaacac atggacatgc ctagccattc ctccgcctgc gccctttcaa   360
caggcgaccc gccaggtcca acactttac cgtaacaatt tctacgaagt ggttcccatc   420
caggatggca cccttctcac aatctaccac tgggatgacc ctgaatatgg ccccctcctgg  480
tgcctagcaa gtacccacgg atatgatgtg agtaactact gttggatagg cgacaaaacc   540
ttcgccgagc ttgtatacga attgctgcag cagcactcta cctgcgacgt caccctggaa   600
aaaaataaaa cgcggggaac gcgtctttc tttgataact taaatcccga ttactgctaa    660
acgattggaa tccggcacca taatttacag ccgctcatct atgaccctca aaatatttgg   720
gcgattcaat ctacaaacct aaaaacgctt aaaacggtat atccagaata ctacggctat   780
ataggcattc caggaattca gagtcaagtt cctgagcttc cccagtatga tttacccttat  840
ctaatacgat cttataaaac tgctatgaat caagccataa atgctataaa aatggcaag    900
aaagacaagg gatactttaa ttatggctat ttactcattt cgcgagcgcc tgccattact   960
aaaagtactt ctaatgtttt gttaaaatcg cctctgctgg tatttttaca aaaaagtgtg  1020
taccagaaaa aacacaatat ctctaacagc agcgactag aatttattat actgcaaaac   1080
tacttgatgc agcattttcg agatcatttc attgctctat ttccgcagta catatcctat  1140
tatacgaaat accaaaacat gttgaatatg attatccata gtattgcaac taaagataaa  1200
gatcatccct ttgcaggagc cgtggtaaaa aagtgttgg aagatattga aaacgccgaa   1260
aacattattg atcatacaac cattcaaaac tatgcccatc aaagcaagta cgccatgctt  1320
tacttgtcaa ttattccca tttttaa                                      1347

SEQ ID NO: 570          moltype = AA  length = 19
FEATURE                 Location/Qualifiers
source                  1..19
                        mol_type = protein
                        organism = African swine fever virus
SEQUENCE: 570
LQMAPGGSYF ITDNMTEEF                                                19

SEQ ID NO: 571          moltype = DNA  length = 57
FEATURE                 Location/Qualifiers
source                  1..57
                        mol_type = unassigned DNA
                        organism = African swine fever virus
SEQUENCE: 571
ctacaaatgg ctccaggagg atcttatttt attacagata atatgactga ggagttt       57

SEQ ID NO: 572          moltype = AA  length = 141
FEATURE                 Location/Qualifiers
source                  1..141
                        mol_type = protein
                        organism = African swine fever virus
SEQUENCE: 572
MGNKESKYLE MCSEEAWLNI PNIFKCIFIR KLFYNKWLKY QEKKLKKSLK LLSFYHPKKD    60
FVGIRDMLQM APGGSYFITD NMTEEFLMLV VKHPEDGSAE FTKLCLKGSC IVIDGYYYDN   120
LHIFISETPD IYKYPLIRYD R                                             141

SEQ ID NO: 573          moltype = DNA  length = 426
FEATURE                 Location/Qualifiers
source                  1..426
                        mol_type = unassigned DNA
                        organism = African swine fever virus
SEQUENCE: 573
atgggaaaca aagaaagtaa gtatctggag atgtgctcgg aagaagcatg gttaaacatt    60
cccaatattt tcaaatgcat tttcataaga aaactgtttt ataacaaatg gcttaaatac   120
caggaaaaaa aactaaaaaa gagtttgaaa ctgctgagtt tttaccatcc caaaaaagat   180
tttgtaggaa taagagacat gctacaaatg gctccaggag gatcttattt tattacagat   240
```

```
                                              -continued
aatatgactg aggagttttt aatgttagtt gtaaagcatc cagaagatgg gagtgctgag    300
tttactaaat tatgccttaa aggaagttgc attgtgattg atggatacta ctatgataat    360
cttcatatct ttatttcaga aactcctgat atacaaaat atcccttgat tcgttatgat    420
agataa                                                               426

SEQ ID NO: 574          moltype = AA  length = 11
FEATURE                 Location/Qualifiers
source                  1..11
                        mol_type = protein
                        organism = African swine fever virus
SEQUENCE: 574
YLMRYTQIYK Y                                                         11

SEQ ID NO: 575          moltype = AA  length = 19
FEATURE                 Location/Qualifiers
source                  1..19
                        mol_type = protein
                        organism = African swine fever virus
SEQUENCE: 575
YINIYMYLMR YTQIYKYPL                                                 19

SEQ ID NO: 576          moltype = AA  length = 124
FEATURE                 Location/Qualifiers
source                  1..124
                        mol_type = protein
                        organism = African swine fever virus
SEQUENCE: 576
MVRLFRNPIK CLFYRRSRKI QEKKLRKSLK KLNFYHPPED CCQIYRLLEN VPGGTYFITE    60
NMTNDLIMVV KDSVDKKIKS IKLYLHGSYI KIHQHYYINI YMYLMRYTQI YKYPLICFNK   120
YYNI                                                                124

SEQ ID NO: 577          moltype = AA  length = 11
FEATURE                 Location/Qualifiers
source                  1..11
                        mol_type = protein
                        organism = African swine fever virus
SEQUENCE: 577
SIARYFDRCM Y                                                         11

SEQ ID NO: 578          moltype = AA  length = 119
FEATURE                 Location/Qualifiers
source                  1..119
                        mol_type = protein
                        organism = African swine fever virus
SEQUENCE: 578
MKLLALLCIL IWLSQPGLNR PLSIFYMKQN LPRTYTPPIR ELEYWCTYGK HCDFCWECRN    60
GICKNKVWDD MPLIKQNDYI SQCSIARYFD RCMYFIKPKS PYIHYMDCFQ PTAYKGFSH    119

SEQ ID NO: 579          moltype = AA  length = 11
FEATURE                 Location/Qualifiers
source                  1..11
                        mol_type = protein
                        organism = African swine fever virus
SEQUENCE: 579
YQSPTTPWCF Y                                                         11

SEQ ID NO: 580          moltype = AA  length = 119
FEATURE                 Location/Qualifiers
source                  1..119
                        mol_type = protein
                        organism = African swine fever virus
SEQUENCE: 580
MKVFLGLLLG YSTILILTYQ SPTTPWCFYE ISLKIPNHHS MKCCSYPRLY EHEMFMEKWR    60
DKNWPIIIRY YCFYLVFSFV FAGCVAFAIC KNLRLSTTMK LLMLLSILVL LLSQPILNN    119

SEQ ID NO: 581          moltype = AA  length = 11
FEATURE                 Location/Qualifiers
source                  1..11
                        mol_type = protein
                        organism = African swine fever virus
SEQUENCE: 581
IVNRNSWGCF Y                                                         11

SEQ ID NO: 582          moltype = AA  length = 116
FEATURE                 Location/Qualifiers
source                  1..116
                        mol_type = protein
                        organism = African swine fever virus
SEQUENCE: 582
```

```
MKVLGLLLGY SVLILAHELP ELPRTQHPPK EELPYWCTYV KNCDFCWDCQ NGICKNKITN   60
ESNSMNSIVN CIVNRNSWGC FYEISVKMPN HHNMECSHPR PYTGNEIFME KWGGGG      116

SEQ ID NO: 583          moltype = AA  length = 10
FEATURE                 Location/Qualifiers
source                  1..10
                        mol_type = protein
                        organism = African swine fever virus
SEQUENCE: 583
LSIPTLLYTY                                                         10

SEQ ID NO: 584          moltype = AA  length = 11
FEATURE                 Location/Qualifiers
source                  1..11
                        mol_type = protein
                        organism = African swine fever virus
SEQUENCE: 584
SVFRHNEFCT Y                                                       11

SEQ ID NO: 585          moltype = AA  length = 214
FEATURE                 Location/Qualifiers
source                  1..214
                        mol_type = protein
                        organism = African swine fever virus
SEQUENCE: 585
MLGLQIFTLL SIPTLLYTYE LELLDLTRTP PEKELEYWCT YANHCRFCWD CQDGICKNKV   60
FENHSPILEN DYIANCSVFR HNEFCTYYVT SIKPHEVYRT ECPQHNHEWH EAVIRKWQKL  120
LTYGFYLVGC VLVANYIRKR SLQTIIYLMV LLVIFFLLSQ LMLYRELEAK KHKIGSIPPE  180
RELEHWCTHG KYCDFCWDCQ NGICRNKVFK MIPP                              214

SEQ ID NO: 586          moltype = AA  length = 9
FEATURE                 Location/Qualifiers
source                  1..9
                        mol_type = protein
                        organism = African swine fever virus
SEQUENCE: 586
RKEWKKDEL                                                          9

SEQ ID NO: 587          moltype = AA  length = 118
FEATURE                 Location/Qualifiers
source                  1..118
                        mol_type = protein
                        organism = African swine fever virus
SEQUENCE: 587
MLVIFLGILG LLASQVSSQL VGQLRPTEDP PEEELEYWCA YMESCQFCWD CQDGTCINKI   60
DGSAIYKNEY VKACLVSRWL DKCMYDLDKG IYHTMNCSQP WSWNPYKYFR KEWKKDEL    118

SEQ ID NO: 588          moltype = AA  length = 205
FEATURE                 Location/Qualifiers
source                  1..205
                        mol_type = protein
                        organism = African swine fever virus
SEQUENCE: 588
MLVIFLGILG LLASQVSSQL VGQLRPTEEP PEEELEYWCA YMESCQFCWD CQDGTCINKI   60
DGSVIYKNEY VKSCLVSRWL DKCMYDLDKG IYHTMNCNQV LGLPNQPAGQ LHPTDNPPQE  120
ELEYWCTYTE NCKFCWNCQN GLCEGKLENT TILENEYVQS CIVSRWLNKC MYDLGQGIHH  180
VMACSEPKPW NPYKILKREW KENNS                                        205

SEQ ID NO: 589          moltype = AA  length = 11
FEATURE                 Location/Qualifiers
source                  1..11
                        mol_type = protein
                        organism = African swine fever virus
SEQUENCE: 589
TVSRWNGICS Y                                                       11

SEQ ID NO: 590          moltype = AA  length = 127
FEATURE                 Location/Qualifiers
source                  1..127
                        mol_type = protein
                        organism = African swine fever virus
SEQUENCE: 590
VATIKVLILV LLGVVVLQAA PIRKLEDLLP TRYPPEHELV YWCTYANQCD FCWECVHGIC   60
RNRIQTDWPV IHQNDWIINC TVSRWNGICS YYEGPKNHTD HQMDCANPTS HTYPHREYMK  120
IYERDDL                                                            127

SEQ ID NO: 591          moltype = AA  length = 10
FEATURE                 Location/Qualifiers
source                  1..10
```

```
                             mol_type = protein
                             organism = African swine fever virus
SEQUENCE: 591
HIMSCTNPTY                                                                 10

SEQ ID NO: 592            moltype = AA    length = 18
FEATURE                   Location/Qualifiers
source                    1..18
                          mol_type = protein
                          organism = African swine fever virus
SEQUENCE: 592
HIMSCTNPTY YDWFDELM                                                        18

SEQ ID NO: 593            moltype = AA    length = 10
FEATURE                   Location/Qualifiers
source                    1..10
                          mol_type = protein
                          organism = African swine fever virus
SEQUENCE: 593
MIATIALISY                                                                 10

SEQ ID NO: 594            moltype = AA    length = 8
FEATURE                   Location/Qualifiers
source                    1..8
                          mol_type = protein
                          organism = African swine fever virus
SEQUENCE: 594
ATIALISY                                                                    8

SEQ ID NO: 595            moltype = AA    length = 18
FEATURE                   Location/Qualifiers
source                    1..18
                          mol_type = protein
                          organism = African swine fever virus
SEQUENCE: 595
KQYSRMRMQA ATRLLIFL                                                        18

SEQ ID NO: 596            moltype = AA    length = 11
FEATURE                   Location/Qualifiers
source                    1..11
                          mol_type = protein
                          organism = African swine fever virus
SEQUENCE: 596
MQAATRLLIF L                                                               11

SEQ ID NO: 597            moltype = AA    length = 11
FEATURE                   Location/Qualifiers
source                    1..11
                          mol_type = protein
                          organism = African swine fever virus
SEQUENCE: 597
CMYEAHFRIH Y                                                               11

SEQ ID NO: 598            moltype = AA    length = 290
FEATURE                   Location/Qualifiers
source                    1..290
                          mol_type = protein
                          organism = African swine fever virus
SEQUENCE: 598
MKVIVFLLVL AVMQPVIQSQ SFPGTGELPM TRRPPKRELE YWCTYAKSCD FCWNCRHGVC           60
KNKVFEKHPL IKKNDYIQIC RVSRYNERCS YFTDSRIRRF HIMSCTNPTY YDWFDELMQI          120
KEDRVIDTEN IKHTCLCMIA TIALISYVRK QYSRMRMQAA TRLLIFLGFY VLLGILMTNI          180
IMNLPLSTDN PMQMRRPPER DLKFWCTYAK HCDFCWTCKD GMCKNKVFSD HPIITQNDYI          240
VNCTVSRWHD RCMYEAHFRI HYQHNMNCSQ PKDLEWFIEL KRHVINQDDL                    290

SEQ ID NO: 599            moltype = AA    length = 19
FEATURE                   Location/Qualifiers
source                    1..19
                          mol_type = protein
                          organism = African swine fever virus
SEQUENCE: 599
YAKNYSLSTL YCIFLAIYY                                                       19

SEQ ID NO: 600            moltype = AA    length = 11
FEATURE                   Location/Qualifiers
source                    1..11
                          mol_type = protein
                          organism = African swine fever virus
SEQUENCE: 600
```

```
                                   -continued
STLYCIFLAI Y                                                         11

SEQ ID NO: 601            moltype = AA   length = 10
FEATURE                   Location/Qualifiers
source                    1..10
                          mol_type = protein
                          organism = African swine fever virus
SEQUENCE: 601
LLSWGASPEY                                                           10

SEQ ID NO: 602            moltype = AA   length = 268
FEATURE                   Location/Qualifiers
source                    1..268
                          mol_type = protein
                          organism = African swine fever virus
SEQUENCE: 602
MVSLTTCCLK NIVNQHAYVE NTVLLYHLGL RWNCKTLYQC TQCNGVNYTN SHSDQCKNKD     60
LFLIKVIVKK NLAVARTLLS WGASPEYARL FCRNTEEEQA LNVQHVADVP SSKILERLTM    120
SYKGNDEQLL ITFYLLNLST NFSTNLREQV RPKIVSYIIC DLAIHQTFKI FYAKNYSLST    180
LYCIFLAIYY KLYTALRKMV KIYPGLKSFA YLTGFMFDDE TVMETYNSTD DEISECKNRI    240
ITIKGYYGNI HCRSDIDHMY AFSQNNFW                                      268

SEQ ID NO: 603            moltype = AA   length = 12
FEATURE                   Location/Qualifiers
source                    1..12
                          mol_type = protein
                          organism = African swine fever virus
SEQUENCE: 603
RLYVYSKTFY RK                                                        12

SEQ ID NO: 604            moltype = AA   length = 8
FEATURE                   Location/Qualifiers
source                    1..8
                          mol_type = protein
                          organism = African swine fever virus
SEQUENCE: 604
YVYSKTFY                                                              8

SEQ ID NO: 605            moltype = AA   length = 330
FEATURE                   Location/Qualifiers
source                    1..330
                          mol_type = protein
                          organism = African swine fever virus
SEQUENCE: 605
MQSLFNIALK ALTLKNHVEF LKRDKEVLTR LGLCCKNYDL IHKCSECGNI CPNGQQHGTC     60
ININYLLIYA VKRDNYMLAY RLLCWGANEK FAHYFRRPLP NLKPLLPKKE LTPKDIKQLA    120
YEHFHSDSEL ITVFEVFRKS RNINDCLEFF YKKNIEFEIY FARLYVYSKT FYRKSWYWFC    180
IFMAVKHSME HALKKITKTY IPTFYNKTTL PLVLFLSACF YENVEWMKNF FYKANKKIQQ    240
KMLSYGMEWA ATHGKVRTFV CCYTLGGTAS LKMYQKAYQN ERYMIMALCS YLGNIQINNP    300
WDSLNPYMMV QNKEKFLPLK FSEETQYFYI                                    330

SEQ ID NO: 606            moltype = AA   length = 9
FEATURE                   Location/Qualifiers
source                    1..9
                          mol_type = protein
                          organism = African swine fever virus
SEQUENCE: 606
NKLFDLHNL                                                             9

SEQ ID NO: 607            moltype = AA   length = 11
FEATURE                   Location/Qualifiers
source                    1..11
                          mol_type = protein
                          organism = African swine fever virus
SEQUENCE: 607
KLFNDNPFPA Y                                                         11

SEQ ID NO: 608            moltype = AA   length = 12
FEATURE                   Location/Qualifiers
source                    1..12
                          mol_type = protein
                          organism = African swine fever virus
SEQUENCE: 608
AISYVYQHFK YL                                                        12

SEQ ID NO: 609            moltype = AA   length = 9
FEATURE                   Location/Qualifiers
source                    1..9
                          mol_type = protein
```

-continued

```
                          organism = African swine fever virus
SEQUENCE: 609
AMLACVRFY                                                                  9

SEQ ID NO: 610           moltype = AA   length = 356
FEATURE                  Location/Qualifiers
source                   1..356
                         mol_type = protein
                         organism = African swine fever virus
SEQUENCE: 610
MVPSLQSFAK KVLASQHVSI DYHVILERCG LWWYKAPISL DCKHMLIKLP NFADGLDLNT          60
ALMLATKENN YQLIKMFTDW GADINYGLIC ANTPPIREFC WELGAKYQVD KKKIMHIFFK         120
LIHPNTTSNN IILCLKFFND NPFSAYVIIR EIKSCIHWKL KNLAEDTNVL SNISDGDMLT         180
IYCFIVALQD NLREAISYVY QHFKYLNTWW LTCALCYNKL FDLHNLYEKE KIRMDMDEMM         240
RIACTKDNNF LTIYYCFILG ANINLAMIAS IRFYNMDNLF FCIDLGADAF EEAKALAEQQ         300
NYYLISHRLS LDIYSPDSSL LTLKEADPNK IYRLLKNYKS KSMLAYLNYD INDTSL             356

SEQ ID NO: 611           moltype = AA   length = 345
FEATURE                  Location/Qualifiers
source                   1..345
                         mol_type = protein
                         organism = African swine fever virus
SEQUENCE: 611
MFPSLQSFAK KVLARQQVSI EYHVILERCG LWWYKAPISL DCKHMLIKLP SFADGLDLNT          60
ALMLATKENN YQLIKLFTEW GADINYGLIC ANTPPVREFC WELGAKYRVD KKKIMHMFFK         120
LIHPGTTSSN IILCLKLFND NPFPAYVIIR EIRSSIYWKL KRLVEDTDIL SNMSDGDMLT         180
IYCFIVALQD NLREAISYVY QHFKYLNTWW LICALCFNKL FDLHNLYEKE KIRMDVDEMM         240
RMACTKDNNF LTIYYCFLLG ANINSAMLAC VRFYNMDNLF FCIDLGADAF EEAKALAEQR         300
NYYLISHHLS LDIYSADSSL LTLKEADPNK IYHLLKNYKL KSMLA                        345

SEQ ID NO: 612           moltype = AA   length = 9
FEATURE                  Location/Qualifiers
source                   1..9
                         mol_type = protein
                         organism = African swine fever virus
SEQUENCE: 612
NVFDLHELY                                                                  9

SEQ ID NO: 613           moltype = AA   length = 21
FEATURE                  Location/Qualifiers
source                   1..21
                         mol_type = protein
                         organism = African swine fever virus
SEQUENCE: 613
EMMHIACIQD YSYSAIYYCF I                                                   21

SEQ ID NO: 614           moltype = AA   length = 11
FEATURE                  Location/Qualifiers
source                   1..11
                         mol_type = protein
                         organism = African swine fever virus
SEQUENCE: 614
IQDYSYSAIY Y                                                              11

SEQ ID NO: 615           moltype = AA   length = 353
FEATURE                  Location/Qualifiers
source                   1..353
                         mol_type = protein
                         organism = African swine fever virus
SEQUENCE: 615
MLPSLQSLTK KVLAGQCIPV DQYHVLKCCG LWWHNGPIML HIRRNKLFIR STCFSQGIEL          60
NIGLMKAVKE NNHDLIKLFT EWGADINYGM ICALTENTRD LCKELGAKEY LEREYILKIF         120
FDTTRDKTSS NIIFCHEVFS NNPNLRIIDN LDLRGEIMWE LRGLMEITFM LDHDDSFSTV         180
LTKYWYAIAV DYDLKDAIRY FYQKYPRLHR WRLMCALFYN NVFDLHELYE IERVRMDIDE         240
MMHIACIQDY SYSAIYYCFI MGANINQAML VSIQNYNLGN LFFCIDLGAD AFEEGKALAE         300
QKENYLIAHA LSLKHYNPVI SLLSIVTDPE KINCMLKNYH SINMGIFLDY EQR                353

SEQ ID NO: 616           moltype = AA   length = 22
FEATURE                  Location/Qualifiers
source                   1..22
                         mol_type = protein
                         organism = African swine fever virus
SEQUENCE: 616
KTDLLNNEFS LSTLLLKYWY AI                                                  22

SEQ ID NO: 617           moltype = AA   length = 9
FEATURE                  Location/Qualifiers
source                   1..9
                         mol_type = protein
```

```
                        -continued
                        organism = African swine fever virus
SEQUENCE: 617
SLSTLLLKY                                                         9

SEQ ID NO: 618          moltype = AA   length = 11
FEATURE                 Location/Qualifiers
source                  1..11
                        mol_type = protein
                        organism = African swine fever virus
SEQUENCE: 618
SLSTLLLKYW Y                                                      11

SEQ ID NO: 619          moltype = AA   length = 9
FEATURE                 Location/Qualifiers
source                  1..9
                        mol_type = protein
                        organism = African swine fever virus
SEQUENCE: 619
AMLSSIQYY                                                         9

SEQ ID NO: 620          moltype = AA   length = 350
FEATURE                 Location/Qualifiers
source                  1..350
                        mol_type = protein
                        organism = African swine fever virus
SEQUENCE: 620
MLPSLQSLTK KVLAGQCVPT NQHYLLKCYD LWWHDAPITF DHNLRLIKSA GIKEGLNLNT   60
ALVKAVRENN YNLIKLFAEW GADINYGLVS VNTEHTWDLC RELGAKETLN EEEILQIFID  120
LKFHKTSSNI ILCHEVFSNN PILQKVNNIK MRIEIFWELR ELIVKTDLLN NEFSLSTLLL  180
KYWYAIAIRY NLKEAIQYFY QKYTHLNTWR LTCALCFNNV FDLHEAYEKD KIHMDIEEMM  240
RIACIKDHNL STMYYCYVLG ANINQAMLSS IQYYNIENMF FCIDLGADVF EEGTTALGEG  300
YELIKNILSL KIYSPATTPL PKSTDPEIID HALKNYVSKN MMIFLTYDLR            350

SEQ ID NO: 621          moltype = AA   length = 11
FEATURE                 Location/Qualifiers
source                  1..11
                        mol_type = protein
                        organism = African swine fever virus
SEQUENCE: 621
VQYYNIGNIF F                                                      11

SEQ ID NO: 622          moltype = AA   length = 353
FEATURE                 Location/Qualifiers
source                  1..353
                        mol_type = protein
                        organism = African swine fever virus
SEQUENCE: 622
MSLPLSLQTL VKKTIASQCL SIDEHCILKY CGLWWHDAPL KLCMDRGRIQ IKSGFLGEDI   60
DLRVALIIAV KENNYSLIKL FTEWGANINY GLLSINTKHI RELCRQLGAK ETLEDNDIFR  120
IFTRIMHNKT SGSIILCHEI FMNNPILENK FVIQLRGLIY KRLWGLIEIK ETDELNGLLV  180
KYWYAKAVQY DCKDAICFLD EKYTDLNEWR LKCLLYYNKI YELHEMYHKE NIQIDVHDMI  240
CLASTKDNNP LTIYYCYALG GNINQAMLTS VQYYNIGNIF FCIDLGGNAF EEGRAIAEQK  300
GYNFLSHSLA LDIYSSDASL PLNLKDPEEI SSLLKDYKSK NLSIIWEYSH NIL         353

SEQ ID NO: 623          moltype = AA   length = 12
FEATURE                 Location/Qualifiers
source                  1..12
                        mol_type = protein
                        organism = African swine fever virus
SEQUENCE: 623
YFYKRHKNHL YW                                                     12

SEQ ID NO: 624          moltype = AA   length = 357
FEATURE                 Location/Qualifiers
source                  1..357
                        mol_type = protein
                        organism = African swine fever virus
SEQUENCE: 624
MLSLQTLAKK VVACNYLSSD YDYTLQRFGL WWDLGPIHLC NNCKQVFSYK HLQCFSEDDL   60
CLEAALVKAV KSDNLELIRL FVDWGANPEY GLIRVPAVYL KRLCAELGGL TPVSEPRLLE  120
ILKEVARLKS CAGVLLGYDM FCHNPLLETV TRTTLDTVTY TCSNIPLTGD TAHHLLTKFW  180
FALALRHNFT KAIHYFYKRH KNHLYWRVAC SLYFNNIFDI HELCREKEIC ISPNLMMKFA  240
CLREKNYAAI YYCHRLGASL DYGMNLSIYN NNTLNMFFCI DLGAADFDRA QLIAHKAYMY  300
NLSNIFLVKQ LFSRDVTLVL DVTEPQEIYD MLKTYTSKNL KRAEEYLTAH PEIIVID    357

SEQ ID NO: 625          moltype = AA   length = 10
FEATURE                 Location/Qualifiers
source                  1..10
                        mol_type = protein
```

```
                                    -continued
                         organism = African swine fever virus
SEQUENCE: 625
LIEFLTGFFY                                                                  10

SEQ ID NO: 626           moltype = AA   length = 10
FEATURE                  Location/Qualifiers
source                   1..10
                         mol_type = protein
                         organism = African swine fever virus
SEQUENCE: 626
VMDMICLDYY                                                                  10

SEQ ID NO: 627           moltype = AA   length = 11
FEATURE                  Location/Qualifiers
source                   1..11
                         mol_type = protein
                         organism = African swine fever virus
SEQUENCE: 627
HEWEISIDYA L                                                                11

SEQ ID NO: 628           moltype = AA   length = 289
FEATURE                  Location/Qualifiers
source                   1..289
                         mol_type = protein
                         organism = African swine fever virus
SEQUENCE: 628
MNKIFLNITE TINMVLIEFL TGFFYLYGKR LFSISKVMDM ICLDYYTIIP APLAMMLAAR            60
LKNYDLMKRL HEWEISIDYA LLVVDDVPSI DYCLSLGARS PTRAQKRELL RDNTFNPVYK           120
YLMNCSGFPT KREKNIPCDV QCERLQKNII KELVFNCSVL LEMVLHTERE YAYALHCAAK           180
HNQLPILMYC WQQSTDAESI LLKTCCSDKN INCFNYCILY GGAQNLDAAM VEAAKHDARM           240
LINYCVMLGG RSLNEAKETA AMFGHIECAQ HCFKLQSYVV DTSNTDDTD                       289

SEQ ID NO: 629           moltype = AA   length = 9
FEATURE                  Location/Qualifiers
source                   1..9
                         mol_type = protein
                         organism = African swine fever virus
SEQUENCE: 629
QVMYLLYKY                                                                    9

SEQ ID NO: 630           moltype = AA   length = 8
FEATURE                  Location/Qualifiers
source                   1..8
                         mol_type = protein
                         organism = African swine fever virus
SEQUENCE: 630
RLYDANIY                                                                     8

SEQ ID NO: 631           moltype = AA   length = 237
FEATURE                  Location/Qualifiers
source                   1..237
                         mol_type = protein
                         organism = African swine fever virus
SEQUENCE: 631
MLEIVLATLL GDLQRLRVLT PQQRAVAFFR ANTKELEDFL CSDGQSEEVL SGPLLNRLLE            60
PSGPLDILTG YHLFRQNPKA GQLRGLEVKM LERLYDANIY NILSRLRPEK VRNKAIELYW           120
VFRAIHICHA PLVLDIVRYE EPDFAELAFI CAAYFGEPQV MYLLYKYMPL TRAVLTDAIR           180
ISLESNNQVG ICYAYLMGGS LKGLVSAPLR KRLRAKLRSQ RKKKDVLSPH DFLLLLQ              237

SEQ ID NO: 632           moltype = AA   length = 9
FEATURE                  Location/Qualifiers
source                   1..9
                         mol_type = protein
                         organism = African swine fever virus
SEQUENCE: 632
YSMAILYKL                                                                    9

SEQ ID NO: 633           moltype = AA   length = 11
FEATURE                  Location/Qualifiers
source                   1..11
                         mol_type = protein
                         organism = African swine fever virus
SEQUENCE: 633
ILYKLTEAIQ Y                                                                11

SEQ ID NO: 634           moltype = AA   length = 9
FEATURE                  Location/Qualifiers
source                   1..9
                         mol_type = protein
```

```
                        organism = African swine fever virus
SEQUENCE: 634
LTEAIQYFY                                                                  9

SEQ ID NO: 635          moltype = AA   length = 9
FEATURE                 Location/Qualifiers
source                  1..9
                        mol_type = protein
                        organism = African swine fever virus
SEQUENCE: 635
AIQYFYQRY                                                                  9

SEQ ID NO: 636          moltype = AA   length = 11
FEATURE                 Location/Qualifiers
source                  1..11
                        mol_type = protein
                        organism = African swine fever virus
SEQUENCE: 636
CMYDCNYTTI Y                                                              11

SEQ ID NO: 637          moltype = AA   length = 360
FEATURE                 Location/Qualifiers
source                  1..360
                        mol_type = protein
                        organism = African swine fever virus
SEQUENCE: 637
MPSTLQALTK KVLATQPVLK DDYCILERCG LWWHEAPITI YHTCIDEQIL IKTASFKHGL           60
TLNVALMKAV QENNHGLIEL FTEWGADISF GLVTVNMECT RTYAKVRCEE KALSENKILE          120
IFYNVQYVKT SSNIILCHEL LSDNPLFLNN AQLKLRIFGE LDTLSINFTL DNISFNEMLT          180
RYWYSMAILY KLTEAIQYFY QRYSHFKDWR LICGVAYNNV FDLHEIYNKE KTNIDIDEMM          240
QLACMYDCNY TTIYYCFMLG ADINRAMITS VMNFCEGNLF LCIDLGADAF EESMEIASQT          300
NNWILINILL FKNYSPDSSL LSIKTTDPEK INALLDEEKY KSKNMLIYEE SLFHIYGVNI          360

SEQ ID NO: 638          moltype = AA   length = 10
FEATURE                 Location/Qualifiers
source                  1..10
                        mol_type = protein
                        organism = African swine fever virus
SEQUENCE: 638
FSEMLTRYWY                                                                10

SEQ ID NO: 639          moltype = AA   length = 11
FEATURE                 Location/Qualifiers
source                  1..11
                        mol_type = protein
                        organism = African swine fever virus
SEQUENCE: 639
SEMLTRYWYS M                                                              11

SEQ ID NO: 640          moltype = AA   length = 9
FEATURE                 Location/Qualifiers
source                  1..9
                        mol_type = protein
                        organism = African swine fever virus
SEQUENCE: 640
YSMAILYNL                                                                  9

SEQ ID NO: 641          moltype = AA   length = 11
FEATURE                 Location/Qualifiers
source                  1..11
                        mol_type = protein
                        organism = African swine fever virus
SEQUENCE: 641
ILYNLTEAIQ Y                                                              11

SEQ ID NO: 642          moltype = AA   length = 11
FEATURE                 Location/Qualifiers
source                  1..11
                        mol_type = protein
                        organism = African swine fever virus
SEQUENCE: 642
IQYFYQRYRH F                                                              11

SEQ ID NO: 643          moltype = AA   length = 11
FEATURE                 Location/Qualifiers
source                  1..11
                        mol_type = protein
                        organism = African swine fever virus
SEQUENCE: 643
```

-continued

```
STYDGNYSTI Y                                                                11

SEQ ID NO: 644          moltype = AA  length = 356
FEATURE                 Location/Qualifiers
source                  1..356
                        mol_type = protein
                        organism = African swine fever virus
SEQUENCE: 644
MSTPLSLQTL VKKVLATQHI SKEHYFILKY CGLWWHEAPI TICIDEDSQI LIKSASFKEG    60
LSLDIALMKV VQENNHDLIE LFTKWGADIN SSLVTVNTEY TRNLCQKLGA KEALNERDIL   120
QIFYKTRHLK TSSNIILYNE LFSNNLLFQN IERLSLIVYR GLKNLSINFI LDDISFSEML   180
TRYWYSMAIL YNLTEAIQYF YQRYRHFKDW RLICGLSFNN LSDLHEVYNL EKTDIDIDEM   240
MKLTCSTYDG NYSTIYYCFM LGADINRAML TSVINFHIGN LFLCIDLGAD AFEDSMELAK   300
QKNNNILVEI LSFKNYYSSN TSLLSIKTTD PEKINALLDE EKYESKNMLM YEELSH       356

SEQ ID NO: 645          moltype = AA  length = 8
FEATURE                 Location/Qualifiers
source                  1..8
                        mol_type = protein
                        organism = African swine fever virus
SEQUENCE: 645
KLTEAIQY                                                             8

SEQ ID NO: 646          moltype = AA  length = 17
FEATURE                 Location/Qualifiers
source                  1..17
                        mol_type = protein
                        organism = African swine fever virus
SEQUENCE: 646
KLTEAIQYFY QRYSHFK                                                  17

SEQ ID NO: 647          moltype = AA  length = 8
FEATURE                 Location/Qualifiers
source                  1..8
                        mol_type = protein
                        organism = African swine fever virus
SEQUENCE: 647
IQYFYQRY                                                             8

SEQ ID NO: 648          moltype = AA  length = 362
FEATURE                 Location/Qualifiers
source                  1..362
                        mol_type = protein
                        organism = African swine fever virus
SEQUENCE: 648
MSTPISLQAL AKKILATQHI SKEHYFILKY CGLWWHGAPI MLSTNEDNQL MIKSAIFKDG    60
LELNLALMKT VQENNYDLIE LFTEWGADIN SSLVTVNTEH TWNFCRELGA KILNEMDIVQ   120
IFYKIHRIKT SSNIILCHKL LSNNPLFQNI EELKVIICCF LEKISINFIL NEITFNEMLT   180
RYWYSIAILC KLTEAIQYFY QRYSHFKDWR LICGLSFNNV SDLHEMYHIK KVDMNIDEMI   240
YLACMRDSNF LTIYYCFVLG ADINRAMVTS VKNFYMNNLF FCIDLGANAF EESLELAKQK   300
NHDILVEILS FKDYYSSNVS LLSLKTTDPE KINALLKNYR SKNIMRYKKL CPEIIRWARF   360
II                                                                  362

SEQ ID NO: 649          moltype = AA  length = 20
FEATURE                 Location/Qualifiers
source                  1..20
                        mol_type = protein
                        organism = African swine fever virus
SEQUENCE: 649
TTNSMLNEIS FSEMLTKYWY                                               20

SEQ ID NO: 650          moltype = AA  length = 356
FEATURE                 Location/Qualifiers
source                  1..356
                        mol_type = protein
                        organism = African swine fever virus
SEQUENCE: 650
MQPSTLQALA KRALATQHVS KDDYYILERY GLWWHEAPIS MYIDDDNQIM IRTLCFKEGI    60
RLNTALVLAV KENNDDLIML FTEWGANINY GLLFINNEHT RNLCRKLGAK EELETSEILR   120
FFFETKCKIT SSNVILCHEL FSNNPFLQNV NMVDLRMIIY WELKDLTTNS MLNEISFSEM   180
LTKYWYGIAV KYNLKEAIQY FCQEYRHFDE WRLICALSFN NVFDLHEICN TTKIHMSINK   240
MMELACMRDN NFLTIYYCFA LGANANRAML ISVKNFCIEN MFFCMDLGAN VIEHSKTLAD   300
IYGYSIIVNI LSLKIYKANP ILLSKETNPE KINTLLKNYY SKNMLAYDIC CIDNYL       356

SEQ ID NO: 651          moltype = AA  length = 9
FEATURE                 Location/Qualifiers
source                  1..9
                        mol_type = protein
                        organism = African swine fever virus
```

```
SEQUENCE: 651
FVYNRFILY                                                                           9

SEQ ID NO: 652           moltype = AA   length = 10
FEATURE                  Location/Qualifiers
source                   1..10
                         mol_type = protein
                         organism = African swine fever virus
SEQUENCE: 652
STYKNTESFY                                                                         10

SEQ ID NO: 653           moltype = AA   length = 387
FEATURE                  Location/Qualifiers
source                   1..387
                         mol_type = protein
                         organism = African swine fever virus
SEQUENCE: 653
MNSLQVLTKK VLIETKAFSN YHEDDIFILQ QLGLWWENGP IGFCKQCKMV TGGSMSCSDV                    60
DSYELDRALV KAVKENQTDL IKLFVLWGAD INFGIMCAKT KQTKDLCIQL GANPEFLDVG                   120
LYNMFVYLVK RKKVLLAIEI YYDNILILDS FNSNDFHLLI DFVYNRFILY LDEKEEEMTR                   180
NTLVLKFWYK FAIDFNLTKP IHYLSKKFPH LDLWRLQTAI YLGNIDEVHH AYFQENIRLG                   240
LNVMMFLACA RPGNKLGIYY CFALGADLDR ALERLISFNS INREINRKIR GEKRLCIEGS                   300
YLSNVYFCIG LGANPYTKKI QEIIKQKHSN IMILLFSKKK ILSPHSVLQN KILDPSDVHK                   360
MISTYKNTES FYPFSSLAVK LIQQANI                                                      387

SEQ ID NO: 654           moltype = AA   length = 13
FEATURE                  Location/Qualifiers
source                   1..13
                         mol_type = protein
                         organism = African swine fever virus
SEQUENCE: 654
SFDSHDFYVL IDF                                                                     13

SEQ ID NO: 655           moltype = AA   length = 9
FEATURE                  Location/Qualifiers
source                   1..9
                         mol_type = protein
                         organism = African swine fever virus
SEQUENCE: 655
STYEYTETF                                                                           9

SEQ ID NO: 656           moltype = AA   length = 375
FEATURE                  Location/Qualifiers
source                   1..375
                         mol_type = protein
                         organism = African swine fever virus
SEQUENCE: 656
MNSLQVLTKK VLIENKAFSN YHEDDIFILQ QLGLWWENGP IGFCKQCKMV TSGSMSCSDV                    60
DSYELDRALV RAVKKNQTDL IKLFVLWGAN INYGIICAKT ERTKVLCIQL GADPKFLDVG                   120
LYNMFVDLIK QQKVLLAIDI YYDNISILDS FDSHDFYVLI DFIYNRFILN LDEKEKMIKN                   180
TYVLKFWFKI AIEFNLIKPI RFLSKKFPHL DYWRLKTAVY LGNVDEIHHA YFQENIRLDP                   240
NDMMSLACMY PQNKLGIYYC FALGANINTA LETLIGFINH EVNREITFFS NYGIWSNVHF                   300
CISLGANPYT KKIQETLLRQ EKNVMMKLLF KKGLLSPHSI LHKKILEPSE VRKIISTYEY                   360
TETFHSFSSL RDNLR                                                                   375

SEQ ID NO: 657           moltype = AA   length = 9
FEATURE                  Location/Qualifiers
source                   1..9
                         mol_type = protein
                         organism = African swine fever virus
SEQUENCE: 657
DVIRLFTEW                                                                           9

SEQ ID NO: 658           moltype = AA   length = 9
FEATURE                  Location/Qualifiers
source                   1..9
                         mol_type = protein
                         organism = African swine fever virus
SEQUENCE: 658
VPMNIFVKY                                                                           9

SEQ ID NO: 659           moltype = AA   length = 10
FEATURE                  Location/Qualifiers
source                   1..10
                         mol_type = protein
                         organism = African swine fever virus
SEQUENCE: 659
RAISFFYQTY                                                                         10
```

| | | |
|---|---|---|
| SEQ ID NO: 660 | moltype = AA length = 12 | |
| FEATURE | Location/Qualifiers | |
| source | 1..12 | |
| | mol_type = protein | |
| | organism = African swine fever virus | |
| SEQUENCE: 660 | | |
| YQTYGHLSMW RL | | 12 |
| | | |
| SEQ ID NO: 661 | moltype = AA length = 11 | |
| FEATURE | Location/Qualifiers | |
| source | 1..11 | |
| | mol_type = protein | |
| | organism = African swine fever virus | |
| SEQUENCE: 661 | | |
| QTYGHLSMWR L | | 11 |
| | | |
| SEQ ID NO: 662 | moltype = AA length = 11 | |
| FEATURE | Location/Qualifiers | |
| source | 1..11 | |
| | mol_type = protein | |
| | organism = African swine fever virus | |
| SEQUENCE: 662 | | |
| TEWGANIYYG L | | 11 |
| | | |
| SEQ ID NO: 663 | moltype = AA length = 319 | |
| FEATURE | Location/Qualifiers | |
| source | 1..319 | |
| | mol_type = protein | |
| | organism = African swine fever virus | |
| SEQUENCE: 663 | | |
| MLSLQTLAKK AVAKQSVPEE YHYILKYCGL WWQNKPISLC HYCNYVILSS TPFKGELLHL | | 60 |
| DVALIMAIKE NNYDVIRLFT EWGANIYYGL TCARTEQTQE LCRKLGAKDG LNNKEIFAGL | | 120 |
| MRHKTSNNII LCHEIFDKNP MLEALNVQEM GEEIHRELKL FIFYILDNVP MNIFVKYWYA | | 180 |
| IAVKYKLKRA IFFFYQTYGH LSMWRLMCAI YFNNVFDLHE IYEQKIVHMD IDKMMQLACM | | 240 |
| QDYNFLTIYY CFVLGADIDQ AITVTQWHYH TNNLYFCKDL KDLKQNTLTA RPLLLPNITD | | 300 |
| PKKIYTMLKN YLPTSSNSL | | 319 |
| | | |
| SEQ ID NO: 664 | moltype = AA length = 319 | |
| FEATURE | Location/Qualifiers | |
| source | 1..319 | |
| | mol_type = protein | |
| | organism = African swine fever virus | |
| SEQUENCE: 664 | | |
| MLSLQTLAKK AVAKQSVPEE YHYILKYCGL WWQNKPISLC HYCNYVILSS TPFKGELLHL | | 60 |
| DVALIMAIKE NNYDVIRLFT EWGANIYYGL TCARTEQTQE LCRKLGAKDS LNNKEIFTGL | | 120 |
| MRHKTSNNII LCHEIFDKNP MLEALNVQEM GEEIHRELKF FIFYILDNVP MNVFVKYCYA | | 180 |
| IAVKYKLKRA ISFFYQTYGH LSMWRLMCAI YFNNVFDLHE IYEQKIVHMD IDKMMQLACM | | 240 |
| KDYNFLTIYY CFVLGGDIDQ AITATQWHHQ TNNLYFCKDL KDLKQNTLTA RPLLLPNITD | | 300 |
| PKKIYTMLKN YLPTSSNSL | | 319 |
| | | |
| SEQ ID NO: 665 | moltype = AA length = 11 | |
| FEATURE | Location/Qualifiers | |
| source | 1..11 | |
| | mol_type = protein | |
| | organism = African swine fever virus | |
| SEQUENCE: 665 | | |
| QRYAHLHRWR L | | 11 |
| | | |
| SEQ ID NO: 666 | moltype = AA length = 11 | |
| FEATURE | Location/Qualifiers | |
| source | 1..11 | |
| | mol_type = protein | |
| | organism = African swine fever virus | |
| SEQUENCE: 666 | | |
| NQAMFHSIQF Y | | 11 |
| | | |
| SEQ ID NO: 667 | moltype = AA length = 13 | |
| FEATURE | Location/Qualifiers | |
| source | 1..13 | |
| | mol_type = protein | |
| | organism = African swine fever virus | |
| SEQUENCE: 667 | | |
| NQAMFHSIQF YNI | | 13 |
| | | |
| SEQ ID NO: 668 | moltype = AA length = 9 | |
| FEATURE | Location/Qualifiers | |
| source | 1..9 | |
| | mol_type = protein | |
| | organism = African swine fever virus | |

```
SEQUENCE: 668
AMFHSIQFY                                                                           9

SEQ ID NO: 669         moltype = AA  length = 11
FEATURE                Location/Qualifiers
source                 1..11
                       mol_type = protein
                       organism = African swine fever virus
SEQUENCE: 669
IQFYNIGNIF F                                                                       11

SEQ ID NO: 670         moltype = AA  length = 8
FEATURE                Location/Qualifiers
source                 1..8
                       mol_type = protein
                       organism = African swine fever virus
SEQUENCE: 670
SMLSLNCY                                                                            8

SEQ ID NO: 671         moltype = AA  length = 350
FEATURE                Location/Qualifiers
source                 1..350
                       mol_type = protein
                       organism = African swine fever virus
SEQUENCE: 671
MVLSLQTLTK KVLASQYPAK CHPHFLKCCG LWWHNGPIMY HQKKIWTPYF KNGTNLNAAL                   60
VKAVEENNHD LIELFTEWGA NINYGLLSVN TEHTRDLCRQ LGAKEQLNDQ EILRFFYTLK                  120
RDLTSSNIIF CHEVFSNNPI LDTINRFEVK GMIYEQLEGL MVETDILSEM FTKYWYAMAI                  180
ECNLKEAICY FYQRYAHLHR WRLMCALFYN NVFELHEVYE KERIRIDMNE MLKWACRKNY                  240
NYLTIYYCCV VLGADINQAM FHSIQFYNIG NIFFCIDLGA NAFEEGKTLA HQKDNSFIAS                  300
MLSLNCYNMN DSLSLKETDP EVIKRMLKDY HSKNLSIAHK HYINDGFNDI                             350

SEQ ID NO: 672         moltype = AA  length = 11
FEATURE                Location/Qualifiers
source                 1..11
                       mol_type = protein
                       organism = African swine fever virus
SEQUENCE: 672
IVDDYIRFLF Y                                                                       11

SEQ ID NO: 673         moltype = AA  length = 542
FEATURE                Location/Qualifiers
source                 1..542
                       mol_type = protein
                       organism = African swine fever virus
SEQUENCE: 673
MFSLQELCRK NIYILPYPLA KHVLQQLGLY WKGHGSLQRI GDDHVLLQQD LIFSINEALR                   60
MAGEEGNNEV VKLLLLWEGN LHYAIIGALE GDRYDLIHKY YDQIGDCHKI LPLIQDPQIF                  120
EKCHELSNSC NIRCLLEHAV KHDMLSILQK HKEQIRLHMA LTQILFELAC HERKNDIIRW                  180
IGYSLHIHHL ETIFDVAFAH KNLSLYVLGY ELLMHKVNTE AAYIELPNLL SYHLRTAAAG                  240
GLLNFMLETI KHGGYLDKTV LSAAIRYKHR KIVAHFIHQV PRKTVKKLLL YAVQARAPKK                  300
TLNLLLSSLN YSVHTITKQL VHNVVIYSST LIVKLLLMRR KNKLNLVDAV LARLVKYSTY                  360
TDIVQFMGEF SVSPERVIKM AARESRTFLI EMISKAAWGN HPQTLIHHLK QLTNTMKPQS                  420
GKDHIIYTIH YIYLNSNMLV AEEEKNIFKL AKFYANHNAV NRFKQICEDY YILDARFKTL                  480
ILECFEIAVQ KNYPRIANIV DDYIRFLFYR GNITEEEIRE AYSLKDAEVY VDLKWLQQGE                  540
MV                                                                                542

SEQ ID NO: 674         moltype = AA  length = 19
FEATURE                Location/Qualifiers
source                 1..19
                       mol_type = protein
                       organism = African swine fever virus
SEQUENCE: 674
HIMHLTSSQE LFEFFHLFI                                                               19

SEQ ID NO: 675         moltype = AA  length = 8
FEATURE                Location/Qualifiers
source                 1..8
                       mol_type = protein
                       organism = African swine fever virus
SEQUENCE: 675
LLYAATLY                                                                            8

SEQ ID NO: 676         moltype = AA  length = 18
FEATURE                Location/Qualifiers
source                 1..18
                       mol_type = protein
                       organism = African swine fever virus
SEQUENCE: 676
```

```
ISMMQTAIQK NYFRFFKK                                                         18

SEQ ID NO: 677          moltype = AA   length = 11
FEATURE                 Location/Qualifiers
source                  1..11
                        mol_type = protein
                        organism = African swine fever virus
SEQUENCE: 677
SMMQTAIQKN Y                                                                11

SEQ ID NO: 678          moltype = AA   length = 20
FEATURE                 Location/Qualifiers
source                  1..20
                        mol_type = protein
                        organism = African swine fever virus
SEQUENCE: 678
SQLDSQMTVI DSVYYSIIKY                                                       20

SEQ ID NO: 679          moltype = AA   length = 11
FEATURE                 Location/Qualifiers
source                  1..11
                        mol_type = protein
                        organism = African swine fever virus
SEQUENCE: 679
SQMTVIDSVY Y                                                                11

SEQ ID NO: 680          moltype = AA   length = 8
FEATURE                 Location/Qualifiers
source                  1..8
                        mol_type = protein
                        organism = African swine fever virus
SEQUENCE: 680
TVIDSVYY                                                                    8

SEQ ID NO: 681          moltype = AA   length = 9
FEATURE                 Location/Qualifiers
source                  1..9
                        mol_type = protein
                        organism = African swine fever virus
SEQUENCE: 681
SVYYSIIKY                                                                   9

SEQ ID NO: 682          moltype = AA   length = 11
FEATURE                 Location/Qualifiers
source                  1..11
                        mol_type = protein
                        organism = African swine fever virus
SEQUENCE: 682
LIDSLIERFR Y                                                                11

SEQ ID NO: 683          moltype = AA   length = 542
FEATURE                 Location/Qualifiers
source                  1..542
                        mol_type = protein
                        organism = African swine fever virus
SEQUENCE: 683
MFSLQKKALQ HIYMTPENAS QLTKDLLQHL GLYWNGPIVK MDTVIHLHNN IFSNRSVLKY           60
ALAKQANISI IETLVLWVEP EYALAQALKH NRKDVLECIF SYHLTTPKYH HIMHLTSSQE           120
LFEFFHLFIC KSKNYNARME CLLYAATLYN FPNILEKNRE YIIRHSIGNS LFAIACKERH           180
IHLIAWFVTA GVLDTYDDST LFNTAFRLGD YSLLEVACDL PIIYPDYLII SMMQTAIQKN           240
YFRFFKKLLT HFNIYRPIII TDAAYYNRRK ILLLLLNQNV FNNFAILCAL SAAIKGHASK           300
KTLNLLISQL DSQMTVIDSV YYSIIKYNNI DCILLLMQIK TFRLETLVSI AVHGDNIDII           360
AACKAFLPKD TLYHLVLKMA IISRNHKLFK LYTEKENPMY IFTTMKAIIS NLVNYTVVQA           420
VAIEYLRKFH QEKQLPIVPL LMVLAEHNYI TKFKKACYAA NMSDQKVKRA LIKCLFIASQ           480
KNYCQIFKYC FGSLLKVLSK HERVKFFNSV VFAKKLASYY DHQNMIHLID SLIERFRYLI           540
KD                                                                          542

SEQ ID NO: 684          moltype = AA   length = 9
FEATURE                 Location/Qualifiers
source                  1..9
                        mol_type = protein
                        organism = African swine fever virus
SEQUENCE: 684
TNINIVNKY                                                                   9

SEQ ID NO: 685          moltype = AA   length = 9
FEATURE                 Location/Qualifiers
source                  1..9
                        mol_type = protein
```

-continued

```
                             organism = African swine fever virus
SEQUENCE: 685
YAIHHAPKL                                                                    9

SEQ ID NO: 686           moltype = AA  length = 9
FEATURE                  Location/Qualifiers
source                   1..9
                         mol_type = protein
                         organism = African swine fever virus
SEQUENCE: 686
YAIHHAPKL                                                                    9

SEQ ID NO: 687           moltype = AA  length = 9
FEATURE                  Location/Qualifiers
source                   1..9
                         mol_type = protein
                         organism = African swine fever virus
SEQUENCE: 687
TNINIVNKY                                                                    9

SEQ ID NO: 688           moltype = AA  length = 11
FEATURE                  Location/Qualifiers
source                   1..11
                         mol_type = protein
                         organism = African swine fever virus
SEQUENCE: 688
ATYNHRKILI Y                                                                11

SEQ ID NO: 689           moltype = AA  length = 11
FEATURE                  Location/Qualifiers
source                   1..11
                         mol_type = protein
                         organism = African swine fever virus
SEQUENCE: 689
RLMNFIYDRC Y                                                                11

SEQ ID NO: 690           moltype = AA  length = 10
FEATURE                  Location/Qualifiers
source                   1..10
                         mol_type = protein
                         organism = African swine fever virus
SEQUENCE: 690
LLAWEGNLYY                                                                  10

SEQ ID NO: 691           moltype = AA  length = 531
FEATURE                  Location/Qualifiers
source                   1..531
                         mol_type = protein
                         organism = African swine fever virus
SEQUENCE: 691
MFSLQNLCRK TLPDCKLPEF FDDYILQLLG LYWENHGTIQ RAGNNCVLIQ QHTLIPVNEA           60
LRIAASEENY EIVGLLLAWE GNLYYAIIGA LEGNRYNLIR KYDDQIKDHH DILPFIDDPI          120
IFHKCHIMRR CFFDCILYQA VKYSKFRVLL YFKYTLEDDL PLVHLLIEKA CEDHNYEVIK          180
WIYENLHVCH IIDTFDCAIA HKDLRLYCLG YTFIYNRIVP YKYHHLDILI LSSLQLLHKV          240
AAKGYLDFIL ETLKYDHNID NLDVILTQAA TYNHRKILTY FIPQSTYAQI EQCLFVAIKT          300
KSSKKTLNLL LSHLNLSIKL IQKISQYVAT FNSTNIIGIL SMKRKKKIYL DIILTKFVKN          360
AIFNKFVVRC MERFSINPER IVKMAARINK MMLVKKISEH VWKNHAARLK HLKHAVHTMK          420
HKDGKNRLMN FIYEHCYYHM QGEEIFSLAR FYAIHHAPKL FDVFYNCCIL DTIRFKSLLL          480
DCSHIIGKNA HDATNINIVN KYIGNLFAMG VLSKKEILQD YPSIYSKHYM P                   531

SEQ ID NO: 692           moltype = AA  length = 531
FEATURE                  Location/Qualifiers
source                   1..531
                         mol_type = protein
                         organism = African swine fever virus
SEQUENCE: 692
MFSLQNLCRK TLPNRKLPEF FDEYILQLLG LYWENHGTIQ RAGNNCVLIQ QHTLIPVNEA           60
LRTAASEENY EIVSLLLAWE GNLYYAIIGA LEGNRHDLIR KYDDQIKDHH EILPFIDDPV          120
IFHKCHIMRQ CFFDCILYQA VKYSKFRVLL YFKHRLEDDL PFTHLLIEKA CKDHNYEVIK          180
WIYENLHIYN MIDTFECAIA HKDLHLYCLG YRFIYNRIVP DKYHHLDIRM LSSLQLLHKV          240
AAKGYLDFIL ETLKYDHNKD NINIILTQAA TYNHRKILIY FIPQSTHAQI EQCLLVAIKA          300
KSSRKTLNLL LSHLNLSINL IKKISHYVAT YNSTNIIGIL SMRRKKKIYL DIILTKFVKK          360
AIFNKFVVRC MDTFSINPER ILKIAARINR MMLVKKISEH VWKNHAVRLK YLKHAVHTMK          420
HKDGKNRLMN FIYDRCYYHM QGEEIFSLAR FYAIHHAPKL FDVFYDCCIL DTIRFKSLLL          480
DCSHIIGKNA HDATNINIVN KYIGNLFVMG VLSKKEILQD YPSIYSKQYM P                   531

SEQ ID NO: 693           moltype = AA  length = 9
FEATURE                  Location/Qualifiers
source                   1..9
```

-continued

```
                         mol_type = protein
                         organism = African swine fever virus
SEQUENCE: 693
RKHIEKLLL                                                                9

SEQ ID NO: 694           moltype = AA  length = 9
FEATURE                  Location/Qualifiers
source                   1..9
                         mol_type = protein
                         organism = African swine fever virus
SEQUENCE: 694
YLHETLFEL                                                                9

SEQ ID NO: 695           moltype = AA  length = 10
FEATURE                  Location/Qualifiers
source                   1..10
                         mol_type = protein
                         organism = African swine fever virus
SEQUENCE: 695
AISKRDLTMY                                                              10

SEQ ID NO: 696           moltype = AA  length = 9
FEATURE                  Location/Qualifiers
source                   1..9
                         mol_type = protein
                         organism = African swine fever virus
SEQUENCE: 696
KLPRYVIEY                                                                9

SEQ ID NO: 697           moltype = AA  length = 526
FEATURE                  Location/Qualifiers
source                   1..526
                         mol_type = protein
                         organism = African swine fever virus
SEQUENCE: 697
MFSLQDLCRK HLFILPDVFG EHVLQRLGLY WRCHGSLQRI GDDHILIRRD LILSTNEALR        60
MAGEEGNNEV VKLLLLWKGN LHYAVIGALQ GDQYDLIHKY ENQIGDFHFI LPLIQDANTF       120
EKCHALERFC GVSCLLKHAT KYNMLPILQK YQEELSMRAY LHETLFELAC LWQRYDVLKW       180
IEQTMHVYDL KIMFNIAISK RDLTMYSLGY IFLFDRGNTE ATLLTQHLEK TAAKGLLHFV       240
LETLKYGGNI DTVLTQAVKY NHRKLLDYFL RQLPRKHIEK LLLLAVQEKA SKKTLNLLLS       300
HLNYSVKRIK KLLRYVIEYE STLVIKILLK KRVNLIDAML EKMVRYFSAT KVRTIMDELS       360
ISPERVIKMA IQKMRTDIVI HTSYVWEDDL ERLTRLKNMV YTIKYEHGKK MLIKVMHGIY       420
KNLLYGEREK VMFHLAKLYV AQNAATQFRD ICKDCYKLDV ARFKPRFKQL ILDCLEIVTK       480
KSCYSILEIL EKHIISLFTM KVMTEEEKNL CLEILYKVIH YKTIQC                     526

SEQ ID NO: 698           moltype = AA  length = 531
FEATURE                  Location/Qualifiers
source                   1..531
                         mol_type = protein
                         organism = African swine fever virus
SEQUENCE: 698
MFSLQNLCRK TLPNRKLPEF FDEYILQLLG LYWENHGTIQ RAGNNCVLIQ QHTLIPVNEA        60
LRTAASEENY EIVSLLLAWE GNLYYAIIGA LEGNRHDLIR KYDDQIKDHH EILPFIDDPV       120
IFHKCHIMRQ CFFDCILYQA VKYSKFRVLL YFKHRLEDDL PFTHLLIEKA CKDHNYEVIK       180
WIYENLHIYN MIDTFECAIA HKDLHLYCLG YRFIYNRIVP DKYHHLDIRM LSSLQLLHKV       240
AAKGYLDFIL ETLKYDHNKD NINIILTQAA TYNHRKILIY FIPQSTHAQI EQCLLVAIKA       300
KSSRKTLNLL LSHLNLSINL IKKISHYVAT YNSTNIIGIL SMRRKKKIYL DIILTKFVKK       360
AIFNKFVVRC MDTFSINPER ILKIAARINR MMLVKKISEH VWKNHAVRLK YLKHAVHTMK       420
HKDGKNRLMN FIYDRCYYHM QGEEIFSLAR FYAIHHAPKL FDVFYDCCIL DTIRFKSLLL       480
DCSHIIGKNA HDATNININVN KYIGNLFVMG VLSKKEILQD YPSIYSKQYM P              531

SEQ ID NO: 699           moltype = AA  length = 9
FEATURE                  Location/Qualifiers
source                   1..9
                         mol_type = protein
                         organism = African swine fever virus
SEQUENCE: 699
KKYQHKHIL                                                                9

SEQ ID NO: 700           moltype = AA  length = 11
FEATURE                  Location/Qualifiers
source                   1..11
                         mol_type = protein
                         organism = African swine fever virus
SEQUENCE: 700
LLLSWEADPR Y                                                            11

SEQ ID NO: 701           moltype = AA  length = 10
FEATURE                  Location/Qualifiers
```

```
source                    1..10
                          mol_type = protein
                          organism = African swine fever virus
SEQUENCE: 701
AVVGALESKY                                                                      10

SEQ ID NO: 702            moltype = AA   length = 280
FEATURE                   Location/Qualifiers
source                    1..280
                          mol_type = protein
                          organism = African swine fever virus
SEQUENCE: 702
MSSSLQELCR KKLPDCILPE FFDDYVLQLL GLHWQDHGSL QRIEKNQILV QQEPIHINEA               60
LKVAASEGNY EIVELLLSWE ADPRYAVVGA LESKYYDLVY KYYDLVKDCH DILPLIQNPE              120
TFEKCHELNN PCSLKCLFKH AVIHDMLPIL QKYTYFLDGW EYCNQMLFEL ACSKKKYEMV              180
VWIEGVLGIG KVTSLFTIAI SNRDLHLYSL GHLIILERMQ SCGQDPTFLL NHFLRDVSIK              240
GLLPFVLKTI EYGGSKEIAI TLAKKYQHKH ILKYFETGKC                                    280

SEQ ID NO: 703            moltype = AA   length = 280
FEATURE                   Location/Qualifiers
source                    1..280
                          mol_type = protein
                          organism = African swine fever virus
SEQUENCE: 703
MSSSLQELCR KKLPDCILPE FFDDYVLQLL GLHWQDHGSL QRIEKNQILV QQEPIHINEA               60
LKVAASEGNY EIVELLLSWE ADPRYAVVGA LESKYYDLVY KYYDQVKDCH DILPLIQNPE              120
TFERCHELNS TCSLKCLFKH AVINDMLPIL QKYTDYLDRW EYCSQMLFEL ACSKKKYEMV              180
VWIEGVLGVG KVTSLFTIAI SNRDLQLYSL GYSIILENLY SCGQDPKFLL NHFLRDVSIK              240
GLLPFVIKTI EYGGSKEIAI TLAKKYQHKH ILKYFETWES                                    280

SEQ ID NO: 704            moltype = AA   length = 9
FEATURE                   Location/Qualifiers
source                    1..9
                          mol_type = protein
                          organism = African swine fever virus
SEQUENCE: 704
LTMGYSLLF                                                                        9

SEQ ID NO: 705            moltype = AA   length = 11
FEATURE                   Location/Qualifiers
source                    1..11
                          mol_type = protein
                          organism = African swine fever virus
SEQUENCE: 705
LTGFIDYYYS Y                                                                    11

SEQ ID NO: 706            moltype = AA   length = 506
FEATURE                   Location/Qualifiers
source                    1..506
                          mol_type = protein
                          organism = African swine fever virus
SEQUENCE: 706
MFSLQDICRK HLFQLPDAFD EYILQALGLY WEKHGSLQRI RKDAVFVQRN IVLSTNEALR               60
IAASEGNERV IKLLLSWEGN FHYVIIGALE GDQYDLIHKY DSQIKDYHMI LSLIQNANTF              120
EKCHQLSNSN MWCLIQNAIK YNMLPILQKH RNILTHEGEN QELFEMACEE QKYDIVLWIG              180
QTLMLNEPEF IFDIAFERID FSLLTMGYSL LFDNKMSSID IHDEEDLTSL PTEHLEKAAT              240
KGCFFPMLET LKHGGNVNMA VLSKAVEYNH RKILDHFIRR QKCLSREEIE NLLLTAITNC              300
ASIKTLNLLL SYLNYSVKNI IGKIVQHVIK DGDYTIILLL KKKKINLVEP VLTGFIDYYY              360
SYCFIKHFIQ EFAIRPEKLI KMAARKGKLN MIIEFLNEKY VHKDDLGTIF KYLKTLVCTM              420
KHKKGKETLI VLIHKIYQDI HLETKEKFKL LRFYVMHDAT IQFLSMCKDC FNLAGFKPFV              480
LECLDIAIKK NYPDMIQYIE ILSKSE                                                   506

SEQ ID NO: 707            moltype = AA   length = 11
FEATURE                   Location/Qualifiers
source                    1..11
                          mol_type = protein
                          organism = African swine fever virus
SEQUENCE: 707
DWLSEHVIQR L                                                                    11

SEQ ID NO: 708            moltype = AA   length = 9
FEATURE                   Location/Qualifiers
source                    1..9
                          mol_type = protein
                          organism = African swine fever virus
SEQUENCE: 708
NVSLLSIGY                                                                        9

SEQ ID NO: 709            moltype = AA   length = 9
```

```
FEATURE                    Location/Qualifiers
source                     1..9
                           mol_type = protein
                           organism = African swine fever virus
SEQUENCE: 709
LSIGYTLLF                                                                     9

SEQ ID NO: 710             moltype = AA  length = 11
FEATURE                    Location/Qualifiers
source                     1..11
                           mol_type = protein
                           organism = African swine fever virus
SEQUENCE: 710
ILADFIGYHS Y                                                                 11

SEQ ID NO: 711             moltype = AA  length = 13
FEATURE                    Location/Qualifiers
source                     1..13
                           mol_type = protein
                           organism = African swine fever virus
SEQUENCE: 711
HSYTYMVDFM REF                                                               13

SEQ ID NO: 712             moltype = AA  length = 498
FEATURE                    Location/Qualifiers
source                     1..498
                           mol_type = protein
                           organism = African swine fever virus
SEQUENCE: 712
MFSLQEICRK NIYFLPDWLS EHVIQRLGLY WEKHGSLQRI GDDYVLIQQD LIIPINEALR             60
MAGEEGNDEV VQLLLLWEGN IHYAIIGALE SDHYSLIRKL YDQIEDCHDI LPLIQDPKIF            120
EKCHELDKFC NILCLVLHAV KNDMLCILQE YKMHLSGEDI QVVFETACRS QKNDIVSWMG            180
QNIAIYNSGV IFDIAFDKMN VSLLSIGYTL LFNHHINNTN ENINSLLTQH LEWAAGMGLL            240
HPFMLETLKYG GDVTIIVLSE AVKYDHRKIL DYFLRRKNLY QEDLEELLLL AIRADCSKKT           300
LNLLLSYLNY SINNIRKKIL QCVKEYETTV IIKILWKRKI NLIEPILADF IGYHSYTYMV            360
DFMREFSIHP EKMIKMAARE SREDLIIKFS KKVCKEPKDR LHYLKSLVYT MRHKEGKQLL            420
IYTIHNLYKA CHLESKEMFN LARFYARHNA VIQFKSICHD LSKLNINIKN LLLECLGIAI            480
KKNYFQLIKT IETDMRYE                                                         498

SEQ ID NO: 713             moltype = AA  length = 498
FEATURE                    Location/Qualifiers
source                     1..498
                           mol_type = protein
                           organism = African swine fever virus
SEQUENCE: 713
MFSLQEICRK NIYFLPDWLG EHVIQRLGLY WEKHGSLQRI GDNYVLIQQD LIIPINEALR             60
MAGEEGNDEV VQLLLLWEGN IHYAIIGALE SDHYSLIRKL YDQIEDCHDI LPLIQDPKIF            120
EKCHELDKSC NILCLVLHAV KNDMLCILQE YKMHLSGEDI QVVFETACRS QKNDIVSWMG            180
QNIAIYNPEV IFDIAFDKMN VSLLSIGYTL LFNHHINNTN ENINSLLTQH LEWAAGMGLL            240
HPFMLETLKYG GDVTIIVLSE AVKYDHRKIL DYFLRRKNLY QEDLEELLLL AIRADCSKKT           300
LNLLLSYLNY SINNIRKKIL QCVKEYETTV IIKILRKKRI NLIEPILADF IGYHSYTYMV            360
DFMREFSIHP EKMIKMAARE SREDLIIKFS KKVCKEPKDR LHYLKSLVYT MRHKEGKQLL            420
IYTIHNLYKA CHLESKEMFN LARFYARHNA VIQFKSICHD LSKLNINIKN LLLECLGIAI            480
KKNYFQLIKT IETDMRYE                                                         498

SEQ ID NO: 714             moltype = AA  length = 10
FEATURE                    Location/Qualifiers
source                     1..10
                           mol_type = protein
                           organism = African swine fever virus
SEQUENCE: 714
SQIQDWHILL                                                                   10

SEQ ID NO: 715             moltype = AA  length = 9
FEATURE                    Location/Qualifiers
source                     1..9
                           mol_type = protein
                           organism = African swine fever virus
SEQUENCE: 715
LVDIIHSIY                                                                     9

SEQ ID NO: 716             moltype = AA  length = 525
FEATURE                    Location/Qualifiers
source                     1..525
                           mol_type = protein
                           organism = African swine fever virus
SEQUENCE: 716
MFSLQDLCRK NIFFLPNDFS KHTLQWLGLY WKEHGSVHRA EKDSIMIQNE LVLSINDALQ             60
LAGEEGDTDV VQLLLLWEGN LHYAIIGALK TEKYNLICEY HSQIQDWHIL LPMIQDPETF            120
```

```
EKCHDLSLGC DFICLLQHAV KYNMLSILVK YKEDLLNARI RHRIQSLFVL ACENRRIEII  180
DWIGQNLPIP EPDAIFSIAV ATRDLELFSL GYKIIFDYMQ RQGIIQLTNG VRMVVLNRHI  240
SMAIDNGLLP FVLETKHGG NIHRALSYAV THNRRKILDY LIRQKNIAPN TIERLLYLAV   300
KNQSSRKTLN LLLSYINYKV KNVKKLVEHV VNEKSTLVLK ILLEKKENLV DAVLTRLVKH  360
STYFQVREFI QEFSISPEKF IKIAVREKKN VLIEAISEDI WENPTERITY LKQIVHTIKY  420
ESGRRFLVDI IHSIYQSYSL KHEDILKLAT FYVKHNAITH FKDLCKYLWL NRGTESKKLF  480
LECLEIADEK EFPDIKSIVS EYINYLFTAG AITKEEIMQA YDALE                 525

SEQ ID NO: 717              moltype = AA  length = 8
FEATURE                     Location/Qualifiers
source                      1..8
                            mol_type = protein
                            organism = African swine fever virus
SEQUENCE: 717
NSTLVIRI                                                          8

SEQ ID NO: 718              moltype = DNA  length = 24
FEATURE                     Location/Qualifiers
source                      1..24
                            mol_type = unassigned DNA
                            organism = African swine fever virus
SEQUENCE: 718
aactctactc ttgtgataag aatc                                        24

SEQ ID NO: 719              moltype = AA  length = 8
FEATURE                     Location/Qualifiers
source                      1..8
                            mol_type = protein
                            organism = African swine fever virus
SEQUENCE: 719
NSTLVIRL                                                          8

SEQ ID NO: 720              moltype = DNA  length = 24
FEATURE                     Location/Qualifiers
source                      1..24
                            mol_type = unassigned DNA
                            organism = African swine fever virus
SEQUENCE: 720
aactctactc ttgtgataag actc                                        24

SEQ ID NO: 721              moltype = AA  length = 10
FEATURE                     Location/Qualifiers
source                      1..10
                            mol_type = protein
                            organism = African swine fever virus
SEQUENCE: 721
SQIQDWHVLL                                                        10

SEQ ID NO: 722              moltype = AA  length = 469
FEATURE                     Location/Qualifiers
source                      1..469
                            mol_type = protein
                            organism = African swine fever virus
SEQUENCE: 722
MFSLQDLCRK NTFFLPDNFS KHTLYLLGLY WKGHGSIQRT MNDGVLIEHN LNLSINEALI  60
LAGEEGNNDV VQLLLLWEGN LHYAIIGALK TEKYGLICEY HSQIQDWHVL LPLIQDPETF  120
EKCHDLSLEC DLSCLLQHAV KYNMLSILVK YKEDLLNVLF RQQIQGLFIL ACEHRRIEIL  180
TWMGQNLPIP DPEPIFSIAV VTKDLEMFSL GYKIVFEYME NQGLFHLTQV VRMVMLNHHL  240
GMVINKGLLP FVLETLKHGG NVNRALSYAV TQNKRRIDLN VVRQKNIPHK TIERMLHLAV  300
KKHAPRKTLN LLLSYINYKV KNVKKLLEHV VKYNSTLVIR ILLEKKKNLL DATLTRYVKD  360
STYFQVKEFM QDFSISPEKF IKIAVREKRN VLIKGISEDI WENPAERIRN LKQIVCTIKY  420
ESGRQFLINI IHTIYQSYSL KPEEILKLAT FMSNTMQPPI LKISANIFG             469

SEQ ID NO: 723              moltype = DNA  length = 1410
FEATURE                     Location/Qualifiers
source                      1..1410
                            mol_type = unassigned DNA
                            organism = African swine fever virus
SEQUENCE: 723
atgttctccc ttcaggacct ctgtcggaag aacaccttct tccttccaga taattttagc  60
aagcataccc tgtatttgct ggggttatac tggaagggac atggatctat ccaaagaaca  120
atgaatgatg gtgtactgat agagcataat cttaatcttt ccatcaatga agccttaatc  180
cttgcaggag aagagggaaa caatgatgta gtacaactct tattgctatg ggaaggaaat  240
cttcattatg ccatcatagg agctttgaag actgagaaat atggcttaat atgtgagtac  300
catagccaaa ttcaggactg gcatgttctc ctcccttga ttcagatcc agaaacattc  360
gaaaatgtc atgattaag ccttgaatgt gatctcat gccttctcca acatgctgta  420
aaatataaca tgctttctat tcttgttaaa tataaagag atctattaaa tgtactattt  480
aggcaacaaa ttcaaggact atttatttta gcatgtgaac atcggaggat tgagattctt  540
acgtggatgg gtcaaaatct gccaattcct gatcctgagc ctattttag cattgctgtt  600
```

```
gtcacaaaag atttagaaat gttttcctta gggtacaaga ttgttttttga atacatggaa   660
aatcaaggac tatttcattt aacccaggta gttcgtatgg ttatgctaaa tcatcacctt   720
ggcatggtaa taaataaagg acttttaccc tttgtgctgg aaactttaaa acatggtggg   780
aatgtaaata gagccttatc ttatgctgtc acacaaaaca aaagaaagat tttagaccat   840
gttgttcgcc aaaagaatat accccataaa accattgaaa gaatgttgca tctggctgta   900
aaaaagcatg ctcccaggaa aactctgaac ttgttactat cttacataaa ttacaaggtg   960
aaaaatgtta aaaagttgtt agaacatgta gtgaaataca actctactct tgtgataaga  1020
atcttgttag aaaaaaagaa aaacctgctg gatgctactt tgacaagata tgtcaaagat  1080
tctacatact ttcaggtgaa agaatttatg caagacttct ccatcagccc agaaaaattc  1140
attaaaatag ctgtgcggga aaagaggaat gtgttgatca agggtatttc tgaagatatt  1200
tgggaaaatc ccgcggaaag aatcaggaat cttaagcaga tagtgtgtac cataaaatat  1260
gaaagtggaa gacaattcct gataaatatc attcacacca tttaccgagt tattctttg   1320
aaacctgaag aaattcttaa actggcaaca tttatgtcaa acacaatgca accacccatt  1380
ttaaagatct ctgcaaatat ctttggctga                                   1410

SEQ ID NO: 724          moltype = AA  length = 527
FEATURE                 Location/Qualifiers
source                  1..527
                        mol_type = protein
                        organism = African swine fever virus
SEQUENCE: 724
MFSLQDLCRK NTFFLPSDFS KHTLHLLGLY WKGHGSIQRI KNDGVLIEHD LTLSINEALI    60
LAGEEGNNEV VKLLLLWEGN LHYAIIGALR TENYNLVCEY HSQIQDWHVL LPLIQDPETF   120
EKCHDLSLEC DLSCLLQHAV KYNMLSILVK YKEDLLNVLF RQQIQGLFIL ACENRKLEIL   180
TWMGQNLPIP DPEPIFSIAV VTKDLEMFSL GYKIVFEYME NQGLHLTQVV RMVMLNHHFG   240
MVINKGLLPF VLEILNYGGN VNRALSYAVT QNKRKILDHV VRQKNIPHKT IERMLHLAVK   300
KHAPRKTLNL LLSYINYKVK NVKKLLEHVV KYNSTLVIRL LLEKKKNLLD ATLTRYVKDS   360
TYFQVKEFMQ DFSISPEKFI KIAVREKRNV LIKGISEDIW ENPAERIRNL KQIVCTIKYE   420
SGRQFLINII HTIYQSYSLK PEEILKLATF YVKHNATTHF KDLCKYLWLN RRTESKKLFL   480
ECLEIADKKE FPDIKSIVSE YINYLFTAGA ITKEEIMQAY ALEYAMY                 527

SEQ ID NO: 725          moltype = DNA  length = 1584
FEATURE                 Location/Qualifiers
source                  1..1584
                        mol_type = unassigned DNA
                        organism = African swine fever virus
SEQUENCE: 725
atgttctccc ttcaggacct ctgtcggaag aacaccttct tccttccaag tgattttagc    60
aagcataccc tgcatttgct gggggttatac tggaaggggc atggatctat ccaaaggata   120
aagaatgatg gtgtgcttat agagcatgat cttactcttt ccatcaatga agccttaatt   180
cttgcaggag aagagggaaa caatgaagta gtaaagctct tgttactatg ggaaggaaat   240
cttcattatg ccatcatagg agctttgagg actgagaact ataacctagt atgtgagtac   300
catagtcaaa ttcaggactg gcatgttctc ctcccttttga ttcaagatcc agaaacattc   360
gaaaaatgtc atgatttaag ccttgaatgt gatctttcat gccttctcca acatgctgta   420
aaatataaca tgctttcgat tcttgttaaa tataaagagg atctactaaa tgtactattt   480
aggcaacaaa ttcaaggact atttatttta gcatgtgaaa atcggaagct tgagattctt   540
acgtggatgg gtcaaaatct gccaattcct gatcctgacg ctattttttag cattgctgtt   600
gtcacaaaag atttagaaat gttttcctta gggtacaaga ttgttttttga atacatggaa   660
aaccaaggac ttcattaac ccaggtagtt cgtatggtta tgctaaatca tcactttggc   720
atggtaataa ataaaggact tttaccctttg tgctgaaaa ttttaaatta tggtgggaat   780
gtaaatagag ccttatctta tgctgtcaca caaaataaa gaaagatttt agaccatgag   840
gttcgccaaa agaatatacc ccataaaacc attgaaagaa tgttgcatct ggctgtaaaa   900
aagcatgctc ccaggaaaac tctgaacttg ttactatctt acataaatta caaggtgaaa   960
aatgttaaaa agttgttaga acatgtagtg aaatacaact ctactcttgt gataagactc  1020
ttgttagaaa aaagaaaaa cctgctggat gctactttga caagatatgt caaagattct  1080
acatactttc aggtgaaaga atttatgcaa gacttctcca tcagcccaga aaaattcatt  1140
aaaatagctg tgcggaaaa gagaaatgtg ttgatcaagg gtatttctga agatatttgg  1200
gaaaatcccg cggaaagaat caggaatctt aagcagatag tgtgtaccat aaaatatgaa  1260
agtggaagac aattcctgat aaatatcatt cacaccattt accagagtta ttctttgaaa  1320
cctgaagaaa ttcttaaatt ggcaacattt tatgtcaaac acaatgcaac cacccatttt  1380
aaagatctct gcaaatatct ttggctgaac agaagaacag aaagtaagaa actgttttta  1440
gagtgcttgg aaattgctga taagaaggag tttcctgata ttaaaagtat tgtgagtgaa  1500
tacattaact atttgtttac tgcaggagct attaccaagg aagaaatcat gcaagcctat  1560
gctttggagt atgccatgta ttaa                                         1584

SEQ ID NO: 726          moltype = AA  length = 9
FEATURE                 Location/Qualifiers
source                  1..9
                        mol_type = protein
                        organism = African swine fever virus
SEQUENCE: 726
YNIHNITGY                                                             9

SEQ ID NO: 727          moltype = AA  length = 9
FEATURE                 Location/Qualifiers
source                  1..9
                        mol_type = protein
                        organism = African swine fever virus
SEQUENCE: 727
```

```
RQYDLIQKY                                                                    9

SEQ ID NO: 728          moltype = AA  length = 9
FEATURE                 Location/Qualifiers
source                  1..9
                        mol_type = protein
                        organism = African swine fever virus
SEQUENCE: 728
NMLPIFQKY                                                                    9

SEQ ID NO: 729          moltype = AA  length = 10
FEATURE                 Location/Qualifiers
source                  1..10
                        mol_type = protein
                        organism = African swine fever virus
SEQUENCE: 729
SSINYCVNPF                                                                  10

SEQ ID NO: 730          moltype = AA  length = 9
FEATURE                 Location/Qualifiers
source                  1..9
                        mol_type = protein
                        organism = African swine fever virus
SEQUENCE: 730
YNIHNITGY                                                                    9

SEQ ID NO: 731          moltype = AA  length = 9
FEATURE                 Location/Qualifiers
source                  1..9
                        mol_type = protein
                        organism = African swine fever virus
SEQUENCE: 731
STYTEIVKY                                                                    9

SEQ ID NO: 732          moltype = AA  length = 506
FEATURE                 Location/Qualifiers
source                  1..506
                        mol_type = protein
                        organism = African swine fever virus
SEQUENCE: 732
MFSLQDLCRK NLFLPLEPLG KHVVQRLGLY WEGHGSLKRV GDCFICVDKI WILSIHKAIQ            60
IAASEGNENI VKLFLLWKGS LQYAIIGALE GRQYDLIQKY YNQIGDCHEI LPLIQDPEIY           120
ERCHELNVTC TFQCLFQHAI RDNMLPIFQK YGEDLNGNRR MVQLLYEMAC RLQNYDIIKW           180
IGFNLHVYNL EAIFSIAFVR KDLTYSLGY MLLLGRMSTE DRNFISIITR HLEYASKKGL            240
FDFVLESLKY GGQVDTVLFQ AVKYNHRKIL AHFIHEIPRE TVEKLILHAV ESRASRKTFN           300
LLLSSINYCV NPFVKKLLHT VVKHKYMLII KLLLERPKKK INLVDAALFK LVKYSTYAEI           360
VKFMKEFSVD PERVVKMAAR LMRVDLIKKI SNDAWENKLE RIKHLKQMVN TMNHRNGKNL           420
LMYNIHNITG YTCLNTKEAF NLTRFYAVHN ATCLFKEMCK SCFVHDKIQF RELLEDCLHI           480
ANRHDYIQIA ETADECIKYI DLITPK                                                506

SEQ ID NO: 733          moltype = AA  length = 506
FEATURE                 Location/Qualifiers
source                  1..506
                        mol_type = protein
                        organism = African swine fever virus
SEQUENCE: 733
MFSLQDLCRK NLFLPLEPLG KHVVQRLGLY WEGHGSVKRV GDCFICVDQI WMLSIHKAIQ            60
IAASEGNENI VKLFLLWKGS LQYAIIGALE GRQYDLIQKY YNQIGDCHQI LPLIQDPEIY           120
ERCHELNVTC TFQCLFQHAI RDNMLPIFQK YGEDLNGNRR MVQLLYEMAC RLQNYDIIKW           180
IGSNLHVYNL EAIFSIAFVR KDLTYSLGY MLLLGRMSTE DRNFISIITR HLEYASKKGL            240
FDFVLESLKY GGQVDTVLFQ AVKYNHRKIL AHFIHEIPRE TVEKLILHAV ESRASRKTFN           300
LLLSSINYCV NPFVKKLLHA VVKHKYMLII KLLLERPKKK INLVDAALFK LVKYSTYTEI           360
VKYMGEFSVD PKRVVKMAAR LMRVDLIKKI SNDAWEDKLE RIKHLKQMVN TMNHRNGKNL           420
LMYNIHNITG YTYLNTKEAF NLTRFYAVHN ATCLFKEMCK SCFVHDKIQL RELLEDCLHI           480
ANRHDYIQIA ETADECIKYI DLITFK                                                506

SEQ ID NO: 734          moltype = AA  length = 103
FEATURE                 Location/Qualifiers
source                  1..103
                        mol_type = protein
                        organism = African swine fever virus
SEQUENCE: 734
MKVFLGLLLG YSTILILTYQ SPTTQWCFYE ISLKILNHHS MEKWRDKNWS IIIRYYCFYL            60
VFSFAFAGCV AFAICKNLRL CTTMKLLMLL NILVLLSQPI LNN                             103

SEQ ID NO: 735          moltype = AA  length = 119
FEATURE                 Location/Qualifiers
source                  1..119
                        mol_type = protein
```

```
                       organism = African swine fever virus
SEQUENCE: 735
MKVFLGLLLG YSTILILTYQ SPTTPWCFYE ISLKIPNHHS MKCCSYPRLY EHEMFMEKWR     60
DKNWPIIIRY YCFYLVFSFV FAGCVAFAIC KNLRLSTTMK LLMLLSILVL LLSQPILNN     119

SEQ ID NO: 736         moltype = AA  length = 158
FEATURE                Location/Qualifiers
source                 1..158
                       mol_type = protein
                       organism = African swine fever virus
SEQUENCE: 736
MGGGGDYWPI IIRHCCFYLV FSIAFVGYIV FAYYKNLHLN TAMKLLALLC ILIWLSQPGL     60
NRPLSIFYMK QNLPRTYTPP IRELEYWCTY GKHCDFCWEC RNGICKNKVW DDMSSVQEHS     120
YPMEHCMIHR QCKYIRDGPI FQVECTMQTS DATHLINA                            158

SEQ ID NO: 737         moltype = AA  length = 274
FEATURE                Location/Qualifiers
source                 1..274
                       mol_type = protein
                       organism = African swine fever virus
SEQUENCE: 737
MKVLLGLLLG YSVLILAHEL PDLPRTQHPP KSELSYWCTY VPQCDFCWDC QDGICKNKIT     60
ESRFIDSNHS IVNCRVFRDS KTQSCLYEIS SKMPNHFSME CLHPRPYTGN EIFMQTWGGG     120
GGDHQQLSIK QYCLYFIIGI AYTGCFVCAL CKNLRLSTTM KLFVLLSILV WLAQPVLNRP     180
LSIFYTKQIL PRTYTPPMRE LEYWCTYGKH CDFCWDCKNG ICKNKVLDDM PLIVQNDYIS     240
KCSITRFIDR CMYFIEPKIP YIHYMNCSLP TYFS                                274

SEQ ID NO: 738         moltype = AA  length = 128
FEATURE                Location/Qualifiers
source                 1..128
                       mol_type = protein
                       organism = African swine fever virus
SEQUENCE: 738
MKVLLGLLLG HSVLILAHEL PDLPRTQHPP KSELSYWCTY VPQCDFCWDC QDGICKNKIT     60
ESRFIDSNHS IVNCRVFRDS KTQSCLYEIS SKMPNHFSME CLHPRSYTGN EIFMQTWGGG     120
GVTINNYL                                                             128

SEQ ID NO: 739         moltype = AA  length = 116
FEATURE                Location/Qualifiers
source                 1..116
                       mol_type = protein
                       organism = African swine fever virus
SEQUENCE: 739
MKVLGLLLGY SVLILAHELP ELPRTQHPPK EELPYWCTYV KNCDFCWDCQ NGICKNKITN     60
ESNSMNSIVN CIVNRNSWGC FYEISVKMPN HHNMECSHPR PYTGNEIFME KWGGGG        116

SEQ ID NO: 740         moltype = AA  length = 270
FEATURE                Location/Qualifiers
source                 1..270
                       mol_type = protein
                       organism = African swine fever virus
SEQUENCE: 740
MLGLQIFTLL SIPTLLYTYE IEPLERTSTP PEKELGYWCT YANHCRFCWD CQDGICRNKA     60
FKNHSPILEN DYIANCSIYR RNDFCIYYIT SIKPHKTYRT ECPQHINHER HEADIRKWQK    120
LLTYGFYLAG CILAVNYIRK RSLQTVMYLL VFLVISFLLS QLMLYGELED KKHKIGSIPP    180
KRELEHWCTH GKYCNFCWDC QNGICKNKAF KNHPPIGEND FIRYDCWTTH LPNKCSYEKI    240
YKHFNTHIME CSQPTHFKWY DNLMKKQDIM                                     270

SEQ ID NO: 741         moltype = AA  length = 214
FEATURE                Location/Qualifiers
source                 1..214
                       mol_type = protein
                       organism = African swine fever virus
SEQUENCE: 741
MLGLQIFTLL SIPTLLYTYE LELLDLTRTP PEKELEYWCT YANHCRFCWD CQDGICKNKV     60
FENHSPILEN DYIANCSVFR HNEFCTYYVT SIKPHEVYRT ECPQHNHEWH EAVIRKWQKL    120
LTYGFYLVGC VLVANYIRKR SLQTIIYLMV LLVIFFLLSQ LMLYRELEAK KHKIGSIPPE    180
RELEHWCTHG KYCDFCWDCQ NGICRNKVFK MIPP                                214

SEQ ID NO: 742         moltype = AA  length = 268
FEATURE                Location/Qualifiers
source                 1..268
                       mol_type = protein
                       organism = African swine fever virus
SEQUENCE: 742
MVSLTTCCLK NIVNQHACVE NTVLLYHLGL RWNCKTLYQC TQCNGVNYTN SHSDQCKNKD     60
LFLMKVIVKK NLAVTRTLLS WGASPEYARL FCRNTEEEQA LNVQHVADVS SSKILERLTM    120
SYKENDEQLL ITFYLLNLST KFSTNLREQV RFNIVSYIIC DLAIHQTFKT FYAKNYSLST    180
LYCIFLAIYY KLYTALRKMV KIYPGLKRFA YLIGFMFDDE TVMETYNSTD DEISECKNRI    240
```

```
IAIKGYYGNI HCRSDIDHMY AFSQNDYW                                                   268

SEQ ID NO: 743          moltype = AA  length = 268
FEATURE                 Location/Qualifiers
source                  1..268
                        mol_type = protein
                        organism = African swine fever virus
SEQUENCE: 743
MVSLTTCCLK NIVNQHAYVE NTVLLYHLGL RWNCKTLYQC TQCNGVNYTN SHSDQCKNKD                 60
LFLIKVIVKK NLAVARTLLS WGASPEYARL FCRNTEEEQA LNVQHVADVP SSKILERLTM                120
SYKGNDEQLL ITFYLLNLST NFSTNLREQV RFKIVSYIIC DLAIHQTFKI FYAKNYSLST                180
LYCIFLAIYY KLYTALRKMV KIYPGLKSFA YLTGFMFDDE TVMETYNSTD DEISECKNRI                240
ITIKGYYGNI HCRSDIDHMY AFSQNNFW                                                   268

SEQ ID NO: 744          moltype = AA  length = 328
FEATURE                 Location/Qualifiers
source                  1..328
                        mol_type = protein
                        organism = African swine fever virus
SEQUENCE: 744
MLSLFNIALK TLKNHIEFLK HDKDILTHLG LCCKNYDLIH KCSECGNICP NRQQHGTCIN                 60
INYLLIYAVK CDNYMLAYRL LCWGANEKFA HYFRRPLPNL KPLLPKKELT PKDIKQLAYE                120
HFYSDSELIT VFEVFRRCRN INDCLEFFYK KNLEFEIYFA RLHVYSKTFY RKSWYWFCIF                180
MAVKHGMKQA LKKITKTYIP TFYNKTTLNL VLFLSACFYE NVEWMKYFFY KANKKIQQRM                240
LSYGMEWAAT HGKVRTFVCC YTLGGTASLK MYQKAYQNER YMIMALCSYL GNIQINNPWD                300
NLNPYMMMQN KEKFLPLKFS EETQYFYI                                                   328

SEQ ID NO: 745          moltype = AA  length = 387
FEATURE                 Location/Qualifiers
source                  1..387
                        mol_type = protein
                        organism = African swine fever virus
SEQUENCE: 745
MNSLQVLTKK VLIETKAFSN YHEDDIFILQ QLGLWWENGP IGFCKQCKMV TGGSMSCSDV                 60
DSYELDRALV KAVKENQTDL IKLFVLWGAD INFGIMCAKT KQTKDLCIQL GANPEFLDVG                120
LYNMFVYLVK RKKVLLAIEI YYDNILILDS FNSNDFHLLI DFVYNRFILY LDEKEEEMTR                180
NTLVLKFWYK FAIDFNLTKP IHYLSKKFPH LDLWRLQTAI YLGNIDEVHH AYFQENIRLG                240
LNVMMFLACA RPGNKLGIYY CFALGADLDR ALERLISFNS INREINRKIR GEKRLCIEGS                300
YLSNVYFCIG LGANPYTKKI QEIIKQKHSN IMILLFSKKK ILSPHSVLQN KILDPSDVHK                360
MISTYKNTES FYPFSSLAVK LIQQANI                                                    387

SEQ ID NO: 746          moltype = AA  length = 356
FEATURE                 Location/Qualifiers
source                  1..356
                        mol_type = protein
                        organism = African swine fever virus
SEQUENCE: 746
MVPSLQSFAK KVLASQHVSI DYHVILERCG LWWYKAPISL DCKHMLIKLP NFADGLDLNT                 60
ALMLATKENN YQLIKMFTDW GADINYGLIC ANTPPIREFC WELGAKYQVD KKKIMHIFFK                120
LIHPNTTSNN IILCLKFFND NPFSAYVIIR EIKSCIHWKL KNLAEDTNVL SNISDGDMLT                180
IYCFIVALQD NLREAISYVY QHFKYLNTWW LTCALCYNKL FDLHNLYEKE KIRMDMDEMM                240
RIACTKDNNF LTIYYCFILG ANINLAMIAS IRFYNMDNLF FCIDLGADAF EEAKALAEQQ                300
NYYLISHRLS LDIYSPDSSL LTLKEADPNK IYRLLKNYKS KSMLAYLNYD INDTSL                    356

SEQ ID NO: 747          moltype = AA  length = 345
FEATURE                 Location/Qualifiers
source                  1..345
                        mol_type = protein
                        organism = African swine fever virus
SEQUENCE: 747
MFPSLQSFAK KVLARQQVSI EYHVILERCG LWWYKAPISL DCKHMLIKLP SFADGLDLNT                 60
ALMLATKENN YQLIKLFTEW GADINYGLIC ANTPPVREFC WELGAKYRVD KKKIMHMFFK                120
LIHPGTTSSN IILCLKLFND NPFPAYVIIR EIRSSIYWKL KRLVEDTDIL SNMSDGDMLT                180
IYCFIVALQD NLREAISYVY QHFKYLNTWW LICALCFNKL FDLHNLYEKE KIRMDVDEMM                240
RMACTKDNNF LTIYYCFLLG ANINSAMLAC VRFYNMDNLF FCIDLGADAF EEAKALAEQR                300
NYYLISHHLS LDIYSADSSL LTLKEADPNK IYHLLKNYKL KSMLA                                345

SEQ ID NO: 748          moltype = AA  length = 353
FEATURE                 Location/Qualifiers
source                  1..353
                        mol_type = protein
                        organism = African swine fever virus
SEQUENCE: 748
MLPSLQSLTK KVLAGQCVSV DHYHILKCCG LWWHNGPIML HIRRNKLFIR STCFSQGIEL                 60
NIGLMKAVKE NNHDLIKLFT EWGADINYGM ICALTENTRD LCKELGAKEY LEREYILKIF                120
FDTTRDKTSS NIIFCHEVFS NNPNLRIIDN LDLRGEIMWE LRGLMEITFM LDHDDSFSTV                180
LTKYWYAIAV DYDLKDAIRY FYQKYPRLHR WRLMCALFYN NVFDLHELYE IERVRMDIDE                240
MMHIACIQDY SYSAIYYCFI MGANINQAML VSIQNYNLGN LFFCIDLGAN AFEEGKALAE                300
QKENYLIAHA LSLKHYNPVI SLLSNVMDPE KINYMLKNYH SINMGIFLDY EQR                       353
```

```
SEQ ID NO: 749            moltype = AA  length = 353
FEATURE                   Location/Qualifiers
source                    1..353
                          mol_type = protein
                          organism = African swine fever virus
SEQUENCE: 749
MLPSLQSLTK KVLAGQCIPV DQYHVLKCCG LWWHNGPIML HIRRNKLFIR STCFSQGIEL    60
NIGLMKAVKE NNHDLIKLFT EWGADINYGM ICALTENTRD LCKELGAKEY LEREYILKIF   120
FDTTRDKTSS NIIFCHEVFS NNPNLRIIDN LDLRGEIMWE LRGLMEITFM LDHDDSFSTV   180
LTKYWYAIAV DYDLKDAIRY FYQKYPRLHR WRLMCALFYN NVFDLHELYE IERVRMDIDE   240
MMHIACIQDY SYSAIYYCFI MGANINQAML VSIQNYNLGN LFFCIDLGAD AFEEGKALAE   300
QKENYLIAHA LSLKHYNPVI SLLSIVTDPE KINCMLKNYH SINMGIFLDY EQR          353

SEQ ID NO: 750            moltype = AA  length = 117
FEATURE                   Location/Qualifiers
source                    1..117
                          mol_type = protein
                          organism = African swine fever virus
SEQUENCE: 750
MDIEEMMRIA CIKDHNLSTM YYCYMLGANI NQAMLTSIQY YNIENMFFCM DLGADVFEEG    60
TTALGEGYEL IKNILSLKIY SPTTIPLPKS TDPEIIDHAL KNYFSKNMMI FLSYDLR      117

SEQ ID NO: 751            moltype = AA  length = 350
FEATURE                   Location/Qualifiers
source                    1..350
                          mol_type = protein
                          organism = African swine fever virus
SEQUENCE: 751
MLPSLQSLTK KVLAGQCVPT NQHYLLKCYD LWWHDAPITF DHNLRLIKSA GIKEGLNLNT    60
ALVKAVRENN YNLIKLFAEW GADINYGLVS VNTEHTWDLC RELGAKETLN EEEILQIFID   120
LKFHKTSSNI ILCHEVFSNN PILQKVNNIK MRIEIFWELR ELIVKTDLLN NEFSLSTLLL   180
KYWYAIAIRY NLKEAIQYFY QKYTHLNTWR LTCALCFNNV FDLHEAYEKD KIHMDIEEMM   240
RIACIKDHNL STMYYCYVLG ANINQAMLSS IQYYNIENMF FCIDLGADVF EEGTTALGEG   300
YELIKNILSL KIYSPATTPL PKSTDPEIID HALKNYVSKN MMIFLTYDLR              350

SEQ ID NO: 752            moltype = AA  length = 357
FEATURE                   Location/Qualifiers
source                    1..357
                          mol_type = protein
                          organism = African swine fever virus
SEQUENCE: 752
MLSLQTLAKK VVACNYLSSD YDYTLQRFGL WWDLGPIHLC NNCKQVFSYK HLQCFSEDDL    60
CLEAALVKAV KSDNLELIRL FVDWGANPEY GLIRVPAVYL KRLCAELGGL TPVSEPRLLE   120
ILKEVANLKS CAGVLLGYDM FCHNPLLETV TRTTLDTVTY TCSNIPLTGD TAHHLLLTKFW  180
FALALRHNFT KAIHYFYKRH KNQLYWRVAC SLYFNNIFDI HELCREKEIC ISPNLMMKFA   240
CLREKNYAAI YYCHRLGASL DYGMNLSIYN NNTLNMFFCI DLGAADFDRA QLIAHKAYMY   300
NLSNIFLVKQ LFSRDVTLVL DVTEPQEIYD MLKTYTSKNM KRAEEYLTAH PEIIVID      357

SEQ ID NO: 753            moltype = AA  length = 357
FEATURE                   Location/Qualifiers
source                    1..357
                          mol_type = protein
                          organism = African swine fever virus
SEQUENCE: 753
MLSLQTLAKK VVACNYLSSD YDYTLQRFGL WWDLGPIHLC NNCKQVFSYK HLQCFSEDDL    60
CLEAALVKAV KSDNLELIRL FVDWGANPEY GLIRVPAVYL KRLCAELGGL TPVSEPRLLE   120
ILKEVARLKS CAGVLLGYDM FCHNPLLETV TRTTLDTVTY TCSNIPLTGD TAHHLLLTKFW  180
FALALRHNFT KAIHYFYKRH KNHLYWRVAC SLYFNNIFDI HELCREKEIC ISPNLMMKFA   240
CLREKNYAAI YYCHRLGASL DYGMNLSIYN NNTLNMFFCI DLGAADFDRA QLIAHKAYMY   300
NLSNIFLVKQ LFSRDVTLVL DVTEPQEIYD MLKTYTSKNL KRAEEYLTAH PEIIVID      357

SEQ ID NO: 754            moltype = AA  length = 276
FEATURE                   Location/Qualifiers
source                    1..276
                          mol_type = protein
                          organism = African swine fever virus
SEQUENCE: 754
MVLIEFLTGF FYLYGKRLFS ISKVMDMICL DYYTIIPAPL AMMLAARIKN YDLMKRLHEW    60
EISVDYALLV VDDVPSIDFC LSLGAKSPTR AQKRQLLRDN TFNPVYKYLM NCSGFPTRRE   120
KNIPCDVQCE RLQKNIIKEL VFNCSVLLEM VLHTEREYAY ALHCAAKHNQ LPILMYCWQQ   180
STDAESILLK TCCSDKNINC FNYCILYGGA QNLNAAMVEA AKHDARMLIN YCVMLGGRSL   240
NEAKETAAMF GHIECAQHCF ELQSYVMDAL NADDAD                            276

SEQ ID NO: 755            moltype = AA  length = 289
FEATURE                   Location/Qualifiers
source                    1..289
                          mol_type = protein
                          organism = African swine fever virus
```

```
SEQUENCE: 755
LNKIFLNITE TINMVLIEFL TGFFYLYGKR LFSISKVMDM ICLDYYTIIP APLAMMLAAR      60
LKNYDLMKRL HEWEISIDYA LLVVDDVPSI DYCLSLGARS PTRAQKRELL RDNTFNPVYK    120
YLMNCSGFPT KREKNIPCDV QCERLQKNII KELVFNCSVL LEMVLHTERE YAYALHCAAK    180
HNQLPILMYC WQQSTDAESI LLKTCCSDKN INCFNYCILY GGAQNLDAAM VEAAKHDARM    240
LINYCVMLGG RSLNEAKETA AMFGHIECAQ HCFKLQSYVV DTSNTDDTD                289

SEQ ID NO: 756          moltype = AA  length = 360
FEATURE                 Location/Qualifiers
source                  1..360
                        mol_type = protein
                        organism = African swine fever virus
SEQUENCE: 756
MSTPLSLQAL AKKILATQHI SKNHYFILKY CGLWWHGAPI MFSTNEDNQL MIKSAIFKDG     60
LELNLALMKA VQENNYDLIE LFTEWGADIN SSLVTVNTEH TWNFCRELGA KILNEMDIVQ    120
IFYKIHRIKT SSNIILCHKL LSNNPLFQNI EELKIIICCF LEKISINFIL NEITLNEMLA    180
RLWYSMAVRY HLTEAIQYFY QRYRHFKDWR LICGVAYNNV FDLHEIYNKE KTNIDIDEMM    240
QLACMYDCNY TTIYYCCMLG ADINRAMITS VMNFCEGNLF LCIDLGADAF EESMEIASQT    300
NNWILINILL FKNYSPDSSL LSIKTTDPEK INALLDEEKY KSKNMLIYEE SLFHIYGVNI    360

SEQ ID NO: 757          moltype = AA  length = 362
FEATURE                 Location/Qualifiers
source                  1..362
                        mol_type = protein
                        organism = African swine fever virus
SEQUENCE: 757
MSTPISLQAL AKKILATQHI SKEHYFILKY CGLWWHGAPI MLSTNEDNQL MIKSAIFKDG     60
LELNLALMKT VQENNYDLIE LFTEWGADIN SSLVTVNTEH TWNFCRELGA KILNEMDIVQ    120
IFYKIHRIKT SSNIILCHKL LSNNPLFQNI EELKVIICCF LEKISINFIL NEITFNEMLT    180
RYWYSIAILC KLTEAIQYFY QRYSHFKDWR LICGLSFNNV FDLHEMYHIK KVDMNIDEMI    240
YLACMRDSNF LTIYYCFVLG ADINRAMVTS VKNFYMNNLF FCIDLGANAF EESLELAKQK    300
NHDILVEILS FKDYYSSNVS LLSLKTTDPE KINALLKNYR SKNIMRYKKL CPEIIRWARF    360
II                                                                  362

SEQ ID NO: 758          moltype = AA  length = 267
FEATURE                 Location/Qualifiers
source                  1..267
                        mol_type = protein
                        organism = African swine fever virus
SEQUENCE: 758
MGYFLLITSI LETYAENWGA KEELETSEIL RFFFETKCKI TSSNVILCHE LFSNNPFLQN     60
VNMVDLRMII YWELKDLPTN SMLNEISFSE MLTKYWYGIA VKYNLKEAIQ YFCQEYRHFD    120
EWRLICALSF NNVFDLHEIC NTTKIHMSIN KMMELACMRD NNFLTIYYCF ALGANANRAM    180
LISVKNFCIE NMFFCMDLGA NVIEHSKTLA DIYGYSIIVN ILSLKIYKAN PILLSKETNP    240
EKINTLLKNY YSKNMLAYDI CCIDNYL                                       267

SEQ ID NO: 759          moltype = AA  length = 356
FEATURE                 Location/Qualifiers
source                  1..356
                        mol_type = protein
                        organism = African swine fever virus
SEQUENCE: 759
MQPSTLQALA KRALATQHVS KDDYYILERY GLWWHEAPIS MYIDDDNQIM IRTLCFKEGI     60
RLNTALVLAV KENNDDLIML FTEWGANINY GLLFINNEHT RNLCRKLGAK EELETSEILR    120
FFFETKCKIT SSNVILCHEL FSNNPFLQVN NMVDLRMIIY WELKDLPTN SMLNEISFSE    180
LTKYWYGIAV KYNLKEAIQY FCQEYRHFDE WRLICALSFN NVFDLHEICN TTKIHMSINK    240
MMELACMRDN NFLTIYYCFA LGANANRAML ISVKNFCIEN MFFCMDLGAN VIEHSKTLAD    300
IYGYSIIVNI LSLKIYKANP ILLSKETNPE KINTLLKNYY SKNMLAYDIC CIDNYL        356

SEQ ID NO: 760          moltype = AA  length = 386
FEATURE                 Location/Qualifiers
source                  1..386
                        mol_type = protein
                        organism = African swine fever virus
SEQUENCE: 760
MNSLQVLTKK VLIETKAFSK YHEDDIFILQ QLGLWWENGP IGFCKQCKMV TDGSMSCSDV     60
NSYELDRALV KAVKENQTDL IKIFLSWGAE INFGIMCAKT KQTKDLCIQL GADPEFLDVG    120
LYNMFVYLIK QKKVLLAIDI YYDNISILDS FDSHDFHVLI DPVYNRFILY LDEKEEMTR    180
NTLVLKFWYK FAIDFKLTKP IRYLSKKFPH LDLWRLQTAI YLGNIDEVHH AYFQENIRLS    240
LNVMMFLACA RPGNKLGIYY CFALGADLDR ALERLISFNS INREINRKIS GETRLCIEGS    300
YLSNVYFCIG LGANPYTKKI QETIKQKHSN IMILLFSKKK ILSPHSVLQN KILDPSDVRK    360
MISTYKNTES FYPFSSLAVK LIQQAK                                        386

SEQ ID NO: 761          moltype = AA  length = 387
FEATURE                 Location/Qualifiers
source                  1..387
                        mol_type = protein
                        organism = African swine fever virus
SEQUENCE: 761
```

```
MNSLQVLTKK VLIETKAFSN YHEDDIFILQ QLGLWWENGP IGFCKQCKMV TGGSMSCSDV    60
DSYELDRALV KAVKENQTDL IKLFVLWGAD INFGIMCAKT KQTKDLCIQL GANPEFLDVG   120
LYNMFVYLVK RKKVLLAIEI YYDNILILDS FNSNDFHLLI DFVYNRFILY LDEKEEEMTR   180
NTLVLKFWYK FAIDFNLTKP IHYLSKKFPH LDLWRLQTAI YLGNIDEVHH AYFQENIRLG   240
LNVMMPLACA RPGNKLGIYY CFALGADLDR ALERLISFNS INREINRKIR GEKRLCIEGS   300
YLSNVYFCIG LGANPYTKKI QEIIKQKHSN IMILLFSKKK ILSPHSVLQN KILDPSDVHK   360
MISTYKNTES FYPFSSLAVK LIQQANI                                      387

SEQ ID NO: 762          moltype = AA  length = 375
FEATURE                 Location/Qualifiers
source                  1..375
                        mol_type = protein
                        organism = African swine fever virus
SEQUENCE: 762
MNSLQVLTKK VLIENKAFSE YHEDDIFILQ QLGLWWHNGP IGFCKQCKMV TSGSMSCSDV    60
DSYELDRALV RAVKKNQTDL IKLFVLWGAN INYGIICAKT ERTKDLCIEL GANPEFLDVG   120
LYNMFVDLIK QQKVLLAIDI YYDNISILDS FDSHDFYVLI DFIYNCFILN LDEKEKMIKN   180
TYVLKFWFKI AIEFNLIKPI RFLSKKFPHL DYWRLKTAVY LGNVDEIHHA YFQENIRLDP   240
NDMMSLACMY PQNKLGIYYC FALGANINTA LETLIGFINH EVNREITFFS NYGIWSNVHF   300
CISLGANPYT KKIQETLLRQ EKNVIMKLLF KKGLLSPHSI LHKKILEPSE VRKIISTYEY   360
TETFHSFSLL RDNLR                                                   375

SEQ ID NO: 763          moltype = AA  length = 375
FEATURE                 Location/Qualifiers
source                  1..375
                        mol_type = protein
                        organism = African swine fever virus
SEQUENCE: 763
MNSLQVLTKK VLIENKAFSN YHEDDIFILQ QLGLWWENGP IGFCKQCKMV TSGSMSCSDV    60
DSYELDRALV RAVKKNQTDL IKLFVLWGAN INYGIICAKT ERTKVLCIQL GADPKFLDVG   120
LYNMFVDLIK QQKVLLAIDI YYDNISILDS FDSHDFYVLI DFIYNRFILN LDEKEKMIKN   180
TYVLKFWFKI AIEFNLIKPI RFLSKKFPHL DYWRLKTAVY LGNVDEIHHA YFQENIRLDP   240
NDMMSLACMY PQNKLGIYYC FALGANINTA LETLIGFINH EVNREITFFS NYGIWSNVHF   300
CISLGANPYT KKIQETLLRQ EKNVMMKLLF KKGLLSPHSI LHKKILEPSE VRKIISTYEY   360
TETFHSFSSL RDNLR                                                   375

SEQ ID NO: 764          moltype = AA  length = 319
FEATURE                 Location/Qualifiers
source                  1..319
                        mol_type = protein
                        organism = African swine fever virus
SEQUENCE: 764
MLSLQTLAKK AVAKQSVPEE YHYILKYCGL WWQNKPISLC HYCNYVILSS TPFKGELLHL    60
DVALIMAIKE NNYDVIRLFT EWGANIYYGL TCARTEQTQE LCRKLGAKDG LNNKEIFAGL   120
MRHKTSNNII LCHEIFDKNP MLEALNVQEM GEEIHRELKL FIFYILDNVP MNIFVKYWYA   180
IAVKYKLKRA IFFFYQTYGH LSMWRLMCAI YFNNVFDLHE IYEQKIVHMD IDKMMQLACM   240
QDYNFLTIYY CFVLGADIDQ AITVTRWHYH TNNLYFCKDL KDLKQNTLTA RPLLLPNITD   300
PKKIYTMLKN YLPTSSNSL                                               319

SEQ ID NO: 765          moltype = AA  length = 319
FEATURE                 Location/Qualifiers
source                  1..319
                        mol_type = protein
                        organism = African swine fever virus
SEQUENCE: 765
MLSLQTLAKK AVAKQSVPEE YHYILKYCGL WWQNKPISLC HYCNYVILSS TPFKGELLHL    60
DVALIMAIKE NNYDVIRLFT EWGANIYYGL TCARTEQTQE LCRKLGAKDS LNNKEIFTGL   120
MRHKTSNNII LCHEIFDKNP MLEALNVQEM GEEIHRELKF FIFYILDNVP MNVFVKYCYA   180
IAVKYKLKRA ISFFYQTYGH LSMWRLMCAI YFNNVFDLHE IYEQKIVHMD IDKMMQLACM   240
KDYNFLTIYY CFVLGGDIDQ AITATQWHHQ TNNLYFCKDL KDLKQNTLTA RPLLLPNITD   300
PKKIYTMLKN YLPTSSNSL                                               319

SEQ ID NO: 766          moltype = AA  length = 357
FEATURE                 Location/Qualifiers
source                  1..357
                        mol_type = protein
                        organism = African swine fever virus
SEQUENCE: 766
MFSLQDLCRK HLFILPDVFG EHVLQRLGLY WRCHGSLQRI GDDHILIRRD LILSTNEALR    60
MAGEEGNNEV VKLLLLWKGN LHYAVIGALQ GDQYDLIHKY ENQIGDFHFI LPLIQDANTF   120
EKCHALERFC GVSCLLKHAT KYNMLPILQK YQEELSMRAY LHETLFELAC LWQRYDVLKW   180
IEQTMHVYDL KIMFNIAISK RDLTMYSLGY IFLFDRGNTE ATLLTQHLEK TAAKGLLHFV   240
LETLKYGGNI DTVLTQAVKY NHRKLLDYFL RQLPRKHIEK LLLLAVQEKA SKKTLNLLLS   300
HLNYSVKRIK KLLRYVIEYE STLVIKILLK KKSKPDRCHV GKDGKIFFCD ESEDDHG      357

SEQ ID NO: 767          moltype = AA  length = 526
FEATURE                 Location/Qualifiers
source                  1..526
                        mol_type = protein
```

```
                            organism = African swine fever virus
SEQUENCE: 767
MFSLQDLCRK HLFILPDVFG EHVLQRLGLY WRCHGSLQRI GDDHILIRRD LILSTNEALR      60
MAGEEGNNEV VKLLLLWKGN LHYAVIGALQ GDQYDLIHKY ENQIGDFHFI LPLIQDANTF     120
EKCHALERFC GVSCLLKHAT KYNMLPILQK YQEELSMRAY LHETLFELAC LWQRYDVLKW     180
IEQTIHVYDL KIMFNIAISK RDLTMYSLGY IFLFDRGNTE ATLLTQHLKK TAAKGLLHFV     240
LETLKYGGNI DTVLTQAVKY NHRKLLDYFL RQLPRKHIEK LLLLAVQEKA SKKTLNLLLS     300
HLNYSVKRIK KLPRYVIEYE STLVIKILLK KRVNLIDAML EKMVRYFSAT KVRTIMDELS     360
ISPERVIKMA IQKMRTDIVI HTSYVWEDDL ERLTRLKNMV YTIKYEHGKK MLIKVMHGIY     420
KNLLYGEREK VMFYLAKLYV AQNAATQFRD ICKDCYKLDV ARFKPRFKQL ILDCLEIITK     480
KSCYSILEIL EKHIISLFTM KVMTEEEKNL CLEILYKVIH YKTIQC                    526

SEQ ID NO: 768              moltype = AA  length = 505
FEATURE                     Location/Qualifiers
source                      1..505
                            mol_type = protein
                            organism = African swine fever virus
SEQUENCE: 768
MFSLQDICRK YLFQLPDSFD EYTLQVLGLY WEKHGSLQRI RKDAVFVQRN LIISINEALR      60
IAASEGNGRV VKLLLSWEGN FHYVIIGALE GDHYDLIHKY GSQIEDYHMI LSSIHNANTF     120
EKCHELSNCD MWCLIQNAIK YNMLPILQKH RNILTHEGEN QELFEMACEE QKYDIVLWIG     180
QTLMLNEPEF IFDIAFERID FSLLTMGYSL LFNNKMSSID IHDEEDLISL LTEHLEKAAT     240
KGCFFFMLET LKHGGNVNMA VLSKAVEYNH RKILDYFIRQ KCLSRKDIEK LLLVAISNSA     300
SKKTLNLLLS YLNHSVKNII GKIVQSVLKN GDFTIIIFLK KKKINLVEPA LIGFINYYYS     360
YCFLEQFIHE FDIRPEKMIK MAARKGKLNM IIEFLNEKYV HKDDLGAIFK FLKNLVCTMK     420
HKKGKETLIV LIHKIYQVIQ LETKEKFKLL RFYVMHDATI QFISMYKDCF NLAGFKPFLL     480
ECLDIAIKKN YPDMIRNIET LLKCE                                          505

SEQ ID NO: 769              moltype = AA  length = 506
FEATURE                     Location/Qualifiers
source                      1..506
                            mol_type = protein
                            organism = African swine fever virus
SEQUENCE: 769
MFSLQDICRK HLFQLPDAFD EYILQALGLY WEKHGSLQRI RKDAVFVQRN IVLSTNEALR      60
IAASEGNERV IKLLLSWEGN FHYVIIGALE GDQYDLIHKY DSQIKDYHMI LSLIQNANTF     120
EKCHQLSNSN MWCLIQNAIK YNMLPILQKH RNILTHEGEN QELFEMACEE QKYDIVLWIG     180
QTLMLNEPEF IFDIAFERID FSLLTMGYSL LFDNKMSSID IHDEEDLTSL PTEHLEKAAT     240
KGCFFFMLET LKHGGNVNMA VLSKAVEYNH RKILDHFIRR QKCLSREEIE NLLLTAITNC     300
ASIKTLNLLL SYLNYSVKNI IGKIVQHVIK DGDYTIILLL KKKKINLVEP VLTGFIDYYY     360
SYCFIKHFIQ EFAIRPEKLI KMAARKGKLN MIIEFLNEKY VHKDDLGTIF KYLKTLVCTM     420
KHKKGKETLI VLIHKIYQDI HLETKEKFKL LRFYVMHDAT IQFLSMCKDC FNLAGFKPFV     480
LECLDIAIKK NYPDMIQYIE ILSKSE                                         506

SEQ ID NO: 770              moltype = AA  length = 528
FEATURE                     Location/Qualifiers
source                      1..528
                            mol_type = protein
                            organism = African swine fever virus
SEQUENCE: 770
MFSLQDLCRK NTFFLPNDFS KHTLQRLGLY WKEHGSVHRI EKDSIMIQNE LVLSINDALQ      60
LAGEEGDTDV VQLLLLWEGN LHYAIIGALK TENYNLVCEY HSQIQDWHIL LPLIQDPETF     120
EKCHDLSLGC DLICLLQHAV KCDMLSILVK YKEDLLNVRI RHRTQSLFVL ACENRRFEII     180
EWIGQNLSIP EPEAIFSIAI VTKDVELFSL GYKIIFDYMQ RQGIFQLTNV VRMLLLNRHI     240
GMAIEKGLLP FILETLKYGG SVKRALSYAV IDNKRKIIDY LVRHENIPRG TIERLLHLAV     300
KKQSSRKTLN LLLSYINYKV KNVKKLVEHV VDHKSTLVLK ILLEKKENLV DAVLTRLVKH     360
STYFQVREFI QEFSISPEKF IKIAVREKKN VLIEAISEDI WENPTERITY LKQIVHTIKY     420
ESGRRFLIDI IHSIYQSYSL KHEDILKLAT FYVKHNAITH FKDLCKYLWL NRGTESKKLF     480
LECLEIADEK EFPDIKSIVS EYINYLFTAG AITKEEIMQA YALEYDMY                  528

SEQ ID NO: 771              moltype = AA  length = 525
FEATURE                     Location/Qualifiers
source                      1..525
                            mol_type = protein
                            organism = African swine fever virus
SEQUENCE: 771
MFSLQDLCRK NIFFLPNDFS KHTLQWLGLY WKEHGSVHRA EKDSIMIQNE LVLSINDALQ      60
LAGEEGDTDV VQLLLLWEGN LHYAIIGALK TEKYNLICEY HSQIQDWHIL LPMIQDPETF     120
EKCHDLSLGC DFICLLQHAV KYNMLSILVK YKEDLLNARI RHRIQSLFVL ACENRRIEII     180
DWIGQNLPIP EPDAIFSIAV ATRDLELFSL GYKIIFDYMQ RQGIIQLTNG VRMVVLNRHI     240
SMAIDNGLLP FVLETLKHGG NIHRALSYAV THNRRKILDY LIRQKNIAPN TIERLLYLAV     300
KNQSSRKTLN LLLSYINYKV KNVKKLVEHV VNEKSTLVLK ILLEKKENLV DAVLTRLVKH     360
STYFQVREFI QEFSISPEKF IKIAVREKKN VLIEAISEDI WENPTERITY LKQIVHTIKY     420
ESGRRFLVDI IHSIYQSYSL KHEDILKLAT FYVKHNAITH FKDLCKYLWL NRGTESKKLF     480
LECLEIADEK EFPDIKSIVS EYINYLFTAG AITKEEIMQA YDALE                     525

SEQ ID NO: 772              moltype = AA  length = 528
FEATURE                     Location/Qualifiers
source                      1..528
```

```
                        mol_type = protein
                        organism = African swine fever virus
SEQUENCE: 772
MFSLQDLCRK NTFFLPDNFS KHTLYLLGLY WKGHGSIQRT MNDGVLIEHN LNLSINEALI    60
LAGEEGNNDV VQLLLLWEGN LHYAIIGALK TEKYGLICEY HSQIQDWHVL LPLIQDPETF   120
EKCHDLSLEC DLSCLLQHAV KYNMLSILVK YKEDLLNVLF RQQIQGLFIL ACEYRRIEIL   180
TWMGQNLPIP DPEPIFSIAV VTKDLEMFSL GYKIVFEYME NQGLFHLTQV VRMVMLNHHL   240
GMVINKGLLP FVLETLKHGG NVNRALSYAV TQNKRKILDH VVRQKNIPHK TIERMLHLAV   300
KKHAPRKTLN LLLSYINYKV KNVKKLLEHV VKYNSTLVIR ILLEKKKNLL DATLTRYVKD   360
STYFQVKEFM QDFSISPEKF IKIAVREKRN VLIKGISEDI WENPAERIRN LKQIVCTIKY   420
ESGRQFLINI IHTIYQSYSL KPEEILKLAT FYVKHNATTH FKDLCKYLWL NRGTESKKLF   480
LECLEIADEK EFPDIKSIVS EYINYLFTAG AITKEEIMQV YALEYAMY               528

SEQ ID NO: 773          moltype = DNA   length = 1587
FEATURE                 Location/Qualifiers
source                  1..1587
                        mol_type = unassigned DNA
                        organism = African swine fever virus
SEQUENCE: 773
atgttctccc ttcaggacct ctgtcggaag aacaccttct tccttccaga taatttagc    60
aagcataccc tgtatttgct ggggttatac tggaagggac atggatctat ccaaagaaca   120
atgaatgatg gtgtactgat agagcataat cttaatcttt ccatcaatga agccttaatc   180
cttgcaggag aagagggaaa caatgatgta gtacaactct tattgctatg gaaggaaat   240
cttcattatg ccatcatagg agctttgaag actgagaaat atggcttaat atgtgagtac   300
catagccaaa tcaggactg gcatgttctc ctcccttga ttcaagatcc agaaacattc   360
gaaaaatgtc atgatttaag ccttgaatgt gatctttcca gccttctcca acatgctgta   420
aaatataaca tgcttttctat tcttgttaaa tataaagaag atctattaaa tgtactattt   480
aggcaacaaa ttcaaggact attttatttta gcatgtgaat atcggaggat tgagattctt   540
acgtggatgg gtcaaaatct gccaattcct gatcctgagc ctattttag cattgctgtt   600
gtcacaaaag atttagaaat gttttcctta gggtacaaga ttgttttga atacatggaa   660
aatcaaggac tatttcattt aacccaggta gttcgtatgg ttatgctaaa tcatcacctt   720
ggcatggtaa taaataaagg acttttaccc tttgtgctgg aaactttaaa acatggtggg   780
aatgtaaata gagccttatc ttatgctgtc acacaaaaca aaagaaagat tttagaccat   840
gttgttcgcc aaaagaatat accccataaa accattgaaa gaatgttgca tctggctgta   900
aaaaagcatg ctcccaggaa aactctgaac ttgttactat cttacataaa ttacaaggta   960
aaaaatgtta aaaagttgtt agaacatgta gtgaaataca actctactct tgtgataaga   1020
atcttgttag aaaaaagaa aaacctgctg gatgctactt tgacaagata tgtcaaagat   1080
tctacatact ttcaggtgaa agaatttatg caagacttct ccatcagccc agaaaaattc   1140
attaaaatag ctgtgcggga aaagaggaat gtgttgatca agggtatttc tgaagatatt   1200
tgggaaaatc ccgcggaaag aatcaggaat cttaagcaga tagtgtgtac cataaaatat   1260
gaaagtggaa gacaattcct gataaatatc attcacacca tttaccagag ttattctttg   1320
aaacctgaag aaattcttaa actggcaaca ttttatgtca aacacaatgc aaccacccat   1380
tttaaagatc tctgcaaata tctttggctg aacagaggaa cagaaagtaa gaaactgttc   1440
ttagagtgct tggaaattgc tgatgagaag gagtttcctg atattaaaag tattgtgagt   1500
gaatatatta actacttgtt tactgcagga gctattacca aggaagaaat catgcaagtc   1560
tatgctttgg agtatgccat gtattaa                                     1587

SEQ ID NO: 774          moltype = AA    length = 527
FEATURE                 Location/Qualifiers
source                  1..527
                        mol_type = protein
                        organism = African swine fever virus
SEQUENCE: 774
MFSLQDLCRK NTFFLPSDFS KHTLHLLGLY WKGHGSIQRI KNDGVLIEHD LTLSINEALI    60
LAGEEGNNEV VKLLLLWEGN LHYAIIGALR TENYNLVCEY HSQIQDWHVL LPLIQDPETF   120
EKCHDLSLEC DLSCLLQHAV KYNMLSILVK YKEDLLNVLF RQQIQGLFIL ACENRKLEIL   180
TWMGQNLPIP DPEPIFSIAV VTKDLEMFSL GYKIVFEYME NQGLHLTQVV RMVMLNHHFG   240
MVINKGLLPF VLEILNYGGN VNRALSYAVT QNKRKILDHV VRQKNIPHKT IERMLHLAVK   300
KHAPRKTLNL LLSYINYKVK NVKKLLEHVV KYNSTLVIRL LEKKKNLLD ATLTRYVKDS   360
TYFQVKEFMQ DFSISPEKFI KIAVREKRNV LIKGISEDIW ENPAERIRNL KQIVCTIKYE   420
SGRQFLINII HTIYQSYSLK PEEILKLATF YVKHNATTHF KDLCKYLWLN RRTESKKLFL   480
ECLEIADKKE FPDIKSIVSE YINYLFTAGA ITKEEIMQAY ALEYAMY                 527

SEQ ID NO: 775          moltype = DNA   length = 1584
FEATURE                 Location/Qualifiers
source                  1..1584
                        mol_type = unassigned DNA
                        organism = African swine fever virus
SEQUENCE: 775
atgttctccc ttcaggacct ctgtcggaag aacaccttct tccttccaag tgatttagc    60
aagcataccc tgcatttgct ggggttatac tggaagggc atggatctat ccaaggata   120
aagaatgatg gtgtgcttat agagcatgat cttactcttt ccatcaatga agccttaatt   180
cttgcaggag aagagggaaa caatgaagta gtaaagctct tgttactatg gaaggaaat   240
cttcattatg ccatcatagg agctttgagg actgagaaat ataacctagt atgtgagtac   300
catagtcaaa tcaggactg gcatgttctc ctcccttga ttcaagatcc agaaacattc   360
gaaaaatgtc atgatttaag ccttgaatgt gatctttcat gccttctcca acatgctgta   420
aaatataaca tgcttttcgat tcttgttaaa tataaagagg atctactaaa tgtactattt   480
aggcaacaaa ttcaaggact attttatttta gcatgtgaaa tcggaagct tgagattctt   540
acgtggatgg gtcaaaatct gccaattcct gatcctgagc ctattttag cattgctgtt   600
```

```
gtcacaaaag atttagaaat gttttcctta gggtacaaga ttgttttga atacatggaa    660
aaccaaggac ttcatttaac ccaggtagtt cgtatggtta tgctaaatca tcactttggc   720
atggtaataa ataaaggact tttacccttt gtgctggaaa ttttaaatta tggtgggaat   780
gtaaatagag cctatctta tgctgtcaca caaaataaaa gaaagatttt agaccatgtt    840
gttcgccaaa agaatatacc ccataaaacc attgaaagaa tgttgcatct ggctgtaaaa   900
aagcatgctc ccaggaaaac tctgaacttg ttactatctt acataaatta caaggtgaaa   960
aatgttaaaa agttgttaga acatgtagtg aaatacaact ctactcttgt gataagactc  1020
ttgttagaaa aaagaaaaa cctgctggat gctactttga caagatatgt caaagattct  1080
acatactttc aggtgaaaga attatgcaa gacttctcca tcagcccaga aaaattcatt   1140
aaaatagctg tgcgggaaaa gagaaatgtg ttgatcaagg gtatttctga agatatttgg  1200
gaaaatcccg cggaaagaat caggaatctt aagcagatag tgtgtaccat aaaatatgaa  1260
agtgaagac aattcctgat aaatatcatt cacaccattt accagagtta ttctttgaaa   1320
cctgaagaaa ttcttaaatt ggcaacattt tatgtcaaac acaatgcaac cacccatttta 1380
aaagatctct gcaaatatct ttggctgaac agaagaacag aaagtaagaa actgttttta  1440
gagtgcttgg aaattgctga taagaaggag tttcctgata ttaaaagtat tgtgagtgaa  1500
tacattaact atttgtttac tgcaggagct attaccaagg aagaaatcat gcaagcctat  1560
gctttggagt atgccatgta ttaa                                         1584

SEQ ID NO: 776          moltype = AA  length = 9
FEATURE                 Location/Qualifiers
source                  1..9
                        mol_type = protein
                        organism = African swine fever virus
SEQUENCE: 776
RAKHPNTYI                                                             9

SEQ ID NO: 777          moltype = AA  length = 9
FEATURE                 Location/Qualifiers
source                  1..9
                        mol_type = protein
                        organism = African swine fever virus
SEQUENCE: 777
MRMLIRIEL                                                             9

SEQ ID NO: 778          moltype = AA  length = 9
FEATURE                 Location/Qualifiers
source                  1..9
                        mol_type = protein
                        organism = African swine fever virus
SEQUENCE: 778
RRWLRVICL                                                             9

SEQ ID NO: 779          moltype = AA  length = 9
FEATURE                 Location/Qualifiers
source                  1..9
                        mol_type = protein
                        organism = African swine fever virus
SEQUENCE: 779
ILDLIRLQY                                                             9

SEQ ID NO: 780          moltype = AA  length = 11
FEATURE                 Location/Qualifiers
source                  1..11
                        mol_type = protein
                        organism = African swine fever virus
SEQUENCE: 780
ILQWHLLYET Y                                                         11

SEQ ID NO: 781          moltype = AA  length = 10
FEATURE                 Location/Qualifiers
source                  1..10
                        mol_type = protein
                        organism = African swine fever virus
SEQUENCE: 781
SSIGDTMELY                                                           10

SEQ ID NO: 782          moltype = AA  length = 13
FEATURE                 Location/Qualifiers
source                  1..13
                        mol_type = protein
                        organism = African swine fever virus
SEQUENCE: 782
INYQRAPTWY SEV                                                       13

SEQ ID NO: 783          moltype = AA  length = 9
FEATURE                 Location/Qualifiers
source                  1..9
                        mol_type = protein
                        organism = African swine fever virus
```

-continued

```
SEQUENCE: 783
ATQQLALNY                                                                         9

SEQ ID NO: 784          moltype = AA  length = 9
FEATURE                 Location/Qualifiers
source                  1..9
                        mol_type = protein
                        organism = African swine fever virus
SEQUENCE: 784
FSFGRTLVY                                                                         9

SEQ ID NO: 785          moltype = AA  length = 1450
FEATURE                 Location/Qualifiers
source                  1..1450
                        mol_type = protein
                        organism = African swine fever virus
SEQUENCE: 785
MEAGYAEIAA VQFNIAGDND HKRQGVMEVT ISNLFEGTLP AEGGIYDARM GTTDHHYKCI    60
TCSHQRKQCM GHPGILQMHA PVLQPLFIAE IRRWLRVICL NCGAPIVDLK RYEHLIRPKR   120
LIEAASSQTE GKQCYVCKAV HPKIVKDSED YFTFWVDQQG KIDKLYPQII REIFSRVTYD   180
TVVKLGRSKN SHPEKLVLKA IQIPPISIRP GIRLGIGSGP QSFHDINNVI QYLVRKNLLI   240
PKDLQIVRGQ KIPLNIDRNL QTIQQLYYNF LLDSVSTTAT QGGTGKRGIV MGARPAPSIM   300
RRLPRKEGRI RKSLLGSQVW SISRSTICGN SDLHLDEVGY PISFARTLQV AETVQHYNIN   360
RLMPYFLNGK RQYPGCSRVY KQITQSVHDI EGLKQDFRLE VGDILYRDVV TGDVAFFNRQ   420
PSLERSSIGV HRIVVLENPK ISTFQMNVSA CAWYNADFDG DQMNLWVPWS VMSRVEAELL   480
CSVRNWFIST KSSGPVNGQV QDSTVGSFLL TRTNTPMGKN VMNKLHAMGL FQTTQTDPPC   540
FANYSPTDLL DGKSVVSMLL KQTPINYQRA PTWYSEVYAP YMHYNKQDIS TQIRNGELIE   600
GVLDKKAVGA GSSGGIYHLI SRRYGPQQAL KMIFATQQLA LNYVRNAGFT VSTADMLLTP   660
EAHQEVQEII NELLLESEEI NNRLLHGDIM PPIGLTTHDF YEKLQLNALK FPDRILKPIM   720
NSINPETNGL FQMVATGAKG SNPNMIHIMA GIGQIEINTQ RIQPQFSFGR TLVYYPRFAL   780
EAQAYGFICN SYIAGLTSPE FIFGEMNGRF DLINKALSTS STGYANRKAI FGLQSCIVDY   840
YRRVSIDTRL VQQLYGEDGL DARQLETVRF ETIMLSDQEL EDKFKYTGIQ SPLFEEEFSR   900
LKKDRDKYRQ IFLNVENFNF SQLLTDVRQV PVNVASIVKN ILLSSTSGVL PFDEKSILQK   960
YAMVKTFCKN LPYVFINNIQ ERLQTPIPVY LKRAAALMRL LIRIELATVK TLNITCEQMS  1020
AILDLIRLQY TQSLINYGEA VGILAAQSVS EPLTQYMLDS HHRSVAGGTN KSGIVRPQEI  1080
FSAKPVEAEQ SSEMLLRLKN PEVETNKTYA QEIANSIELI TFERLILQWH LLYETYSSTK  1140
KNVMYPDFAS DVEWMTDFLE NHPLLQPPED IANWCIRLEL NKTTMILKSI SLESIINSLR  1200
AKHPNTYIMH SVENTASGIP IIIRIYLRES AFRRSTNTRM ATDEKIAVNV VDKLLNSTIR  1260
GIPGIKNANV VKLMRHRVDA QGKLVRLDNI YAIKTNGTNI FGAMLDDNID PYTIVSSSIG  1320
DTMELYGIEA ARQKIISEIR TVMGDKGPNH RHLLMYADLM TRTGQVTSLE KAGLNAREPS  1380
NVLLRMALSS PVQVLTDAAV DSAVNPIYGI AAPTLMGSVP RIGTMYSDII MDEKYITENY  1440
KSVDSMIDML                                                        1450

SEQ ID NO: 786          moltype = AA  length = 1438
FEATURE                 Location/Qualifiers
source                  1..1438
                        mol_type = protein
                        organism = African swine fever virus
SEQUENCE: 786
FNIAGDNDHK RQGVMEVTIS NLFEGTLPAE GGIYDARMGT TDHHYKCITC SHQRKQCMGH    60
PGILQMHAPV LQPLFIAEIR RWLRVICLNC GAPIVDLKRY EHLIRPKRLI EAASSQTEGK   120
QCYVCKAVHP KIVKDSEDYF TFWADQQGKI DKLYPQIIRE IFSRVTYDTV VKLGRSKNSH   180
PEKLVLKAIQ IPPISIRPGI RLGIGSGPQS FHDINNVIQY LVRKNLLIPK DLQIVRGQKI   240
PLNIDRNLQT IQQLYYNFLL DSVSTTATQG GTGKRGIVMG ARPAPSIMRR LPRKEGRIRK   300
SLLGSQVWSI SRSTICGNSD LHLDEVGYPI SFARTLQVAE TVQHYNINRL MPYFLNGKRQ   360
YPGCSRVYKQ ITQSVHDIEG LKQDFRLEVG DILYRDVVTG DVAFFNRQPS LERSSIGVHR   420
IVVLENPKIS TFQMNVSACA WYNADFDGDQ MNLWVPWSVM SRVEAELLCS VRNWFISTKS   480
SGPVNGQVQD STVGSFLLTR TNTPMGKNVM NKLHAMGLFQ TTQTDPPCFA NYSPTDLLDG   540
KSVVSMLLRQ TPINYQRAPT WYSEVYAPYM HYNKQDISTQ IRNGELIEGV LDKKAVGAGS   600
SGGIYHLISR RYGPQQALKM IFATQQLALN YVRNAGFTVS TADMLLTPEA HQEVQEIINE   660
LLLESEEINN RLLHGDIMPP IGLTTHDFYE KLQLNALKFP DRILKPIMNS INPETNGLFQ   720
MVATGAKGSN PNMIHIMAGI GQIEINTQRI QPQFSFGRTL VYYPRFALEA QAYGFICNSY   780
IAGLTSPEFI FGEMNGRFDL INKALSTSST GYANRKAIFG LQSCIVDYYR RVSIDTRLVQ   840
QLYGEDGLDA RQLETVRFET IMLSDQELED KFKYTGIQSP LFEEEFSRLK KDRDKYRQIF   900
LNVENFNFSQ LLTDVRQVPV NVASIVKNIL LSSTSGVLPF DEKSILQKYA MVKTFCKNLP   960
YVFINNIQER LQTPIPVYLK RAASLMRMLI RIELATVKTL NITCEQMSAI LDLIRLQYTQ  1020
SLINYGEAVG ILAAQSVSEP LTQYMLDSHH RSVAGGTNKS GIVRPQEIFS AKPVEAEQSS  1080
EMLLRLKNPE VETNKTYAQE IANSIELITF ERLILQWHLL YETYSSTKKN VMYPDFASDV  1140
EWMTDFLENH PLLQPPEDIA NWCIRLELNK TTMILKSISL ESIINSLRAK HPNTYIMHSV  1200
ENTASGIPII IRIYLRESAF RRSTNTRMAT DEKIAVNVVD KLLNSTIRGI PGIKNANVVK  1260
LMRHRVDAQG KLVRLDNIYA IKTNGTNIFG AMLDDNIDPY TIVSSSIGDT MELYGIEAAR  1320
QKIISEIRTV MGDKGPNHRH LLMYADLMTR TGQVTSLEKA GLNAREPSNV LLRMALSSPV  1380
QVLTDAAVDS AVNPIYGIAA PTLMGSVPRI GTMYSDIIMD EKYITENYKS VDSLIDML    1438

SEQ ID NO: 787          moltype = AA  length = 10
FEATURE                 Location/Qualifiers
source                  1..10
                        mol_type = protein
                        organism = African swine fever virus
```

```
SEQUENCE: 787
TPALFKKHLY                                                                  10

SEQ ID NO: 788         moltype = AA  length = 9
FEATURE                Location/Qualifiers
source                 1..9
                       mol_type = protein
                       organism = African swine fever virus
SEQUENCE: 788
VVTPKHLTY                                                                    9

SEQ ID NO: 789         moltype = AA  length = 16
FEATURE                Location/Qualifiers
source                 1..16
                       mol_type = protein
                       organism = African swine fever virus
SEQUENCE: 789
YADRYALFQK LTPALF                                                           16

SEQ ID NO: 790         moltype = AA  length = 419
FEATURE                Location/Qualifiers
source                 1..419
                       mol_type = protein
                       organism = African swine fever virus
SEQUENCE: 790
MLNQFPGQYS NNIFCFPPIE SETKSGKKAS WIICVQVVQH NTIIPITDEM FSTDVKDAVA           60
EIFTKFFVEE GAVRISKMTR VTEGKNLGKK NATTVVHQAF KDALSKYNRH ARQKRGAHTN          120
RGMIPPMLVK YFNIIPKTFF EEETDPIVQR KRNGVRAVAC QQGDGCILLY SRTEKEFLGL          180
DNIKKELKQL YLFIDVRVYL DGELYLHRKP LQWIAGQANA KTDSSELHFY VFDCFWSDQL          240
QMPSNKRQQL LTNIFKQKED LTFIHQVENF SVKNVDEALR LKAQFIKEGY EGAIVRNANG          300
PYEPGYNNYH SAHLAKLKPL LDAEFILVDY TQGKKGKDLG AILWVCELPN KKRFVVTPKH          360
LTYADRYALF QKLTPALFKK HLYGKELTVE YAELSPKTGI PLQARAVGFR EPINVLEII           419

SEQ ID NO: 791         moltype = AA  length = 419
FEATURE                Location/Qualifiers
source                 1..419
                       mol_type = protein
                       organism = African swine fever virus
SEQUENCE: 791
MLNQFPGQYS NNIFCFPPIE SETKSGKKAS WIICVQVVQH NTIIPITDEM FSTDVKDAVA           60
EIFTKFFVEE GAVRISKMTR VTEGKNLGKK NATTVVHQAF KDALSKYNRH ARQKRGAHTN          120
RGIIPPMLVK YFNIIPKTFF EEETDPIVQR KRNGVRAVAC QQGDGSILLY SRTKKEFLGL          180
DNIKKELKQL YLFIDVRVYL DGELYLHRKP LQWIAGQANA KTDSSELHFY VFDCFWSDQL          240
QMPSNKRQQL LTNIFKQKED LTFIHQVENF SVKNVDEALR LKAQFIKEGY EGAIVRNANG          300
PYEPGYNNYH SAHLAKLKPL LDAEFILVDY TQGKKGKDLG AILWVCELPN KKRFVVTPKH          360
LTYADRYALF QKLTPALFKK HLYGKELTVE YAELSPKTGI PLQARAVGFR EPINVLEII           419

SEQ ID NO: 792         moltype = AA  length = 11
FEATURE                Location/Qualifiers
source                 1..11
                       mol_type = protein
                       organism = African swine fever virus
SEQUENCE: 792
TLINPDDEYL Y                                                                11

SEQ ID NO: 793         moltype = AA  length = 9
FEATURE                Location/Qualifiers
source                 1..9
                       mol_type = protein
                       organism = African swine fever virus
SEQUENCE: 793
YLYEIEIEY                                                                    9

SEQ ID NO: 794         moltype = AA  length = 21
FEATURE                Location/Qualifiers
source                 1..21
                       mol_type = protein
                       organism = African swine fever virus
SEQUENCE: 794
QFQPSDFPLA FLYYHPDTSS F                                                     21

SEQ ID NO: 795         moltype = AA  length = 10
FEATURE                Location/Qualifiers
source                 1..10
                       mol_type = protein
                       organism = African swine fever virus
SEQUENCE: 795
YMDPFSFEEL                                                                  10
```

| | | |
|---|---|---|
| SEQ ID NO: 796 | moltype = AA  length = 868 | |
| FEATURE | Location/Qualifiers | |
| source | 1..868 | |
| | mol_type = protein | |
| | organism = African swine fever virus | |
| SEQUENCE: 796 | | |

```
MASLDNLVAR YQRCFNDQSL KNSTIELEIR FQQINFLLFK TVYEALVAQE IPSTISHSIR   60
CIKKVHHENH CREKILPSEN LYFKKQPLMF FKFSEPASLG CKVSLAIEQP IRKFILDSSI  120
LVRLKNRTTF RVSELWKIEL TIVKQLMGSE VSAKLAAFKT LLFDTPEQQT TKNMMTLINP  180
DDEYLYEIEI EYTGKPESLT AADVIKIKNT VLTLISPNHL MLTAYHQAIE FIASHILSSE  240
ILLARIKSGK WGLKRLLPQV KSMTKADYMK FYPPVGYYVT DKADGIRGIA VIQDTQIYVV  300
ADQLYSLGTT GIEPLKPTIL DGEFMPEKKE FYGFDVIMYE GNLLTQQGFE TRIESLSKGI  360
KVLQAFNIKA EMKPFISLTS ADPNVLLKNF ESIFKKKTRP YSIDGIILVE PGNSYLNTNT  420
FKWKPTWDNT LDFLVRKCPE SLNVPEYAPK KGFSLHLLFV GISGELFKKL ALNWCPGYTK  480
LFPVTQRNQN YFPVQFQPSD FPLAFLYYHP DTSSFSNIDG KVLEMRCLKR EINHVSWEIV  540
KIREDRQQDL KTGGYFGNDF KTAELTWLNY MDPFSFEELA KGPSGMYFAG AKTGIYRAQT  600
ALISFIKQEI IQKISHQSWV IDLGIGKGQD LGRYLDAGIR HLVGIDKDQT ALAELVYRKF  660
SHATTRQHKH ATNIYVLHQD LAEPAKEISE KVHQIYGFPK EGASSIVSNL FIHYLMKNTQ  720
QVENLAVLCH KLLQPGGMVW FTTMLGEQVL ELLHENRIEL NEVWEARENE VVKFAIKRLF  780
KEDILQETGQ EIGVLLPFSN GDFYNEYLVN TAFLIKIFKH HGFSLVQKQS FKDWIPEFQN  840
FSKSLYKILT EADKTWTSLF GFICLRKN                                    868
```

| | | |
|---|---|---|
| SEQ ID NO: 797 | moltype = AA  length = 9 | |
| FEATURE | Location/Qualifiers | |
| source | 1..9 | |
| | mol_type = protein | |
| | organism = African swine fever virus | |
| SEQUENCE: 797 | | |
| YQLDLFTAL | | 9 |

| | | |
|---|---|---|
| SEQ ID NO: 798 | moltype = AA  length = 174 | |
| FEATURE | Location/Qualifiers | |
| source | 1..174 | |
| | mol_type = protein | |
| | organism = African swine fever virus | |
| SEQUENCE: 798 | | |

```
MLTLIQGKKI VNDLRSRLAF EYNGQLIKIL SKNIVAVGSL RREEKMLNDV DLLIIVPEKK   60
LLKHVLPNIR IKDLSFSVKV CGERKCVLFI EWKKNTYQLD LFTALAEEKP YAVLHFTGPV  120
SYLIRIRAAL KKKNYKLNQY GLFKNQTLVP LKITTEKELI KELGFTYRIP KKRL        174
```

| | | |
|---|---|---|
| SEQ ID NO: 799 | moltype = AA  length = 16 | |
| FEATURE | Location/Qualifiers | |
| source | 1..16 | |
| | mol_type = protein | |
| | organism = African swine fever virus | |
| SEQUENCE: 799 | | |
| VVIMAIMLYY FWWMPR | | 16 |

| | | |
|---|---|---|
| SEQ ID NO: 800 | moltype = AA  length = 61 | |
| FEATURE | Location/Qualifiers | |
| source | 1..61 | |
| | mol_type = protein | |
| | organism = African swine fever virus | |
| SEQUENCE: 800 | | |

```
MALDGSSGGG SNVETLLIVA IIVVIMAIML YYFWWMPRQQ KKCSKAEECT CNNGSCSLKT   60
S                                                                  61
```

| | | |
|---|---|---|
| SEQ ID NO: 801 | moltype = AA  length = 10 | |
| FEATURE | Location/Qualifiers | |
| source | 1..10 | |
| | mol_type = protein | |
| | organism = African swine fever virus | |
| SEQUENCE: 801 | | |
| AAYVGKGTTI | | 10 |

| | | |
|---|---|---|
| SEQ ID NO: 802 | moltype = AA  length = 9 | |
| FEATURE | Location/Qualifiers | |
| source | 1..9 | |
| | mol_type = protein | |
| | organism = African swine fever virus | |
| SEQUENCE: 802 | | |
| NSTIHTATI | | 9 |

| | | |
|---|---|---|
| SEQ ID NO: 803 | moltype = AA  length = 9 | |
| FEATURE | Location/Qualifiers | |
| source | 1..9 | |
| | mol_type = protein | |
| | organism = African swine fever virus | |
| SEQUENCE: 803 | | |

| | | |
|---|---|---|
| VIKKFQQTI | | 9 |
| SEQ ID NO: 804<br>FEATURE<br>source<br><br>SEQUENCE: 804<br>AAYVGKGTTI | moltype = AA  length = 10<br>Location/Qualifiers<br>1..10<br>mol_type = protein<br>organism = African swine fever virus | <br><br><br><br><br>10 |
| SEQ ID NO: 805<br>FEATURE<br>source<br><br>SEQUENCE: 805<br>TIMVRNEQL | moltype = AA  length = 9<br>Location/Qualifiers<br>1..9<br>mol_type = protein<br>organism = African swine fever virus | <br><br><br><br><br>9 |
| SEQ ID NO: 806<br>FEATURE<br>source<br><br>SEQUENCE: 806<br>IEFNTYYEIL YAWLPYRR | moltype = AA  length = 18<br>Location/Qualifiers<br>1..18<br>mol_type = protein<br>organism = African swine fever virus | <br><br><br><br><br>18 |
| SEQ ID NO: 807<br>FEATURE<br>source<br><br>SEQUENCE: 807<br>NTYYEILY | moltype = AA  length = 8<br>Location/Qualifiers<br>1..8<br>mol_type = protein<br>organism = African swine fever virus | <br><br><br><br><br>8 |
| SEQ ID NO: 808<br>FEATURE<br>source<br><br>SEQUENCE: 808<br>ILYAWLPY | moltype = AA  length = 8<br>Location/Qualifiers<br>1..8<br>mol_type = protein<br>organism = African swine fever virus | <br><br><br><br><br>8 |
| SEQ ID NO: 809<br>FEATURE<br>source<br><br>SEQUENCE: 809<br>REHAVLKL | moltype = AA  length = 8<br>Location/Qualifiers<br>1..8<br>mol_type = protein<br>organism = African swine fever virus | <br><br><br><br><br>8 |
| SEQ ID NO: 810<br>FEATURE<br>source<br><br>SEQUENCE: 810<br>RIIMETAIVR Y | moltype = AA  length = 11<br>Location/Qualifiers<br>1..11<br>mol_type = protein<br>organism = African swine fever virus | <br><br><br><br><br>11 |
| SEQ ID NO: 811<br>FEATURE<br>source<br><br>SEQUENCE: 811<br>REMFTRIEL | moltype = AA  length = 9<br>Location/Qualifiers<br>1..9<br>mol_type = protein<br>organism = African swine fever virus | <br><br><br><br><br>9 |
| SEQ ID NO: 812<br>FEATURE<br>source<br><br>SEQUENCE: 812<br>SIAENVFKTH Y | moltype = AA  length = 11<br>Location/Qualifiers<br>1..11<br>mol_type = protein<br>organism = African swine fever virus | <br><br><br><br><br>11 |
| SEQ ID NO: 813<br>FEATURE<br>source | moltype = AA  length = 9<br>Location/Qualifiers<br>1..9<br>mol_type = protein<br>organism = African swine fever virus | |

```
SEQUENCE: 813
KTMPVEFYY                                                                     9

SEQ ID NO: 814        moltype = AA  length = 10
FEATURE               Location/Qualifiers
source                1..10
                      mol_type = protein
                      organism = African swine fever virus
SEQUENCE: 814
SLANHTVKYY                                                                   10

SEQ ID NO: 815        moltype = AA  length = 8
FEATURE               Location/Qualifiers
source                1..8
                      mol_type = protein
                      organism = African swine fever virus
SEQUENCE: 815
YVADHMFY                                                                      8

SEQ ID NO: 816        moltype = AA  length = 1192
FEATURE               Location/Qualifiers
source                1..1192
                      mol_type = protein
                      organism = African swine fever virus
SEQUENCE: 816
MEAFEISDFK EHAKKKSMWA GALNKVTISG LMGVFTEDED LMALPIHRDH CPALLKIFDE             60
LIVNATDHER ACHSKTKKVT YIKISFDKGV FSCENDGPGI PIAKHEQASL IAKRDVYVPE            120
VASCFFLAGT NINKAKDCIK GGTNGVGLKL AMVHSQWAIL TTADGAQKYV QQINQRLDII            180
EPPTITPSRE MFTRIELMPV YQELGYAEPL SETEQADLSA WIYLRACQCA AYVGKGTTIY            240
YNDKPCRTGS VMALAKMYTL LSAPNSTIHT ATIKADAKPY SLHPLQVAAV VSPKFKKFEH            300
VSIINGVNCV KGEHVTFLKK TINEMVIKKF QQTIKDKNRK TTLRDSCSNI FVVIVGSIPG            360
IEWTGQRKDE LSIAENVFKT HYSIPSSFLT SMTRSIVDIL LQSISKKDNH KQVDVDKYTR            420
ARNAGGKRAQ DCMLLAAEGD SALSLLRTGL TLGKSNPSGP SFDFCGMISL GGVIMNACKK            480
VTNITTDSGE TIMVRNEQLT NNKVLQGIVQ VLGLDFNCHY KTQEERAKLR YGCIVACVDQ            540
DLDGCGKILG LLLAYFHLFW PQLIIHGFVK RLLTPLIRVY EKGKTMPVEF YYEQEFDAWA            600
KKQTSLVNHT VKYYKGLAAH DTHEVKSMPK HFDNMVYTFT LDDSAKELFH IYFGGESELR            660
KRELCTGVVP LTEQTQSIH SVRRIPCSLH LQVDTKAYKL DAIERQIPNF LDGMTRARRK             720
ILAGGVKCFA SNNRERKVFQ FGGYVADHMF YHHGDMSLNT SIIKAAQYYP GSSHLYPVFI            780
GIGSFGSRHL GGKDAGSPRY ISVQLASEFI KTMFPAEDSW LLPYVFEDGQ RAEPEYYVPV            840
LPLAIMEYGA NPSEGWKYTT WARQLEDILA LVRAYVDKDN PKHELLYHAI KHKITILPLR            900
PSNYNFKGHL KRFGQYYYSY GTYDISEQRN IITITELPLR VPTVAYIESI KKSSNRMTFI            960
EEIIDYSSSE TIEILVKLKP NSLNRIVEEF KETEEQDSIE NFLRLRNCLH SHLNFVKPKG           1020
GIIEFNSYYE ILYAWLPYRR ELYQKRLMRE HAVLKLRIIM ETAIVRYINE SAELNLSHYE           1080
DEKEASRILS EHGFPPLNHT LIISPEFASI EELNQKALQG CYTYILSLQA RELLIAAKTR           1140
RVEKIKKMQA RLDKVEQLLQ ESPFPGASVW LEEIDAVEKA IIKGRNTQWK FH                   1192

SEQ ID NO: 817        moltype = AA  length = 1192
FEATURE               Location/Qualifiers
source                1..1192
                      mol_type = protein
                      organism = African swine fever virus
SEQUENCE: 817
MEAFEISDFK EHAKKKSMWA GALNKVTISG LMGVFTEDED LMALPIHRDH CPALLKIFDE             60
IIVNATDHER ACHNKTKKVT YIKISFDKGV FSCENDGPGI PIAKHEQASL IAKRDVYVPE            120
VASCFFLAGT NINKAKDCIK GGTNGVGLKL AMVHSQWAIL TTADGAQKYV QHINQRLDII            180
EPPTITPSRE MFTRIELMPV YQELGYAEPL SETEQADLSA WIYLRACQCA AYVGKGTTIY            240
YNDKPCRTGS VMALAKMYTL LSAPNSTIHT ATIKADAKPY SLHPLQVAAV VSPKFKKFEH            300
VSVINGVNCV KGEHVTFLKK TINEMVVKKF QQTIKDKNRK TTLRDSCSNI FIVIVGSIPG            360
IEWTGQRKDE LSIAENVFKT HYSIPSSFLT SMTKSIVDIL LQSISKKDNH KQVDVDKYTR            420
ARNAGGKRAQ DCMLLAAEGD SALSLLRTGL TLGKSNPSGP SFDFCGMISL GGVIMNACKK            480
VTNITTDSGE TIMVRNEQLT NNKVLQGIVQ VLGLDFNCHY KTQEERAKLR YGCIVACVDQ            540
DLDGCGKILG LLLAYFHLFW PQLIIHGFVK RLLTPLIRVY EKGKTMPVEF YYEQEFDAWA            600
KKQTSLANHT VKYYKGLAAH DTHEVKSMPK HFDNMVYTFT LDDSAKELFH IYFGGESELR            660
KRELCTGVVP LTEQTQSIH SVRRIPCSLH LQVDTKAYKL DAIERQIPNF LDGMTRARRK             720
ILAGGVKCFA SNNRERKVFQ FGGYVADHMF YHHGDMSLNT SIIKAAQYYP GSSHLYPVFI            780
GIGSFGSRHL GGKDAGSPRY ISVQLASEFI KTMFPAEDSW LLPYVFEDGQ RAEPEYYVPV            840
LPLAIMEYGA NPSEGWKYTT WARQLEDILA LVRAYVDKDN PKHELLYHAI KHKITILPLR            900
PSNYNFKGHL KRFGQYYYSY GTYVISEQRN IITITELPLR VPTVAYIESI KKSSNRMTFI            960
EEIIDYSSSE TIEILVKLKP NSLNRIVEEF KETEEQDSIE NFLRLRNCLH SHLNFVKPKG           1020
GIIEFNTYYE ILYAWLPYRR ELYQKRLMRE HAVLKLRIIM ETAIVRYINE SAELNLSHYE           1080
DEKEASRILS EHGFPPLNHT LIISPEFASI EELNQKALQG CYTYILSLQA RELLIAAKTR           1140
RVEKIKKMQA RLDKVEQLLQ ESPFPGASVW LEEIDAVEKA IIKGRNTQWK FH                   1192

SEQ ID NO: 818        moltype = AA  length = 9
FEATURE               Location/Qualifiers
source                1..9
                      mol_type = protein
                      organism = African swine fever virus
SEQUENCE: 818
```

-continued

```
AKNIRILFL                                                                 9

SEQ ID NO: 819         moltype = AA  length = 8
FEATURE                Location/Qualifiers
source                 1..8
                       mol_type = protein
                       organism = African swine fever virus
SEQUENCE: 819
RRFRFVSL                                                                  8

SEQ ID NO: 820         moltype = AA  length = 11
FEATURE                Location/Qualifiers
source                 1..11
                       mol_type = protein
                       organism = African swine fever virus
SEQUENCE: 820
LTARFARALK Y                                                             11

SEQ ID NO: 821         moltype = AA  length = 9
FEATURE                Location/Qualifiers
source                 1..9
                       mol_type = protein
                       organism = African swine fever virus
SEQUENCE: 821
YQFLIYTAF                                                                 9

SEQ ID NO: 822         moltype = AA  length = 706
FEATURE                Location/Qualifiers
source                 1..706
                       mol_type = protein
                       organism = African swine fever virus
SEQUENCE: 822
MSCVHNNTSF PVQIEAYLKE VYEKYKELQE SKDTSLTARF ARALKYYQFL IYTAFSDPKF    60
GIGQGENTRG LLIYHQMGMG KTILSLSLAI SLSHIYNPIL IAPKSLHSNF QQSLLKLIKL   120
LYPETTDHSK ELQKISRRFR FVSLDAYNMG QQIIKAGGSL NGCLLIVDEA HNLFRGIINS   180
ANDKTNARQL YNNIMQAKNI RILFLTGTPC SKDPFEMVPC FNMLSGRILL PLHYERFYTA   240
YVNKTTNSPL NADKLLNRLV GMISYAGNQN ELNKLFPTEL PLIIEKVEMS PEQYRQYLLA   300
RDVENAEKHA SSGMYEKINA AALCLPGSEQ ESGSSYYVRS RMISIFASEM LTVKEDEKLS   360
EAVQQLPKEA FTENSSPKIV RMLKNIKTSP GPVLIYSQFV ELGLHVVARF LEIEGYQCLQ   420
PLKVLEEGHN TILLHKDGKD LMVKNFAEDG PTHTLVLSSK ITRFTLITGK ILSKERDMIQ   480
QVWNSPLNIH GEVIKILLVS KTGAEGLDLK YGRQVHILEP YWDKAREDQV KARIIRIGSH   540
DALPPEEKTV QPFLYIAVAN QKMFYSIPEG SQEQKTIDER FHERGLEKSH LNSAFRDLLK   600
RAAIECAFNG ESGCLMCQPT NALLFHENFE RDLRLPNPCQ PLVKAEVKAY SISYEGKQFF   660
YQKNKDVGLG YTFYEYNPII KAYIEIKPSN PLYIKLIKHV QAGTTA                  706

SEQ ID NO: 823         moltype = AA  length = 706
FEATURE                Location/Qualifiers
source                 1..706
                       mol_type = protein
                       organism = African swine fever virus
SEQUENCE: 823
MSCVHNNTSF PVQIEAYLKE VYEKYKELQE SKDTSLTARF ARALKYYQFL IYTAFSDPKF    60
GIGQGENTRG LLIYHQMGMG KTILSLSLAI SLSHIYNPIL IAPKSLHSNF QQSLLKLIKL   120
LYPETTDHSK ELQKISRRFR FVSLDAYNMG QQIIKAGGSL NGCLLIVDEA HNLFRGIINS   180
ANDKTNARQL YNNIMQAKNI RILFLTGTPC SKDPFEMVPC FNMLSGRILL PLHYERFYTA   240
YVNKTTNSPL NADKLLNRLV GMISYAGNQN ELNKLFPTEL PLIIEKVEMS PEQYRQYLLA   300
RDVENAEKHA SSGMYEKINA AALCLPGSEQ ESGSSYYVRS RMISIFASEM LTVKEDEKLS   360
EAVQQLPKEA FTENSSPKIV RMLKNIKTSP GPVLIYSQFV ELGLHVVARF LEIEGYQCLQ   420
PLKVLEEGHN TILLHKDGKD LMVKNFAEDG PTHTLVLSSK ITRFTLITGK ILSKERDMIQ   480
QLWNSPLNIH GEVIKILLVS KTGAEGLDLK YGRQVHILEP YWDKAREDQV KARIIRIGSH   540
DALPPEEKTV QPFLYIAVAN QKMFYSIPEG SQEQKTIDER FHERGLEKSH LNSAFRDLLK   600
RAAIECAFNG ESGCLMCQPT NALLFHENFE RDLRLPNPCQ PLVKAEVKAY SISYEGKQFF   660
YQKNKDVGLG YTFYEYNPII KAYIEIKPSN PLYIKLIKHV QAGTTA                  706

SEQ ID NO: 824         moltype = AA  length = 9
FEATURE                Location/Qualifiers
source                 1..9
                       mol_type = protein
                       organism = African swine fever virus
SEQUENCE: 824
KKINTIHKL                                                                 9

SEQ ID NO: 825         moltype = AA  length = 10
FEATURE                Location/Qualifiers
source                 1..10
                       mol_type = protein
                       organism = African swine fever virus
SEQUENCE: 825
NKLQDISKVL                                                               10
```

```
SEQ ID NO: 826          moltype = AA  length = 9
FEATURE                 Location/Qualifiers
source                  1..9
                        mol_type = protein
                        organism = African swine fever virus
SEQUENCE: 826
PSMKKINTI                                                                 9

SEQ ID NO: 827          moltype = AA  length = 383
FEATURE                 Location/Qualifiers
source                  1..383
                        mol_type = protein
                        organism = African swine fever virus
SEQUENCE: 827
MASILALDGL YAEVPKFLPE ALREGCAGKN PLSFYIQQIL NLMGCDGNEY HVLFTGSSEE         60
ANTHMIMAAV RRHLLRTQQR PHVIIGAAEP PSVTECVKAL AQEKRCVYTI IPLKNFEIDP        120
VAVYDAIQSN TCLACISGTN AVVKTFNKLQ DISKVLKGIP LHSEVSELVY QGCIKQNPPA        180
DSFSINSLYG FLGVGVLGMK KKVMQGLGPL IFGGGLRGGS PNIPGIHAMY RTLTQQRPSM        240
KKINTIHKLF MKTLKKHQHV YLPIGGVSAE DTSAENISTK DIPVEGPKEL PGYILFSVGR        300
RAEELQKKIF TKFNIKVGRI VDLQEILFRI KIPQKYWETL LFIQLRDNLT KEDIKRVMVV        360
LMHLDTITPR GSLPPPSYSS SFS                                               383

SEQ ID NO: 828          moltype = AA  length = 383
FEATURE                 Location/Qualifiers
source                  1..383
                        mol_type = protein
                        organism = African swine fever virus
SEQUENCE: 828
MASILTLDGL YAEVPKFLPE ALREGCAGKN PLSFYIQQIL NLMGCDGNEY HVLFTSSSEE         60
ANTHMIMAAV RRHLLRTQQR PHVIIGAAEP PSVTECVKAL AQEKRCVYTI IPLKNFEIDP        120
VAVYDAIQSN TCLACISGTN AVVKTFNKLQ DISNVLKGIP LHSEVSDLVY QGCIQQNPPA        180
DSFSINSLYG FLGVGVLGMK KKVMQGLGPL IFGGGLRGGS PNIPGIHAMY KTLTQQRPSM        240
KKNKYNTYAV HENFKKHQHV YLPIGGVSAE DTSAENISTK DMPVEGPKGL PGYILFSVGR        300
RAEELQKKIF TKFNIKVGRV VDLQEILFRI KIPQKYWETL LFIQLRDNLT KEDIKRVMVV        360
LMHLDTITPR GSLPPPSHSS SFS                                               383

SEQ ID NO: 829          moltype = AA  length = 19
FEATURE                 Location/Qualifiers
source                  1..19
                        mol_type = protein
                        organism = African swine fever virus
SEQUENCE: 829
ALSQAHSASI ILLTYGYGR                                                     19

SEQ ID NO: 830          moltype = AA  length = 9
FEATURE                 Location/Qualifiers
source                  1..9
                        mol_type = protein
                        organism = African swine fever virus
SEQUENCE: 830
SIILLTYGY                                                                 9

SEQ ID NO: 831          moltype = AA  length = 13
FEATURE                 Location/Qualifiers
source                  1..13
                        mol_type = protein
                        organism = African swine fever virus
SEQUENCE: 831
ETAFTLQGEY IYF                                                           13

SEQ ID NO: 832          moltype = AA  length = 10
FEATURE                 Location/Qualifiers
source                  1..10
                        mol_type = protein
                        organism = African swine fever virus
SEQUENCE: 832
MVYTTRPVSL                                                               10

SEQ ID NO: 833          moltype = AA  length = 509
FEATURE                 Location/Qualifiers
source                  1..509
                        mol_type = protein
                        organism = African swine fever virus
SEQUENCE: 833
MEAIISFAGI GINYKKLQSK LQHDFGRVLK ALTVTARALP GQPKHIAIRQ ETAFTLQGEY         60
IYFPILLQKQ FEMFNMVYTT RPVSLRALPC VETEFPLFNY QQEMVDKIHK KLLSPYGRFY        120
LHLNTGLGKT RIAISIIQKL LYPTLVIVPT KAIQIQWIDE LTLLLPHLRV AAYNNAACKK        180
KDMTSKEYDV IVGIINTLRK KPEQFFEPFG LVVLDEAHEL HSPENYKIFW KIQLSRILGL        240
```

```
SATPLDRPDG MDKIIIHHLG QPQRTVSPTT TFSGYVREIE YQGHPDFVSP VYINEKVSAI   300
ATIDKLLQDP SRIQLVVNEA KRLYSLHTAE PHKWGTDEPY GIIIFVEFRK LLEIFYQALS   360
KEFKDVQIIV PEVALLCGGV SNTALSQAHS ASIILLTYGY GRRGISFKHM TSIIMATPRR   420
NNMEQILGRI TRQGSDEKKV RIVVDIKDTL SPLSSQVYDR HRIYKKKGYP IFKCSASYQQ   480
PYSSNEVLIW DPYNESCLAC TTTPPSPSK                                    509

SEQ ID NO: 834         moltype = AA   length = 298
FEATURE                Location/Qualifiers
source                 1..298
                       mol_type = protein
                       organism = African swine fever virus
SEQUENCE: 834
MSRPEQQLKK MLKNPQAQYA FYPTAKVERI STTQHMYFIA TRPMFEGGRN NVFLGHQVGQ    60
PIIFKYVSKK EIPGNEVIVL KALQDTPGVI KLIEYTENAM YHILIIEYIP NSVDLLHYHY   120
FKKLEETEAK KIIFQLILII QNIYEKGFIH GDIKDENLII DINQKIIKVI DFGSAVRLDE   180
TRPQYNMFGT WEYVCPEFYY YGYYYQLPLT VWTIGMVAVN LFRFRAENFY LNDILKRENY   240
IPENISETGK QFITECLTIN ENKRLSFKSL VSHPWFKGLK KEIQPISELG VDYKNVIT    298

SEQ ID NO: 835         moltype = AA   length = 11
FEATURE                Location/Qualifiers
source                 1..11
                       mol_type = protein
                       organism = African swine fever virus
SEQUENCE: 835
GTWEYVCPEF Y                                                        11

SEQ ID NO: 836         moltype = AA   length = 26
FEATURE                Location/Qualifiers
source                 1..26
                       mol_type = protein
                       organism = African swine fever virus
SEQUENCE: 836
GTWEYVCPEF YYYGYYYQLP LTVWTI                                        26

SEQ ID NO: 837         moltype = AA   length = 9
FEATURE                Location/Qualifiers
source                 1..9
                       mol_type = protein
                       organism = African swine fever virus
SEQUENCE: 837
YVCPEFYYY                                                            9

SEQ ID NO: 838         moltype = AA   length = 11
FEATURE                Location/Qualifiers
source                 1..11
                       mol_type = protein
                       organism = African swine fever virus
SEQUENCE: 838
YVCPEFYYYG Y                                                        11

SEQ ID NO: 839         moltype = AA   length = 10
FEATURE                Location/Qualifiers
source                 1..10
                       mol_type = protein
                       organism = African swine fever virus
SEQUENCE: 839
FYYYGYYYQL                                                          10

SEQ ID NO: 840         moltype = AA   length = 10
FEATURE                Location/Qualifiers
source                 1..10
                       mol_type = protein
                       organism = African swine fever virus
SEQUENCE: 840
YQLPLTVWTI                                                          10

SEQ ID NO: 841         moltype = AA   length = 11
FEATURE                Location/Qualifiers
source                 1..11
                       mol_type = protein
                       organism = African swine fever virus
SEQUENCE: 841
NLFRFRAENF Y                                                        11

SEQ ID NO: 842         moltype = AA   length = 10
FEATURE                Location/Qualifiers
source                 1..10
                       mol_type = protein
                       organism = African swine fever virus
```

```
SEQUENCE: 842
AMYHILIIEY                                                                  10

SEQ ID NO: 843          moltype = AA  length = 298
FEATURE                 Location/Qualifiers
source                  1..298
                        mol_type = protein
                        organism = African swine fever virus
SEQUENCE: 843
MSRPEQQLKK MLKNPQAQYA FYPTAKVERI STTQHMYFIA TRPMFEGGRN NVFLGHQVGQ            60
PIIFKYVSKK EIPGNEVIVL KALQDTPGVI KLIEYTENAM YHILIIEYIP NSVDLLHYHY           120
FKKLEETEAK KIIFQLILII QNIYEKGFIH GDIKDENLII DINQKIIKVI DFGSAVRLDE           180
TRPQYNMFGT WEYVCPEFYY YGYYYQLPLT VWTIGMVAVN LRFRAENFY LNDILKRENY            240
IPENISETGK QFITECLTIN ENKRLSFKSL VSHPWFKGLK KEIQPISELG VDYKNVIT             298

SEQ ID NO: 844          moltype = AA  length = 9
FEATURE                 Location/Qualifiers
source                  1..9
                        mol_type = protein
                        organism = African swine fever virus
SEQUENCE: 844
YSLNNWARY                                                                    9

SEQ ID NO: 845          moltype = AA  length = 9
FEATURE                 Location/Qualifiers
source                  1..9
                        mol_type = protein
                        organism = African swine fever virus
SEQUENCE: 845
QAFEHLYAF                                                                    9

SEQ ID NO: 846          moltype = AA  length = 183
FEATURE                 Location/Qualifiers
source                  1..183
                        mol_type = protein
                        organism = African swine fever virus
SEQUENCE: 846
MSVVVGGVEY SLNNWARYEI KRRAAELESV NYYPHCEYIM PEDIVVSILG SKPNCPFLEA            60
LKRFHDFLKK RRIIFKGEYL VIPWMGAQDV ADMIHHVENR INLDHLEDLA HMLKLITYHR           120
SFDTCINQAF EHLYAFKFPD ANIETHELKH IRQLEKKMYG YILRLEKLQT VLTFYIEFLL           180
KQV                                                                        183

SEQ ID NO: 847          moltype = AA  length = 10
FEATURE                 Location/Qualifiers
source                  1..10
                        mol_type = protein
                        organism = African swine fever virus
SEQUENCE: 847
SMMDFERVHY                                                                  10

SEQ ID NO: 848          moltype = AA  length = 9
FEATURE                 Location/Qualifiers
source                  1..9
                        mol_type = protein
                        organism = African swine fever virus
SEQUENCE: 848
TLQRWAIKY                                                                    9

SEQ ID NO: 849          moltype = AA  length = 273
FEATURE                 Location/Qualifiers
source                  1..273
                        mol_type = protein
                        organism = African swine fever virus
SEQUENCE: 849
MSILEKITSS PSECAEHLTN KDSCLSKKIQ KELTSFLEKK ETLGCDSESC VITHPAVKAY            60
AQQKGLDLSK ELETRFKAPG PRNNTGLLTN FNIDETLQRW AIKYTKFFNC PFSMMDFERV           120
HYKFNQVDMV KVYKGEELQY VEGKVVKRPC NTFGCVLNTD FSTGTGKHWV AIFVDMRGDC           180
WSIEYFNSTG NSPPGPVIRW MERVKQQLLK IHHTVKTLAV TNIRHQRSQT ECGPYSLFYI           240
RARLDNVSYA HFISARITDE DMYKFRTHLF RIA                                       273

SEQ ID NO: 850          moltype = AA  length = 11
FEATURE                 Location/Qualifiers
source                  1..11
                        mol_type = protein
                        organism = African swine fever virus
SEQUENCE: 850
NEYWAIHLFF I                                                                11

SEQ ID NO: 851          moltype = AA  length = 8
```

```
FEATURE                 Location/Qualifiers
source                  1..8
                        mol_type = protein
                        organism = African swine fever virus
SEQUENCE: 851
SQFWNYTM                                                                            8

SEQ ID NO: 852          moltype = AA  length = 69
FEATURE                 Location/Qualifiers
source                  1..69
                        mol_type = protein
                        organism = African swine fever virus
SEQUENCE: 852
MLLYIVIIVA CIISKLVPNE YWAIHLFFII MIFMVYMYEK LDIHQKSQFW NYTMSGLSGH                    60
NVQVTCKCY                                                                           69

SEQ ID NO: 853          moltype = AA  length = 209
FEATURE                 Location/Qualifiers
source                  1..209
                        mol_type = protein
                        organism = African swine fever virus
SEQUENCE: 853
MRGILITIEG INGVGKSTQA MRLKKALECM DYNAVCIRFP NPDTTTGGLI LQVLNKMTEM                    60
SSEQLHKLFT KHHSEFSAEI AALLKLNFIV IVDHYIWSGL AYAQADGITI ETKNIFKPDY                   120
TFFLSSKKPL NEKPLTLQRL FETKEKQETI FTNFTIIMND VPKNRLCIIP ATLNKEIIHT                   180
MILTKTIKVF DNNSCLNYIK MYDDKYLNV                                                    209

SEQ ID NO: 854          moltype = AA  length = 236
FEATURE                 Location/Qualifiers
source                  1..236
                        mol_type = protein
                        organism = African swine fever virus
SEQUENCE: 854
MRGILIAIEG INGVGKSTQA MKLKETLECM DYNAICIHFP NPDTTTGDLI LQVLNKTIEM                    60
SSEQLHKLFT KHRSEFIAEI AVLLKLNYIV IVDRYIWSGL VYAQADGITI ETKNTFKPDY                   120
TFFLSSKKPL NEKPLTLQRL FETKEKQETI FTNFTIIMDD VPKNRFCIIP ATLNKEIIHM                   180
IILTKTLKVF DNNSCLNYIK MYDDKYLNVQ DLNLFDFDWQ KYIEDNNDKE EYDFIV                       236

SEQ ID NO: 855          moltype = DNA  length = 6594
FEATURE                 Location/Qualifiers
misc_feature            1..6594
                        note = Expression plasmid pCMV
source                  1..6594
                        mol_type = other DNA
                        organism = synthetic construct
SEQUENCE: 855
gacggatcgg gagatctccc gatcccctat ggtgcactct cagtacaatc tgctctgatg              60
ccgcatagtt aagccagtat ctgctccctg cttgtgtgtt ggaggtcgct gagtagtgcg             120
cgagcaaaat ttaagctaca acaaggcaag gcttgaccga caattgcatg aagaatctgc             180
ttagggttag gcgttttgcg ctgcttcgcg atgtacgggc cagatatacg cgttgacatt             240
gattattgac tagttattaa tagtaatcaa ttacggggtc attagttcat agcccatata             300
tggagttccg cgttacataa cttacggtaa atggcccgcc tggctgaccg cccaacgacc             360
cccgcccatt gacgtcaata atgacgtatg ttcccatagt aacgccaata gggactttcc             420
attgacgtca atgggtggag tatttacggt aaactgccca cttggcagta catcaagtgt             480
atcatatgcc aagtacgccc cctattgacg tcaatgacgg taaatggccc gcctggcatt             540
atgcccagta catgacctta tgggactttc ctacttggca gtacatctac gtattagtca             600
tcgctattac catggtgatg cggttttggc agtacatcaa tgggcgtgga tagcggtttg             660
actcacgggg atttccaagt ctccacccca ttgacgtcaa tgggagtttg ttttggcacc             720
aaaatcaacg ggactttcca aaatgtcgta acaactccgc cccattgacg caaatgggcg             780
gtaggcgtgt acggtgggag gtctatataa gcagagctct ctggctaact agagaaccca             840
ctgcttactg gcttatcgaa attaatacga ctcactatag ggagacccaa gctggctagc             900
gtttaaactt aagcttgcca catgcagatc tttgtgaaaa ccctgaccgg gaaaccatt              960
accctggaag tggaaccctc gacaccattg aaaacgtgag aggctaagat ccaggacaag            1020
gagggcatcc cccagacca gcagaggctg atcttcgccg gcaagcagct gggggacggc            1080
agaaccctga gcgactacaa catccagaag gagtccaccc tgcacctggt gctgaggctg            1140
aggggagctg cctactgcag caactactcc accagcatct acaacatcac caacaactgc            1200
tccctgacca tcttccccca acgacgtg ttcgccgcct acacctacca ggtggtgtgg             1260
aaccagatca tcaactacgc cgcctacatc tacctgaaca tcaacgacac cttcgtgaag            1320
tacaccaacg agagcatcct ggagtacaac tgggccgcct accgctacca gtacaacacc            1380
ccaatctact acatgaggcc atccaccag ccactggctg cttacgagac cccctgatc              1440
aactgcacct acctgaccct gtccagcaac tacttctaca ccttcttcaa gctgtacgct            1500
gcttaccacg ctgacgacct gctgcaggcc ctgcagcagg ctaaggccga agaacttc              1560
tccagcgtgt tcagcctgga ctgggacaag ctgaggaccg ccaagagaaa caccaccgtg            1620
aagtacgtga ccgtgaacgt ggccgcctac tgcatcagca acatgggcat ctccttccc            1680
ctgtgcctgg agatgggcgt ggtgaaggtg ttcgagaaga acaacggcat cgacgtgaac            1740
tccatctacg cagcgacga catctccacc ctggctgcct acaagctgtt caccaagcac            1800
cgcagcgagt tcatcgccga gatcgccgtg ctgctgaagc tgaactacat cgtgatcgtg            1860
gaccgctaca tctggtccgg actggtgtac gctcaggctg acggcatcac catcgagacc            1920
aagaacacct tcaagcccga ctacaccttc ttcctgtcca gcaagaagcc actgaacgag            1980
```

```
aaggccgcct acaaggagat catccacatg atcatcctga ccaagaccct gaaggtgttc   2040
gacaataact cctgcctcaa ctatatcaag atgtacgatg acaaatactg aggatccact   2100
agtccagtgt ggtggaattc tgcagatatc cagcacagtg gcggccgctc gagtctagag   2160
ggcccgttta aacccgctga tcagcctcga ctgtgccttc tagttgccag ccatctgttg   2220
tttgcccctc ccccgtgcct tccttgaccc tggaaggtgc cactcccact gtcctttcct   2280
aataaaatga ggaaattgca tcgcattgtc tgagtaggtg tcattctatt ctgggggtg   2340
gggtggggca ggacagcaag ggggaggatt gggaagacaa tagcaggcat gctgggtccg   2400
atgcggtggg ctctatggct tctgaggcgg aagaaccag ctggggctct aggggggtatc   2460
cccacgcgcc ctgtagcggc gcattaagcg cggcgggtgt ggtggttacg cgcagcgtga   2520
ccgctacact tgccagcgcc ctagcgcccg ctcctttcgc tttcttccct tcctttctcg   2580
ccacgttcgc cggctttccc cgtcaagctc taaatcgggg ctccctttta gggttccgat   2640
ttagtgcttt acggcacctc gaccccaaaa aacttgatta gggtgatggt tcacgtagtg   2700
ggccatcgcc ctgatagacg gttttcgcc ctttgacgtt ggagtccacg ttctttaata   2760
gtggactctt gttccaaact ggaacaacac tcaaccctat ctcggtctat tcttttgatt   2820
tataagggat tttgccgatt tcggcctatt ggttaaaaaa tgagctgatt taacaaaaat   2880
ttaacgcgaa ttaattctgt ggaatgtgtg tcagttaggg tgtggaaagt ccccaggctc   2940
cccagcaggc agaagtatgc aaagcatgca tctcaattag tcagcaacca ggtgtggaaa   3000
gtccccaggc tccccagcag gcagaagtat gcaaagcatg catctcaatt agtcagcaac   3060
catagtcccg ccctaactc cgcccatccc gcccctaact ccgcccagtt ccgcccattc   3120
tccgccccat ggctgactaa ttttttttat ttatgcagag gccgaggccg cctctgcctc   3180
tgagctattc cagaagtagt gaggaggctt ttttggaggc ctaggctttt gcaaaaagct   3240
cccgggagct tgtatatcca ttttcggatc tgatcaagag acaggatgag gatcgtttcg   3300
catgattgaa caagatggat tgcacgcagg ttctccggcc gcttgggtgg agaggctatt   3360
cggctatgac tgggcacaac agacaatcgg ctgctctgat gccgccgtgt tccggctgtc   3420
agcgcagggg cgcccggttc tttttgtcaa gaccgacctg tccggtgccc tgaatgaact   3480
gcaggacgag gcagcgcggc tatcgtggct ggccacgacg ggcgttcctt gcgcagctgt   3540
gctcgacgtt gtcactgaag cgggaaggga ctggctgcta ttgggcgaag tgccggggca   3600
ggatctcctg tcatctcacc ttgctcctgc cgagaaagta tccatcatgg ctgatgcaat   3660
gcggcggctg catacgcttg atccggctac ctgcccattc gaccaccaag cgaaacatcg   3720
catcgagcga gcacgtactc ggatggaagc cggtcttgtc gatcaggatg atctggacga   3780
agagcatcag gggctcgcgc cagccgaact gttcgccagg ctcaaggcgc gcatgcccga   3840
cggcgaggat ctcgtcgtga cccatggcga tgcctgcttg ccgaatatca tggtggaaaa   3900
tggccgcttt tctggattca tcgactgtgg ccggctgggt gtggcggacc gctatcagga   3960
catagcgttg gctacccgtg atattgctga agagcttggc ggcgaatggg ctgaccgctt   4020
cctcgtgctt tacggtatcg ccgctcccga ttcgcagcgc atcgccttct atcgccttct   4080
tgacgagttc ttctgagcgg gactctgggg ttcgaaatga ccgaccaagc gacgcccaac   4140
ctgccatcac gagatttcga ttccaccgcc gccttctatg aaaggttggg cttcggaatc   4200
gttttccggg acgccggctg gatgatcctc cagcgcgggg atctcatgct ggagttcttc   4260
gcccacccca acttgtttat tgcagcttat aatggttaca aataaagcaa tagcatcaca   4320
aatttcacaa ataaagcatt ttttcactg cattctagtt gtggtttgtc caaactcatc   4380
aatgtatctt atcatgtctg tataccgtcg acctctagct agagcttggc gtaatcatgg   4440
tcatagctgt ttcctgtgtg aaattgttat ccgctcacaa ttccacacaa catacgagcc   4500
ggaagcataa agtgtaaagc ctggggtgcc taatgagtga gctaactcac attaattgcg   4560
ttgcgctcac tgcccgcttt ccagtcggga aacctgtcgt gccagctgca ttaatgaatc   4620
ggccaacgcg cggggagagg cggtttgcgt attgggcgct cttccgcttc ctcgctcact   4680
gactcgctgc gctcggtcgt tcggctgcgg cgagcggtat cagctcactc aaaggcggta   4740
atacggttat ccacagaatc aggggataac gcaggaaaga acatgtgagc aaaaggccag   4800
caaaaggcca ggaaccgtaa aaaggccgcg ttgctggcgt ttttccatag gctccgcccc   4860
cctgacgagc atcacaaaaa tcgacgctca agtcagaggt ggcgaaaccc gacaggacta   4920
taaagatacc aggcgtttcc ccctggaagc tccctcgtgc gctctcctgt tccgaccctg   4980
ccgcttaccg gatacctgtc cgcctttctc cttcgggaag cgtggcgctt tctcatagc   5040
tcacgctgta ggtatctcag ttcggtgtag tcgttcgct ccaagctggg ctgtgtgcac   5100
gaacccccg ttcagcccga ccgctgcgcc ttatccggta actatcgtct tgagtccaac   5160
ccggtaagac acgacttatc gccactggca gcagccactg gtaacaggat tagcagagcg   5220
aggtatgtag gcggtgctac agagttcttg aagtggtggc ctaactacgg ctacactaga   5280
agaacagtat ttggtatctg cgctctgctg aagccagtta ccttcggaaa aagagttggt   5340
agctcttgat ccggcaaaca aaccaccgct ggtagcggtt ttttgtttg caagcagcag   5400
attacgcgca gaaaaaaagg atctcaagaa gatcctttga tcttttctac ggggtctgac   5460
gctcagtgga acgaaaactc acgttaaggg attttggtca tgagattatc aaaaaggatc   5520
ttcacctaga tccttttaaa ttaaaaatga agttttaaat caatctaaag tatatatgag   5580
taaacttggt ctgacagtta ccaatgctta atcagtgagg cacctatctc agcgatctgt   5640
ctatttcgtt catccatagt tgcctgactc ccgtcgtgt agataactac gatacggag   5700
ggcttaccat ctggccccag tgctgcaatg ataccgcgag acccacgctc accggctcca   5760
gatttatcag caataaacca gccagccgga agggccgagc gcagaagtgg tcctgcaact   5820
ttatccgcct ccatccagtc tattaattgt tgccgggaag ctagagtaag tagttcgcca   5880
gttaatagtt tgcgcaacgt tgttgccatt gctacaggca tcgtggtgtc acgctcgtcg   5940
tttggtatgg cttcattcag ctccggttcc caacgatcaa ggcgagttac atgatccccc   6000
atgttgtgca aaaaagcggt tagctccttc ggtcctccga tcgttgtcag aagtaagttg   6060
gccgcagtgt tatcactcat ggttatggca gcactgcata attctcttac tgtcatgcca   6120
tccgtaagat gcttttctgt gactggtgag tactcaacca agtcattctg agaatagtgt   6180
atgcggcgac cgagttgctc ttgcccggcg tcaatacggg ataataccgc gccacatagc   6240
agaactttaa aagtgctcat cattggaaaa cgttcttcgg ggcgaaaact ctcaaggatc   6300
ttaccgctgt tgagatccag ttcgatgtaa cccactcgtg cacccaactg atcttcagca   6360
tcttttactt tcaccagcgt ttctgggtga gcaaaaacag gaaggcaaaa tgccgcaaaa   6420
aagggaataa gggcgacacg gaaatgttga atactcatac tcttcctttt tcaatattat   6480
tgaagcattt atcagggtta ttgtctcatg agcggataca tatttgaatg tatttagaaa   6540
aataaacaaa tagggggttcc gcgcacattt ccccgaaaag tgccacctga cgtc          6594

SEQ ID NO: 856        moltype = DNA   length = 11072
```

```
FEATURE               Location/Qualifiers
misc_feature          1..11072
                      note = Expression plasmid pCMV
source                1..11072
                      mol_type = other DNA
                      organism = synthetic construct SEQUENCE: 856
gacggatcgg gagatctccc gatccctat ggtgcactct cagtacaatc tgctctgatg    60
ccgcatagtt aagccagtat ctgctcctg cttgtgtgtt ggaggtcgct gagtagtgcg   120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa gctggctagc               660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag tctatataa gcagagctct ctggctaact agagaaccca   840
ctgcttactg gcttatcgaa attaatacga ctcactatag ggagacccaa gctggctagc   900
gtttaaactt aagcttgcca ccatgcagat tttcgtgaag accctgaccg gaagagccat   960
taccctggaa gtggaaccat ccgataccat tgagaacgtg aagctaaga tccaggacaa  1020
ggagggcatc cccccagacc agcagcggct gatcttcgct ggcaagcagc tggaggacgg  1080
aaggaccctg tccgactaca acatccagaa ggagagcacc ctgcacctgg tgctgaggct  1140
gagaggagct gcttacaccg agctgctta ccactccatc gtgaccgagt accagtacca   1200
ggtgaaggc tacatcctgg gcgtgaagca gaacaagaag ctgtacgaga gatgctgga   1260
cagcttctac aagtacttcg ccgcctactt ctccaacttc gtgaccacca tcgtggacag  1320
cttcatcccc aaggagtaca gccagtccat cagcctggag aagaaggagt ccatcctgga  1380
gctgctgctg tgcgactaca tcagcaacct gggccacttc atcaccaccg agaagatgct  1440
gccctatcat atcaagaacc ggaaggagaa ctaccacaag gtgaccaagg agatgcagga  1500
ctactccctg accttcctgc tgaagaagag aatggagctg tacaacaagt cgctgctta   1560
caggcagtcc gagtaccgcc ggctggtgca gctgctgtac cagcagatcc agagaagctc  1620
caccagcaag agctcctacc ccctgaccaa gttcatcgaa accctgcct ccgagcactt   1680
cagcaacgag gagtaccaga aggaaacccc cgccgaccag aaggaggtgg tggagatgga  1740
gctgctgcgc aagcaggagc tgctgaccag ccaggagctg acctccaaga gccccaacaa  1800
cgctgcttac gccttcttcc catgcgaccc atacgcttcc ccattcccca gcatcaaggg  1860
cctgcagctc cacaacgccc agctgttcgt gcagaacttc cagaacccca acacccccta  1920
ctcccggctg ctgctgaact ggcagaccgg aaccggcaag agcatcgctg ctatcgccat  1980
cgccaggcag ttcatgaatc actacatgaa cttcatcgag aacgcccct ggatcttcgt   2040
ggtggccgcc tacaggatct cgccggcaa gatgctgtcc tacaaggacg aaaccctgcc  2100
ctacctgcac ttcatcgagt ccccatgag cgagtaccag ctggaaaccc tgaagcagct  2160
gggcccgac cccaagatca gctccaacgc ctactccatc tacgacatgg tgttccccaa  2220
ccccaagttc agcaagcaga ccgagccaaa ggcctacggc ctgttcgctg cctacgtgct  2280
ggacatcgaa acctacatca gggacttcca gccaccagct atgcactcca tcaggatcac  2340
caagtaccct gagcacagcc agaccaagga gccccttcgc gtgctgtacg agaagttcca  2400
gaaggacttc caggacgagc ccatggagca ggtgctgatc cactaccccg cctccttcca  2460
ctacaccatg ctggaggccc tgatcatcga aacctggct ggaatgggcg ccctggtgga   2520
ggtgtacgcc gcctacagcc aggtggacct gaaccaggcc atcaacacct tcatgtacta  2580
ctactacctg gcccagatct actccaacct gacccacaac aagcaggagt tccagagcta  2640
cgaggagaac tacgccacca tcctgggcga cgctatcgct ggccggctga tgcagctggc  2700
tgcttacgct accgtgtccg ccatcggagc tggagtacgac gtgaagagga gattctacag  2760
ggccctggag ggcctggacc tgtacctgaa gaacatcacc aagaccttcg tgaacaacat  2820
cgctgcttac ttcaccgaca acgctccagc tggacactac tacgagaagg tggccgcga   2880
gatccagcag ggcagatccg tgggcaccct gcgcccgtg agggctagcc aggccaagaa   2940
catccgggac ctgatcggca ggtccctgag caacttccag gccctgaagg ctgcttacac  3000
cgctgaggag gctgctcagc gggtgtacct gtccaccgtg agggtgaacg acgtctgag   3060
caccagatgg gaaaccgagg acgtgttctt caccttcatg ctgaagagca tggccgccaa  3120
gatcttcatc gtgctgggca tctacgacat gttcgagagg gctgcttacg aagtgatccc  3180
agaggccgcc gagctgtact tcagactgcc ccgcctggcc gagttctacc agaagctgtt  3240
ctccttcagg gacgagaacg tgcagatcag catgctgcca gagctggctg cttacggcct  3300
gtcccagcac ctgatcagca ccctgaccga gatccccatc tacctgaagg agaactaccg  3360
cgccaacctg ccccctgttca acaaggctgc ttacgctgca atccagagg gacggcgagg  3420
gtgggccac cccatgtcca tctacatcaa ccaggcctg cacgagatcg tgcggaccat   3480
caggctggct gaaaccgtgc gcggcctggc tgcttacaag gagttcatca cctgctgaa   3540
ccaggccctg gcttccaccc agctgtacag gagcatccag cagctgttcc tgaccatgta  3600
caagctggac cccatcggct tcatcaacta catcaagacc agcaagcagg agtacctgtg  3660
cctgctgatc aaccccaagc tggtgaccaa gttcctgaag atcacctcct tcaagatcta  3720
catcaacttc agactgaaga ccttctacat cagccccaac aagtacaaca acttctacgc  3780
cgcctacgcc ctggtggacg atctactc caccctgaag ggcagcaacg acatcaagaa    3840
catcagactg atcgacttcc tgttcacct gaaggacttc gtgaaccacg tgcgcgctga  3900
gcagtccaag ctgcccgacc tgagcatgcc catcgaggcc tacatcgccg cctacctgct  3960
gaccgagagc tgcctgacc ccatgtacga ctacgctgct accggcaat ctcaagagag    4020
aagcatcccc atgcacaagc caggacccc aaaggaggct gagtacgagt caagaccgt    4080
gatcggaagg accccagctg agctgctgtc ccagaaggga ttctacgaca agatctacac  4140
cagcaagtac agaccggact tcacccagct gaccgcctg aacgatatct acgccgccta   4200
ctccatcatg gacagaagcg agatcgtggc ccgcagaac cccgtgatca cccagagagt   4260
gaccaacctg ctgcagacca acgccccct gctgttcatg cccatcgaca tccacgaggt  4320
```

```
gcgctacggc gcctacaccc tgttcatgta cggctccctg gagaacggct acaaggccgc   4380
ctacagcctg ctgaccgccg agaacatcgt gtacgagaga ctggaaaccc tgacccagcg   4440
gcccgtgatg ggctacaggg agaaggagaa ggagttcgcc ccctacatcc gcatcttctt   4500
caagtccctg tacgagcgcc ggaaggccat cacctacctg aacaacatgg gctacaacac   4560
cgccgccgac gacaccacct gctactacag aatggtgagc cgcgagctga agctgccccct   4620
gacctcctgg atccagctgc agcactacag ctacgagccc agaggcctgg tgcaccgctt   4680
ctccgtgacc ccagaggacc tggtgagcta ccagaacgac ggcccaccg accactccat   4740
cgtgatggcc tacgacatcg aaacctactc ccccgtggcc gcctacagcc tgtaccagaa   4800
cctgctggag agcgtgtact tcgccgtgga aaccatccac ctgaagcagc agatcgagtt   4860
cctgaacttc ggcatgaagt gctaccggca cttctacaac aagatcaagc tgctgaacga   4920
ctacctggcc cccaagaaga agatcttcca ggacagatgg cgcgtgctga acaagctgta   4980
cgtgctggag aagaagcaca agctggccgc ctacaacaag atcgagagct ccgtgcacct   5040
gctgaggaag aacttcaaca cctactactc cgactacgg ggcagcggct acaacccac   5100
catcatcatg gagcagtaca tcaaggacat ctcccaggac agcaagaaca tctcccccag   5160
aatcagctac cagttccgca ccatcatcaa gtactaccgg gacatgatcg ccaccaggca   5220
ccagaccatg gacccacagg tgctgaacct ggtggctgcc taccagcaga tccaggagat   5280
cctgtacctg ctgcggatgc acatctacga aaccaacctg tacctgaagc aggagctgag   5340
cagactgatc taccccaacc gccagctgtc cttcgtgctg ctgatgcccc tgacctgct   5400
gagaaactgg gacgacatcg agtacgccgc ctacaagctg aacaagaagc agcgccactc   5460
cttctacgag gtgctggtga ccagcgaaac cctgaacaac tacgagaacc tgtccaagaa   5520
catcctgaac accctgatgt cgccgtgcg gtacgtgttc aagccaaccc caaactacg   5580
tgcttacagg ctgatgaact tcatctacga taggtgctac tccacatgc aggggcgaagga   5640
gatcttcagc ctggccaggt tctacgctat ccaccacgct ccaaagctgg ctgcttacgc   5700
caccaacatc aacatcgtga acaagtacat cggcaacctg ttcgtgatgg gcgtgctgtc   5760
caagaaggag atcctgcagg actacccctc catctacagc aagcagtaca tggccgccta   5820
cttcctgctg tggaagggca gcctgcagta cgctatcatc ggcgccctgg agggccggca   5880
gtacgacctg atccagaagt actacgccgc ctacgtgacc tgcaccttcc agtgcctgtt   5940
ccagcacgcc atccgggaca acatgctgcc tatcttccag aagtacgccg cctacgcctc   6000
caggaagacc ttcaacctgc tgctgagctc catcaactac tgcgtgaacc ccttcgtgaa   6060
gaaggccgcc tacatggtga acaccatgaa ccacaggaag ggcaagaacc tgctgatgta   6120
caacatccac aacatcaccg gctacaccta cctgaacacc aaggaggcct tcaacctgac   6180
cagattctac gccgtgcaca acgccacctg cctgttcaag gagatgtgca agctcctgct   6240
cgtgcacgac aagatccagc tgagggagct ggctgcttac agggagatgt tcaccaggat   6300
cgagctgatg cccgtgtacc aggagctggg atacgctgag ccactgtccg aaaccgagca   6360
ggccgacctg agcgcctgga tctacctgag agcttccaac tgcgctgctt acgtgggcaa   6420
gggaaccacc atctactacg ccgcctacac caccgacagc ggcgaaacca tcatggtgcg   6480
caacgagcag ctgaccaaca caaggtgct gcagggcatc gtgcaggtgc tgggactcga   6540
cttcaactgt cattacaaga cccaggagga aagagccaaa ctgagatact gagaattctg   6600
cagatatcca gcacagtggc ggccgctcga tctctagaggg cccgtttaaa cccgctgatc   6660
agcctcgact gtgccttcta gttgccagcc atctgttgtt tgcccctccc ccgtgccttc   6720
cttgaccctg gaaggtgcca ctcccactgt ccttttcctaa taaatgagg aaattgcatc   6780
gcattgtctg agtaggtgtc attctattct ggggggtggg gtgggcagg acagcaaggg   6840
ggaggattgg gaagacaata gcaggcatgc tggggtggct ctatggcttc   6900
tgaggcggaa agaaccagct ggggctctag ggggtatccc cacgcgccct gtagcggcgc   6960
attaagcgcg gcgggtgtgg tggttacgcg cagcgtgacc gctacacttg ccagcgccct   7020
agcgcccgct cctttcgctt tcttcccttc ctttctcgcc acgttcgccg gctttccccg   7080
tcaagctcta aatcggggc tccctttagg gttccgattt agtgctttac ggcacctcga   7140
ccccaaaaaa cttgattagg gtgatggttc acgtagtggg ccatcgccct gatagacggt   7200
ttttcgccct ttgacgttgg agtccacgtt ctttaatagt ggactcttgt tccaaactgg   7260
aacaacactc aaccctatct cggtctattc ttttgattta aagggattt tgccgatttc   7320
ggcctattgg ttaaaaaatg agctgattta acaaaaattt aacgcgaatt aattctgtga   7380
aatgtgtgtc agttagggtg tggaaagtcc caggctccc cagcaggcag aagtatgcaa   7440
agcatgcatc tcaattagtc agcaaccagg tgtggaaagt ccccaggctc cccagcaggc   7500
agaagtatgc aaagcatgca tctcaattag tcagcaacca gtagtcccgcc cctaactccg   7560
cccatcccgc ccctaactcc gcccagttcc gcccattctc cgccccatgg ctgactaatt   7620
ttttttattt atgcagaggc cgaggccgcc tctgcctctg agctattcca gaagtagtga   7680
ggaggctttt ttggaggcct aggcttttgc aaaaagctcc cgggagcttg tatatccatt   7740
ttcggatctg atcaagagac aggatgagga tcgtttcgca tgattgaaca agatggattg   7800
cacgcaggtt ctccggccgc ttgggtggag aggctattcg gctatgactg ggcacaacag   7860
acaatcggct gctctgatgc cgccgtgttc cggctgtcag cgcaggggcg cccggttctt   7920
tttgtcaaga ccgacctgtc cggtgccctg aatgaactgc aggacgaggc agcgcggcta   7980
tcgtggctgg ccacgacggg cgttccttgc gcagctgtgc tcgacgttgt cactgaagcg   8040
ggaagggact ggctgctatt gggcgaagtg ccggggcagg atctcctgtc atctcacctt   8100
gctcctgccg agaaagtatc catcatggct gatgcaatgc ggcggctgca tacgcttgat   8160
ccggctacct gcccattcga ccaccaagcg aaacatcgca tcgagcgagc acgtactcgg   8220
atggaagccg gtcttgtcga tcaggatgat ctggacgaag agcatcaggg gctcgcgcca   8280
gccgaactgt tcgccaggct caaggcgcgc atgcccgacg gcgaggatct cgtcgtgacc   8340
catggcgatg cctgcttgcc gaatatcatg gtggaaaatg gccgcttttc tggattcatc   8400
gactgtggcc ggctgggtgt ggcggaccgc tatcaggaca tagcgttggc tacccgtgat   8460
attgctgaag agcttggcgg cgaatgggct gaccgcttcc tcgtgcttta cggtatcgcc   8520
gctcccgatt cgcagcgcat cgccttctat cgccttcttg acgagttctt ctgagcggga   8580
ctctggggtt cgaaatgacc gaccaagcga cgcccaacct gccatcacga tttcgatt   8640
ccaccgccgc cttctatgaa aggttgggct tcggaatcgt tttccgggac gccggctgga   8700
tgatcctcca gcgcggggat ctcatgctgg agttcttcgc ccaccccaac ttgtttattg   8760
cagcttataa tggttacaaa taaagcaata gcatcacaaa tttcacaaat aaagcatttt   8820
tttcactgca ttctagttgt ggtttgtcca aactcatcaa tgtatcttat catgtctgta   8880
taccgtcgac ctctagctag agcttggcgt aatcatggtc atagctgttt cctgtgtgaa   8940
attgttatcc gctcacaatt ccacacaaca tacgagccgg aagcataaag tgtaaagcct   9000
ggggtgccta atgagtgagc taactcacat taattgcgtt gcgctcactg cccgctttcc   9060
```

```
agtcgggaaa cctgtcgtgc cagctgcatt aatgaatcgg ccaacgcgcg gggagaggcg   9120
gtttgcgtat tgggcgctct tccgcttcct cgctcactga ctcgctgcgc tcggtcgttc   9180
ggctgcggcg agcggtatca gctcactcaa aggcggtaat acggttatcc acagaatcag   9240
gggataacgc aggaaagaac atgtgagcaa aaggccagca aaaggccagg aaccgtaaaa   9300
aggccgcgtt gctggcgttt ttccataggc tccgcccccc tgacgagcat cacaaaaatc   9360
gacgctcaag tcagaggtgg cgaaacccga caggactata agataccagg cgtttcccc    9420
ctggaagctc cctcgtgcgc tctcctgttc cgaccctgcc gcttaccgga tacctgtccg   9480
cctttctccc ttcgggaagc gtggcgcttt ctcatagctc acgctgtagg tatctcagtt   9540
cggtgtaggt cgttcgctcc aagctgggct gtgtgcacga accccccgtt cagcccgacc   9600
gctgcgcctt atccggtaac tatcgtcttg agtccaaccc ggtaagacac gacttatcgc   9660
cactggcagc agccactggt aacaggatta gcagagcgag gtatgtaggc ggtgctacag   9720
agttcttgaa gtggtggcct aactacggct acactagaag aacagtattt ggtatctgcg   9780
ctctgctgaa gccagttacc ttcggaaaaa gagttggtag ctcttgatcc ggcaaacaaa   9840
ccaccgctgg tagcggtttt tttgtttgca agcagcagat tacgcgcaga aaaaaaggat   9900
ctcaagaaga tcctttgatc ttttctacgg gtctgacgct cagtggaac gaaaactcac   9960
gttaaggat tttggtcatg agattatcaa aaaggatctt cacctagatc cttttaaatt    10020
aaaaatgaag ttttaaatca atctaaagta tatatgagta aacttggtct gacagttacc   10080
aatgcttaat cagtgaggca cctatctcag cgatctgtct atttcgttca tccatagttg   10140
cctgactccc cgtcgtgtag ataactacga tacgggaggg cttaccatct ggccccagtg   10200
ctgcaatgat accgcgagac ccacgctcac cggctccaga tttatcagca ataaaccagc   10260
cagccggaag ggccgagcgc agaagtggtc ctgcaacttt atccgcctcc atccagtcta   10320
ttaattgttg ccgggaagct agagtaagta gttcgccagt taatagtttg cgcaacgttg   10380
ttgccattgc tacaggcatc gtggtgtcac gctcgtcgtt tggtatggct tcattcagct   10440
ccggttccca acgatcaagg cgagttacat gatccccat gttgtgcaaa aaagcggtta    10500
gctccttcgg tcctccgatc gttgtcagaa gtaagttggc cgcagtgtta tcactcatgg   10560
ttatgcagc actgcataat tctcttactg tcatgccatc cgtaagatgc ttttctgtga    10620
ctggtgagta ctcaaccaag tcattctgag aatagtgtat gcggcgaccg agttgctctt   10680
gcccggcgtc aatacgggat aataccgcgc cacatagcag aactttaaaa gtgctcatca   10740
ttggaaaacg ttcttcgggg cgaaaactct caaggatctt accgctgttg agatccagtt   10800
cgatgtaacc cactcgtgca cccaactgat cttcagcatc ttttactttc accagcgttt   10860
ctgggtgagc aaaaacagga aggcaaaatg ccgcaaaaaa gggaataagg gcgacacgga   10920
aatgttgaat actcatactc ttcctttttc aatattattg aagcatttat cagggttatt   10980
gtctcatgag cggatacata tttgaatgta tttagaaaaa taaacaaata ggggttccgc   11040
gcacatttcc ccgaaaagtg ccacctgacg tc                                 11072

SEQ ID NO: 857         moltype = DNA   length = 1584
FEATURE                Location/Qualifiers
source                 1..1584
                       mol_type = unassigned DNA
                       organism = African swine fever virus
SEQUENCE: 857
atgttctctc tgcaggactt gtgtcgcaag aataccttct tcctgccttc agacttcagt   60
aagcacacct tgcatctgct tggcctctat tggaaggagc atggatcaat ccagcgcatc   120
aagaatgacg gtgtgctgat cgaacacgat ctgacactct ccattaacga agccctgatt   180
ctggcaggcg aggaaggcaa taatgaggtc gttaaactgc tcttgctttg ggaagggaat   240
ctccactatg cgatcattgg tgccctgaga acggagaact acaatctggt gtgtgagtat   300
cacagccaga tccaggattg gcactgtttg ctgccactga tccaagaccc cagagactttc   360
gagaagtgcc atgacctgag tcttgagtgc gacctgtctt gtctcctgca acatgctgtg   420
aaatacaaca tgctgagcat cctcgtcaag tataaggagg atctcctgaa cgtgctgttt   480
cgccagcaga ttcagggcct gttttatcctg gcttgtgaga accgcaaact ggagattctg   540
acttggatgg ggcagaatct gcccattcct gatcccgaac ccatcttcag catcgccgtt   600
gtcaccaaag acctggagat gttctccttg ggctacaaaa tcgtgtttga gtatatggaa   660
aaccaaggac tgcacctcac tcaggtagtc cggatggtga tgctgaatca ccactttggc   720
atggtgataa acaaggact gctgcccttt gtcctgaaaa tcctgaacta tggtggaaac    780
gtgaaccggg cttttgagcta cgccgtaacg cagaataagc gcaaaatcct ggatcacgtt   840
gttagacaga agaacatccc gcacaaaacc atagagagga tgctgcattt ggccgtaaag   900
aagcatgctc ctagaaagac cctgaatctc ctgctgagct acatcaacta caaagtgaag   960
aacgtgaaga aacttctgga gcacgtcgtc aagtacaatt ccacactggt catacggctg   1020
ctgctggaga agaagaagaa ccttccttgac gcgacactta cccgatacgt gaaggattca   1080
acctactttc aggtgaaaga gtttatgcag gatttctcca tttcccctga gaagttcatc   1140
aagatcgcgg ttagggagaa gaggaacgtc ctcataaagg ggattagtga ggacatttgg   1200
gaaaacccag ctgaacgaat caggaacttg aagcagattg tgtgcaccat caaatatgaa   1260
tccgggagac agttcctgat aacatcatt cacactatct accaaagcta ctctcctcaaa   1320
ccggaagaaa tcctcaaact cgccaccttc tatgtcaaaa agtcaac aacccattgt      1380
aaagatctgt gcaaataccct ttggcttaat cgccggacag agagcaagaa gctgttcctc   1440
gagtgcctcg aaatcgccga caagaaggaa tttccagaca tcaaaagcat cgtgtctgag   1500
tacataaact acctctttac tgcagggcgc ataacgaagg aggagattat gcaggcctat   1560
gcattggagt acgccatgta ctga                                          1584

SEQ ID NO: 858         moltype = DNA   length = 1347
FEATURE                Location/Qualifiers
source                 1..1347
                       mol_type = unassigned DNA
                       organism = African swine fever virus
SEQUENCE: 858
atgagcaatg agtcctttcc ggagacactg gagaacctcc tgtccatgct gcagactaag   60
cagcagaatc ccattcagtc cgaagtgatt gaatggctgc acagcttctg cgaaacgttc   120
cacctgaaaa tccactgcca taaacagttc attcccagtg gggagaagaa acgggctaaa   180
atccctgctc aggagactca gggcaatacc cagccatctc accatgtgta ccgcgttgta   240
```

```
ctgtccagag cccaacctgt caaagcccaa gagtcactct tgaccacaat gtgcaatgga    300
cttgtgctgg atgcgaacac ctggacctgt cttgctatcc cacctcctgc acccttcag    360
caagcaactc gccaggtgca acacttctac aggaacaact tctacgaggt agtccccatt    420
caagacggaa cactgctgac aatctatcac tgggatgacc ctgagtatgg tccctcctgg    480
tgtctggcct ctacccatgg ctatgacgtg agtaattact gttggatagg ggataaaacc    540
tttgctgagc tggtctacga gcttctgcag caacacagca cttgcgatgt tacactggaa    600
aagaacaaga ccagaggaac acgcctcttc ttcgataacc tcaacccaga ctattgctac    660
actatcggga tcaggcacca taacttgcag cccctcatct acgatccgca gaacatttgg    720
gccattcaga gcaccaatct gaaaacgctc aaaaccgtct atcccgaata ctatggctac    780
atcggcattc caggcatcca gtctccagtc ccagaacttc ctcagtacga cttgccctat    840
ctcatacgga gctataaaac cgccatgaat caggcgaaga atgctattaa gaatgggaag    900
aaggacaagg gctactttaa ctacggttac ttgctgatat cacgagcacc agcgataaca    960
aagagcacta gcaacgttct cctgaagagt ccctgctgg tgttccttca gaagtctgtg    1020
taccagaaga agcacaatat cagcaacagt caacgcctgg aattcatcat cctgcagaac    1080
tacctgatgc agcattttcg ggaccacttc atcgccctgt ttccccagta catatcctac    1140
tacacgaaat accagaacat gctcaacatg atcatccact ccattgccac caaagacaag    1200
gaccatccgt tgctggagc agtggtgaag aaggtgctgg aggatatcga gaatgccgag    1260
aacatcattg accacaccac gatccagaac tatgcccatc agtcaaagta tgccatgctg    1320
tatttgtcta ttatcagcca cttctga                                        1347

SEQ ID NO: 859         moltype = DNA  length = 3402
FEATURE                Location/Qualifiers
source                 1..3402
                       mol_type = unassigned DNA
                       organism = African swine fever virus
SEQUENCE: 859
atggcatatc ccgagctgga cgctgctgac ttcctccaac aattggctcg gcgcaaggag     60
ttcaagtccc tgatctcccc tcccgtggat cagaaagaac tgattcggga tctgagagcc    120
cactttgtgc agatcggagg cccaggatgt gaaaagggag gcagggcctt cttttccctgt   180
gatccgtacg cctctccttt tccttccatc aaagggctc agctgcataa tgcccagctc     240
ttcgtgcaga atttccagaa tccaaacacc cctatagtc gcctcttgct caattggcaa     300
accggcaccg gcaaatccat cgccgcaatt gccattgccc gacagttcat gaatcactac    360
atgaacttca tcgagaacgc accttggatc ttcgtggtgg gcttcactag agccatcatc    420
cagaccgaga tgctgcgacg ccccgaactc ggattcgtca gttataaaga agtggctgag    480
cttccacaggc tgcttcatat cgcgaagcaa tccgggtcaa ccacaagtgt cgagtcacgg   540
cacctcaatg gcttcgtgag cacccctgaag aggaggctta ccgaccggaa tcgcggcgga  600
ttctttcagt tttacggcta caaggaattt gccagcaaac tgttcaacat tacctctaaa    660
ggcgaggaaa agaactttga tgtgttgagc ctcttccacc ggtctgacga agccgaggac    720
acgctgaacg aaaacgacat ctcccagttt gtccagaaaa tttccgagc cgaaaccaat    780
ggactcataa gagtcaacca gaaaatcatg gagcagctca gaggcggact gctcatcgct    840
gacgagattc acaacgtgta caatatccag gagcgcaaca actatggtat agccctgcag    900
tacgttctgg atgcattccc accccatcag gctccaaggg ctgtgttcat gagtgccact    960
ccggttacag gttccgtgat ggagtacgtt gatctgctga atttgcttgt gcctcggctc   1020
gaattgccca atgggcagcc actgcaacgg cagcagctgt ttgacagcag cggccattct   1080
gtgaagtgga agaaggacgc tctcgctctc gtggaacgac tgagcacggg aagagtttcc   1140
ttcctgctgg atacgaatac aaacttttat cccgaacgca tcttcgcagg aaagatgctt    1200
agctacaaag acgagacact gccgtatctc cactttattg agtgcccat gtctgagtac    1260
cagctggaaa ccctgaagca gctgggcc gaccctaaaa tctcttccaa tgcctactca    1320
atctatgata tggtattccc gaacccaaag tttagcaagc aaacagaacc aaaggcgtat    1380
gggctcttca cagcactga gactccaacc gcgttgtcta tggcatccac ggactggctg    1440
ctggaaacg gagtccagat aatagagccg agtcgccgga caccctcaa cgtcagcggc    1500
tcttttctgt cactgcaacc acccaccat atcagcgggc ttgcctttta cagtggcaag   1560
tatcccaga tgatgaagga catactgtcc ataattcgac aggggagggg caagattctg    1620
atctaccaca acagggtacg catgagtggg gtgttgatac tgcaggaaat ccttcagagc   1680
aatgggattc tgaacgaagt ctcatctccc gtcgggacca ctcgctgttc catttgcgct   1740
gcaattaggg acgaacacac acacagcgac caccagttta tccctgttcg cttcaccatc    1800
ctgcatagcg aaatcgagcc cgccgtgcgc gagcgctccc tggccctgtt caatgccagc    1860
agtaaccttg aaggtcacca actgcgcatt ctgatcgggt ccaaggtcat cgtcgaggga   1920
ctgaacttcc aggctgtgcg ctatgcagga attatgtctc tgcccttga tacccgcgg   1980
ctgatccagg tatttgggcg cgttgtgcgg aagaacagcc atatggagct tccacccagt   2040
gagcggaatg tgaccatcta cctgtacgtc agcaccacac ccgatggtgg cccggagctg   2100
gccaaatacg cccagaaatt gaaggagtac atcctcatcc aggagggtga caagcgctg    2160
agaaagcacg caattgatgg ttttaccaac cagatcaaga tcgacaagcc tatgctcgag   2220
tcttttgccc tgagtccctc cattactcct gccaatgcag gctgaatacc                2280
tttgaggcct atggctacgg tgagcaggag gttaaaacta tttccaacat cattatcagc   2340
cttttcatgg caaggcctgt gtggacatac agcgaactct ggaaggcggt gtccacacct   2400
aagcttatac agggtatcac gattgacaac aaactcttca gcgaggacaa tttcgccctt   2460
gcgctgataa gcctctgcta tagcaagaat caatgcaaag agttgtggat acagaacagg   2520
ctgtcgcacta ttatgcacgt gcccgccaaa cccgagcacc tgtacgttgc tgcggtgctg   2580
aaccataaga aagagcctgt cctggacatc gagacataca tccgcgattt tcagccacca   2640
gcaatgcaca gcatcaggat cactaaatac ttggagcata gccaaacgaa ggagcccttc   2700
caggtcctct acgagaaatt tcaaaaggac ttccaggatg agccgatgga gcaagtcctc   2760
atccattatc ccgcctcatt ccactacaca atgctcgagg ccctatcat cgacaatctg    2820
gctgggatgg gagctctggt ggaggtcatt aagaaattct tcatcgcatt ttcaaagaag   2880
gatatccagc ccttcccaga catctttaag atcatcagcc acgtgcctgg cgacgacaat   2940
accctggtgg gatatgccac cgaggatagc gtgagactga tcacgtcaag agaggacaaa   3000
acgtggcacg agataccact gtacatgctc aacattaacg tgaagagaaa agagaacgac   3060
atagtcattg gctacatgga atccaagggg aaagctctga aattcaagat ccggccaccg   3120
attcaggttc tgaagaagaa cgaaattacc gatattcgga tgctcaatag aggcgcggtc    3180
```

```
tgcgaaacta ggggccgcga agagcagcaa aagatcgccg atcagctggg catctcactg   3240
aacctgacca agatctctgc cattaagctc tgtctgttga tccggaacaa cctgctgcag   3300
aaagaaatgg aagcccgaaa ccagcctaat gggatgcagg atggcattag atggttctat   3360
ctctttaacg acaagatgcc ttccctggtg cacacttctt ga                      3402

SEQ ID NO: 860           moltype = DNA   length = 711
FEATURE                  Location/Qualifiers
source                   1..711
                         mol_type = unassigned DNA
                         organism = African swine fever virus
SEQUENCE: 860
atgagaggga tactcatagc gatcgaaggc atcaatggcg taggaaagtc cactcaggcc   60
atgaaactga aggagactct ggaatgtatg gactataacg ccatttgcat ccactttccc   120
aatcctgata caaccactgg tgacctgatt ctccaagtgc tcaataagac gattgagatg   180
tccagcgaac agctgcacaa gctgttcacc aaacatcgga gtgagtttat cgccgaaata   240
gcagtgctgt tgaagctgaa ctacatcgtc atcgtggata ggtacatttg gtcaggactg   300
gtctatgccc aagctgatgg gattacgatc gagacaaaga acacctttaa acccgattat   360
accttctttc tgtctagcaa gaaacctttg aatgagaaac cacttacact tcagcgactt   420
ttcgaaacca aggagaagca ggagacaatc ttcacgaact tcaccattat catggatgac   480
gttccgaaga accgcttttg cattattcca gctactctga acaaggagat catccacatg   540
atcatcctca ccaaaaccct gaaagtgttc acaacaatag ctgtctgaa ctacatcaag   600
atgtacgacg acaagtatct gaatgtgcag gacttgaacc tctttgactt cgattggcag   660
aaatacatag aggacaacaa tgataaggag gaatacgact tcatcgtgtg a            711

SEQ ID NO: 861           moltype = DNA   length = 924
FEATURE                  Location/Qualifiers
source                   1..924
                         mol_type = unassigned DNA
                         organism = African swine fever virus
SEQUENCE: 861
atgacaaccc acatatttca tgctgatgac ctccttcagg ccttgcaaca ggctaaggcc   60
gagaagaact tttcctccgt attcagcctt gattgggaca aactgagaac tgcgaagcgc   120
aatactacgg taaagtacgt cactgtcaac gtgatcgtca agggcaagaa ggctcccctg   180
atgttcaact tccagaatga gaagcacgtt ggcaccattc caccatctac cgacgaagaa   240
gtgattcgaa tgaacgcaga gaacccgaaa ttcctggtca gaaacgggta tagggaccct   300
tgtctgcagt tcaacaagta caagatcagc cctccacttg aggacgatgg tctgaccgtt   360
aagaagaaca acaaggggga agagatttat cccggccgatg aggagaaaag caaactcttc   420
cagataatcg agctgttgga ggaggcgttt gaggacgccg ttcagaaagg acccgaagcc   480
atgaaaacca aacacgtgat caaactgatt cagcggaaaa tctccaacag tgctgtgaag   540
aatgcagaca agccactccc gaatcccata gccagaatcc gcattaagat caatcccgca   600
acatccattc tgcacccat cctgctggac aagaacaaac ctatcaccct gcagaatggc   660
aaaacgtctt cgaagagct caaggatgaa gatggggtca agccaatcc tgacaacatt   720
cacaagttga tcgaaagcca ctcaattcat gacggaatca tcaacgcaag gagcatctgc   780
attagcaaca tgggcatttc ctttcctctg tgcctcgaga tgggtgtggt gaaggtgttt   840
gagaagaaca acgggatcga cgtgaatagt atctacggat ctgacgatat ctcaacactg   900
gtgaatcaga tagccatcgc ctga                                          924

SEQ ID NO: 862           moltype = AA   length = 117
FEATURE                  Location/Qualifiers
source                   1..117
                         mol_type = protein
                         organism = African swine fever virus
SEQUENCE: 862
MDTETSPLLS HNLSTREGIK QSTQGLLAHT IAKYPGTTAI LLGILILLII ILIIVAIVYY   60
NRTIDCKSSI PKPPPSYYVQ QPEPHHHFPV FFRKRKNSTS LQSHIPSDEQ LAELAHS      117

SEQ ID NO: 863           moltype = DNA   length = 354
FEATURE                  Location/Qualifiers
source                   1..354
                         mol_type = unassigned DNA
                         organism = African swine fever virus
SEQUENCE: 863
atggacactg aaacgtctcc actgctttct cataacctgt caacccgcga gggaattaaa   60
caaagcaccc aaggccttttt agcccataca atcgccaaat atcccggaac aactgcgatt   120
ctcctgggca ttttgatttt gctcattatt attcttatca tcgttgccat cgtttactat   180
aaccggacta ttgactgcaa gtcgagcata cctaaacctc ctcctagcta ctatgtacaa   240
caacctgagc tcaccacca tttccccgta ttctttagaa aaaggaaaaa ctccacctcc   300
ctgcagtccc acattccaag cgacgaacaa ttagctgaac ttgcgcattc ataa         354

SEQ ID NO: 864           moltype = AA   length = 117
FEATURE                  Location/Qualifiers
source                   1..117
                         mol_type = protein
                         organism = African swine fever virus
SEQUENCE: 864
MDTETSPLLS HNLSTREGIK QSTQGFLAHT IVKYPGITAI ILGILILLVI ILIVVAIVYY   60
NRSVDCKSTM PKLPPPGYYV QQPEPHHHFP VFFRKRKNST SQQHIPSDEQ LAELAHS      117

SEQ ID NO: 865           moltype = DNA   length = 354
```

```
FEATURE                 Location/Qualifiers
source                  1..354
                        mol_type = unassigned DNA
                        organism = African swine fever virus
SEQUENCE: 865
atggacactg aaacttctcc actgctttct cataatctgt caacccgcga gggaattaaa    60
caaagcaccc aaggcttttt agcccatacg atcgtgaagt atcccggaat aactgcgatc   120
atcctaggca ttttgatttt gctggttatt attcttatcg tcgttgccat cgtttactac   180
aaccggtctg ttgactgcaa gtcgaccatg cctaaacttc ctcctcctgg ctactatgta   240
caacacccg agcctcacca ccatttccca gtattcttta gaaaaaggaa aaactccacc    300
tcccagcagc acattccaag cgacgaacaa ttagctgaac ttgcgcattc ataa          354

SEQ ID NO: 866          moltype = DNA  length = 1428
FEATURE                 Location/Qualifiers
source                  1..1428
                        mol_type = unassigned DNA
                        organism = African swine fever virus
SEQUENCE: 866
atggatcagg aagaatccca cgttataagt atttttgaaa cccttggtgc gtattttatc    60
aacatttttt ataacttttt atacaaaaat gcactataca aaaaacattc cattgttacg   120
gaatatcagt atcaagtaaa gggctatatt ttaggggtta acaaaataa aaaacttat     180
gaaaaaatgc tagatagttt ttacaaatat ttttgtaaca ttacccaaat taacagcaaa   240
acattaaact tttcaaactt cgtaacaacg attgttgatt cttcatacc taagaaatac    300
agccaatcta taagccttga aaagaaagaa tctatcttgg aattgctact gtgcgactac   360
attagcaatc tgggcacctt tatcacaaca gaaaaaatgc tgcccttat tatcaaaaac    420
cggaaagaaa actaccataa agttacgaaa gaaatgcaag attatagtct tacctttctg   480
ctcaaaaaaa gaatgggaact atacaataaa tttctgcgaa acaggccta tgtggagccg    540
gagacagaat tagaagaaac gtatgcaaga cttagttcat acaatcgcag ccttcttcat   600
caaattgaag aattaacatc tgaaaacaag tcgctcttag cagatctctc cacgctacgt   660
aaaaaatatg aaaaaagaca gagtgaatac cggcgacttg ttcaactcct ttatcagcaa   720
attcaacgct cttctacatc aaagagcagc tatccactca caaagtttat tgaaacatta   780
ccctctgaac atttttctaa tgaagaatac caaaagaga caccggcgga tcaaaaagaa    840
gtagtagaga tggaattatt gagaaaacaa gaactattaa caagccaaga gctaaccagc   900
aagtcaccaa acaattatcc cgtgccacat tcgaggacta gtaagtaa accattagat    960
aactatcccg tgccacggtc taggacaaca actaaaatag attttgataa ttctcttcaa   1020
aaccaagagc ttcacactaa aaacggattt agcgagaaag atattgttga gtttggtcag   1080
gataaacctg aagaagaaaa tattcttgcg attgatcagg ataaacctga ggaagaaact   1140
attcttgcga ttaaacagga tatatctgaa gaagataata tttttgcgat tgatcaggat   1200
aaacctgagt ttaatcaaga tacacctgag tttaaagaag ctgttcttga tatcaaagaa   1260
aatatccttg aagaagaaaa tcaagatgag cctattgttc aaaatccatt cttgaaaat   1320
ttttggaaac ctgagcagaa gacattcaac cagtcgggcc ttttttgaaga atcttcaaat   1380
tttagcaatg attggtccgg cggagatgta actctaaatt tttcataa                1428

SEQ ID NO: 867          moltype = DNA  length = 1428
FEATURE                 Location/Qualifiers
source                  1..1428
                        mol_type = unassigned DNA
                        organism = African swine fever virus
SEQUENCE: 867
atggatcagg aagaatccca cgttataagt atttttgaaa cccttggtgc gtatttatc     60
aacatttttt ataacttttt atacaaaaat gcactataca aaaaacattc cattgttacg   120
gaatatcagt atcaagtaaa gggctatatt ttaggggtta acaaaataa aaaacttat     180
gaaaaaatgc tagatagttt ttacaaatat ttttgtaaca ttacccaaat taacagcaaa   240
acattaaact tttcaaactt cataacaacg attgttgatt cttcatacc taagaatac     300
agccaatcta taagccttga aaagaaagaa tctatcttgg aattgctact gtgcgactac   360
attagcaatt tgggcacctt tatcacaaca gaaaaaatgc tgcccttat tatcaaaaac    420
cggaaagaaa actaccataa agttacgaaa gaaatgcaag attatagtct tacctttctg   480
ctcaaaaaaa gaatgggaact atacaacaaa ttttttgcgaa acaggccta tgtggagccg    540
gagacagaat tagaagaaac gtatgcaaga cttagttcat acaatcgcag ccttcttcat   600
caaattgaag aattaacatc tgaaaaaaag tcgctcttag cggatctctc cacgctacgt   660
aaaaaatatg aaaaaagaca gagtgaatac cggcgacttg ttcaactcct ttatcagcaa   720
attcaacgct cttctacatc aaagagcagc tatccactca caaagtttat tgaaacatta   780
ccctctgaac atttttctaa tgaagaatac caaaagaga caccggcgga tcaaaaagaa    840
gtagtagaga tggaattatt gagaaaacaa gaactattaa caagccaaga gctaaccagc   900
aagtcaccaa acaattatcc cgtgccacat tcgaggacta gtaagtaa accaccagat    960
aactatcctg tgccacgatc tagaacaaca actaaactag attttgataa ttctcttcaa   1020
aaccaagaac ttcacactaa aaacggattt agcgagaaag atattgttga gtttggtcag   1080
gataaacctg aggaagaaaa tattcttgcg attgatcagg ataaacctga ggaagaaat    1140
attcttgcga ttaaacagga tatacctgaa gaagaaaata ttcttgcgat tgatcaggat   1200
aaacctgagt ttaatcaaga tacacctgag tttaaagaag ctgttcttga taccaaagaa   1260
aatatccttg aagaagaaaa tcaagatgag cctattgttc aaaatccatt cttgaaaat   1320
ttttggaaac ctgagcagaa gacattcaac cagtcgggcc ttttttgaaga atcttcaaat   1380
tttagcaatg attggtccgg cggagatgta acttaaatt tttcataa                 1428

SEQ ID NO: 868          moltype = DNA  length = 1104
FEATURE                 Location/Qualifiers
source                  1..1104
                        mol_type = unassigned DNA
                        organism = African swine fever virus
```

```
SEQUENCE: 868
gccctaacag ttgaagagct tgggctcagc aaggccgcgc gatcgcaggt tgacctcaac    60
caggcaatta acacctttat gtattactat tatgtggccc agatttactc caatttaacg   120
cataacaaac aggagtttca atcctacgag gaaaactatg ccactattct cggagatgct   180
attgcgggac gcctcatgca gttggatacg gaaaaaaatg cgcgcattaa ttctccggct   240
gtagatcttg ccagaggaca cgtgggccca atcctggag gtgcccagga agtagactgg   300
aaggcaaccg taagcgccat cgagctggag tatgatgtaa aacgccgatt ctatcgagct   360
ctggaagggc tagatcttta tcttaaaaac attaccaaaa cgtttgtaaa caacatagat   420
tctattcaaa cagtccaaca gatgctggat ggcgtgcgca ttataggacg atggttcacc   480
gagacaacag gggacacgct tgcacaagtc tttgaaagtt ttcccacctc cacaggcaac   540
gactccaacg tctttacgga taatgctcct gcgggccact actacgaaaa agttgcggct   600
gaaatccaac aaggccgaag cgttggtacc ctccgtcccg tcagcaag ccaggctaaa    660
aacattcgcg acccttatcgg gcgctctctt tctaactttc aggcgcttaa aaatatcatc   720
aatgcctttg cccggattgg ggacatgctt gggggagagg agctgcggca aatggtgccc   780
atgtcgcccc tgcaaatcta taaaaccttg cttgaatatc ttcaacattc tgcgctttcc   840
gtgggactta aaaatctaaa tcaatcagaa attggaggac aaaggatggc gcttgcacag   900
actgccgagg aagcggctca gcgggtctac ctctctactg tgagagttaa cgacgcccta   960
tcaacccgct gggaaaccga ggacgtcttc ttccccttcg tgctgaaaag tatggccgcc  1020
aagatttttta ttgtattagg gatttacgac atgtttgaac ggcctgagcc cgtgtacaaa  1080
cttataccca cgcgtatgat attg                                          1104

SEQ ID NO: 869                moltype = DNA  length = 1104
FEATURE                       Location/Qualifiers
source                        1..1104
                              mol_type = unassigned DNA
                              organism = African swine fever virus
SEQUENCE: 869
gctctcacag ttgaagagct tgggctcagc aaggccgcgc ggtcgcaggt tgacctcaac    60
caggcaatta atacttttat gtattactac tatgtggccc agatttactc caatttaacg   120
cataacaaac aggagtttca atcctacgag gaaaactatg ccactattct cggagatgct   180
attgcgggac gcctcatgca gttggatacg gaaaaaaatg cgcgcattaa ttctccggct   240
gtagatcttg ccagaggaca cgtgggccca aaccctggag gtgcccagga agcagactgg   300
aaggcagctg taagcgccat cgagctggag tacgatgtaa aacgccgctt ctatcgagct   360
ctggaagggc tagaccttta tcttaaaaac attaccaaaa cgtttgtaaa caacatagat   420
tctattcaaa cagtccagca gatgttggat ggcgtgcgca ttataggacg atggttcacc   480
gaggcaacag gggacacgct tgcacaagtc tttgaaagtt ttcccacctc cgcaggtaac   540
gactccaacg tctttacgga taatgctcct gcgggccact actacgaaaa agttgcggct   600
gaaatccaac aaggccgaag cgttggtacc ctccgtcccg tcagcaagc caggctaaa    660
aacattcgcg accttatcgg gcgttctctt tccaacttct aggcgcttaa aaatatcatc   720
aatgcttttg cccggattgg agacatgctt gggggagagg agctgcggca aatggtgccc   780
atgtcgccct tgcagatcta taaaaccttg cttgaatata ttcaacattc tgcgctttcc   840
gtgggactta aaaatctaaa tcaatctgaa attgagggc aaaggggtagc gcttgcacga   900
actcccgagg aagcggctca gcgggtctac ctctctactg tgagagttaa cgacgcccta   960
tcaacccgct gggaaaccga ggacgtcttc ttccaccttca tgctgaaaag tatggccgct  1020
aagatttttca ttgtattagg catttatgat atgtttgaac ggcctgagcc tgtgtacaaa  1080
cttataccca cacgtatgat actg                                          1104

SEQ ID NO: 870                moltype = DNA  length = 4746
FEATURE                       Location/Qualifiers
source                        1..4746
                              mol_type = unassigned DNA
                              organism = African swine fever virus
SEQUENCE: 870
gatgagctag agcccgaggt aattcccgag gcagcagagc tttacttccg ccttcccgc     60
ctcgccgaat tttatcaaaa gttgttttcc tttagagatg aaaatgtaca gatctcgatg   120
cttcctgagc tggaaggaat cttctcagga cttattcgca ttatctttat gcgtcctatt   180
gagcttatta acattggtga ctactcagaa accgaaattc gtcagcttat caaagaaata   240
aacgtcattt accaacactt taacttagag tatggtgaac aagaagcaac caaaaaagcg   300
cttatccatt ttgtaaatga aataaaccgc agattcggtg tacacg caccgaatgg      360
gaaaaatttc aacgcattgt tcaggaagcg cgaactatga tgattttgg aatgatgatg   420
caaaccaact actccattct tcctgatgag gatggctata cacaatcctc acaattactt   480
ccctccgata ggtttattag tccttcaacc cagcctaccc caagtggcg cccggcacta   540
tacaatatag actctgtgga tgtccaaaca ggaatgctgc agcccaactc ccagtgggat   600
ttggtacaaa aatttaggaa acagcttagt gagatgtttg aagatcccag tctgcaacaa   660
gaattgggca aaatttccta ccaagaactc attcgccagg ctatcaatga actcaaaaag   720
gagcataccg ataaaattca aatcgtttca aaacttattc aaggctctga gtcactggca   780
gatacagatg ttaacaaaat atttctgttt catgaaaccg ttattacagg tcttaactta   840
ttgagtgcta tttacgtact tcttaataac tttcgtaata acattaaagg tttagaccta   900
gatcgattc aaaaagcat tatcgaatgg ttacgagaga cacaagctgc caacgtgaac   960
cgcgccaatc ttattgactg gctcggaaga aaacacgggg ccatctctga gattagaaat  1020
ccaggattag tcattaaaga aatcaatatg cggctttcta tggtgtaccc tgatcccact  1080
accgaagcgg ctgcagcagc caagaccga aatttaacca cagaaactct ttttgcttgg  1140
attgtaccat atgtgggtat tcctgctggt ggaggagttc gtccggagca agagtggcc  1200
gcaaggtatt tagtagataa tcagcgaatc atgcagctcc tgttgaccaa tatcttcgaa  1260
atgaccttcca gttttaacaa aatggttcaa gttcgcttcc ctgaaaccag caccgctcaa  1320
gtgcattta g attttacagg tcttattcc ttaattgatt ctttgatggc cgacacgaag  1380
tattttcttg atcttctacg cccgcatatt gataaaaaca ttattcaata ctatgaaaat  1440
agatctaatc ctggctcatt ttactggttg gaagaacatt taattgacaa acttattaaa  1500
ccacctaccg atgccggagg aaggccgctt cctggcggtg aattgggcct ggaggggtt  1560
```

```
aaccaaatca ttaataaaac ctacaccttg cttacaaagc cttataatgt actgcaactt    1620
cgaggtgggg cgcaaagaag ggacgcggct aatattcaaa taaataacaa tccccaatcc    1680
tctgaacgct ttgaacaata cggaagagta ttcagtagac tcgtatttta cgatgctttg    1740
gagaataact ctggacttcg tgtagagcag gtggcactag gagactttag actctccaat    1800
cttattcgta ccaacaacgc ccaggaggaa aatactctta gctactggga caacatagcg    1860
ctcagaacct atgccaatgt caatgatgcc gcaaacaacc ttcgacgtta tcgcctatac    1920
ggatcagact atggtattca aaataatcgt agtatgatga tggtgtttaa ccagctcata    1980
gcttcatata ttacccgatt ttatgatgct cccagcggaa aaatatatct aaatcttatt    2040
aatgcattcg ctaatgggaa cttttagccaa gcagtgatgg agatgggata tgctcaccct    2100
gacttagcac gcaataacaa cgtctcttgg catagaggcg accccacaga gcagtcggtc    2160
cttcttctgt ctttgggact tatacttcag cggcttatta aggataccaa tcgccagggc    2220
ctgagtcagc atcttatttc tactttaaca gaaattccca tttaccttaa agaaaattat    2280
agagccaatc ttccactatt taacaaaatg tttaatattc ttattagcca gggagagctt    2340
ctaaaacaat ttatacaata cacaaatgtc caactagctc gcccctaatct gacggcactc    2400
ttgggagcca ataatgattc cgttatttat tataataata acaatgttcc tgcgacagga    2460
ctatccgtcg gtcaggcggc cctgcgggga attggcggcg tatttcgtcc caatgttacg    2520
cttatgcccc taggagacgc acaaaataat acgagcgatg ttgtgcgaaa gcgactggtc    2580
gcagtgatcg acgggatcat tagaggctct cacactctgg cagattctgc catggaggtc    2640
ctgcacgagc ttaccgatca tcccatctat cttgaaacag aagaacactt cattcaaaac    2700
tatatgtccc ggtacaataa ggagcctctt atgccatttt cactttcgct ctattattta    2760
catgacctaa gaatagaaaa taatgaggta tatgatcctc ttctttaccc gaaccttgaa    2820
agcggctccc ccgagtttaa actactatac ggcacaagaa aattactggg aaatgatccg    2880
gtacagctct cagatatgcc cggagtacag cttatcatga aaaactataa tgaaacggta    2940
gttgctcgcg aacaaattac tcccacgcga tttgaacact tttatcccca cgccattcag    3000
gctctccgat ttatcataaa tatccgtagt tttaaaacag tgatgatgta caatgaaaat    3060
acttttggtg gagttaatct tattagcgag aacagagcg ataaacccat tataacagcg    3120
ggaataggga tgaatgcagt gtattcgctt cgtaaaacat tgcaagacgt aatttccttc    3180
gtggaaagct cttaccaaga ggagcaaatc aatcatattc acaaaatagt gtcgccgaaa    3240
ggtcaaacac gcactcttgg ctctaataga gagcgcgagc gcatatttaa cttgtttgat    3300
atgaatatta tacctatcaa tgtaaatgcg ctgatgcgat ctataccact tgccaatatt    3360
tacaactatg actatagttt tgaagaaatt gcttgtctta tgtacggcat ttcggctgaa    3420
aaagtacgat ctctggacac cacggctcct caaccagatg ttgcagaggt attaaacatt    3480
ccgaatcgtc cccccataaa tactcgagaa tttatgctaa aacttcttat aaaccccata    3540
gtctcggtct ctattactca caaaggcaa gagttactat ccaaaggcaa cgccggatac    3600
atgtcacgca tctttagagg ggacaacgcg ctaaatatgg gccgccctaa atttctttct    3660
gaccaaattt tcaataaagt gctatttgga agcttttatc ctacacaatt tgattatgac    3720
gaggcaggtc ctagtttggc cgcaggtatt caacgtggac gtgagcggtg gggccatccc    3780
atgtcaatat acataaacca ggcctacat gaaattgtgc gtactatacg attggctgaa    3840
acagttcgag gtttaagaaa tgttattgat agaaaaccaa ttataggcga gttaaatgca    3900
tttaggactc agcttgaaga tacacgaaga gaagtgaata atctaataca aacacctgaa    3960
attcaaaaca atccaacccc tgagatcatc gctgccattc aaaactgggt acaacaatat    4020
cgaggtcaaa taaccaattt aatcgatctt ataggaaatg ccgggcaagc caattcgatg    4080
ataaattaa tacaaaatat tacgcccaa acagccggtg cacaattaac cgcttattc     4140
aacatacgtg gattacctgc cccgcctccc cgtcaagcat acaaaatga tattgaagca    4200
atgcaatggt ttatgacaat ggttataaac catccacctg ttttaatagc cccttcatg    4260
ctactcgtaa ataaccttaa ggaattttta aatacgctag aacgatatgt ttataaaact    4320
ccacgatggt tgggtcccgg tacagcccga attgcacaac cgccagttgg aatggcacca    4380
ggtattaata tgcgacatca tacctcatat acagaaaata gtgtgctgac ctatatcacg    4440
gaacaaaatc gggaagaagg accctggtcc atcgttaaac aagtgggagt tggaatacaa    4500
aagcccacct tagtacaaat tggaaaggat cgctttgaca ctcgcctcat acgcaatcta    4560
atatttatta caaatataca gcgactatta cgactgcgtc taaacctaga actctcgcag    4620
ttcagaaatg tgcttgtcag tcctgaccac attataaacc ccagcattac agagtatggg    4680
ttctccatca caggacccag tgagaccttc tcagataaac agtatgatag tgatattcgg    4740
atttta                                                               4746

SEQ ID NO: 871         moltype = DNA   length = 4743
FEATURE                Location/Qualifiers
source                 1..4743
                       mol_type = unassigned DNA
                       organism = African swine fever virus
SEQUENCE: 871
gatgagctag aacctgaggt aattcccgag gcagcggaac tttacttccg ccttcctcgc      60
ctcgccgagt tttatcaaaa actgttttcc ttcagagatg aaaatgtaca gatctcgatg     120
cttcctgagc tggaaggaat attctcagga cttattcgca ttactcttat ggtgtcctatt    180
gagcttatta acattggtga ctactcagaa accgaaattc gtcagcttat caaagaaata     240
aacgtcattt accaacactt taacttagag tatggtgaac aagaagcaac caaaaaagcg     300
cttatccatt ttgtaaatga aataaaccgc aggttcggcg ttatcacacg cactgaatgg     360
gaaaaatttc aacgcattgt tcaggaagcg cgaactatga atgacttcgg aatgatgaat     420
caaaccaact actccattct tcctgatgag gacggcttata caatcctc gcaattactt     480
ccctccgata ggtttattag tccttcaacc caacctaccc ccaagtggcg cccggcacta     540
tacaatatag actctgtgga tgtccaaaca ggaatgctgc agcccaactc ccagtgggac     600
ttggtacaaa aatttaggaa acagcttagt gagatgtttg aagatcccag cctacaacaa     660
gaattgggca agtttcccta ccaggaactc attcgccagg ctatcaatga actcactaaag    720
gagcataccg acaaaattca aattgtttca aaacttttat aggctctga gtcactggtca    780
gatacagatg ttaacaaaat atttctgttt catgaaaccg ttattacagg tcttaactta     840
ttaagtgcta tttacgtact tcttaataac tttcgtaata acattaaagg tttagaccta     900
gatacgattc aaaaagcat cattgaatgg ttacgagaaa cgcaagccgc taacgtgaac     960
cgagccaatc ttattgactg gctcggaaga aaacacgggg ccatctctga gattagaaat    1020
ccaggattgg ttgttaagga aaatgatgtg cggctttcta gggtgtatcc tgatccaact    1080
```

```
accaatgcga ctgcacccca agaccaaaat ttagtcacag agactctttt tgcctggatt 1140
gtaccatatg tgggtattcc tgctggtgga ggagttcgtg cggagcaaga attagccgca 1200
agatatttgg tagacaatca gcgaatcatg cagctcctgt tgaccaatat cttcgaaatg 1260
acctctagtt ttaacaaaat ggttcaagtt cgctttcccg aaactagcac cgctcaagtg 1320
cacttagatt ttacgggtct tatttcctta attgattctt tgatggccga cactaagtat 1380
tttcttaatc ttctacgccc acatattgat aaaaacatta ttcaatacta cgaaaaatga 1440
tccaatcctg gctcatttta ctggctggaa gaacatttga ttgacaagct tattaaacca 1500
cccaccgatg ccgggggaag gccgcttcct ggcggtgaat taggcctgga gggagttaac 1560
caaatcatta ataaaaccta catcttgctt acaaaaccct ataatgtact gcaacttcga 1620
ggtggggtac aaagaagaga tgcagctaat attcaaataa ataacaatcc ccaaccctct 1680
gagcgctttg aacaatatgg aagagtattt agtagactcg tatttacga tgctttggag 1740
aataactctg gactccgtgt agagcaagtg gtactaggag actttagact ctccaatctt 1800
attcgtacca acaatgccca ggaggaaaat actcttagct actgggacaa tatggcgccc 1860
agaacctatg ccaacgtcaa tgatgccgca aacaaccttc gacgttatcg cctatatgga 1920
tcagactatg gtattcaaaa taatcgtagt atgatgatgg tgtttaacca gcttgtagcc 1980
tcgtacattg cccggtttta tgacgctccc agcggaaaaa tatatcttaa tcttatcaat 2040
gcattcgcca acgggaactt tagccaagcg gtgatggagc tggggtacac tcatcccgac 2100
ctagcacgtg ataacatcgc cttttggccat aggggcgagc ccacagagca gtcggtgctc 2160
cttttgtcct tgggtctcat gcttcagcgg cttattaagg atactaaccg ccaaggcctg 2220
agtcaacatc ttatttccac gttaacagaa attcctatct atcttaaaga aaattataga 2280
gccaatcttc cactatttaa caaatgtttt aatattctta ttagtcaggg ggagcttta 2340
aaacaattca tacaatacac aaatgtccaa ctggctcgtc tcaatctgat ggggctcttg 2400
ggggccaata atgattccgt tatttactat aataataata ttaatgttcc tatgacagga 2460
ctatccgtcg gtcaggcggc cctgcgggga attggcggcg tatttcgtcc caatgttacg 2520
cttatgcccc taggagacgc acaaaataat acgagcgatg ttgtgcgaaa gcgattggtc 2580
gcagtgatcg acgggatcat tagaggctcc cacactctgc cagactctgc catggaagtc 2640
ctacatgaac ttaccgacca tcccatctat cttgaaacag aagaacactt cattcaaaac 2700
tatatgtccc ggtacaataa ggagcctctt atgccatttt cactttcgct ctattatttg 2760
cgtgacctaa gaatagagaa taatgaggta tatgatcctc ttctttaccc aaaccttgaa 2820
agcggctccc ccgagtttaa actactatac ggcacaagaa aattactggg aaatgatccg 2880
gtacagctct cagatatgcc cggagtacga cttatcatga aaaattataa tgaaacagtg 2940
gttgctcacg aacaaattac tcccacgcga ttcgaacact tttataccca tgctattcag 3000
gctcttcgat ttatcgtaaa tatccgtagt tttaaaacag tgatgatgta caatgaaaat 3060
actttggtg gagttaatct tattagcgag aacagagacg ataaacctat tataacacg 3120
ggaatagga tgaatgcagt gtattcgctt cgtaaaacat tgcaagacgt gatttccttc 3180
gtggaaagct cttaccaaga ggagcaaatc aatcatattc acaaaatagt atcgccgaaa 3240
ggccaaacac gcactcttgg ctctaataga gagcgcgagc gcatatttaa cttgtttgat 3300
atgaatatta tacctatcaa tgtaaatgcg ctgatgcgat ctataccact tgcgaatatt 3360
tacaactatg actatgtttt tgaagaaatt gcttgtctta tgtacggcat ttcggccgaa 3420
aaggtacgat cgctaaacac cgcggctcct cagccagata ttgcagaggt attaaacatt 3480
ccgaatcgtc cccccatgaa cactcgagaa tttatgctaa aacttcttat aaaccccta 3540
gtttcagtct ctatcaccca atatggaaac gaattgatga gcaagggcag tgctggatat 3600
atgtcaccga ttttttagag agataatgcg ctgaacatgg gagtg gtttctttcc 3660
gaccaaattt ttaataaagt gttatttgga agtctgtacc ccacacagtt tgactatgat 3720
gaagcaggcc cgggtttggc cgcaggtatt caacgtggac gtgaacaatg ggggcaaccc 3780
ttatcagaat acatcaatca ggcttacat gaacttgtcc gtaccataag aataacctcag 3840
aaacttcgag ttctaagaaa tattattgtt aaaaaccaac ttatagcgga tttaactaca 3900
attagagagc agcttgtaag tatgcgaaga gaagttaaa acatgataca aactcctgaa 3960
attcaaaaca atccaacccc tgaggtcatt gcagccgctc aaaactggac acagcaatac 4020
cgagctcggg tagataccctt aattaattt ataggaaata ttgggcaacc caattcaatg 4080
ttagacttaa tacaaactat tacgcccgta acagtgcgag cacaattagg cgtcattttt 4140
aatagacatg gaatccctgt tccacatccc cgtcagatac tacaaactga tgatgaagcc 4200
actcaatggt ttatgaccaa tatttaaac atacctgcca ttataatgac cccttacg 4260
gacctcgcaa atgatcttag aacattttta gaaactttgg aacgatatgt ttaatgtt 4320
ccaagatgt tgggtcctag cacaggacga gttgcacgag caccccgttcg tatggcacct 4380
agagatatgc gacatcccat ttcatatacg gaaaatagtg tgctcaccta tatcacggaa 4440
caaaatcggg aagaaggacc ctggtccatc gttaaacaag tgggagttgg aatacaaaag 4500
cccaccttag tacaaatcgg aaaggatcgc tttgacactc gcctcatacg caatctaata 4560
tttattacaa atatacagcg actattacga ctgcgtctaa acctagaact ctcgcagttc 4620
agaaatgtgc tcgtcagtcc tgaccacatt ataaaccca gcattacaga gtacgggttc 4680
tccatcacag gacccagtga gaccttctca gataaacagt atgatagcga tattcgaatt 4740
tta                                                                  4743
```

```
SEQ ID NO: 872        moltype = DNA   length = 3750
FEATURE               Location/Qualifiers
source                1..3750
                      mol_type = unassigned DNA
                      organism = African swine fever virus
SEQUENCE: 872
atggaggaag taattacgat cgcgcaaata gtccaccgtg gcacagatat cttatcgctc    60
aataatgagg aaatcgaggc actagtggat gaaatctact ctacccttaa agggtctaat   120
gatataaaaa acatacgttt aatagacttt cttttcactc taaagatttt tgtgaaccat   180
gttcgcgccg agcagtcaaa gctgcccgat ctatccatgc ccatagaggc ctacatacgt   240
caactgctgg tagaccccga tgtggtcccc atcgtgagtg aaaaaaaaaa ggaattacgt   300
gttcgcccta gcacacgcaa agaaattttt taattaatg ggacgcacct ggccgttccc   360
gcagaagccc ccattgaaat ctatggactt aagttcggc taaaaacttt tccccgcag    420
tgttttatgc gtatggctga gataggctcc ttctcgcctg aaaccttggg ctacgtcgcc   480
tcaggagcca atttgaccaa ttttattcga gtatttatga aatgcgttgga tcaagaaacc   540
tggaaaaaaa acgagaagg ggttgtcgta accaccaagg aaaacatcat ccagtttacg   600
```

```
caccagtata tcgaacttta taagtttttg cggagcggcg ggcatagctg gctcattaat   660
cggctagcag aggagatggt acaccgaaag ctagaccgtg aggatcaggg cagtcatata   720
tctaatatcg ttgaaaccga ggagattgaa ccggaggaga acattaagcg cgtgatattt   780
tttttaaaag agttgtctac gatgtactcg gtgtccccgg ttttacatc gggatacatg    840
cccttgcttt atgacctata tagagcaggc tatttggagg tgcttttgaa ccctgtagaa    900
caaaagtttt tacaacatgc tgaacagcgt gaaaaggagc aaatgattct gcagcaggtg   960
gacatgaagc tcacagaggt cattacccag gcgagacagt attttaaaat tatgaagaa   1020
aaaataggta gggtgcagtc ggatgctata cgtgaaattc ttacaatgga gggtaaagtg  1080
gatgaccccta acagcatcct tcaagaagtc attaaagcct gtgggaaaca ggaggcagaa  1140
cttattacaa cagaatacct aaacattaaa aaacagtggg aactccaaga aaaaaatgca  1200
tgtgctcatc tcaagctggt aaaacagttg cgttcgggtc ttcaatacgc ggagttatta  1260
aaagtattag aaagtattcg tgtactctac aaggaaaaaa acaataccac caattggaat  1320
ctatgcaaag cctgcgggtt taagctgctt tgtcccatg tggacatgct tatacagctt   1380
caagcggcag aagcgtccta cgacaccatg cgaaccaagc taatgaaatt ttcaggaata  1440
aacaaggaga aagaaaacaa ccaggggctt atttactcct actttgcaa aatttgtggc   1500
gaagagctgg cccatttat tcaagaggat cgtacggcag atgtgggcat catccggcgat  1560
cttaatagta agctccgtgt ttttatttgg caggaaacca tgaaggcctg cacgtttatc  1620
cactttggaa agcttgtaga cgtgaaacag tttgccaata tagccgtaaa tgtctgcctg  1680
ccgctcgtgt atagcatcga aaatattaaa aaggaagagg attacgatcc tttaacgcag  1740
ctgtatgctg tgatctacat ctatgcctat attttgaatc tcatttatag ctcgcaaaaa  1800
aataaagaat ttcttacgat taccattcat ggaatgaagg cggatagctc tttgaatgca  1860
tacgtgacct ttcttttgga gaaaatgatg cagcaatata gcggtataat aaatcagcta  1920
tctgagatta cggatcagtg gattgctaat aattttcggg aggctttcaa aaaaattatc  1980
caccaaaatg ggctacaagg gcttagcgtg caggacgaca ccaaggtact tttgacagag  2040
attctgctga accccatgta tgattatgct gccacagtgg cccgtattga cggcagcatc  2100
cctatgcaca aaccacggac tcccaaggag gctgaatatg agtttaaaac cgtgatagga  2160
cgtaccccgg ccgagctatt atcgcaaaaa gaatttatg ataaaattta tacctctaaa  2220
tatcggcctg attttacgca gttgacgcgt ctgaatgaca tctattttca agaagaaagc  2280
ctgcgggtgt ggtggggagg acgggatgag gaaaaaacct caactctcat ttaccttaga  2340
gcctatgaat tatttcttaa gtatttacaa aatgccaccta attttaactc cgaacttgca  2400
gaattcaaaa cgtacgaaaa tgcttatggc gagcaaaagg ccctgcttgc tcagcaagga  2460
ttttataaca tatttgatcc taacacagga agagccgacc aacggactcg gctgtttgag  2520
tataaaaggc ttcccatttc aaccctatac gatgaaaggg ggcttcctca taagtggacc  2580
atttacgttt acaaggccgt agacgttcg cagaaacccg ccgagattga agtaacacgc  2640
aaagacgtca taaaaaaaat tgacaaccat tatgccacttg ccgatctacg ctgttctgta  2700
tgccacgtgc tacaacatga ggtggggcaa ttaaacataa aaaaggtcca aacagcccta  2760
aaggcgagct tagaatttaa caccttttat gccttctacg agtcacgctg ccccaaggga  2820
ggattacacg acttccagga taaaaatgt gtcaagtgcg gactttttac ctatattata  2880
tacgatcatc tttctcaacc cgaattagtt catgactatt ataataatta taaagaccag  2940
tacgataagg aaaagatgtc gatccgttct attcaaataa agaaagatat gaccacgccc  3000
tccaccgaaa cacaacccaa gcctccacag gagccatgga ctttcgatta cggaaaaata  3060
atcaagacgg ccaagatttt ggatatcagt cctgctgtga tagaggccat aggggccatg  3120
gagggcgct cctacgcaga catcagggaa ggccagggtg ccccgccacc acctacctca  3180
atggatgatc caaggctcat ggcggtcgac tctgccgtac gtatttctt atataattat  3240
aactgtttgc ggcacgttag tacatttaac aagcctccta tacatgttga aaggcttgta  3300
aagcaccgt cgtacgagga aaaggaggat ttggaaaagg tgctgcctaa cgttgtgaat  3360
gaatatcaca ctacatttaa acacctacgg gtaacagctc ctgccagcgc cttgctttac  3420
tctatagaat ttttatgtat aagtttctta acgctgtatg aaattaaaga gccctcctgg  3480
gttgtgaata ttgtgagaga gtttgcgctg acagaactca acactattat tcaaagcgaa  3540
aagctgttaa gtaagcccgg tgcatttaac tttatgattt ttggagagga ctttgtgtgc  3600
tctggggaag atagctccat ggacgacatc tcggcctaca gttctcccgg acttttttggg  3660
gaagacatta ttgaccggct cgatgacccct tttagcatcg aggatgttga catttcttta  3720
gatgtgttgg acaacttagc gccccagtag                                   3750
SEQ ID NO: 873        moltype = DNA    length = 3750
FEATURE               Location/Qualifiers
source                1..3750
                      mol_type = unassigned DNA
                      organism = African swine fever virus
SEQUENCE: 873
atggaggaag taattacgat cgcgcaaata gtccaccgtg gcacagatat cttatcgctc    60
aataatgagg aaatcgaggc actagtggat gaaatctact ctacccttaa agggtctaat   120
gatataaaaa acatacgttt aatagacttt cttttcactc taaaagattt tgtgaaccat   180
gttcgcgccg agcagtcaaa gctgcccgat ctatccatgc ccatggagcc ctacatcgtg   240
caactgctag tagaccccga tgtggtcccc atcgtgagcg aaaaaaaaa ggaattacgt   300
gttcgcccta gcacacgcaa agaaattttt ttaattaatg ggacgcacct ggccgttccc   360
gcagaagccc ccattgaaat ctatggactt aagttgcggc taaaaagttt ttccccgcag   420
tgctttatgc gtatggctga gataggctcc ttctcgcctg aaaccttggg ctacgtcgcc   480
tcaggagcca atttgaccaa ttttattcga gtattatga atgcgtgga ccaagaaacc   540
tggaaaaaaa acggggaagg ggttgtcgta accaccaagg aaaacatcat ccagtttacg   600
caccagtata tcgaacttta taagtttttg cggagcggcg ggcatagctg gctcattaat   660
cggctagcag aggagatggt acaccgaaag ctagaccgtg aggatcaggg cagtcatata   720
tctaatatcg ttgaaaccga ggagattgaa ccggaggaga acattaagcg cgtgatattt   780
tttttaaaag agttgtctac gatgtactcg gtgtccccgg ttttacatc gggatacatg    840
cccttgcttt atgacctata tagagcaggc tatttggagg tgcttttgaa ccctgtagaa    900
caaaagtttt tacaacatgc tgaacagcgt gaaaaggagc aaatgattct gcagcaggtg   960
gacatgaagc tcacgaggt cattacccag gcgagacagt attttaaaat tatgaagaa   1020
aaaataggta gggtgcagtc ggatgctata cgtgaaattc ttacaatgga gggtaaagtg  1080
gatgaccccta acagcatcct tcaagaagtc attaaagcct gtgggaaaca ggaggcagaa  1140
```

```
cttattacaa cagaatacct aaacattaaa aaacagtggg aactccaaga aaaaaacgca  1200
tgtgctcatc tcaagctggt aaaacagttg cgttcgggtc ttcaatacgc ggagttatta  1260
aaagtattag aaagtattcg tgtactctac aaggaaaaaa acaataccac caattggaat  1320
ctatgcaaag cctgcgggtt taagctgctt tgccccatg tggacatgct tatacagctt   1380
caagcggcag aagcgtccta cgacaccatg cgaaccaagc taatgaaatt ttcaggaata  1440
aacaaggaga aagaaaacaa ccaggggctt atttactcct acttttgcaa aatttgtggc  1500
gaagagctgg cccatttat tcaagaggat cgtacggcag atgtgggcgt catccggcgat  1560
cttaatagta agctccgtat ttttatttgg caggaaacca tgaaggcctg cacgtttatc  1620
cactttggaa agcttgtgga cgtgaaacag tttgccaata tagccgtaaa tgtctgcctg  1680
ccgctcgtgt atagcatcga aaatattaaa aaggaggagg attacgatcc tttaacgcag  1740
ctgtatgctg tgatctacat ctatgcctat attttgaatc tcatttatag ctcgcaaaaa  1800
aataaagaat ttcttacgat taccattcat ggaatgaagg cggatagctc gttgaatgca  1860
tacgtgacct ttcttttgga aaaaatgatg cagcaatata gcggtataat aaatcagcta  1920
tctgagatta cggatcagtg gattgctaat aattttcggg aggctttcaa aaaaattatc  1980
caccaaaatg ggctacaagg gcttagcgtg caggacgaca ccaaggtact tttgacagag  2040
attctgctgg accccatgta tgattatgct gccactgtgg cccgtattga cggcagcatc  2100
cctatgcata agccacggac tcccaaggag gctgaatatg agtttaaaac cgtgatagga  2160
cgtacccccgg ccgagctatt atcgcaaaaa gaattttatg ataaaattta tacctctaaa  2220
tatcggcctg attttacgca gttggcgcgt ctgaatgaca tctatttca agaagaaagc  2280
ctgcgggtgt ggtggggagg acgggatgag gaaaaaacct caactctcat ttaccttaga  2340
gcctatgaat tatttcttaa gtatttacaa aatgcaccta attttaactc cgaacttgca  2400
gaattcaaaa cgtacgaaaa tgcttatggc gagcaaaagg ccctgcttgc tcagcaagga  2460
ttttataaca tatttgatcc taacacagga agagccgacc aacggactcg gctgtttgag  2520
tataaaaggc ttcccatttc aacectatat gatgaaaggg ggcttcctca taagtggacc  2580
atttacgttt acaaggccgt cgacagttcg cagaaacccg ccgagattga agtaacacgc  2640
aaagacgtca taaaaaaaat tgacaaccat tatgcgcttg ccgatctacg ctgttctgta  2700
tgccacgtgc tacaacatga ggtgggggcaa ttaaacataa aaaaggtcca aacagcccta  2760
aaggcgagct tagaatttaa caccttttat gccttctacg agtcacgctg ccccaagggg  2820
ggattacacg acttccagga taaaaaatgt gtcaagtgcg gactttttac ctatattata  2880
tacgatcatc tttctcaacc cgaattagtt catgatcatt ataataatta taaagatcag  2940
tacgataagg aaaagatgtc gatccgttct attcaaataa agaaagatat gaccacgccc  3000
tccagcgaaa cacaacccaa gcctccacag gagccatgga ccttcgatta cggaaaaata  3060
atcaagacgg ccaagatttt ggatatcagt cctgctgtga tagaggccat aggagccatg  3120
gaggggcgct cctacgcaga catcaggaa ggccagggtg ccccgccacc acctacctca   3180
atggatgatc caaggctcat ggcggtcgac tctgccgtac gtattttctt atataattat  3240
aactgtttgc ggcatgttag tacatttaac aagcctccta tgcatgttga aaggcttgta  3300
aagcatctgt cgtatgagga aaaggaggat ttggaaaaag tgctgcctaa cgtcgtgaat  3360
gaatatcaca ctacatttaa acacctacgg gtaacagatc ctgccagcgc cttgctttac  3420
tctataagat tttatgtgt aagtttctta acgctgtatg aaattaaaga gccttcctgg  3480
gttgtgaata ttgtgagaga atttgcgctg acagagctca acactattat tcaaagcgaa  3540
aagctgttaa gtaagcccgg tgcatttaac tttatgattt tggggagga cttttgtgtgc  3600
tctggggaag atagctccat ggattacatc tcggcctaca gttctcccgg acttttggc   3660
gaagacatta ttgaccggct cgatgacect tttagcatcg aggatgttga catttcttta  3720
gatgtgttgg ataacttagc gccccagtag                                    3750

SEQ ID NO: 874          moltype = DNA  length = 1521
FEATURE                 Location/Qualifiers
source                  1..1521
                        mol_type = unassigned DNA
                        organism = African swine fever virus
SEQUENCE: 874
atgttctccc tacaggatct ctgtcggaag aacctttttc ttccacttga gcccttaggc   60
aagcatgtgg ttcaacggct gggattatac tgggaaggcc atggttcagt taacgagtg   120
ggtgattgct ttatatgtgt agaccagatt tggatgctat caatccataa ggctatacaa  180
attgcagcct cggaaggaaa tgagaacatt gtcaagcttt tcttactatg gaaggggagt  240
ctacaatatg ccatcatagg agccttagag ggcaggcaat atgatctgat tcaaaaatat  300
tacaaccaaa ttggggactg ccatcagatt ctaccactga ttcaagatcc agaaatttac  360
gaaagatgtc atgaattaaa tgttacatgt accttccaat gcttatttca acatgctata  420
agagataaca tgctgcccat tttccaaaaa tatggagaag atctgaatgg aaacaggaga  480
atggttcaac ttctgtatga gatggcatgc cgattacaaa attatgatat catcaaatgg  540
ataggatcta acctgcatgt ttataacttg aagccattt tagcattgc ttttgttaga   600
aaggatttaa ctttgtattc tttaggctac atgcttcttc tgggtagaat gagtactgaa  660
gatagaaact ttatctcaat cataacacgc atcttgaat acgcatcaaa aagggacttt  720
tttgactttg tactagaatc tttgaaatat ggaggtcaag tgtacagt gttgtttcag  780
gctgtaaaat acaaccatag gaaaattttg gcccatttta ttcatgaaat tccccgtgaa  840
acggttgaaa agctgatact ccatgctgtg gagtcacggg cctccagaaa acattcaac   900
ctgctttat cttccataaa ctactgtgtg aacccttttg tcaaaaaact actgcacgct   960
gtggtgaaac acaagtacat gcttatcata aagcttttgc tcgagcggcc caaaaagaag  1020
ataaacctgg tagatgctgc tctattcaaa cttgtaaaat actctactta tacagaaata  1080
gtaaaataca tgggtgagtt ttctgtggac ccaaaaaggg tggtcaaaat ggcagcacga  1140
ctcatgagag tggacctgat taaaaagatt tctaatgatg catgggaaga taaactagag  1200
agaatcaagc accttaaaca gatggtaaat accatgaacc acagaaatgg aaaaaatcta  1260
ttgatgtaca atattcacaa tattactgga tatacctatc tgaacaccaa agaagctttt  1320
aacttaacaa gatttttagc tgtgtccacaat gcaacatgtt tgtttaaaga aatgtgtaaa  1380
agctgtttttg tacatgataa aatacagctc agagaattgc ttgaagattg tttacatatt  1440
gctaataggc atgattatat ccagattgca gaaaccgcag atgaatgtat caaatatata  1500
gatcttatta catttaagta a                                              1521

SEQ ID NO: 875          moltype = DNA  length = 1521
```

| FEATURE | Location/Qualifiers |
|---|---|
| source | 1..1521<br>mol_type = unassigned DNA<br>organism = African swine fever virus |

SEQUENCE: 875

```
atgttctccc tacaggatct ctgtcggaag aacctttttc ttccacttga gcccttaggc    60
aagcatgtgg ttcaacggct gggattatac tgggaaggcc atggttcact taaacgagtg   120
ggtgattgct ttatatgtgt agacaagatt tggatcctat ccatccataa ggctatacaa   180
attgcagcct cggaaggaaa tgagaacatt gtcaagcttt tcttactgtg gaaggggagt   240
ctacaatatg ccatcatagg agccttagag ggcaggcaat atgatctgat tcaaaaatat   300
tacaaccaaa ttggggactg ccatgagatt ttaccactga ttcaagatcc agaaatttac   360
gaaagatgcc atgaattaaa tgttacatgt acctttcaat gcttatttca acatgctata   420
agagataaca tgctgcccat tttccaaaaa tatggagaag atctgaatgg aaacagaaga   480
atggttcaac ttctatatga aatggcatgc cgattacaaa attatgatat catcaaatgg   540
ataggattta acctgcatgt ttataacttg gaagccattt ttagcattgc ttttgttaga   600
aaggatttaa ctttgtattc tttaggctac atgcttcttc tgggtagaat gagtactgaa   660
gatagaaact ttatttcaat cataacacgc catcttgaat acgcatcaaa aagggacttt   720
tttgactttg tactagaatc tttgaaatac ggaggtcaag tggatacagt gttgttttcag  780
gctgtaaaat acaaccatag aaaaattttg gcccatttta ttcatgaaat tccgcgtgaa   840
acagttgaaa agctgatact ccatgctgta gaatcgcggg cctccaggaa aacattcaac   900
ctgcttttat cttccataaa ctactgtgta aacccttttg tcaaaaaact actgcacacc   960
gtggtgaaac acaagtacat gcttatcata aagctttttgc tcgagcgggcc caaaaagaag 1020
ataaacctgg tagatgctgc tctattcaaa cttgtaaaat actctactta tgcagaaata  1080
gtaaaattca tgaaagagtt ttctgtggac ccagaaaggg tggtcaaaat ggcagcacga  1140
ctcatgagag tggacctgat taaaagatt tctaacgatg catgggaaaa taactagag   1200
agaatcaagc accttaaaca gatggtaaat accatgagcc cagggaaatgg aaaaaatcta 1260
ttgatgtaca atattcacaa tattactgga tatacctgct gaacaccaa agaagctttt  1320
aacttaacaa gattttatgc tgtccacaat gcaacatgtt tgtttaaaga aatgtgtaaa  1380
agctgttttg tacatgataa aatacagttc agagaattgc ttgaagattg tttacatatt  1440
gctaataggc atgattatat ccagattgca gaaaccgcag atgaatgtat caaatatata  1500
gatcttatta cacctaagta a                                            1521
```

| SEQ ID NO: 876 | moltype = DNA length = 3579 |
|---|---|
| FEATURE | Location/Qualifiers |
| source | 1..3579<br>mol_type = unassigned DNA<br>organism = African swine fever virus |

SEQUENCE: 876

```
atggaagcgt ttgaaatcag cgatttcaaa gagcatgcga agaaaaaaag catgtgggct    60
ggcgccctca acaaagtcac tatttcgggt cttatgggggg tctttaccga agatgaggac  120
cttatgcgct tacccattca cagagaccac tgccccgctt tgttaaaaat ttttgacgag   180
atcatcgtaa atgccacgga tcatgaaaga gcttgccata caaaaacaaa aaaggtaact   240
tacattaaaa tttcgtttga taaaggtgtg ttttcttgcg aaaacgatgg cccgggaatc   300
cccattgcaa agcatgagca agccagtctt atcgccaagc gcgatgtgta tgttcccgag   360
gtggcttcat gtcactttt agccggaacg aacatcaata aggccaagga ctgtatcaag   420
gggggaacca acggcgtcgg gctgaagctc gccatggtgc attcgcagtg ggccattctt   480
accaccgccg acggcgcgca aaagtatgtt caacatatca accaacgcct agatatcatt   540
gagcctccta ccattacacc ctccaggaa atgtttacac gtatcgagct catgcccgta   600
taccaggaac tagggtacgc ggagcctctg tctgaaacag agcaggcgga tctttccgcc   660
tggatttacc ttcgcgcctg ccaatgcgcg gcctacgtgg gaaaaggcac cacccatttat  720
tacaatgata agccttgccg cacgggctct gtgatggcgc tagccaaaat gtacaccctg   780
ttgagcgcgc taatagcac gatcacatacg gcgaccatta aggccgacgc aaagccctat   840
agcctgcacc ctgcaggt tgcggcggtc gtgtccccca gtttaaaaa atttgaacac   900
gtgtccgtta tcaacggggt aaattgcgta aaggagaac atgtcacctt tttgaaaaag   960
actattaatg aaatggtcgt taaaaaattt caacaaacga ttaaagataa aaaccgcaaa  1020
acaacattac gagacagctg ttcaaacatc tttatcgtta tagtgggttc cattccagga  1080
atagaatgga ccggccagcg gaaggatgaa cttagcatcg cggaaaatgt ttttaaaacg  1140
cattactcca ttccttctag ttttttaaca agtatgacaa agtctatcgt ggatattctt  1200
ctgcaatcca tttctaaaaa agataaccat aaacaggtcg acgtagacaa atatacgcgt  1260
gcccgcaatg cgggaggaaa aagggcgcag gactgcatgc tactcgcggc ggaagggat  1320
agcgcacttt ccctgctgcg cacgggacta accctgggaa agtccaaccc aagcgggccc  1380
tcctttgact tctgcggcat gatctccctg ggaggagtca tcatgaatgc ctgcaaaaag  1440
gtgacaaaca ttacaacgga ctctggagaa accattatgg tgcgcaacga acagcttacc  1500
aataataaag tgttgcaggg aatcgtgcag tgattggtgt cagtacttcaa ctgccattac  1560
aaaacacagg aagagcgagc aaagctgaga tacggctgca ttgttgcgtg cgttgatcaa  1620
gatctggatg gtgtgtggaa aatccttgga ctgctgctgg cctactttca cctgttttgg  1680
cctcagctta ttatccatgg ttttcgtaaaaa cgactgctta ccccgctgat acgtgtgtat  1740
gaaaagggta agaccatgcc cgtggaattt tactatgaac aagagtttgt tgcctgggca  1800
aaaaagcagc ccagcttagc caaccatacc gtaaaatatt acaagggatt gggcgcgaaa  1860
gacacccatg aagtaaaaag catgttcaaa cattttgaca acatggtgta cacgtttacc  1920
ctggatgact cagcaaagga gttgtttcat attttattg gcggggagtc ggagttgcga  1980
aaaagagagc tttgcaccgg cgtggtgccg ctcaccgaaa cccagacgca gtccattcat  2040
agtgtccgac gaattccttg cagcctgcat ctgcaagtag ataccaaggc ttacaagctg  2100
gatgccatcg agcggcagat tcccaacttc ttagacggga ggcgcggc cgcgcgcaaa  2160
attttagccg gggggtgaa atgcttcgcc tccaacaacc gtgaacgaaa ggttttcag   2220
ttcgggggct acgttgcaga tcacatgttt tatcaccatg cgacatgtc gttaaacaca  2280
agtattataa aagccgccca gtattcccca ggctcctccc acctctatcc ggtattcata  2340
ggcataggaa gttttggctc caggcacctg ggaggaaagg atgcaggatc cccaagatac  2400
atcagtgtgc agcttgcgtc tgaattttatt aaaacaatgt tccccgcgga ggactcatgg  2460
```

```
cttctcccct acgtctttga ggacggccag cgggcggaac cagagtacta cgtgcctgtg  2520
ttgccgcttg ctattatgga gtacggcgcc aacccatcgg agggctggaa gtacaccact  2580
tgggcccggc aactggaaga cattttggcc ttggtgaggg cctacgtcga caaagacaac  2640
ccaaaacacg agctactgca ctatgcaata aaacataaga ttactatact cccgctgcgg  2700
ccctccaatt acaatttcaa gggccatttg aagcggtttg ccaatacta ctacagctac  2760
ggcacgtacg tcatctcaga gcagcgaaat ataattacta ttacggagct tcctctgcgt  2820
gttcctacgg ttgcatacat cgaaagtata aaaaaatcga gtaaccgcat gacatttatt  2880
gaagaaatca tcgactacag tagttcagaa actattgaaa ttctggtgaa attaaagcca  2940
aatagtctta accgtatcgt ggaagaattt aaggagactg aagagcaaga ttccataga  3000
aattttctgc gcctgcgcaa ttgtttacat tcacatctaa actttgtaaa acctaaaggt  3060
ggcattatcg agtttaacac gtattatgaa attttgtatg cgtggctacc ttacaggcgt  3120
gagctttacc aaaagcgtct tatgcgtgag cacgcggtgc ttaagctgcg cattatcatg  3180
gaaactgcta ttgtacgcta catcaatgag tctgcagagc taaatctttc ccattatgag  3240
gatgaaaagg aggcaagccg cattctaagc gagcatggat ttccccgct gaaccacacg  3300
ctgatcattt cccctgagtt tgcctctata gaggaactca atcaaaaagc actgcagggc  3360
tgttataccct atatactatc tttgcaggct cgagaattgc ttatcgcagc caaaactcgt  3420
cgggtggaaa aaataaaaaa aatgcaagct cgtcttgata aggttgagca gcttttgcaa  3480
gagtctccct ttcccggcgc cagcgtatgg ctggaggaaa ttgatgcggt ggaaaaggct  3540
attataaaag gaagaaatac tcagtggaaa tttcattaa                         3579

SEQ ID NO: 877     moltype = DNA  length = 3579
FEATURE            Location/Qualifiers
source             1..3579
                   mol_type = unassigned DNA
                   organism = African swine fever virus
SEQUENCE: 877
atggaagcgt ttgaaatcag cgatttcaaa gagcatgcga agaaaaaaag catgtgggct    60
ggcgccctca acaaagtcac tatttcgggt cttatgggggg tctttaccga agatgaggac   120
cttatgcgt tacccattca cagagaccac tgtcccgctt tgttaaaaat ttttgacgag   180
ctcatcgtaa atgccacgga tcatgaaaga gcttgccata gcaaaacaaa aaaggtaacc   240
tacatcaaaa tttcgtttga taaaggcgtg ttttccttgcg aaaacgatgg cccgggaatc   300
cccattgcaa agcatgagca ggccagtctt atcgccaagc gcgatgtgta tgttcccgag   360
gtggcttcat gcttctttct agccggaacg aacatcaata aggccaagga ctgtatcaag   420
gggggaacca acggcgtcgg gctgaagctc gccatggtgc attcgcagtg ggccattctt   480
accaccgccg acggcgcgca aaagtatgtt caacaaatca accagcgcct agatatcatt   540
gagcctccta ccattacacc ctccaggaaa atgtttacac gtatcgagct catgcccgta   600
taccaggaac tagggtacgc ggagcctctg tctgaaacgg agcaagcaga tctttccgcc   660
tggatttatc ttcgcgcctg ccaatgcgcg gcctacgtgg aaaaaggcac caccatttat   720
tacaatgata agccttgccg cacgggctct gtgatggccc tggccaaaat gtacaccctg   780
ttgagcgcgc ctaatagcac gatacatacg gcgaccatta aggccgacgc aaaacccctat  840
agcctgcacc ctctgcaggt tgcggcggtc gtgtccccca gtttaaaaaa atttgaacac   900
gtgtccatta tcaacgggt aaattgtgta aaggagaaac atgttacctt tttgaaaaag   960
accattaatg aaaatggtcat taaaaaattt caacagacga ttaaagataa aaaccgcaaa  1020
acaacattac gtgacagctg ttcaaacatc tttgtcgtta tagtgggttc cattccaggc  1080
atagaatgga ccgccagcg aaggatgaa cttagcatcg cagaaaatgt ttttaaaacg  1140
cattactcca tccctctag ttttttaaca agcatgacaa ggtctatcgt ggatattctt  1200
ctgcaatcca tttctaaaaa agataaccat acgtagaaca atatacgcgt  1260
gcccgcaatg cggagggaa aagggcgcag gactgcatgc tactcgcggc ggaaggggat  1320
agcgcacttt ccctgttgcg cacgggactg accctgggaa agtccaaccc aagcggggcc  1380
tccttttgact tctgcggcat gatctcctg ggagggtgta tcatgaatgc ctgcaaaag  1440
gtgacaacta ttacaacgga ctctggaaaa accatcatgg tgcgcaacga acagcttaca  1500
aataataaag tgttcaggg aattgtgcag gtatgggtc tagacttcaa ctgccattac  1560
aaaacgcagg aagagcgagc aaagctgaga tacggctgca ttgttgcgtg cgttgatcaa  1620
gatctgatgt ggtgtggaaa aatccttgga ctgctgctgg cctactttca cctgtttgg  1680
cctcagctta ttatccatgg tttcgtaaaa cgactgctta ccccgctgat acgtgtgtac  1740
gaaaagggca agactatgcc cgtagaattt tactatgaac aggagttta tgcctgggca  1800
aaaaagcaga ccagccttagt caatcatact gtaaatatt caagggatt ggcggcgcat  1860
gacacccatg aagtaaaaag catgttcaaa cattttgaca acatggtgta cacgtttacc  1920
ctggatgact cggcaaagga gttgtttcat attatttg gcggggagtc ggagttgcga  1980
aaaagagagc tttgcaccgg cgtggtgccg ctcactgaaa ccccagacga gtccattcat  2040
agtgtccgac gaattccttg cagcctgcat ctgcaggtag ataccaaggc ttacaagctg  2100
gatgccatcg agcggcagat tcccaactc ttagacggaa tgacgcgggc gcggcgcaaa  2160
atttagccg gggggggtgaa atgcttcgct tccaacaacc gtgaacgaaa ggttttcag   2220
ttcgggggct acgttgcgga tcacatgttt tatcaccatg gcgacatgtc gttaaacaca  2280
agtattataa aagccgccca gtattaccg ggctcctccc acctctatcc agtattcata  2340
ggcataggaa gcttcggctc caggcacctg ggaggaaagg atgcaggatc cccaagatac  2400
atcagtgtgc agcttgcgtc tgaatttatt aaaacaatgt tccccgcgga ggactcatgg  2460
cttctcccct acgtctttga ggacggccag cgggcggaac cagagtacta cgtgcctgta  2520
ttgccgcttg ctattatgga gtacggcgcc aacccatcgg agggctggaa gtacaccact  2580
tgggcccggc aactggaaga cattttggcc ttggtgaggg cctacgtcga caaagacaac  2640
ccaaaacacg agctactgca ctatgcaata aaacataaga ttactatact cccgctgcgg  2700
ccctccaatt acaatttcaa gggccatttg aagcggtttg ccaatacta ctacagctac  2760
ggcacgtacg acatctcaga gcagcgaaat ataattacta ttacggagct tcctctgcgt  2820
gttcctacgg ttgcatatat cgaaagtata aaaaaatcga gtaaccgcat gacatttatt  2880
gaagaaatca tcgactacag tagttcagaa accattgaaa ttctggtgaa actaaagcca  2940
aatagtctca accgtatcgt ggaagaattt aaggagactg aagagcaaga ttccataga   3000
aattttctgc gcctgcgcaa ttgtttacat tcgcatctaa actttgtaaa acctaaaggt  3060
ggtattatcg agtttaactc atattatgaa attttatatg cgtggctacc ttacaggcgt  3120
gagctttacc aaaagcgtct tatgcgtgag cacgcggtgc ttaagctgcg cattatcatg  3180
```

```
gaaactgcta ttgtacgcta catcaatgag tctgcagagc taaatctttc ccattatgag  3240
gatgaaaagg aggcaagccg cattctaagc gagcatggat ttcccccgct gaaccacacg  3300
ctgatcattt cccctgagtt tgcctctata gaggaactca atcaaaaagc gctgcagggc  3360
tgttatacct atatactatc tttgcaggct cgagaattgc ttatcgcagc caaaactcgt  3420
cgggtggaaa aaataaaaaa aatgcaagct cgtcttgata aggttgagca gcttttgcag  3480
gagtctccct ttcccggcgc cagcgtatgg ctggaggaaa ttgatgcggt ggaaaaggct  3540
attataaaag gaagaaatac tcagtggaaa tttcattaa                         3579

SEQ ID NO: 878          moltype = DNA   length = 1596
FEATURE                 Location/Qualifiers
source                  1..1596
                        mol_type = unassigned DNA
                        organism = African swine fever virus
SEQUENCE: 878
atgttctctc tccagaactt atgtcgaaaa acattaccta accgtaaact tcctgaattt   60
tttgacgaat atatattaca actgctggga ttatactggg aaaaccatgg aactattcaa  120
cgagcaggaa acaactgtgt gcttatacag caacataccc tcattcccgt aaatgaagcc  180
ctgagaacag cagcatctga agaaaattat gagatcgtac gcctttattt agcgtgggag  240
gggaaccttt actatgctat tagggggct ctagagggca accgccacga cttaattcgt  300
aaatatgatg accaaatcaa ggaccatcat gaaattctgc cattcattga cgatccagtc  360
atatttcaca aatgccatat catgcggcaa tgcttttttg attgtatttt atatcaagct  420
gtaaaatata gtaagtttcg cgttcttctt tactttaaaa atagattaga ggatgatttg  480
cccttcactc atttacttat tgaaaaggca tgtaaagatc ataattatga agttattaaa  540
tggatatatg aaaacctaca tatctacaat atgatagata cctttgaatg tgctattgcc  600
cataaggatc tacatctata ttgtttgggg tatagattta tatataacag aatcgtaccc  660
gataagtatc atcatttaga tattcgcatg ctttcaagcc tacaactcct acataaggtg  720
gcagccaaag gatacttaga ttttatccta gaaaccttaa agtatgatca taatataagat  780
aatataaata ttattctaac acaagctgca acctataacc atagaaaaat ttaatctat   840
ttcattcctc aatcaaccca cgcacagata gaacaatgtt tactagtggc gataaaagca  900
aaatcttcca ggaaaacctt gaacttacta ctgtctcacc taaaccttc catcaacctc   960
atcaaaaaaa taagccatta tgttgccact tacaattcaa caaatataat aggcattctg  1020
agtatgcggc ggaaaaagaa gatatattta gatatcatat tgacaaaatt tgtaaaaaaa  1080
gctatttta ataagtttgt cgttcgatgt atggatacat ttctataaa cccggaaaga   1140
atccttaaaa tagccgcgcg aataaatagg atgatgttag tgaaaaaaat atctgaacat  1200
gtttggaaaa atcatgcggt tagacttaaa taccttaaac atgcggtaca cacgatgaag  1260
cataaagatg ggaaaaatag actcatgaac tttatctatg atcgctgtta ttaccatatg  1320
caaggggaag aaatctttag cctcgcaaga ttttatgcaa tccatcatgc accaaagttg  1380
tttgacgttt tttatgattg ttgtatccta gatcgatac gattcaaaag ccttctttta   1440
gattgttcac atatcatagg taaaaacgct catgatgcca caatcaa catcgtgaac    1500
aagtatatcg gcaacctgtt tgttatggga gttcttagca aaaagaaat cttacaggac  1560
tatccatcca tttattctaa acaatacatg ccttag                            1596

SEQ ID NO: 879          moltype = DNA   length = 1596
FEATURE                 Location/Qualifiers
source                  1..1596
                        mol_type = unassigned DNA
                        organism = African swine fever virus
SEQUENCE: 879
atgttctctc tccagaactt atgtcgaaaa acattacctg actgtaaact tcctgaattt   60
tttgacgatt atatattaca actgctggga ttatactggg aaaaccatgg aactattcaa  120
cgggcaggaa acaactgtgt gcttatacaa caacataccc tcattcccgt aaatgaagcc  180
ctaagaatag cagcatctga agaaaattat gagatcgtgg gccttttatt agcgtgggag  240
gggaaccttt actatgctat tagggggct ctagagggta accgctacaa cttaattcgt  300
aaatatgatg atcaaatcaa ggaccatcat gacattctgc cattcattga tgatccaatc  360
atatttcaca aatgccatat catgcggcga tgcttttttg attgtatttt atatcaagct  420
gtaaaatata gtaagtttcg tgttcttctt tatttaaat atacattaga ggatgatttg  480
cccctcgttc atttacttat tgaaaaggca tgtgaagatc ataattatga agttattaaa  540
tggatatatg aaaacctaca tgtctgccat ataatagata cctttgactg tgctattgcc  600
cataaagatc tacgtttata ttgtttgggg tatacattta tacaacag gattgtaccc  660
tataagtatc atcatttaga tattctcata ctttcaagcc tacaactcct acataaggtg  720
gcggccaaag gatacttaga ttttatccta gaaaccttaa agtatgatca taatatagat  780
aatttagatg ttattctaac acaagctgca acatataacc atagaaaaat ttaacctat   840
tttattcctc aatcaaccta cgcacaaata gaacaatgtt tgttcgtggc gataaaaaca  900
aaatcttcca agaaaacctt gaacttacta ctgtctcacc taaaccttc catcaacctc   960
atccaaaaaa tcagccaata tgttgccact ttcaattcaa caaatataat aggcattctg  1020
agtatgaagc ggaaaaagaa gatatatttg gatatcatat tgacaaaatt tgtaaaaaat  1080
gctatttta ataatttgt cgttcgatgt atggagagat tttctataaa cccggaaaga   1140
atcgtcaaaa tggctgcgcg tataaataag atgatgttag tgaaaaaat atctgaacat  1200
gtttggaaaa atcatgcggc tagacttaaa caccttaaac atgcggtaca cacgatgaag  1260
cataaagatg ggaaaaatag actcatgaac tttatctatg aacactgcta ttaccatatg  1320
caaggggaag aaattttag cctcgcaaga ttttatgcaa tccatcatgc accaaagttg  1380
ttcgacgttt tttataattg ttgtatccta gatcgatac gattcaaaag ccttctttta   1440
gattgttcac atatcatagg taaaaacgct catgatgcta ctaatatcaa catcgtgaac  1500
aagtatattg gcaacctgtt tgtctatggga gttcttagca aaaagaaat cttacaggac  1560
tatccatcca tctattctaa acattatatg ccttag                            1596

SEQ ID NO: 880          moltype = DNA   length = 843
FEATURE                 Location/Qualifiers
source                  1..843
```

```
                              mol_type = unassigned DNA
                              organism = African swine fever virus
SEQUENCE: 880
atgtcctctt ctcttcagga actttgtcga aaaaagctgc ctgactgcat acttccagag    60
ttttttgacg actatgtatt gcaactgtta ggactgcact ggcaagatca tggttccctt   120
cagcgtatcg agaagaacca gatacttgtt caacaggaac ccatccatat caatgaagca   180
ctcaaagtag cagcatcgga agggaactat gaaatcgtag agctgttgtt gtcatgggag   240
gcagatcccc gctacgccgt cgtaggagcc ctagaaagca aatactatga cctggtttac   300
aaatactatg accaagttaa agactgccat gatatcttgc cgctgattca aaatccggaa   360
acattcgaaa gatgtcatga gttaaacagc acctgttcac tgaaatgctt attcaagcat   420
gctgtgataa atgacatgct gccgattctt caaaaatata cagactatct ggataggtgg   480
gagtattgca gccagatgct gttcgaactg gcatgtagta aaaaaaaata tgagatggtt   540
gtgtggatag agggagttct aggcgtcggc aaagttacat ctcttttcac cattgcgatt   600
agcaacagag acctacagct gtattctctg ggctactcaa ttatccttga gaatttgtac   660
tcctgtggac aggaccccaa gttttttacta aatcatttcc tgcgagacgt ttcaataaaa   720
gggcttctac cctttgtaat caaaaccata gaatatggtg aagcaagga gatagccata    780
actctggcta aaaaatatca gcataaacat atttttgaaat acttcgaaac ctgggaaagc   840
tag                                                                  843

SEQ ID NO: 881        moltype = DNA   length = 843
FEATURE               Location/Qualifiers
source                1..843
                      mol_type = unassigned DNA
                      organism = African swine fever virus
SEQUENCE: 881
atgtcctctt cccttcagga actttgtcga aaaaagctgc ctgactgcat acttccagag    60
ttttttgacg actatgtatt gcaactgtta ggactgcact ggcaagatca tggttccctt   120
cagcgtatcg agaagaacca gatacttgtt caacaggaac ccatccatat caatgaagca   180
ctcaaagtag cagcatcgga agggaactat gaaatcgtag agctgttgtt gtcatgggag   240
gcagatcccc gctacgccgt cgtaggagct ctagaaagca aatactatga cctggtttac   300
aaatactatg acctggttaa agactgccat gatatcttgc cgctgattca aaatccggaa   360
acatttgaaa aatgtcatga gttaaacaac ccctgttctc ttaaatgctt attcaagcat   420
gctgtgatac atgacatgct gccgattctt caaaaatata catactttct ggatgggtgg   480
gagtattgca accagatgct gttcgaactg gcatgtagta aaaaaaaata tgagatggtt   540
gtgtggatag agggagttct aggcatcggc aaagttacat ctcttttcac tattgcgatt   600
agcaacagag acctgcacct gtattccctg ggccacttaa tcattcttga gagaatgcag   660
tcctgtggac aagaccccac gttttttacta aatcatttcc tgcgagacgt ttcaataaaa   720
gggcttctcc cttttgtact gaaaaccata gaatatggtg aagcaagga gatagccata    780
actctggcta aaaaatatca gcataaacat atttttgaaat acttcgaaac cgggaaatgc   840
taa                                                                  843

SEQ ID NO: 882        moltype = DNA   length = 1257
FEATURE               Location/Qualifiers
source                1..1257
                      mol_type = unassigned DNA
                      organism = African swine fever virus
SEQUENCE: 882
atgtccaatt actattatta ctatggcggg gggagatatg attggttaaa aacagtagaa    60
cccactaatt ttttaaaaat cgggttgcct taccaggcac acccattaca tcttcaacat   120
caggcaacta ctcccccatc tatcttagaa aaatttaaac gagcagacat tcttcttaat   180
gaggtgaacg ccgaaatgga cccactcatg ttacaaccga aaccgaaaa aaaactattc   240
cagatattga gtagtattga tatgttcaaa ggtctgcgaa aaaaagtaga attcacgtac   300
aatgctcaaa ttgttacgaa tgcttggctt aaaatgtatg agctgctaaa taccatgaat   360
tttaataata catctcaggc attttgcaat tgtgagcttc caggagggtt tataagtgca   420
attaaccatt ttaattatac aatgatgcat taccctactt ttaactgagt agcttcctcc   480
ctttacccca gttcggaaac agatgccctg gaagatcact atggtcttta tcagtgcaat   540
ccggataact ggttgatgca atctccttta ctgaaaaaaa atatagatta taataacggg   600
gacgtaacca tcgctagcaa tgtaaaaaac ctagcgctta gagccacaca aaggctgacg   660
cccatccatc tatatacggc tgatggggggt attaatgtag gacatgacta caataaacag   720
gaagaattaa atcttaagct tcactttggt caagcccttg cgggtttgtt gagtcttagc   780
aaaggcggaa acatgatact caaacactat accttaaatc atgcatttac tctttctttta   840
atatgtgtat tttctcactt ttttgaggaa ctatacatta ccaaacctac ctcctctcgg   900
cccacaaact ctgaaaccta tattgtgggt aaaaacagat tacgcttatt taccccccaag   960
gaagaacaag tccttctaaa acggctagaa ttttttaatg atacgccccct cgtagaccta  1020
agtctttacc aaaaatttact tgaaagcgtt tactttgccg tagaaacaat acatctaaaa  1080
caacaaatag aatttctaaa cttcggaatg aaatgttatc gacatttttta taacaagatt  1140
aaaactactta acgattattt agctccgaaa aaaaagattt ttcaggatag gtggcgtgtg  1200
cttaataagc tttatgttct tgaaaaaaag cataaactta gctttgtgc ctcctag      1257

SEQ ID NO: 883        moltype = DNA   length = 1275
FEATURE               Location/Qualifiers
source                1..1275
                      mol_type = unassigned DNA
                      organism = African swine fever virus
SEQUENCE: 883
atgtccaatt actattatta ctatggcggg gggagatatg attggttaaa aacagtagaa    60
cccactaatt ttttaaaaat cgggttgcct taccaggcac acccattaca cctccaacat   120
caggcaacta ctactccccc atctatccta gaaaaattta acgagcaga tattcttctt   180
aatgaggtga aggccgaaat ggacccactc atgttacaac cagaaaccga aaaaaaatta   240
```

```
taccagatat taggtagtat tgatatgttc aaaggtctgc gaaaaaaagt agaatttacg    300
tacaatgctc aaattgttac gaatgcttgg cttaaaatgt atgagctgct aaataccatg    360
aattttaata atacatctca ggcattttgc aattgtgagc ttccaggagg gtttataagt    420
gcaattaatc attttaatta tacaatgatg cattacccta cttttaactg ggtagcctcc    480
tccctttacc ccagttcgga aacagatgcc ctggaagacc actatggtct ttatcagtgc    540
aatccggata actggctgat gcaatctcct ttactaaaaa aaaatgtgga ttataatgac    600
ggggacgtaa ccattgctag caatgtaaaa aatctagcgc ttagagccac acagaggctg    660
acgcccatcc atctatatac cgctgacgga ggtattaatg tagggcatga ctacaataaa    720
caggaagaat taaatcttaa gcttcacttt ggtcaagctc ttacaggttt gttgagcctt    780
agcaaaggcg gaaacatgat actcaaacac tataccttaa atcatgcatt tactcttttt    840
ttaatatgcg tatttttctca cttttttgag gaactataca ttaccaaacc tacctcctct    900
cggcccacga actctgaaac ctatattgtg ggtaaaaaca ggctacgcct atttactccc    960
aaggaagaac aaatactttt gaaacgacta gaattttta atgatacgcc cctcgtagac   1020
ctaagtcttt accaaaattt acttgaaagc atttactttg ccgtagaaac aatacatcta   1080
aaacagcaaa tagagtttct aaacttcgga atgaaatgtt accgacattt ttataacaag   1140
attaaactac ttaacgaata tttagctccg aaaaaaaaga tttttcagga taggtggcgt   1200
gtgcttaata agctttatgt tcttgaaaaa aagcataaac ttaagctttg tgcccctcag   1260
ggatctgttg cctaa                                                    1275

SEQ ID NO: 884          moltype = DNA  length = 1428
FEATURE                 Location/Qualifiers
source                  1..1428
                        mol_type = unassigned DNA
                        organism = African swine fever virus
SEQUENCE: 884
atgacgtctt tactaaagac tgattttaat gtttctaagt accggctcat tgctcaaaaa     60
cgtgaggcaa atgccgtgga gattgaggcg gctttggagg tggtccgcga atttatcata    120
aagaaaaagc ttattttgta cgggggggatt gccattgatt atgccctgca tcttaaaggc    180
agctcaattt atcccgaggg agaaagaccc gactttgata tgttttcccc caaccacgtt    240
gaggacgcct acgaacttgc tgacattttt tatgaaaagg gcttcaagca ggtgggcacg    300
gtgcgcgcca tccatgtgca gaccatgcgg gtgcgcacgg acttttgtgt ggttgctgat    360
cttttcatata tgcccccccaa tatctttaac accataccca cattaacgta taaaaacctt    420
aaaatcattc accccgatta ccagcgggcc gggctacacc tagcattttg ctttcctttt    480
gataacccac caagggaaga tgttttttagc aggtttaaaa aggatttgca gcggtataac    540
ctcatagaaa aatattaccc cattcccgtt gttcctgtga agtcgacata cgaaagtaaa    600
acgttttcaa ttcccttttaa acaagtggcc atacacggct ttgcggcata cgccctcctg    660
taccagactc taaatgagct gagaattacc tgcaaagtcc cggagtggaa aacagaattt    720
ccacaaccat cttactccta ccataagaat gataaaaaca taacacttac cgtggatatg    780
cccaaagcct atcccgcgct ggtgttagcg acgtacaacc cggaagaagt cataaaagaa    840
atgggccttc acctgactga gatatgtgag ccctacatgg actatagtcc ccctatattc    900
aagacgaacg acatacattt ttttagcact atgtttaaag agctagcgat atctatcatt    960
caagataacc ttattgtggt gtctccccag tacttactgc tttattttct atacggcgct   1020
tttgcaacgc ctgccgataa gtcgctattt ttatttttact acaatgcgac gctttggatt   1080
ctcgaaaagg cagactccct gctaaacatc atacaaaaac aaacaagtcc ggaagagttt   1140
acgaggtttg ctaataccag tccatttgta ttaacaacgc gcgtactaag ttgttcacag   1200
gaacgttgca ccttttagccc ggcatataga atctccctgg ccaacgacgt acaacagtcg   1260
cagttacccc tcccaaaaac ccattttttta agcaattctc tcccagacgt ttcaacactc   1320
ccttataatt attatccggg caagggaaaa gataggccca caaatttcag ctatgaaaaa   1380
aatttattgt ttaacatagg aggaaaatgt actccgtctg cgatgtag                1428

SEQ ID NO: 885          moltype = DNA  length = 1428
FEATURE                 Location/Qualifiers
source                  1..1428
                        mol_type = unassigned DNA
                        organism = African swine fever virus
SEQUENCE: 885
atgtcgtctt tactaaagac tgattttaat gtttctaagt atcggctcat tgctcaaaag     60
cgtgaggcaa atgccgtgga gattgaggcg gctttggagg tggtccgcga atttatcata    120
aagaaaaagc ttattttgta cgggggggatt gccattgatt atgccctgca tcttaaaggc    180
agctcgattt atcccgaggg agaaagaccc gactttgata tgttttcccc caaccacgtt    240
gaggatgcct acgaacttgc tgacattttt tatgaaaagg gcttcaagca ggtgggcacg    300
gtgcgcgcca tccatgtgca gaccatgcgg gtgcgcacgg acttttgtgt ggttgctgac    360
cttttcatata tgcccccccaa tatctttaac accataccca cattaacgta taaaaacctt    420
aaaatcattc accccgatta ccagcgggcc gggctacacc tagcattttg ctttcctttt    480
gataacccac caagggaaga tgttttttagc aggtttaaaa aggatttgca gcggtataac    540
ctcatagaaa aatattaccc cattcccgtt gttcctgtga agtcgatata cgaaagtaaa    600
acgttttcaa ttcccttttaa acaagtggcc atacacggct ttgcggcata cgccctcctg    660
taccagactt taaatgaact gagaattacc tgcaaggtcc cggagtggaa aacagaattt    720
ccacaaccat cttactccta ccataagaat gataaaaaca taacacttac cgtggatatg    780
cccaaagcct atcccgcgct ggtgttagcc acgtacaacc cggaagaagt cataaaagaa    840
atgggccttc acctgactga gatatgtgag ccctacatgg actatagtcc ccctatattc    900
aagacgaacg acatacattt ttttagcacc atgtttaaag agctagcgat atctatcatt    960
caggataacc ttattgtggt gtctccccag tacttactgc tttattttct atacggcgct   1020
tttgcaacgc ctgccgataa gtcgctattt ttatttttact acaatgcgac gctttggatt   1080
ctcgaaaagg cagactccct gctaaacatc atacaaaaac aaacaagtcc ggaagagttt   1140
acgaggtttg ctaataccag tccatttgta ttaacaacgc gcgtactaag ttgttcacag   1200
gaacgttgca ccttttagccc ggcatataga atctccctgg ctaacgacgt acaacagtcg   1260
cagttacccc tcccaaaaac ccattttttta agcaattctc tcccgacgt ttcaacactc   1320
ccttataatt attatccggg caagggaaaa gataggccca caaatttcag ctatgaaaaa   1380
```

```
aatttattgt taacatagg aggaaaatgt actccgtctg cgatgtag        1428

SEQ ID NO: 886          moltype = DNA   length = 1593
FEATURE                 Location/Qualifiers
source                  1..1593
                        mol_type = unassigned DNA
                        organism = African swine fever virus
SEQUENCE: 886
atggcagaat ttaatattga tgagcttctc aaaaacgtat tggaggatcc ctctactgaa    60
atatccgaag aaacgcttaa acagctttac caaggacga acccttacaa acagttcaaa    120
aatgatagca gggtggcctt ttgctctttt acaaatttgc gggagcagta tattcgacgt   180
cttataatga ctagctttat tggatatgtc ttcaaagctc tgcaggaatg gatgccttcc   240
tattcaaaac ctacccacac gaccaaaact cttctcagtg agctaataac gttagttgat   300
actttgaaac aggaaactaa tgatgttccc tctgaatcgg tagtaaatac aatttttatct  360
atagcagata gctgcaaaac ccagacgcag aaaagcaagg aagctaaaac aacgatcgat   420
agcttttac gagaacattt tgtgtttgat cctaatcttc atgctcaaag tgcgtatact    480
tgtgcagata ccaatgtaga cacttgtgca agcatgtgtg cagataccaa tgtagacacc   540
tgtgcaagca tgtgtgcaga taccaatgta gatacctgtg caagcacttg tacaagcaca   600
gaatacaccg atttagcaga tcctgagcgc atcccttac acatcatgca aaaaacatta   660
aatgtgccta atgagcttca ggccgatatt gatgcaatca cccaaacccc acagggctat   720
agggcagcag cccacatatt acaaaatata gaacttcacc aaagcattaa acatatgctt   780
gaaaatccga gggcgtttaa acccattctc tttaacacaa aaattactag atatctttcg   840
cagcatattc caccctcagga tacttttat aagtggaatt attacattga ggataattac   900
gaagagttgc gggccgctac ggaaagcatc tacccagaaa acccgacct agagtttgcc   960
ttcattattt atgatgtggt ggatagcagc aaccaacaaa aggttgatga atttattat   1020
aaatataaag accagatttt ctcagaggtt tcatccattc aattaggcaa ctggacactc  1080
ctgggaagct ttaaggccaa cagagagcgc tacaattatt ttaatcaaaa taatgaaata  1140
ataaaacgga ttttggaccg tcatgaggaa gacctaaaga taggaaaaga gattttacga  1200
aatactattt accacaaaaa agcaaaaaat atacaagaaa ctggcccgga tgctccgggg  1260
ctctccatct ataattcaac cttttcacacg gatagcggta ttaagggact gcttccttt   1320
aaggagctaa aaaacctaga aaagcatctt ggaaatatca aaaactcg agagtatgat   1380
tttatagacg actgcgaaga aaaaattaag caactgctta gtaaagaaaa tttaacccc   1440
gatgaagaaa gcgagctgat aaaaacaaaa aaacagttag ataatgcgct tgaaatgctc  1500
aatgtgcctg atgatacgat acgggtagat atgtgggtca acaataataa taaactcgaa  1560
aaagaaattt tatatacaaa agcagaattg taa                              1593

SEQ ID NO: 887          moltype = DNA   length = 1809
FEATURE                 Location/Qualifiers
source                  1..1809
                        mol_type = unassigned DNA
                        organism = African swine fever virus
SEQUENCE: 887
atggcagaat ttaatattga tgagcttctc aaaaacgtat tggaggatcc ctctactgaa    60
atatccgaag aaacgcttaa acagctttat caaaggacga accccttacaa acagttcaaa   120
aatgatagca gggtggcctt ttgctctttt acaaatttgc gggagcagta tattcgacgt   180
cttataatga ctagctttat tggatatgtc ttcaaagctc tgcaggaatg gatgccttcc   240
tattcaaaac ctacccacac gaccaaaact cttctcagtg agctaataac gttagttgat   300
actttgaaac aggaaactaa tgatgttccc tctgaatcgg tagtaaatac aatttttatct  360
atagcggata gctgcaaaac ccagacgcag aaaagcaagg aagctaaaac aacgatcgat   420
agcttttac gagaacattt tgtgtttgat cctaatcttc atgctcaaag tgcgtatact    480
tgtgcaagca cttgtgcaga taccaatgta gacacctgtg caagcacttg tgcaagcact   540
tgtgcaagca cttgtgcaag cacaggtgca agcacttgtg cagataccaa tgtagacacc   600
tgtgcaagca cttgtgcaga taccaatgta gacacctgtg caagcacttg tgcagatacc   660
aatgtagaca cctgtgcaag cacttgtgca gataccaatg tagacacctg tgcaagcact   720
tgtgcagata ccaatgtaaa cacttgtgca agcatgtgtg cagataccaa tgtagacacc   780
tgtgcaagca cctgtgcaaa cacctgtgca agcacagaat acaccgatt agcagatcct   840
gagcgcatcc cttacacat catgcaaaaa acattaaatg tgcctaatga gcttcaggcc   900
gatattgatg caattaccca aacccacag gctataggg cagcagccca catattcaa     960
aatatagaac ttcatcaaag cattaaacat atgcttgaaa atccgagggc gtttaaaccc  1020
attctcttta acacaaaaat tactagatat ctttcgcagc atattccacc tcaggatact  1080
ttttataagt ggaattatta cattgaggat aattacgaag agttgcgggc cgctacggaa  1140
agcatctacc cagaaaagcc cgacctgag tttgccttca ttatttatga tgtggtggat   1200
agcagcaacc aacaaaaggt tgatgaattt tattataaat ataaagacca gattttctca  1260
gaggtttcat ccattcaatt aggcaactgg cactcctgg gaagctttaa ggccaacaga   1320
gagcgctaca attattttaa tcaaaataat gaataataa acgatttt ggaccgtcat     1380
gaggaagacc taaagatagg aaaagagatt ctacgaaata ccatttacca caaaaaagca  1440
aaaaatatac aagaaaccgg cccggatgct ccggggctct ccatctataa ttcaaccttt  1500
cacacggata gcgggattaa gggactgctt cctttaagg agctaaaaaa cctagaaaaa   1560
gcatctggaa atatcaaaa agctcgagag tatgatttta tagacgactg cgaagaaaaa   1620
attaagcaac tgcttagtaa agaaaattta ccccgatg aagaaagcga gctgataaaa    1680
acaaaaaaac agttaaataa tgcgcttgaa atgctcaatg tgcctgatga tacgatacgg   1740
gtagatatgt gggtcaacaa taataataaa ctcgaaaag aaattttata tacaaagca    1800
gaattgtaa                                                          1809

SEQ ID NO: 888          moltype = DNA   length = 1593
FEATURE                 Location/Qualifiers
source                  1..1593
                        mol_type = unassigned DNA
                        organism = African swine fever virus
```

```
SEQUENCE: 888
atgccctcta atatgaaaca gttttgcaag atttctgtat ggctacagca gcacgatcca      60
gatttattag aaattatcaa caacttatgt atgcttggca atttatccgc ggcaaagtac     120
aaacacggag ttaccttcat ttaccccaaa caggcaaaga tccgcgatga aataaaaaaa     180
catgcctact ccaatgaccc ttcacaagcc ataaagacct tagaatcact catccttcca     240
ttttacattc ccactccagc ggagttcacc ggggaaatcg gctcctacac cggagtgaaa     300
ttagaggttg aaaaaacgga ggcgaataaa gttattttaa aaaatggaga agcggtccta     360
gtaccggcgg ccgattttaa gccctttcct gatcgccgac tagcggtctg gatcatggag     420
tcaggctcta tgcccctgga gggtccccc tataagcgga aaaaggaggg tgggggaat      480
gacccgccgg ttcctaagca tatctcgccg tatactccgc gcacgcgtat tgccattgag     540
gtggaaaagg cctttgatga ctgtatgcgt caaaactggt gtagtgtcaa taatccctat     600
cttgccaagt cggtctcctt gctgtctttc ttgtcgctca accatcccac cgagtttatt     660
aaggtactgc cgcttataga ctttgacccc ttggtgacct tttatctact tcttgagccc     720
tataaaacgc atggggatga ctttttaatt ccggaaacca tttattcgg ccctaccgga     780
tggaatggta cagatctgta tcaaagtgcc atgctggagt ttaaaaagtt tttttaccag     840
attactcgcc aaacctttat ggacatagcc gattcggcta ctaaggaggt agatgttccc     900
atatgttact cggatcccga aaccgtacat tcctatgcca atcacgtgcg tactgaaatt     960
ttgcatcaca atgccgtcaa taaggttaca cacctaacc tcgtcgtgca ggcctataat   1020
gagctcgagc aaaccaatac catacgacat tacggcccta ttttcccgga aagtaccatc     1080
aacgcactgc gttttggaa aaagctgtgg caggatgaac agcgatttgt tatccacggc     1140
ctgcaccgca cgttgatgga tcaacccacc tatgaaacct ctgagtttgc agagatcgtt     1200
agaaatttac ggttttcgcg tcccggcaat aactatatta acgagcttaa tattacaagt   1260
cccgctatgt acggcgacaa gcataccacc ggagatattg cgcccaatga tagatttgcc   1320
atgttggtgg cctttatcaa cagtactgac ttttatataca ccgcgattcc cgaggaaaag   1380
gtaggggga atgaaaccca aaccagtagc cttacgacc tagtccaac acggctacac   1440
tctttttaa atcataatct aagcaaactt aaaatcttaa accgcgcgca gcaaacggtt   1500
agaaatattc tttcaatga ttgtcttaat caactgaaac attatgttaa acacacggga   1560
aaaaatgaaa tactaaagtt acttcaagaa taa                                 1593

SEQ ID NO: 889        moltype = DNA length = 1593
FEATURE               Location/Qualifiers
source                1..1593
                      mol_type = unassigned DNA
                      organism = African swine fever virus
SEQUENCE: 889
atgccctcta atatgaaaca gttttgcaag atttctgtat ggctgcagca gcacgatcca      60
gatttattag aaattatcaa caacttatgt atgcttggca atttatccgc ggcaaagtac     120
aaacacggag ttaccttcat ttatcccaaa caggcaaaga tccgcgatga aataaaaaaa     180
catgcctact ccaatgaccc ctcacaggcc ataaagacct tagaatcact catccttcca     240
ttttacattc ccactccagc ggagttcacc ggggaaatcg gctcctacac cggagtgaaa     300
ttagaggtcg aaaaaacgga ggcgaataaa gttattttga aaaatggaga agcagtcctg     360
gttccggcgg ccgattttaa gccctttcct gatcgccgac tagcggtctg gatcatggag     420
tcaggctcta tgcccctgga gggtccccc tataagcgga aaaaggaggg tgggggaat      480
gacccgccgg ttcctaagca tatctcgccg tatactccgc gcacgcgtat tgccattgag     540
gtggaaaagg cctttgatga ctgtatgcgt caaaactggt gtagtgtcaa taatccctat     600
cttgccaaat cagtttcctt gctgtctttc ttgtcgctca accatcccac cgagtttatt     660
aaggtactgc cgcttataga ctttgacccc ttggtgacct tttatctact tcttgagccc     720
tataaaacgc atggggatga ctttttaatt ccggaaacca ttttattcgg tcctaccgga     780
tggaatggta cagatctgta tcaaagtgct atgctggaat taaaaagtt tttttaccag     840
attactcgcc aaacctttat ggacatagcc gattcggcta ctaaggaggt ggatgttcct     900
atatgttatt cggatcccga aaccgtacat tcctatacca atcacgtgcg tactgaaatt     960
ttgcatcaca atgccgtcaa taaggttaca cacctaacc tagtcgtgca ggcctataat   1020
gagctcgagc aaaccaatac catacgacat tacggcccta ttttcccgga aagtaccatc   1080
aacgcactgc gttctggaa aaagctgtgg caggatgaac agcgatttgt tattcacggc   1140
ctgcaccgca cgttgatgga tcaacccacc tatgaaacct ctgagtttgc agagatcgtt   1200
agaaatttac ggttttcgcg tcccggcaat aactatata acgagcttaa tattacaagt   1260
cctgctatgt acggcgataa gcataccacc ggagatattg cgcccaatga tagatttgcc   1320
atgttggtgg cctttatcaa cagtactgac ttttatataca ccgccattcc cgaagaaaag   1380
gtaggggga atgaaaccca aaccagtagc cttacgacc tagttccaac acggctacac   1440
tctttttaa atcataatct aagcaaactt aaaatcttaa accgcgcgca gcaaacggtt   1500
agaaacattc tttcaatga ttgtcttaat caactgaaac attatgttaa acacacggga   1560
aaaaatgaaa tactaaagtt acttcaagaa taa                                 1593

SEQ ID NO: 890        moltype = DNA length = 1020
FEATURE               Location/Qualifiers
source                1..1020
                      mol_type = unassigned DNA
                      organism = African swine fever virus
SEQUENCE: 890
atgatcgacc aaaaaatttt tgagacaacg ttgaatattg atgatcctac caatttttgt      60
acaaatgtgg aggctcatct tttgaaggag cttgaaaaca tttatgtggg taagtgtttc     120
aaaaacagtt ttattcttaa tattactggc gttatacaac gctccccttg ttttattatg     180
cgtacgaata atagcggaag aggatatatg catgtaaagt tttctgctgt tgtttcttac     240
ttaaatgcct ttgatttaat agcggccgtt aaaattatta aaatgacag taatattatt     300
ctcggcgaaa gccattgac tgaacccgta actattgtca tacctcgtc cgaatccgcaa     360
aataatgttg cagaagtggg gcaaattgtg ccggtacagc ttgctaacag cagcgtgtac     420
tatataccctg gcagacaaca ggccagtgcc acgggagta ttttcattcc taagcacact    480
ttttcagtct atcacgtgca agaggagctt acacaggaac aggcctaaaa cctaacaaaa     540
cttgttaaca ttatagaaat gcttcttgaa agtcgttcta aaaaagactt caagcagata     600
```

```
tgcttttttg aaaaacttta ctatacctac tctataagct cggatgagat cttagatcta    660
aaaatatgga aagggcccaa ggggaaggag atgtcgcggc ttaagccttg caatgtgctt    720
tcatttcttt atgacgccct aaaaaacaag aacagcagcc tagggttttg ggcaagaccc    780
ccaaatctcc ttaagtcctc gccattggcg tatcaacaag atcaaaattc ttttaacgcc    840
actgaattac ctattatatg ttctgctgaa gtaatgtttg ttactctctt gaaagaaata    900
ataaactatc tgcaatttat aaatgatctt tgtgatacgt tcaataatga acaattaata    960
aaacgccatg aaaatatttg gatgcttatt gagcaaagaa aaataggaca tgattttttaa  1020

SEQ ID NO: 891          moltype = DNA   length = 1020
FEATURE                 Location/Qualifiers
source                  1..1020
                        mol_type = unassigned DNA
                        organism = African swine fever virus
SEQUENCE: 891
atgatcgacc aaaaaatttt tgagacaacg ttgaatattg atgatcctac caatttttgt     60
acaaatgtgg aggctcatct tttgaaggag cttgaaaaca tttatgtggg taagtgtttc    120
aaaaacagtt ttattcttaa tattactggc gttatacaac gctccccttg ttttattatg    180
cgtacgaata atagcggaag aggatatatg catgtaagat tttctgctgt tgtttcttac    240
ttaaatgcct ttgatttaat agcggccgtt aaaattatta aaaatgacag taatatattt    300
ctcggcgaaa gccttattga ctgaacccgta actattgtca taccctcgtc cgaatcgcaa    360
aataatgttg cagaagtagg gcaaattgtg ccggtacagc ttgctaacag cagcgtgtac    420
tatataccgt gcagacaaca ggccagtgcc acggggcagta ttttcattcc taagcacact    480
ttttcagtct atcacgtgca agaggagctt acacaggaac aggccttaaa cctaacaaaa    540
cttgttaaca ttagaaaat gcttcttgaa agtcgttcta aaaaagactt caagcagata    600
tgcttttttg aaaaacttta ctatacctac tctataagct cggatgagat cttagatcta    660
aaaatatgga aagggcccaa ggggaaggag atgtcgcggc ttaagccttg caatgtgctt    720
tcatttcttt atgacgccct aaaaaacaag agcagcagcc tagggttttg ggcaagaccc    780
ccgaatctcc ttaagtcctc gccattggcg tatcaacaag atcaaaattc ttttaacgcc    840
actgaattac ctattatatg ttctgctgaa gtaatgtttg ttactctctt gaagaaata    900
ataaactatc tgcaatttat gaatgatctt tgtgatacgt tcaataatga acaattaata    960
aaacgccatg aaaatatttg gatgcttatt gagcaaagaa aaataggaca tgattttttaa  1020

SEQ ID NO: 892          moltype = DNA   length = 732
FEATURE                 Location/Qualifiers
source                  1..732
                        mol_type = unassigned DNA
                        organism = African swine fever virus
SEQUENCE: 892
atgaaaatgc atatagcccg cgattctatc gtattttgc taaataagta tttgcaaaat     60
actatcctta caaataagat tgaacaagaa tgttttttac aggctgacac gcctaaaaaa    120
tatttacaat atattaaacc attttttaata aattgtatga ctaagaatat taccaccgat    180
ctagttatga aagattccaa aagactagaa ccctatatta ttttgaaat gcgtgatatc    240
atccaaatga tgtttttag aacgcttcaa aaacatatgt tttttaagga acatactgat    300
ttatgcaccg aatacgcgca aaaaatcgag gcctcgtgtt atcattatac gtaccagcaa    360
caagaaaaa ccttttttaga agaatattca acccgttgtg ggacgatcaa tcatattatt    420
aactgcgaaa aaaaagtca ccaacaacag gataacgatg cccttaataa gctaatttct    480
ggcgagctaa aaccggaggc aattggtagc atgacgttcg ccgagctttg ccctctgcc    540
gccttaaagg agaagacaga aattactcta cgttcgcagc aaaaggtcgc cgaaagacg    600
tcacaacttt ataagtgtcc caactgcaag cagcgtatgt gtacctacag agaagtacaa    660
acacgcgccc tcgatgagcc atccacgata ttttgtacct gtaaaaaatg cgggcatgag    720
tttattggct aa                                                        732

SEQ ID NO: 893          moltype = DNA   length = 732
FEATURE                 Location/Qualifiers
source                  1..732
                        mol_type = unassigned DNA
                        organism = African swine fever virus
SEQUENCE: 893
atgaaaatgc atatagcccg cgattctatc gtattttgc taaataagca tttgcaaaat     60
actatcctta caaataagat tgaacaagaa tgttttttac aggctgacac gcctaaaaaa    120
tatttacaat atattaagcc attttttaata aattgtatga ctaagaatat taccaccgat    180
ctagttatga aagattccaa aagattagaa ccctatatta ttttgaaat gcgtgatatc    240
atccaaatga tgtttttag aacgcttcaa aaacatatgt tttttaagga acatactgat    300
ttatgcaccg aatacgcgca aaaaatcgag gcctcgtgtt atcattatac gtaccagcaa    360
caagaaaaa ccttttttaga agaatattca acccgttgtg ggacgatcaa tcatattatt    420
aattgcgaaa aaaaagtca ccagcagcag gataacgatg cccttaataa gctaatttct    480
ggcgagctaa aaccggaggc aattggtagc atgacgttcg ccgagctttg tccctctgcc    540
gccttaaagg agaagacaga aattactcta cgttcgcagc aaaaggtcgc cgaaagacg    600
tcacaacttt ataagtgtcc caactgcaag cagcgtatgt gcacctacag agaagtacaa    660
acacgcgccc tcgatgagcc ttccacgata ttttgtacct gtaaaaaatg cgggcatgag    720
tttattggct aa                                                        732

SEQ ID NO: 894          moltype = DNA   length = 219
FEATURE                 Location/Qualifiers
source                  1..219
                        mol_type = unassigned DNA
                        organism = African swine fever virus
SEQUENCE: 894
atggagactc agaagttgat ttccatggtt aaggaagcct tagaaaaata tcaatacccct    60
```

```
cttactgcta aaaatattaa agtagtgata caaaaagagc acaatgtcgt cttacctaca    120
ggatctataa atagcatact gtacagtaac tcagaacttt ttgagaagat tgataagaca    180
aataccattt atccccgct ttggatacgg aaaaactaa                            219

SEQ ID NO: 895          moltype = DNA  length = 222
FEATURE                 Location/Qualifiers
source                  1..222
                        mol_type = unassigned DNA
                        organism = African swine fever virus
SEQUENCE: 895
atggagactc agaagttgat ttccatggtt aaggaagcct tggaaaaata tcaatacccct   60
cttactgcta aaaatattaa agtagtgata caaaaagagt acaatgttgt cttacctaca    120
ggttctataa atagcatact gtacagtaac tcagaacttt ttgaaaagat tgataagaca    180
aatactattt atccccgct ttggatacgg aaaactaact aa                        222

SEQ ID NO: 896          moltype = DNA  length = 717
FEATURE                 Location/Qualifiers
source                  1..717
                        mol_type = unassigned DNA
                        organism = African swine fever virus
SEQUENCE: 896
atggctcgtg gtcaaaatat tcgtaagagg acgttctccg atatggacac tccttcagat    60
aaaaatatag gaatccatac taattcttta cctaagaata acttgtatag aagaatatta    120
tttaaaggta aaatatctaa ctatagtata tccaaggaca gcttggctaa agatcattca    180
tctaatcata gtatctcgaa aaacggttta attggaaaaa agcgtccagc tccccttgat    240
atatcgtttc agaatatgaa ttcctctatt tcatctagta cccaaaaaaa gacaagaatt    300
ttagacgaag aaatcaaaga tcaaagttta tcaaatgaaa atgatagaga ttctcctgtt    360
attgtggata taaccttaaa accatcttac atgtcaaaaa catcacggat tacggaaatt    420
atacataaga tgaaggaact taacatgaac cgtattgagg acggttcatc tttcaacaaa    480
aaaagaagtg agcatgatga taaaaatatt ctcctacaca ctatggaaat ggaggaggag    540
gattgcgaga tagaagagga tattgctata gatagtccat atttaaatac ttctctttct    600
gaggatgaca ccgattctat tgtaggaaca gattattctg aggaagaaaa agaaactatc    660
tctgaaacgg aatcttcatc cgacgatgag tcctattcac tttatgatag tttctaa       717

SEQ ID NO: 897          moltype = DNA  length = 717
FEATURE                 Location/Qualifiers
source                  1..717
                        mol_type = unassigned DNA
                        organism = African swine fever virus
SEQUENCE: 897
atggctcgtg gtcaaaatat tcgtaagagg acgttctccg atatggacac tccttcagat    60
aaaaatatag gaatccatac taattcttta cctaagaata acttgtatag aagaatatta    120
tttaaaggta aaatatctaa ctatagtata tccaaggaca gcttggctaa agatcattca    180
tctaaacata gtatctcgaa aaacggttta attggaaaaa agcgtccagc tccccttgat    240
atatcgtttc agagtatgaa ttcctcgatt tcatctagta cccaaaaaaa gacaagaatt    300
ttagacgaag aaatcaaaga tcaaagttta tcaaatgaaa atgatacaga ttctcctgtt    360
attgtggata taaccttaaa accatcttac atgtcaaaaa catcacggat tacggaaatt    420
attcataaga tgaaggaact taacatgaac cgcattgagg acggttcatc tttcaacaaa    480
aaaagaagtg aacatgatga taaaaatatt ctcctacaca ctatggaaat ggaggaggag    540
gattgcgaga tagaagagga tattgctata gatagtccat atttaaatac ttctctttct    600
gaggatgaca ccgattctat tgtaggaaca gattattctg agaaagaaaa agaaactatc    660
tctgaaacgg aatcttcatc cgacgatgag tcctattcac tttatgatag tttctaa       717

SEQ ID NO: 898          moltype = DNA  length = 291
FEATURE                 Location/Qualifiers
source                  1..291
                        mol_type = unassigned DNA
                        organism = African swine fever virus
SEQUENCE: 898
atgggaactt tttcagtaac tgcctctgca aaagtgacg atgctgtttg taagtattta     60
gaagaaccaa tagatgaaaa ttacagaaac atattaagaa atgagcatgt taaaaaaaat    120
ttaaatgagg ctctgaatcg acatattact acctataatc cagtagttga ttggtgtaat    180
aactattcaa cattttcatc tcaggatttc gatgaatata aaatttatat acatagcgat    240
cttatggatg gacgacctcg tccaaaaaaa acatggtgtg tcatcatgta a              291

SEQ ID NO: 899          moltype = DNA  length = 297
FEATURE                 Location/Qualifiers
source                  1..297
                        mol_type = unassigned DNA
                        organism = African swine fever virus
SEQUENCE: 899
atggaaacct tttcagtaac tgcctctgcg aaaagtgacg atgctgtttg taagtatcta    60
gaagaaccaa tagatgaaaa taaaaattct agaaacatat taagaaatga catggtaaa    120
aaaaaattaa atgaggctct gaatcgacat ataattgctt ataatccagt agttgattgg    180
tgtaataact attcaacata ttcatctcag tatttcgatg aatataaaat ttatatacat    240
agcgatctta tggatggacg acctcgtcca aaaaaaacat ggtgtgtcat catgtaa       297

SEQ ID NO: 900          moltype = DNA  length = 45
FEATURE                 Location/Qualifiers
```

```
source          1..45
                mol_type = unassigned DNA
                organism = African swine fever virus
SEQUENCE: 900
tcatttccgc tttgcttgga aatgggagtt gtaaaagttt ttgaa                45

SEQ ID NO: 901      moltype = DNA  length = 45
FEATURE             Location/Qualifiers
source          1..45
                mol_type = unassigned DNA
                organism = African swine fever virus
SEQUENCE: 901
aaaaataatg ggattgatgt gaactccatt tatggctcag acgat                45
```